US012529074B2

(12) United States Patent
Gu et al.

(10) Patent No.: US 12,529,074 B2
(45) Date of Patent: Jan. 20, 2026

(54) ADENO-ASSOCIATED VIRUS (AAV) PRODUCER CELL LINE AND RELATED METHODS

(71) Applicant: LONZA WALKERSVILLE, INC., Walkersville, MD (US)

(72) Inventors: Bingnan Gu, Manvel, TX (US); Caitlin M. Guenther, Houston, TX (US); Anandita Seth, Sugar Land, TX (US)

(73) Assignee: Lonza Walkersville, Inc., Walkersville, MD (US)

(*) Notice: Subject to any disclaimer, the term of this patent is extended or adjusted under 35 U.S.C. 154(b) by 0 days.

(21) Appl. No.: 18/352,657

(22) Filed: Jul. 14, 2023

(65) Prior Publication Data

US 2024/0018545 A1 Jan. 18, 2024

Related U.S. Application Data

(63) Continuation of application No. 16/719,251, filed on Dec. 18, 2019, now Pat. No. 11,739,347.

(60) Provisional application No. 62/866,092, filed on Jun. 25, 2019, provisional application No. 62/783,589, filed on Dec. 21, 2018.

(51) Int. Cl.

*C12N 15/86* (2006.01)
*C12N 15/113* (2010.01)
*C12N 15/864* (2006.01)

(52) U.S. Cl.

CPC ............ *C12N 15/86* (2013.01); *C12N 15/113* (2013.01); *C12N 15/8645* (2013.01); *C12N 2710/10343* (2013.01); *C12N 2830/008* (2013.01)

(58) Field of Classification Search

CPC ................ C12N 15/86; C12N 15/8645; C12N 2750/14152; C12N 2830/006
See application file for complete search history.

(56) References Cited

U.S. PATENT DOCUMENTS 5,622,856 A 4/1997 Natsoulis
2021/0062161 A1 3/2021 Vink

FOREIGN PATENT DOCUMENTS

WO 2003/104392 A2 12/2003
WO 2006/083800 A2 8/2006
WO 2015/162211 A1 10/2015
WO 2018/136566 A1 7/2018
WO 2018/192982 A2 10/2018

OTHER PUBLICATIONS

Smith, A. D., et al., 2007, Tissue-specific regulatory elements in mammalian promoters, Mol. Sys. Biol. 3:Article 73, pp. 1-8.*

Li, J., et al., Jul. 1997, Role for Highly Regulated rep Gene Expression in Adeno-Associated Virus Vector Production, J. Virol. 71(7):5236-5243.*

Chu et al., "SV40 DNA Transfection of Cells in Suspension: Analysis of the Efficiency of Transcription and Translation of T Antigen," Gene 13(2): 197-202 (1981).

Clark et al., "Cell Lines for the Production of Recombinant Adeno-Associated Virus," Human Gene Therapy 6:1329-1341 (1995).

Deuschle et al., "Tetracycline-Reversible Silencing of Eukaryotic Promoters," Mol. Cell Biol. 15(4): 1907-1914 (1995).

Graham et al., "A New Technique for the Assay of Infectivity of Human Adenovirus 5 DNA," Virology, 52(2):456-457 (1973).

Guido et al., "Human bocavirus: Current knowledge and future challenges," World J. Gateroenterol 22:8684-8697.

Huang et al., "Adenovirus early region 4 encodes two gene products with redundant effects in lytic infection," Journal of Virology 63(6):2605-2615 (1989).

Ishibashi et al., "Adenoviruses of animals," The Adenoviruses, Ginsberg, ed., Plenum Press, New York, N.Y., pp. 497-562 (1984).

Kotin, R. M., "Prospects for the Use of Adeno-Associated Virus as a Vector for Human Gene Therapy," Human Gene Therapy 5:793-801 (1994).

Li et al., "Role for Highly Regulated rep Gene Expression in Adeno-Associated Virus Vector Production," Journal of Virology 71:5236-5243 (1997).

Machitani et al., "Development of an adenovirus vector lacking the expression of virus-associates RNAs," Journal of Controlled Release 154(3):285-289 (2011).

Mullick et al., "The cumate gene-switch: a system for regulated expression in mammalian cells," BMC Biotechnology 6:43 (1-18) (2006).

Muzyczka, N., "Use of Adeno-Associated Virus as a General Transduction Vector for Mammalian Cells," Current Topics in Microbiol. and Immunol. 158:97-129 (1992).

Nakamura et al., "Development of packaging cell lines for generation of adeno-associated virus vectors by lentiviral gene transfer of trans-complementary components," Eur. J. Haematol. 73:285-294 (2004).

Robert et al., "Manufacturing of Recombinant Adeno-Associated Viruses Using Mammalian Expression Platforms," Biotechnology Journal 12(1600193): 1-16 (2017).

Smith and Katin, "An adeno-associated virus (AAV) initiator protein, Rep 78, catalyzes the cleavage and ligation of single-stranded AAV ori Dna," J. Viral. 74(7):3122-3129 (2002).

Strauss, "Adenovirus infections in humans," In The Adenoviruses, Ginsberg, ed., Plenum Press, New York, N.Y., pp. 451-596 (1984).

Szulc et al., "A versatile tool for conditional gene expression and knockdown," Nature Methods 3:109-116 (2006).

Tetracycline On, "Tetracycline (Tet) Inducible Expression". Addgene. Retrieved from https://www.addgene.org/collections/tetracycline/ on Jun. 2, 2023.

(Continued)

*Primary Examiner* — Jeffrey S Parkin
(74) *Attorney, Agent, or Firm* — Medler Ferro Woodhouse & Mills PLLC

(57) ABSTRACT

The present disclosure relates to a mammalian cell line for producing adeno-associated virus (AAV), suitably including nucleic acids encoding helper genes and AAV genes, under the control of derepressible promoters. The disclosure also relates to isolated nucleic acid molecules that encode such genes, as well as methods of using the mammalian cells for producing AAVs.

9 Claims, 15 Drawing Sheets

Specification includes a Sequence Listing.

(56) References Cited

OTHER PUBLICATIONS

Tordo et al., "A Novel Adeno-Associated Virus Capsid with Enhanced Neurotropism Corrects a Lysosomal Transmembrane Enzyme Deficiency," Brain ePub 141(7): 2014-2031 (2018).
Urabe et al., "Insect Cells as a Factory to Produce Adeno-Associated Virus Type 2 Vectors," Human Gene Therapy 13: 193501943 (2002).
Wiederschain et al., "Single-vector inducible lentiviral RNAi system for oncology target validation," Cell Cycle 8:498-504 (2009).
Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9:1939-1950 (1998).
Zhou et al., "A New Vector System with Inducible E2a Cell Line for Production of Higher Titer and Safer Adenoviral Vectors," Virology 275(2):348-357 (2000).
Restriction Requirement issued in U.S. Appl. No. 18/498,577, dated Feb. 26, 2024.
Non-Final Office Action issued in U.S. Appl. No. 18/498,577, dated May 22, 2024.

* cited by examiner pcDNA3.1-E2A-E4-VA-TetR
11,986 bp pcDNA3.1-E2A-E4-VA-TetR-V2
11,641 bp

| | pHelper | | piHelper1 | |
|---|---|---|---|---|
| | - Dox | + Dox | - Dox | + Dox |
| **AAV titer (vg/ml)** | **1.04E+10** | **1.26E+10** | **1.50E+09** | **3.35E+09** |

pPBBG7
18,281 bp pcPBBG8
17,936 bp

PBBG-iHelper-Puro
11,801 bp

PBBG-ITRGFP
7798 bp

SEQUENCE LISTING

```
Sequence total quantity: 32
SEQ ID NO: 1            moltype = DNA  length = 11986
FEATURE                 Location/Qualifiers
misc_feature            1..11986
                        note = Description of Artificial Sequence: Synthetic
                         polynucleotide
source                  1..11986
                        mol_type = other DNA
                        organism = synthetic construct
SEQUENCE: 1
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
```

```
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgagctcgg atccactagt ccagtgtggt ggaattcctg  960
cttcgcgatg tacgggccag atatacgcgt tgacattgat tattgactag ttattaatag  1020
taatcaatta cggggtcatt agttcatagc ccatatatgg agttccgcgt tacataactt  1080
acggtaaatg gcccgcctgg ctgaccgccc aacgaccccc gcccattgac gtcaataatg  1140
acgtatgttc ccatagtaac gccaataggg actttccatt gacgtcaatg ggtggagtat  1200
ttacggtaaa ctgcccactt ggcagtacat caagtgtatc atatgccaag tacgccccct  1260
attgacgtca atgacggtaa atggcccgcc tggcattatg cccagtacat gaccttatgg  1320
gactttccta cttggcagta catctacgta ttagtcatcg ctattaccat ggtgatgcgg  1380
ttttggcagt acatcaatgg gcgtggatag cggtttgact cacggggatt tccaagtctc  1440
caccccattg acgtcaatgg gagtttgttt tggaaccaaa atcaacggga ctttccaaaa  1500
tgtcgtaaca actccgcccc attgacgcaa atgggcggta ggcgtgtacg gtgggaggtc  1560
tatataagca gagctctccc tatcagtgat agagatctcc ctatcagtga tagagatcgt  1620
cgacgagctc gtttagtgaa ccgtcagatc gcctggagac gccatccacg ctgttttgac  1680
ctccatagaa gacaccggga ccgatccagc ctccggactc tagcgtttaa acttaagctt  1740
gccaccatgg ccagtcggga agaggagcag cgcgaaacca cccccgagcg cggacgcggt  1800
gcggcgcgac gtcccccaac catggaggac gtgtcgtccc cgtccccgtc gccgccgcct  1860
ccccgggcgc ccccaaaaaa gcggatgagg cggcgtatcg agtccgagga cgaggaagac  1920
tcatcacaag acgcgctggt gccgcgcaca cccagcccgc ggccatcgac ctcggcggcg  1980
gatttggcca ttgcgcccaa gaagaaaaag aagcgccctt ctcccaagcc cgagcgcccg  2040
ccatcaccag aggtaatcgt ggacagcgag gaagaaagag aagatgtggc gctacaaatg  2100
gtgggtttca gcaacccacc ggtgctaatc aagcatggca aggaggtaa gcgcacagtg  2160
cggcggctga atgaagacga cccagtggcg cgtggtatgc ggacgcaaga ggaagaggaa  2220
gagcccagcg aagcggaaag tgaaattacg gtgatgaacc cgctgagtgt gccgatcgtg  2280
tctgcgtggg agaagggcat ggaggctgcg cgcgcgctga tggacaagta ccacgtggat  2340
aacgatctaa aggcgaactt caaactactg cctgaccaag tggaagctct ggcggccgta  2400
tgcaagacct ggctgaacga ggagcaccgc gggttgcagc tgaccttcac cagcaacaag  2460
acctttgtga cgatgatggg gcgattcctg caggcgtacc tgcagtcgtt tgcagaggtg  2520
acctacaagc atcacgagcc cacgggctgc gcgttgtggc tgcaccgctg cgctgagatc  2580
gaaggcgagc ttaagtgtct acacggaagc attatgataa ataaggagca cgtgattgaa  2640
atggatgtga cgagcgaaaa cgggcagcgc gcgctgaagg agcagtctag caaggccaag  2700
atcgtgaaga accggtgggg ccgaaatgtg gtgcagatct ccaacaccga cgcaaggtgc  2760
tgcgtgcacg acgcggcctg tccggccaat cagttttccg gcaagtcttg cggcatgttc  2820
ttctctgaag gcgcaaaggc tcaggtggct tttaagcaga tcaaggcttt tatgcaggcg  2880
ctgtatccta acgcccagac cgggcacggt cacctttga tgccactacg gtgcgagtgc  2940
aactcaaagc ctgggcacgc gcccttttg ggaaggcagc taccaaagtt gactccgttc  3000
gccctgagca acgcggagga cctggacgcg gatctgatct ccgacaagag cgtgctggcc  3060
agcgtgcacc acccggcgct gatagtgttc cagtgctgca accctgtgta tcgcaactcg  3120
cgcgcgcagg gcggaggccc caactgcgac ttcaagatat cggcgcccga cctgctaaac  3180
gcgttggtga tggtgcgcag cctgtggagt gaaaacttca ccgagctgcc gcggatggtt  3240
gtgcctgagt ttaagtggag cactaaacac cagtatcgca acgtgtccct gccagtggcg  3300
catagcgatg cgcggcagaa cccctttgat ttttaacccg ggagttctag ggatctgccc  3360
ctctccctcc cccccccta acgttactgg ccgaagccgc ttggaataag gccggtgtgc  3420
gtttgtctat atgttatttt ccaccatatt gccgtctttt ggcaatgtga gggcccggaa  3480
acctggccct gtcttcttga cgagcattcc taggggtctt tcccctctcg ccaaaggaat  3540
gcaaggtctg ttgaatgtcg tgaaggaagc agttcctctg gaagcttctt gaagacaaac  3600
aacgtctgta gcgacccttt gcaggcagcg gaacccccca cctggcgaca ggtgcctctg  3660
cggccaaaag ccacgtgtat aagatacacc tgcaaaggcg gcacaacccc agtgccacgt  3720
tgtgagttgg atagttgtgg aaagagtcaa atggctctcc tcaagcgtat tcaacaaggg  3780
gctgaaggat gcccagaagg taccccattg tatgggatct gatctggggc ctcggtgcac  3840
atgctttaca tgtgtttagt cgaggttaaa aaaacgtcta ggccccccga accacgggga  3900
cgtggttttc ctttgaaaaa cacgatgata aggatccacc ggaggccacc atgactacgt  3960
ccggcgttcc atttggcatg acactacgac caacacgatc tcggttgtct cggcgcactc  4020
cgtacagtag ggatcgtcta cctccttttg agacagaaac ccgcgctacc atactggagg  4080
atcatccgct gctgcccgaa tgtaacactt tgacaatgca caacgtgagt tacgtgcgag  4140
gtcttccctg cagtgtggga tttacgctga ttcaggaatg ggttgttccc tgggatatgg  4200
ttctaacgcg ggaggagctt gtaatcctga ggaagtgtat gcacgtgtgc ctgtgttgtg  4260
ccaacattga tatcatgacg agcatgatga tccatggtta cgagtcctgg gctctccact  4320
gtcattgttc cagtcccggt tccctgcagt gtatagccgg cgggcaggtt ttggccagct  4380
ggtttaggat ggtggtggat ggcgccatgt ttaatcagag gtttatatgg taccgggagg  4440
tggtgaatta caacatgcca aaagaggtaa tgtttatgtc cagcgtgttt atgaggggtc  4500
gccacttaat ctacctgcgc ttgtggtatg atggccacgt gggttctgtg gtccccgcca  4560
tgagctttgg atacagcgcc ttgcactgtg ggattttgaa caatattgtg gtgctgtgct  4620
gcagttactg tgctgattta agtgagatca gggtgcgctg ctgtgcccgg aggacaaggc  4680
gccttatgct gcgggcggtg cgaatcatcg ctgaggagac cactgccatg ttgtattcct  4740
gcaggacgga gcggcggcgg cagcagttta ttcgcgcgct gctgcagcac caccgcccta  4800
tcctgatgca cgattatgac tctaccccca tgtaggcggc cgctcgagtc tagagggccc  4860
gtttaaaccc gctgatcagc ctcgactgtg ccttctagtt gccagccatc tgttgtttgc  4920
ccctcccccg tgccttcctt gaccctggaa ggtgccactc ccactgtcct ttcctaataa  4980
aatgaggaaa ttgcatcgca ttgtctgagt aggtgtcatt ctattctggg gggtggggtg  5040
gggcaggaca gcaaggggga ggattgggaa gacaatagca ggcatgctgg ggatgcggtg  5100
ggctctatgg cttctgaggc ggaaagaacc agctggggct ctaggggta tccccggggt  5160
tggggttgcg ccttttccaa ggcatccagc acagtggcgg ccgcaatatt tgcatgtcgc  5220
tatgtgttct gggaaatcac cataaacgtg aaatccctat cagtgataga gacttataag  5280
```

-continued

```
ttccctatca gtgatagaga accggtgggc actcttccgt ggtctggtgg ataaattcgc  5340
aagggtatca tggcggacga ccggggttcg agccccgtat ccggccgtcc gccgtgatcc  5400
atgcggttac cgcccgcgtg tcgaacccag gtgtgcgacg tcagacaacg ggggagtgct  5460
cctttttgaa ttccactttg gccgcggctc gagggggttg ggttgcgcc ttttccaagg  5520
cagccctggg tttgcgcagg gacgcggctg ctctgggcgt ggttccggga aacgcagcgg  5580
cgccgaccct gggtctcgca cattcttcac gtccgttcgc agcgtcaccc ggatcttcgc  5640
cgctaccctt gtgggccccc cggcgacgct tcctgctccg cccctaagtc gggaaggttc  5700
cttgcggttc gcggcgtgcc ggacgtgaca aacggaagcc gcacgtctca ctagtaccct  5760
cgcagacgga cagcgccagg gagcaatggc agcgcgccga ccgcgatggg ctgtggccaa  5820
tagcggctgc tcagcagggc gcgccgagag cagcggccgg gaaggggcgg tgcgggaggc  5880
ggggtgtggg gcggtagtgt gggccctgtt cctgcccgcg cggtgttccg cattctgcaa  5940
gcctccggag cgcacgtcgg cagtcggctc cctcgttgac cgaatcaccg acctctctcc  6000
ccagggggat ctgtgagttt ggggaccctt gattgttctt tctttttcgc tattgtaaaa  6060
ttcatgttat atggaggggg caaagttttc agggtgttgt ttagaatggg aagatgtccc  6120
ttgtatcacc atggaccctc atgataattt tgtttcttc actttctact ctgttgacaa  6180
ccattgtctc ctcttatttt cttttcattt tctgtaactt tttcgttaaa ctttagcttg  6240
catttgtaac gaatttttaa attcactttt gtttatttgt cagattgtaa gtactttctc  6300
taatcacttt tttttcaagg caatcagggt atattatatt gtacttcagc acagttttag  6360
agaacaattg ttataattaa atgataaggt agaatatttc tgcatataaa ttctggctgg  6420
cgtggaaata ttcttattgg tagaaacaac tacatcctgg tcatcatcct gcctttctct  6480
ttatggttac aatgatatac actgtttgag atgaggataa aatactctga gtccaaaccg  6540
ggcccctctg ctaaccatgt tcatgccttc ttctttttcc tacagctcct gggcaacgtg  6600
ctggttattg tgctgtctca tcattttggc aaagaattgt aatacgactc actatagggc  6660
gagccaccat ggctagatta gataaaagta aagtgattaa cagcgcatta gagctgctta  6720
atgaggtcgg aatcgaaggt ttaacaaccc gtaaactcgc ccagaagcta ggtgtagagc  6780
agcctacatt gtattggcat gtaaaaaata agcgggcttt gctcgacgcc ttagccattg  6840
agatgttaga taggcaccat actcactttt gccctttaga aggggaaagc tggcaagatt  6900
ttttacgtaa taacgctaaa agttttagat gtgctttact aagtcatcgc gatggagcaa  6960
aagtacattt aggtacacgg cctacagaaa aacagtatga aactctcgaa aatcaattag  7020
cctttttatg ccaacaaggt ttttcactag agaatgcctt atatgcactc agcgccgtgg  7080
ggcattttac tttaggttgc gtattggaag atcaagagca tcaagtcgct aaagaagaaa  7140
gggaaacacc tactactgat agtatgccgc cattattacg acaagctatc gaattatttg  7200
atcaccaagg tgcagagcca gccttcttat tcggccttga attgatcata tgcggattag  7260
aaaaacaact taaatgtgaa agtgggtccc caaaaaagaa gagaaaggtc gacggcggtg  7320
gtgctttgtc tcctcagcac tctgctgtca ctcaaggaag tatcatcaag aacaaggagg  7380
gcatggatgc taagtcacta actgcctggt cccggacact ggtgaccttc aaggatgtat  7440
ttgtggactt caccagggag gagtggaagc tgctggacac tgctcagcag atcgtgtaca  7500
gaaatgtgat gctggagaac tataagaacc tggtttcctt gggttatcag cttactaagc  7560
cagatgtgat cctccggttg gagaagggag aagagccctg gctggtggag agagaaattc  7620
accaagagac ccatcctgat tcagagactg catttgaaat caaatcatca gtttaagcgt  7680
acagcggctc ccgggagttc tagggatctg cccctctccc tcccccccc ctaacgttac  7740
tggccgaagc cgcttggaat aaggccggtg tgcgtttgtc tatatgttat tttccaccat  7800
attgccgtct tttggcaatg tgagggcccg gaaacctggc cctgtcttct tgacgagcat  7860
tcctaggggt ctttcccctc tcgccaaagg aatgcaaggt ctgttgaatg tcgtgaagga  7920
agcagttcct ctggaagctt cttgaagaca aacaacgtct gtagcgaccc tttgcaggca  7980
gcggaacccc ccacctggcg acaggtgcct ctgcggccaa aagccacgtg tataagatac  8040
acctgcaaag gcggcacaac cccagtgcca cgttgtgagt tggatagttg tggaaagagt  8100
caaatggctc tcctcaagcg tattcaacaa ggggctgaag gatgcccaga aggtacccca  8160
ttgtatggga tctgatctgg ggcctcggtg cacatgcttt acatgtgttt agtcgaggtt  8220
aaaaaaacgt ctaggccccc cgaaccacgg ggacgtggtt ttcctttgaa aaacacgatg  8280
ataaggatcc accggaggcc accatgaccg agtacaagcc cacggtgcgc ctcgccaccc  8340
gcgacgacgt ccccagggcc gtacgcaccc tcgccgccgc gttcgccgac taccccgcca  8400
cgcgccacac cgtcgatccg gaccgccaca tcgagcgggt caccgagctg caagaactct  8460
tcctcacgcg cgtcgggctc gacatcggca aggtgtgggt cgcggacgac ggcgccgcgg  8520
tggcggtctg gaccacgccg gagagcgtcg aagcgggggc ggtgttcgcc gagatcggcc  8580
cgcgcatggc cgagttgagc ggttcccggc tggccgcgca gcaacagatg gaaggcctcc  8640
tggcgccgca ccggcccaag gagcccgcgt ggttcctggc caccgtcggc gtctcgcccg  8700
accaccaggg caagggtctg ggcagcgccg tcgtgctccc cggagtggag gcggccgagc  8760
gcgccggggt gcccgccttc ctggagacct ccgcgccccg caacctcccc ttctacgagc  8820
ggctcggctt caccgtcacc gccgacgtcg aggtgcccga aggaccgcgc acctggtgca  8880
tgacccgcaa gcccggtgcc tgaccgcgtc tggaacaatc aacctctgga ttacaaaatt  8940
tgtgaaagat tgactggtat tcttaactat gttgctcctt ttacgctatg tggatacgct  9000
gctttaatgc ctttgtatca tgctattgct tcccgtatgg ctttcatttt ctcctccttg  9060
tataaatcct ggttgctgtc tctttatgag gagttgtggc ccgttgtcag gcaacgtggc  9120
gtggtgtgca ctgtgtttgc tgacgcaacc cccactggtt ggggcattgc caccacctgt  9180
cagctccttt ccgggacttt cgctttcccc ctccctattg ccacggcgga actcatcgcc  9240
gcctgccttg cccgctgctg gacaggggct cggctgttgg gcactgacaa ttccgtggtg  9300
ttgtcgggga agctgacgtc ctttccatgg ctgctcgcct gtgttgccac ctggattctg  9360
cgcgggacgt ccttctgcta cgtcccttcg gccctcaatc cagcggacct tccttcccgc  9420
ggcctgctgc cggctctgcg gcctcttccg cgtcttcgcc ttcgccctca gacgagtcgg  9480
atctcccttt gggccgcctc cccgcaaaat gaccgaccaa gcgacgccca acctgccatc  9540
acgagatttc gattccaccg ccgccttcta tgaaaggttg ggcttcggaa tcgttttccg  9600
ggacgccggc tggatgatcc tccagcgcgg ggatctcatg ctggagttct tcgcccaccc  9660
caacttgttt attgcagctt ataatggtta caaataaagc aatagcatca caaatttcac  9720
aaataaagca tttttttcac tgcattctag ttgtggtttg tccaaactca tcaatgtatc  9780
ttatcatgtc tgtataccgt cgacctctag ctagagcttg gcgtaatcat ggtcatagct  9840
gtttcctgtg tgaaattgtt atccgctcac aattccacac aacatacgag ccggaagcat  9900
aaagtgtaaa gcctggggtg cctaatgagt gagctaactc acattaattg cgttgcgctc  9960
actgcccgct ttccagtcgg gaaacctgtc gtgccagctg cattaatgaa tcggccaacg  10020
```

```
cgcggggaga ggcggtttgc gtattgggcg ctcttccgct tcctcgctca ctgactcgct  10080
gcgctcggtc gttcggctgc ggcgagcggt atcagctcac tcaaaggcgg taatacggtt  10140
atccacagaa tcaggggata acgcaggaaa gaacatgtga gcaaaaggcc agcaaaaggc  10200
caggaaccgt aaaaaggccg cgttgctggc gtttttccat aggctccgcc cccctgacga  10260
gcatcacaaa aatcgacgct caagtcagag gtggcgaaac ccgacaggac tataaagata  10320
ccaggcgttt ccccctggaa gctccctcgt gcgctctcct gttccgaccc tgccgcttac  10380
cggatacctg tccgcctttc tcccttcggg aagcgtggcg ctttctcata gctcacgctg  10440
taggtatctc agttcggtgt aggtcgttcg ctccaagctg ggctgtgtgc acgaaccccc  10500
cgttcagccc gaccgctgcg ccttatccgg taactatcgt cttgagtcca acccggtaag  10560
acacgactta tcgccactgg cagcagccac tggtaacagg attagcagag cgaggtatgt  10620
aggcggtgct acagagttct tgaagtggtg gcctaactac ggctacacta gaagaacagt  10680
atttggtatc tgcgctctgc tgaagccagt taccttcgga aaaagagttg gtagctcttg  10740
atccggcaaa caaaccaccg ctggtagcgg tttttttgtt tgcaagcagc agattacgcg  10800
cagaaaaaaa ggatctcaag aagatccttt gatcttttct acggggtctg acgctcagtg  10860
gaacgaaaac tcacgttaag ggattttggt catgagatta tcaaaaagga tcttcaccta  10920
gatcctttta aattaaaaat gaagttttaa atcaatctaa agtatatatg agtaaacttg  10980
gtctgacagt taccaatgct taatcagtga ggcacctatc tcagcgatct gtctatttcg  11040
ttcatccata gttgcctgac tccccgtcgt gtagataact acgatacggg agggcttacc  11100
atctggcccc agtgctgcaa tgataccgcg agacccacgc tcaccggctc cagatttatc  11160
agcaataaac cagccagccg gaagggccga gcgcagaagt ggtcctgcaa ctttatccgc  11220
ctccatccag tctattaatt gttgccggga agctagagta agtagttcgc cagttaatag  11280
tttgcgcaac gttgttgcca ttgctacagg catcgtggtg tcacgctcgt cgtttggtat  11340
ggcttcattc agctccggtt cccaacgatc aaggcgagtt acatgatccc ccatgttgtg  11400
caaaaaagcg gttagctcct tcggtcctcc gatcgttgtc agaagtaagt tggccgcagt  11460
gttatcactc atggttatgg cagcactgca taattctctt actgtcatgc catccgtaag  11520
atgcttttct gtgactggtg agtactcaac caagtcattc tgagaatagt gtatgcggcg  11580
accgagttgc tcttgcccgg cgtcaatacg ggataatacc gcgccacata gcagaacttt  11640
aaaagtgctc atcattggaa aacgttcttc ggggcgaaaa ctctcaagga tcttaccgct  11700
gttgagatcc agttcgatgt aacccactcg tgcacccaac tgatcttcag catcttttac  11760
tttcaccagc gtttctgggt gagcaaaaac aggaaggcaa aatgccgcaa aaaagggaat  11820
aagggcgaca cggaaatgtt gaatactcat actcttcctt tttcaatatt attgaagcat  11880
ttatcagggt tattgtctca tgagcggata catatttgaa tgtatttaga aaaataaaca  11940
aataggggtt ccgcgcacat ttccccgaaa agtgccacct gacgtc                11986

SEQ ID NO: 2           moltype = DNA  length = 11641
FEATURE                Location/Qualifiers
misc_feature           1..11641
                       note = Description of Artificial Sequence: Synthetic
                        polynucleotide
source                 1..11641
                       mol_type = other DNA
                       organism = synthetic construct
SEQUENCE: 2
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgagctcgg atccactagt ccagtgtggt ggaattcctg  960
cttcgcgatg tacgggccag atatacgcgt tgacattgat tattgactag ttattaatag  1020
taatcaatta cggggtcatt agttcatagc ccatatatgg agttccgcgt tacataactt  1080
acggtaaatg gcccgcctgg ctgaccgccc aacgaccccc gcccattgac gtcaataatg  1140
acgtatgttc ccatagtaac gccaataggg actttccatt gacgtcaatg ggtggagtat  1200
ttacggtaaa ctgcccactt ggcagtacat caagtgtatc atatgccaag tacgcccct  1260
attgacgtca atgacggtaa atggcccgcc tggcattatg cccagtacat gaccttatgg  1320
gactttccta cttggcagta catctacgta ttagtcatcg ctattaccat ggtgatgcgg  1380
ttttggcagt acatcaatgg gcgtggatag cggtttgact cacggggatt tccaagtctc  1440
caccccattg acgtcaatgg gagtttgttt tggaaccaaa atcaacggga ctttccaaaa  1500
tgtcgtaaca actccgcccc attgacgcaa atgggcggta ggcgtgtacg gtgggaggtc  1560
tatataagca gagctctccc tatcagtgat agagatctcc ctatcagtga tagagatcgt  1620
cgacgagctc gtttagtgaa ccgtcagatc gcctggagac gccatccacg ctgttttgac  1680
ctccatagaa gacaccggga ccgatccagc ctccggactc tagcgtttaa acttaagctt  1740
gccaccatgg ccagtcggga agaggagcag cgcgaaacca cccccgagcg cggacgcggt  1800
gcggcgcgac gtcccccaac catggaggac gtgtcgtccc cgtccccgtc gccgccgcct  1860
ccccgggcgc ccccaaaaaa gcggatgagg cggcgtatcg agtccgagga cgaggaagac  1920
tcatcacaag acgcgctggt gccgcgcaca cccagcccgc ggccatcgac ctcggcggcg  1980
gatttggcca ttgcgcccaa gaagaaaaag aagcgccctt ctcccaagcc cgagcgcccg  2040
ccatcaccag aggtaatcgt ggacagcgag gaagaaagag aagatgtggc gctacaaatg  2100
gtgggtttca gcaacccacc ggtgctaatc aagcatggca aaggaggtaa gcgcacagtg  2160
```

```
cggcggctga atgaagacga cccagtggcg cgtggtatgc ggacgcaaga ggaagaggaa  2220
gagcccagcg aagcggaaag tgaaattacg gtgatgaacc cgctgagtgt gccgatcgtg  2280
tctgcgtggg agaagggcat ggaggctgcg cgcgcgctga tggacaagta ccacgtggat  2340
aacgatctaa aggcgaactt caaactactg cctgaccaag tggaagctct ggcggccgta  2400
tgcaagacct ggctgaacga ggagcaccgc gggttgcagc tgaccttcac cagcaacaag  2460
acctttgtga cgatgatggg gcgattcctg caggcgtacc tgcagtcgtt tgcagaggtg  2520
acctacaagc atcacgagcc cacgggctgc gcgttgtggc tgcaccgctg cgctgagatc  2580
gaaggcgagc ttaagtgtct acacggaagc attatgataa ataaggagca cgtgattgaa  2640
atggatgtga cgagcgaaaa cgggcagcgc gcgctgaagg agcagtctag caaggccaag  2700
atcgtgaaga accggtgggg ccgaaatgtg gtgcagatct ccaacaccga cgcaaggtgc  2760
tgcgtgcacg acgcggcctg tccggccaat cagttttccg gcaagtcttg cggcatgttc  2820
ttctctgaag gcgcaaaggc tcaggtggct tttaagcaga tcaaggcttt tatgcaggcg  2880
ctgtatccta acgcccagac cgggcacggt cacctttga tgccactacg gtgcgagtgc  2940
aactcaaagc ctgggcacgc gcccttttg ggaaggcagc taccaaagtt gactccgttc  3000
gccctgagca acgcggagga cctggacgcg gatctgatct ccgacaagag cgtgctggcc  3060
agcgtgcacc acccggcgct gatagtgttc cagtgctgca accctgtgta tcgcaactcg  3120
cgcgcgcagg gcggaggccc caactgcgac ttcaagatat cggcgcccga cctgctaaac  3180
gcgttggtga tggtgcgcag cctgtggagt gaaaacttca ccgagctgcc gcggatggtt  3240
gtgcctgagt ttaagtggag cactaaacac cagtatcgca acgtgtccct gccagtggcg  3300
catagcgatg cgcggcagaa cccctttgat ttttaacccg ggagttctag ggatctgccc  3360
ctctccctcc cccccccta acgttactgg ccgaagccgc ttggaataag gccggtgtgc  3420
gtttgtctat atgttatttt ccaccatatt gccgtctttt ggcaatgtga gggcccggaa  3480
acctggccct gtcttcttga cgagcattcc taggggtctt tcccctctcg ccaaaggaat  3540
gcaaggtctg ttgaatgtcg tgaaggaagc agttcctctg gaagcttctt gaagacaaac  3600
aacgtctgta gcgacccttt gcaggcagcg gaacccccca cctggcgaca ggtgcctctg  3660
cggccaaaag ccacgtgtat aagatacacc tgcaaaggcg gcacaacccc agtgccacgt  3720
tgtgagttgg atagttgtgg aaagagtcaa atggctctcc tcaagcgtat tcaacaaggg  3780
gctgaaggat gcccagaagg taccccattg tatgggatct gatctggggc ctcggtgcac  3840
atgctttaca tgtgtttagt cgaggttaaa aaaacgtcta ggccccccga accacgggga  3900
cgtggttttc ctttgaaaaa cacgatgata aggatccacc ggaggccacc atgactacgt  3960
ccggcgttcc atttggcatg acactacgac caacacgatc tcggttgtct cggcgcactc  4020
cgtacagtag ggatcgtcta cctccttttg agacagaaac ccgcgctacc atactggagg  4080
atcatccgct gctgcccgaa tgtaacactt tgacaatgca caacgtgagt tacgtgcgag  4140
gtcttccctg cagtgtggga tttacgctga ttcaggaatg ggttgttccc tgggatatgg  4200
ttctaacgcg ggaggagctt gtaatcctga ggaagtgtat gcacgtgtgc ctgtgttgtg  4260
ccaacattga tatcatgacg agcatgatga tccatggtta cgagtcctgg gctctccact  4320
gtcattgttc cagtcccggt tccctgcagt gtatagccgg cgggcaggtt ttggccagct  4380
ggtttaggat ggtggtggat ggcgccatgt ttaatcagag gtttatatgg taccgggagg  4440
tggtgaatta caacatgcca aaagaggtaa tgtttatgtc cagcgtgttt atgaggggtc  4500
gccacttaat ctacctgcgc ttgtggtatg atggccacgt gggttctgtg gtccccgcca  4560
tgagctttgg atacagcgcc ttgcactgtg ggattttgaa caatattgtg gtgctgtgct  4620
gcagttactg tgctgattta agtgagatca gggtgcgctg ctgtgcccgg aggacaaggc  4680
gccttatgct gcgggcggtg cgaatcatcg ctgaggagac cactgccatg ttgtattcct  4740
gcaggacgga gcggcggcgg cagcagttta ttcgcgcgct gctgcagcac caccgcccta  4800
tcctgatgca cgattatgac tctacccca tgtaggcggc cgctcgagtc tagagggccc  4860
gtttaaaccc gctgatcagc ctcgactgtg ccttctagtt gccagccatc tgttgtttgc  4920
ccctcccccg tgccttcctt gaccctggaa ggtgccactc ccactgtcct ttcctaataa  4980
aatgaggaaa ttgcatcgca ttgtctgagt aggtgtcatt ctattctggg gggtggggtg  5040
gggcaggaca gcaaggggga ggattgggaa gacaatagca ggcatgctgg ggatgcggtg  5100
ggctctatgg cttctgaggc ggaaagaacc agctggggct ctagggggta tccccggggt  5160
tggggttgcg cctttttccaa ggcatccagc acagtggcgg ccgcaatatt tgcatgtcgc  5220
tatgtgttct gggaaatcac cataaacgtg aaatccctat cagtgataga gacttataag  5280
ttccctatca gtgatagaga accggtgggc actcttccgt ggtctggtgg ataaattcgc  5340
aagggtatca tggcggacga ccggggttcg agccccgtat ccggccgtcc gccgtgatcc  5400
atgcggttac cgcccgcgtg tcgaacccag gtgtgcgacg tcagacaacg ggggagtgct  5460
cctttttgaa ttccactttg gccgcggctc gagggggttg ggttgcgcc ttttccaagg  5520
cagccctggg tttgcgcagg gacgcggctg ctctgggcgt ggttccggga aacgcagcgg  5580
cgccgaccct gggtctcgca cattcttcac gtccgttcgc agcgtcaccc ggatcttcgc  5640
cgctacccctt gtgggcccc cggcgacgct tcctgctccg cccctaagtc gggaaggttc  5700
cttgcggttc gcggcgtgcc ggacgtgaca aacggaagcc gcacgtctca ctagtaccct  5760
cgcagacgga cagcgccagg gagcaatggc agcgcgccga ccgcgatggg ctgtggccaa  5820
tagcggctgc tcagcagggc gcgccgagag cagcggccgg gaaggggcgg tgcgggaggc  5880
ggggtgtggg gcggtagtgt gggccctgtt cctgcccgcg cggtgttccg cattctgcaa  5940
gcctccggag cgcacgtcgg cagtcggctc cctcgttgac cgaatcaccg acctctctcc  6000
ccagggggat ctgtgagttt ggggaccctt gattgttctt tctttttcgc tattgtaaaa  6060
ttcatgttat atggaggggg caaagttttc agggtgttgt ttagaatggg aagatgtccc  6120
ttgtatcacc atggaccctc atgataattt tgtttctttc actttctact ctgttgacaa  6180
ccattgtctc ctcttatttt cttttcattt tctgtaactt tttcgttaaa ctttagcttg  6240
catttgtaac gaatttttaa attcactttt gtttatttgt cagattgtaa gtactttctc  6300
taatcacttt tttttcaagg caatcagggt atattatatt gtacttcagc acagttttag  6360
agaacaattg ttataattaa atgataaggt agaatatttc tgcatataaa ttctggctgg  6420
cgtggaaata ttcttattgg tagaaacaac tacatcctgg tcatcatcct gcctttctct  6480
ttatggttac aatgatatac actgtttgag atgaggataa aatactctga gtccaaaccg  6540
ggcccctctg ctaaccatgt tcatgccttc ttctttttcc tacagctcct gggcaacgtg  6600
ctggttattg tgctgtctca tcattttggc aaagaattgt aatacgactc actatagggc  6660
gagccaccat ggctagatta gataaaagta aagtgattaa cagcgcatta gagctgctta  6720
atgaggtcgg aatcgaaggt ttaacaaccc gtaaactcgc ccagaagcta ggtgtagagc  6780
agcctacatt gtattggcat gtaaaaaata agcgggcttt gctcgacgcc ttagccattg  6840
agatgttaga taggcaccat actcactttt gcccttttaga aggggaaagc tggcaagatt  6900
```

-continued

```
ttttacgtaa taacgctaaa agttttagat gtgctttact aagtcatcgc gatggagcaa  6960
aagtacattt aggtacacgg cctacagaaa aacagtatga aactctcgaa aatcaattag  7020
cctttttatg ccaacaaggt ttttcactag agaatgcctt atatgcactc agcgccgtgg  7080
ggcattttac tttaggttgc gtattggaag atcaagagca tcaagtcgct aaagaagaaa  7140
gggaaacacc tactactgat agtatgccgc cattattacg acaagctatc gaattatttg  7200
atcaccaagg tgcagagcca gccttcttat tcggccttga attgatcata tgcggattag  7260
aaaaacaact taaatgtgaa agtgggtccc caaaaaagaa gagaaaggtc gacggcggtg  7320
gttcagttta agcgtacagc ggctcccggg agttctaggg atctgcccct ctccctcccc  7380
ccccccctaac gttactggcc gaagccgctt ggaataaggc cggtgtgcgt ttgtctatat  7440
gttattttcc accatattgc cgtcttttgg caatgtgagg gcccggaaac ctggccctgt  7500
cttcttgacg agcattccta ggggtctttc ccctctcgcc aaaggaatgc aaggtctgtt  7560
gaatgtcgtg aaggaagcag ttcctctgga agcttcttga agacaaacaa cgtctgtagc  7620
gaccctttgc aggcagcgga acccccccacc tggcgacagg tgcctctgcg gccaaaagcc  7680
acgtgtataa gatacacctg caaaggcggc acaaccccag tgccacgttg tgagttggat  7740
agttgtggaa agagtcaaat ggctctcctc aagcgtattc aacaaggggc tgaaggatgc  7800
ccagaaggta ccccattgta tgggatctga tctggggcct cggtgcacat gctttacatg  7860
tgtttagtcg aggttaaaaa aacgtctagg ccccccgaac cacggggacg tggttttcct  7920
ttgaaaaaca cgatgataag gatccaccgg aggccaccat gaccgagtac aagcccacgg  7980
tgcgcctcgc cacccgcgac gacgtcccca gggccgtacg caccctcgcc gccgcgttcg  8040
ccgactaccc cgccacgcgc cacaccgtcg atccggaccg ccacatcgag cgggtcaccg  8100
agctgcaaga actcttcctc acgcgcgtcg ggctcgacat cggcaaggtg tgggtcgcgg  8160
acgacggcgc cgcggtggcg gtctggacca cgccggagag cgtcgaagcg ggggcggtgt  8220
tcgccgagat cggcccgcgc atggccgagt tgagcggttc ccggctggcc gcgcagcaac  8280
agatggaagg cctcctggcg ccgcaccggc ccaaggagcc cgcgtggttc ctggccaccg  8340
tcggcgtctc gcccgaccac cagggcaagg gtctgggcag cgccgtcgtg ctccccggag  8400
tggaggcggc cgagcgcgcc ggggtgcccg ccttcctgga gacctccgcg ccccgcaacc  8460
tccccttcta cgagcggctc ggcttcaccg tcaccgccga cgtcgaggtg cccgaaggac  8520
cgcgcacctg gtgcatgacc cgcaagcccg gtgcctgacc gcgtctggaa caatcaacct  8580
ctggattaca aaatttgtga aagattgact ggtattctta actatgttgc tccttttacg  8640
ctatgtggat acgctgcttt aatgcctttg tatcatgcta ttgcttcccg tatggctttc  8700
attttctcct ccttgtataa atcctggttg ctgtctcttt atgaggagtt gtggcccgtt  8760
gtcaggcaac gtggcgtggt gtgcactgtg tttgctgacg caacccccac tggttggggc  8820
attgccacca cctgtcagct cctttccggg actttcgctt tccccctccc tattgccacg  8880
gcggaactca tcgccgcctg ccttgcccgc tgctggacag gggctcggct gttgggcact  8940
gacaattccg tggtgttgtc ggggaagctg acgtcctttc catggctgct cgcctgtgtt  9000
gccacctgga ttctgcgcgg gacgtccttc tgctacgtcc cttcggccct caatccagcg  9060
gaccttcctt cccgcggcct gctgccggct ctgcggcctc ttccgcgtct tcgccttcgc  9120
cctcagacga gtcggatctc cctttgggcc gcctccccgc aaaatgaccg accaagcgac  9180
gcccaacctg ccatcacgag atttcgattc caccgccgcc ttctatgaaa ggttgggctt  9240
cggaatcgtt ttccgggacg ccggctggat gatcctccag cgcggggatc tcatgctgga  9300
gttcttcgcc caccccaact tgtttattgc agcttataat ggttacaaat aaagcaatag  9360
catcacaaat ttcacaaata aagcattttt ttcactgcat tctagttgtg gtttgtccaa  9420
actcatcaat gtatcttatc atgtctgtat accgtcgacc tctagctaga gcttggcgta  9480
atcatggtca tagctgtttc ctgtgtgaaa ttgttatccg ctcacaattc cacacaacat  9540
acgagccgga agcataaagt gtaaagcctg gggtgcctaa tgagtgagct aactcacatt  9600
aattgcgttg cgctcactgc ccgctttcca gtcgggaaac ctgtcgtgcc agctgcatta  9660
atgaatcggc caacgcgcgg ggagaggcgg tttgcgtatt gggcgctctt ccgcttcctc  9720
gctcactgac tcgctgcgct cggtcgttcg gctgcggcga gcggtatcag ctcactcaaa  9780
ggcggtaata cggttatcca cagaatcagg ggataacgca ggaaagaaca tgtgagcaaa  9840
aggccagcaa aaggccagga accgtaaaaa ggccgcgttg ctggcgtttt tccataggct  9900
ccgcccccct gacgagcatc acaaaaatcg acgctcaagt cagaggtggc gaaacccgac  9960
aggactataa agataccagg cgtttccccc tggaagctcc ctcgtgcgct ctcctgttcc  10020
gaccctgccg cttaccggat acctgtccgc ctttctccct tcgggaagcg tggcgctttc  10080
tcatagctca cgctgtaggt atctcagttc ggtgtaggtc gttcgctcca agctgggctg  10140
tgtgcacgaa ccccccgttc agcccgaccg ctgcgcctta tccggtaact atcgtcttga  10200
gtccaacccg gtaagacacg acttatcgcc actggcagca gccactggta acaggattag  10260
cagagcgagg tatgtaggcg gtgctacaga gttcttgaag tggtggccta actacggcta  10320
cactagaaga acagtatttg gtatctgcgc tctgctgaag ccagttacct tcggaaaaag  10380
agttggtagc tcttgatccg gcaaacaaac caccgctggt agcggttttt ttgtttgcaa  10440
gcagcagatt acgcgcagaa aaaaaggatc tcaagaagat cctttgatct tttctacggg  10500
gtctgacgct cagtggaacg aaaactcacg ttaagggatt ttggtcatga gattatcaaa  10560
aaggatcttc acctagatcc ttttaaatta aaaatgaagt tttaaatcaa tctaaagtat  10620
atatgagtaa acttggtctg acagttacca atgcttaatc agtgaggcac ctatctcagc  10680
gatctgtcta tttcgttcat ccatagttgc ctgactcccc gtcgtgtaga taactacgat  10740
acgggagggc ttaccatctg gccccagtgc tgcaatgata ccgcgagacc cacgctcacc  10800
ggctccagat ttatcagcaa taaaccagcc agccggaagg gccgagcgca gaagtggtcc  10860
tgcaacttta tccgcctcca tccagtctat taattgttgc cgggaagcta gagtaagtag  10920
ttcgccagtt aatagtttgc gcaacgttgt tgccattgct acaggcatcg tggtgtcacg  10980
ctcgtcgttt ggtatggctt cattcagctc cggttcccaa cgatcaaggc gagttacatg  11040
atcccccatg ttgtgcaaaa aagcggttag ctccttcggt cctccgatcg ttgtcagaag  11100
taagttggcc gcagtgttat cactcatggt tatggcagca ctgcataatt ctcttactgt  11160
catgccatcc gtaagatgct tttctgtgac tggtgagtac tcaaccaagt cattctgaga  11220
atagtgtatg cggcgaccga gttgctcttg cccggcgtca atacgggata ataccgcgcc  11280
acatagcaga actttaaaag tgctcatcat tggaaaacgt tcttcggggc gaaaactctc  11340
aaggatctta ccgctgttga gatccagttc gatgtaaccc actcgtgcac ccaactgatc  11400
ttcagcatct tttactttca ccagcgtttc tgggtgagca aaaacaggaa ggcaaaatgc  11460
cgcaaaaaag ggaataaggg cgacacggaa atgttgaata ctcatactct tcctttttca  11520
```

```
atattattga agcatttatc agggttattg tctcatgagc ggatacatat ttgaatgtat  11580
ttagaaaaat aaacaaatag gggttccgcg cacatttccc cgaaaagtgc cacctgacgt  11640
c                                                                  11641

SEQ ID NO: 3            moltype = DNA  length = 110
FEATURE                 Location/Qualifiers
misc_feature            1..110
                        note = Description of Artificial Sequence: Synthetic
                         polynucleotide
source                  1..110
                        mol_type = other DNA
                        organism = synthetic construct
SEQUENCE: 3
tatttaatct ccctatcagt gatagagatc tccctatcag tgatagagat cgcccgagtg  60
agcacgcagg gtctccattt tgaagcggga ggtttgaacg cgcagccgcc             110

SEQ ID NO: 4            moltype = DNA  length = 108
FEATURE                 Location/Qualifiers
misc_feature            1..108
                        note = Description of Artificial Sequence: Synthetic
                         polynucleotide
source                  1..108
                        mol_type = other DNA
                        organism = synthetic construct
SEQUENCE: 4
tatttaatct ccctatcagt gatagagatc gcccgagtga gcacgcaggg tctccatttt  60
gatccctatc agtgatagag aagcgggagg tttgaacgcg cagccgcc               108

SEQ ID NO: 5            moltype = DNA  length = 106
FEATURE                 Location/Qualifiers
misc_feature            1..106
                        note = Description of Artificial Sequence: Synthetic
                         polynucleotide
source                  1..106
                        mol_type = other DNA
                        organism = synthetic construct
SEQUENCE: 5
tccctatcag tgatagagat ctatttaagc ccgagtgagc acgcagtccc tatcagtgat  60
agagaggtct ccattttgaa gcgggaggtt tgaacgcgca gccgcc                 106

SEQ ID NO: 6            moltype = DNA  length = 183
FEATURE                 Location/Qualifiers
misc_feature            1..183
                        note = Description of Artificial Sequence: Synthetic
                         polynucleotide
source                  1..183
                        mol_type = other DNA
                        organism = synthetic construct
SEQUENCE: 6
ccagaaatgg cgccggaggc gggaacaagg tggtggatga gtgctacatc cccaattact  60
tgctccccaa aacccagcct gagctccagt gggcgtggac taatatggaa cagtatttaa  120
gcgcctgtcc ctatcagtga tagagatctc cctatcagtg atagagattt gaatctcacg  180
gag                                                                183

SEQ ID NO: 7            moltype = DNA  length = 181
FEATURE                 Location/Qualifiers
misc_feature            1..181
                        note = Description of Artificial Sequence: Synthetic
                         polynucleotide
source                  1..181
                        mol_type = other DNA
                        organism = synthetic construct
SEQUENCE: 7
ccagaaatgg cgccggaggc gggaacaagg tggtggatga gtgctacatc cccaattact  60
tgctccccaa aacccagcct gagtccctat cagtgataga gactccagtg ggcgtggact  120
aatatggaac agtatttaag cgcctgtccc tatcagtgat agagatttga atctcacgga  180
g                                                                  181

SEQ ID NO: 8            moltype = DNA  length = 181
FEATURE                 Location/Qualifiers
misc_feature            1..181
                        note = Description of Artificial Sequence: Synthetic
                         polynucleotide
source                  1..181
                        mol_type = other DNA
                        organism = synthetic construct
SEQUENCE: 8
ccagaaatgg cgccggaggc gggaacaagg tggtggatga gtgctacatc cccaattact  60
tgctccccaa aacccagcct gagctccagt gggcgtggac taatatggaa tccctatcag  120
```

```
tgatagagac agtatttaag cgcctgtccc tatcagtgat agagatttga atctcacgga  180
g                                                                  181

SEQ ID NO: 9           moltype = DNA  length = 221
FEATURE                Location/Qualifiers
misc_feature           1..221
                       note = Description of Artificial Sequence: Synthetic
                        polynucleotide
source                 1..221
                       mol_type = other DNA
                       organism = synthetic construct
SEQUENCE: 9
ccagaaatgg cgccggaggc gggaacaagg tggtggatga gtgctacatc cccaattact  60
tgctccccaa aacccagcct gagctccagt gggcgtggac taatatggaa cagtatttaa  120
ggtaagttcc ctatcagtga tagagatctc cctatcagtg atagagatac tgacatccac  180
tttgcctttc tctccacagc gcctgtttga atctcacgga g                      221

SEQ ID NO: 10          moltype = DNA  length = 223
FEATURE                Location/Qualifiers
misc_feature           1..223
                       note = Description of Artificial Sequence: Synthetic
                        polynucleotide
source                 1..223
                       mol_type = other DNA
                       organism = synthetic construct
SEQUENCE: 10
ccagaaatgg cgccggaggc gggaacaagg tggtggatga gtgctacatc cccaattact  60
tgctccccaa aacccagcct gagctccagt gggcgtggac taatatggaa cagtatttaa  120
gcgcctgttt gaatctcacg gaaaggtaag ttccctatca gtgatagaga tctccctatc  180
agtgatagag atactgacat ccactttgcc tttctctcca cag                    223

SEQ ID NO: 11          moltype = DNA  length = 18281
FEATURE                Location/Qualifiers
misc_feature           1..18281
                       note = Description of Artificial Sequence: Synthetic
                        polynucleotide
source                 1..18281
                       mol_type = other DNA
                       organism = synthetic construct
SEQUENCE: 11
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcgtttaaac ttaagcttgg taccgagctc ggatccacta  1560
gtccagtgtg gtggaattcc tgcttcgcga tgtacgggcc agatatacgc gttgacattg  1620
attattgact agttattaat agtaatcaat tacggggtca ttagttcata gcccatatat  1680
ggagttccgc gttacataac ttacggtaaa tggcccgcct ggctgaccgc ccaacgaccc  1740
ccgcccattg acgtcaataa tgacgtatgt tcccatagta acgccaatag ggactttcca  1800
ttgacgtcaa tgggtggagt atttacggta aactgcccac ttggcagtac atcaagtgta  1860
tcatatgcca agtacgcccc ctattgacgt caatgacggt aaatggcccg cctggcatta  1920
tgcccagtac atgaccttat gggactttcc tacttggcag tacatctacg tattagtcat  1980
cgctattacc atggtgatgc ggttttggca gtacatcaat gggcgtggat agcggtttga  2040
ctcacgggga tttccaagtc tccaccccat tgacgtcaat gggagtttgt tttggaacca  2100
aaatcaacgg gactttccaa aatgtcgtaa caactccgcc ccattgacgc aaatgggcgg  2160
taggcgtgta cggtgggagg tctatataag cagagctctc cctatcagtg atagagatct  2220
ccctatcagt gatagagatc gtcgacgagc tcgtttagtg aaccgtcaga tcgcctggag  2280
acgccatcca cgctgttttg acctccatag aagacaccgg gaccgatcca gcctccggac  2340
```

```
tctagcgttt aaacttaagc ttgccaccat ggccagtcgg gaagaggagc agcgcgaaac  2400
cacccccgag cgcggacgcg gtgcggcgcg acgtccccca accatggagg acgtgtcgtc  2460
cccgtccccg tcgccgccgc ctccccgggc gcccccaaaa aagcggatga ggcggcgtat  2520
cgagtccgag gacgaggaag actcatcaca agacgcgctg gtgccgcgca cacccagccc  2580
gcggccatcg acctcggcgg cggatttggc cattgcgccc aagaagaaaa agaagcgccc  2640
ttctcccaag cccgagcgcc cgccatcacc agaggtaatc gtggacagcg aggaagaaag  2700
agaagatgtg gcgctacaaa tggtgggttt cagcaaccca ccggtgctaa tcaagcatgg  2760
caaaggaggt aagcgcacag tgcggcggct gaatgaagac gacccagtgg cgcgtggtat  2820
gcggacgcaa gaggaagagg aagagcccag cgaagcggaa agtgaaatta cggtgatgaa  2880
cccgctgagt gtgccgatcg tgtctgcgtg ggagaagggc atggaggctg cgcgcgcgct  2940
gatggacaag taccacgtgg ataacgatct aaaggcgaac ttcaaactac tgcctgacca  3000
agtggaagct ctggcggccg tatgcaagac ctggctgaac gaggagcacc gcgggttgca  3060
gctgaccttc accagcaaca agacctttgt gacgatgatg gggcgattcc tgcaggcgta  3120
cctgcagtcg tttgcagagg tgacctacaa gcatcacgag cccacgggct gcgcgttgtg  3180
gctgcaccgc tgcgctgaga tcgaaggcga gcttaagtgt ctacacggaa gcattatgat  3240
aaataaggag cacgtgattg aaatggatgt gacgagcgaa aacgggcagc gcgcgctgaa  3300
ggagcagtct agcaaggcca agatcgtgaa gaaccggtgg ggccgaaatg tggtgcagat  3360
ctccaacacc gacgcaaggt gctgcgtgca cgacgcggcc tgtccggcca atcagttttc  3420
cggcaagtct tgcggcatgt tcttctctga aggcgcaaag gctcaggtgg cttttaagca  3480
gatcaaggct tttatgcagg cgctgtatcc taacgcccag accgggcacg gtcacctttt  3540
gatgccacta cggtgcgagt gcaactcaaa gcctgggcac gcgccctttt tgggaaggca  3600
gctaccaaag ttgactccgt tcgccctgag caacgcggag gacctggacg cggatctgat  3660
ctccgacaag agcgtgctgg ccagcgtgca ccacccggcg ctgatagtgt tccagtgctg  3720
caaccctgtg tatcgcaact cgcgcgcgca gggcggaggc cccaactgcg acttcaagat  3780
atcggcgccc gacctgctaa acgcgttggt gatggtgcgc agcctgtgga gtgaaaactt  3840
caccgagctg ccgcggatgg ttgtgcctga gtttaagtgg agcactaaac accagtatcg  3900
caacgtgtcc ctgccagtgg cgcatagcga tgcgcggcag aaccccttg atttttaacc  3960
cgggagttct agggatctgc cctctccct cccccccccc taacgttact ggccgaagcc  4020
gcttggaata aggccggtgt gcgtttgtct atatgttatt ttccaccata ttgccgtctt  4080
ttggcaatgt gagggcccgg aaacctggcc ctgtcttctt gacgagcatt cctaggggtc  4140
tttcccctct cgccaaagga atgcaaggtc tgttgaatgt cgtgaaggaa gcagttcctc  4200
tggaagcttc ttgaagacaa acaacgtctg tagcgaccct ttgcaggcag cggaaccccc  4260
cacctggcga caggtgcctc tgcggccaaa agccacgtgt ataagataca cctgcaaagg  4320
cggcacaacc ccagtgccac gttgtgagtt ggatagttgt ggaaagagtc aaatggctct  4380
cctcaagcgt attcaacaag gggctgaagg atgcccagaa ggtaccccat tgtatgggat  4440
ctgatctggg gcctcggtgc acatgcttta catgtgttta gtcgaggtta aaaaaacgtc  4500
taggcccccc gaaccacggg gacgtggttt tcctttgaaa aacacgatga taaggatcca  4560
ccggaggcca ccatgactac gtccggcgtt ccatttggca tgacactacg accaacacga  4620
tctcggttgt ctcggcgcac tccgtacagt agggatcgtc tacctccttt tgagacagaa  4680
acccgcgcta ccatactgga ggatcatccg ctgctgcccg aatgtaacac tttgacaatg  4740
cacaacgtga gttacgtgcg aggtcttccc tgcagtgtgg gatttacgct gattcaggaa  4800
tgggttgttc cctgggatat ggttctaacg cgggaggagc ttgtaatcct gaggaagtgt  4860
atgcacgtgt gcctgtgttg tgccaacatt gatatcatga cgagcatgat gatccatggt  4920
tacgagtcct gggctctcca ctgtcattgt tccagtcccg gttccctgca gtgtatagcc  4980
ggcgggcagg ttttggccag ctggtttagg atggtggtgg atggcgccat gtttaatcag  5040
aggtttatat ggtaccggga ggtggtgaat tacaacatgc caaaagaggt aatgtttatg  5100
tccagcgtgt ttatgagggg tcgccactta atctacctgc gcttgtggta tgatggccac  5160
gtgggttctg tggtccccgc catgagcttt ggatacagcg ccttgcactg tgggattttg  5220
aacaatattg tggtgctgtg ctgcagttac tgtgctgatt taagtgagat cagggtgcgc  5280
tgctgtgccc ggaggacaag gcgccttatg ctgcgggcgg tgcgaatcat cgctgaggag  5340
accactgcca tgttgtattc ctgcaggacg gagcggcggc ggcagcagtt tattcgcgcg  5400
ctgctgcagc accaccgccc tatcctgatg cacgattatg actctacccc catgtaggcg  5460
gccgctcgag tctagagggc ccgtttaaac ccgctgatca gcctcgactg tgccttctag  5520
ttgccagcca tctgttgttt gcccctcccc cgtgccttcc ttgaccctgg aaggtgccac  5580
tcccactgtc ctttcctaat aaaatgagga aattgcatcg cattgtctga gtaggtgtca  5640
ttctattctg gggggtgggg tggggcagga cagcaagggg gaggattggg aagacaatag  5700
caggcatgct ggggatgcgg tgggctctat ggcttctgag gcggaaagaa ccagctgggg  5760
ctctaggggg tatccccggg gttggggttg cgccttttcc aaggcatcca gcacagtggc  5820
ggccgcaata tttgcatgtc gctatgtgtt ctgggaaatc accataaacg tgaaatccct  5880
atcagtgata gagacttata agttccctat cagtgataga gaaccggtgg gcactcttcc  5940
gtggtctggt ggataaattc gcaagggtat catggcggac gaccggggtt cgagccccgt  6000
atccggccgt ccgccgtgat ccatgcggtt accgcccgcg tgtcgaaccc aggtgtgcga  6060
cgtcagacaa cgggggagtg ctcctttttg aattccactt tggccgcggc tcgagggggt  6120
tggggttgcg ccttttccaa ggcagccctg ggtttgcgca gggacgcggc tgctctgggc  6180
gtggttccgg gaaacgcagc ggcgccgacc ctgggtctcg cacattcttc acgtccgttc  6240
gcagcgtcac ccggatcttc gccgctaccc ttgtgggccc cccggcgacg cttcctgctc  6300
cgccccctaag tcgggaaggt tccttgcggt tcgcggcgtg ccggacgtga caaacggaag  6360
ccgcacgtct cactagtacc ctcgcagacg gacagcgcca gggagcaatg gcagcgcgcc  6420
gaccgcgatg ggctgtggcc aatagcggct gctcagcagg gcgcgccgag agcagcggcc  6480
gggaaggggc ggtgcgggag gcggggtgtg gggcggtagt gtgggccctg ttcctgcccg  6540
cgcggtgttc cgcattctgc aagcctccgg agcgcacgtc ggcagtcggc tccctcgttg  6600
accgaatcac cgacctctct ccccaggggg atctgtgagt ttggggaccc ttgattgttc  6660
tttcttttc gctattgtaa aattcatgtt atatggaggg ggcaaagttt tcagggtgtt  6720
gtttagaatg ggaagatgtc ccttgtatca ccatggaccc tcatgataat tttgtttctt  6780
tcactttcta ctctgttgac aaccattgtc tcctcttatt ttcttttcat tttctgtaac  6840
tttttcgtta aactttagct tgcatttgta acgaattttt aaattcactt ttgtttattt  6900
gtcagattgt aagtactttc tctaatcact ttttttcaa ggcaatcagg gtatattata  6960
ttgtacttca gcacagtttt agagaacaat tgttataatt aaatgataag gtagaatatt  7020
tctgcatata aattctggct ggcgtggaaa tattcttatt ggtagaaaca actacatcct  7080
```

-continued

```
ggtcatcatc ctgcctttct ctttatggtt acaatgatat acactgtttg agatgaggat  7140
aaaatactct gagtccaaac cggggcccctc tgctaaccat gttcatgcct tcttcttttt  7200
cctacagctc ctgggcaacg tgctggttat tgtgctgtct catcattttg gcaaagaatt  7260
gtaatacgac tcactatagg gcgagccacc atggctagat tagataaaag taaagtgatt  7320
aacagcgcat tagagctgct taatgaggtc ggaatcgaag gtttaacaac ccgtaaactc  7380
gcccagaagc taggtgtaga gcagcctaca ttgtattggc atgtaaaaaa taagcgggct  7440
ttgctcgacg ccttagccat tgagatgtta gataggcacc atactcactt ttgcccttta  7500
gaaggggaaa gctggcaaga tttttacgt aataacgcta aaagttttag atgtgcttta  7560
ctaagtcatc gcgatggagc aaaagtacat ttaggtacac ggcctacaga aaaacagtat  7620
gaaactctcg aaaatcaatt agccttttta tgccaacaag gtttttcact agagaatgcc  7680
ttatatgcac tcagcgccgt ggggcatttt actttaggtt gcgtattgga agatcaagag  7740
catcaagtcg ctaaagaaga aagggaaaca cctactactg atagtatgcc gccattatta  7800
cgacaagcta tcgaattatt tgatcaccaa ggtgcagagc cagccttctt attcggcctt  7860
gaattgatca tatgcggatt agaaaaacaa cttaaatgtg aaagtgggtc cccaaaaaag  7920
aagagaaagg tcgacggcgg tggtgctttg tctcctcagc actctgctgt cactcaagga  7980
agtatcatca agaacaagga gggcatggat gctaagtcac taactgcctg gtcccggaca  8040
ctggtgacct tcaaggatgt atttgtggac ttcaccaggg aggagtggaa gctgctggac  8100
actgctcagc agatcgtgta cagaaatgtg atgctggaga actataagaa cctggtttcc  8160
ttgggttatc agcttactaa gccagatgtg atcctccggt tggagaaggg agaagagccc  8220
tggctggtgg agagagaaat tcaccaagag acccatcctg attcagagac tgcatttgaa  8280
atcaaatcat cagtttaagc gtacagcggc tcccgggagt tctagggatc tgcccctctc  8340
cctccccccc ccctaacgtt actggccgaa gccgcttgga ataaggccgg tgtgcgtttg  8400
tctatatgtt attttccacc atattgccgt cttttggcaa tgtgagggcc cggaaacctg  8460
gccctgtctt cttgacgagc attcctaggg gtctttcccc tctcgccaaa ggaatgcaag  8520
gtctgttgaa tgtcgtgaag gaagcagttc ctctggaagc ttcttgaaga caaacaacgt  8580
ctgtagcgac cctttgcagg cagcggaacc ccccacctgg cgacaggtgc ctctgcggcc  8640
aaaagccacg tgtataagat acacctgcaa aggcggcaca accccagtgc cacgttgtga  8700
gttggatagt tgtggaaaga gtcaaatggc tctcctcaag cgtattcaac aaggggctga  8760
aggatgccca gaaggtaccc cattgtatgg gatctgatct ggggcctcgg tgcacatgct  8820
ttacatgtgt ttagtcgagg ttaaaaaaac gtctaggccc cccgaaccac ggggacgtgg  8880
ttttcctttg aaaaacacga tgataaggat ccaccggagg ccaccatgac cgagtacaag  8940
cccacggtgc gcctcgccac ccgcgacgac gtccccaggg ccgtacgcac cctcgccgcc  9000
gcgttcgccg actaccccgc cacgcgccac accgtcgatc cggaccgcca catcgagcgg  9060
gtcaccgagc tgcaagaact cttcctcacg cgcgtcgggc tcgacatcgg caaggtgtgg  9120
gtcgcggacg acggcgccgc ggtggcggtc tggaccacgc cggagagcgt cgaagcgggg  9180
gcggtgttcg ccgagatcgg cccgcgcatg gccgagttga gcggttcccg gctggccgcg  9240
cagcaacaga tggaaggcct cctggcgccg caccggccca aggagcccgc gtggttcctg  9300
gccaccgtcg gcgtctcgcc cgaccaccag ggcaagggtc tgggcagcgc cgtcgtgctc  9360
cccggagtgg aggcggccga gcgcgccggg gtgcccgcct tcctggagac ctccgcgccc  9420
cgcaacctcc ccttctacga gcggctcggc ttcaccgtca ccgccgacgt cgaggtgccc  9480
gaaggaccgc gcacctggtg catgacccgc aagcccggtg cctgaccgcg tctggaacaa  9540
tcaacctctg gattacaaaa tttgtgaaag attgactggt attcttaact atgttgctcc  9600
ttttacgcta tgtggatacg ctgctttaat gcctttgtat catgctattg cttcccgtat  9660
ggctttcatt ttctcctcct tgtataaatc ctggttgctg tctctttatg aggagttgtg  9720
gcccgttgtc aggcaacgtg gcgtggtgtg cactgtgttt gctgacgcaa cccccactgg  9780
ttggggcatt gccaccacct gtcagctcct ttccgggact ttcgctttcc ccctccctat  9840
tgccacggcg gaactcatcg ccgcctgcct tgcccgctgc tggacagggg ctcggctgtt  9900
gggcactgac aattccgtgg tgttgtcggg gaagctgacg tcctttccat ggctgctcgc  9960
ctgtgttgcc acctggattc tgcgcgggac gtccttctgc tacgtccctt cggccctcaa  10020
tccagcggac cttccttccc gcggcctgct gccggctctg cggcctcttc cgcgtcttcg  10080
ccttcgccct cagacgagtc ggatctccct ttgggccgcc tccccgcaaa atgaccgacc  10140
aagcgacgcc caacctgcca tcacgagatt tcgattccac cgccgccttc tatgaaaggt  10200
tgggcttcgg aatcgttttc cgggacgccg gctggatgat cctccagcgc ggggatctca  10260
tgctggagtt cttcgcccac cccaacttgt ttattgcagc ttataatggt tacaaataaa  10320
gcaatagcat cacaaatttc acaaataaag cattttttc actgcattct agttgtggtt  10380
tgtccaaact catcaatgta tcttatcatg tctgtagctg atcaattggc gcgccgaatt  10440
cgttatctgc agaattcggc ttggcggctg cgcgttcaaa cctcccgctt caaaatggag  10500
accctgcgtg ctcactcggg cttaaatacc cagcgtgacc acatggtgtc gcaaaatgtc  10560
gcaaaacact cacgtgacct ctaatacagg acctctagag catggaaact agataagaaa  10620
gaaatacgca gagaccaaag ttcaactgaa acgaattaaa cggtttattg attaacaagc  10680
aaactagttt acagattacg ggtgaggtaa cgggtgccga tggggcgagg ctcagaataa  10740
acgccatttg tgtcaacagc aaagtccaca tttgtagatt tgttgtagtt ggaagtgtat  10800
tgaatctctg ggttccagcg tttgctgttt tctttctgca gctcccattc aatttccacg  10860
ctgacctgtc cggtgctgta ctgcgtgatg aacgacgcaa acttagctgg actgaaggta  10920
gttggaggat tcgcgggaac aggtgtattc ttaatcagga tctgaggagg cgggtgtttc  10980
agtccaaagc ctcccatcag cggcgaggga tgaaagtgtc cgtccgtgtg aggaatcttg  11040
gcccagatag gaccctgcag gtacacgtcc cggtcctgcc agaccatgcc aggtaaggct  11100
ccttgactgt tgacggtccc tgtagcagga gcggtgttgg ccgattgcag gttagtggcc  11160
accgtgccgt actcttctgt ggccactggg ttggtggttt taatttcttc ctcgttggtt  11220
atcataacgt tgtcaaggtc cacgttgcta tttccagctc cctgtttccc aaatattaag  11280
actccgctca tcggaaaaaa tttgtcttcg tcgtccttgt gggttgccat agcgggaccg  11340
ggatttacca gagagtctct gccattcaga tgatacttgg tggcaccggt ccaggcaaag  11400
ttgctgttgt tattttgatt ggttgtcttg gagacgcgtt gctgccggta gcagggcccg  11460
ggtagccagt ttttggcctg attcgccatg ctactaggcc cggcctgaga aaattgcaac  11520
gtccgatttc ctgcggtacc actcgtggtc tgagtccgag acaggtagta caggtactgg  11580
tcgatgaggg ggttcatcag ccggtccagg ctttggctgt gcgcgtagct gctgtgaaaa  11640
ggcacgtcct caaacgtgta gctgaactga aagttgttgc ccgttctcag catttgagaa  11700
ggaaagtatt ccaggcagta gaaggaggaa cggcccacgg cctgactgcc attgttcaga  11760
gtcaggtacc cgtactgagg aatcatgaag acgtccgccg ggaacggagg caggcagccc  11820
```

-continued

```
tggtgcgcag agccgaggac gtacgggagc tggtattccg agtccgtaaa gacctgaacc  11880
gtgctggtaa ggttattggc gatggtcgtg gtgccatcat tcgtcgtgac ctccttgacc  11940
tggatgttga agagcttgaa gttgagcttc ttgggccgga atccccagtt gttgttgatg  12000
agtcgctgcc agtcacgtgg tgagaagtgg cagtggaatc tgttaaagtc aaaatacccc  12060
cagggggtgc tgtagccgaa gtaggtgttg tcgttggtgc tgcctcccga ttggctggag  12120
atttgcttgt agaggtggtt gttgtaggtg gggagggccc aggttcgggt gctggtggtg  12180
atgactctgt cgcccagcca tgtggaatcg caatgccaat ttcctgaggc gttacccact  12240
ccgtcggcgc cttcgttatt gtctgccatt ggagcgccac cgcctgcagc cattgtatta  12300
gatcccacac cagagggggc tgcggggggt tctccgagtg gttgagggtc gggcactgac  12360
tctgagtcgc cagtctgccc aaagttgagt ctctttctcg cgggctgctg gcctttcttg  12420
ccgatgcccg aagaggagtc tggttcctgg ggtgattgct ctaccggtct cttctttcca  12480
ggagccgtct tagcgccttc ctcaaccaga ccgagaggtt cgagaacccg cttcttggcc  12540
tggaagactg ctcgcccgag gttgccccca aaagacgtat cttcttgcag acgctcctga  12600
aactcggcgt cggcgtggtt ataccgcagg tacggattgt cacccgcttt gagctgctgg  12660
tcgtaggcct tgtcgtgctc gagggccgct gcgtccgccg cgttgacggg ctcccccttg  12720
tcgagtccgt tgaagggtcc gaggtacttg tagccaggaa gcaccagacc ccggccgtcg  12780
tcctgctttt gctggttggc tttgggtttc ggggctccag gtttcaagtc ccaccactcg  12840
cgaatgccct cagagaggtt gtcctcgagc caatctggaa gataaccatc ggcagccata  12900
cctgatttaa atcatttatt gttcaaagat gcagtcatcc aaatccacat tgaccagatc  12960
gcaggcagtg caagcgtctg gcacctttcc catgatatga tgaatgtagc acagtttctg  13020
atacgccttt ttgacgacag aaacgggttg agattctgac acgggaaagc actctaaaca  13080
gtctttctgt ccgtgagtga agcagatatt tgaattctga ttcattctct cgcattgtct  13140
gcagggaaac agcatcagat tcatgcccac gtgacgagaa catttgtttt ggtacctgtc  13200
tgcgtagttg atcgaagctt ccgcgtctga cgtcgatggc tgcgcaactg actcgcgcac  13260
ccgtttgggc tcacttatat ctgcgtcact gggggcgggt cttttcttgg ctccacccctt  13320
tttgacgtag aattcatgct ccacctcaac cacgtgatcc tttgcccacc ggaaaaagtc  13380
tttgacttcc tgcttggtga ccttcccaaa gtcatgatcc agacggcggg tgagttcaaa  13440
tttgaacatc cggtcttgca acggctgctg gtgttcgaag gtcgttgagt tcccgtcaat  13500
cacggcgcac atgttggtgt tggaggtgac gatcacggga gtcgggtcta tctgggccga  13560
ggacttgcat ttctggtcca cgcgcacctt gcttcctccg agaatggctt tggccgactc  13620
cacgaccttg gcggtcatct tcccctcctc ccaccagatc accatcttgt cgacacagtc  13680
gttgaaggga aagttctcat tggtccagtt tacgcacccg tagaagggca cagtgtgggc  13740
tatggcctcc gcgatgttgg tcttcccggt agttgcaggc ccaaacagcc agatggtgtt  13800
cctcttgccg aactttttcg tggcccatcc cagaaagacg gaagccgcat attggggatc  13860
gtacccgttt agttccaaaa ttttataaat ccgattgctg gaaatgtcct ccacgggctg  13920
ctggcccacc aggtagtcgg gggcggtttt agtcaggctc ataatctttc ccgcattgtc  13980
caaggcagcc ttgatttggg accgcgagtt ggaggccgca ttgaaggaga tgtatgaggc  14040
ctggtcctcc tggatccact gcttctccga ggtaatcccc ttgtccacga gccacccgac  14100
cagctccatg tacctggctg aagtttttga tctgatcacc ggcgcatcag aattgggatt  14160
ctgattctct ttgttctgct cctgcgtctg cgacacgtgc gtcagatgct gcgccaccaa  14220
ccgtttacgc tccgtgagat tcaaacaggc gctgtggaga gaaaggcaaa gtggatgtca  14280
gtatctctat cactgatagg gagatctcta tcactgatag ggaacttacc ttaaatactg  14340
ttccatatta gtccacgccc actggagctc aggctgggtt ttggggagca agtaattggg  14400
gatgtagcac tcatccacca ccttgttccc gcctccggcg ccatttctgg tctttgtgac  14460
cgcgaaccag tttggcaaag tcggctcgat cccgcggtaa attctctgaa tcagtttttc  14520
gcgaatctga ctcaggaaac gtcccaaaac catggatttc accccggtgg tttccacgag  14580
cacgtgcatg tggaagtagc tctctccctt ctcaaattgc acaaagaaaa gagcctccgg  14640
ggccttactc acacggcgcc attccgtcag aaagtcgcgc tgcagcttct cggccacggt  14700
caggggtgcc tgctcaatca gattcagatc catgtcagaa tctggcggca actcccattc  14760
cttctcggcc acccagttca caaagctgtc agaaatgccg ggcagatgct cgtcaaggtc  14820
gctggggacc ttaatcacaa tctcgtaaaa ccccggcatg gcggctgcgc gttcaaacct  14880
cccgcttcaa aatggagacc ctgcgtgctc actcgggcga tctctatcac tgatagggag  14940
atctctatca ctgataggga gattaaatag aatggctagg atccggccgg cctgcaggtg  15000
tcctcacagg aacgaagtcc ctaaagaaac agtggcagcc aggtttagcc ccggaattga  15060
ctggattcct tttttagggc ccattggtat ggctttttcc ccgtatcccc ccaggtgtct  15120
gcaggctcaa agagcagcga gaagcgttca gaggaaagcg atcccgtgcc accttccccg  15180
tgcccgggct gtccccgcac gctgccggct cggggatgcg gggggagcgc cggaccggag  15240
cggagccccg ggcggctcgc tgctgccccc tagcgggggga gggacgtaat tacatccctg  15300
ggggctttgg gggggggctg tccctctaga gcggccgcca ccgcggtgga gctccagctt  15360
ttgttccctt tagtgagggt taattagatc ttaatacgac tcactatagg gcgaattggg  15420
taccgggccc cccctcgagg tcgacggtat cgataagctt gatatctata acaagaaaat  15480
atatatataa taagttatca cgtaagtaga acatgaaata acaatataat tatcgtatga  15540
gttaaatctt aaaagtcacg taaaagataa tcatgcgtca ttttgactca cgcggtcgtt  15600
atagttcaaa atcagtgaca cttaccgcat tgacaagcac gcctcacggg agctccaagc  15660
ggcgactgag atgtcctaaa tgcacagcga cggattcgcg ctatttagaa agagagagca  15720
atatttcaag aatgcatgcg tcaattttac gcagactatc tttctagggt taatctagct  15780
gcatcaggat catatcgtcg ggtctttttt ccggctcagt catcgcccaa gctggcgcta  15840
tctgggcatc ggggaggaag aagcccgtgc cttttcccgc gaggttgaag cggcatggaa  15900
agagtttgcc gaggatgact gctgctgcat tgacgttgag cgaaaacgca cgtttaccat  15960
gatgattcgg gaaggtgtgg ccatgcacgc ctttaacggt gaactgttcg ttcaggccac  16020
ctgggatacc agttcgtcgc ggcttttccg gacacagttc cggatggtca gcccgaagcg  16080
catcagcaac ccgaacaata ccggcgacag ccggaactgc cgtgccggtg tgcagattaa  16140
tgacagcggt gcggcgctgg gatattacgt cagcgaggac gggtatcctg gctggatgcc  16200
gcagaaatgg acatggatac cccgtgagtt acccggcggg cgcgcttggc gtaatcatgg  16260
tcatagctgt ttcctgtgtg aaattgttat ccgctcacaa ttccacacaa catacgagcc  16320
ggaagcataa agtgtaaagc ctggggtgcc taatgagtga gctaactcac attaattgcg  16380
ttgcgctcac tgcccgcttt ccagtcggga aacctgtcgt gccagctgca ttaatgaatc  16440
ggccaacgcg cggggagagg cggtttgcgt attgggcgct cttccgcttc ctcgctcact  16500
gactcgctgc gctcggtcgt tcggctgcgg cgagcggtat cagctcactc aaaggcggta  16560
```

```
atacggttat ccacagaatc aggggataac gcaggaaaga acatgtgagc aaaaggccag  16620
caaaaggcca ggaaccgtaa aaaggccgcg ttgctggcgt ttttccatag gctccgcccc  16680
cctgacgagc atcacaaaaa tcgacgctca agtcagaggt ggcgaaaccc gacaggacta  16740
taaagatacc aggcgtttcc ccctggaagc tccctcgtgc gctctcctgt tccgaccctg  16800
ccgcttaccg gatacctgtc cgcctttctc ccttcgggaa gcgtggcgct ttctcatagc  16860
tcacgctgta ggtatctcag ttcggtgtag gtcgttcgct ccaagctggg ctgtgtgcac  16920
gaaccccccg ttcagcccga ccgctgcgcc ttatccggta actatcgtct tgagtccaac  16980
ccggtaagac acgacttatc gccactggca gcagccactg gtaacaggat tagcagagcg  17040
aggtatgtag gcggtgctac agagttcttg aagtggtggc ctaactacgg ctacactaga  17100
aggacagtat ttggtatctg cgctctgctg aagccagtta ccttcggaaa aagagttggt  17160
agctcttgat ccggcaaaca aaccaccgct ggtagcggtg gtttttttgt ttgcaagcag  17220
cagattacgc gcagaaaaaa aggatctcaa gaagatcctt tgatcttttc tacggggtct  17280
gacgctcagt ggaacgaaaa ctcacgttaa gggattttgg tcatgagatt atcaaaaagg  17340
atcttcacct agatcctttt aaattaaaaa tgaagtttta aatcaatcta aagtatatat  17400
gagtaaactt ggtctgacag ttaccaatgc ttaatcagtg aggcacctat ctcagcgatc  17460
tgtctatttc gttcatccat agttgcctga ctccccgtcg tgtagataac tacgatacgg  17520
gagggcttac catctggccc cagtgctgca atgataccgc gagacccacg ctcaccggct  17580
ccagatttat cagcaataaa ccagccagcc ggaagggccg agcgcagaag tggtcctgca  17640
actttatccg cctccatcca gtctattaat tgttgccggg aagctagagt aagtagttcg  17700
ccagttaata gtttgcgcaa cgttgttgcc attgctacag gcatcgtggt gtcacgctcg  17760
tcgtttggta tggcttcatt cagctccggt tcccaacgat caaggcgagt tacatgatcc  17820
cccatgttgt gcaaaaaagc ggttagctcc ttcggtcctc cgatcgttgt cagaagtaag  17880
ttggccgcag tgttatcact catggttatg gcagcactgc ataattctct tactgtcatg  17940
ccatccgtaa gatgcttttc tgtgactggt gagtactcaa ccaagtcatt ctgagaatag  18000
tgtatgcggc gaccgagttg ctcttgcccg gcgtcaatac gggataatac cgcgccacat  18060
agcagaactt taaaagtgct catcattgga aaacgttctt cggggcgaaa actctcaagg  18120
atcttaccgc tgttgagatc cagttcgatg taacccactc gtgcacccaa ctgatcttca  18180
gcatctttta ctttcaccag cgtttctggg tgagcaaaaa caggaaggca aaatgccgca  18240
aaaaagggaa taagggcgac acggaaatgt tgaatactca t                      18281

SEQ ID NO: 12          moltype = DNA  length = 17936
FEATURE                Location/Qualifiers
misc_feature           1..17936
                       note = Description of Artificial Sequence: Synthetic
                        polynucleotide
source                 1..17936
                       mol_type = other DNA
                       organism = synthetic construct
SEQUENCE: 12
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcgtttaaac ttaagcttgg taccgagctc ggatccacta  1560
gtccagtgtg gtggaattcc tgcttcgcga tgtacgggcc agatatacgc gttgacattg  1620
attattgact agttattaat agtaatcaat tacggggtca ttagttcata gcccatatat  1680
ggagttccgc gttacataac ttacggtaaa tggcccgcct ggctgaccgc ccaacgaccc  1740
ccgcccattg acgtcaataa tgacgtatgt tcccatagta acgccaatag ggactttcca  1800
ttgacgtcaa tgggtggagt atttacggta aactgcccac ttggcagtac atcaagtgta  1860
tcatatgcca agtacgcccc ctattgacgt caatgacggt aaatggcccg cctggcatta  1920
tgcccagtac atgaccttat gggactttcc tacttggcag tacatctacg tattagtcat  1980
cgctattacc atggtgatgc ggttttggca gtacatcaat gggcgtggat agcggtttga  2040
ctcacgggga tttccaagtc tccaccccat tgacgtcaat gggagtttgt tttggaacca  2100
aaatcaacgg gactttccaa aatgtcgtaa caactccgcc ccattgacgc aaatgggcgg  2160
taggcgtgta cggtgggagg tctatataag cagagctctc cctatcagtg atagagatct  2220
ccctatcagt gatagagatc gtcgacgagc tcgtttagtg aaccgtcaga tcgcctggag  2280
acgccatcca cgctgttttg acctccatag aagacaccgg gaccgatcca gcctccggac  2340
tctagcgttt aaacttaagc ttgccaccat ggccagtcgg gaagaggagc agcgcgaaac  2400
```

-continued

```
caccccgag cgcggacgcg gtgcggcgcg acgtcccca accatggagg acgtgtcgtc  2460
cccgtccccg tcgccgccgc ctccccgggc gcccccaaaa aagcggatga ggcggcgtat  2520
cgagtccgag gacgaggaag actcatcaca agacgcgctg gtgccgcgca cacccagccc  2580
gcggccatcg acctcggcgg cggatttggc cattgcgccc aagaagaaaa agaagcgccc  2640
ttctcccaag cccgagcgcc cgccatcacc agaggtaatc gtggacagcg aggaagaaag  2700
agaagatgtg gcgctacaaa tggtgggttt cagcaaccca ccggtgctaa tcaagcatgg  2760
caaaggaggt aagcgcacag tgcggcggct gaatgaagac gacccagtgg cgcgtggtat  2820
gcggacgcaa gaggaagagg aagagcccag cgaagcggaa agtgaaatta cggtgatgaa  2880
cccgctgagt gtgccgatcg tgtctgcgtg ggagaagggc atggaggctg cgcgcgcgct  2940
gatggacaag taccacgtgg ataacgatct aaaggcgaac ttcaaactac tgcctgacca  3000
agtggaagct ctggcggccg tatgcaagac ctggctgaac gaggagcacc gcgggttgca  3060
gctgaccttc accagcaaca agacctttgt gacgatgatg gggcgattcc tgcaggcgta  3120
cctgcagtcg tttgcagagg tgacctacaa gcatcacgag cccacgggct gcgcgttgtg  3180
gctgcaccgc tgcgctgaga tcgaaggcga gcttaagtgt ctacacggaa gcattatgat  3240
aaataaggag cacgtgattg aaatggatgt gacgagcgaa aacgggcagc gcgcgctgaa  3300
ggagcagtct agcaaggcca agatcgtgaa gaaccggtgg ggccgaaatg tggtgcagat  3360
ctccaacacc gacgcaaggt gctgcgtgca cgacgcggcc tgtccggcca atcagttttc  3420
cggcaagtct tgcggcatgt tcttctctga aggcgcaaag gctcaggtgg cttttaagca  3480
gatcaaggct tttatgcagg cgctgtatcc taacgcccag accgggcacg gtcacctttt  3540
gatgccacta cggtgcgagt gcaactcaaa gcctgggcac gcgccctttt tgggaaggca  3600
gctaccaaag ttgactccgt tcgccctgag caacgcggag gacctggacg cggatctgat  3660
ctccgacaag agcgtgctgg ccagcgtgca ccacccggcg ctgatagtgt tccagtgctg  3720
caaccctgtg tatcgcaact cgcgcgcgca gggcggaggc cccaactgcg acttcaagat  3780
atcggcgccc gacctgctaa acgcgttggt gatggtgcgc agcctgtgga gtgaaaactt  3840
caccgagctg ccgcggatgg ttgtgcctga gtttaagtgg agcactaaac accagtatcg  3900
caacgtgtcc ctgccagtgg cgcatagcga tgcgcggcag aaccccttttg atttttaacc  3960
cgggagttct agggatctgc cctctccct cccccccccc taacgttact ggccgaagcc  4020
gcttggaata aggccggtgt gcgtttgtct atatgttatt ttccaccata ttgccgtctt  4080
ttggcaatgt gagggcccgg aaacctggcc ctgtcttctt gacgagcatt cctaggggtc  4140
tttcccctct cgccaaagga atgcaaggtc tgttgaatgt cgtgaaggaa gcagttcctc  4200
tggaagcttc ttgaagacaa acaacgtctg tagcgaccct ttgcaggcag cggaaccccc  4260
cacctggcga caggtgcctc tgcggccaaa agccacgtgt ataagataca cctgcaaagg  4320
cggcacaacc ccagtgccac gttgtgagtt ggatagttgt ggaaagagtc aaatggctct  4380
cctcaagcgt attcaacaag gggctgaagg atgcccagaa ggtaccccat tgtatgggat  4440
ctgatctggg gcctcggtgc acatgcttta catgtgttta gtcgaggtta aaaaaacgtc  4500
taggcccccc gaaccacggg gacgtggttt tcctttgaaa aacacgatga taaggatcca  4560
ccggaggcca ccatgactac gtccggcgtt ccatttggca tgacactacg accaacacga  4620
tctcggttgt ctcggcgcac tccgtacagt agggatcgtc tacctccttt tgagacagaa  4680
acccgcgcta ccatactgga ggatcatccg ctgctgcccg aatgtaacac tttgacaatg  4740
cacaacgtga gttacgtgcg aggtcttccc tgcagtgtgg gatttacgct gattcaggaa  4800
tgggttgttc cctgggatat ggttctaacg cgggaggagc ttgtaatcct gaggaagtgt  4860
atgcacgtgt gcctgtgttg tgccaacatt gatatcatga cgagcatgat gatccatggt  4920
tacgagtcct gggctctcca ctgtcattgt tccagtcccg gttccctgca gtgtatagcc  4980
ggcgggcagg ttttggccag ctggtttagg atggtggtgg atggcgccat gtttaatcag  5040
aggtttatat ggtaccggga ggtggtgaat tacaacatgc caaaagaggt aatgtttatg  5100
tccagcgtgt ttatgagggg tcgccactta atctacctgc gcttgtggta tgatggccac  5160
gtgggttctg tggtccccgc catgagcttt ggatacagcg ccttgcactg tgggattttg  5220
aacaatattg tggtgctgtg ctgcagttac tgtgctgatt taagtgagat cagggtgcgc  5280
tgctgtgccc ggaggacaag gcgccttatg ctgcgggcgg tgcgaatcat cgctgaggag  5340
accactgcca tgttgtattc ctgcaggacg gagcggcggc ggcagcagtt tattcgcgcg  5400
ctgctgcagc accaccgccc tatcctgatg cacgattatg actctacccc catgtaggcg  5460
gccgctcgag tctagagggc ccgtttaaac ccgctgatca gcctcgactg tgccttctag  5520
ttgccagcca tctgttgttt gcccctcccc cgtgccttcc ttgaccctgg aaggtgccac  5580
tcccactgtc ctttcctaat aaaatgagga aattgcatcg cattgtctga gtaggtgtca  5640
ttctattctg gggggtgggg tggggcagga cagcaagggg gaggattggg aagacaatag  5700
caggcatgct ggggatgcgg tgggctctat ggcttctgag gcggaaagaa ccagctgggg  5760
ctctaggggg tatccccggg gttggggttg cgcctttttcc aaggcatcca gcacagtggc  5820
ggccgcaata tttgcatgtc gctatgtgtt ctgggaaatc accataaacg tgaaatccct  5880
atcagtgata gagacttata agttccctat cagtgataga gaaccggtgg gcactcttcc  5940
gtggtctggt ggataaattc gcaagggtat catggcggac gaccggggtt cgagccccgt  6000
atccggccgt ccgccgtgat ccatgcggtt accgcccgcg tgtcgaaccc aggtgtgcga  6060
cgtcagacaa cgggggagtg ctcctttttg aattccactt tggccgcggc tcgagggggt  6120
tggggttgcg ccttttccaa ggcagccctg ggtttgcgca gggacgcggc tgctctgggc  6180
gtggttccgg gaaacgcagc ggcgccgacc ctgggtctcg cacattcttc acgtccgttc  6240
gcagcgtcac ccggatcttc gccgctaccc ttgtgggccc cccggcgacg cttcctgctc  6300
cgcccctaag tcgggaaggt tccttgcggt tcgcggcgtg ccggacgtga caaacggaag  6360
ccgcacgtct cactagtacc ctcgcagacg gacagcgcca gggagcaatg gcagcgcgcc  6420
gaccgcgatg ggctgtggcc aatagcggct gctcagcagg gcgcgccgag agcagcggcc  6480
gggaaggggc ggtgcgggag gcggggtgtg gggcggtagt gtgggccctg ttcctgcccg  6540
cgcggtgttc cgcattctgc aagcctccgg agcgcacgtc ggcagtcggc tccctcgttg  6600
accgaatcac cgacctctct ccccaggggg atctgtgagt ttggggaccc ttgattgttc  6660
tttcttttc gctattgtaa aattcatgtt atatggaggg ggcaaagttt tcagggtgtt  6720
gtttagaatg ggaagatgtc ccttgtatca ccatggaccc tcatgataat tttgtttctt  6780
tcactttcta ctctgttgac aaccattgtc tcctcttatt ttcttttcat tttctgtaac  6840
tttttcgtta aactttagct tgcatttgta acgaattttt aaattcactt ttgtttattt  6900
gtcagattgt aagtactttc tctaatcact ttttttcaa ggcaatcagg gtatattata  6960
ttgtacttca gcacagtttt agagaacaat tgttataatt aaatgataag gtagaatatt  7020
tctgcatata aattctggct ggcgtggaaa tattcttatt ggtagaaaca actacatcct  7080
ggtcatcatc ctgcctttct ctttatggtt acaatgatat acactgtttg agatgaggat  7140
```

```
aaaatactct gagtccaaac cgggcccctc tgctaaccat gttcatgcct tcttcttttt  7200
cctacagctc ctgggcaacg tgctggttat tgtgctgtct catcattttg gcaaagaatt  7260
gtaatacgac tcactatagg gcgagccacc atggctagat tagataaaag taaagtgatt  7320
aacagcgcat tagagctgct taatgaggtc ggaatcgaag gtttaacaac ccgtaaactc  7380
gcccagaagc taggtgtaga gcagcctaca ttgtattggc atgtaaaaaa taagcgggct  7440
ttgctcgacg ccttagccat tgagatgtta gataggcacc atactcactt ttgccccttta  7500
gaaggggaaa gctggcaaga tttttttacgt aataacgcta aaagttttag atgtgcttta  7560
ctaagtcatc gcgatggagc aaaagtacat ttaggtacac ggcctacaga aaaacagtat  7620
gaaactctcg aaaatcaatt agcctttttta tgccaacaag gtttttcact agagaatgcc  7680
ttatatgcac tcagcgccgt ggggcatttt actttaggtt gcgtattgga agatcaagag  7740
catcaagtcg ctaaagaaga aagggaaaca cctactactg atagtatgcc gccattatta  7800
cgacaagcta tcgaattatt tgatcaccaa ggtgcagagc cagccttctt attcggcctt  7860
gaattgatca tatgcggatt agaaaaacaa cttaaatgtg aaagtgggtc cccaaaaaag  7920
aagagaaagg tcgacggcgg tggttcagtt taagcgtaca gcggctcccg ggagttctag  7980
ggatctgccc ctctccctcc cccccccta acgttactgg ccgaagccgc ttggaataag  8040
gccggtgtgc gtttgtctat atgttatttt ccaccatatt gccgtctttt ggcaatgtga  8100
gggcccggaa acctggccct gtcttcttga cgagcattcc taggggtctt tcccctctcg  8160
ccaaaggaat gcaaggtctg ttgaatgtcg tgaaggaagc agttcctctg gaagcttctt  8220
gaagacaaac aacgtctgta gcgacccttt gcaggcagcg gaacccccca cctggcgaca  8280
ggtgcctctg cggccaaaag ccacgtgtat aagatacacc tgcaaaggcg gcacaacccc  8340
agtgccacgt tgtgagttgg atagttgtgg aaagagtcaa atggctctcc tcaagcgtat  8400
tcaacaaggg gctgaaggat gcccagaagg taccccattg tatgggatct gatctggggc  8460
ctcggtgcac atgctttaca tgtgtttagt cgaggttaaa aaaacgtcta ggccccccga  8520
accacgggga cgtggttttc ctttgaaaaa cacgatgata aggatccacc ggaggccacc  8580
atgaccgagt acaagcccac ggtgcgcctc gccacccgcg acgacgtccc cagggccgta  8640
cgcaccctcg ccgccgcgtt cgccgactac cccgccacgc gccacaccgt cgatccggac  8700
cgccacatcg agcgggtcac cgagctgcaa gaactcttcc tcacgcgcgt cgggctcgac  8760
atcggcaagg tgtgggtcgc ggacgacggc gccgcggtgg cggtctggac cacgccggag  8820
agcgtcgaag cgggggcggt gttcgccgag atcggcccgc gcatggccga gttgagcggt  8880
tcccggctgg ccgcgcagca acagatggaa ggcctcctgg cgccgcaccg gcccaaggag  8940
cccgcgtggt tcctggccac cgtcggcgtc tcgcccgacc accagggcaa gggtctgggc  9000
agcgccgtcg tgctccccgg agtggaggcg gccgagcgcg ccggggtgcc cgccttcctg  9060
gagacctccg cgccccgcaa cctccccttc tacgagcggc tcggcttcac cgtcaccgcc  9120
gacgtcgagg tgcccgaagg accgcgcacc tggtgcatga cccgcaagcc cggtgcctga  9180
ccgcgtctgg aacaatcaac ctctggatta caaaatttgt gaaagattga ctggtattct  9240
taactatgtt gctcctttta cgctatgtgg atacgctgct ttaatgcctt tgtatcatgc  9300
tattgcttcc cgtatggctt tcattttctc ctccttgtat aaatcctggt tgctgtctct  9360
ttatgaggag ttgtggcccg ttgtcaggca acgtggcgtg gtgtgcactg tgtttgctga  9420
cgcaaccccc actggttggg gcattgccac cacctgtcag ctcctttccg ggactttcgc  9480
tttccccctc cctattgcca cggcggaact catcgccgcc tgccttgccc gctgctggac  9540
aggggctcgg ctgttgggca ctgacaattc cgtggtgttg tcggggaagc tgacgtcctt  9600
tccatggctg ctcgcctgtg ttgccacctg gattctgcgc gggacgtcct tctgctacgt  9660
cccttcggcc ctcaatccag cggaccttcc ttcccgcggc ctgctgccgg ctctgcggcc  9720
tcttccgcgt cttcgccttc gccctcagac gagtcggatc tccctttggg ccgcctcccc  9780
gcaaaatgac cgaccaagcg acgcccaacc tgccatcacg agatttcgat tccaccgccg  9840
ccttctatga aaggttgggc ttcggaatcg ttttccggga cgccggctgg atgatcctcc  9900
agcgcgggga tctcatgctg gagttcttcg cccaccccaa cttgtttatt gcagcttata  9960
atggttacaa ataaagcaat agcatcacaa atttcacaaa taaagcattt ttttcactgc  10020
attctagttg tggtttgtcc aaactcatca atgtatctta tcatgtctgt agctgatcaa  10080
ttggcgcgcc gaattcgtta tctgcagaat tcggcttggc ggctgcgcgt tcaaacctcc  10140
cgcttcaaaa tggagaccct gcgtgctcac tcgggcttaa atacccagcg tgaccacatg  10200
gtgtcgcaaa atgtcgcaaa acactcacgt gacctctaat acaggacctc tagagcatgg  10260
aaactagata agaaagaaat acgcagagac caaagttcaa ctgaaacgaa ttaaacggtt  10320
tattgattaa caagcaaact agtttacaga ttacgggtga ggtaacgggt gccgatgggg  10380
cgaggctcag aataaacgcc atttgtgtca acagcaaagt ccacatttgt agatttgttg  10440
tagttggaag tgtattgaat ctctgggttc cagcgtttgc tgttttcttt ctgcagctcc  10500
cattcaattt ccacgctgac ctgtccggtg ctgtactgcg tgatgaacga cgcaaactta  10560
gctggactga aggtagttgg aggattcgcg ggaacaggtg tattcttaat caggatctga  10620
ggaggcgggt gtttcagtcc aaagcctcca atcagcggcg agggatgaaa gtgtccgtcc  10680
gtgtgaggaa tcttggccca gataggaccc tgcaggtaca cgtcccggtc ctgccagacc  10740
atgccaggta aggctccttg actgttgacg gtccctgtag caggagcggt gttggccgat  10800
tgcaggttag tggccaccgt gccgtactct tctgtggcca ctgggttggt ggttttaatt  10860
tcttcctcgt tggttatcat aacgttgtca aggtccacgt tgctatttcc agctccctgt  10920
ttcccaaata ttaagactcc gctcatcgga aaaaatttgt cttcgtcgtc cttgtgggtt  10980
gccatagcgg gaccgggatt taccagagag tctctgccat tcagatgata cttggtggca  11040
ccggtccagg caaagttgct gttgttattt tgattggttg tcttggagac gcgttgctgc  11100
cggtagcagg gcccgggtag ccagtttttg gcctgattcg ccatgctact aggcccggcc  11160
tgagaaaatt gcaacgtccg atttcctgcg gtaccactcg tggtctgagt ccgagacagg  11220
tagtacaggt actggtcgat gagggggttc atcagccggt ccaggctttg gctgtgcgcg  11280
tagctgctgt gaaaaggcac gtcctcaaac gtgtagctga actgaaagtt gttgcccgtt  11340
ctcagcattt gagaaggaaa gtattccagg cagtagaagg aggaacggcc cacggcctga  11400
ctgccattgt tcagagtcag gtacccgtac tgaggaatca tgaagacgtc cgcccgggaac  11460
ggaggcaggc agccctggtg cgcagagccg aggacgtacg ggagctggta ttccgagtcc  11520
gtaaagacct gaaccgtgct ggtaaggtta ttggcgatgg tcgtggtgcc atcattcgtc  11580
gtgacctcct tgacctggat gttgaagagc ttgaagttga gcttcttggg ccggaatccc  11640
cagttgttgt tgatgagtcg ctgccagtca cgtggtgaga agtggcagtg gaatctgtta  11700
aagtcaaaat acccccaggg ggtgctgtag ccgaagtagg tgttgtcgtt ggtgctgcct  11760
cccgattggc tggagatttg cttgtagagg tggttgttgt aggtggggag ggcccaggtt  11820
cgggtgctgg tggtgatgac tctgtcgccc agccatgtgg aatcgcaatg ccaatttcct  11880
```

-continued

```
gaggcgttac ccactccgtc ggcgccttcg ttattgtctg ccattggagc gccaccgcct  11940
gcagccattg tattagatcc cacaccagag gggggctgcgg ggggttctcc gagtggttga  12000
gggtcgggca ctgactctga gtcgccagtc tgcccaaagt tgagtctctt tctcgcgggc  12060
tgctggcctt tcttgccgat gcccgaagag gagtctggtt cctggggtga ttgctctacc  12120
ggtctcttct ttccaggagc cgtcttagcg ccttcctcaa ccagaccgag aggttcgaga  12180
acccgcttct tggcctggaa gactgctcgc ccgaggttgc ccccaaaaga cgtatcttct  12240
tgcagacgct cctgaaactc ggcgtcggcg tggttatacc gcaggtacgg attgtcaccc  12300
gctttgagct gctggtcgta ggccttgtcg tgctcgaggg ccgctgcgtc cgccgcgttg  12360
acgggctccc ccttgtcgag tccgttgaag ggtccgaggt acttgtagcc aggaagcacc  12420
agaccccggc cgtcgtcctg cttttgctgg ttggctttgg gtttcggggc tccaggtttc  12480
aagtcccacc actcgcgaat gccctcagag aggttgtcct cgagccaatc tggaagataa  12540
ccatcggcag ccatacctga tttaaatcat ttattgttca aagatgcagt catccaaatc  12600
cacattgacc agatcgcagg cagtgcaagc gtctggcacc tttcccatga tatgatgaat  12660
gtagcacagt ttctgatacg ccttttttgac gacagaaacg ggttgagatt ctgacacggg  12720
aaagcactct aaacagtctt tctgtccgtg agtgaagcag atatttgaat tctgattcat  12780
tctctcgcat tgtctgcagg gaaacagcat cagattcatg cccacgtgac gagaacattt  12840
gttttggtac ctgtctgcgt agttgatcga agcttccgcg tctgacgtcg atggctgcgc  12900
aactgactcg cgcacccgtt tgggctcact tatatctgcg tcactggggg cgggtctttt  12960
cttggctcca cccttttttga cgtagaattc atgctccacc tcaaccacgt gatcctttgc  13020
ccaccggaaa aagtctttga cttcctgctt ggtgaccttc ccaaagtcat gatccagacg  13080
gcgggtgagt tcaaatttga acatccggtc ttgcaacggc tgctggtgtt cgaaggtcgt  13140
tgagttcccg tcaatcacgg cgcacatgtt ggtgttggag gtgacgatca cgggagtcgg  13200
gtctatctgg gccgaggact tgcatttctg gtccacgcgc accttgcttc ctccgagaat  13260
ggctttggcc gactccacga ccttggcggt catcttcccc tcctcccacc agatcaccat  13320
cttgtcgaca cagtcgttga agggaaagtt ctcattggtc cagtttacgc acccgtagaa  13380
gggcacagtg tgggctatgg cctccgcgat gttggtcttc ccggtagttg caggcccaaa  13440
cagccagatg gtgttcctct tgccgaactt tttcgtggcc catcccagaa agacggaagc  13500
cgcatattgg ggatcgtacc cgtttagttc caaaatttta taaatccgat tgctggaaat  13560
gtcctccacg ggctgctggc ccaccaggta gtcggggggcg gttttagtca ggctcataat  13620
ctttcccgca ttgtccaagg cagccttgat ttgggaccgc gagttggagg ccgcattgaa  13680
ggagatgtat gaggcctggt cctcctggat ccactgcttc tccgaggtaa tccccttgtc  13740
cacgagccac ccgaccagct ccatgtacct ggctgaagtt tttgatctga tcaccggcgc  13800
atcagaattg ggattctgat tctctttgtt ctgctcctgc gtctgcgaca cgtgcgtcag  13860
atgctgcgcc accaaccgtt tacgctccgt gagattcaaa caggcgctgt ggagagaaag  13920
gcaaagtgga tgtcagtatc tctatcactg atagggagat ctctatcact gatagggaac  13980
ttaccttaaa tactgttcca tattagtcca cgcccactgg agctcaggct gggttttggg  14040
gagcaagtaa ttggggatgt agcactcatc caccaccttg ttcccgcctc cggcgccatt  14100
tctggtcttt gtgaccgcga accagtttgg caaagtcggc tcgatcccgc ggtaaattct  14160
ctgaatcagt ttttcgcgaa tctgactcag gaaacgtccc aaaaccatgg atttcacccc  14220
ggtggtttcc acgagcacgt gcatgtggaa gtagctctct cccttctcaa attgcacaaa  14280
gaaaagagcc tccggggcct tactcacacg gcgccattcc gtcagaaagt cgcgctgcag  14340
cttctcggcc acggtcaggg gtgcctgctc aatcagattc agatccatgt cagaatctgg  14400
cggcaactcc cattccttct cggccaccca gttcacaaag ctgtcagaaa tgccgggcag  14460
atgctcgtca aggtcgctgg ggaccttaat cacaatctcg taaaaccccg gcatggcggc  14520
tgcgcgttca aacctcccgc ttcaaaatgg agaccctgcg tgctcactcg ggcgatctct  14580
atcactgata gggagatctc tatcactgat agggagatta aatagaatgg ctaggatccg  14640
gccggcctgc aggtgtcctc acaggaacga agtccctaaa gaaacagtgg cagccaggtt  14700
tagccccgga attgactgga ttcctttttt agggcccatt ggtatggctt tttccccgta  14760
tccccccagg tgtctgcagg ctcaaagagc agcgagaagc gttcagagga aagcgatccc  14820
gtgccacctt ccccgtgccc gggctgtccc cgcacgctgc cggctcgggg atgcgggggg  14880
agcgccggac cggagcggag ccccgggcgg ctcgctgctg cccccctagcg ggggagggac  14940
gtaattacat ccctgggggc tttgggggggg ggctgtccct ctagagcggc cgccaccgcg  15000
gtggagctcc agcttttgtt ccctttagtg agggttaatt agatcttaat acgactcact  15060
atagggcgaa ttgggtaccg ggccccccct cgaggtcgac ggtatcgata agcttgatat  15120
ctataacaag aaaatatata tataataagt tatcacgtaa gtagaacatg aaataacaat  15180
ataattatcg tatgagttaa atcttaaaag tcacgtaaaa gataatcatg cgtcattttg  15240
actcacgcgg tcgttatagt tcaaaatcag tgacacttac cgcattgaca agcacgcctc  15300
acgggagctc caagcggcga ctgagatgtc ctaaatgcac agcgacggat tcgcgctatt  15360
tagaaagaga gagcaatatt tcaagaatgc atgcgtcaat tttacgcaga ctatctttct  15420
agggttaatc tagctgcatc aggatcatat cgtcgggtct tttttccggc tcagtcatcg  15480
cccaagctgg cgctatctgg gcatcgggga ggaagaagcc cgtgcctttt cccgcgaggt  15540
tgaagcggca tggaaagagt ttgccgagga tgactgctgc tgcattgacg ttgagcgaaa  15600
acgcacgttt accatgatga ttcgggaagg tgtggccatg cacgccttta acggtgaact  15660
gttcgttcag gccacctggg ataccagttc gtcgcggctt ttccggacac agttccggat  15720
ggtcagcccg aagcgcatca gcaacccgaa caataccggc gacagccgga actgccgtgc  15780
cggtgtgcag attaatgaca gcggtgcggc gctgggatat tacgtcagcg aggacgggta  15840
tcctggctgg atgccgcaga aatggacatg gataccccgt gagttacccg gcgggcgcgc  15900
ttggcgtaat catggtcata gctgtttcct gtgtgaaatt gttatccgct cacaattcca  15960
cacaacatac gagccggaag cataaagtgt aaagcctggg gtgcctaatg agtgagctaa  16020
ctcacattaa ttgcgttgcg ctcactgccc gctttccagt cgggaaacct gtcgtgccag  16080
ctgcattaat gaatcggcca acgcgcgggg agaggcggtt tgcgtattgg gcgctcttcc  16140
gcttcctcgc tcactgactc gctgcgctcg gtcgttcggc tgcggcgagc ggtatcagct  16200
cactcaaagg cggtaatacg gttatccaca gaatcagggg ataacgcagg aaagaacatg  16260
tgagcaaaag gccagcaaaa ggccaggaac cgtaaaaagg ccgcgttgct ggcgtttttc  16320
cataggctcc gcccccctga cgagcatcac aaaaatcgac gctcaagtca gaggtggcga  16380
aacccgacag gactataaag ataccaggcg tttccccctg gaagctccct cgtgcgctct  16440
cctgttccga ccctgccgct taccggatac ctgtccgcct ttctcccttc gggaagcgtg  16500
gcgctttctc atagctcacg ctgtaggtat ctcagttcgg tgtaggtcgt tcgctccaag  16560
ctgggctgtg tgcacgaacc ccccgttcag cccgaccgct gcgccttatc cggtaactat  16620
```

```
cgtcttgagt ccaacccggt aagacacgac ttatcgccac tggcagcagc cactggtaac  16680
aggattagca gagcgaggta tgtaggcggt gctacagagt tcttgaagtg gtggcctaac  16740
tacggctaca ctagaaggac agtatttggt atctgcgctc tgctgaagcc agttaccttc  16800
ggaaaaagag ttggtagctc ttgatccggc aaacaaacca ccgctggtag cggtggtttt  16860
tttgtttgca agcagcagat tacgcgcaga aaaaaaggat ctcaagaaga tcctttgatc  16920
ttttctacgg ggtctgacgc tcagtggaac gaaaactcac gttaagggat tttggtcatg  16980
agattatcaa aaaggatctt cacctagatc cttttaaatt aaaaatgaag ttttaaatca  17040
atctaaagta tatatgagta aacttggtct gacagttacc aatgcttaat cagtgaggca  17100
cctatctcag cgatctgtct atttcgttca tccatagttg cctgactccc cgtcgtgtag  17160
ataactacga tacgggaggg cttaccatct ggccccagtg ctgcaatgat accgcgagac  17220
ccacgctcac cggctccaga tttatcagca ataaaccagc cagccggaag ggccgagcgc  17280
agaagtggtc ctgcaacttt atccgcctcc atccagtcta ttaattgttg ccgggaagct  17340
agagtaagta gttcgccagt taatagtttg cgcaacgttg ttgccattgc tacaggcatc  17400
gtggtgtcac gctcgtcgtt tggtatggct tcattcagct ccggttccca acgatcaagg  17460
cgagttacat gatcccccat gttgtgcaaa aaagcggtta gctccttcgg tcctccgatc  17520
gttgtcagaa gtaagttggc cgcagtgtta tcactcatgg ttatggcagc actgcataat  17580
tctcttactg tcatgccatc cgtaagatgc ttttctgtga ctggtgagta ctcaaccaag  17640
tcattctgag aatagtgtat gcggcgaccg agttgctctt gcccggcgtc aatacgggat  17700
aataccgcgc cacatagcag aactttaaaa gtgctcatca ttggaaaacg ttcttcgggg  17760
cgaaaactct caaggatctt accgctgttg agatccagtt cgatgtaacc cactcgtgca  17820
cccaactgat cttcagcatc ttttactttc accagcgttt ctgggtgagc aaaaacagga  17880
aggcaaaatg ccgcaaaaaa gggaataagg gcgacacgga aatgttgaat actcat      17936

SEQ ID NO: 13          moltype = DNA  length = 21391
FEATURE                Location/Qualifiers
misc_feature           1..21391
                       note = Description of Artificial Sequence: Synthetic
                        polynucleotide
source                 1..21391
                       mol_type = other DNA
                       organism = synthetic construct
SEQUENCE: 13
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcgtttaaac ttaagcttgg taccgagctc ggatccacta  1560
gtccagtgtg gtggaattcc tgcttcgcga tgtacgggcc agatatacgc gttgacattg  1620
attattgact agttattaat agtaatcaat tacggggtca ttagttcata gcccatatat  1680
ggagttccgc gttacataac ttacggtaaa tggcccgcct ggctgaccgc ccaacgaccc  1740
ccgcccattg acgtcaataa tgacgtatgt tcccatagta acgccaatag ggactttcca  1800
ttgacgtcaa tgggtggagt atttacggta aactgcccac ttggcagtac atcaagtgta  1860
tcatatgcca agtacgcccc ctattgacgt caatgacggt aaatggcccg cctggcatta  1920
tgcccagtac atgaccttat gggactttcc tacttggcag tacatctacg tattagtcat  1980
cgctattacc atggtgatgc ggttttggca gtacatcaat gggcgtggat agcggtttga  2040
ctcacgggga tttccaagtc tccaccccat tgacgtcaat gggagtttgt tttggaacca  2100
aaatcaacgg gactttccaa aatgtcgtaa caactccgcc ccattgacgc aaatgggcgg  2160
taggcgtgta cggtgggagg tctatataag cagagctctc cctatcagtg atagagatct  2220
ccctatcagt gatagagatc gtcgacgagc tcgtttagtg aaccgtcaga tcgcctggag  2280
acgccatcca cgctgttttg acctccatag aagacaccgg gaccgatcca gcctccggac  2340
tctagcgttt aaacttaagc ttgccaccat ggccagtcgg gaagaggagc agcgcgaaac  2400
cacccccgag cgcggacgcg gtgcggcgcg acgtccccca accatggagg acgtgtcgtc  2460
cccgtccccg tcgccgccgc ctccccgggc gcccccaaaa aagcggatga ggcggcgtat  2520
cgagtccgag gacgaggaag actcatcaca agacgcgctg gtgccgcgca cacccagccc  2580
gcggccatcg acctcggcgg cggatttggc cattgcgccc aagaagaaaa agaagcgccc  2640
ttctcccaag cccgagcgcc cgccatcacc agaggtaatc gtggacagcg aggaagaaag  2700
agaagatgtg gcgctacaaa tggtgggttt cagcaaccca ccggtgctaa tcaagcatgg  2760
caaaggaggt aagcgcacag tgcggcggct gaatgaagac gacccagtgg cgcgtggtat  2820
```

```
gcggacgcaa gaggaagagg aagagcccag cgaagcggaa agtgaaatta cggtgatgaa  2880
cccgctgagt gtgccgatcg tgtctgcgtg ggagaagggc atggaggctg cgcgcgcgct  2940
gatggacaag taccacgtgg ataacgatct aaaggcgaac ttcaaactac tgcctgacca  3000
agtggaagct ctggcggccg tatgcaagac ctggctgaac gaggagcacc gcgggttgca  3060
gctgaccttc accagcaaca agacctttgt gacgatgatg gggcgattcc tgcaggcgta  3120
cctgcagtcg tttgcagagg tgacctacaa gcatcacgag cccacgggct gcgcgttgtg  3180
gctgcaccgc tgcgctgaga tcgaaggcga gcttaagtgt ctacacggaa gcattatgat  3240
aaataaggag cacgtgattg aaatggatgt gacgagcgaa aacgggcagc gcgcgctgaa  3300
ggagcagtct agcaaggcca agatcgtgaa gaaccggtgg ggccgaaatg tggtgcagat  3360
ctccaacacc gacgcaaggt gctgcgtgca cgacgcggcc tgtccggcca atcagttttc  3420
cggcaagtct tgcggcatgt tcttctctga aggcgcaaag gctcaggtgg cttttaagca  3480
gatcaaggct tttatgcagg cgctgtatcc taacgcccag accgggcacg gtcacctttt  3540
gatgccacta cggtgcgagt gcaactcaaa gcctgggcac gcgccctttt tgggaaggca  3600
gctaccaaag ttgactccgt tcgccctgag caacgcggag gacctggacg cggatctgat  3660
ctccgacaag agcgtgctgg ccagcgtgca ccacccggcg ctgatagtgt tccagtgctg  3720
caaccctgtg tatcgcaact cgcgcgcgca gggcggaggc cccaactgcg acttcaagat  3780
atcggcgccc gacctgctaa acgcgttggt gatggtgcgc agcctgtgga gtgaaaactt  3840
caccgagctg ccgcggatgg ttgtgcctga gtttaagtgg agcactaaac accagtatcg  3900
caacgtgtcc ctgccagtgg cgcatagcga tgcgcggcag aacccctttg atttttaacc  3960
cgggagttct agggatctgc ccctctccct cccccccccc taacgttact ggccgaagcc  4020
gcttggaata aggccggtgt gcgtttgtct atatgttatt ttccaccata ttgccgtctt  4080
ttggcaatgt gagggcccgg aaacctggcc ctgtcttctt gacgagcatt cctaggggtc  4140
tttcccctct cgccaaagga atgcaaggtc tgttgaatgt cgtgaaggaa gcagttcctc  4200
tggaagcttc ttgaagacaa acaacgtctg tagcgaccct ttgcaggcag cggaaccccc  4260
cacctggcga caggtgcctc tgcggccaaa agccacgtgt ataagataca cctgcaaagg  4320
cggcacaacc ccagtgccac gttgtgagtt ggatagttgt ggaaagagtc aaatggctct  4380
cctcaagcgt attcaacaag gggctgaagg atgcccagaa ggtaccccat tgtatgggat  4440
ctgatctggg gcctcggtgc acatgcttta catgtgttta gtcgaggtta aaaaaacgtc  4500
taggcccccc gaaccacggg gacgtggttt tcctttgaaa aacacgatga taaggatcca  4560
ccggaggcca ccatgactac gtccggcgtt ccatttggca tgacactacg accaacacga  4620
tctcggttgt ctcggcgcac tccgtacagt agggatcgtc tacctccttt tgagacagaa  4680
acccgcgcta ccatactgga ggatcatccg ctgctgcccg aatgtaacac tttgacaatg  4740
cacaacgtga gttacgtgcg aggtcttccc tgcagtgtgg gatttacgct gattcaggaa  4800
tgggttgttc cctgggatat ggttctaacg cgggaggagc ttgtaatcct gaggaagtgt  4860
atgcacgtgt gcctgtgttg tgccaacatt gatatcatga cgagcatgat gatccatggt  4920
tacgagtcct gggctctcca ctgtcattgt tccagtcccg gttccctgca gtgtatagcc  4980
ggcgggcagg ttttggccag ctggtttagg atggtggtgg atggcgccat gtttaatcag  5040
aggtttatat ggtaccggga ggtggtgaat tacaacatgc caaaagaggt aatgtttatg  5100
tccagcgtgt ttatgagggg tcgccactta atctacctgc gcttgtggta tgatggccac  5160
gtgggttctg tggtccccgc catgagcttt ggatacagcg ccttgcactg tgggattttg  5220
aacaatattg tggtgctgtg ctgcagttac tgtgctgatt taagtgagat cagggtgcgc  5280
tgctgtgccc ggaggacaag gcgccttatg ctgcgggcgg tgcgaatcat cgctgaggag  5340
accactgcca tgttgtattc ctgcaggacg gagcggcggc ggcagcagtt tattcgcgcg  5400
ctgctgcagc accaccgccc tatcctgatg cacgattatg actctacccc catgtaggcg  5460
gccgctcgag tctagagggc ccgtttaaac ccgctgatca gcctcgactg tgccttctag  5520
ttgccagcca tctgttgttt gcccctcccc cgtgccttcc ttgaccctgg aaggtgccac  5580
tcccactgtc ctttcctaat aaaatgagga aattgcatcg cattgtctga gtaggtgtca  5640
ttctattctg gggggtgggg tggggcagga cagcaagggg gaggattggg aagacaatag  5700
caggcatgct ggggatgcgg tgggctctat ggcttctgag gcggaaagaa ccagctgggg  5760
ctctaggggg tatccccggg gttggggttg cgccttttcc aaggcatcca gcacagtggc  5820
ggccgcaata tttgcatgtc gctatgtgtt ctgggaaatc accataaacg tgaaatccct  5880
atcagtgata gagacttata agttccctat cagtgataga gaaccggtgg gcactcttcc  5940
gtggtctggt ggataaattc gcaagggtat catggcggac gaccggggtt cgagccccgt  6000
atccggccgt ccgccgtgat ccatgcggtt accgcccgcg tgtcgaaccc aggtgtgcga  6060
cgtcagacaa cgggggagtg ctcctttttg aattccactt tggccgcggc tcgagggggt  6120
tggggttgcg ccttttccaa ggcagccctg ggtttgcgca gggacgcggc tgctctgggc  6180
gtggttccgg gaaacgcagc ggcgccgacc ctgggtctcg cacattcttc acgtccgttc  6240
gcagcgtcac ccggatcttc gccgctaccc ttgtgggccc cccggcgacg cttcctgctc  6300
cgcccctaag tcgggaaggt tccttgcggt tcgcggcgtg ccggacgtga caaacggaag  6360
ccgcacgtct cactagtacc ctcgcagacg gacagcgcca gggagcaatg gcagcgcgcc  6420
gaccgcgatg ggctgtggcc aatagcggct gctcagcagg gcgcgccgag agcagcggcc  6480
gggaaggggc ggtgcgggag gcggggtgtg gggcggtagt gtgggccctg ttcctgcccg  6540
cgcggtgttc cgcattctgc aagcctccgg agcgcacgtc ggcagtcggc tccctcgttg  6600
accgaatcac cgacctctct ccccaggggg atctgtgagt ttggggaccc ttgattgttc  6660
tttctttttc gctattgtaa aattcatgtt atatggaggg ggcaaagttt tcagggtgtt  6720
gtttagaatg ggaagatgtc ccttgtatca ccatggaccc tcatgataat tttgtttctt  6780
tcactttcta ctctgttgac aaccattgtc tcctcttatt ttcttttcat tttctgtaac  6840
tttttcgtta aactttagct tgcatttgta acgaattttt aaattcactt ttgtttattt  6900
gtcagattgt aagtactttc tctaatcact ttttttcaa ggcaatcagg gtatattata  6960
ttgtacttca gcacagtttt agagaacaat tgttataatt aaatgataag gtagaatatt  7020
tctgcatata aattctggct ggcgtggaaa tattcttatt ggtagaaaca actacatcct  7080
ggtcatcatc ctgcctttct ctttatggtt acaatgatat acactgtttg agatgaggat  7140
aaaatactct gagtccaaac cgggcccctc tgctaaccat gttcatgcct tcttcttttt  7200
cctacagctc ctgggcaacg tgctggttat tgtgctgtct catcattttg gcaaagaatt  7260
gtaatacgac tcactatagg gcgagccacc atggctagat tagataaaag taaagtgatt  7320
aacagcgcat tagagctgct taatgaggtc ggaatcgaag gtttaacaac ccgtaaactc  7380
gcccagaagc taggtgtaga gcagcctaca ttgtattggc atgtaaaaaa taagcgggct  7440
ttgctcgacg ccttagccat tgagatgtta gataggcacc atactcactt ttgcccttta  7500
gaaggggaaa gctggcaaga tttttacgt aataacgcta aaagttttag atgtgcttta  7560
```

-continued

```
ctaagtcatc gcgatggagc aaaagtacat ttaggtacac ggcctacaga aaaacagtat  7620
gaaactctcg aaaatcaatt agccttttta tgccaacaag gtttttcact agagaatgcc  7680
ttatatgcac tcagcgccgt ggggcatttt actttaggtt gcgtattgga agatcaagag  7740
catcaagtcg ctaaagaaga aagggaaaca cctactactg atagtatgcc gccattatta  7800
cgacaagcta tcgaattatt tgatcaccaa ggtgcagagc cagccttctt attcggcctt  7860
gaattgatca tatgcggatt agaaaaacaa cttaaatgtg aaagtgggtc cccaaaaaag  7920
aagagaaagg tcgacggcgg tggtgctttg tctcctcagc actctgctgt cactcaagga  7980
agtatcatca agaacaagga gggcatggat gctaagtcac taactgcctg gtcccggaca  8040
ctggtgacct tcaaggatgt atttgtggac ttcaccaggg aggagtggaa gctgctggac  8100
actgctcagc agatcgtgta cagaaatgtg atgctggaga actataagaa cctggtttcc  8160
ttgggttatc agcttactaa gccagatgtg atcctccggt tggagaaggg agaagagccc  8220
tggctggtgg agagagaaat tcaccaagag acccatcctg attcagagac tgcatttgaa  8280
atcaaatcat cagtttaagc gtacagcggc tcccgggagt tctagggatc tgcccctctc  8340
cctccccccc ccctaacgtt actggccgaa gccgcttgga ataaggccgg tgtgcgtttg  8400
tctatatgtt attttccacc atattgccgt cttttggcaa tgtgagggcc cggaaacctg  8460
gccctgtctt cttgacgagc attcctaggg gtctttcccc tctcgccaaa ggaatgcaag  8520
gtctgttgaa tgtcgtgaag gaagcagttc ctctggaagc ttcttgaaga caaacaacgt  8580
ctgtagcgac cctttgcagg cagcggaacc ccccacctgg cgacaggtgc ctctgcggcc  8640
aaaagccacg tgtataagat acacctgcaa aggcggcaca accccagtgc cacgttgtga  8700
gttggatagt tgtggaaaga gtcaaatggc tctcctcaag cgtattcaac aaggggctga  8760
aggatgccca gaaggtaccc cattgtatgg gatctgatct ggggcctcgg tgcacatgct  8820
ttacatgtgt ttagtcgagg ttaaaaaaac gtctaggccc cccgaaccac ggggacgtgg  8880
ttttcctttg aaaaacacga tgataaggat ccaccggagg ccaccatgac cgagtacaag  8940
cccacggtgc gcctcgccac ccgcgacgac gtccccaggg ccgtacgcac cctcgccgcc  9000
gcgttcgccg actaccccgc cacgcgccac accgtcgatc cggaccgcca catcgagcgg  9060
gtcaccgagc tgcaagaact cttcctcacg cgcgtcgggc tcgacatcgg caaggtgtgg  9120
gtcgcggacg acggcgccgc ggtggcggtc tggaccacgc cggagagcgt cgaagcgggg  9180
gcggtgttcg ccgagatcgg cccgcgcatg gccgagttga gcggttcccg gctggccgcg  9240
cagcaacaga tggaaggcct cctggcgccg caccggccca aggagcccgc gtggttcctg  9300
gccaccgtcg gcgtctcgcc cgaccaccag ggcaagggtc tgggcagcgc cgtcgtgctc  9360
cccggagtgg aggcggccga gcgcgccggg gtgcccgcct tcctggagac ctccgcgccc  9420
cgcaacctcc ccttctacga gcggctcggc ttcaccgtca ccgccgacgt cgaggtgccc  9480
gaaggaccgc gcacctggtg catgacccgc aagcccggtg cctgaccgcg tctggaacaa  9540
tcaacctctg gattacaaaa tttgtgaaag attgactggt attcttaact atgttgctcc  9600
ttttacgcta tgtggatacg ctgctttaat gcctttgtat catgctattg cttcccgtat  9660
ggctttcatt ttctcctcct tgtataaatc ctggttgctg tctctttatg aggagttgtg  9720
gcccgttgtc aggcaacgtg gcgtggtgtg cactgtgttt gctgacgcaa cccccactgg  9780
ttggggcatt gccaccacct gtcagctcct ttccgggact ttcgctttcc ccctccctat  9840
tgccacggcg gaactcatcg ccgcctgcct tgcccgctgc tggacagggg ctcggctgtt  9900
gggcactgac aattccgtgg tgttgtcggg gaagctgacg tcctttccat ggctgctcgc  9960
ctgtgttgcc acctggattc tgcgcgggac gtccttctgc tacgtccctt cggccctcaa  10020
tccagcggac cttccttccc gcggcctgct gccggctctg cggcctcttc cgcgtcttcg  10080
ccttcgccct cagacgagtc ggatctccct ttgggccgcc tccccgcaaa atgaccgacc  10140
aagcgacgcc caacctgcca tcacgagatt tcgattccac cgccgccttc tatgaaaggt  10200
tgggcttcgg aatcgttttc cgggacgccg gctggatgat cctccagcgc ggggatctca  10260
tgctggagtt cttcgcccac cccaacttgt ttattgcagc ttataatggt tacaaataaa  10320
gcaatagcat cacaaatttc acaaataaag catttttttc actgcattct agttgtggtt  10380
tgtccaaact catcaatgta tcttatcatg tctgtagctg atcaattggc gcgccgaatt  10440
cgttatctgc agaattcggc ttggcggctg cgcgttcaaa cctcccgctt caaaatggag  10500
accctgcgtg ctcactcggg cttaaatacc cagcgtgacc acatggtgtc gcaaaatgtc  10560
gcaaaacact cacgtgacct ctaatacagg acctctagag catggaaact agataagaaa  10620
gaaatacgca gagaccaaag ttcaactgaa acgaattaaa cggtttattg attaacaagc  10680
aaactagttt acagattacg ggtgaggtaa cgggtgccga tggggcgagg ctcagaataa  10740
acgccatttg tgtcaacagc aaagtccaca tttgtagatt tgttgtagtt ggaagtgtat  10800
tgaatctctg ggttccagcg tttgctgttt tctttctgca gctcccattc aatttccacg  10860
ctgacctgtc cggtgctgta ctgcgtgatg aacgacgcaa acttagctgg actgaaggta  10920
gttggaggat tcgcgggaac aggtgtattc ttaatcagga tctgaggagg cgggtgtttc  10980
agtccaaagc ctcccatcag cggcgaggga tgaaagtgtc cgtccgtgtg aggaatcttg  11040
gcccagatag gaccctgcag gtacacgtcc cggtcctgcc agaccatgcc aggtaaggct  11100
ccttgactgt tgacggtccc tgtagcagga gcggtgttgg ccgattgcag gttagtggcc  11160
accgtgccgt actcttctgt ggccactggg ttggtggttt taatttcttc ctcgttggtt  11220
atcataacgt tgtcaaggtc cacgttgcta tttccagctc cctgtttccc aaatattaag  11280
actccgctca tcggaaaaaa tttgtcttcg tcgtccttgt gggttgccat agcgggaccg  11340
ggatttacca gagagtctct gccattcaga tgatacttgg tggcaccggt ccaggcaaag  11400
ttgctgttgt tattttgatt ggttgtcttg gagacgcgtt gctgccggta gcagggcccg  11460
ggtagccagt ttttggcctg attcgccatg ctactaggcc cggcctgaga aaattgcaac  11520
gtccgatttc ctgcggtacc actcgtggtc tgagtccgag acaggtagta caggtactgg  11580
tcgatgaggg ggttcatcag ccggtccagg ctttggctgt gcgcgtagct gctgtgaaaa  11640
ggcacgtcct caaacgtgta gctgaactga aagttgttgc ccgttctcag catttgagaa  11700
ggaaagtatt ccaggcagta gaaggaggaa cggcccacgg cctgactgcc attgttcaga  11760
gtcaggtacc cgtactgagg aatcatgaag acgtccgccg ggaacggagg caggcagccc  11820
tggtgcgcag agccgaggac gtacgggagc tggtattccg agtccgtaaa gacctgaacc  11880
gtgctggtaa ggttattggc gatggtcgtg gtgccatcat tcgtcgtgac ctccttgacc  11940
tggatgttga agagcttgaa gttgagcttc ttgggccgga atccccagtt gttgttgatg  12000
agtcgctgcc agtcacgtgg tgagaagtgg cagtggaatc tgttaaagtc aaaatacccc  12060
cagggggtgc tgtagccgaa gtaggtgttg tcgttggtgc tgcctcccga ttggctggag  12120
atttgcttgt agaggtggtt gttgtaggtg gggagggccc aggttcgggt gctggtggtg  12180
atgactctgt cgcccagcca tgtggaatcg caatgccaat ttcctgaggc gttacccact  12240
ccgtcggcgc cttcgttatt gtctgccatt ggagcgccac cgcctgcagc cattgtatta  12300
```

-continued

```
gatcccacac cagaggggc tgcgggggt tctccgagtg gttgagggtc gggcactgac  12360
tctgagtcgc cagtctgccc aaagttgagt ctctttctcg cgggctgctg gcctttcttg  12420
ccgatgcccg aagaggagtc tggttcctgg ggtgattgct ctaccggtct cttctttcca  12480
ggagccgtct tagcgccttc ctcaaccaga ccgagaggtt cgagaacccg cttcttggcc  12540
tggaagactg ctcgcccgag gttgccccca aaagacgtat cttcttgcag acgctcctga  12600
aactcggcgt cggcgtggtt ataccgcagg tacggattgt cacccgcttt gagctgctgg  12660
tcgtaggcct tgtcgtgctc gagggccgct gcgtccgccg cgttgacggg ctccccccttg  12720
tcgagtccgt tgaagggtcc gaggtacttg tagccaggaa gcaccagacc ccggccgtcg  12780
tcctgctttt gctggttggc tttgggtttc ggggctccag gtttcaagtc ccaccactcg  12840
cgaatgccct cagagaggtt gtcctcgagc caatctggaa gataaccatc ggcagccata  12900
cctgatttaa atcatttatt gttcaaagat gcagtcatcc aaatccacat tgaccagatc  12960
gcaggcagtg caagcgtctg gcacctttcc catgatatga tgaatgtagc acagtttctg  13020
atacgccttt ttgacgacag aaacgggttg agattctgac acgggaaagc actctaaaca  13080
gtctttctgt ccgtgagtga agcagatatt tgaattctga ttcattctct cgcattgtct  13140
gcagggaaac agcatcagat tcatgcccac gtgacgagaa catttgtttt ggtacctgtc  13200
tgcgtagttg atcgaagctt ccgcgtctga cgtcgatggc tgcgcaactg actcgcgcac  13260
ccgtttgggc tcacttatat ctgcgtcact gggggcgggt cttttcttgg ctccaccctt  13320
tttgacgtag aattcatgct ccacctcaac cacgtgatcc tttgcccacc ggaaaaagtc  13380
tttgacttcc tgcttggtga ccttcccaaa gtcatgatcc agacggcggg tgagttcaaa  13440
tttgaacatc cggtcttgca acggctgctg gtgttcgaag gtcgttgagt tcccgtcaat  13500
cacggcgcac atgttggtgt tggaggtgac gatcacggga gtcgggtcta tctgggccga  13560
ggacttgcat ttctggtcca cgcgcacctt gcttcctccg agaatggctt tggccgactc  13620
cacgaccttg gcggtcatct tcccctcctc ccaccagatc accatcttgt cgacacagtc  13680
gttgaaggga aagttctcat tggtccagtt tacgcacccg tagaagggca cagtgtgggc  13740
tatggcctcc gcgatgttgg tcttcccggt agttgcaggc ccaaacagcc agatggtgtt  13800
cctcttgccg aactttttcg tggcccatcc cagaaagacg gaagccgcat attggggatc  13860
gtacccgttt agttccaaaa ttttataaat ccgattgctg gaaatgtcct ccacgggctg  13920
ctggcccacc aggtagtcgg gggcggtttt agtcaggctc ataatctttc ccgcattgtc  13980
caaggcagcc ttgatttggg accgcgagtt ggaggccgca ttgaaggaga tgtatgaggc  14040
ctggtcctcc tggatccact gcttctccga ggtaatcccc ttgtccacga gccacccgac  14100
cagctccatg tacctggctg aagtttttga tctgatcacc ggcgcatcag aattgggatt  14160
ctgattctct ttgttctgct cctgcgtctg cgacacgtgc gtcagatgct gcgccaccaa  14220
ccgtttacgc tccgtgagat tcaaacaggc gctgtggaga gaaaggcaaa gtggatgtca  14280
gtatctctat cactgatagg gagatctcta tcactgatag ggaacttacc ttaaatactg  14340
ttccatatta gtccacgccc actggagctc aggctgggtt ttggggagca agtaattggg  14400
gatgtagcac tcatccacca ccttgttccc gcctccggcg ccatttctgg tctttgtgac  14460
cgcgaaccag tttggcaaag tcggctcgat cccgcggtaa attctctgaa tcagtttttc  14520
gcgaatctga ctcaggaaac gtcccaaaac catggatttc accccggtgg tttccacgag  14580
cacgtgcatg tggaagtagc tctctccctt ctcaaattgc acaaagaaaa gagcctccgg  14640
ggccttactc acacggcgcc attccgtcag aaagtcgcgc tgcagcttct cggccacggt  14700
caggggtgcc tgctcaatca gattcagatc catgtcagaa tctggcggca actcccattc  14760
cttctcggcc acccagttca caaagctgtc agaaatgccg ggcagatgct cgtcaaggtc  14820
gctggggacc ttaatcacaa tctcgtaaaa ccccggcatg gcggctgcgc gttcaaacct  14880
cccgcttcaa aatggagacc ctgcgtgctc actcgggcga tctctatcac tgatagggag  14940
atctctatca ctgataggga gattaaatag aatggctagg atccggccgg cctgcaggtg  15000
tcctcacagg aacgaagtcc ctaaagaaac agtggcagcc aggtttagcc ccggaattga  15060
ctggattcct tttttagggc ccattggtat ggcttttttcc ccgtatcccc ccaggtgtct  15120
gcaggctcaa agagcagcga gaagcgttca gaggaaagcg atcccgtgcc accttccccg  15180
tgcccgggct gtccccgcac gctgccggct cggggatgcg gggggagcgc cggaccggag  15240
cggagccccg ggcggctcgc tgctgccccc tagcggggga gggacgtaat tacatccctg  15300
ggggctttgg gggggggctg tccctctaga gcggccgcca ccgcggtgga gctccagctt  15360
ttgttccctt tagtgagggt taattagatc ttaatacgac tcactatagg gcgaattggg  15420
taccgggccc cccctcgagg tcgacggtat cgcctccaag gccagcttcc cacaataagt  15480
tgggtgaatt ttggctcatt cctcctttct ataggattga ggtcagagct ttgtgatggg  15540
aattctgtgg aatgtgtgtc agttagggtg tggaaagtcc cgcgatcgct agcaaacgcc  15600
agcaacgcgg ccttttttacg gttcctggcc ttttgctggc cttttgctca catgtcctgc  15660
aggcagctgc gcgctcgctc gctcactgag gccgcccggg caaagcccgg gcgtcgggcg  15720
acctttggtc gcccggcctc agtgagcgag cgagcgcgca gagagggagt ggccaactcc  15780
atcactaggg gttcctgcgg ccgcacgcgt ggagctagtt attaatagta atcaattacg  15840
gggtcattag ttcatagccc atatatggag ttccgcgtta cataacttac ggtaaatggc  15900
ccgcctggct gaccgcccaa cgacccccgc ccattgacgt caataatgac gtatgttccc  15960
atagtaacgt caatagggac tttccattga cgtcaatggg tggagtattt acggtaaact  16020
gcccacttgg cagtacatca agtgtatcat atgccaagta cgccccctat tgacgtcaat  16080
gacggtaaat ggcccgcctg gcattatgcc cagtacatga ccttatggga ctttcctact  16140
tggcagtaca tctacgtatt agtcatcgct attaccatgg tgatgcggtt ttggcagtac  16200
atcaatgggc gtggatagcg gtttgactca cggggatttc caagtctcca ccccattgac  16260
gtcaatggga gtttgttttg caccaaaatc aacgggactt tccaaaatgt cgtaacaact  16320
ccgccccatt gacgcaaatg ggcggtaggc gtgtacggtg ggaggtctat ataagcagag  16380
ctcgtttagt gaaccgtcag atcgcctgga gacgccatcc acgctgtttt gacctccata  16440
gaagacaccg ggaccgatcc agcctccgcg gattcgaatc ccggccggga acggtgcatt  16500
ggaacgcgga ttccccgtgc caagagtgac gtaagtaccg cctatagagt ctataggccc  16560
acaaaaaatg ctttcttctt ttaatatact tttttgttta tcttatttct aatactttcc  16620
ctaatctctt tctttcaggg caataatgat acaatgtatc atgcctcttt gcaccattct  16680
aaagaataac agtgataatt tctgggttaa ggcaatagca atatttctgc atataaatat  16740
ttctgcatat aaattgtaac tgatgtaaga ggtttcatat tgctaatagc agctacaatc  16800
cagctaccat tctgctttta ttttatggtt gggataaggc tggattattc tgagtccaag  16860
ctaggccctt ttgctaatca tgttcatacc tcttatcttc ctcccacagc tcctgggcaa  16920
cgtgctggtc tgtgtgctgg cccatcactt tggcaaagaa ttgggattcg aacatcgatt  16980
gaattctgaa tggtgagcaa gggcgaggag ctgttcaccg gggtggtgcc catcctggtc  17040
```

```
gagctggacg gcgacgtaaa cggccacaag ttcagcgtgt ccggcgaggg cgagggcgat  17100
gccacctacg gcaagctgac cctgaagttc atctgcacca ccggcaagct gcccgtgccc  17160
tggcccaccc tcgtgaccac cctgacctac ggcgtgcagt gcttcagccg ctaccccgac  17220
cacatgaagc agcacgactt cttcaagtcc gccatgcccg aaggctacgt ccaggagcgc  17280
accatcttct tcaaggacga cggcaactac aagacccgcg ccgaggtgaa gttcgagggc  17340
gacaccctgg tgaaccgcat cgagctgaag ggcatcgact tcaaggagga cggcaacatc  17400
ctggggcaca agctggagta caactacaac agccacaacg tctatatcat ggccgacaag  17460
cagaagaacg gcatcaaggt gaacttcaag atccgccaca acatcgagga cggcagcgtg  17520
cagctcgccg accactacca gcagaacacc cccatcggcg acggccccgt gctgctgccc  17580
gacaaccact acctgagcac ccagtccgcc ctgagcaaag accccaacga gaagcgcgat  17640
cacatggtcc tgctggagtt cgtgaccgcc gccgggatca ctctcggcat ggacgagctg  17700
tacaagtact cagatctcga gctcaagtag ggatcctcta gagtcgacct gcagaagctt  17760
gcctcgagca gcgctgctcg agagatctac gggtggcatc cctgtgaccc ctccccagtg  17820
cctctcctgg ccctggaagt tgccactcca gtgcccacca gccttgtcct aataaaatta  17880
agttgcatca ttttgtctga ctaggtgtcc ttctataata ttatggggtg gaggggggtg  17940
gtatggagca aggggcaagt tgggaagaca acctgtaggg cctgcggggt ctattgggaa  18000
ccaagctgga gtgcagtggc acaatcttgg ctcactgcaa tctccgcctc ctgggttcaa  18060
gcgattctcc tgcctcagcc tcccgagttg ttgggattcc aggcatgcat gaccaggctc  18120
agctaatttt tgtttttttg gtagagacgg ggtttcacca tattggccag gctggtctcc  18180
aactcctaat ctcaggtgat ctacccacct tggcctccca aattgctggg attacaggcg  18240
tgaaccactg ctcccttccc tgtccttctg attttgtagg taaccacgtg cggaccgagc  18300
ggccgcagga acccctagtg atggagttgg ccactccctc tctgcgcgct cgctcgctca  18360
ctgaggccgg gcgaccaaag gtcgcccgac gcccgggctt tgcccgggcg gcctcagtga  18420
gcgagcgagc gcgcagctgc ctgcaggggc gcctgatgcg gtattttctc cttacgcatc  18480
tgtgcggtat ttcacaccgc atacgtcgta gctgatcaat tggcgcgccg aattcgttaa  18540
caagctttaa ttaacgcgta cgataagctt gatatctata acaagaaaat atatatataa  18600
taagttatca cgtaagtaga acatgaaata acaatataat tatcgtatga gttaaatctt  18660
aaaagtcacg taaaagataa tcatgcgtca ttttgactca cgcggtcgtt atagttcaaa  18720
atcagtgaca cttaccgcat tgacaagcac gcctcacggg agctccaagc ggcgactgag  18780
atgtcctaaa tgcacagcga cggattcgcg ctatttagaa agagagagca atatttcaag  18840
aatgcatgcg tcaattttac gcagactatc tttctagggt taatctagct gcatcaggat  18900
catatcgtcg ggtctttttt ccggctcagt catcgcccaa gctggcgcta tctgggcatc  18960
ggggaggaag aagcccgtgc cttttcccgc gaggttgaag cggcatggaa agagtttgcc  19020
gaggatgact gctgctgcat tgacgttgag cgaaaacgca cgtttaccat gatgattcgg  19080
gaaggtgtgg ccatgcacgc ctttaacggt gaactgttcg ttcaggccac ctgggatacc  19140
agttcgtcgc ggcttttccg gacacagttc cggatggtca gcccgaagcg catcagcaac  19200
ccgaacaata ccggcgacag ccggaactgc cgtgccggtg tgcagattaa tgacagcggt  19260
gcggcgctgg gatattacgt cagcgaggac gggtatcctg gctggatgcc gcagaaatgg  19320
acatggatac cccgtgagtt acccggcggg cgcgcttggc gtaatcatgg tcatagctgt  19380
ttcctgtgtg aaattgttat ccgctcacaa ttccacacaa catacgagcc ggaagcataa  19440
agtgtaaagc ctggggtgcc taatgagtga gctaactcac attaattgcg ttgcgctcac  19500
tgcccgcttt ccagtcggga aacctgtcgt gccagctgca ttaatgaatc ggccaacgcg  19560
cggggagagg cggtttgcgt attgggcgct cttccgcttc ctcgctcact gactcgctgc  19620
gctcggtcgt tcggctgcgg cgagcggtat cagctcactc aaaggcggta atacggttat  19680
ccacagaatc aggggataac gcaggaaaga acatgtgagc aaaaggccag caaaaggcca  19740
ggaaccgtaa aaaggccgcg ttgctggcgt ttttccatag gctccgcccc cctgacgagc  19800
atcacaaaaa tcgacgctca agtcagaggt ggcgaaaccc gacaggacta taaagatacc  19860
aggcgtttcc ccctggaagc tccctcgtgc gctctcctgt tccgaccctg ccgcttaccg  19920
gatacctgtc cgcctttctc ccttcgggaa gcgtggcgct ttctcatagc tcacgctgta  19980
ggtatctcag ttcggtgtag gtcgttcgct ccaagctggg ctgtgtgcac gaaccccccg  20040
ttcagcccga ccgctgcgcc ttatccggta actatcgtct tgagtccaac ccggtaagac  20100
acgacttatc gccactggca gcagccactg gtaacaggat tagcagagcg aggtatgtag  20160
gcggtgctac agagttcttg aagtggtggc ctaactacgg ctacactaga aggacagtat  20220
ttggtatctg cgctctgctg aagccagtta ccttcggaaa aagagttggt agctcttgat  20280
ccggcaaaca aaccaccgct ggtagcggtg gtttttttgt ttgcaagcag cagattacgc  20340
gcagaaaaaa aggatctcaa gaagatcctt tgatcttttc tacggggtct gacgctcagt  20400
ggaacgaaaa ctcacgttaa gggattttgg tcatgagatt atcaaaaagg atcttcacct  20460
agatcctttt aaattaaaaa tgaagtttta aatcaatcta aagtatatat gagtaaactt  20520
ggtctgacag ttaccaatgc ttaatcagtg aggcacctat ctcagcgatc tgtctatttc  20580
gttcatccat agttgcctga ctccccgtcg tgtagataac tacgatacgg gagggcttac  20640
catctggccc cagtgctgca atgataccgc gagacccacg ctcaccggct ccagatttat  20700
cagcaataaa ccagccagcc ggaagggccg agcgcagaag tggtcctgca actttatccg  20760
cctccatcca gtctattaat tgttgccggg aagctagagt aagtagttcg ccagttaata  20820
gtttgcgcaa cgttgttgcc attgctacag gcatcgtggt gtcacgctcg tcgtttggta  20880
tggcttcatt cagctccggt tcccaacgat caaggcgagt tacatgatcc cccatgttgt  20940
gcaaaaaagc ggttagctcc ttcggtcctc cgatcgttgt cagaagtaag ttggccgcag  21000
tgttatcact catggttatg gcagcactgc ataattctct tactgtcatg ccatccgtaa  21060
gatgcttttc tgtgactggt gagtactcaa ccaagtcatt ctgagaatag tgtatgcggc  21120
gaccgagttg ctcttgcccg gcgtcaatac gggataatac cgcgccacat agcagaactt  21180
taaaagtgct catcattgga aaacgttctt cggggcgaaa actctcaagg atcttaccgc  21240
tgttgagatc cagttcgatg taacccactc gtgcacccaa ctgatcttca gcatctttta  21300
ctttcaccag cgtttctggg tgagcaaaaa caggaaggca aaatgccgca aaaaagggaa  21360
taagggcgac acggaaatgt tgaatactca t                                 21391
```

```
SEQ ID NO: 14          moltype = DNA  length = 21046
FEATURE                Location/Qualifiers
misc_feature           1..21046
                       note = Description of Artificial Sequence: Synthetic
                        polynucleotide
```

```
source                  1..21046
                        mol_type = other DNA
                        organism = synthetic construct
SEQUENCE: 14
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcgtttaaac ttaagcttgg taccgagctc ggatccacta  1560
gtccagtgtg gtggaattcc tgcttcgcga tgtacgggcc agatatacgc gttgacattg  1620
attattgact agttattaat agtaatcaat tacggggtca ttagttcata gcccatatat  1680
ggagttccgc gttacataac ttacggtaaa tggcccgcct ggctgaccgc ccaacgaccc  1740
ccgcccattg acgtcaataa tgacgtatgt tcccatagta acgccaatag ggactttcca  1800
ttgacgtcaa tgggtggagt atttacggta aactgcccac ttggcagtac atcaagtgta  1860
tcatatgcca agtacgcccc ctattgacgt caatgacggt aaatggcccg cctggcatta  1920
tgcccagtac atgaccttat gggactttcc tacttggcag tacatctacg tattagtcat  1980
cgctattacc atggtgatgc ggttttggca gtacatcaat gggcgtggat agcggtttga  2040
ctcacgggga tttccaagtc tccaccccat tgacgtcaat gggagtttgt tttggaacca  2100
aaatcaacgg gactttccaa aatgtcgtaa caactccgcc ccattgacgc aaatgggcgg  2160
taggcgtgta cggtgggagg tctatataag cagagctctc cctatcagtg atagagatct  2220
ccctatcagt gatagagatc gtcgacgagc tcgtttagtg aaccgtcaga tcgcctggag  2280
acgccatcca cgctgttttg acctccatag aagacaccgg gaccgatcca gcctccggac  2340
tctagcgttt aaacttaagc ttgccaccat ggccagtcgg gaagaggagc agcgcgaaac  2400
cacccccgag cgcggacgcg gtgcggcgcg acgtccccca accatggagg acgtgtcgtc  2460
cccgtccccg tcgccgccgc ctccccgggc gcccccaaaa aagcggatga ggcggcgtat  2520
cgagtccgag gacgaggaag actcatcaca agacgcgctg gtgccgcgca cacccagccc  2580
gcggccatcg acctcggcgg cggatttggc cattgcgccc aagaagaaaa agaagcgccc  2640
ttctcccaag cccgagcgcc cgccatcacc agaggtaatc gtggacagcg aggaagaaag  2700
agaagatgtg gcgctacaaa tggtgggttt cagcaaccca ccggtgctaa tcaagcatgg  2760
caaaggaggt aagcgcacag tgcggcggct gaatgaagac gacccagtgg cgcgtggtat  2820
gcggacgcaa gaggaagagg aagagcccag cgaagcggaa agtgaaatta cggtgatgaa  2880
cccgctgagt gtgccgatcg tgtctgcgtg ggagaagggc atggaggctg cgcgcgcgct  2940
gatggacaag taccacgtgg ataacgatct aaaggcgaac ttcaaactac tgcctgacca  3000
agtggaagct ctggcggccg tatgcaagac ctggctgaac gaggagcacc gcgggttgca  3060
gctgaccttc accagcaaca agacctttgt gacgatgatg gggcgattcc tgcaggcgta  3120
cctgcagtcg tttgcagagg tgacctacaa gcatcacgag cccacgggct gcgcgttgtg  3180
gctgcaccgc tgcgctgaga tcgaaggcga gcttaagtgt ctacacggaa gcattatgat  3240
aaataaggag cacgtgattg aaatggatgt gacgagcgaa aacgggcagc gcgcgctgaa  3300
ggagcagtct agcaaggcca agatcgtgaa gaaccggtgg ggccgaaatg tggtgcagat  3360
ctccaacacc gacgcaaggt gctgcgtgca cgacgcggcc tgtccggcca atcagttttc  3420
cggcaagtct tgcggcatgt tcttctctga aggcgcaaag gctcaggtgg cttttaagca  3480
gatcaaggct tttatgcagg cgctgtatcc taacgcccag accgggcacg gtcacctttt  3540
gatgccacta cggtgcgagt gcaactcaaa gcctgggcac gcgccctttt tgggaaggca  3600
gctaccaaag ttgactccgt tcgccctgag caacgcggag gacctggacg cggatctgat  3660
ctccgacaag agcgtgctgg ccagcgtgca ccacccggcg ctgatagtgt tccagtgctg  3720
caaccctgtg tatcgcaact cgcgcgcgca gggcggaggc cccaactgcg acttcaagat  3780
atcggcgccc gacctgctaa acgcgttggt gatggtgcgc agcctgtgga gtgaaaactt  3840
caccgagctg ccgcggatgg ttgtgcctga gtttaagtgg agcactaaac accagtatcg  3900
caacgtgtcc ctgccagtgg cgcatagcga tgcgcggcag aaccccttttg atttttaacc  3960
cgggagttct agggatctgc ccctctccct cccccccccc taacgttact ggccgaagcc  4020
gcttggaata aggccggtgt gcgtttgtct atatgttatt ttccaccata ttgccgtctt  4080
ttggcaatgt gagggcccgg aaacctggcc ctgtcttctt gacgagcatt cctaggggtc  4140
tttcccctct cgccaaagga atgcaaggtc tgttgaatgt cgtgaaggaa gcagttcctc  4200
tggaagcttc ttgaagacaa acaacgtctg tagcgaccct ttgcaggcag cggaaccccc  4260
cacctggcga caggtgcctc tgcggccaaa agccacgtgt ataagataca cctgcaaagg  4320
cggcacaacc ccagtgccac gttgtgagtt ggatagttgt ggaaagagtc aaatggctct  4380
cctcaagcgt attcaacaag gggctgaagg atgcccagaa ggtaccccat tgtatgggat  4440
ctgatctggg gcctcggtgc acatgcttta catgtgttta gtcgaggtta aaaaaacgtc  4500
```

-continued

```
taggcccccc gaaccacggg gacgtggttt tcctttgaaa aacacgatga taaggatcca  4560
ccggaggcca ccatgactac gtccggcgtt ccatttggca tgacactacg accaacacga  4620
tctcggttgt ctcggcgcac tccgtacagt agggatcgtc tacctccttt tgagacagaa  4680
acccgcgcta ccatactgga ggatcatccg ctgctgcccg aatgtaacac tttgacaatg  4740
cacaacgtga gttacgtgcg aggtcttccc tgcagtgtgg gatttacgct gattcaggaa  4800
tgggttgttc cctgggatat ggttctaacg cgggaggagc ttgtaatcct gaggaagtgt  4860
atgcacgtgt gcctgtgttg tgccaacatt gatatcatga cgagcatgat gatccatggt  4920
tacgagtcct gggctctcca ctgtcattgt tccagtcccg gttccctgca gtgtatagcc  4980
ggcgggcagg ttttggccag ctggtttagg atggtggtgg atggcgccat gtttaatcag  5040
aggtttatat ggtaccggga ggtggtgaat tacaacatgc caaaagaggt aatgtttatg  5100
tccagcgtgt ttatgagggg tcgccactta atctacctgc gcttgtggta tgatggccac  5160
gtgggttctg tggtccccgc catgagcttt ggatacagcg ccttgcactg tgggattttg  5220
aacaatattg tggtgctgtg ctgcagttac tgtgctgatt taagtgagat cagggtgcgc  5280
tgctgtgccc ggaggacaag gcgccttatg ctgcgggcgg tgcgaatcat cgctgaggag  5340
accactgcca tgttgtattc ctgcaggacg gagcggcggc ggcagcagtt tattcgcgcg  5400
ctgctgcagc accaccgccc tatcctgatg cacgattatg actctacccc catgtaggcg  5460
gccgctcgag tctagagggc ccgtttaaac ccgctgatca gcctcgactg tgccttctag  5520
ttgccagcca tctgttgttt gcccctcccc cgtgccttcc ttgaccctgg aaggtgccac  5580
tcccactgtc ctttcctaat aaaatgagga aattgcatcg cattgtctga gtaggtgtca  5640
ttctattctg gggggtgggg tggggcagga cagcaagggg gaggattggg aagacaatag  5700
caggcatgct ggggatgcgg tgggctctat ggcttctgag gcggaaagaa ccagctgggg  5760
ctctaggggg tatccccggg gttggggttg cgccttttcc aaggcatcca gcacagtggc  5820
ggccgcaata tttgcatgtc gctatgtgtt ctgggaaatc accataaacg tgaaatccct  5880
atcagtgata gagacttata agttccctat cagtgataga gaaccggtgg gcactcttcc  5940
gtggtctggt ggataaattc gcaagggtat catggcggac gaccggggtt cgagccccgt  6000
atccggccgt ccgccgtgat ccatgcggtt accgcccgcg tgtcgaaccc aggtgtgcga  6060
cgtcagacaa cgggggagtg ctcctttttg aattccactt tggccgcggc tcgagggggt  6120
tggggttgcg ccttttccaa ggcagccctg ggtttgcgca gggacgcggc tgctctgggc  6180
gtggttccgg gaaacgcagc ggcgccgacc ctgggtctcg cacattcttc acgtccgttc  6240
gcagcgtcac ccggatcttc gccgctaccc ttgtgggccc cccggcgacg cttcctgctc  6300
cgcccctaag tcgggaaggt tccttgcggt tcgcggcgtg ccggacgtga caaacggaag  6360
ccgcacgtct cactagtacc ctcgcagacg gacagcgcca gggagcaatg gcagcgcgcc  6420
gaccgcgatg ggctgtggcc aatagcggct gctcagcagg gcgcgccgag agcagcggcc  6480
gggaagggc ggtgcgggag gcggggtgtg gggcggtagt gtgggccctg ttcctgcccg  6540
cgcggtgttc cgcattctgc aagcctccgg agcgcacgtc ggcagtcggc tccctcgttg  6600
accgaatcac cgacctctct ccccaggggg atctgtgagt ttggggaccc ttgattgttc  6660
tttcttttc gctattgtaa aattcatgtt atatggaggg ggcaaagttt tcagggtgtt  6720
gtttagaatg ggaagatgtc ccttgtatca ccatggaccc tcatgataat ttgtttctt  6780
tcactttcta ctctgttgac aaccattgtc tcctcttatt ttcttttcat tttctgtaac  6840
tttttcgtta aactttagct tgcatttgta acgaattttt aaattcactt ttgtttattt  6900
gtcagattgt aagtactttc tctaatcact tttttttcaa ggcaatcagg gtatattata  6960
ttgtacttca gcacagtttt agagaacaat tgttataatt aaatgataag gtagaatatt  7020
tctgcatata aattctggct ggcgtggaaa tattcttatt ggtagaaaca actacatcct  7080
ggtcatcatc ctgcctttct ctttatggtt acaatgatat acactgtttg agatgaggat  7140
aaaatactct gagtccaaac cgggcccctc tgctaaccat gttcatgcct tcttcttttt  7200
cctacagctc ctgggcaacg tgctggttat tgtgctgtct catcattttg gcaaagaatt  7260
gtaatacgac tcactatagg gcgagccacc atggctagat tagataaaag taaagtgatt  7320
aacagcgcat tagagctgct taatgaggtc ggaatcgaag gtttaacaac ccgtaaactc  7380
gcccagaagc taggtgtaga gcagcctaca ttgtattggc atgtaaaaaa taagcgggct  7440
ttgctcgacg ccttagccat tgagatgtta gataggcacc atactcactt ttgcccttta  7500
gaaggggaaa gctggcaaga ttttttacgt aataacgcta aaagttttag atgtgcttta  7560
ctaagtcatc gcgatggagc aaaagtacat ttaggtacac ggcctacaga aaaacagtat  7620
gaaactctcg aaaatcaatt agcctttta tgccaacaag gtttttcact agagaatgcc  7680
ttatatgcac tcagcgccgt ggggcatttt actttaggtt gcgtattgga agatcaagag  7740
catcaagtcg ctaaagaaga aagggaaaca cctactactg atagtatgcc gccattatta  7800
cgacaagcta tcgaattatt tgatcaccaa ggtgcagagc cagccttctt attcggcctt  7860
gaattgatca tatgcggatt agaaaaacaa cttaaatgtg aaagtgggtc cccaaaaaag  7920
aagagaaagg tcgacggcgg tggttcagtt taagcgtaca gcggctcccg ggagttctag  7980
ggatctgccc ctctccctcc cccccccta acgttactgg ccgaagccgc ttggaataag  8040
gccggtgtgc gtttgtctat atgttatttt ccaccatatt gccgtctttt ggcaatgtga  8100
gggcccggaa acctggccct gtcttcttga cgagcattcc taggggtctt tcccctctcg  8160
ccaaaggaat gcaaggtctg ttgaatgtcg tgaaggaagc agttcctctg gaagcttctt  8220
gaagacaaac aacgtctgta gcgacccttt gcaggcagcg gaacccccca cctggcgaca  8280
ggtgcctctg cggccaaaag ccacgtgtat aagatacacc tgcaaaggcg gcacaacccc  8340
agtgccacgt tgtgagttgg atagttgtgg aaagagtcaa atggctctcc tcaagcgtat  8400
tcaacaaggg gctgaaggat gcccagaagg taccccattg tatgggatct gatctggggc  8460
ctcggtgcac atgctttaca tgtgtttagt cgaggttaaa aaaacgtcta ggccccccga  8520
accacgggga cgtggttttc ctttgaaaaa cacgatgata aggatccacc ggaggccacc  8580
atgaccgagt acaagcccac ggtgcgcctc gccacccgcg acgacgtccc cagggccgta  8640
cgcaccctcg ccgccgcgtt cgccgactac cccgccacgc gccacaccgt cgatccggac  8700
cgccacatcg agcgggtcac cgagctgcaa gaactcttcc tcacgcgcgt cgggctcgac  8760
atcggcaagg tgtgggtcgc ggacgacggc gccgcggtgg cggtctggac cacgccggag  8820
agcgtcgaag cgggggcggt gttcgccgag atcggcccgc gcatggccga gttgagcggt  8880
tcccggctgg ccgcgcagca acagatggaa ggcctcctgg cgccgcaccg gcccaaggag  8940
cccgcgtggt tcctggccac cgtcggcgtc tcgcccgacc accagggcaa gggtctgggc  9000
agcgccgtcg tgctccccgg agtggaggcg gccgagcgcg ccggggtgcc cgccttcctg  9060
gagacctccg cgccccgcaa cctccccttc tacgagcggc tcggcttcac cgtcaccgcc  9120
gacgtcgagg tgcccgaagg accgcgcacc tggtgcatga cccgcaagcc cggtgcctga  9180
ccgcgtctgg aacaatcaac ctctggatta caaaatttgt gaaagattga ctggtattct  9240
```

-continued

```
taactatgtt gctcctttta cgctatgtgg atacgctgct ttaatgcctt tgtatcatgc  9300
tattgcttcc cgtatggctt tcattttctc ctccttgtat aaatcctggt tgctgtctct  9360
ttatgaggag ttgtggcccg ttgtcaggca acgtggcgtg gtgtgcactg tgtttgctga  9420
cgcaaccccc actggttggg gcattgccac cacctgtcag ctcctttccg ggactttcgc  9480
tttccccctc cctattgcca cggcggaact catcgccgcc tgccttgccc gctgctggac  9540
aggggctcgg ctgttgggca ctgacaattc cgtggtgttg tcggggaagc tgacgtcctt  9600
tccatggctg ctcgcctgtg ttgccacctg gattctgcgc gggacgtcct tctgctacgt  9660
cccttcggcc ctcaatccag cggaccttcc ttcccgcggc ctgctgccgg ctctgcggcc  9720
tcttccgcgt cttcgccttc gccctcagac gagtcggatc tccctttggg ccgcctcccc  9780
gcaaaatgac cgaccaagcg acgcccaacc tgccatcacg agatttcgat tccaccgccg  9840
ccttctatga aaggttgggc ttcggaatcg ttttccggga cgccggctgg atgatcctcc  9900
agcgcgggga tctcatgctg gagttcttcg cccaccccaa cttgtttatt gcagcttata  9960
atggttacaa ataaagcaat agcatcacaa atttcacaaa taaagcattt ttttcactgc  10020
attctagttg tggtttgtcc aaactcatca atgtatctta tcatgtctgt agctgatcaa  10080
ttggcgcgcc gaattcgtta tctgcagaat tcggcttggc ggctgcgcgt tcaaacctcc  10140
cgcttcaaaa tggagaccct gcgtgctcac tcgggcttaa atacccagcg tgaccacatg  10200
gtgtcgcaaa atgtcgcaaa acactcacgt gacctctaat acaggacctc tagagcatgg  10260
aaactagata agaaagaaat acgcagagac caaagttcaa ctgaaacgaa ttaaacggtt  10320
tattgattaa caagcaaact agtttacaga ttacgggtga ggtaacgggt gccgatgggg  10380
cgaggctcag aataaacgcc atttgtgtca acagcaaagt ccacatttgt agatttgttg  10440
tagttggaag tgtattgaat ctctgggttc cagcgtttgc tgttttcttt ctgcagctcc  10500
cattcaattt ccacgctgac ctgtccggtg ctgtactgcg tgatgaacga cgcaaactta  10560
gctggactga aggtagttgg aggattcgcg ggaacaggtg tattcttaat caggatctga  10620
ggaggcgggt gtttcagtcc aaagcctccc atcagcggcg agggatgaaa gtgtccgtcc  10680
gtgtgaggaa tcttggccca gataggaccc tgcaggtaca cgtcccggtc ctgccagacc  10740
atgccaggta aggctccttg actgttgacg gtccctgtag caggagcggt gttggccgat  10800
tgcaggttag tggccaccgt gccgtactct tctgtggcca ctgggttggt ggttttaatt  10860
tcttcctcgt tggttatcat aacgttgtca aggtccacgt tgctatttcc agctccctgt  10920
ttcccaaata ttaagactcc gctcatcgga aaaaatttgt cttcgtcgtc cttgtgggtt  10980
gccatagcgg gaccgggatt taccagagag tctctgccat tcagatgata cttggtggca  11040
ccggtccagg caaagttgct gttgttattt tgattggttg tcttggagac gcgttgctgc  11100
cggtagcagg gcccgggtag ccagtttttg gcctgattcg ccatgctact aggcccggcc  11160
tgagaaaatt gcaacgtccg atttcctgcg gtaccactcg tggtctgagt ccgagacagg  11220
tagtacaggt actggtcgat gagggggttc atcagccggt ccaggctttg gctgtgcgcg  11280
tagctgctgt gaaaaggcac gtcctcaaac gtgtagctga actgaaagtt gttgcccgtt  11340
ctcagcattt gagaaggaaa gtattccagg cagtagaagg aggaacggcc cacggcctga  11400
ctgccattgt tcagagtcag gtacccgtac tgaggaatca tgaagacgtc cgccgggaac  11460
ggaggcaggc agccctggtg cgcagagccg aggacgtacg ggagctggta ttccgagtcc  11520
gtaaagacct gaaccgtgct ggtaaggtta ttggcgatgg tcgtggtgcc atcattcgtc  11580
gtgacctcct tgacctggat gttgaagagc ttgaagttga gcttcttggg ccggaatccc  11640
cagttgttgt tgatgagtcg ctgccagtca cgtggtgaga agtggcagtg gaatctgtta  11700
aagtcaaaat acccccaggg ggtgctgtag ccgaagtagg tgttgtcgtt ggtgctgcct  11760
cccgattggc tggagatttg cttgtagagg tggttgttgt aggtggggag ggcccaggtt  11820
cgggtgctgg tggtgatgac tctgtcgccc agccatgtgg aatcgcaatg ccaatttcct  11880
gaggcgttac ccactccgtc ggcgccttcg ttattgtctg ccattggagc gccaccgcct  11940
gcagccattg tattagatcc cacaccagag ggggctgcgg ggggttctcc gagtggttga  12000
gggtcgggca ctgactctga gtcgccagtc tgcccaaagt tgagtctctt tctcgcgggc  12060
tgctggcctt tcttgccgat gcccgaagag gagtctggtt cctggggtga ttgctctacc  12120
ggtctcttct ttccaggagc cgtcttagcg ccttcctcaa ccagaccgag aggttcgaga  12180
acccgcttct tggcctggaa gactgctcgc ccgaggttgc ccccaaaaga cgtatcttct  12240
tgcagacgct cctgaaactc ggcgtcggcg tggttatacc gcaggtacgg attgtcaccc  12300
gctttgagct gctggtcgta ggccttgtcg tgctcgaggg ccgctgcgtc cgccgcgttg  12360
acgggctccc ccttgtcgag tccgttgaag ggtccgaggt acttgtagcc aggaagcacc  12420
agaccccggc cgtcgtcctg cttttgctgg ttggctttgg gtttcggggc tccaggtttc  12480
aagtcccacc actcgcgaat gccctcagag aggttgtcct cgagccaatc tggaagataa  12540
ccatcggcag ccatacctga tttaaatcat ttattgttca aagatgcagt catccaaatc  12600
cacattgacc agatcgcagg cagtgcaagc gtctggcacc tttcccatga tatgatgaat  12660
gtagcacagt ttctgatacg ccttttttgac gacagaaacg ggttgagatt ctgacacggg  12720
aaagcactct aaacagtctt tctgtccgtg agtgaagcag atatttgaat tctgattcat  12780
tctctcgcat tgtctgcagg gaaacagcat cagattcatg cccacgtgac gagaacattt  12840
gttttggtac ctgtctgcgt agttgatcga agcttccgcg tctgacgtcg atggctgcgc  12900
aactgactcg cgcacccgtt tgggctcact tatatctgcg tcactggggg cgggtctttt  12960
cttggctcca cccttttga cgtagaattc atgctccacc tcaaccacgt gatcctttgc  13020
ccaccggaaa aagtctttga cttcctgctt ggtgaccttc ccaaagtcat gatccagacg  13080
gcgggtgagt tcaaatttga acatccggtc ttgcaacggc tgctggtgtt cgaaggtcgt  13140
tgagttcccg tcaatcacgg cgcacatgtt ggtgttggag gtgacgatca cgggagtcgg  13200
gtctatctgg gccgaggact tgcatttctg gtccacgcgc accttgcttc ctccgagaat  13260
ggctttggcc gactccacga ccttggcggt catcttcccc tcctcccacc agatcaccat  13320
cttgtcgaca cagtcgttga agggaaagtt ctcattggtc cagtttacgc acccgtagaa  13380
gggcacagtg tgggctatgg cctccgcgat gttggtcttc ccggtagttg caggcccaaa  13440
cagccagatg gtgttcctct tgccgaactt tttcgtggcc catcccagaa agacggaagc  13500
cgcatattgg ggatcgtacc cgtttagttc caaaatttta taaatccgat tgctggaaat  13560
gtcctccacg ggctgctggc ccaccaggta gtcgggggcg gttttagtca ggctcataat  13620
ctttcccgca ttgtccaagg cagccttgat ttgggaccgc gagttggagg ccgcattgaa  13680
ggagatgtat gaggcctggt cctcctggat ccactgcttc tccgaggtaa tccccttgtc  13740
cacgagccac ccgaccagct ccatgtacct ggctgaagtt tttgatctga tcaccggcgc  13800
atcagaattg ggattctgat tctctttgtt ctgctcctgc gtctgcgaca cgtgcgtcag  13860
atgctgcgcc accaaccgtt tacgctccgt gagattcaaa caggcgctgt ggagagaaag  13920
gcaaagtgga tgtcagtatc tctatcactg atagggagat ctctatcact gatagggaac  13980
```

```
ttaccttaaa tactgttcca tattagtcca cgcccactgg agctcaggct gggttttggg  14040
gagcaagtaa ttggggatgt agcactcatc caccaccttg ttcccgcctc cggcgccatt  14100
tctggtcttt gtgaccgcga accagtttgg caaagtcggc tcgatcccgc ggtaaattct  14160
ctgaatcagt tttcgcgaa tctgactcag gaaacgtccc aaaaccatgg atttcacccc  14220
ggtggtttcc acgagcacgt gcatgtggaa gtagctctct cccttctcaa attgcacaaa  14280
gaaaagagcc tccggggcct tactcacacg gcgccattcc gtcagaaagt cgcgctgcag  14340
cttctcggcc acggtcaggg gtgcctgctc aatcagattc agatccatgt cagaatctgg  14400
cggcaactcc cattccttct cggccaccca gttcacaaag ctgtcagaaa tgccgggcag  14460
atgctcgtca aggtcgctgg ggaccttaat cacaatctcg taaaaccccg gcatggcggc  14520
tgcgcgttca aacctcccgc ttcaaaatgg agaccctgcg tgctcactcg ggcgatctct  14580
atcactgata gggagatctc tatcactgat agggagatta aatagaatgg ctaggatccg  14640
gccggcctgc aggtgtcctc acaggaacga agtccctaaa gaaacagtgg cagccaggtt  14700
tagccccgga attgactgga ttcctttttt agggcccatt ggtatggctt tttccccgta  14760
tccccccagg tgtctgcagg ctcaaagagc agcgagaagc gttcagagga aagcgatccc  14820
gtgccacctt ccccgtgccc gggctgtccc cgcacgctgc cggctcgggg atgcgggggg  14880
agcgccggac cggagcggag ccccgggcgg ctcgctgctg cccccctagcg ggggagggac  14940
gtaattacat ccctgggggc tttgggggg ggctgtccct ctagagcggc cgccaccgcg  15000
gtggagctcc agcttttgtt ccctttagtg agggttaatt agatcttaat acgactcact  15060
atagggcgaa ttgggtaccg ggcccccct cgaggtcgac ggtatcgcct ccaaggccag  15120
cttcccacaa taagttgggt gaattttggc tcattcctcc tttctatagg attgaggtca  15180
gagctttgtg atgggaattc tgtggaatgt gtgtcagtta gggtgtggaa agtcccgcga  15240
tcgctagcaa acgccagcaa cgcggccttt ttacggttcc tggccttttg ctggcctttt  15300
gctcacatgt cctgcaggca gctgcgcgct cgctcgctca ctgaggccgc ccgggcaaag  15360
cccgggcgtc gggcgacctt tggtcgcccg gcctcagtga gcgagcgagc gcgcagagag  15420
ggagtggcca actccatcac taggggttcc tgcggccgca cgcgtggagc tagttattaa  15480
tagtaatcaa ttacggggtc attagttcat agcccatata tggagttccg cgttacataa  15540
cttacggtaa atggcccgcc tggctgaccg cccaacgacc cccgcccatt gacgtcaata  15600
atgacgtatg ttcccatagt aacgtcaata gggactttcc attgacgtca atgggtggag  15660
tatttacggt aaactgccca cttggcagta catcaagtgt atcatatgcc aagtacgccc  15720
cctattgacg tcaatgacgg taaatggccc gcctggcatt atgcccagta catgacctta  15780
tgggactttc ctacttggca gtacatctac gtattagtca tcgctattac catggtgatg  15840
cggttttggc agtacatcaa tgggcgtgga tagcggtttg actcacgggg atttccaagt  15900
ctccacccca ttgacgtcaa tgggagtttg ttttgcacca aaatcaacgg gactttccaa  15960
aatgtcgtaa caactccgcc ccattgacgc aaatgggcgg taggcgtgta cggtgggagg  16020
tctatataag cagagctcgt ttagtgaacc gtcagatcgc ctggagacgc catccacgct  16080
gttttgacct ccatagaaga caccgggacc gatccagcct ccgcggattc gaatcccggc  16140
cgggaacggt gcattggaac gcggattccc cgtgccaaga gtgacgtaag taccgcctat  16200
agagtctata ggcccacaaa aaatgctttc ttcttttaat atactttttt gtttatctta  16260
tttctaatac tttccctaat ctctttcttt cagggcaata atgatacaat gtatcatgcc  16320
tctttgcacc attctaaaga ataacagtga taatttctgg gttaaggcaa tagcaatatt  16380
tctgcatata aatatttctg catataaatt gtaactgatg taagaggttt catattgcta  16440
atagcagcta caatccagct accattctgc ttttatttta tggttgggat aaggctggat  16500
tattctgagt ccaagctagg cccttttgct aatcatgttc atacctctta tcttcctccc  16560
acagctcctg ggcaacgtgc tggtctgtgt gctggcccat cactttggca aagaattggg  16620
attcgaacat cgattgaatt ctgaatggtg agcaagggcg aggagctgtt caccggggtg  16680
gtgcccatcc tggtcgagct ggacggcgac gtaaacggcc acaagttcag cgtgtccggc  16740
gagggcgagg gcgatgccac ctacggcaag ctgaccctga agttcatctg caccaccggc  16800
aagctgcccg tgccctggcc caccctcgtg accaccctga cctacggcgt gcagtgcttc  16860
agccgctacc ccgaccacat gaagcagcac gacttcttca agtccgccat gcccgaaggc  16920
tacgtccagg agcgcaccat cttcttcaag gacgacggca actacaagac ccgcgccgag  16980
gtgaagttcg agggcgacac cctggtgaac cgcatcgagc tgaagggcat cgacttcaag  17040
gaggacggca acatcctggg gcacaagctg gagtacaact acaacagcca caacgtctat  17100
atcatggccg acaagcagaa gaacggcatc aaggtgaact tcaagatccg ccacaacatc  17160
gaggacggca gcgtgcagct cgccgaccac taccagcaga acacccccat cggcgacggc  17220
cccgtgctgc tgcccgacaa ccactacctg agcacccagt ccgccctgag caaagacccc  17280
aacgagaagc gcgatcacat ggtcctgctg gagttcgtga ccgccgccgg gatcactctc  17340
ggcatggacg agctgtacaa gtactcagat ctcgagctca agtagggatc ctctagagtc  17400
gacctgcaga agcttgcctc gagcagcgct gctcgagaga tctacgggtg gcatccctgt  17460
gacccctccc cagtgcctct cctggccctg gaagttgcca ctccagtgcc caccagcctt  17520
gtcctaataa aattaagttg catcattttg tctgactagg tgtccttcta taatattatg  17580
gggtggaggg gggtggtatg gagcaagggg caagttggga agacaacctg tagggcctgc  17640
ggggtctatt gggaaccaag ctggagtgca gtggcacaat cttggctcac tgcaatctcc  17700
gcctcctggg ttcaagcgat tctcctgcct cagcctcccg agttgttggg attccaggca  17760
tgcatgacca ggctcagcta atttttgttt ttttggtaga gacggggttt caccatattg  17820
gccaggctgg tctccaactc ctaatctcag gtgatctacc caccttggcc tcccaaattg  17880
ctgggattac aggcgtgaac cactgctccc ttccctgtcc ttctgatttt gtaggtaacc  17940
acgtgcggac cgagcggccg caggaacccc tagtgatgga gttggccact ccctctctgc  18000
gcgctcgctc gctcactgag gccgggcgac caaaggtcgc ccgacgcccg ggctttgccc  18060
gggcggcctc agtgagcgag cgagcgcgca gctgcctgca ggggcgcctg atgcggtatt  18120
ttctccttac gcatctgtgc ggtatttcac accgcatacg tcgtagctga tcaattggcg  18180
cgccgaattc gttaacaagc tttaattaac gcgtacgata agcttgatat ctataacaag  18240
aaaatatata tataataagt tatcacgtaa gtagaacatg aaataacaat ataattatcg  18300
tatgagttaa atcttaaaag tcacgtaaaa gataatcatg cgtcattttg actcacgcgg  18360
tcgttatagt tcaaaatcag tgacacttac cgcattgaca agcacgcctc acgggagctc  18420
caagcggcga ctgagatgtc ctaaatgcac agcgacggat tcgcgctatt tagaaagaga  18480
gagcaatatt tcaagaatgc atgcgtcaat tttacgcaga ctatctttct agggttaatc  18540
tagctgcatc aggatcatat cgtcgggtct tttttccggc tcagtcatcg cccaagctgg  18600
cgctatctgg gcatcgggga ggaagaagcc cgtgcctttt cccgcgaggt tgaagcggca  18660
tggaaagagt ttgccgagga tgactgctgc tgcattgacg ttgagcgaaa acgcacgttt  18720
```

```
accatgatga ttcgggaagg tgtggccatg cacgccttta acggtgaact gttcgttcag  18780
gccacctggg ataccagttc gtcgcggctt ttccggacac agttccggat ggtcagcccg  18840
aagcgcatca gcaacccgaa caataccggc gacagccgga actgccgtgc cggtgtgcag  18900
attaatgaca gcggtgcggc gctgggatat tacgtcagcg aggacgggta tcctggctgg  18960
atgccgcaga aatggacatg gataccccgt gagttacccg gcgggcgcgc ttggcgtaat  19020
catggtcata gctgtttcct gtgtgaaatt gttatccgct cacaattcca cacaacatac  19080
gagccggaag cataaagtgt aaagcctggg gtgcctaatg agtgagctaa ctcacattaa  19140
ttgcgttgcg ctcactgccc gctttccagt cgggaaacct gtcgtgccag ctgcattaat  19200
gaatcggcca acgcgcgggg agaggcggtt tgcgtattgg gcgctcttcc gcttcctcgc  19260
tcactgactc gctgcgctcg gtcgttcggc tgcggcgagc ggtatcagct cactcaaagg  19320
cggtaatacg gttatccaca gaatcagggg ataacgcagg aaagaacatg tgagcaaaag  19380
gccagcaaaa ggccaggaac cgtaaaaagg ccgcgttgct ggcgtttttc cataggctcc  19440
gcccccctga cgagcatcac aaaaatcgac gctcaagtca gaggtggcga aacccgacag  19500
gactataaag ataccaggcg tttccccctg gaagctccct cgtgcgctct cctgttccga  19560
ccctgccgct taccggatac ctgtccgcct ttctcccttc gggaagcgtg gcgctttctc  19620
atagctcacg ctgtaggtat ctcagttcgg tgtaggtcgt tcgctccaag ctgggctgtg  19680
tgcacgaacc ccccgttcag cccgaccgct gcgccttatc cggtaactat cgtcttgagt  19740
ccaacccggt aagacacgac ttatcgccac tggcagcagc cactggtaac aggattagca  19800
gagcgaggta tgtaggcggt gctacagagt tcttgaagtg gtggcctaac tacggctaca  19860
ctagaaggac agtatttggt atctgcgctc tgctgaagcc agttaccttc ggaaaaagag  19920
ttggtagctc ttgatccggc aaacaaacca ccgctggtag cggtggtttt tttgtttgca  19980
agcagcagat tacgcgcaga aaaaaaggat ctcaagaaga tcctttgatc ttttctacgg  20040
ggtctgacgc tcagtggaac gaaaactcac gttaagggat tttggtcatg agattatcaa  20100
aaaggatctt cacctagatc cttttaaatt aaaaatgaag ttttaaatca atctaaagta  20160
tatatgagta aacttggtct gacagttacc aatgcttaat cagtgaggca cctatctcag  20220
cgatctgtct atttcgttca tccatagttg cctgactccc cgtcgtgtag ataactacga  20280
tacgggaggg cttaccatct ggccccagtg ctgcaatgat accgcgagac ccacgctcac  20340
cggctccaga tttatcagca ataaaccagc cagccggaag ggccgagcgc agaagtggtc  20400
ctgcaacttt atccgcctcc atccagtcta ttaattgttg ccgggaagct agagtaagta  20460
gttcgccagt taatagtttg cgcaacgttg ttgccattgc tacaggcatc gtggtgtcac  20520
gctcgtcgtt tggtatggct tcattcagct ccggttccca acgatcaagg cgagttacat  20580
gatcccccat gttgtgcaaa aaagcggtta gctccttcgg tcctccgatc gttgtcagaa  20640
gtaagttggc cgcagtgtta tcactcatgg ttatggcagc actgcataat tctcttactg  20700
tcatgccatc cgtaagatgc ttttctgtga ctggtgagta ctcaaccaag tcattctgag  20760
aatagtgtat gcggcgaccg agttgctctt gcccggcgtc aatacgggat aataccgcgc  20820
cacatagcag aactttaaaa gtgctcatca ttggaaaacg ttcttcgggg cgaaaactct  20880
caaggatctt accgctgttg agatccagtt cgatgtaacc cactcgtgca cccaactgat  20940
cttcagcatc ttttactttc accagcgttt ctgggtgagc aaaaacagga aggcaaaatg  21000
ccgcaaaaaa gggaataagg gcgacacgga aatgttgaat actcat                21046

SEQ ID NO: 15           moltype = DNA  length = 10497
FEATURE                 Location/Qualifiers
misc_feature            1..10497
                        note = Description of Artificial Sequence: Synthetic
                         polynucleotide
source                  1..10497
                        mol_type = other DNA
                        organism = synthetic construct
SEQUENCE: 15
cctcgagggc tagccattct atttaatctc cctatcagtg atagagatct ccctatcagt  60
gatagagatc gcccgagtga gcacgcaggg tctccatttt gaagcgggag gtttgaacgc  120
gcagccgcca tgccggggtt ttacgagatt gtgattaagg tccccagcga ccttgacgag  180
catctgcccg gcatttctga cagctttgtg aactgggtgg ccgagaagga atgggagttg  240
ccgccagatt ctgacatgga tctgaatctg attgagcagg cacccctgac cgtggccgag  300
aagctgcagc gcgactttct gacggaatgg cgccgtgtga gtaaggcccc ggaggctctt  360
ttctttgtgc aatttgagaa gggagagagc tacttccaca tgcacgtgct cgtggaaacc  420
accggggtga aatccatggt tttgggacgt ttcctgagtc agattcgcga aaaactgatt  480
cagagaattt accgcgggat cgagccgact ttgccaaact ggttcgcggt cacaaagacc  540
agaaatggcg ccggaggcgg gaacaaggtg gtggatgagt gctacatccc caattacttg  600
ctccccaaaa cccagcctga gctccaatgg gcatggacca acatggaaca gtacctcagc  660
gcctgtttga atctcacgga gcgtaaacgg ttggtggcgc agcatctgac gcacgtgtcg  720
cagacgcagg agcagaacaa agagaatcag aatcccaatt ctgatgcgcc ggtgatcaga  780
tcaaaaactt cagccaggta catggagctg gtcgggtggc tcgtggacaa ggggattacc  840
tcggagaagc agtggatcca ggaggaccag gcctcataca tctccttcaa tgcggcctcc  900
aactcgcggt cccaaatcaa ggctgccttg gacaatgcgg gaaagattat gagcctgact  960
aaaaccgccc ccgactacct ggtgggccag cagcccgtgg aggacatttc cagcaatcgg  1020
atttataaaa ttttggaact aaacgggtac gatccccaat atgcggcttc cgtctttctg  1080
ggatgggcca cgaaaaagtt cggcaagagg aacaccatct ggctgtttgg gcctgcaact  1140
accgggaaga ccaacatcgc ggaggccata gcccacactg tgcccttcta cgggtgcgta  1200
aactggacca atgagaactt tcccttcaac gactgtgtcg acaagatggt gatctggtgg  1260
gaggagggga agatgaccgc caaggtcgtg gagtcggcca aagccattct cggaggaagc  1320
aaggtgcgcg tggaccagaa atgcaagtcc tcggcccaga tagacccgac tcccgtgatc  1380
gtcacctcca acaccaacat gtgcgccgtg attgacggga actcaacgac cttcgaacac  1440
cagcagccgt tgcaagaccg gatgttcaaa tttgaactca cccgccgtct ggatcatgac  1500
tttgggaagg tcaccaagca ggaagtcaaa gactttttcc ggtgggcaaa ggatcacgtg  1560
gttgaggtgg agcatgaatt ctacgtcaaa aagggtggag ccaagaaaag acccgccccc  1620
agtgacgcag atataagtga gcccaaacgg gtgcgcgagt cagttgcgca gccatcgacg  1680
tcagacgcgg aagcttcgat caactacgca gacaggtacc aaaacaaatg ttctcgtcac  1740
gtgggcatga atctgatgct gtttccctgc agacaatgcg agagaatgaa tcagaattca  1800
```

```
aatatctgct tcactcacgg acagaaagac tgtttagagt gctttcccgt gtcagaatct  1860
caacccgttt ctgtcgtcaa aaaggcgtat cagaaactgt gctacattca tcatatcatg  1920
ggaaaggtgc cagacgcttg cactgcctgc gatctggtca atgtggattt ggatgactgc  1980
atctttgaac aataaatgat ttaaatcagg tatggctgcc gatggttatc ttccagattg  2040
gctcgaggac aacctctctg agggcattcg cgagtggtgg gacttgaaac ctggagcccc  2100
gaaacccaaa gccaaccagc aaaagcagga cgacggccgg ggtctggtgc ttcctggcta  2160
caagtacctc ggacccttca acggactcga caagggggag cccgtcaacg cggcggacgc  2220
agcggccctc gagcacgaca aggcctacga ccagcagctc aaagcgggtg acaatccgta  2280
cctgcggtat aaccacgccg acgccgagtt tcaggagcgt ctgcaagaag atacgtcttt  2340
tgggggcaac ctcgggcgag cagtcttcca ggccaagaag cgggttctcg aacctctcgg  2400
tctggttgag gaaggcgcta agacggctcc tggaaagaag agaccggtag agcaatcacc  2460
ccaggaacca gactcctctt cgggcatcgg caagaaaggc cagcagcccg cgagaaagag  2520
actcaacttt gggcagactg gcgactcaga gtcagtgccc gaccctcaac cactcggaga  2580
accccccgca gccccctctg gtgtgggatc taatacaatg gctgcaggcg gtggcgctcc  2640
aatggcagac aataacgaag gcgccgacgg agtgggtaac gcctcaggaa attggcattg  2700
cgattccaca tggctgggcg acagagtcat caccaccagc acccgaacct gggccctccc  2760
cacctacaac aaccacctct acaagcaaat ctccagccaa tcgggaggca gcaccaacga  2820
caacacctac ttcggctaca gcacccccctg ggggtatttt gactttaaca gattccactg  2880
ccacttctca ccacgtgact ggcagcgact catcaacaac aactggggat tccggcccaa  2940
gaagctcaac ttcaagctct tcaacatcca ggtcaaggag gtcacgacga atgatggcac  3000
cacgaccatc gccaataacc ttaccagcac ggttcaggtc tttacggact cggaatacca  3060
gctcccgtac gtcctcggct ctgcgcacca gggctgcctg cctccgttcc cggcggacgt  3120
cttcatgatt cctcagtacg ggtacctgac tctgaacaat ggcagtcagg ccgtgggccg  3180
ttcctccttc tactgcctgg aatactttcc ttctcaaatg ctgagaacgg gcaacaactt  3240
tcagttcagc tacacgtttg aggacgtgcc ttttcacagc agctacgcgc acagccaaag  3300
cctggaccgg ctgatgaacc ccctcatcga ccagtacctg tactacctgt ctcggactca  3360
gaccacgagt ggtaccgcag gaaatcggac gttgcaattt tctcaggccg ggcctagtag  3420
catggcgaat caggccaaaa actggctacc cgggccctgc taccggcagc aacgcgtctc  3480
caagacaacc aatcaaaata acaacagcaa ctttgcctgg accggtgcca ccaagtatca  3540
tctgaatggc agagactctc tggtaaatcc cggtcccgct atggcaaccc acaaggacga  3600
cgaagacaaa ttttttccga tgagcggagt cttaatattt gggaaacagg gagctggaaa  3660
tagcaacgtg gaccttgaca acgttatgat aaccaacgag gaagaaatta aaaccaccaa  3720
cccagtggcc acagaagagt acggcacggt ggccactaac ctgcaatcgg ccaacaccgc  3780
tcctgctaca gggaccgtca acagtcaagg agccttacct ggcatggtct ggcaggaccg  3840
ggacgtgtac ctgcagggtc ctatctgggc caagattcct cacacggacg gacactttca  3900
tccctcgccg ctgatgggag gctttggact gaaacacccg cctcctcaga tcctgattaa  3960
gaatacacct gttcccgcga atcctccaac taccttcagt ccagctaagt ttgcgtcgtt  4020
catcacgcag tacagcaccg gacaggtcag cgtggaaatt gaatgggagc tgcagaaaga  4080
aaacagcaaa cgctggaacc cagagattca atacacttcc aactacaaca aatctacaaa  4140
tgtggacttt gctgttgaca caaatggcgt ttattctgag cctcgcccca tcggcacccg  4200
ttacctcacc cgtaatctgt aaactagttt gcttgttaat caataaaccg tttaattcgt  4260
ttcagttgaa ctttggtctc tgcgtatttc tttcttatct agtttccatg ctctagaggt  4320
cctgtattag aggtcacgtg agtgttttgc gacattttgc gacaccatgt ggtcacgctg  4380
ggtatttaag cccgagtgag cacgcagggt ctccattttg aagcgggagg tttgaacgcg  4440
cagccgccaa gccgaattct gcagatatcg ggttggggt tgcgcctttt ccaaggcagc  4500
cctgggtttg cgcagggacg cggctgctct gggcgtggtt ccgggaaacg cagcggcgcc  4560
gaccctgggt ctcgcacatt cttcacgtcc gttcgcagcg tcacccggat cttcgccgct  4620
acccttgtgg gccccccggc gacgcttcct gctccgcccc taagtcggga aggttccttg  4680
cggttcgcgg cgtgccggac gtgacaaacg gaagccgcac gtctcactag taccctcgca  4740
gacggacagc gccagggagc aatggcagcg cgccgaccgc gatgggctgt ggccaatagc  4800
ggctgctcag cagggcgcgc cgagagcagc ggccgggaag gggcggtgcg ggaggcgggg  4860
tgtggggcgg tagtgtgggc cctgttcctg cccgcgcggt gttccgcatt ctgcaagcct  4920
ccggagcgca cgtcggcagt cggctccctc gttgaccgaa tcaccgacct ctctccccag  4980
aagctcccgg gagcttgtat atccattttc ggatctgatc agcacgtgtt gacaattaat  5040
catcggcata gtatatcggc atagtataat acgacaaggt gaggaacgcc accatggcca  5100
agcctttgtc tcaagaagaa tccaccctca ttgaaagagc aacggctaca atcaacagca  5160
tccccatctc tgaagactac agcgtcgcca gcgcagctct ctctagcgac ggccgcatct  5220
tcactggtgt caatgtatat cattttactg ggggaccttg tgcagaactc gtggtgctgg  5280
gcactgctgc tgctgcggca gctggcaacc tgacttgtat cgtcgcgatc ggaaatgaga  5340
acaggggcat cttgagcccc tgcggacggt gccgacaggt gcttctcgat ctgcatcctg  5400
ggatcaaagc catagtgaag gacagtgatg gacagccgac ggcagttggg attcgtgaat  5460
tgctgccctc tggttatgtg tgggagggct aagcacttcg tggccgagga gcaggactga  5520
cacgtgctac gagatttcga ttccaccgcc gccttctatg aaaggttggg cttcggaatc  5580
gttttccggg acgccggctg gatgatcctc cagcgcgggg atctcatgct ggagttcttc  5640
gcccacccca acttgtttat tgcagcttat aatggttaca aataaagcaa tagcatcaca  5700
aatttcacaa ataaagcatt tttttcactg cattctagtt gtggtttgtc caaactcatc  5760
aatgtatctt agcgctcact gcccgctttc cagtcgggaa acctgtcgtg ccagctgcat  5820
taatgaatcg gccaacgcgc ggggagaggc ggtttgcgta ttgggcgctc tcctaggcca  5880
gaaatggcgc cggaggcggg aacaaggtgg tggatgagtg ctacatcccc aattacttgc  5940
tccccaaaac ccagcctgag ctccagtggg cgtggactaa tatggaacag tatttaagcg  6000
cctgtcccta tcagtgatag agatctccct atcagtgata gagatttgaa tctcacggag  6060
cgtaaacggt tggtggcgca gcatctgttt aaacgcagac gcaggagcag aacaaagaga  6120
atcagaatcc caattctgat gcgccggtga tcagatcaaa aacttcagcc aggtacatgg  6180
agctggtcgg gtggctcgtg gacaagggga ttacctcgga gaagcagtgg attcaggagg  6240
accaggcctc atacatctcc ttcaatgcgg cctccaactc gcggtcccaa atcaaggctg  6300
ccttggacaa tgcgggaaag attatgagcc tgactaaaac cgcccccgac tacctggtgg  6360
gccagcagcc cgtggaggac atttccagca atcggattta taaaattttg gaactaaacg  6420
ggtacgatcc ccaatatgcg gcttccgtct ttctgggatg ggccacgaaa aagttcggca  6480
agaggaacac catctggctg tttgggcctg caactaccgg gaagaccaac atcgcggagg  6540
```

```
ccatagccca cactgtgccc ttctacgggt gcgtaaactg gaccaatgag aactttccct  6600
tcaacgactg tgtcgacaag atggtgatct ggtgggagga ggggaagatg accgccaagg  6660
tcgtggagtc ggccaaagcc attctcggag gaagcaaggt gcgcgtggac cagaaatgca  6720
agtcctcggc ccagatagac ccgactcccg tgatcgtcac ctccaacacc aacatgtgcg  6780
ccgtgattga cgggaactca acgaccttcg aacaccagca gccgttgcaa gaccggatgt  6840
tcaaatttga actcacccgc cgtctggatc atgactttgg gaaggtcacc aagcaggaag  6900
tcaaagactt tttccggtgg gcaaaggatc acgtggttga ggtggagcat gaattctacg  6960
tcaaaaaggg tggagccaag aaaagacccg cccccagtga cgcagatata agtgagccca  7020
aacgggtgcg cgagtcagtt gcgcagccat cgacgtcaga cgcggaagct tcgatcaact  7080
acgcagacag gtaccaaaac aaatgttctc gtcacgtggg catgaatctg atgctgtttc  7140
cctgcagaca atgcgagaga atgaatcaga attcaaatat ctgcttcact cacggacaga  7200
aagactgttt agagtgcttt cccgtgtcag aatctcaacc cgtttctgtc gtcaaaaagg  7260
cgtatcagaa actgtgctac attcatcata tcatgggaaa ggtgccagac gcttgcactg  7320
cctgcgatct ggtcaatgtg gatttggatg actgcatctt tgaacaataa actagtttgc  7380
ttgttaatca ataaaccgtt taattcgttt cagttgaact ttggtctctg cgtatttctt  7440
tcttatctag tttccatgct ctagagtata cgatatccat cacactggcg gccgctcgac  7500
tagagcggcc gccaccgcgg tggagctcca gcttttgttc gcgcgcttgg cgtaatcatg  7560
gtcatagctg tttcctgtgt gaaattccac agcctggggt gcctaattgc gttgcgctca  7620
ctgcccgctt tccagtcggg aaacctgtcg tgccagctgc attaatgaat cggccaacgc  7680
gcggggagag gcggtttgcg tattgggcgc tcttccgctt cctcgctcac tgactcgctg  7740
cgctcggtcg ttcggctgcg gcgagcggta tcagctcact caaaggcggt aatacggtta  7800
tccacagaat caggggataa cgcaggaaag aacatgtgag caaaaggcca gcaaaaggcc  7860
aggaaccgta aaaaggccgc gttgctggcg tttttccata ggctccgccc ccctgacgag  7920
catcacaaaa atcgacgctc aagtcagagg tggcgaaacc cgacaggact ataaagatac  7980
caggcgtttc cccctggaag ctccctcgtg cgctctcctg ttccgaccct gccgcttacc  8040
ggatacctgt ccgcctttct cccttcggga agcgtggcgc tttctcatag ctcacgctgt  8100
aggtatctca gttcggtgta ggtcgttcgc tccaagctgg gctgtgtgca cgaacccccc  8160
gttcagcccg accgctgcgc cttatccggt aactatcgtc ttgagtccaa cccggtaaga  8220
cacgacttat cgccactggc agcagccact ggtaacagga ttagcagagc gaggtatgta  8280
ggcggtgcta cagagttctt gaagtggtgg cctaactacg gctacactag aagaacagta  8340
tttggtatct gcgctctgct gaagccagtt accttcggaa aaagagttgg tagctcttga  8400
tccggcaaac aaaccaccgc tggtagcggt ggtttttttg tttgcaagca gcagattacg  8460
cgcagaaaaa aaggatctca agaagatcct ttgatctttt ctacggggtc tgacgctcag  8520
tggaacgaaa actcacgtta agggattttg gtcatgagat tatcaaaaag gatcttcacc  8580
tagatccttt taaattaaaa atgaagttt aaatcaatct aaagtatata tgagtaaact  8640
tggtctgaca gaaataataa aaaagccgga ttaataatct ggctttttat attctctctc  8700
tagtatataa acgcagaaag gcccacccga aggtgagcca gtgtgactct agtattatta  8760
gaaaaactca tcgagcatca aatgaaactg caatttattc atatcaggat tatcaatacc  8820
atatttttga aaaagccgtt tctgtaatga aggagaaaac tcaccgaggc agttccaaag  8880
aatggcaagg tcctggtaac ggtctgcgat tccgacccgt ccaacatcaa tacaacctat  8940
taatttcccc tcgtcaaaaa taaggttatc aagtgagaaa tcaccatgag tgacgactga  9000
atccggtgag aatggcaaga gcttgtgcat ttctttccag acttgttcaa caggccagcc  9060
attacgctcg tcatcaaaat cactcgcatc aaccaaaccg ttattcatgc gtgattgcgc  9120
ctgagcaaga cgaaatacac gatcgctgtt aaaaggacaa ttacaaacag gaatcgaatg  9180
taaccggcgc aggaacacgg ccagcgcatc aacaatattt tcacctgaat caggatattc  9240
ttctaatacc tggaaggctg ttttcccagg aatcgcggtg gtgagtaacc acgcatcatc  9300
aggagtacgg ataaaatgct tgatggtcgg gagaggcata aactccgtca gccagttgag  9360
acggaccatc tcatctgtaa catcattggc aacgctacct ttgccatgtt tcagaaacaa  9420
ctctggcgca tcgggcttcc catacaagcg atagattgtc gcacctgatt gcccgacatt  9480
atcgcgagcc catttatacc catataaatc agcgtccatg ttggagttta agcgcggacg  9540
ggagcaagac gtttcccgtt gaatatggct cataacaccc cttgtattac tgtttatgta  9600
agcagacagt tttattgttc atgatgatat atttttatct tgtgcaatgt aacatcagag  9660
attttgagac acaacgtggc tttgttgaat aaatcgaact tttgctgagt tgaaggatca  9720
gctctagtaa aataataaaa aagccggatt aataatctgg ctttttatat tctctctcta  9780
gtatataaac gcagaaaggc ccacccgaag gtgagccagt gtgacggcac atttccccga  9840
aaagtgccac ctaaattgta agcgttaata ttttgttaaa attcgcgtta aatttttgtt  9900
aaatcagctc attttttaac caataggccg aaatcggcaa aatcccttat aaatcaaaag  9960
aatagaccga gatagggttg agtgttgttc cagtttggaa caagagtcca ctattaaaga  10020
acgtggactc caacgtcaaa gggcgaaaaa ccgtctatca gggcgatggc ccactacgtg  10080
aaccatcacc ctaatcaagt tttttggggt cgaggtgccg taaagcacta aatcggaacc  10140
ctaaagggag cccccgattt agagcttgac ggggaaagcc ggcgaacgtg gcgagaaagg  10200
aagggaagaa agcgaaagga gcgggcgcta gggcgctggc aagtgtagcg gtcacgctgc  10260
gcgtaaccac cacacccgcc gcgcttaatg cgccgctaca gggcgcgtcc cattcgccat  10320
tcaggctgcg caactgttgg gaagggcgat cggtgcgggc ctcttcgcta ttacgccagc  10380
tggcgaaagg gggatgtgct gcaaggcgat taagttgggt aacgccaggg ttttcccagt  10440
cacgacgttg taaaacgacg gccagtgagc gcgcggcgaa ttgggtaccg ggcccc     10497
```

```
SEQ ID NO: 16          moltype = DNA  length = 10495
FEATURE                Location/Qualifiers
misc_feature           1..10495
                       note = Description of Artificial Sequence: Synthetic
                        polynucleotide
source                 1..10495
                       mol_type = other DNA
                       organism = synthetic construct
SEQUENCE: 16
cctcgagggc tagccattct atttaatctc cctatcagtg atagagatcg cccgagtgag  60
cacgcagggt ctccatttg atccctatca gtgatagaga agcgggaggt ttgaacgcgc  120
agccgccatg ccggggtttt acgagattgt gattaaggtc cccagcgacc ttgacgagca  180
```

-continued

```
tctgcccggc atttctgaca gctttgtgaa ctgggtggcc gagaaggaat gggagttgcc  240
gccagattct gacatggatc tgaatctgat tgagcaggca cccctgaccg tggccgagaa  300
gctgcagcgc gactttctga cggaatggcg ccgtgtgagt aaggccccgg aggctctttt  360
ctttgtgcaa tttgagaagg gagagagcta cttccacatg cacgtgctcg tggaaaccac  420
cggggtgaaa tccatggttt tgggacgttt cctgagtcag attcgcgaaa aactgattca  480
gagaatttac cgcgggatcg agccgacttt gccaaactgg ttcgcggtca caaagaccag  540
aaatggcgcc ggaggcggga acaaggtggt ggatgagtgc tacatcccca attacttgct  600
ccccaaaacc cagcctgagc tccaatgggc atggaccaac atggaacagt acctcagcgc  660
ctgtttgaat ctcacggagc gtaaacggtt ggtggcgcag catctgacgc acgtgtcgca  720
gacgcaggag cagaacaaag agaatcagaa tcccaattct gatgcgccgg tgatcagatc  780
aaaaacttca gccaggtaca tggagctggt cgggtggctc gtggacaagg ggattacctc  840
ggagaagcag tggatccagg aggaccaggc ctcatacatc tccttcaatg cggcctccaa  900
ctcgcggtcc caaatcaagg ctgccttgga caatgcggga aagattatga gcctgactaa  960
aaccgccccc gactacctgg tggccagcga gcccgtggag gacatttcca gcaatcggat  1020
ttataaaatt ttggaactaa acgggtacga tccccaatat gcggcttccg tctttctggg  1080
atgggccacg aaaaagttcg gcaagaggaa caccatctgg ctgtttgggc ctgcaactac  1140
cgggaagacc aacatcgcgg aggccatagc ccacactgtg cccttctacg ggtgcgtaaa  1200
ctggaccaat gagaactttc ccttcaacga ctgtgtcgac aagatggtga tctggtggga  1260
ggaggggaag atgaccgcca aggtcgtgga gtcggccaaa gccattctcg gaggaagcaa  1320
ggtgcgcgtg gaccagaaat gcaagtcctc ggcccagata gacccgactc ccgtgatcgt  1380
cacctccaac accaacatgt gcgccgtgat tgacgggaac tcaacgacct tcgaacacca  1440
gcagccgttg caagaccgga tgttcaaatt tgaactcacc cgccgtctgg atcatgactt  1500
tgggaaggtc accaagcagg aagtcaaaga ctttttccgg tgggcaaagg atcacgtggt  1560
tgaggtggag catgaattct acgtcaaaaa gggtggagcc aagaaaagac ccgcccccag  1620
tgacgcagat ataagtgagc ccaaacgggt gcgcgagtca gttgcgcagc catcgacgtc  1680
agacgcggaa gcttcgatca actacgcaga caggtaccaa aacaaatgtt ctcgtcacgt  1740
gggcatgaat ctgatgctgt ttccctgcag acaatgcgag agaatgaatc agaattcaaa  1800
tatctgcttc actcacggac agaaagactg tttagagtgc tttcccgtgt cagaatctca  1860
acccgtttct gtcgtcaaaa aggcgtatca gaaactgtgc tacattcatc atatcatggg  1920
aaaggtgcca gacgcttgca ctgcctgcga tctggtcaat gtggatttgg atgactgcat  1980
ctttgaacaa taaatgattt aaatcaggta tggctgccga tggttatctt ccagattggc  2040
tcgaggacaa cctctctgag ggcattcgcg agtggtggga cttgaaacct ggagccccga  2100
aacccaaagc caaccagcaa aagcaggacg acggccgggg tctggtgctt cctggctaca  2160
agtacctcgg acccttcaac ggactcgaca agggggagcc cgtcaacgcg gcggacgcag  2220
cggccctcga gcacgacaag gcctacgacc agcagctcaa agcgggtgac aatccgtacc  2280
tgcggtataa ccacgccgac gccgagtttc aggagcgtct gcaagaagat acgtcttttg  2340
ggggcaacct cgggcgagca gtcttccagg ccaagaagcg ggttctcgaa cctctcggtc  2400
tggttgagga aggcgctaag acggctcctg gaaagaagag accggtagag caatcacccc  2460
aggaaccaga ctcctcttcg ggcatcggca agaaaggcca gcagcccgcg agaaagagac  2520
tcaactttgg gcagactggc gactcagagt cagtgcccga ccctcaacca ctcggagaac  2580
cccccgcagc cccctctggt gtgggatcta atacaatggc tgcaggcggt ggcgctccaa  2640
tggcagacaa taacgaaggc gccgacggag tgggtaacgc ctcaggaaat tggcattgcg  2700
attccacatg gctgggcgac agagtcatca ccaccagcac ccgaacctgg gccctcccca  2760
cctacaacaa ccacctctac aagcaaatct ccagccaatc gggaggcagc accaacgaca  2820
acacctactt cggctacagc accccctggg ggtattttga ctttaacaga ttccactgcc  2880
acttctcacc acgtgactgg cagcgactca tcaacaacaa ctggggattc cggcccaaga  2940
agctcaactt caagctcttc aacatccagg tcaaggaggt cacgacgaat gatggcacca  3000
cgaccatcgc caataacctt accagcacgg ttcaggtctt tacggactcg gaataccagc  3060
tcccgtacgt cctcggctct gcgcaccagg gctgcctgcc tccgttcccg gcggacgtct  3120
tcatgattcc tcagtacggg tacctgactc tgaacaatgg cagtcaggcc gtgggccgtt  3180
cctccttcta ctgcctggaa tactttcctt ctcaaatgct gagaacgggc aacaactttc  3240
agttcagcta cacgtttgag gacgtgcctt ttcacagcag ctacgcgcac agccaaagcc  3300
tggaccggct gatgaacccc ctcatcgacc agtacctgta ctacctgtct cggactcaga  3360
ccacgagtgg taccgcagga aatcggacgt tgcaattttc tcaggccggg cctagtagca  3420
tggcgaatca ggccaaaaac tggctacccg ggccctgcta ccggcagcaa cgcgtctcca  3480
agacaaccaa tcaaaataac aacagcaact ttgcctggac cggtgccacc aagtatcatc  3540
tgaatggcag agactctctg gtaaatcccg gtcccgctat ggcaacccac aaggacgacg  3600
aagacaaatt ttttccgatg agcggagtct taatatttgg gaaacaggga gctggaaata  3660
gcaacgtgga ccttgacaac gttatgataa ccaacgagga agaaattaaa accaccaacc  3720
cagtggccac agaagagtac ggcacggtgg ccactaacct gcaatcggcc aacaccgctc  3780
ctgctacagg gaccgtcaac agtcaaggag ccttacctgg catggtctgg caggaccggg  3840
acgtgtacct gcagggtcct atctgggcca agattcctca cacggacgga cactttcatc  3900
cctcgccgct gatgggaggc tttggactga aacacccgcc tcctcagatc ctgattaaga  3960
atacacctgt tcccgcgaat cctccaacta ccttcagtcc agctaagttt gcgtcgttca  4020
tcacgcagta cagcaccgga caggtcagcg tggaaattga atgggagctg cagaaagaaa  4080
acagcaaacg ctggaaccca gagattcaat acacttccaa ctacaacaaa tctacaaatg  4140
tggactttgc tgttgacaca aatggcgttt attctgagcc tcgccccatc ggcacccgtt  4200
acctcacccg taatctgtaa actagtttgc ttgttaatca ataaaccgtt taattcgttt  4260
cagttgaact ttggtctctg cgtatttctt tcttatctag tttccatgct ctagaggtcc  4320
tgtattagag gtcacgtgag tgttttgcga cattttgcga caccatgtgg tcacgctggg  4380
tatttaagcc cgagtgagca cgcagggtct ccattttgaa gcgggaggtt tgaacgcgca  4440
gccgccaagc cgaattctgc agatatcggg gttggggttg cgccttttcc aaggcagccc  4500
tgggtttgcg cagggacgcg gctgctctgg gcgtggttcc gggaaacgca gcggcgccga  4560
ccctgggtct cgcacattct tcacgtccgt tcgcagcgtc acccggatct tcgccgctac  4620
ccttgtgggc cccccggcga cgcttcctgc tccgccccta agtcgggaag gttccttgcg  4680
gttcgcggcg tgccggacgt gacaaacgga agccgcacgt ctcactagta ccctcgcaga  4740
cggacagcgc cagggagcaa tggcagcgcg ccgaccgcga tgggctgtgg ccaatagcgg  4800
ctgctcagca gggcgcgccg agagcagcgg ccgggaaggg gcggtgcggg aggcggggtg  4860
tggggcggta gtgtgggccc tgttcctgcc cgcgcggtgt tccgcattct gcaagcctcc  4920
```

```
ggagcgcacg tcggcagtcg gctccctcgt tgaccgaatc accgacctct ctccccagaa  4980
gctcccggga gcttgtatat ccattttcgg atctgatcag cacgtgttga caattaatca  5040
tcggcatagt atatcggcat agtataatac gacaaggtga ggaacgccac catggccaag  5100
cctttgtctc aagaagaatc caccctcatt gaaagagcaa cggctacaat caacagcatc  5160
cccatctctg aagactacag cgtcgccagc gcagctctct ctagcgacgg ccgcatcttc  5220
actggtgtca atgtatatca ttttactggg ggaccttgtg cagaactcgt ggtgctgggc  5280
actgctgctg ctgcggcagc tggcaacctg acttgtatcg tcgcgatcgg aaatgagaac  5340
aggggcatct tgagcccctg cggacggtgc cgacaggtgc ttctcgatct gcatcctggg  5400
atcaaagcca tagtgaagga cagtgatgga cagccgacgg cagttgggat tcgtgaattg  5460
ctgccctctg gttatgtgtg ggagggctaa gcacttcgtg gccgaggagc aggactgaca  5520
cgtgctacga gatttcgatt ccaccgccgc cttctatgaa aggttgggct tcggaatcgt  5580
tttccgggac gccggctgga tgatcctcca gcgcggggat ctcatgctgg agttcttcgc  5640
ccaccccaac ttgtttattg cagcttataa tggttacaaa taaagcaata gcatcacaaa  5700
tttcacaaat aaagcatttt tttcactgca ttctagttgt ggtttgtcca aactcatcaa  5760
tgtatcttag cgctcactgc ccgctttcca gtcgggaaac ctgtcgtgcc agctgcatta  5820
atgaatcggc caacgcgcgg ggagaggcgg tttgcgtatt gggcgctctc ctaggccaga  5880
aatggcgccg gaggcgggaa caaggtggtg gatgagtgct acatccccaa ttacttgctc  5940
cccaaaaccc agcctgagct ccagtgggcg tggactaata tggaacagta tttaagcgcc  6000
tgtccctatc agtgatagag atctccctat cagtgataga gatttgaatc tcacggagcg  6060
taaacggttg gtggcgcagc atctgtttaa acgcagacgc aggagcagaa caaagagaat  6120
cagaatccca attctgatgc gccggtgatc agatcaaaaa cttcagccag gtacatggag  6180
ctggtcgggt ggctcgtgga caaggggatt acctcggaga agcagtggat tcaggaggac  6240
caggcctcat acatctcctt caatgcggcc tccaactcgc ggtcccaaat caaggctgcc  6300
ttggacaatg cgggaaagat tatgagcctg actaaaaccg cccccgacta cctggtgggc  6360
cagcagcccg tggaggacat ttccagcaat cggatttata aaattttgga actaaacggg  6420
tacgatcccc aatatgcggc ttccgtcttt ctgggatggg ccacgaaaaa gttcggcaag  6480
aggaacacca tctggctgtt tggcctgcca actaccggga agaccaacat cgcggaggcc  6540
atagcccaca ctgtgccctt ctacgggtgc gtaaactgga ccaatgagaa ctttcccttc  6600
aacgactgtg tcgacaagat ggtgatctgg tgggaggagg ggaagatgac cgccaaggtc  6660
gtggagtcgg ccaaagccat tctcggagga agcaaggtgc gcgtggacca gaaatgcaag  6720
tcctcggccc agatagaccc gactcccgtg atcgtcacct ccaacaccaa catgtgcgcc  6780
gtgattgacg ggaactcaac gaccttcgaa caccagcagc cgttgcaaga ccggatgttc  6840
aaatttgaac tcacccgccg tctggatcat gactttggga aggtcaccaa gcaggaagtc  6900
aaagactttt tccggtgggc aaaggatcac gtggttgagg tggagcatga attctacgtc  6960
aaaaagggtg gagccaagaa aagacccgcc cccagtgacg cagatataag tgagcccaaa  7020
cgggtgcgcg agtcagttgc gcagccatcg acgtcagacg cggaagcttc gatcaactac  7080
gcagacaggt accaaaacaa atgttctcgt cacgtgggca tgaatctgat gctgtttccc  7140
tgcagacaat gcgagagaat gaatcagaat tcaaatatct gcttcactca cggacagaaa  7200
gactgtttag agtgctttcc cgtgtcagaa tctcaacccg tttctgtcgt caaaaaggcg  7260
tatcagaaac tgtgctacat tcatcatatc atgggaaagg tgccagacgc ttgcactgcc  7320
tgcgatctgg tcaatgtgga tttggatgac tgcatctttg aacaataaac tagtttgctt  7380
gttaatcaat aaaccgttta attcgtttca gttgaacttt ggtctctgcg tatttctttc  7440
ttatctagtt tccatgctct agagtatacg atatccatca cactggcggc cgctcgacta  7500
gagcggccgc caccgcggtg gagctccagc ttttgttcgc gcgcttggcg taatcatggt  7560
catagctgtt tcctgtgtga aattccacag cctggggtgc ctaattgcgt tgcgctcact  7620
gcccgctttc cagtcgggaa acctgtcgtg ccagctgcat taatgaatcg gccaacgcgc  7680
ggggagaggc ggtttgcgta ttgggcgctc ttccgcttcc tcgctcactg actcgctgcg  7740
ctcggtcgtt cggctgcggc gagcggtatc agctcactca aaggcggtaa tacggttatc  7800
cacagaatca ggggataacg caggaaagaa catgtgagca aaaggccagc aaaaggccag  7860
gaaccgtaaa aaggccgcgt tgctggcgtt tttccatagg ctccgccccc ctgacgagca  7920
tcacaaaaat cgacgctcaa gtcagaggtg gcgaaacccg acaggactat aaagatacca  7980
ggcgtttccc cctggaagct ccctcgtgcg ctctcctgtt ccgaccctgc cgcttaccgg  8040
atacctgtcc gcctttctcc cttcgggaag cgtggcgctt tctcatagct cacgctgtag  8100
gtatctcagt tcggtgtagg tcgttcgctc caagctgggc tgtgtgcacg aaccccccgt  8160
tcagcccgac cgctgcgcct tatccggtaa ctatcgtctt gagtccaacc cggtaagaca  8220
cgacttatcg ccactggcag cagccactgg taacaggatt agcagagcga ggtatgtagg  8280
cggtgctaca gagttcttga agtggtggcc taactacggc tacactagaa gaacagtatt  8340
tggtatctgc gctctgctga agccagttac cttcggaaaa agagttggta gctcttgatc  8400
cggcaaacaa accaccgctg gtagcggtgg tttttttgtt tgcaagcagc agattacgcg  8460
cagaaaaaaa ggatctcaag aagatccttt gatcttttct acggggtctg acgctcagtg  8520
gaacgaaaac tcacgttaag ggattttggt catgagatta tcaaaaagga tcttcaccta  8580
gatcctttta aattaaaaat gaagttttaa atcaatctaa agtatatatg agtaaacttg  8640
gtctgacaga aataataaaa aagccggatt aataatctgg ctttttatat tctctctcta  8700
gtatataaac gcagaaaggc ccacccgaag gtgagccagt gtgactctag tattattaga  8760
aaaactcatc gagcatcaaa tgaaactgca atttattcat atcaggatta tcaataccat  8820
atttttgaaa aagccgtttc tgtaatgaag gagaaaactc accgaggcag ttccaaagaa  8880
tggcaaggtc ctggtaacgg tctgcgattc cgacccgtcc aacatcaata caacctatta  8940
atttcccctc gtcaaaaata aggttatcaa gtgagaaatc accatgagtg acgactgaat  9000
ccggtgagaa tggcaagagc ttgtgcattt ctttccagac ttgttcaaca ggccagccat  9060
tacgctcgtc atcaaaatca ctcgcatcaa ccaaaccgtt attcatgcgt gattgcgcct  9120
gagcaagacg aaatacacga tcgctgttaa aaggacaatt acaaacagga atcgaatgta  9180
accggcgcag gaacacggcc agcgcatcaa caatattttc acctgaatca ggatattctt  9240
ctaatacctg gaaggctgtt ttcccaggaa tcgcggtggt gagtaaccac gcatcatcag  9300
gagtacggat aaaatgcttg atggtcggga gaggcataaa ctccgtcagc cagttgagac  9360
ggaccatctc atctgtaaca tcattggcaa cgctaccttt gccatgtttc agaaacaact  9420
ctggcgcatc gggcttccca tacaagcgat agattgtcgc acctgattgc ccgacattat  9480
cgcgagccca tttataccca tataaatcag cgtccatgtt ggagtttaag cgcggacggg  9540
agcaagacgt ttcccgttga atatggctca taacacccct tgtattactg tttatgtaag  9600
cagacagttt tattgttcat gatgatatat ttttatcttg tgcaatgtaa catcagagat  9660
```

```
tttgagacac aacgtggctt tgttgaataa atcgaacttt tgctgagttg aaggatcagc  9720
tctagtaaaa taataaaaaa gccggattaa taatctggct ttttatattc tctctctagt  9780
atataaacgc agaaaggccc acccgaaggt gagccagtgt gacggcacat ttccccgaaa  9840
agtgccacct aaattgtaag cgttaatatt ttgttaaaat tcgcgttaaa tttttgttaa  9900
atcagctcat tttttaacca ataggccgaa atcggcaaaa tcccttataa atcaaaagaa  9960
tagaccgaga tagggttgag tgttgttcca gtttggaaca agagtccact attaaagaac  10020
gtggactcca acgtcaaagg gcgaaaaacc gtctatcagg gcgatggccc actacgtgaa  10080
ccatcaccct aatcaagttt tttggggtcg aggtgccgta aagcactaaa tcggaaccct  10140
aaagggagcc cccgatttag agcttgacgg ggaaagccgg cgaacgtggc gagaaaggaa  10200
gggaagaaag cgaaaggagc gggcgctagg gcgctggcaa gtgtagcggt cacgctgcgc  10260
gtaaccacca cacccgccgc gcttaatgcg ccgctacagg gcgcgtccca ttcgccattc  10320
aggctgcgca actgttggga agggcgatcg gtgcgggcct cttcgctatt acgccagctg  10380
gcgaaagggg gatgtgctgc aaggcgatta agttgggtaa cgccagggtt ttcccagtca  10440
cgacgttgta aaacgacggc cagtgagcgc gcggcgaatt gggtaccggg ccccc       10495

SEQ ID NO: 17          moltype = DNA  length = 10493
FEATURE                Location/Qualifiers
misc_feature           1..10493
                       note = Description of Artificial Sequence: Synthetic
                        polynucleotide
source                 1..10493
                       mol_type = other DNA
                       organism = synthetic construct
SEQUENCE: 17
cctcgagggc tagccattct ccctatcagt gatagagatc tatttaagcc cgagtgagca  60
cgcagtccct atcagtgata gagaggtctc cattttgaag cgggaggttt gaacgcgcag  120
ccgccatgcc ggggttttac gagattgtga ttaaggtccc cagcgacctt gacgagcatc  180
tgcccggcat ttctgacagc tttgtgaact gggtggccga gaaggaatgg gagttgccgc  240
cagattctga catggatctg aatctgattg agcaggcacc cctgaccgtg gccgagaagc  300
tgcagcgcga ctttctgacg gaatggcgcc gtgtgagtaa ggccccggag gctctttttct  360
ttgtgcaatt tgagaaggga gagagctact tccacatgca cgtgctcgtg gaaaccaccg  420
gggtgaaatc catggttttg ggacgtttcc tgagtcagat tcgcgaaaaa ctgattcaga  480
gaatttaccg cgggatcgag ccgactttgc caaactggtt cgcggtcaca aagaccagaa  540
atggcgccgg aggcgggaac aaggtggtgg atgagtgcta catccccaat tacttgctcc  600
ccaaaaccca gcctgagctc caatgggcat ggaccaacat ggaacagtac ctcagcgcct  660
gtttgaatct cacggagcgt aaacggttgg tggcgcagca tctgacgcac gtgtcgcaga  720
cgcaggagca gaacaaagag aatcagaatc ccaattctga tgcgccggtg atcagatcaa  780
aaacttcagc caggtacatg gagctggtcg ggtggctcgt ggacaagggg attacctcgg  840
agaagcagtg gatccaggag gaccaggcct catacatctc cttcaatgcg gcctccaact  900
cgcggtccca aatcaaggct gccttggaca atgcgggaaa gattatgagc ctgactaaaa  960
ccgcccccga ctacctggtg ggccagcagc ccgtggagga catttccagc aatcggattt  1020
ataaaatttt ggaactaaac gggtacgatc cccaatatgc ggcttccgtc tttctgggat  1080
gggccacgaa aaagttcggc aagaggaaca ccatctggct gtttgggcct gcaactaccg  1140
ggaagaccaa catcgcggag gccatagccc acactgtgcc cttctacggg tgcgtaaact  1200
ggaccaatga gaactttccc ttcaacgact gtgtcgacaa gatggtgatc tggtgggagg  1260
aggggaagat gaccgccaag gtcgtggagt cggccaaagc cattctcgga ggaagcaagg  1320
tgcgcgtgga ccagaaatgc aagtcctcgg cccagataga cccgactccc gtgatcgtca  1380
cctccaacac caacatgtgc gccgtgattg acgggaactc aacgaccttc gaacaccagc  1440
agccgttgca agaccggatg ttcaaatttg aactcacccg ccgtctggat catgactttg  1500
ggaaggtcac caagcaggaa gtcaaagact ttttccggtg ggcaaaggat cacgtggttg  1560
aggtggagca tgaattctac gtcaaaaagg gtggagccaa gaaaagaccc gcccccagtg  1620
acgcagatat aagtgagccc aaacgggtgc gcgagtcagt tgcgcagcca tcgacgtcag  1680
acgcggaagc ttcgatcaac tacgcagaca ggtaccaaaa caaatgttct cgtcacgtgg  1740
gcatgaatct gatgctgttt ccctgcagac aatgcgagag aatgaatcag aattcaaata  1800
tctgcttcac tcacggacag aaagactgtt tagagtgctt tcccgtgtca gaatctcaac  1860
ccgtttctgt cgtcaaaaag gcgtatcaga aactgtgcta cattcatcat atcatgggaa  1920
aggtgccaga cgcttgcact gcctgcgatc tggtcaatgt ggatttggat gactgcatct  1980
ttgaacaata aatgatttaa atcaggtatg gctgccgatg gttatcttcc agattggctc  2040
gaggacaacc tctctgaggg cattcgcgag tggtgggact tgaaacctgg agccccgaaa  2100
cccaaagcca accagcaaaa gcaggacgac ggccggggtc tggtgcttcc tggctacaag  2160
tacctcggac ccttcaacgg actcgacaag ggggagcccg tcaacgcggc ggacgcagcg  2220
gccctcgagc acgacaaggc ctacgaccag cagctcaaag cgggtgacaa tccgtacctg  2280
cggtataacc acgccgacgc cgagtttcag gagcgtctgc aagaagatac gtcttttggg  2340
ggcaacctcg ggcgagcagt cttccaggcc aagaagcggg ttctcgaacc tctcggtctg  2400
gttgaggaag gcgctaagac ggctcctgga aagaagagac cggtagagca atcaccccag  2460
gaaccagact cctcttcggg catcggcaag aaaggccagc agcccgcgag aaaagagactc  2520
aactttgggc agactggcga ctcagagtca gtgcccgacc ctcaaccact cggagaaccc  2580
cccgcagccc cctctggtgt gggatctaat acaatggctg caggcggtgg cgctccaatg  2640
gcagacaata acgaaggcgc cgacggagtg ggtaacgcct caggaaattg gcattgcgat  2700
tccacatggc tgggcgacag agtcatcacc accagcaccc gaacctgggc cctccccacc  2760
tacaacaacc acctctacaa gcaaatctcc agccaatcgg gaggcagcac caacgacaac  2820
acctacttcg gctacagcac cccctggggg tattttgact ttaacagatt ccactgccac  2880
ttctcaccac gtgactggca gcgactcatc aacaacaact ggggattccg gcccaagaag  2940
ctcaacttca agctcttcaa catccaggtc aaggaggtca cgacgaatga tggcaccacg  3000
accatcgcca ataaccttac cagcacggtt caggtcttta cggactcgga ataccagctc  3060
ccgtacgtcc tcggctctgc gcaccagggc tgcctgcctc cgttcccggc ggacgtcttc  3120
atgattcctc agtacgggta cctgactctg aacaatggca gtcaggccgt gggccgttcc  3180
tccttctact gcctggaata ctttccttct caaatgctga gaacgggcaa caactttcag  3240
ttcagctaca cgtttgagga cgtgcctttt cacagcagct acgcgcacag ccaaagcctg  3300
```

```
gaccggctga tgaacccccct catcgaccag tacctgtact acctgtctcg gactcagacc  3360
acgagtggta ccgcaggaaa tcggacgttg caattttctc aggccgggcc tagtagcatg  3420
gcgaatcagg ccaaaaactg gctacccggg ccctgctacc ggcagcaacg cgtctccaag  3480
acaaccaatc aaaataacaa cagcaacttt gcctggaccg gtgccaccaa gtatcatctg  3540
aatggcagag actctctggt aaatcccggt cccgctatgg caacccacaa ggacgacgaa  3600
gacaaatttt ttccgatgag cggagtctta atatttggga aacagggagc tggaaatagc  3660
aacgtggacc ttgacaacgt tatgataacc aacgaggaag aaattaaaac caccaaccca  3720
gtggccacag aagagtacgg cacggtggcc actaacctgc aatcggccaa caccgctcct  3780
gctacaggga ccgtcaacag tcaaggagcc ttacctggca tggtctggca ggaccgggac  3840
gtgtacctgc agggtcctat ctgggccaag attcctcaca cggacggaca ctttcatccc  3900
tcgccgctga tgggaggctt tggactgaaa cacccgcctc ctcagatcct gattaagaat  3960
acacctgttc ccgcgaatcc tccaactacc ttcagtccag ctaagtttgc gtcgttcatc  4020
acgcagtaca gcaccggaca ggtcagcgtg gaaattgaat gggagctgca gaaagaaaac  4080
agcaaacgct ggaacccaga gattcaatac acttccaact acaacaaatc tacaaatgtg  4140
gactttgctg ttgacacaaa tggcgtttat tctgagcctc gccccatcgg cacccgttac  4200
ctcacccgta atctgtaaac tagtttgctt gttaatcaat aaaccgttta attcgtttca  4260
gttgaacttt ggtctctgcg tatttctttc ttatctagtt tccatgctct agaggtcctg  4320
tattagaggt cacgtgagtg ttttgcgaca ttttgcgaca ccatgtggtc acgctgggta  4380
tttaagcccg agtgagcacg cagggtctcc attttgaagc gggaggtttg aacgcgcagc  4440
cgccaagccg aattctgcag atatcggggt tggggttgcg ccttttccaa ggcagccctg  4500
ggtttgcgca gggacgcggc tgctctgggc gtggttccgg gaaacgcagc ggcgccgacc  4560
ctgggtctcg cacattcttc acgtccgttc gcagcgtcac ccggatcttc gccgctaccc  4620
ttgtgggccc cccggcgacg cttcctgctc cgcccctaag tcgggaaggt tccttgcggt  4680
tcgcggcgtg ccggacgtga caaacggaag ccgcacgtct cactagtacc ctcgcagacg  4740
gacagcgcca gggagcaatg gcagcgcgcc gaccgcgatg ggctgtggcc aatagcggct  4800
gctcagcagg gcgcgccgag agcagcggcc gggaaggggc ggtgcgggag gcggggtgtg  4860
gggcggtagt gtgggccctg ttcctgcccg cgcggtgttc cgcattctgc aagcctccgg  4920
agcgcacgtc ggcagtcggc tccctcgttg accgaatcac cgacctctct ccccagaagc  4980
tcccgggagc ttgtatatcc attttcggat ctgatcagca cgtgttgaca attaatcatc  5040
ggcatagtat atcggcatag tataatacga caaggtgagg aacgccacca tggccaagcc  5100
tttgtctcaa gaagaatcca ccctcattga aagagcaacg gctacaatca acagcatccc  5160
catctctgaa gactacagcg tcgccagcgc agctctctct agcgacggcc gcatcttcac  5220
tggtgtcaat gtatatcatt ttactggggg accttgtgca gaactcgtgg tgctgggcac  5280
tgctgctgct gcggcagctg gcaacctgac ttgtatcgtc gcgatcggaa atgagaacag  5340
gggcatcttg agcccctgcg gacggtgccg acaggtgctt ctcgatctgc atcctgggat  5400
caaagccata gtgaaggaca gtgatggaca gccgacggca gttgggattc gtgaattgct  5460
gccctctggt tatgtgtggg agggctaagc acttcgtggc cgaggagcag gactgacacg  5520
tgctacgaga tttcgattcc accgccgcct tctatgaaag gttgggcttc ggaatcgttt  5580
tccgggacgc cggctggatg atcctccagc gcggggatct catgctggag ttcttcgccc  5640
accccaactt gtttattgca gcttataatg gttacaaata aagcaatagc atcacaaatt  5700
tcacaaataa agcatttttt tcactgcatt ctagttgtgg tttgtccaaa ctcatcaatg  5760
tatcttagcg ctcactgccc gctttccagt cgggaaacct gtcgtgccag ctgcattaat  5820
gaatcggcca acgcgcgggg agaggcggtt tgcgtattgg gcgctctcct aggccagaaa  5880
tggcgccgga ggcgggaaca aggtggtgga tgagtgctac atccccaatt acttgctccc  5940
caaaacccag cctgagctcc agtgggcgtg gactaatatg gaacagtatt taagcgcctg  6000
tccctatcag tgatagagat ctccctatca gtgatagaga tttgaatctc acggagcgta  6060
aacggttggt ggcgcagcat ctgtttaaac gcagacgcag gagcagaaca aagagaatca  6120
gaatcccaat tctgatgcgc cggtgatcag atcaaaaact tcagccaggt acatggagct  6180
ggtcgggtgg ctcgtggaca aggggattac ctcggagaag cagtggattc aggaggacca  6240
ggcctcatac atctccttca atgcggcctc caactcgcgg tcccaaatca aggctgcctt  6300
ggacaatgcg ggaaagatta tgagcctgac taaaaccgcc cccgactacc tggtgggcca  6360
gcagcccgtg gaggacattt ccagcaatcg gatttataaa attttggaac taaacgggta  6420
cgatccccaa tatgcggctt ccgtctttct gggatgggcc acgaaaaagt tcggcaagag  6480
gaacaccatc tggctgtttg ggcctgcaac taccgggaag accaacatcg cggaggccat  6540
agcccacact gtgcccttct acgggtgcgt aaactggacc aatgagaact ttcccttcaa  6600
cgactgtgtc gacaagatgg tgatctggtg ggaggagggg aagatgaccg ccaaggtcgt  6660
ggagtcggcc aaagccattc tcggaggaag caaggtgcgc gtggaccaga aatgcaagtc  6720
ctcggcccag atagacccga ctcccgtgat cgtcacctcc aacaccaaca tgtgcgccgt  6780
gattgacggg aactcaacga ccttcgaaca ccagcagccg ttgcaagacc ggatgttcaa  6840
atttgaactc acccgccgtc tggatcatga ctttgggaag gtcaccaagc aggaagtcaa  6900
agactttttc cggtgggcaa aggatcacgt ggttgaggtg gagcatgaat tctacgtcaa  6960
aaagggtgga gccaagaaaa gacccgcccc cagtgacgca gatataagtg agcccaaacg  7020
ggtgcgcgag tcagttgcgc agccatcgac gtcagacgcg gaagcttcga tcaactacgc  7080
agacaggtac caaaacaaat gttctcgtca cgtgggcatg aatctgatgc tgtttccctg  7140
cagacaatgc gagagaatga atcagaattc aaatatctgc ttcactcacg gacagaaaga  7200
ctgtttagag tgctttcccg tgtcagaatc tcaacccgtt tctgtcgtca aaaaggcgta  7260
tcagaaactg tgctacattc atcatatcat gggaaaggtg ccagacgctt gcactgcctg  7320
cgatctggtc aatgtggatt tggatgactg catctttgaa caataaacta gtttgcttgt  7380
taatcaataa accgtttaat tcgtttcagt tgaactttgg tctctgcgta tttctttctt  7440
atctagtttc catgctctag agtatacgat atccatcaca ctggcggccg ctcgactaga  7500
gcggccgcca ccgcggtgga gctccagctt ttgttcgcgc gcttggcgta atcatggtca  7560
tagctgtttc ctgtgtgaaa ttccacagcc tggggtgcct aattgcgttg cgctcactgc  7620
ccgctttcca gtcgggaaac ctgtcgtgcc agctgcatta atgaatcggc caacgcgcgg  7680
ggagaggcgg tttgcgtatt gggcgctctt ccgcttcctc gctcactgac tcgctgcgct  7740
cggtcgttcg gctgcggcga gcggtatcag ctcactcaaa ggcggtaata cggttatcca  7800
cagaatcagg ggataacgca ggaaagaaca tgtgagcaaa aggccagcaa aaggccagga  7860
accgtaaaaa ggccgcgttg ctggcgtttt tccataggct ccgcccccct gacgagcatc  7920
acaaaaatcg acgctcaagt cagaggtggc gaaacccgac aggactataa agataccagg  7980
cgtttccccc tggaagctcc ctcgtgcgct ctcctgttcc gaccctgccg cttaccggat  8040
```

```
acctgtccgc ctttctccct tcgggaagcg tggcgctttc tcatagctca cgctgtaggt  8100
atctcagttc ggtgtaggtc gttcgctcca agctgggctg tgtgcacgaa ccccccgttc  8160
agcccgaccg ctgcgcctta tccggtaact atcgtcttga gtccaacccg gtaagacacg  8220
acttatcgcc actggcagca gccactggta acaggattag cagagcgagg tatgtaggcg  8280
gtgctacaga gttcttgaag tggtggccta actacggcta cactagaaga acagtatttg  8340
gtatctgcgc tctgctgaag ccagttacct tcggaaaaag agttggtagc tcttgatccg  8400
gcaaacaaac caccgctggt agcggtggtt tttttgtttg caagcagcag attacgcgca  8460
gaaaaaaagg atctcaagaa gatcctttga tcttttctac ggggtctgac gctcagtgga  8520
acgaaaactc acgttaaggg attttggtca tgagattatc aaaaaggatc ttcacctaga  8580
tccttttaaa ttaaaaatga agttttaaat caatctaaag tatatatgag taaacttggt  8640
ctgacagaaa taataaaaaa gccggattaa taatctggct tttatattc tctctctagt  8700
atataaacgc agaaaggccc acccgaaggt gagccagtgt gactctagta ttattagaaa  8760
aactcatcga gcatcaaatg aaactgcaat ttattcatat caggattatc aataccatat  8820
ttttgaaaaa gccgtttctg taatgaagga gaaaactcac cgaggcagtt ccaaagaatg  8880
gcaaggtcct ggtaacggtc tgcgattccg acccgtccaa catcaataca acctattaat  8940
ttcccctcgt caaaaataag gttatcaagt gagaaatcac catgagtgac gactgaatcc  9000
ggtgagaatg gcaagagctt gtgcatttct ttccagactt gttcaacagg ccagccatta  9060
cgctcgtcat caaaatcact cgcatcaacc aaaccgttat tcatgcgtga ttgcgcctga  9120
gcaagacgaa atacacgatc gctgttaaaa ggacaattac aaacaggaat cgaatgtaac  9180
cggcgcagga acacggccag cgcatcaaca atattttcac ctgaatcagg atattcttct  9240
aatacctgga aggctgtttt cccaggaatc gcggtggtga gtaaccacgc atcatcagga  9300
gtacggataa aatgcttgat ggtcgggaga ggcataaact ccgtcagcca gttgagacgg  9360
accatctcat ctgtaacatc attggcaacg ctacctttgc catgtttcag aaacaactct  9420
ggcgcatcgg gcttcccata caagcgatag attgtcgcac ctgattgccc gacattatcg  9480
cgagcccatt tatacccata taaatcagcg tccatgttgg agtttaagcg cggacgggag  9540
caagacgttt cccgttgaat atggctcata acaccccttg tattactgtt tatgtaagca  9600
gacagtttta ttgttcatga tgatatattt ttatcttgtg caatgtaaca tcagagattt  9660
tgagacacaa cgtggctttg ttgaataaat cgaacttttg ctgagttgaa ggatcagctc  9720
tagtaaaata ataaaaaagc cggattaata atctggcttt ttatattctc tctctagtat  9780
ataaacgcag aaaggcccac ccgaaggtga gccagtgtga cggcacattt ccccgaaaag  9840
tgccacctaa attgtaagcg ttaatatttt gttaaaattc gcgttaaatt tttgttaaat  9900
cagctcattt tttaaccaat aggccgaaat cggcaaaatc ccttataaat caaaagaata  9960
gaccgagata gggttgagtg ttgttccagt ttggaacaag agtccactat taaagaacgt  10020
ggactccaac gtcaaagggc gaaaaaccgt ctatcagggc gatggcccac tacgtgaacc  10080
atcaccctaa tcaagttttt tggggtcgag gtgccgtaaa gcactaaatc ggaaccctaa  10140
agggagcccc cgatttagag cttgacgggg aaagccggcg aacgtggcga gaaaggaagg  10200
gaagaaagcg aaaggagcgg gcgctagggc gctggcaagt gtagcggtca cgctgcgcgt  10260
aaccaccaca cccgccgcgc ttaatgcgcc gctacagggc gcgtcccatt cgccattcag  10320
gctgcgcaac tgttgggaag ggcgatcggt gcgggcctct tcgctattac gccagctggc  10380
gaaaggggga tgtgctgcaa ggcgattaag ttgggtaacg ccagggtttt cccagtcacg  10440
acgttgtaaa acgacggcca gtgagcgcgc ggcgaattgg gtaccgggcc ccc         10493

SEQ ID NO: 18           moltype = DNA  length = 10495
FEATURE                 Location/Qualifiers
misc_feature            1..10495
                        note = Description of Artificial Sequence: Synthetic
                         polynucleotide
source                  1..10495
                        mol_type = other DNA
                        organism = synthetic construct
SEQUENCE: 18
cctcgagggc tagccattct atttaatctc cctatcagtg atagagatct ccctatcagt  60
gatagagatc gcccgagtga gcacgcaggg tctccatttt gaagcgggag gtttgaacgc  120
gcagccgcca tgccggggtt ttacgagatt gtgattaagg tccccagcga ccttgacgag  180
catctgcccg gcatttctga cagctttgtg aactgggtgg ccgagaagga atgggagttg  240
ccgccagatt ctgacatgga tctgaatctg attgagcagg cacccctgac cgtggccgag  300
aagctgcagc gcgactttct gacggaatgg cgccgtgtga gtaaggcccc ggaggctctt  360
ttctttgtgc aatttgagaa gggagagagc tacttccaca tgcacgtgct cgtggaaacc  420
accggggtga aatccatggt tttgggacgt ttcctgagtc agattcgcga aaaactgatt  480
cagagaattt accgcgggat cgagccgact ttgccaaact ggttcgcggt cacaaagacc  540
agaaatggcg ccggaggcgg gaacaaggtg gtggatgagt gctacatccc caattacttg  600
ctccccaaaa cccagcctga gctccaatgg gcatggacca acatggaaca gtacctcagc  660
gcctgtttga atctcacgga gcgtaaacgg ttggtggcgc agcatctgac gcacgtgtcg  720
cagacgcagg agcagaacaa agagaatcag aatcccaatt ctgatgcgcc ggtgatcaga  780
tcaaaaactt cagccaggta catggagctg gtcgggtggc tcgtggacaa ggggattacc  840
tcggagaagc agtggatcca ggaggaccag gcctcataca tctccttcaa tgcggcctcc  900
aactcgcggt cccaaatcaa ggctgccttg gacaatgcgg gaaagattat gagcctgact  960
aaaaccgccc ccgactacct ggtgggccag cagcccgtgg aggacatttc cagcaatcgg  1020
atttataaaa ttttggaact aaacgggtac gatccccaat atgcggcttc cgtctttctg  1080
ggatgggcca cgaaaaagtt cggcaagagg aacaccatct ggctgtttgg gcctgcaact  1140
accgggaaga ccaacatcgc ggaggccata gcccacactg tgcccttcta cgggtgcgta  1200
aactggacca atgagaactt tcccttcaac gactgtgtcg acaagatggt gatctggtgg  1260
gaggagggga agatgaccgc caaggtcgtg gagtcggcca aagccattct cggaggaagc  1320
aaggtgcgcg tggaccagaa atgcaagtcc tcggcccaga tagacccgac tcccgtgatc  1380
gtcacctcca acaccaacat gtgcgccgtg attgacggga actcaacgac cttcgaacac  1440
cagcagccgt tgcaagaccg gatgttcaaa tttgaactca cccgccgtct ggatcatgac  1500
tttgggaagg tcaccaagca ggaagtcaaa gactttttcc ggtgggcaaa ggatcacgtg  1560
gttgaggtgg agcatgaatt ctacgtcaaa aagggtggag ccaagaaaag acccgccccc  1620
agtgacgcag atataagtga gcccaaacgg gtgcgcgagt cagttgcgca gccatcgacg  1680
```

-continued

```
tcagacgcgg aagcttcgat caactacgca gacaggtacc aaaacaaatg ttctcgtcac  1740
gtgggcatga atctgatgct gtttccctgc agacaatgcg agagaatgaa tcagaattca  1800
aatatctgct tcactcacgg acagaaagac tgtttagagt gctttcccgt gtcagaatct  1860
caacccgttt ctgtcgtcaa aaaggcgtat cagaaactgt gctacattca tcatatcatg  1920
ggaaaggtgc cagacgcttg cactgcctgc gatctggtca atgtggattt ggatgactgc  1980
atctttgaac aataaatgat ttaaatcagg tatggctgcc gatggttatc ttccagattg  2040
gctcgaggac aacctctctg agggcattcg cgagtggtgg gacttgaaac ctggagcccc  2100
gaaacccaaa gccaaccagc aaaagcagga cgacggccgg ggtctggtgc ttcctggcta  2160
caagtacctc ggacccttca acggactcga caagggggag cccgtcaacg cggcggacgc  2220
agcggccctc gagcacgaca aggcctacga ccagcagctc aaagcgggtg acaatccgta  2280
cctgcggtat aaccacgccg acgccgagtt tcaggagcgt ctgcaagaag atacgtcttt  2340
tgggggcaac ctcgggcgag cagtcttcca ggccaagaag cgggttctcg aacctctcgg  2400
tctggttgag gaaggcgcta agacggctcc tggaaagaag agaccggtag agcaatcacc  2460
ccaggaacca gactcctctt cgggcatcgg caagaaaggc cagcagcccg cgagaaagag  2520
actcaacttt gggcagactg gcgactcaga gtcagtgccc gaccctcaac cactcggaga  2580
acccccccgca gccccctctg gtgtgggatc taatacaatg gctgcaggcg gtggcgctcc  2640
aatggcagac aataacgaag gcgccgacgg agtgggtaac gcctcaggaa attggcattg  2700
cgattccaca tggctgggcg acagagtcat caccaccagc acccgaacct gggccctccc  2760
cacctacaac aaccacctct acaagcaaat ctccagccaa tcgggaggca gcaccaacga  2820
caacacctac ttcggctaca gcaccccctg ggggtatttt gactttaaca gattccactg  2880
ccacttctca ccacgtgact ggcagcgact catcaacaac aactggggat tccggcccaa  2940
gaagctcaac ttcaagctct tcaacatcca ggtcaaggag gtcacgacga atgatggcac  3000
cacgaccatc gccaataacc ttaccagcac ggttcaggtc tttacggact cggaatacca  3060
gctcccgtac gtcctcggct ctgcgcacca gggctgcctg cctccgttcc cggcggacgt  3120
cttcatgatt cctcagtacg ggtacctgac tctgaacaat ggcagtcagg ccgtgggccg  3180
ttcctccttc tactgcctgg aatactttcc ttctcaaatg ctgagaacgg gcaacaactt  3240
tcagttcagc tacacgtttg aggacgtgcc ttttcacagc agctacgcgc acagccaaag  3300
cctggaccgg ctgatgaacc ccctcatcga ccagtacctg tactacctgt ctcggactca  3360
gaccacgagt ggtaccgcag gaaatcggac gttgcaattt tctcaggccg ggcctagtag  3420
catggcgaat caggccaaaa actggctacc cgggccctgc taccggcagc aacgcgtctc  3480
caagacaacc aatcaaaata acaacagcaa ctttgcctgg accggtgcca ccaagtatca  3540
tctgaatggc agagactctc tggtaaatcc cggtcccgct atggcaaccc acaaggacga  3600
cgaagacaaa tttttccga tgagcggagt cttaatattt gggaaacagg gagctggaaa  3660
tagcaacgtg gaccttgaca acgttatgat aaccaacgag gaagaaatta aaaccaccaa  3720
cccagtggcc acagaagagt acggcacggt ggccactaac ctgcaatcgg ccaacaccgc  3780
tcctgctaca gggaccgtca acagtcaagg agccttacct ggcatggtct ggcaggaccg  3840
ggacgtgtac ctgcagggtc ctatctgggc caagattcct cacacggacg gacactttca  3900
tccctcgccg ctgatgggag gctttggact gaaacacccg cctcctcaga tcctgattaa  3960
gaatacacct gttcccgcga atcctccaac taccttcagt ccagctaagt ttgcgtcgtt  4020
catcacgcag tacagcaccg gacaggtcag cgtggaaatt gaatgggagc tgcagaaaga  4080
aaacagcaaa cgctggaacc cagagattca atacacttcc aactacaaca aatctacaaa  4140
tgtggacttt gctgttgaca caaatggcgt ttattctgag cctcgcccca tcggcacccg  4200
ttacctcacc cgtaatctgt aaactagttt gcttgttaat caataaaccg tttaattcgt  4260
ttcagttgaa ctttggtctc tgcgtatttc tttcttatct agtttccatg ctctagaggt  4320
cctgtattag aggtcacgtg agtgttttgc gacattttgc gacaccatgt ggtcacgctg  4380
ggtatttaag cccgagtgag cacgcagggt ctccattttg aagcgggagg tttgaacgcg  4440
cagccgccaa gccgaattct gcagatatcg ggttggggt tgcgcctttt ccaaggcagc  4500
cctgggtttg cgcagggacg cggctgctct gggcgtggtt ccgggaaacg cagcggcgcc  4560
gaccctgggt ctcgcacatt cttcacgtcc gttcgcagcg tcacccggat cttcgccgct  4620
acccttgtgg gccccccggc gacgcttcct gctccgcccc taagtcggga aggttccttg  4680
cggttcgcgg cgtgccggac gtgacaaacg gaagccgcac gtctcactag taccctcgca  4740
gacggacagc gccagggagc aatggcagcg cgccgaccgc gatgggctgt ggccaatagc  4800
ggctgctcag cagggcgcgc cgagagcagc ggccgggaag ggcggtgcg ggaggcgggg  4860
tgtggggcgg tagtgtgggc cctgttcctg cccgcgcggt gttccgcatt ctgcaagcct  4920
ccggagcgca cgtcggcagt cggctccctc gttgaccgaa tcaccgacct ctctccccag  4980
aagctcccgg gagcttgtat atccatttc ggatctgatc agcacgtgtt gacaattaat  5040
catcggcata gtatatcggc atagtataat acgacaaggt gaggaacgcc accatggcca  5100
agcctttgtc tcaagaagaa tccaccctca ttgaaagagc aacggctaca atcaacagca  5160
tccccatctc tgaagactac agcgtcgcca gcgcagctct ctctagcgac ggccgcatct  5220
tcactggtgt caatgtatat cattttactg ggggaccttg tgcagaactc gtggtgctgg  5280
gcactgctgc tgctgcggca gctggcaacc tgacttgtat cgtcgcgatc ggaaatgaga  5340
acaggggcat cttgagcccc tgcggacggt gccgacaggt gcttctcgat ctgcatcctg  5400
ggatcaaagc catagtgaag gacagtgatg gacagccgac ggcagttggg attcgtgaat  5460
tgctgccctc tggttatgtg tgggagggct aagcacttcg tggccgagga gcaggactga  5520
cacgtgctac gagatttcga ttccaccgcc gccttctatg aaaggttggg cttcggaatc  5580
gttttccggg acgccggctg gatgatcctc cagcgcgggg atctcatgct ggagttcttc  5640
gcccacccca acttgtttat tgcagcttat aatggttaca aataaagcaa tagcatcaca  5700
aatttcacaa ataaagcatt tttttcactg cattctagtt gtggtttgtc caaactcatc  5760
aatgtatctt agcgctcact gcccgctttc cagtcgggaa acctgtcgtg ccagctgcat  5820
taatgaatcg gccaacgcgc ggggagaggc ggtttgcgta ttgggcgctc tcctaggcca  5880
gaaatggcgc cggaggcggg aacaaggtgg tggatgagtg ctacatcccc aattacttgc  5940
tccccaaaac ccagcctgag tccctatcag tgatagagac tccagtgggc gtggactaat  6000
atggaacagt atttaagcgc ctgtccctat cagtgataga gatttgaatc tcacggagcg  6060
taaacggttg gtggcgcagc atctgtttaa acgcagacgc aggagcagaa caaagagaat  6120
cagaatccca attctgatgc gccggtgatc agatcaaaaa cttcagccag gtacatggag  6180
ctggtcgggt ggctcgtgga caaggggatt acctcggaga agcagtggat tcaggaggac  6240
caggcctcat acatctcctt caatgcggcc tccaactcgc ggtcccaaat caaggctgcc  6300
ttggacaatg cgggaaagat tatgagcctg actaaaaccg cccccgacta cctggtgggc  6360
cagcagcccg tggaggacat ttccagcaat cggatttata aaattttgga actaaacggg  6420
```

```
tacgatcccc aatatgcggc ttccgtcttt ctgggatggg ccacgaaaaa gttcggcaag  6480
aggaacacca tctggctgtt tgggcctgca actaccggga agaccaacat cgcggaggcc  6540
atagcccaca ctgtgccctt ctacgggtgc gtaaactgga ccaatgagaa ctttcccttc  6600
aacgactgtg tcgacaagat ggtgatctgg tgggaggagg ggaagatgac cgccaaggtc  6660
gtggagtcgg ccaaagccat tctcggagga agcaaggtgc gcgtggacca gaaatgcaag  6720
tcctcggccc agatagaccc gactcccgtg atcgtcacct ccaacaccaa catgtgcgcc  6780
gtgattgacg ggaactcaac gaccttcgaa caccagcagc cgttgcaaga ccggatgttc  6840
aaatttgaac tcacccgccg tctggatcat gactttggga aggtcaccaa gcaggaagtc  6900
aaagactttt tccggtgggc aaaggatcac gtggttgagg tggagcatga attctacgtc  6960
aaaaagggtg gagccaagaa aagacccgcc cccagtgacg cagatataag tgagcccaaa  7020
cgggtgcgcg agtcagttgc gcagccatcg acgtcagacg cggaagcttc gatcaactac  7080
gcagacaggt accaaaacaa atgttctcgt cacgtgggca tgaatctgat gctgtttccc  7140
tgcagacaat gcgagagaat gaatcagaat tcaaatatct gcttcactca cggacagaaa  7200
gactgtttag agtgctttcc cgtgtcagaa tctcaacccg tttctgtcgt caaaaaggcg  7260
tatcagaaac tgtgctacat tcatcatatc atgggaaagg tgccagacgc ttgcactgcc  7320
tgcgatctgg tcaatgtgga tttggatgac tgcatctttg aacaataaac tagtttgctt  7380
gttaatcaat aaaccgttta attcgtttca gttgaacttt ggtctctgcg tatttctttc  7440
ttatctagtt tccatgctct agagtatacg atatccatca cactggcggc cgctcgacta  7500
gagcggccgc caccgcggtg gagctccagc ttttgttcgc gcgcttggcg taatcatggt  7560
catagctgtt tcctgtgtga aattccacag cctggggtgc ctaattgcgt tgcgctcact  7620
gcccgctttc cagtcgggaa acctgtcgtg ccagctgcat taatgaatcg gccaacgcgc  7680
ggggagaggc ggtttgcgta ttgggcgctc ttccgcttcc tcgctcactg actcgctgcg  7740
ctcggtcgtt cggctgcggc gagcggtatc agctcactca aaggcggtaa tacggttatc  7800
cacagaatca ggggataacg caggaaagaa catgtgagca aaaggccagc aaaaggccag  7860
gaaccgtaaa aaggccgcgt tgctggcgtt tttccatagg ctccgccccc ctgacgagca  7920
tcacaaaaat cgacgctcaa gtcagaggtg gcgaaacccg acaggactat aaagatacca  7980
ggcgtttccc cctggaagct ccctcgtgcg ctctcctgtt ccgaccctgc cgcttaccgg  8040
atacctgtcc gcctttctcc cttcgggaag cgtggcgctt tctcatagct cacgctgtag  8100
gtatctcagt tcggtgtagg tcgttcgctc caagctgggc tgtgtgcacg aaccccccgt  8160
tcagcccgac cgctgcgcct tatccggtaa ctatcgtctt gagtccaacc cggtaagaca  8220
cgacttatcg ccactggcag cagccactgg taacaggatt agcagagcga ggtatgtagg  8280
cggtgctaca gagttcttga agtggtggcc taactacggc tacactagaa gaacagtatt  8340
tggtatctgc gctctgctga agccagttac cttcggaaaa agagttggta gctcttgatc  8400
cggcaaacaa accaccgctg gtagcggtgg tttttttgtt tgcaagcagc agattacgcg  8460
cagaaaaaaa ggatctcaag aagatccttt gatcttttct acggggtctg acgctcagtg  8520
gaacgaaaac tcacgttaag ggattttggt catgagatta tcaaaaagga tcttcaccta  8580
gatcctttta aattaaaaat gaagttttaa atcaatctaa agtatatatg agtaaacttg  8640
gtctgacaga aataataaaa aagccggatt aataatctgg ctttttatat tctctctcta  8700
gtatataaac gcagaaaggc ccacccgaag gtgagccagt gtgactctag tattattaga  8760
aaaactcatc gagcatcaaa tgaaactgca atttattcat atcaggatta tcaataccat  8820
atttttgaaa aagccgtttc tgtaatgaag gagaaaactc accgaggcag ttccaaagaa  8880
tggcaaggtc ctggtaacgg tctgcgattc cgacccgtcc aacatcaata caacctatta  8940
atttcccctc gtcaaaaata aggttatcaa gtgagaaatc accatgagtg acgactgaat  9000
ccggtgagaa tggcaagagc ttgtgcattt ctttccagac ttgttcaaca ggccagccat  9060
tacgctcgtc atcaaaatca ctcgcatcaa ccaaaccgtt attcatgcgt gattgcgcct  9120
gagcaagacg aaatacacga tcgctgttaa aaggacaatt acaaacagga atcgaatgta  9180
accggcgcag gaacacggcc agcgcatcaa caatattttc acctgaatca ggatattctt  9240
ctaatacctg gaaggctgtt ttcccaggaa tcgcggtggt gagtaaccac gcatcatcag  9300
gagtacggat aaaatgcttg atggtcggga gaggcataaa ctccgtcagc cagttgagac  9360
ggaccatctc atctgtaaca tcattggcaa cgctaccttt gccatgtttc agaaacaact  9420
ctggcgcatc gggcttccca tacaagcgat agattgtcgc acctgattgc ccgacattat  9480
cgcgagccca tttataccca tataaatcag cgtccatgtt ggagtttaag cgcggacggg  9540
agcaagacgt ttcccgttga atatggctca taacacccct tgtattactg tttatgtaag  9600
cagacagttt tattgttcat gatgatatat ttttatcttg tgcaatgtaa catcagagat  9660
tttgagacac aacgtggctt tgttgaataa atcgaacttt tgctgagttg aaggatcagc  9720
tctagtaaaa taataaaaaa gccggattaa taatctggct tttatattc tctctctagt  9780
atataaacgc agaaaggccc acccgaaggt gagccagtgt gacggcacat ttccccgaaa  9840
agtgccacct aaattgtaag cgttaatatt ttgttaaaat tcgcgttaaa tttttgttaa  9900
atcagctcat tttttaacca ataggccgaa atcggcaaaa tcccttataa atcaaaagaa  9960
tagaccgaga tagggttgag tgttgttcca gtttggaaca agagtccact attaaagaac  10020
gtggactcca acgtcaaagg gcgaaaaacc gtctatcagg gcgatggccc actacgtgaa  10080
ccatcaccct aatcaagttt tttggggtcg aggtgccgta aagcactaaa tcggaaccct  10140
aaagggagcc cccgatttag agcttgacgg ggaaagccgg cgaacgtggc gagaaaggaa  10200
gggaagaaag cgaaaggagc gggcgctagg gcgctggcaa gtgtagcggt cacgctgcgc  10260
gtaaccacca cacccgccgc gcttaatgcg ccgctacagg gcgcgtccca ttcgccattc  10320
aggctgcgca actgttggga agggcgatcg gtgcgggcct cttcgctatt acgccagctg  10380
gcgaaagggg gatgtgctgc aaggcgatta agttgggtaa cgccagggtt ttcccagtca  10440
cgacgttgta aaacgacggc cagtgagcgc gcggcgaatt gggtaccggg ccccc       10495

SEQ ID NO: 19          moltype = DNA  length = 10493
FEATURE                Location/Qualifiers
misc_feature           1..10493
                       note = Description of Artificial Sequence: Synthetic
                        polynucleotide
source                 1..10493
                       mol_type = other DNA
                       organism = synthetic construct
```

```
SEQUENCE: 19
cctcgagggc tagccattct atttaatctc cctatcagtg atagagatcg cccgagtgag  60
cacgcagggt ctccatttg atccctatca gtgatagaga agcgggaggt ttgaacgcgc  120
agccgccatg ccggggtttt acgagattgt gattaaggtc cccagcgacc ttgacgagca  180
tctgcccggc atttctgaca gctttgtgaa ctgggtggcc gagaaggaat gggagttgcc  240
gccagattct gacatggatc tgaatctgat tgagcaggca cccctgaccg tggccgagaa  300
gctgcagcgc gactttctga cggaatggcg ccgtgtgagt aaggccccgg aggctctttt  360
ctttgtgcaa tttgagaagg gagagagcta cttccacatg cacgtgctcg tggaaaccac  420
cggggtgaaa tccatggttt tgggacgttt cctgagtcag attcgcgaaa aactgattca  480
gagaatttac cgcgggatcg agccgacttt gccaaactgg ttcgcggtca caaagaccag  540
aaatggcgcc ggaggcggga acaaggtggt ggatgagtgc tacatcccca attacttgct  600
ccccaaaacc cagcctgagc tccaatgggc atggaccaac atggaacagt acctcagcgc  660
ctgtttgaat ctcacggagc gtaaacggtt ggtggcgcag catctgacgc acgtgtcgca  720
gacgcaggag cagaacaaag agaatcagaa tcccaattct gatgcgccgg tgatcagatc  780
aaaaacttca gccaggtaca tggagctggt cgggtggctc gtggacaagg ggattacctc  840
ggagaagcag tggatccagg aggaccaggc ctcatacatc tccttcaatg cggcctccaa  900
ctcgcggtcc caaatcaagg ctgccttgga caatgcggga aagattatga gcctgactaa  960
aaccgccccc gactacctgg tgggccagca gcccgtggag gacatttcca gcaatcggat  1020
ttataaaatt ttggaactaa acgggtacga tccccaatat gcggcttccg tctttctggg  1080
atgggccacg aaaaagttcg gcaagaggaa caccatctgg ctgtttgggc ctgcaactac  1140
cgggaagacc aacatcgcgg aggccatagc ccacactgtg cccttctacg ggtgcgtaaa  1200
ctggaccaat gagaactttc ccttcaacga ctgtgtcgac aagatggtga tctggtggga  1260
ggaggggaag atgaccgcca aggtcgtgga gtcggccaaa gccattctcg gaggaagcaa  1320
ggtgcgcgtg gaccagaaat gcaagtcctc ggcccagata gacccgactc ccgtgatcgt  1380
cacctccaac accaacatgt gcgccgtgat tgacgggaac tcaacgacct tcgaacacca  1440
gcagccgttg caagaccgga tgttcaaatt tgaactcacc cgccgtctgg atcatgactt  1500
tgggaaggtc accaagcagg aagtcaaaga ctttttccgg tgggcaaagg atcacgtggt  1560
tgaggtggag catgaattct acgtcaaaaa gggtggagcc aagaaaagac ccgcccccag  1620
tgacgcagat ataagtgagc ccaaacgggt gcgcgagtca gttgcgcagc catcgacgtc  1680
agacgcggaa gcttcgatca actacgcaga caggtaccaa aacaaatgtt ctcgtcacgt  1740
gggcatgaat ctgatgctgt ttccctgcag acaatgcgag agaatgaatc agaattcaaa  1800
tatctgcttc actcacggac agaaagactg tttagagtgc tttcccgtgt cagaatctca  1860
acccgtttct gtcgtcaaaa aggcgtatca gaaactgtgc tacattcatc atatcatggg  1920
aaaggtgcca gacgcttgca ctgcctgcga tctggtcaat gtggatttgg atgactgcat  1980
ctttgaacaa taaatgattt aaatcaggta tggctgccga tggttatctt ccagattggc  2040
tcgaggacaa cctctctgag ggcattcgcg agtggtggga cttgaaacct ggagccccga  2100
aacccaaagc caaccagcaa aagcaggacg acggccgggg tctggtgctt cctggctaca  2160
agtacctcgg acccttcaac ggactcgaca agggggagcc cgtcaacgcg gcggacgcag  2220
cggccctcga gcacgacaag gcctacgacc agcagctcaa agcgggtgac aatccgtacc  2280
tgcggtataa ccacgccgac gccgagtttc aggagcgtct gcaagaagat acgtcttttg  2340
ggggcaacct cgggcgagca gtcttccagg ccaagaagcg ggttctcgaa cctctcggtc  2400
tggttgagga aggcgctaag acggctcctg gaaagaagag accggtagag caatcacccc  2460
aggaaccaga ctcctcttcg ggcatcggca agaaaggcca gcagcccgcg agaaagagac  2520
tcaactttgg gcagactggc gactcagagt cagtgcccga ccctcaacca ctcggagaac  2580
cccccgcagc cccctctggt gtgggatcta atacaatggc tgcaggcggt ggcgctccaa  2640
tggcagacaa taacgaaggc gccgacggag tgggtaacgc ctcaggaaat tggcattgcg  2700
attccacatg gctgggcgac agagtcatca ccaccagcac ccgaacctgg gccctcccca  2760
cctacaacaa ccacctctac aagcaaatct ccagccaatc gggaggcagc accaacgaca  2820
acacctactt cggctacagc acccccctggg ggtattttga ctttaacaga ttccactgcc  2880
acttctcacc acgtgactgg cagcgactca tcaacaacaa ctggggattc cggcccaaga  2940
agctcaactt caagctcttc aacatccagg tcaaggaggt cacgacgaat gatggcacca  3000
cgaccatcgc caataacctt accagcacgg ttcaggtctt tacggactcg gaataccagc  3060
tcccgtacgt cctcggctct gcgcaccagg gctgcctgcc tccgttcccg gcggacgtct  3120
tcatgattcc tcagtacggg tacctgactc tgaacaatgg cagtcaggcc gtgggccgtt  3180
cctccttcta ctgcctggaa tactttcctt ctcaaatgct gagaacgggc aacaactttc  3240
agttcagcta cacgtttgag gacgtgcctt ttcacagcag ctacgcgcac agccaaagcc  3300
tggaccggct gatgaacccc ctcatcgacc agtacctgta ctacctgtct cggactcaga  3360
ccacgagtgg taccgcagga aatcggacgt tgcaattttc tcaggccggg cctagtagca  3420
tggcgaatca ggccaaaaac tggctacccg ggccctgcta ccggcagcaa cgcgtctcca  3480
agacaaccaa tcaaaataac aacagcaact ttgcctggac cggtgccacc aagtatcatc  3540
tgaatggcag agactctctg gtaaatcccg gtcccgctat ggcaacccac aaggacgacg  3600
aagacaaatt ttttccgatg agcggagtct taatatttgg gaaacaggga gctggaaata  3660
gcaacgtgga ccttgacaac gttatgataa ccaacgagga agaaattaaa accaccaacc  3720
cagtggccac agaagagtac ggcacggtgg ccactaacct gcaatcggcc aacaccgctc  3780
ctgctacagg gaccgtcaac agtcaaggag ccttacctgg catggtctgg caggaccggg  3840
acgtgtacct gcagggtcct atctgggcca agattcctca cacggacgga cactttcatc  3900
cctcgccgct gatgggaggc tttggactga aacacccgcc tcctcagatc ctgattaaga  3960
atacacctgt tcccgcgaat cctccaacta ccttcagtcc agctaagttt gcgtcgttca  4020
tcacgcagta cagcaccgga caggtcagcg tggaaattga atgggagctg cagaaagaaa  4080
acagcaaacg ctggaaccca gagattcaat acacttccaa ctacaacaaa tctacaaatg  4140
tggactttgc tgttgacaca aatggcgttt attctgagcc tcgccccatc ggcacccgtt  4200
acctcacccg taatctgtaa actagtttgc ttgttaatca ataaaccgtt taattcgttt  4260
cagttgaact ttggtctctg cgtatttctt tcttatctag tttccatgct ctagaggtcc  4320
tgtattagag gtcacgtgag tgttttgcga cattttgcga caccatgtgg tcacgctggg  4380
tatttaagcc cgagtgagca cgcagggtct ccattttgaa gcgggaggtt tgaacgcgca  4440
gccgccaagc cgaattctgc agatatcggg gttggggttg cgccttttcc aaggcagccc  4500
tgggtttgcg cagggacgcg gctgctctgg gcgtggttcc gggaaacgca gcggcgccga  4560
ccctgggtct cgcacattct tcacgtccgt tcgcagcgtc acccggatct tcgccgctac  4620
ccttgtgggc cccccggcga cgcttcctgc tccgcccta agtcgggaag gttccttgcg  4680
```

-continued

```
gttcgcggcg tgccggacgt gacaaacgga agccgcacgt ctcactagta ccctcgcaga  4740
cggacagcgc cagggagcaa tggcagcgcg ccgaccgcga tgggctgtgg ccaatagcgg  4800
ctgctcagca gggcgcgccg agagcagcgg ccgggaaggg gcggtgcggg aggcggggtg  4860
tggggcggta gtgtgggccc tgttcctgcc cgcgcggtgt tccgcattct gcaagcctcc  4920
ggagcgcacg tcggcagtcg gctccctcgt tgaccgaatc accgacctct ctccccagaa  4980
gctcccggga gcttgtatat ccatttttcgg atctgatcag cacgtgttga caattaatca  5040
tcggcatagt atatcggcat agtataatac gacaaggtga ggaacgccac catggccaag  5100
cctttgtctc aagaagaatc caccctcatt gaaagagcaa cggctacaat caacagcatc  5160
cccatctctg aagactacag cgtcgccagc gcagctctct ctagcgacgg ccgcatcttc  5220
actggtgtca atgtatatca ttttactggg ggaccttgtg cagaactcgt ggtgctgggc  5280
actgctgctg ctgcggcagc tggcaacctg acttgtatcg tcgcgatcgg aaatgagaac  5340
aggggcatct tgagcccctg cggacggtgc cgacaggtgc ttctcgatct gcatcctggg  5400
atcaaagcca tagtgaagga cagtgatgga cagccgacgg cagttgggat tcgtgaattg  5460
ctgccctctg gttatgtgtg ggagggctaa gcacttcgtg gccgaggagc aggactgaca  5520
cgtgctacga gatttcgatt ccaccgccgc cttctatgaa aggttgggct tcggaatcgt  5580
tttccgggac gccggctgga tgatcctcca gcgcggggat ctcatgctgg agttcttcgc  5640
ccaccccaac ttgtttattg cagcttataa tggttacaaa taaagcaata gcatcacaaa  5700
tttcacaaat aaagcatttt tttcactgca ttctagttgt ggtttgtcca aactcatcaa  5760
tgtatcttag cgctcactgc ccgctttcca gtcgggaaac ctgtcgtgcc agctgcatta  5820
atgaatcggc caacgcgcgg ggagaggcgg tttgcgtatt gggcgctctc ctaggccaga  5880
aatggcgccg gaggcgggaa caaggtggtg gatgagtgct acatccccaa ttacttgctc  5940
cccaaaaccc agcctgagtc cctatcagtg atagagactc cagtgggcgt ggactaatat  6000
ggaacagtat ttaagcgcct gtccctatca gtgatagaga tttgaatctc acggagcgta  6060
aacggttggt ggcgcagcat ctgtttaaac gcagacgcag gagcagaaca aagagaatca  6120
gaatcccaat tctgatgcgc cggtgatcag atcaaaaact tcagccaggt acatggagct  6180
ggtcgggtgg ctcgtggaca aggggattac ctcggagaag cagtggattc aggaggacca  6240
ggcctcatac atctccttca atgcggcctc caactcgcgg tcccaaatca aggctgcctt  6300
ggacaatgcg ggaaagatta tgagcctgac taaaaccgcc cccgactacc tggtgggcca  6360
gcagcccgtg gaggacattt ccagcaatcg gatttataaa atttggaac taaacgggta  6420
cgatccccaa tatgcggctt ccgtctttct gggatgggcc acgaaaaagt tcggcaagag  6480
gaacaccatc tggctgtttg ggcctgcaac taccgggaag accaacatcg cggaggccat  6540
agcccacact gtgcccttct acgggtgcgt aaactggacc aatgagaact ttcccttcaa  6600
cgactgtgtc gacaagatgg tgatctggtg ggaggagggg aagatgaccg ccaaggtcgt  6660
ggagtcggcc aaagccattc tcggaggaag caaggtgcgc gtggaccaga aatgcaagtc  6720
ctcggcccag atagacccga ctcccgtgat cgtcacctcc aacaccaaca tgtgcgccgt  6780
gattgacggg aactcaacga ccttcgaaca ccagcagccg ttgcaagacc ggatgttcaa  6840
atttgaactc acccgccgtc tggatcatga ctttgggaag gtcaccaagc aggaagtcaa  6900
agactttttc cggtgggcaa aggatcacgt ggttgaggtg gagcatgaat tctacgtcaa  6960
aaagggtgga gccaagaaaa gacccgcccc cagtgacgca gatataagtg agcccaaacg  7020
ggtgcgcgag tcagttgcgc agccatcgac gtcagacgcg gaagcttcga tcaactacgc  7080
agacaggtac caaaacaaat gttctcgtca cgtgggcatg aatctgatgc tgtttccctg  7140
cagacaatgc gagagaatga atcagaattc aaatatctgc ttcactcacg gacagaaaga  7200
ctgtttagag tgctttcccg tgtcagaatc tcaacccgtt tctgtcgtca aaaaggcgta  7260
tcagaaactg tgctacattc atcatatcat gggaaaggtg ccagacgctt gcactgcctg  7320
cgatctggtc aatgtggatt tggatgactg catctttgaa caataaacta gtttgcttgt  7380
taatcaataa accgtttaat tcgtttcagt tgaactttgg tctctgcgta tttctttctt  7440
atctagtttc catgctctag agtatacgat atccatcaca ctggcggccg ctcgactaga  7500
gcggccgcca ccgcggtgga gctccagctt ttgttcgcgc gcttggcgta atcatggtca  7560
tagctgtttc ctgtgtgaaa ttccacagcc tggggtgcct aattgcgttg cgctcactgc  7620
ccgctttcca gtcgggaaac ctgtcgtgcc agctgcatta atgaatcggc caacgcgcgg  7680
ggagaggcgg tttgcgtatt gggcgctctt ccgcttcctc gctcactgac tcgctgcgct  7740
cggtcgttcg gctgcggcga gcggtatcag ctcactcaaa ggcggtaata cggttatcca  7800
cagaatcagg ggataacgca ggaaagaaca tgtgagcaaa aggccagcaa aaggccagga  7860
accgtaaaaa ggccgcgttg ctggcgtttt tccataggct ccgcccccct gacgagcatc  7920
acaaaaatcg acgctcaagt cagaggtggc gaaacccgac aggactataa agataccagg  7980
cgtttccccc tggaagctcc ctcgtgcgct ctcctgttcc gaccctgccg cttaccggat  8040
acctgtccgc ctttctccct tcgggaagcg tggcgctttc tcatagctca cgctgtaggt  8100
atctcagttc ggtgtaggtc gttcgctcca agctgggctg tgtgcacgaa ccccccgttc  8160
agcccgaccg ctgcgcctta tccggtaact atcgtcttga gtccaacccg gtaagacacg  8220
acttatcgcc actggcagca gccactggta acaggattag cagagcgagg tatgtaggcg  8280
gtgctacaga gttcttgaag tggtggccta actacggcta cactagaaga acagtatttg  8340
gtatctgcgc tctgctgaag ccagttacct tcggaaaaag agttggtagc tcttgatccg  8400
gcaaacaaac caccgctggt agcggtggtt tttttgtttg caagcagcag attacgcgca  8460
gaaaaaaagg atctcaagaa gatcctttga tcttttctac ggggtctgac gctcagtgga  8520
acgaaaactc acgttaaggg attttggtca tgagattatc aaaaaggatc ttcacctaga  8580
tccttttaaa ttaaaaatga agttttaaat caatctaaag tatatatgag taaacttggt  8640
ctgacagaaa taataaaaaa gccggattaa taatctggct ttttatattc tctctctagt  8700
atataaacgc agaaaggccc acccgaaggt gagccagtgt gactctagta ttattagaaa  8760
aactcatcga gcatcaaatg aaactgcaat ttattcatat caggattatc aataccatat  8820
ttttgaaaaa gccgtttctg taatgaagga gaaaactcac cgaggcagtt ccaaagaatg  8880
gcaaggtcct ggtaacggtc tgcgattccg acccgtccaa catcaataca acctattaat  8940
ttcccctcgt caaaaataag gttatcaagt gagaaatcac catgagtgac gactgaatcc  9000
ggtgagaatg gcaagagctt gtgcatttct ttccagactt gttcaacagg ccagccatta  9060
cgctcgtcat caaaatcact cgcatcaacc aaaccgttat tcatgcgtga ttgcgcctga  9120
gcaagacgaa atacacgatc gctgttaaaa ggacaattac aaacaggaat cgaatgtaac  9180
cggcgcagga acacggccag cgcatcaaca atattttcac ctgaatcagg atattcttct  9240
aatacctgga aggctgtttt cccaggaatc gcggtggtga gtaaccacgc atcatcagga  9300
gtacggataa aatgcttgat ggtcgggaga ggcataaact ccgtcagcca gttgagacgg  9360
accatctcat ctgtaacatc attggcaacg ctacctttgc catgtttcag aaacaactct  9420
```

```
ggcgcatcgg gcttcccata caagcgatag attgtcgcac ctgattgccc gacattatcg  9480
cgagcccatt tatacccata taaatcagcg tccatgttgg agtttaagcg cggacgggag  9540
caagacgttt cccgttgaat atggctcata acaccccttg tattactgtt tatgtaagca  9600
gacagtttta ttgttcatga tgatatattt ttatcttgtg caatgtaaca tcagagattt  9660
tgagacacaa cgtggctttg ttgaataaat cgaacttttg ctgagttgaa ggatcagctc  9720
tagtaaaata ataaaaaagc cggattaata atctggcttt ttatattctc tctctagtat  9780
ataaacgcag aaaggcccac ccgaaggtga gccagtgtga cggcacattt ccccgaaaag  9840
tgccacctaa attgtaagcg ttaatatttt gttaaaattc gcgttaaatt tttgttaaat  9900
cagctcattt tttaaccaat aggccgaaat cggcaaaatc ccttataaat caaaagaata  9960
gaccgagata gggttgagtg ttgttccagt ttggaacaag agtccactat taaagaacgt  10020
ggactccaac gtcaaagggc gaaaaaccgt ctatcagggc gatggcccac tacgtgaacc  10080
atcaccctaa tcaagttttt tggggtcgag gtgccgtaaa gcactaaatc ggaaccctaa  10140
agggagcccc cgatttagag cttgacgggg aaagccggcg aacgtggcga gaaaggaagg  10200
gaagaaagcg aaaggagcgg gcgctagggc gctggcaagt gtagcggtca cgctgcgcgt  10260
aaccaccaca cccgccgcgc ttaatgcgcc gctacagggc gcgtcccatt cgccattcag  10320
gctgcgcaac tgttgggaag ggcgatcggt gcgggcctct tcgctattac gccagctggc  10380
gaaaggggga tgtgctgcaa ggcgattaag ttgggtaacg ccagggtttt cccagtcacg  10440
acgttgtaaa acgacggcca gtgagcgcgc ggcgaattgg gtaccgggcc ccc         10493

SEQ ID NO: 20          moltype = DNA  length = 10491
FEATURE                Location/Qualifiers
misc_feature           1..10491
                       note = Description of Artificial Sequence: Synthetic
                        polynucleotide
source                 1..10491
                       mol_type = other DNA
                       organism = synthetic construct
SEQUENCE: 20
cctcgagggc tagccattct ccctatcagt gatagagatc tatttaagcc cgagtgagca  60
cgcagtccct atcagtgata gagaggtctc cattttgaag cgggaggttt gaacgcgcag  120
ccgccatgcc ggggttttac gagattgtga ttaaggtccc cagcgacctt gacgagcatc  180
tgcccggcat ttctgacagc tttgtgaact gggtggccga gaaggaatgg gagttgccgc  240
cagattctga catggatctg aatctgattg agcaggcacc cctgaccgtg gccgagaagc  300
tgcagcgcga ctttctgacg gaatggcgcc gtgtgagtaa ggccccggag gctcttttct  360
ttgtgcaatt tgagaaggga gagagctact tccacatgca cgtgctcgtg gaaaccaccg  420
gggtgaaatc catggttttg ggacgtttcc tgagtcagat tcgcgaaaaa ctgattcaga  480
gaatttaccg cgggatcgag ccgactttgc caaactggtt cgcggtcaca aagaccagaa  540
atggcgccgg aggcgggaac aaggtggtgg atgagtgcta catccccaat tacttgctcc  600
ccaaaaccca gcctgagctc caatgggcat ggaccaacat ggaacagtac ctcagcgcct  660
gtttgaatct cacggagcgt aaacggttgg tggcgcagca tctgacgcac gtgtcgcaga  720
cgcaggagca gaacaaagag aatcagaatc ccaattctga tgcgccggtg atcagatcaa  780
aaacttcagc caggtacatg gagctggtcg ggtggctcgt ggacaagggg attacctcgg  840
agaagcagtg gatccaggag gaccaggcct catacatctc cttcaatgcg gcctccaact  900
cgcggtccca aatcaaggct gccttggaca atgcgggaaa gattatgagc ctgactaaaa  960
ccgcccccga ctacctggtg ggccagcagc ccgtggagga catttccagc aatcggattt  1020
ataaaatttt ggaactaaac gggtacgatc cccaatatgc ggcttccgtc tttctgggat  1080
gggccacgaa aaagttcggc aagaggaaca ccatctggct gtttgggcct gcaactaccg  1140
ggaagaccaa catcgcggag gccatagccc acactgtgcc cttctacggg tgcgtaaact  1200
ggaccaatga gaactttccc ttcaacgact gtgtcgacaa gatggtgatc tggtgggagg  1260
aggggaagat gaccgccaag gtcgtggagt cggccaaagc cattctcgga ggaagcaagg  1320
tgcgcgtgga ccagaaatgc aagtcctcgg cccagataga cccgactccc gtgatcgtca  1380
cctccaacac caacatgtgc gccgtgattg acgggaactc aacgaccttc gaacaccagc  1440
agccgttgca agaccggatg ttcaaatttg aactcacccg ccgtctggat catgactttg  1500
ggaaggtcac caagcaggaa gtcaaagact ttttccggtg ggcaaaggat cacgtggttg  1560
aggtggagca tgaattctac gtcaaaaagg gtggagccaa gaaaagaccc gcccccagtg  1620
acgcagatat aagtgagccc aaacgggtgc gcgagtcagt tgcgcagcca tcgacgtcag  1680
acgcggaagc ttcgatcaac tacgcagaca ggtaccaaaa caaatgttct cgtcacgtgg  1740
gcatgaatct gatgctgttt ccctgcagac aatgcgagag aatgaatcag aattcaaata  1800
tctgcttcac tcacggacag aaagactgtt tagagtgctt tcccgtgtca gaatctcaac  1860
ccgtttctgt cgtcaaaaag gcgtatcaga aactgtgcta cattcatcat atcatgggaa  1920
aggtgccaga cgcttgcact gcctgcgatc tggtcaatgt ggatttggat gactgcatct  1980
ttgaacaata aatgatttaa atcaggtatg gctgccgatg gttatcttcc agattggctc  2040
gaggacaacc tctctgaggg cattcgcgag tggtgggact tgaaacctgg agccccgaaa  2100
cccaaagcca accagcaaaa gcaggacgac ggccggggtc tggtgcttcc tggctacaag  2160
tacctcggac ccttcaacgg actcgacaag ggggagcccg tcaacgcggc ggacgcagcg  2220
gccctcgagc acgacaaggc ctacgaccag cagctcaaag cgggtgacaa tccgtacctg  2280
cggtataacc acgccgacgc cgagtttcag gagcgtctgc aagaagatac gtcttttggg  2340
ggcaacctcg ggcgagcagt cttccaggcc aagaagcggg ttctcgaacc tctcggtctg  2400
gttgaggaag gcgctaagac ggctcctgga aagaagagac cggtagagca atcaccccag  2460
gaaccagact cctcttcggg catcggcaag aaaggccagc agcccgcgag aaagagactc  2520
aactttgggc agactggcga ctcagagtca gtgcccgacc ctcaaccact cggagaaccc  2580
cccgcagccc cctctggtgt gggatctaat acaatggctg caggcggtgg cgctccaatg  2640
gcagacaata acgaaggcgc cgacggagtg ggtaacgcct caggaaattg gcattgcgat  2700
tccacatggc tgggcgacag agtcatcacc accagcaccc gaacctgggc cctccccacc  2760
tacaacaacc acctctacaa gcaaatctcc agccaatcgg gaggcagcac caacgacaac  2820
acctacttcg gctacagcac cccctggggg tattttgact ttaacagatt ccactgccac  2880
ttctcaccac gtgactggca gcgactcatc aacaacaact ggggattccg gcccaagaag  2940
ctcaacttca agctcttcaa catccaggtc aaggaggtca cgacgaatga tggcaccacg  3000
accatcgcca ataaccttac cagcacggtt caggtcttta cggactcgga ataccagctc  3060
```

```
ccgtacgtcc tcggctctgc gcaccagggc tgcctgcctc cgttcccggc ggacgtcttc  3120
atgattcctc agtacgggta cctgactctg aacaatggca gtcaggccgt gggccgttcc  3180
tccttctact gcctggaata ctttccttct caaatgctga gaacgggcaa caactttcag  3240
ttcagctaca cgtttgagga cgtgcctttt cacagcagct acgcgcacag ccaaagcctg  3300
gaccggctga tgaaccccct catcgaccag tacctgtact acctgtctcg gactcagacc  3360
acgagtggta ccgcaggaaa tcggacgttg caattttctc aggccgggcc tagtagcatg  3420
gcgaatcagg ccaaaaactg gctacccggg ccctgctacc ggcagcaacg cgtctccaag  3480
acaaccaatc aaaataacaa cagcaacttt gcctggaccg gtgccaccaa gtatcatctg  3540
aatggcagag actctctggt aaatcccggt cccgctatgg caacccacaa ggacgacgaa  3600
gacaaatttt ttccgatgag cggagtctta atatttggga aacagggagc tggaaatagc  3660
aacgtggacc ttgacaacgt tatgataacc aacgaggaag aaattaaaac caccaaccca  3720
gtggccacag aagagtacgg cacggtggcc actaacctgc aatcggccaa caccgctcct  3780
gctacaggga ccgtcaacag tcaaggagcc ttacctggca tggtctggca ggaccgggac  3840
gtgtacctgc agggtcctat ctgggccaag attcctcaca cggacggaca ctttcatccc  3900
tcgccgctga tgggaggctt tggactgaaa cacccgcctc ctcagatcct gattaagaat  3960
acacctgttc ccgcgaatcc tccaactacc ttcagtccag ctaagtttgc gtcgttcatc  4020
acgcagtaca gcaccggaca ggtcagcgtg gaaattgaat gggagctgca gaaagaaaac  4080
agcaaacgct ggaacccaga gattcaatac acttccaact acaacaaatc tacaaatgtg  4140
gactttgctg ttgacacaaa tggcgtttat tctgagcctc gccccatcgg cacccgttac  4200
ctcacccgta atctgtaaac tagtttgctt gttaatcaat aaaccgttta attcgtttca  4260
gttgaacttt ggtctctgcg tatttctttc ttatctagtt tccatgctct agaggtcctg  4320
tattagaggt cacgtgagtg ttttgcgaca ttttgcgaca ccatgtggtc acgctgggta  4380
tttaagcccg agtgagcacg cagggtctcc attttgaagc gggaggtttg aacgcgcagc  4440
cgccaagccg aattctgcag atatcggggt tggggttgcg ccttttccaa ggcagccctg  4500
ggtttgcgca gggacgcggc tgctctgggc gtggttccgg gaaacgcagc ggcgccgacc  4560
ctgggtctcg cacattcttc acgtccgttc gcagcgtcac ccggatcttc gccgctaccc  4620
ttgtgggccc cccggcgacg cttcctgctc cgcccctaag tcgggaaggt tccttgcggt  4680
tcgcggcgtg ccggacgtga caaacggaag ccgcacgtct cactagtacc ctcgcagacg  4740
gacagcgcca gggagcaatg gcagcgcgcc gaccgcgatg ggctgtggcc aatagcggct  4800
gctcagcagg gcgcgccgag agcagcggcc gggaaggggc ggtgcgggag gcggggtgtg  4860
gggcggtagt gtgggccctg ttcctgcccg cgcggtgttc cgcattctgc aagcctccgg  4920
agcgcacgtc ggcagtcggc tccctcgttg accgaatcac cgacctctct ccccagaagc  4980
tcccgggagc ttgtatatcc attttcggat ctgatcagca cgtgttgaca attaatcatc  5040
ggcatagtat atcggcatag tataatacga caaggtgagg aacgccacca tggccaagcc  5100
tttgtctcaa gaagaatcca ccctcattga aagagcaacg gctacaatca acagcatccc  5160
catctctgaa gactacagcg tcgccagcgc agctctctct agcgacggcc gcatcttcac  5220
tggtgtcaat gtatatcatt ttactggggg accttgtgca gaactcgtgg tgctgggcac  5280
tgctgctgct gcggcagctg gcaacctgac ttgtatcgtc gcgatcggaa atgagaacag  5340
gggcatcttg agcccctgcg gacggtgccg acaggtgctt ctcgatctgc atcctgggat  5400
caaagccata gtgaaggaca gtgatggaca gccgacggca gttgggattc gtgaattgct  5460
gccctctggt tatgtgtggg agggctaagc acttcgtggc cgaggagcag gactgacacg  5520
tgctacgaga tttcgattcc accgccgcct tctatgaaag gttgggcttc ggaatcgttt  5580
tccgggacgc cggctggatg atcctccagc gcggggatct catgctggag ttcttcgccc  5640
accccaactt gtttattgca gcttataatg gttacaaata aagcaatagc atcacaaatt  5700
tcacaaataa agcatttttt tcactgcatt ctagttgtgg tttgtccaaa ctcatcaatg  5760
tatcttagcg ctcactgccc gctttccagt cgggaaacct gtcgtgccag ctgcattaat  5820
gaatcggcca acgcgcgggg agaggcggtt tgcgtattgg gcgctctcct aggccagaaa  5880
tggcgccgga ggcgggaaca aggtggtgga tgagtgctac atccccaatt acttgctccc  5940
caaaacccag cctgagtccc tatcagtgat agagactcca gtgggcgtgg actaatatgg  6000
aacagtattt aagcgcctgt ccctatcagt gatagagatt tgaatctcac ggagcgtaaa  6060
cggttggtgg cgcagcatct gtttaaacgc agacgcagga gcagaacaaa gagaatcaga  6120
atcccaattc tgatgcgccg gtgatcagat caaaaacttc agccaggtac atggagctgg  6180
tcgggtggct cgtggacaag ggattacct cggagaagca gtggattcag gaggaccagg  6240
cctcatacat ctccttcaat gcggcctcca actcgcggtc ccaaatcaag gctgccttgg  6300
acaatgcggg aaagattatg agcctgacta aaaccgcccc cgactacctg gtgggccagc  6360
agcccgtgga ggacatttcc agcaatcgga tttataaaat tttggaacta aacgggtacg  6420
atccccaata tgcggcttcc gtctttctgg gatgggccac gaaaaagttc ggcaagagga  6480
acaccatctg gctgtttggg cctgcaacta ccgggaagac caacatcgcg gaggccatag  6540
cccacactgt gcccttctac gggtgcgtaa actggaccaa tgagaacttt cccttcaacg  6600
actgtgtcga caagatggtg atctggtggg aggaggggaa gatgaccgcc aaggtcgtgg  6660
agtcggccaa agccattctc ggaggaagca aggtgcgcgt ggaccagaaa tgcaagtcct  6720
cggcccagat agacccgact cccgtgatcg tcacctccaa caccaacatg tgcgccgtga  6780
ttgacgggaa ctcaacgacc ttcgaacacc agcagccgtt gcaagaccgg atgttcaaat  6840
ttgaactcac ccgccgtctg gatcatgact ttgggaaggt caccaagcag gaagtcaaag  6900
actttttccg gtgggcaaag gatcacgtgg ttgaggtgga gcatgaattc tacgtcaaaa  6960
agggtggagc caagaaaaga cccgccccca gtgacgcaga tataagtgag cccaaacggg  7020
tgcgcgagtc agttgcgcag ccatcgacgt cagacgcgga agcttcgatc aactacgcag  7080
acaggtacca aaacaaatgt tctcgtcacg tgggcatgaa tctgatgctg tttccctgca  7140
gacaatgcga gagaatgaat cagaattcaa atatctgctt cactcacgga cagaaagact  7200
gtttagagtg ctttcccgtg tcagaatctc aacccgtttc tgtcgtcaaa aaggcgtatc  7260
agaaactgtg ctacattcat catatcatgg gaaaggtgcc agacgcttgc actgcctgcg  7320
atctggtcaa tgtggatttg gatgactgca tctttgaaca ataaactagt ttgcttgtta  7380
atcaataaac cgtttaattc gtttcagttg aactttggtc tctgcgtatt tctttcttat  7440
ctagtttcca tgctctagag tatacgatat ccatcacact ggcggccgct cgactagagc  7500
ggccgccacc gcggtggagc tccagctttt gttcgcgcgc ttggcgtaat catggtcata  7560
gctgtttcct gtgtgaaatt ccacagcctg gggtgcctaa ttgcgttgcg ctcactgccc  7620
gctttccagt cgggaaacct gtcgtgccag ctgcattaat gaatcggcca acgcgcgggg  7680
agaggcggtt tgcgtattgg gcgctcttcc gcttcctcgc tcactgactc gctgcgctcg  7740
gtcgttcggc tgcggcgagc ggtatcagct cactcaaagg cggtaatacg gttatccaca  7800
```

```
gaatcagggg ataacgcagg aaagaacatg tgagcaaaag gccagcaaaa ggccaggaac  7860
cgtaaaaagg ccgcgttgct ggcgtttttc cataggctcc gcccccctga cgagcatcac  7920
aaaaatcgac gctcaagtca gaggtggcga aacccgacag gactataaag ataccaggcg  7980
tttccccctg gaagctccct cgtgcgctct cctgttccga ccctgccgct taccggatac  8040
ctgtccgcct ttctcccttc gggaagcgtg gcgctttctc atagctcacg ctgtaggtat  8100
ctcagttcgg tgtaggtcgt tcgctccaag ctgggctgtg tgcacgaacc ccccgttcag  8160
cccgaccgct gcgccttatc cggtaactat cgtcttgagt ccaacccggt aagacacgac  8220
ttatcgccac tggcagcagc cactggtaac aggattagca gagcgaggta tgtaggcggt  8280
gctacagagt tcttgaagtg gtggcctaac tacggctaca ctagaagaac agtatttggt  8340
atctgcgctc tgctgaagcc agttaccttc ggaaaaagag ttggtagctc ttgatccggc  8400
aaacaaacca ccgctggtag cggtggtttt tttgtttgca agcagcagat tacgcgcaga  8460
aaaaaaggat ctcaagaaga tcctttgatc ttttctacgg ggtctgacgc tcagtggaac  8520
gaaaactcac gttaagggat tttggtcatg agattatcaa aaaggatctt cacctagatc  8580
cttttaaatt aaaaatgaag ttttaaatca atctaaagta tatatgagta aacttggtct  8640
gacagaaata ataaaaaagc cggattaata atctggcttt ttatattctc tctctagtat  8700
ataaacgcag aaaggcccac ccgaaggtga gccagtgtga ctctagtatt attagaaaaa  8760
ctcatcgagc atcaaatgaa actgcaattt attcatatca ggattatcaa taccatattt  8820
ttgaaaaagc cgtttctgta atgaaggaga aaactcaccg aggcagttcc aaagaatggc  8880
aaggtcctgg taacggtctg cgattccgac ccgtccaaca tcaatacaac ctattaattt  8940
cccctcgtca aaaataaggt tatcaagtga gaaatcacca tgagtgacga ctgaatccgg  9000
tgagaatggc aagagcttgt gcatttcttt ccagacttgt tcaacaggcc agccattacg  9060
ctcgtcatca aaatcactcg catcaaccaa accgttattc atgcgtgatt gcgcctgagc  9120
aagacgaaat acacgatcgc tgttaaaagg acaattacaa acaggaatcg aatgtaaccg  9180
gcgcaggaac acggccagcg catcaacaat attttcacct gaatcaggat attcttctaa  9240
tacctggaag gctgttttcc caggaatcgc ggtggtgagt aaccacgcat catcaggagt  9300
acggataaaa tgcttgatgg tcgggagagg cataaactcc gtcagccagt tgagacggac  9360
catctcatct gtaacatcat tggcaacgct acctttgcca tgtttcagaa acaactctgg  9420
cgcatcgggc ttcccataca agcgatagat tgtcgcacct gattgcccga cattatcgcg  9480
agcccattta tacccatata aatcagcgtc catgttggag tttaagcgcg gacgggagca  9540
agacgtttcc cgttgaatat ggctcataac accccttgta ttactgttta tgtaagcaga  9600
cagttttatt gttcatgatg atatattttt atcttgtgca atgtaacatc agagattttg  9660
agacacaacg tggctttgtt gaataaatcg aacttttgct gagttgaagg atcagctcta  9720
gtaaaataat aaaaaagccg gattaataat ctggcttttt atattctctc tctagtatat  9780
aaacgcagaa aggcccaccc gaaggtgagc cagtgtgacg gcacatttcc ccgaaaagtg  9840
ccacctaaat tgtaagcgtt aatattttgt taaaattcgc gttaaatttt tgttaaatca  9900
gctcattttt taaccaatag gccgaaatcg gcaaaatccc ttataaatca aaagaataga  9960
ccgagatagg gttgagtgtt gttccagttt ggaacaagag tccactatta aagaacgtgg  10020
actccaacgt caaagggcga aaaaccgtct atcagggcga tggcccacta cgtgaaccat  10080
caccctaatc aagttttttg gggtcgaggt gccgtaaagc actaaatcgg aaccctaaag  10140
ggagcccccg atttagagct tgacggggaa agccggcgaa cgtggcgaga aaggaaggga  10200
agaaagcgaa aggagcgggc gctagggcgc tggcaagtgt agcggtcacg ctgcgcgtaa  10260
ccaccacacc cgccgcgctt aatgcgccgc tacagggcgc gtcccattcg ccattcaggc  10320
tgcgcaactg ttgggaaggg cgatcggtgc gggcctcttc gctattacgc cagctggcga  10380
aagggggatg tgctgcaagg cgattaagtt gggtaacgcc agggttttcc cagtcacgac  10440
gttgtaaaac gacggccagt gagcgcgcgg cgaattgggt accgggcccc c           10491

SEQ ID NO: 21          moltype = DNA  length = 10495
FEATURE                Location/Qualifiers
misc_feature           1..10495
                       note = Description of Artificial Sequence: Synthetic
                        polynucleotide
source                 1..10495
                       mol_type = other DNA
                       organism = synthetic construct
SEQUENCE: 21
cctcgagggc tagccattct atttaatctc cctatcagtg atagagatct ccctatcagt  60
gatagagatc gcccgagtga gcacgcaggg tctccatttt gaagcgggag gtttgaacgc  120
gcagccgcca tgccggggtt ttacgagatt gtgattaagg tccccagcga ccttgacgag  180
catctgcccg gcatttctga cagctttgtg aactgggtgg ccgagaagga atgggagttg  240
ccgccagatt ctgacatgga tctgaatctg attgagcagg cacccctgac cgtggccgag  300
aagctgcagc gcgactttct gacggaatgg cgccgtgtga gtaaggcccc ggaggctctt  360
ttctttgtgc aatttgagaa gggagagagc tacttccaca tgcacgtgct cgtggaaacc  420
accggggtga aatccatggt tttgggacgt ttcctgagtc agattcgcga aaaactgatt  480
cagagaattt accgcgggat cgagccgact ttgccaaact ggttcgcggt cacaaagacc  540
agaaatggcg ccggaggcgg gaacaaggtg gtggatgagt gctacatccc caattacttg  600
ctccccaaaa cccagcctga gctccaatgg gcatggacca acatggaaca gtacctcagc  660
gcctgtttga atctcacgga gcgtaaacgg ttggtggcgc agcatctgac gcacgtgtcg  720
cagacgcagg agcagaacaa agagaatcag aatcccaatt ctgatgcgcc ggtgatcaga  780
tcaaaaactt cagccaggta catggagctg gtcgggtggc tcgtggacaa ggggattacc  840
tcggagaagc agtggatcca ggaggaccag gcctcataca tctccttcaa tgcggcctcc  900
aactcgcggt cccaaatcaa ggctgccttg gacaatgcgg gaaagattat gagcctgact  960
aaaaccgccc ccgactacct ggtgggccag cagcccgtgg aggacatttc cagcaatcgg  1020
atttataaaa ttttggaact aaacgggtac gatccccaat atgcggcttc cgtctttctg  1080
ggatgggcca cgaaaaagtt cggcaagagg aacaccatct ggctgtttgg gcctgcaact  1140
accgggaaga ccaacatcgc ggaggccata gcccacactg tgcccttcta cgggtgcgta  1200
aactggacca atgagaactt tcccttcaac gactgtgtcg acaagatggt gatctggtgg  1260
gaggagggga agatgaccgc caaggtcgtg gagtcggcca aagccattct cggaggaagc  1320
aaggtgcgcg tggaccagaa atgcaagtcc tcggcccaga tagacccgac tcccgtgatc  1380
gtcacctcca acaccaacat gtgcgccgtg attgacggga actcaacgac cttcgaacac  1440
```

-continued

```
cagcagccgt tgcaagaccg gatgttcaaa tttgaactca cccgccgtct ggatcatgac  1500
tttgggaagg tcaccaagca ggaagtcaaa gactttttcc ggtgggcaaa ggatcacgtg  1560
gttgaggtgg agcatgaatt ctacgtcaaa aagggtggag ccaagaaaag acccgccccc  1620
agtgacgcag atataagtga gcccaaacgg gtgcgcgagt cagttgcgca gccatcgacg  1680
tcagacgcgg aagcttcgat caactacgca gacaggtacc aaaacaaatg ttctcgtcac  1740
gtgggcatga atctgatgct gtttccctgc agacaatgcg agagaatgaa tcagaattca  1800
aatatctgct tcactcacgg acagaaagac tgtttagagt gctttcccgt gtcagaatct  1860
caacccgttt ctgtcgtcaa aaaggcgtat cagaaactgt gctacattca tcatatcatg  1920
ggaaaggtgc cagacgcttg cactgcctgc gatctggtca atgtggattt ggatgactgc  1980
atctttgaac aataaatgat ttaaatcagg tatggctgcc gatggttatc ttccagattg  2040
gctcgaggac aacctctctg agggcattcg cgagtggtgg gacttgaaac ctggagcccc  2100
gaaacccaaa gccaaccagc aaaagcagga cgacggccgg ggtctggtgc ttcctggcta  2160
caagtacctc ggacccttca acggactcga caagggggag cccgtcaacg cggcggacgc  2220
agcggccctc gagcacgaca aggcctacga ccagcagctc aaagcgggtg acaatccgta  2280
cctgcggtat aaccacgccg acgccgagtt tcaggagcgt ctgcaagaag atacgtcttt  2340
tgggggcaac ctcgggcgag cagtcttcca ggccaagaag cgggttctcg aacctctcgg  2400
tctggttgag gaaggcgcta agacggctcc tggaaagaag agaccggtag agcaatcacc  2460
ccaggaacca gactcctctt cgggcatcgg caagaaaggc cagcagcccg cgagaaagag  2520
actcaacttt gggcagactg gcgactcaga gtcagtgccc gaccctcaac cactcggaga  2580
accccccgca gccccctctg gtgtgggatc taatacaatg gctgcaggcg gtggcgctcc  2640
aatggcagac aataacgaag gcgccgacgg agtgggtaac gcctcaggaa attggcattg  2700
cgattccaca tggctgggcg acagagtcat caccaccagc acccgaacct gggccctccc  2760
cacctacaac aaccacctct acaagcaaat ctccagccaa tcgggaggca gcaccaacga  2820
caacacctac ttcggctaca gcaccccctg ggggtatttt gactttaaca gattccactg  2880
ccacttctca ccacgtgact ggcagcgact catcaacaac aactggggat tccggcccaa  2940
gaagctcaac ttcaagctct tcaacatcca ggtcaaggag gtcacgacga atgatggcac  3000
cacgaccatc gccaataacc ttaccagcac ggttcaggtc tttacggact cggaatacca  3060
gctcccgtac gtcctcggct ctgcgcacca gggctgcctg cctccgttcc cggcggacgt  3120
cttcatgatt cctcagtacg ggtacctgac tctgaacaat ggcagtcagg ccgtgggccg  3180
ttcctccttc tactgcctgg aatactttcc ttctcaaatg ctgagaacgg gcaacaactt  3240
tcagttcagc tacacgtttg aggacgtgcc ttttcacagc agctacgcgc acagccaaag  3300
cctggaccgg ctgatgaacc ccctcatcga ccagtacctg tactacctgt ctcggactca  3360
gaccacgagt ggtaccgcag gaaatcggac gttgcaattt tctcaggccg ggcctagtag  3420
catggcgaat caggccaaaa actggctacc cgggccctgc taccggcagc aacgcgtctc  3480
caagacaacc aatcaaaata acaacagcaa ctttgcctgg accggtgcca ccaagtatca  3540
tctgaatggc agagactctc tggtaaatcc cggtcccgct atggcaaccc acaaggacga  3600
cgaagacaaa ttttttccga tgagcggagt cttaatattt gggaaacagg gagctggaaa  3660
tagcaacgtg gaccttgaca acgttatgat aaccaacgag gaagaaatta aaaccaccaa  3720
cccagtggcc acagaagagt acggcacggt ggccactaac ctgcaatcgg ccaacaccgc  3780
tcctgctaca gggaccgtca acagtcaagg agccttacct ggcatggtct ggcaggaccg  3840
ggacgtgtac ctgcagggtc ctatctgggc caagattcct cacacggacg gacactttca  3900
tccctcgccg ctgatgggag gctttggact gaaacacccg cctcctcaga tcctgattaa  3960
gaatacacct gttcccgcga atcctccaac taccttcagt ccagctaagt ttgcgtcgtt  4020
catcacgcag tacagcaccg gacaggtcag cgtggaaatt gaatgggagc tgcagaaaga  4080
aaacagcaaa cgctggaacc cagagattca atacacttcc aactacaaca aatctacaaa  4140
tgtggacttt gctgttgaca caaatggcgt ttattctgag cctcgcccca tcggcacccg  4200
ttacctcacc cgtaatctgt aaactagttt gcttgttaat caataaaccg tttaattcgt  4260
ttcagttgaa ctttggtctc tgcgtatttc tttcttatct agtttccatg ctctagaggt  4320
cctgtattag aggtcacgtg agtgttttgc gacattttgc gacaccatgt ggtcacgctg  4380
ggtatttaag cccgagtgag cacgcagggt ctccattttg aagcgggagg tttgaacgcg  4440
cagccgccaa gccgaattct gcagatatcg ggttggggt tgcgcctttt ccaaggcagc  4500
cctgggtttg cgcagggacg cggctgctct gggcgtggtt ccgggaaacg cagcggcgcc  4560
gaccctgggt ctcgcacatt cttcacgtcc gttcgcagcg tcacccggat cttcgccgct  4620
acccttgtgg gccccccggc gacgcttcct gctccgcccc taagtcggga aggttccttg  4680
cggttcgcgg cgtgccggac gtgacaaacg gaagccgcac gtctcactag taccctcgca  4740
gacggacagc gccagggagc aatggcagcg cgccgaccgc gatgggctgt ggccaatagc  4800
ggctgctcag cagggcgcgc cgagagcagc ggccgggaag gggcggtgcg ggaggcgggg  4860
tgtggggcgg tagtgtgggc cctgttcctg cccgcgcggt gttccgcatt ctgcaagcct  4920
ccggagcgca cgtcggcagt cggctccctc gttgaccgaa tcaccgacct ctctccccag  4980
aagctcccgg gagcttgtat atccattttc ggatctgatc agcacgtgtt gacaattaat  5040
catcggcata gtatatcggc atagtataat acgacaaggt gaggaacgcc accatggcca  5100
agcctttgtc tcaagaagaa tccaccctca ttgaaagagc aacggctaca atcaacagca  5160
tccccatctc tgaagactac agcgtcgcca gcgcagctct ctctagcgac ggccgcatct  5220
tcactggtgt caatgtatat cattttactg gggaccttgg tgcagaactc gtggtgctgg  5280
gcactgctgc tgctgcggca gctggcaacc tgacttgtat cgtcgcgatc ggaaatgaga  5340
acaggggcat cttgagcccc tgcggacggt gccgacaggt gcttctcgat ctgcatcctg  5400
ggatcaaagc catagtgaag gacagtgatg gacagccgac ggcagttggg attcgtgaat  5460
tgctgccctc tggttatgtg tgggagggct aagcacttcg tggccgagga gcaggactga  5520
cacgtgctac gagatttcga ttccaccgcc gccttctatg aaaggttggg cttcggaatc  5580
gttttccggg acgccggctg gatgatcctc cagcgcgggg atctcatgct ggagttcttc  5640
gcccacccca acttgtttat tgcagcttat aatggttaca aataaagcaa tagcatcaca  5700
aatttcacaa ataaagcatt tttttcactg cattctagtt gtggtttgtc caaactcatc  5760
aatgtatctt agcgctcact gcccgctttc cagtcgggaa acctgtcgtg ccagctgcat  5820
taatgaatcg gccaacgcgc ggggagaggc ggtttgcgta ttgggcgctc tcctaggcca  5880
gaaatggcgc cggaggcggg aacaaggtgg tggatgagtg ctacatcccc aattacttgc  5940
tccccaaaac ccagcctgag ctccagtggg cgtggactaa tatggaatcc ctatcagtga  6000
tagagacagt atttaagcgc ctgtccctat cagtgataga gatttgaatc tcacggagcg  6060
taaacggttg gtggcgcagc atctgtttaa acgcagacgc aggagcagaa caaagagaat  6120
cagaatccca attctgatgc gccggtgatc agatcaaaaa cttcagccag gtacatggag  6180
```

```
ctggtcgggt ggctcgtgga caaggggatt acctcggaga agcagtggat tcaggaggac  6240
caggcctcat acatctcctt caatgcggcc tccaactcgc ggtcccaaat caaggctgcc  6300
ttggacaatg cgggaaagat tatgagcctg actaaaaccg cccccgacta cctggtgggc  6360
cagcagcccg tggaggacat ttccagcaat cggatttata aaattttgga actaaacggg  6420
tacgatcccc aatatgcggc ttccgtcttt ctgggatggg ccacgaaaaa gttcggcaag  6480
aggaacacca tctggctgtt tgggcctgca actaccggga agaccaacat cgcggaggcc  6540
atagcccaca ctgtgccctt ctacgggtgc gtaaactgga ccaatgagaa ctttcccttc  6600
aacgactgtg tcgacaagat ggtgatctgg tgggaggagg ggaagatgac cgccaaggtc  6660
gtggagtcgg ccaaagccat tctcggagga agcaaggtgc gcgtggacca gaaatgcaag  6720
tcctcggccc agatagaccc gactcccgtg atcgtcacct ccaacaccaa catgtgcgcc  6780
gtgattgacg ggaactcaac gaccttcgaa caccagcagc cgttgcaaga ccggatgttc  6840
aaatttgaac tcacccgccg tctggatcat gactttggga aggtcaccaa gcaggaagtc  6900
aaagactttt tccggtgggc aaaggatcac gtggttgagg tggagcatga attctacgtc  6960
aaaaagggtg gagccaagaa aagacccgcc cccagtgacg cagatataag tgagcccaaa  7020
cgggtgcgcg agtcagttgc gcagccatcg acgtcagacg cggaagcttc gatcaactac  7080
gcagacaggt accaaaacaa atgttctcgt cacgtgggca tgaatctgat gctgtttccc  7140
tgcagacaat gcgagagaat gaatcagaat tcaaatatct gcttcactca cggacagaaa  7200
gactgtttag agtgctttcc cgtgtcagaa tctcaacccg tttctgtcgt caaaaaggcg  7260
tatcagaaac tgtgctacat tcatcatatc atgggaaagg tgccagacgc ttgcactgcc  7320
tgcgatctgg tcaatgtgga tttggatgac tgcatctttg aacaataaac tagtttgctt  7380
gttaatcaat aaaccgttta attcgtttca gttgaacttt ggtctctgcg tatttctttc  7440
ttatctagtt tccatgctct agagtatacg atatccatca cactggcggc cgctcgacta  7500
gagcggccgc caccgcggtg gagctccagc ttttgttcgc gcgcttggcg taatcatggt  7560
catagctgtt tcctgtgtga aattccacag cctggggtgc ctaattgcgt tgcgctcact  7620
gcccgctttc cagtcgggaa acctgtcgtg ccagctgcat taatgaatcg gccaacgcgc  7680
ggggagaggc ggtttgcgta ttgggcgctc ttccgcttcc tcgctcactg actcgctgcg  7740
ctcggtcgtt cggctgcggc gagcggtatc agctcactca aaggcggtaa tacggttatc  7800
cacagaatca ggggataacg caggaaagaa catgtgagca aaaggccagc aaaaggccag  7860
gaaccgtaaa aaggccgcgt tgctggcgtt tttccatagg ctccgccccc ctgacgagca  7920
tcacaaaaat cgacgctcaa gtcagaggtg gcgaaacccg acaggactat aaagatacca  7980
ggcgtttccc cctggaagct ccctcgtgcg ctctcctgtt ccgaccctgc cgcttaccgg  8040
atacctgtcc gcctttctcc cttcgggaag cgtggcgctt tctcatagct cacgctgtag  8100
gtatctcagt tcggtgtagg tcgttcgctc caagctgggc tgtgtgcacg aaccccccgt  8160
tcagcccgac cgctgcgcct tatccggtaa ctatcgtctt gagtccaacc cggtaagaca  8220
cgacttatcg ccactggcag cagccactgg taacaggatt agcagagcga ggtatgtagg  8280
cggtgctaca gagttcttga agtggtggcc taactacggc tacactagaa gaacagtatt  8340
tggtatctgc gctctgctga agccagttac cttcggaaaa agagttggta gctcttgatc  8400
cggcaaacaa accaccgctg gtagcggtgg tttttttgtt tgcaagcagc agattacgcg  8460
cagaaaaaaa ggatctcaag aagatccttt gatcttttct acggggtctg acgctcagtg  8520
gaacgaaaac tcacgttaag ggattttggt catgagatta tcaaaaagga tcttcaccta  8580
gatcctttta aattaaaaat gaagttttaa atcaatctaa agtatatatg agtaaacttg  8640
gtctgacaga aataataaaa aagccggatt aataatctgg ctttttatat tctctctcta  8700
gtatataaac gcagaaaggc ccacccgaag gtgagccagt gtgactctag tattattaga  8760
aaaactcatc gagcatcaaa tgaaactgca atttattcat atcaggatta tcaataccat  8820
atttttgaaa aagccgtttc tgtaatgaag gagaaaactc accgaggcag ttccaaagaa  8880
tggcaaggtc ctggtaacgg tctgcgattc cgacccgtcc aacatcaata caacctatta  8940
atttcccctc gtcaaaaata aggttatcaa gtgagaaatc accatgagtg acgactgaat  9000
ccggtgagaa tggcaagagc ttgtgcattt ctttccagac ttgttcaaca ggccagccat  9060
tacgctcgtc atcaaaatca ctcgcatcaa ccaaaccgtt attcatgcgt gattgcgcct  9120
gagcaagacg aaatacacga tcgctgttaa aaggacaatt acaaacagga atcgaatgta  9180
accggcgcag gaacacggcc agcgcatcaa caatattttc acctgaatca ggatattctt  9240
ctaatacctg gaaggctgtt ttcccaggaa tcgcggtggt gagtaaccac gcatcatcag  9300
gagtacggat aaaatgcttg atggtcggga gaggcataaa ctccgtcagc cagttgagac  9360
ggaccatctc atctgtaaca tcattggcaa cgctaccttt gccatgtttc agaaacaact  9420
ctggcgcatc gggcttccca tacaagcgat agattgtcgc acctgattgc ccgacattat  9480
cgcgagccca tttataccca tataaatcag cgtccatgtt ggagtttaag cgcggacggg  9540
agcaagacgt ttcccgttga atatggctca taacacccct tgtattactg tttatgtaag  9600
cagacagttt tattgttcat gatgatatat ttttatcttg tgcaatgtaa catcagagat  9660
tttgagacac aacgtggctt tgttgaataa atcgaacttt tgctgagttg aaggatcagc  9720
tctagtaaaa taataaaaaa gccggattaa taatctggct ttttatattc tctctctagt  9780
atataaacgc agaaaggccc acccgaaggt gagccagtgt gacggcacat ttccccgaaa  9840
agtgccacct aaattgtaag cgttaatatt ttgttaaaat tcgcgttaaa tttttgttaa  9900
atcagctcat tttttaacca ataggccgaa atcggcaaaa tcccttataa atcaaaagaa  9960
tagaccgaga tagggttgag tgttgttcca gtttggaaca agagtccact attaaagaac  10020
gtggactcca acgtcaaagg gcgaaaaacc gtctatcagg gcgatggccc actacgtgaa  10080
ccatcaccct aatcaagttt tttggggtcg aggtgccgta aagcactaaa tcggaaccct  10140
aaagggagcc cccgatttag agcttgacgg ggaaagccgg cgaacgtggc gagaaaggaa  10200
gggaagaaag cgaaaggagc gggcgctagg gcgctggcaa gtgtagcggt cacgctgcgc  10260
gtaaccacca cacccgccgc gcttaatgcg ccgctacagg gcgcgtccca ttcgccattc  10320
aggctgcgca actgttggga agggcgatcg gtgcgggcct cttcgctatt acgccagctg  10380
gcgaaagggg gatgtgctgc aaggcgatta agttgggtaa cgccagggtt ttcccagtca  10440
cgacgttgta aaacgacggc cagtgagcgc gcggcgaatt gggtaccggg ccccc       10495
```

```
SEQ ID NO: 22          moltype = DNA  length = 10493
FEATURE                Location/Qualifiers
misc_feature           1..10493
                       note = Description of Artificial Sequence: Synthetic
                        polynucleotide
```

```
source                  1..10493
                        mol_type = other DNA
                        organism = synthetic construct
SEQUENCE: 22
cctcgagggc tagccattct atttaatctc cctatcagtg atagagatcg cccgagtgag  60
cacgcagggt ctccattttg atccctatca gtgatagaga agcgggaggt ttgaacgcgc  120
agccgccatg ccggggtttt acgagattgt gattaaggtc cccagcgacc ttgacgagca  180
tctgcccggc atttctgaca gctttgtgaa ctgggtggcc gagaaggaat gggagttgcc  240
gccagattct gacatggatc tgaatctgat tgagcaggca cccctgaccg tggccgagaa  300
gctgcagcgc gactttctga cggaatggcg ccgtgtgagt aaggccccgg aggctctttt  360
ctttgtgcaa tttgagaagg gagagagcta cttccacatg cacgtgctcg tggaaaccac  420
cggggtgaaa tccatggttt tgggacgttt cctgagtcag attcgcgaaa aactgattca  480
gagaatttac cgcgggatcg agccgacttt gccaaactgg ttcgcggtca caaagaccag  540
aaatggcgcc ggaggcggga acaaggtggt ggatgagtgc tacatcccca attacttgct  600
ccccaaaacc cagcctgagc tccaatgggc atggaccaac atggaacagt acctcagcgc  660
ctgtttgaat ctcacggagc gtaaacggtt ggtggcgcag catctgacgc acgtgtcgca  720
gacgcaggag cagaacaaag agaatcagaa tcccaattct gatgcgccgg tgatcagatc  780
aaaaacttca gccaggtaca tggagctggt cgggtggctc gtggacaagg ggattacctc  840
ggagaagcag tggatccagg aggaccaggc ctcatacatc tccttcaatg cggcctccaa  900
ctcgcggtcc caaatcaagg ctgccttgga caatgcggga aagattatga gcctgactaa  960
aaccgccccc gactacctgg tgggccagca gcccgtggag gacatttcca gcaatcggat  1020
ttataaaatt ttggaactaa acgggtacga tccccaatat gcggcttccg tctttctggg  1080
atgggccacg aaaaagttcg gcaagaggaa caccatctgg ctgtttgggc ctgcaactac  1140
cgggaagacc aacatcgcgg aggccatagc ccacactgtg cccttctacg ggtgcgtaaa  1200
ctggaccaat gagaactttc ccttcaacga ctgtgtcgac aagatggtga tctggtggga  1260
ggaggggaag atgaccgcca aggtcgtgga gtcggccaaa gccattctcg gaggaagcaa  1320
ggtgcgcgtg gaccagaaat gcaagtcctc ggcccagata gacccgactc ccgtgatcgt  1380
cacctccaac accaacatgt gcgccgtgat tgacgggaac tcaacgacct tcgaacacca  1440
gcagccgttg caagaccgga tgttcaaatt tgaactcacc cgccgtctgg atcatgactt  1500
tgggaaggtc accaagcagg aagtcaaaga ctttttccgg tgggcaaagg atcacgtggt  1560
tgaggtggag catgaattct acgtcaaaaa gggtggagcc aagaaaagac ccgcccccag  1620
tgacgcagat ataagtgagc ccaaacgggt gcgcgagtca gttgcgcagc catcgacgtc  1680
agacgcggaa gcttcgatca actacgcaga caggtaccaa aacaaatgtt ctcgtcacgt  1740
gggcatgaat ctgatgctgt ttccctgcag acaatgcgag agaatgaatc agaattcaaa  1800
tatctgcttc actcacggac agaaagactg tttagagtgc tttcccgtgt cagaatctca  1860
acccgtttct gtcgtcaaaa aggcgtatca gaaactgtgc tacattcatc atatcatggg  1920
aaaggtgcca gacgcttgca ctgcctgcga tctggtcaat gtggatttgg atgactgcat  1980
ctttgaacaa taaatgattt aaatcaggta tggctgccga tggttatctt ccagattggc  2040
tcgaggacaa cctctctgag ggcattcgcg agtggtggga cttgaaacct ggagccccga  2100
aacccaaagc caaccagcaa aagcaggacg acggccgggg tctggtgctt cctggctaca  2160
agtacctcgg acccttcaac ggactcgaca agggggagcc cgtcaacgcg gcggacgcag  2220
cggccctcga gcacgacaag gcctacgacc agcagctcaa agcgggtgac aatccgtacc  2280
tgcggtataa ccacgccgac gccgagtttc aggagcgtct gcaagaagat acgtcttttg  2340
ggggcaacct cgggcgagca gtcttccagg ccaagaagcg ggttctcgaa cctctcggtc  2400
tggttgagga aggcgctaag acggctcctg gaaagaagag accggtagag caatcacccc  2460
aggaaccaga ctcctcttcg ggcatcggca agaaaggcca gcagcccgcg agaaagagac  2520
tcaactttgg gcagactggc gactcagagt cagtgcccga ccctcaacca ctcggagaac  2580
cccccgcagc cccctctggt gtgggatcta atacaatggc tgcaggcggt ggcgctccaa  2640
tggcagacaa taacgaaggc gccgacggag tgggtaacgc ctcaggaaat tggcattgcg  2700
attccacatg gctgggcgac agagtcatca ccaccagcac ccgaacctgg gccctcccca  2760
cctacaacaa ccacctctac aagcaaatct ccagccaatc gggaggcagc accaacgaca  2820
acacctactt cggctacagc acccccctggg ggtattttga ctttaacaga ttccactgcc  2880
acttctcacc acgtgactgg cagcgactca tcaacaacaa ctggggattc cggcccaaga  2940
agctcaactt caagctcttc aacatccagg tcaaggaggt cacgacgaat gatggcacca  3000
cgaccatcgc caataacctt accagcacgg ttcaggtctt tacggactcg gaataccagc  3060
tcccgtacgt cctcggctct gcgcaccagg gctgcctgcc tccgttcccg gcggacgtct  3120
tcatgattcc tcagtacggg tacctgactc tgaacaatgg cagtcaggcc gtgggccgtt  3180
cctccttcta ctgcctggaa tactttcctt ctcaaatgct gagaacgggc aacaactttc  3240
agttcagcta cacgtttgag gacgtgcctt ttcacagcag ctacgcgcac agccaaagcc  3300
tggaccggct gatgaacccc ctcatcgacc agtacctgta ctacctgtct cggactcaga  3360
ccacgagtgg taccgcagga aatcggacgt tgcaattttc tcaggccggg cctagtagca  3420
tggcgaatca ggccaaaaac tggctacccg ggccctgcta ccggcagcaa cgcgtctcca  3480
agacaaccaa tcaaaataac aacagcaact ttgcctggac cggtgccacc aagtatcatc  3540
tgaatggcag agactctctg gtaaatcccg gtcccgctat ggcaacccac aaggacgacg  3600
aagacaaatt ttttccgatg agcggagtct taatatttgg gaaacaggga gctggaaata  3660
gcaacgtgga ccttgacaac gttatgataa ccaacgagga agaaattaaa accaccaacc  3720
cagtggccac agaagagtac ggcacggtgg ccactaacct gcaatcggcc aacaccgctc  3780
ctgctacagg gaccgtcaac agtcaaggag ccttacctgg catggtctgg caggaccggg  3840
acgtgtacct gcagggtcct atctgggcca agattcctca cacggacgga cactttcatc  3900
cctcgccgct gatgggaggc tttggactga aacacccgcc tcctcagatc ctgattaaga  3960
atacacctgt tcccgcgaat cctccaacta ccttcagtcc agctaagttt gcgtcgttca  4020
tcacgcagta cagcaccgga caggtcagcg tggaaattga atgggagctg cagaaagaaa  4080
acagcaaacg ctggaaccca gagattcaat acacttccaa ctacaacaaa tctacaaatg  4140
tggactttgc tgttgacaca aatggcgttt attctgagcc tcgccccatc ggcacccgtt  4200
acctcacccg taatctgtaa actagtttgc ttgttaatca ataaaccgtt taattcgttt  4260
cagttgaact tggtctctg cgtatttctt tcttatctag tttccatgct ctagaggtcc  4320
tgtattagag gtcacgtgag tgttttgcga catttgcga caccatgtgg tcacgctggg  4380
tatttaagcc cgagtgagca cgcagggtct ccattttgaa gcgggaggtt tgaacgcgca  4440
gccgccaagc cgaattctgc agatatcggg gttggggttg cgccttttcc aaggcagccc  4500
```

-continued

```
tgggtttgcg cagggacgcg gctgctctgg gcgtggttcc gggaaacgca gcggcgccga 4560
ccctgggtct cgcacattct tcacgtccgt tcgcagcgtc acccggatct tcgccgctac 4620
ccttgtgggc cccccggcga cgcttcctgc tccgccccta agtcgggaag gttccttgcg 4680
gttcgcggcg tgccggacgt gacaaacgga agccgcacgt ctcactagta ccctcgcaga 4740
cggacagcgc cagggagcaa tggcagcgcg ccgaccgcga tgggctgtgg ccaatagcgg 4800
ctgctcagca gggcgcgccg agagcagcgg ccgggaaggg gcggtgcggg aggcggggtg 4860
tggggcggta gtgtgggccc tgttcctgcc cgcgcggtgt tccgcattct gcaagcctcc 4920
ggagcgcacg tcggcagtcg gctccctcgt tgaccgaatc accgacctct ctccccagaa 4980
gctcccggga gcttgtatat ccattttcgg atctgatcag cacgtgttga caattaatca 5040
tcggcatagt atatcggcat agtataatac gacaaggtga ggaacgccac catggccaag 5100
cctttgtctc aagaagaatc caccctcatt gaaagagcaa cggctacaat caacagcatc 5160
cccatctctg aagactacag cgtcgccagc gcagctctct ctagcgacgg ccgcatcttc 5220
actggtgtca atgtatatca ttttactggg ggaccttgtg cagaactcgt ggtgctgggc 5280
actgctgctg ctgcggcagc tggcaacctg acttgtatcg tcgcgatcgg aaatgagaac 5340
aggggcatct tgagcccctg cggacggtgc cgacaggtgc ttctcgatct gcatcctggg 5400
atcaaagcca tagtgaagga cagtgatgga cagccgacgg cagttgggat tcgtgaattg 5460
ctgccctctg gttatgtgtg ggagggctaa gcacttcgtg gccgaggagc aggactgaca 5520
cgtgctacga gatttcgatt ccaccgccgc cttctatgaa aggttgggct tcggaatcgt 5580
tttccgggac gccggctgga tgatcctcca gcgcggggat ctcatgctgg agttcttcgc 5640
ccaccccaac ttgtttattg cagcttataa tggttacaaa taaagcaata gcatcacaaa 5700
tttcacaaat aaagcatttt tttcactgca ttctagttgt ggtttgtcca aactcatcaa 5760
tgtatcttag cgctcactgc ccgctttcca gtcgggaaac ctgtcgtgcc agctgcatta 5820
atgaatcggc caacgcgcgg ggagaggcgg tttgcgtatt gggcgctctc ctaggccaga 5880
aatggcgccg gaggcgggaa caaggtggtg gatgagtgct acatccccaa ttacttgctc 5940
cccaaaaccc agcctgagct ccagtgggcg tggactaata tggaatccct atcagtgata 6000
gagacagtat ttaagcgcct gtccctatca gtgatagaga tttgaatctc acggagcgta 6060
aacggttggt ggcgcagcat ctgtttaaac gcagacgcag gagcagaaca aagagaatca 6120
gaatcccaat tctgatgcgc cggtgatcag atcaaaaact tcagccaggt acatggagct 6180
ggtcgggtgg ctcgtggaca aggggattac ctcggagaag cagtggattc aggaggacca 6240
ggcctcatac atctccttca atgcggcctc caactcgcgg tcccaaatca aggctgcctt 6300
ggacaatgcg ggaaagatta tgagcctgac taaaaccgcc cccgactacc tggtgggcca 6360
gcagcccgtg gaggacattt ccagcaatcg gatttataaa attttggaac taaacgggta 6420
cgatccccaa tatgcggctt ccgtctttct gggatgggcc acgaaaaagt tcggcaagag 6480
gaacaccatc tggctgtttg ggcctgcaac taccgggaag accaacatcg cggaggccat 6540
agcccacact gtgcccttct acgggtgcgt aaactggacc aatgagaact ttcccttcaa 6600
cgactgtgtc gacaagatgg tgatctggtg ggaggagggg aagatgaccg ccaaggtcgt 6660
ggagtcggcc aaagccattc tcggaggaag caaggtgcgc gtggaccaga aatgcaagtc 6720
ctcggcccag atagacccga ctcccgtgat cgtcacctcc aacaccaaca tgtgcgccgt 6780
gattgacggg aactcaacga ccttcgaaca ccagcagccg ttgcaagacc ggatgttcaa 6840
atttgaactc acccgccgtc tggatcatga ctttgggaag gtcaccaagc aggaagtcaa 6900
agactttttc cggtgggcaa aggatcacgt ggttgaggtg gagcatgaat tctacgtcaa 6960
aaagggtgga gccaagaaaa gacccgcccc cagtgacgca gatataagtg agcccaaacg 7020
ggtgcgcgag tcagttgcgc agccatcgac gtcagacgcg gaagcttcga tcaactacgc 7080
agacaggtac caaaacaaat gttctcgtca cgtgggcatg aatctgatgc tgtttccctg 7140
cagacaatgc gagagaatga atcagaattc aaatatctgc ttcactcacg gacagaaaga 7200
ctgtttagag tgctttcccg tgtcagaatc tcaacccgtt tctgtcgtca aaaaggcgta 7260
tcagaaactg tgctacattc atcatatcat gggaaaggtg ccagacgctt gcactgcctg 7320
cgatctggtc aatgtggatt tggatgactg catctttgaa caataaacta gtttgcttgt 7380
taatcaataa accgtttaat tcgtttcagt tgaactttgg tctctgcgta tttctttctt 7440
atctagtttc catgctctag agtatacgat atccatcaca ctggcggccg ctcgactaga 7500
gcggccgcca ccgcggtgga gctccagctt ttgttcgcgc gcttggcgta atcatggtca 7560
tagctgtttc ctgtgtgaaa ttccacagcc tggggtgcct aattgcgttg cgctcactgc 7620
ccgctttcca gtcgggaaac ctgtcgtgcc agctgcatta atgaatcggc caacgcgcgg 7680
ggagaggcgg tttgcgtatt gggcgctctt ccgcttcctc gctcactgac tcgctgcgct 7740
cggtcgttcg gctgcggcga gcggtatcag ctcactcaaa ggcggtaata cggttatcca 7800
cagaatcagg ggataacgca ggaaagaaca tgtgagcaaa aggccagcaa aaggccagga 7860
accgtaaaaa ggccgcgttg ctggcgtttt tccataggct ccgcccccct gacgagcatc 7920
acaaaaatcg acgctcaagt cagaggtggc gaaacccgac aggactataa agataccagg 7980
cgtttccccc tggaagctcc ctcgtgcgct ctcctgttcc gaccctgccg cttaccggat 8040
acctgtccgc ctttctccct tcgggaagcg tggcgctttc tcatagctca cgctgtaggt 8100
atctcagttc ggtgtaggtc gttcgctcca agctgggctg tgtgcacgaa ccccccgttc 8160
agcccgaccg ctgcgcctta tccggtaact atcgtcttga gtccaacccg gtaagacacg 8220
acttatcgcc actggcagca gccactggta acaggattag cagagcgagg tatgtaggcg 8280
gtgctacaga gttcttgaag tggtggccta actacggcta cactagaaga acagtatttg 8340
gtatctgcgc tctgctgaag ccagttacct tcggaaaaag agttggtagc tcttgatccg 8400
gcaaacaaac caccgctggt agcggtggtt tttttgtttg caagcagcag attacgcgca 8460
gaaaaaaagg atctcaagaa gatcctttga tcttttctac ggggtctgac gctcagtgga 8520
acgaaaactc acgttaaggg attttggtca tgagattatc aaaaaggatc ttcacctaga 8580
tccttttaaa ttaaaaatga agttttaaat caatctaaag tatatatgag taaacttggt 8640
ctgacagaaa taataaaaaa gccggattaa taatctggct ttttatattc tctctctagt 8700
atataaacgc agaaaggccc acccgaaggt gagccagtgt gactctagta ttattagaaa 8760
aactcatcga gcatcaaatg aaactgcaat ttattcatat caggattatc aataccatat 8820
ttttgaaaaa gccgtttctg taatgaagga gaaaactcac cgaggcagtt ccaaagaatg 8880
gcaaggtcct ggtaacggtc tgcgattccg acccgtccaa catcaataca acctattaat 8940
ttcccctcgt caaaaataag gttatcaagt gagaaatcac catgagtgac gactgaatcc 9000
ggtgagaatg gcaagagctt gtgcatttct ttccagactt gttcaacagg ccagccatta 9060
cgctcgtcat caaaatcact cgcatcaacc aaaccgttat tcatgcgtga ttgcgcctga 9120
gcaagacgaa atacacgatc gctgttaaaa ggacaattac aaacaggaat cgaatgtaac 9180
cggcgcagga acacggccag cgcatcaaca atattttcac ctgaatcagg atattcttct 9240
```

```
aatacctgga aggctgtttt cccaggaatc gcggtggtga gtaaccacgc atcatcagga  9300
gtacggataa aatgcttgat ggtcgggaga ggcataaact ccgtcagcca gttgagacgg  9360
accatctcat ctgtaacatc attggcaacg ctacctttgc catgtttcag aaacaactct  9420
ggcgcatcgg gcttcccata caagcgatag attgtcgcac ctgattgccc gacattatcg  9480
cgagcccatt tatacccata taaatcagcg tccatgttgg agtttaagcg cggacgggag  9540
caagacgttt cccgttgaat atggctcata acaccccttg tattactgtt tatgtaagca  9600
gacagtttta ttgttcatga tgatatattt ttatcttgtg caatgtaaca tcagagattt  9660
tgagacacaa cgtggctttg ttgaataaat cgaactttgg ctgagttgaa ggatcagctc  9720
tagtaaaata ataaaaaagc cggattaata atctggcttt ttatattctc tctctagtat  9780
ataaacgcag aaaggcccac ccgaaggtga gccagtgtga cggcacattt ccccgaaaag  9840
tgccacctaa attgtaagcg ttaatatttt gttaaaattc gcgttaaatt tttgttaaat  9900
cagctcattt tttaaccaat aggccgaaat cggcaaaatc ccttataaat caaaagaata  9960
gaccgagata gggttgagtg ttgttccagt ttggaacaag agtccactat taaagaacgt  10020
ggactccaac gtcaaagggc gaaaaaccgt ctatcagggc gatggcccac tacgtgaacc  10080
atcaccctaa tcaagttttt tggggtcgag gtgccgtaaa gcactaaatc ggaaccctaa  10140
agggagcccc cgatttagag cttgacgggg aaagccggcg aacgtggcga gaaaggaagg  10200
gaagaaagcg aaaggagcgg gcgctagggc gctggcaagt gtagcggtca cgctgcgcgt  10260
aaccaccaca cccgccgcgc ttaatgcgcc gctacagggc gcgtcccatt cgccattcag  10320
gctgcgcaac tgttgggaag ggcgatcggt gcgggcctct tcgctattac gccagctggc  10380
gaaaggggga tgtgctgcaa ggcgattaag ttgggtaacg ccagggtttt cccagtcacg  10440
acgttgtaaa acgacggcca gtgagcgcgc ggcgaattgg gtaccgggcc ccc         10493

SEQ ID NO: 23          moltype = DNA  length = 10491
FEATURE                Location/Qualifiers
misc_feature           1..10491
                       note = Description of Artificial Sequence: Synthetic
                        polynucleotide
source                 1..10491
                       mol_type = other DNA
                       organism = synthetic construct
SEQUENCE: 23
cctcgagggc tagccattct ccctatcagt gatagagatc tatttaagcc cgagtgagca  60
cgcagtccct atcagtgata gagaggtctc cattttgaag cgggaggttt gaacgcgcag  120
ccgccatgcc ggggttttac gagattgtga ttaaggtccc cagcgacctt gacgagcatc  180
tgcccggcat ttctgacagc tttgtgaact gggtggccga gaaggaatgg gagttgccgc  240
cagattctga catggatctg aatctgattg agcaggcacc cctgaccgtg gccgagaagc  300
tgcagcgcga ctttctgacg gaatggcgcc gtgtgagtaa ggccccggag gctctttttct  360
ttgtgcaatt tgagaaggga gagagctact tccacatgca cgtgctcgtg gaaaccaccg  420
ggtgaaatc catggttttg ggacgtttcc tgagtcagat tcgcgaaaaa ctgattcaga  480
gaatttaccg cgggatcgag ccgactttgc caaactggtt cgcggtcaca aagaccagaa  540
atggcgccgg aggcgggaac aaggtggtgg atgagtgcta catccccaat tacttgctcc  600
ccaaaaccca gcctgagctc caatgggcat ggaccaacat ggaacagtac ctcagcgcct  660
gtttgaatct cacggagcgt aaacggttgg tggcgcagca tctgacgcac gtgtcgcaga  720
cgcaggagca gaacaaagag aatcagaatc ccaattctga tgcgccggtg atcagatcaa  780
aaacttcagc caggtacatg gagctggtcg ggtggctcgt ggacaagggg attacctcgg  840
agaagcagtg gatccaggag gaccaggcct catacatctc cttcaatgcg gcctccaact  900
cgcggtccca aatcaaggct gccttggaca atgcgggaaa gattatgagc ctgactaaaa  960
ccgcccccga ctacctggtg ggccagcagc ccgtggagga catttccagc aatcggattt  1020
ataaaatttt ggaactaaac gggtacgatc cccaatatgc ggcttccgtc tttctgggat  1080
gggccacgaa aaagttcggc aagaggaaca ccatctggct gtttgggcct gcaactaccg  1140
ggaagaccaa catcgcggag gccatagccc acactgtgcc cttctacggg tgcgtaaact  1200
ggaccaatga gaactttccc ttcaacgact gtgtcgacaa gatggtgatc tggtgggagg  1260
aggggaagat gaccgccaag gtcgtggagt cggccaaagc cattctcgga ggaagcaagg  1320
tgcgcgtgga ccagaaatgc aagtcctcgg cccagataga cccgactccc gtgatcgtca  1380
cctccaacac caacatgtgc gccgtgattg acgggaactc aacgaccttc gaacaccagc  1440
agccgttgca agaccggatg ttcaaatttg aactcacccg ccgtctggat catgactttg  1500
ggaaggtcac caagcaggaa gtcaaagact ttttccggtg ggcaaaggat cacgtggttg  1560
aggtggagca tgaattctac gtcaaaaagg gtggagccaa gaaaagaccc gcccccagtg  1620
acgcagatat aagtgagccc aaacgggtgc gcgagtcagt tgcgcagcca tcgacgtcag  1680
acgcggaagc ttcgatcaac tacgcagaca ggtaccaaaa caaatgttct cgtcacgtgg  1740
gcatgaatct gatgctgttt ccctgcagac aatgcgagag aatgaatcag aattcaaata  1800
tctgcttcac tcacggacag aaagactgtt tagagtgctt tcccgtgtca gaatctcaac  1860
ccgtttctgt cgtcaaaaag gcgtatcaga aactgtgcta cattcatcat atcatgggaa  1920
aggtgccaga cgcttgcact gcctgcgatc tggtcaatgt ggatttggat gactgcatct  1980
ttgaacaata aatgatttaa atcaggtatg gctgccgatg gttatcttcc agattggctc  2040
gaggacaacc tctctgaggg cattcgcgag tggtgggact tgaaacctgg agccccgaaa  2100
cccaaagcca accagcaaaa gcaggacgac ggccggggtc tggtgcttcc tggctacaag  2160
tacctcggac ccttcaacgg actcgacaag ggggagcccg tcaacgcggc ggacgcagcg  2220
gccctcgagc acgacaaggc ctacgaccag cagctcaaag cgggtgacaa tccgtacctg  2280
cggtataacc acgccgacgc cgagtttcag gagcgtctgc aagaagatac gtcttttggg  2340
ggcaacctcg ggcgagcagt cttccaggcc aagaagcggg ttctcgaacc tctcggtctg  2400
gttgaggaag gcgctaagac ggctcctgga aagaagagac cggtagagca atcaccccag  2460
gaaccagact cctcttcggg catcggcaag aaaggccagc agcccgcgag aaagagactc  2520
aactttgggc agactggcga ctcagagtca gtgcccgacc ctcaaccact cggagaaccc  2580
cccgcagccc cctctggtgt gggatctaat acaatggctg caggcggtgg cgctccaatg  2640
gcagacaata acgaaggcgc cgacggagtg ggtaacgcct caggaaattg gcattgcgat  2700
tccacatggc tgggcgacag agtcatcacc accagcaccc gaacctgggc cctccccacc  2760
tacaacaacc acctctacaa gcaaatctcc agccaatcgg gaggcagcac caacgacaac  2820
acctacttcg gctacagcac cccctggggg tattttgact ttaacagatt ccactgccac  2880
```

```
ttctcaccac gtgactggca gcgactcatc aacaacaact ggggattccg gcccaagaag  2940
ctcaacttca agctcttcaa catccaggtc aaggaggtca cgacgaatga tggcaccacg  3000
accatcgcca ataaccttac cagcacggtt caggtcttta cggactcgga ataccagctc  3060
ccgtacgtcc tcggctctgc gcaccagggc tgcctgcctc cgttcccggc ggacgtcttc  3120
atgattcctc agtacgggta cctgactctg aacaatggca gtcaggccgt gggccgttcc  3180
tccttctact gcctggaata ctttccttct caaatgctga gaacgggcaa caactttcag  3240
ttcagctaca cgtttgagga cgtgcctttt cacagcagct acgcgcacag ccaaagcctg  3300
gaccggctga tgaacccccct catcgaccag tacctgtact acctgtctcg gactcagacc  3360
acgagtggta ccgcaggaaa tcggacgttg caattttctc aggccgggcc tagtagcatg  3420
gcgaatcagg ccaaaaactg gctacccggg ccctgctacc ggcagcaacg cgtctccaag  3480
acaaccaatc aaaataacaa cagcaacttt gcctggaccg gtgccaccaa gtatcatctg  3540
aatggcagag actctctggt aaatcccggt cccgctatgg caacccacaa ggacgacgaa  3600
gacaaatttt ttccgatgag cggagtctta atatttggga aacagggagc tggaaatagc  3660
aacgtggacc ttgacaacgt tatgataacc aacgaggaag aaattaaaac caccaaccca  3720
gtggccacag aagagtacgg cacggtggcc actaacctgc aatcggccaa caccgctcct  3780
gctacaggga ccgtcaacag tcaaggagcc ttacctggca tggtctggca ggaccgggac  3840
gtgtacctgc agggtcctat ctgggccaag attcctcaca cggacggaca ctttcatccc  3900
tcgccgctga tgggaggctt tggactgaaa cacccgcctc ctcagatcct gattaagaat  3960
acacctgttc ccgcgaatcc tccaactacc ttcagtccag ctaagtttgc gtcgttcatc  4020
acgcagtaca gcaccggaca ggtcagcgtg gaaattgaat gggagctgca gaaagaaaac  4080
agcaaacgct ggaacccaga gattcaatac acttccaact acaacaaatc tacaaatgtg  4140
gactttgctg ttgacacaaa tggcgtttat tctgagcctc gccccatcgg cacccgttac  4200
ctcacccgta atctgtaaac tagtttgctt gttaatcaat aaaccgttta attcgtttca  4260
gttgaacttt ggtctctgcg tatttctttc ttatctagtt tccatgctct agaggtcctg  4320
tattagaggt cacgtgagtg ttttgcgaca ttttgcgaca ccatgtggtc acgctgggta  4380
tttaagcccg agtgagcacg cagggtctcc attttgaagc gggaggtttg aacgcgcagc  4440
cgccaagccg aattctgcag atatcggggt tggggttgcg ccttttccaa ggcagccctg  4500
ggtttgcgca gggacgcggc tgctctgggc gtggttccgg gaaacgcagc ggcgccgacc  4560
ctgggtctcg cacattcttc acgtccgttc gcagcgtcac ccggatcttc gccgctaccc  4620
ttgtgggccc cccggcgacg cttcctgctc cgcccctaag tcgggaaggt tccttgcggt  4680
tcgcggcgtg ccggacgtga caaacggaag ccgcacgtct cactagtacc ctcgcagacg  4740
gacagcgcca gggagcaatg gcagcgcgcc gaccgcgatg ggctgtggcc aatagcggct  4800
gctcagcagg gcgcgccgag agcagcggcc gggaaggggc ggtgcgggag gcggggtgtg  4860
gggcggtagt gtgggccctg ttcctgcccg cgcggtgttc cgcattctgc aagcctccgg  4920
agcgcacgtc ggcagtcggc tccctcgttg accgaatcac cgacctctct ccccagaagc  4980
tcccgggagc ttgtatatcc attttcggat ctgatcagca cgtgttgaca attaatcatc  5040
ggcatagtat atcggcatag tataatacga caaggtgagg aacgccacca tggccaagcc  5100
tttgtctcaa gaagaatcca ccctcattga aagagcaacg gctacaatca acagcatccc  5160
catctctgaa gactacagcg tcgccagcgc agctctctct agcgacggcc gcatcttcac  5220
tggtgtcaat gtatatcatt ttactggggg accttgtgca gaactcgtgg tgctgggcac  5280
tgctgctgct gcggcagctg gcaacctgac ttgtatcgtc gcgatcggaa atgagaacag  5340
gggcatcttg agcccctgcg gacggtgccg acaggtgctt ctcgatctgc atcctgggat  5400
caaagccata gtgaaggaca gtgatggaca gccgacggca gttgggattc gtgaattgct  5460
gccctctggt tatgtgtggg agggctaagc acttcgtggc cgaggagcag gactgacacg  5520
tgctacgaga tttcgattcc accgccgcct tctatgaaag gttgggcttc ggaatcgttt  5580
tccgggacgc cggctggatg atcctccagc gcggggatct catgctggag ttcttcgccc  5640
accccaactt gtttattgca gcttataatg gttacaaata aagcaatagc atcacaaatt  5700
tcacaaataa agcatttttt tcactgcatt ctagttgtgg tttgtccaaa ctcatcaatg  5760
tatcttagcg ctcactgccc gctttccagt cgggaaacct gtcgtgccag ctgcattaat  5820
gaatcggcca acgcgcgggg agaggcggtt tgcgtattgg gcgctctcct aggccagaaa  5880
tggcgccgga ggcgggaaca aggtggtgga tgagtgctac atccccaatt acttgctccc  5940
caaaacccag cctgagctcc agtgggcgtg gactaatatg gaatccctat cagtgataga  6000
gacagtattt aagcgcctgt ccctatcagt gatagagatt tgaatctcac ggagcgtaaa  6060
cggttggtgg cgcagcatct gtttaaacgc agacgcagga gcagaacaaa gagaatcaga  6120
atcccaattc tgatgcgccg gtgatcagat caaaaacttc agccaggtac atggagctgg  6180
tcgggtggct cgtggacaag gggattacct cggagaagca gtggattcag gaggaccagg  6240
cctcatacat ctccttcaat gcggcctcca actcgcggtc ccaaatcaag gctgccttgg  6300
acaatgcggg aaagattatg agcctgacta aaaccgcccc cgactacctg gtgggccagc  6360
agcccgtgga ggacatttcc agcaatcgga tttataaaat tttggaacta aacgggtacg  6420
atccccaata tgcggcttcc gtctttctgg gatgggccac gaaaaagttc ggcaagagga  6480
acaccatctg gctgtttggg cctgcaacta ccgggaagac caacatcgcg gaggccatag  6540
cccacactgt gcccttctac gggtgcgtaa actggaccaa tgagaacttt cccttcaacg  6600
actgtgtcga caagatggtg atctggtggg aggaggggaa gatgaccgcc aaggtcgtgg  6660
agtcggccaa agccattctc ggaggaagca aggtgcgcgt ggaccagaaa tgcaagtcct  6720
cggcccagat agacccgact cccgtgatcg tcacctccaa caccaacatg tgcgccgtga  6780
ttgacgggaa ctcaacgacc ttcgaacacc agcagccgtt gcaagaccgg atgttcaaat  6840
ttgaactcac ccgccgtctg gatcatgact ttgggaaggt caccaagcag gaagtcaaag  6900
actttttccg gtgggcaaag gatcacgtgg ttgaggtgga gcatgaattc tacgtcaaaa  6960
agggtggagc caagaaaaga cccgcccccca gtgacgcaga tataagtgag cccaaacggg  7020
tgcgcgagtc agttgcgcag ccatcgacgt cagacgcgga agcttcgatc aactacgcag  7080
acaggtacca aaacaaatgt tctcgtcacg tgggcatgaa tctgatgctg tttccctgca  7140
gacaatgcga gagaatgaat cagaattcaa atatctgctt cactcacgga cagaaagact  7200
gtttagagtg ctttcccgtg tcagaatctc aacccgtttc tgtcgtcaaa aaggcgtatc  7260
agaaactgtg ctacattcat catatcatgg gaaaggtgcc agacgcttgc actgcctgcg  7320
atctggtcaa tgtggatttg gatgactgca tctttgaaca ataaactagt ttgcttgtta  7380
atcaataaac cgtttaattc gtttcagttg aactttggtc tctgcgtatt tctttcttat  7440
ctagtttcca tgctctagag tatacgatat ccatcacact ggcggccgct cgactagagc  7500
ggccgccacc gcggtggagc tccagctttt gttcgcgcgc ttggcgtaat catggtcata  7560
gctgtttcct gtgtgaaatt ccacagcctg gggtgcctaa ttgcgttgcg ctcactgccc  7620
```

```
gctttccagt cgggaaacct gtcgtgccag ctgcattaat gaatcggcca acgcgcgggg  7680
agaggcggtt tgcgtattgg gcgctcttcc gcttcctcgc tcactgactc gctgcgctcg  7740
gtcgttcggc tgcggcgagc ggtatcagct cactcaaagg cggtaatacg gttatccaca  7800
gaatcagggg ataacgcagg aaagaacatg tgagcaaaag gccagcaaaa ggccaggaac  7860
cgtaaaaagg ccgcgttgct ggcgtttttc cataggctcc gcccccctga cgagcatcac  7920
aaaaatcgac gctcaagtca gaggtggcga aacccgacag gactataaag ataccaggcg  7980
tttccccctg gaagctccct cgtgcgctct cctgttccga ccctgccgct taccggatac  8040
ctgtccgcct ttctcccttc gggaagcgtg gcgctttctc atagctcacg ctgtaggtat  8100
ctcagttcgg tgtaggtcgt tcgctccaag ctgggctgtg tgcacgaacc ccccgttcag  8160
cccgaccgct gcgccttatc cggtaactat cgtcttgagt ccaacccggt aagacacgac  8220
ttatcgccac tggcagcagc cactggtaac aggattagca gagcgaggta tgtaggcggt  8280
gctacagagt tcttgaagtg gtggcctaac tacggctaca ctagaagaac agtatttggt  8340
atctgcgctc tgctgaagcc agttaccttc ggaaaaagag ttggtagctc ttgatccggc  8400
aaacaaacca ccgctggtag cggtggtttt tttgtttgca agcagcagat tacgcgcaga  8460
aaaaaaggat ctcaagaaga tcctttgatc ttttctacgg ggtctgacgc tcagtggaac  8520
gaaaactcac gttaagggat tttggtcatg agattatcaa aaaggatctt cacctagatc  8580
cttttaaatt aaaaatgaag ttttaaatca atctaaagta tatatgagta aacttggtct  8640
gacagaaata ataaaaaagc cggattaata atctggcttt ttatattctc tctctagtat  8700
ataaacgcag aaaggcccac ccgaaggtga gccagtgtga ctctagtatt attagaaaaa  8760
ctcatcgagc atcaaatgaa actgcaattt attcatatca ggattatcaa taccatattt  8820
ttgaaaaagc cgtttctgta atgaaggaga aaactcaccg aggcagttcc aaagaatggc  8880
aaggtcctgg taacggtctg cgattccgac ccgtccaaca tcaatacaac ctattaattt  8940
cccctcgtca aaaataaggt tatcaagtga gaaatcacca tgagtgacga ctgaatccgg  9000
tgagaatggc aagagcttgt gcatttcttt ccagacttgt tcaacaggcc agccattacg  9060
ctcgtcatca aaatcactcg catcaaccaa accgttattc atgcgtgatt gcgcctgagc  9120
aagacgaaat acacgatcgc tgttaaaagg acaattacaa acaggaatcg aatgtaaccg  9180
gcgcaggaac acggccagcg catcaacaat attttcacct gaatcaggat attcttctaa  9240
tacctggaag gctgttttcc caggaatcgc ggtggtgagt aaccacgcat catcaggagt  9300
acggataaaa tgcttgatgg tcgggagagg cataaactcc gtcagccagt tgagacggac  9360
catctcatct gtaacatcat tggcaacgct acctttgcca tgtttcagaa acaactctgg  9420
cgcatcgggc ttcccataca agcgatagat tgtcgcacct gattgcccga cattatcgcg  9480
agcccattta tacccatata aatcagcgtc catgttggag tttaagcgcg gacgggagca  9540
agacgtttcc cgttgaatat ggctcataac accccttgta ttactgttta tgtaagcaga  9600
cagttttatt gttcatgatg atatattttt atcttgtgca atgtaacatc agagattttg  9660
agacacaacg tggctttgtt gaataaatcg aacttttgct gagttgaagg atcagctcta  9720
gtaaaataat aaaaaagccg gattaataat ctggcttttt atattctctc tctagtatat  9780
aaacgcagaa aggcccaccc gaaggtgagc cagtgtgacg gcacatttcc ccgaaaagtg  9840
ccacctaaat tgtaagcgtt aatattttgt taaaattcgc gttaaatttt tgttaaatca  9900
gctcattttt taaccaatag gccgaaatcg gcaaaatccc ttataaatca aaagaataga  9960
ccgagatagg gttgagtgtt gttccagttt ggaacaagag tccactatta aagaacgtgg  10020
actccaacgt caaagggcga aaaaccgtct atcagggcga tggcccacta cgtgaaccat  10080
caccctaatc aagttttttg gggtcgaggt gccgtaaagc actaaatcgg aaccctaaag  10140
ggagcccccg atttagagct tgacggggaa agccggcgaa cgtggcgaga aaggaaggga  10200
agaaagcgaa aggagcgggc gctagggcgc tggcaagtgt agcggtcacg ctgcgcgtaa  10260
ccaccacacc cgccgcgctt aatgcgccgc tacagggcgc gtcccattcg ccattcaggc  10320
tgcgcaactg ttgggaaggg cgatcggtgc gggcctcttc gctattacgc cagctggcga  10380
aagggggatg tgctgcaagg cgattaagtt gggtaacgcc agggttttcc cagtcacgac  10440
gttgtaaaac gacggccagt gagcgcgcgg cgaattgggt accgggcccc c           10491

SEQ ID NO: 24          moltype = DNA  length = 7567
FEATURE                Location/Qualifiers
misc_feature           1..7567
                       note = Description of Artificial Sequence: Synthetic
                        polynucleotide
source                 1..7567
                       mol_type = other DNA
                       organism = synthetic construct
SEQUENCE: 24
cctcgagggc tagccattct atttaatctc cctatcagtg atagagatct ccctatcagt  60
gatagagatc gcccgagtga gcacgcaggg tctccatttt gaagcgggag gtttgaacgc  120
gcagccgcca tgccggggtt ttacgagatt gtgattaagg tccccagcga ccttgacgag  180
catctgcccg gcatttctga cagctttgtg aactgggtgg ccgagaagga atgggagttg  240
ccgccagatt ctgacatgga tctgaatctg attgagcagg cacccctgac cgtggccgag  300
aagctgcagc gcgactttct gacggaatgg cgccgtgtga gtaaggcccc ggaggctctt  360
ttctttgtgc aatttgagaa gggagagagc tacttccaca tgcacgtgct cgtggaaacc  420
accggggtga aatccatggt tttgggacgt ttcctgagtc agattcgcga aaaactgatt  480
cagagaattt accgcgggat cgagccgact ttgccaaact ggttcgcggt cacaaagacc  540
agaaatggcg ccggaggcgg gaacaaggtg gtggatgagt gctacatccc caattacttg  600
ctccccaaaa cccagcctga gctccagtgg gcgtggacta atatggaaca gtatttaagg  660
taagttccct atcagtgata gagatctccc tatcagtgat agagatactg acatccactt  720
tgcctttctc tccacagcgc ctgtttgaat ctcacggagc gtaaacggtt ggtggcgcag  780
catctgacgc acgtgtcgca gacgcaggag cagaacaaag agaatcagaa tcccaattct  840
gatgcgccgg tgatcagatc aaaaacttca gccaggtaca tggagctggt cgggtggctc  900
gtggacaagg ggattacctc ggagaagcag tggatccagg aggaccaggc ctcatacatc  960
tccttcaatg cggcctccaa ctcgcggtcc caaatcaagg ctgccttgga caatgcggga  1020
aagattatga gcctgactaa aaccgccccc gactacctgg tgggccagca gcccgtggag  1080
gacatttcca gcaatcggat ttataaaatt ttggaactaa acgggtacga tccccaatat  1140
gcggcttccg tctttctggg atgggccacg aaaaagttcg gcaagaggaa caccatctgg  1200
ctgtttgggc ctgcaactac cgggaagacc aacatcgcgg aggccatagc ccacactgtg  1260
```

```
cccttctacg ggtgcgtaaa ctggaccaat gagaactttc ccttcaacga ctgtgtcgac  1320
aagatggtga tctggtggga ggaggggaag atgaccgcca aggtcgtgga gtcggccaaa  1380
gccattctcg gaggaagcaa ggtgcgcgtg gaccagaaat gcaagtcctc ggcccagata  1440
gacccgactc ccgtgatcgt cacctccaac accaacatgt gcgccgtgat tgacgggaac  1500
tcaacgacct tcgaacacca gcagccgttg caagaccgga tgttcaaatt tgaactcacc  1560
cgccgtctgg atcatgactt tgggaaggtc accaagcagg aagtcaaaga ctttttccgg  1620
tgggcaaagg atcacgtggt tgaggtggag catgaattct acgtcaaaaa gggtggagcc  1680
aagaaaagac ccgcccccag tgacgcagat ataagtgagc ccaaacgggt gcgcgagtca  1740
gttgcgcagc catcgacgtc agacgcggaa gcttcgatca actacgcaga caggtaccaa  1800
aacaaatgtt ctcgtcacgt gggcatgaat ctgatgctgt ttccctgcag acaatgcgag  1860
agaatgaatc agaattcaaa tatctgcttc actcacggac agaaagactg tttagagtgc  1920
tttcccgtgt cagaatctca acccgtttct gtcgtcaaaa aggcgtatca gaaactgtgc  1980
tacattcatc atatcatggg aaaggtgcca gacgcttgca ctgcctgcga tctggtcaat  2040
gtggatttgg atgactgcat ctttgaacaa taaatgattt aaatcaggta tggctgccga  2100
tggttatctt ccagattggc tcgaggacaa cctctctgag ggcattcgcg agtggtggga  2160
cttgaaacct ggagccccga aacccaaagc caaccagcaa aagcaggacg acggccgggg  2220
tctggtgctt cctggctaca agtacctcgg acccttcaac ggactcgaca agggggagcc  2280
cgtcaacgcg gcggacgcag cggccctcga gcacgacaag gcctacgacc agcagctcaa  2340
agcgggtgac aatccgtacc tgcggtataa ccacgccgac gccgagtttc aggagcgtct  2400
gcaagaagat acgtcttttg ggggcaacct cgggcgagca gtcttccagg ccaagaagcg  2460
ggttctcgaa cctctcggtc tggttgagga aggcgctaag acggctcctg gaaagaagag  2520
accggtagag caatcacccc aggaaccaga ctcctcttcg ggcatcggca agaaaggcca  2580
gcagcccgcg agaaagagac tcaactttgg gcagactggc gactcagagt cagtgcccga  2640
ccctcaacca ctcggagaac cccccgcagc cccctctggt gtgggatcta atacaatggc  2700
tgcaggcggt ggcgctccaa tggcagacaa taacgaaggc gccgacggag tgggtaacgc  2760
ctcaggaaat tggcattgcg attccacatg gctgggcgac agagtcatca ccaccagcac  2820
ccgaacctgg gccctcccca cctacaacaa ccacctctac aagcaaatct ccagccaatc  2880
gggaggcagc accaacgaca acacctactt cggctacagc accccctggg ggtattttga  2940
ctttaacaga ttccactgcc acttctcacc acgtgactgg cagcgactca tcaacaacaa  3000
ctggggattc cggcccaaga agctcaactt caagctcttc aacatccagg tcaaggaggt  3060
cacgacgaat gatggcacca cgaccatcgc caataacctt accagcacgg ttcaggtctt  3120
tacggactcg gaataccagc tcccgtacgt cctcggctct gcgcaccagg gctgcctgcc  3180
tccgttcccg gcggacgtct tcatgattcc tcagtacggg tacctgactc tgaacaatgg  3240
cagtcaggcc gtgggccgtt cctccttcta ctgcctggaa tactttcctt ctcaaatgct  3300
gagaacgggc aacaactttc agttcagcta cacgtttgag gacgtgcctt ttcacagcag  3360
ctacgcgcac agccaaagcc tggaccggct gatgaacccc ctcatcgacc agtacctgta  3420
ctacctgtct cggactcaga ccacgagtgg taccgcagga aatcggacgt tgcaattttc  3480
tcaggccggg cctagtagca tggcgaatca ggccaaaaac tggctacccg ggccctgcta  3540
ccggcagcaa cgcgtctcca agacaaccaa tcaaaataac aacagcaact ttgcctggac  3600
cggtgccacc aagtatcatc tgaatggcag agactctctg gtaaatcccg gtcccgctat  3660
ggcaacccac aaggacgacg aagacaaatt ttttccgatg agcggagtct taatatttgg  3720
gaaacaggga gctggaaata gcaacgtgga ccttgacaac gttatgataa ccaacgagga  3780
agaaattaaa accaccaacc cagtggccac agaagagtac ggcacggtgg ccactaacct  3840
gcaatcggcc aacaccgctc ctgctacagg gaccgtcaac agtcaaggag ccttacctgg  3900
catggtctgg caggaccggg acgtgtacct gcagggtcct atctgggcca agattcctca  3960
cacggacgga cactttcatc cctcgccgct gatgggaggc tttggactga aacacccgcc  4020
tcctcagatc ctgattaaga atacacctgt tcccgcgaat cctccaacta ccttcagtcc  4080
agctaagttt gcgtcgttca tcacgcagta cagcaccgga caggtcagcg tggaaattga  4140
atgggagctg cagaaagaaa acagcaaacg ctggaaccca gagattcaat acacttccaa  4200
ctacaacaaa tctacaaatg tggactttgc tgttgacaca aatggcgttt attctgagcc  4260
tcgccccatc ggcacccgtt acctcacccg taatctgtaa actagtttgc ttgttaatca  4320
ataaaccgtt taattcgttt cagttgaact ttggtctctg cgtatttctt tcttatctag  4380
tttccatgct ctagaggtcc tgtattagag gtcacgtgag tgttttgcga cattttgcga  4440
caccatgtgg tcacgctggg tatttaagcc cgagtgagca cgcagggtct ccattttgaa  4500
gcgggaggtt tgaacgcgca gccgccaagc cgaattctgc agatatccat cacactggcg  4560
gccgctcgac tagagcggcc gccaccgcgg tggagctcca gcttttgttc gcgcgcttgg  4620
cgtaatcatg gtcatagctg tttcctgtgt gaaattccac agcctggggt gcctaattgc  4680
gttgcgctca ctgcccgctt tccagtcggg aaacctgtcg tgccagctgc attaatgaat  4740
cggccaacgc gcggggagag gcggtttgcg tattgggcgc tcttccgctt cctcgctcac  4800
tgactcgctg cgctcggtcg ttcggctgcg gcgagcggta tcagctcact caaaggcggt  4860
aatacggtta tccacagaat caggggataa cgcaggaaag aacatgtgag caaaaggcca  4920
gcaaaaggcc aggaaccgta aaaaggccgc gttgctggcg tttttccata ggctccgccc  4980
ccctgacgag catcacaaaa atcgacgctc aagtcagagg tggcgaaacc cgacaggact  5040
ataaagatac caggcgtttc cccctggaag ctccctcgtg cgctctcctg ttccgaccct  5100
gccgcttacc ggatacctgt ccgcctttct cccttcggga agcgtggcgc tttctcatag  5160
ctcacgctgt aggtatctca gttcggtgta ggtcgttcgc tccaagctgg gctgtgtgca  5220
cgaacccccc gttcagcccg accgctgcgc cttatccggt aactatcgtc ttgagtccaa  5280
cccggtaaga cacgacttat cgccactggc agcagccact ggtaacagga ttagcagagc  5340
gaggtatgta ggcggtgcta cagagttctt gaagtggtgg cctaactacg gctacactag  5400
aagaacagta tttggtatct gcgctctgct gaagccagtt accttcggaa aaagagttgg  5460
tagctcttga tccggcaaac aaaccaccgc tggtagcggt ggtttttttg tttgcaagca  5520
gcagattacg cgcagaaaaa aaggatctca agaagatcct ttgatctttt ctacggggtc  5580
tgacgctcag tggaacgaaa actcacgtta agggattttg gtcatgagat tatcaaaaag  5640
gatcttcacc tagatccttt taaattaaaa atgaagtttt aaatcaatct aaagtatata  5700
tgagtaaact tggtctgaca gaaataataa aaaagccgga ttaataatct ggctttttat  5760
attctctctc tagtatataa acgcagaaag gcccacccga aggtgagcca gtgtgactct  5820
agtattatta gaaaaactca tcgagcatca aatgaaactg caatttattc atatcaggat  5880
tatcaatacc atatttttga aaaagccgtt tctgtaatga aggagaaaac tcaccgaggc  5940
agttccaaag aatggcaagg tcctggtaac ggtctgcgat tccgacccgt ccaacatcaa  6000
```

```
tacaacctat taatttcccc tcgtcaaaaa taaggttatc aagtgagaaa tcaccatgag  6060
tgacgactga atccggtgag aatggcaaga gcttgtgcat ttctttccag acttgttcaa  6120
caggccagcc attacgctcg tcatcaaaat cactcgcatc aaccaaaccg ttattcatgc  6180
gtgattgcgc ctgagcaaga cgaaatacac gatcgctgtt aaaaggacaa ttacaaacag  6240
gaatcgaatg taaccggcgc aggaacacgg ccagcgcatc aacaatattt tcacctgaat  6300
caggatattc ttctaatacc tggaaggctg ttttcccagg aatcgcggtg gtgagtaacc  6360
acgcatcatc aggagtacgg ataaaatgct tgatggtcgg gagaggcata aactccgtca  6420
gccagttgag acggaccatc tcatctgtaa catcattggc aacgctacct ttgccatgtt  6480
tcagaaacaa ctctggcgca tcgggcttcc catacaagcg atagattgtc gcacctgatt  6540
gcccgacatt atcgcgagcc catttatacc catataaatc agcgtccatg ttggagttta  6600
agcgcggacg ggagcaagac gtttcccgtt gaatatggct cataacaccc cttgtattac  6660
tgtttatgta agcagacagt tttattgttc atgatgatat atttttatct tgtgcaatgt  6720
aacatcagag attttgagac acaacgtggc tttgttgaat aaatcgaact tttgctgagt  6780
tgaaggatca gctctagtaa aataataaaa aagccggatt aataatctgg ctttttatat  6840
tctctctcta gtatataaac gcagaaaggc ccacccgaag gtgagccagt gtgacggcac  6900
atttccccga aaagtgccac ctaaattgta agcgttaata ttttgttaaa attcgcgtta  6960
aatttttgtt aaatcagctc attttttaac caataggccg aaatcggcaa aatcccttat  7020
aaatcaaaag aatagaccga gatagggttg agtgttgttc cagtttggaa caagagtcca  7080
ctattaaaga acgtggactc caacgtcaaa gggcgaaaaa ccgtctatca gggcgatggc  7140
ccactacgtg aaccatcacc ctaatcaagt tttttggggt cgaggtgccg taaagcacta  7200
aatcggaacc ctaaagggag cccccgattt agagcttgac ggggaaagcc ggcgaacgtg  7260
gcgagaaagg aagggaagaa agcgaaagga gcgggcgcta gggcgctggc aagtgtagcg  7320
gtcacgctgc gcgtaaccac cacacccgcc gcgcttaatg cgccgctaca gggcgcgtcc  7380
cattcgccat tcaggctgcg caactgttgg gaagggcgat cggtgcgggc ctcttcgcta  7440
ttacgccagc tggcgaaagg gggatgtgct gcaaggcgat taagttgggt aacgccaggg  7500
ttttcccagt cacgacgttg taaaacgacg gccagtgagc gcgcggcgaa ttgggtaccg  7560
ggccccc                                                            7567

SEQ ID NO: 25          moltype = DNA  length = 7567
FEATURE                Location/Qualifiers
misc_feature           1..7567
                       note = Description of Artificial Sequence: Synthetic
                        polynucleotide
source                 1..7567
                       mol_type = other DNA
                       organism = synthetic construct
SEQUENCE: 25
cctcgagggc tagccattct atttaatctc cctatcagtg atagagatct ccctatcagt  60
gatagagatc gcccgagtga gcacgcaggg tctccatttt gaagcgggag gtttgaacgc  120
gcagccgcca tgccggggtt ttacgagatt gtgattaagg tccccagcga ccttgacgag  180
catctgcccg gcatttctga cagctttgtg aactgggtgg ccgagaagga atgggagttg  240
ccgccagatt ctgacatgga tctgaatctg attgagcagg caccccctgac cgtggccgag  300
aagctgcagc gcgactttct gacggaatgg cgccgtgtga gtaaggcccc ggaggctctt  360
ttctttgtgc aatttgagaa gggagagagc tacttccaca tgcacgtgct cgtggaaacc  420
accggggtga aatccatggt tttgggacgt ttcctgagtc agattcgcga aaaactgatt  480
cagagaattt accgcgggat cgagccgact ttgccaaact ggttcgcggt cacaaagacc  540
agaaatggcg ccggaggcgg gaacaaggtg gtggatgagt gctacatccc caattacttg  600
ctccccaaaa cccagcctga gctccagtgg gcgtggacta atatggaaca gtatttaagc  660
gcctgtttga atctcacgga aaggtaagtt ccctatcagt gatagagatc tccctatcag  720
tgatagagat actgacatcc actttgcctt tctctccaca ggaaacggtt ggtggcgcag  780
catctgacgc acgtgtcgca gacgcaggag cagaacaaag agaatcagaa tcccaattct  840
gatgcgccgg tgatcagatc aaaaacttca gccaggtaca tggagctggt cgggtggctc  900
gtggacaagg ggattacctc ggagaagcag tggatccagg aggaccaggc ctcatacatc  960
tccttcaatg cggcctccaa ctcgcggtcc caaatcaagg ctgccttgga caatgcggga  1020
aagattatga gcctgactaa aaccgccccc gactacctgg tgggccagca gcccgtggag  1080
gacatttcca gcaatcggat ttataaaatt ttggaactaa acgggtacga tccccaatat  1140
gcggcttccg tctttctggg atgggccacg aaaaagttcg gcaagaggaa caccatctgg  1200
ctgtttgggc ctgcaactac cgggaagacc aacatcgcgg aggccatagc ccacactgtg  1260
cccttctacg ggtgcgtaaa ctggaccaat gagaactttc ccttcaacga ctgtgtcgac  1320
aagatggtga tctggtggga ggaggggaag atgaccgcca aggtcgtgga gtcggccaaa  1380
gccattctcg gaggaagcaa ggtgcgcgtg gaccagaaat gcaagtcctc ggcccagata  1440
gacccgactc ccgtgatcgt cacctccaac accaacatgt gcgccgtgat tgacgggaac  1500
tcaacgacct tcgaacacca gcagccgttg caagaccgga tgttcaaatt tgaactcacc  1560
cgccgtctgg atcatgactt tgggaaggtc accaagcagg aagtcaaaga ctttttccgg  1620
tgggcaaagg atcacgtggt tgaggtggag catgaattct acgtcaaaaa gggtggagcc  1680
aagaaaagac ccgccccag tgacgcagat ataagtgagc ccaaacgggt gcgcgagtca  1740
gttgcgcagc catcgacgtc agacgcggaa gcttcgatca actacgcaga caggtaccaa  1800
aacaaatgtt ctcgtcacgt gggcatgaat ctgatgctgt ttccctgcag acaatgcgag  1860
agaatgaatc agaattcaaa tatctgcttc actcacggac agaaagactg tttagagtgc  1920
tttcccgtgt cagaatctca acccgtttct gtcgtcaaaa aggcgtatca gaaactgtgc  1980
tacattcatc atatcatggg aaaggtgcca gacgcttgca ctgcctgcga tctggtcaat  2040
gtggatttgg atgactgcat ctttgaacaa taaatgattt aaatcaggta tggctgccga  2100
tggttatctt ccagattggc tcgaggacaa cctctctgag ggcattcgcg agtggtggga  2160
cttgaaacct ggagccccga aacccaaagc caaccagcaa aagcaggacg acggccgggg  2220
tctggtgctt cctggctaca agtacctcgg acccttcaac ggactcgaca agggggagcc  2280
cgtcaacgcg gcggacgcag cggccctcga gcacgacaag gcctacgacc agcagctcaa  2340
agcgggtgac aatccgtacc tgcggtataa ccacgccgac gccgagtttc aggagcgtct  2400
gcaagaagat acgtcttttg gggcaacct cgggcgagca gtcttccagg ccaagaagcg  2460
ggttctcgaa cctctcggtc tggttgagga aggcgctaag acggctcctg gaaagaagag  2520
```

```
accggtagag caatcacccc aggaaccaga ctcctcttcg ggcatcggca agaaaggcca  2580
gcagcccgcg agaaagagac tcaactttgg gcagactggc gactcagagt cagtgcccga  2640
ccctcaacca ctcggagaac cccccgcagc cccctctggt gtgggatcta atacaatggc  2700
tgcaggcggt ggcgctccaa tggcagacaa taacgaaggc gccgacggag tgggtaacgc  2760
ctcaggaaat tggcattgcg attccacatg gctgggcgac agagtcatca ccaccagcac  2820
ccgaacctgg gccctcccca cctacaacaa ccacctctac aagcaaatct ccagccaatc  2880
gggaggcagc accaacgaca acacctactt cggctacagc accccctggg ggtattttga  2940
ctttaacaga ttccactgcc acttctcacc acgtgactgg cagcgactca tcaacaacaa  3000
ctggggattc cggcccaaga agctcaactt caagctcttc aacatccagg tcaaggaggt  3060
cacgacgaat gatggcacca cgaccatcgc caataacctt accagcacgg ttcaggtctt  3120
tacggactcg gaataccagc tcccgtacgt cctcggctct gcgcaccagg gctgcctgcc  3180
tccgttcccg gcggacgtct tcatgattcc tcagtacggg tacctgactc tgaacaatgg  3240
cagtcaggcc gtgggccgtt cctccttcta ctgcctggaa tactttcctt ctcaaatgct  3300
gagaacgggc aacaactttc agttcagcta cacgtttgag gacgtgcctt ttcacagcag  3360
ctacgcgcac agccaaagcc tggaccggct gatgaacccc ctcatcgacc agtacctgta  3420
ctacctgtct cggactcaga ccacgagtgg taccgcagga aatcggacgt tgcaattttc  3480
tcaggccggg cctagtagca tggcgaatca ggccaaaaac tggctacccg ggccctgcta  3540
ccggcagcaa cgcgtctcca agacaaccaa tcaaaataac aacagcaact ttgcctggac  3600
cggtgccacc aagtatcatc tgaatggcag agactctctg gtaaatcccg gtcccgctat  3660
ggcaacccac aaggacgacg aagacaaatt ttttccgatg agcggagtct taatatttgg  3720
gaaacaggga gctggaaata gcaacgtgga ccttgacaac gttatgataa ccaacgagga  3780
agaaattaaa accaccaacc cagtggccac agaagagtac ggcacggtgg ccactaacct  3840
gcaatcggcc aacaccgctc ctgctacagg gaccgtcaac agtcaaggag ccttacctgg  3900
catggtctgg caggaccggg acgtgtacct gcagggtcct atctgggcca agattcctca  3960
cacggacgga cactttcatc cctcgccgct gatgggaggc tttggactga aacacccgcc  4020
tcctcagatc ctgattaaga atacacctgt tcccgcgaat cctccaacta ccttcagtcc  4080
agctaagttt gcgtcgttca tcacgcagta cagcaccgga caggtcagcg tggaaattga  4140
atgggagctg cagaaagaaa acagcaaacg ctggaaccca gagattcaat acacttccaa  4200
ctacaacaaa tctacaaatg tggactttgc tgttgacaca aatggcgttt attctgagcc  4260
tcgccccatc ggcacccgtt acctcacccg taatctgtaa actagtttgc ttgttaatca  4320
ataaaccgtt taattcgttt cagttgaact ttggtctctg cgtatttctt tcttatctag  4380
tttccatgct ctagaggtcc tgtattagag gtcacgtgag tgttttgcga cattttgcga  4440
caccatgtgg tcacgctggg tatttaagcc cgagtgagca cgcagggtct ccattttgaa  4500
gcgggaggtt tgaacgcgca gccgccaagc cgaattctgc agatatccat cacactggcg  4560
gccgctcgac tagagcggcc gccaccgcgg tggagctcca gcttttgttc gcgcgcttgg  4620
cgtaatcatg gtcatagctg tttcctgtgt gaaattccac agcctggggt gcctaattgc  4680
gttgcgctca ctgcccgctt tccagtcggg aaacctgtcg tgccagctgc attaatgaat  4740
cggccaacgc gcggggagag gcggtttgcg tattgggcgc tcttccgctt cctcgctcac  4800
tgactcgctg cgctcggtcg ttcggctgcg gcgagcggta tcagctcact caaaggcggt  4860
aatacggtta tccacagaat caggggataa cgcaggaaag aacatgtgag caaaaggcca  4920
gcaaaaggcc aggaaccgta aaaaggccgc gttgctggcg tttttccata ggctccgccc  4980
ccctgacgag catcacaaaa atcgacgctc aagtcagagg tggcgaaacc cgacaggact  5040
ataaagatac caggcgtttc cccctggaag ctccctcgtg cgctctcctg ttccgaccct  5100
gccgcttacc ggatacctgt ccgcctttct cccttcggga agcgtggcgc tttctcatag  5160
ctcacgctgt aggtatctca gttcggtgta ggtcgttcgc tccaagctgg gctgtgtgca  5220
cgaacccccc gttcagcccg accgctgcgc cttatccggt aactatcgtc ttgagtccaa  5280
cccggtaaga cacgacttat cgccactggc agcagccact ggtaacagga ttagcagagc  5340
gaggtatgta ggcggtgcta cagagttctt gaagtggtgg cctaactacg gctacactag  5400
aagaacagta tttggtatct gcgctctgct gaagccagtt accttcggaa aaagagttgg  5460
tagctcttga tccggcaaac aaaccaccgc tggtagcggt ggtttttttg tttgcaagca  5520
gcagattacg cgcagaaaaa aaggatctca agaagatcct ttgatctttt ctacggggtc  5580
tgacgctcag tggaacgaaa actcacgtta agggattttg gtcatgagat tatcaaaaag  5640
gatcttcacc tagatccttt taaattaaaa atgaagtttt aaatcaatct aaagtatata  5700
tgagtaaact tggtctgaca gaaataataa aaaagccgga ttaataatct ggctttttat  5760
attctctctc tagtatataa acgcagaaag gcccacccga aggtgagcca gtgtgactct  5820
agtattatta gaaaaactca tcgagcatca aatgaaactg caatttattc atatcaggat  5880
tatcaatacc atatttttga aaaagccgtt tctgtaatga aggagaaaac tcaccgaggc  5940
agttccaaag aatggcaagg tcctggtaac ggtctgcgat tccgacccgt ccaacatcaa  6000
tacaacctat taatttcccc tcgtcaaaaa taaggttatc aagtgagaaa tcaccatgag  6060
tgacgactga atccggtgag aatggcaaga gcttgtgcat ttctttccag acttgttcaa  6120
caggccagcc attacgctcg tcatcaaaat cactcgcatc aaccaaaccg ttattcatgc  6180
gtgattgcgc ctgagcaaga cgaaatacac gatcgctgtt aaaaggacaa ttacaaacag  6240
gaatcgaatg taaccggcgc aggaacacgg ccagcgcatc aacaatattt tcacctgaat  6300
caggatattc ttctaatacc tggaaggctg ttttcccagg aatcgcggtg gtgagtaacc  6360
acgcatcatc aggagtacgg ataaaatgct tgatggtcgg gagaggcata aactccgtca  6420
gccagttgag acggaccatc tcatctgtaa catcattggc aacgctacct ttgccatgtt  6480
tcagaaacaa ctctggcgca tcgggcttcc catacaagcg atagattgtc gcacctgatt  6540
gcccgacatt atcgcgagcc catttatacc catataaatc agcgtccatg ttggagttta  6600
agcgcggacg ggagcaagac gtttcccgtt gaatatggct cataacaccc cttgtattac  6660
tgtttatgta agcagacagt tttattgttc atgatgatat atttttatct tgtgcaatgt  6720
aacatcagag attttgagac acaacgtggc tttgttgaat aaatcgaact tttgctgagt  6780
tgaaggatca gctctagtaa aataataaaa aagccggatt aataatctgg ctttttatat  6840
tctctctcta gtatataaac gcagaaaggc ccacccgaag gtgagccagt gtgacggcac  6900
atttccccga aaagtgccac ctaaattgta agcgttaata ttttgttaaa attcgcgtta  6960
aatttttgtt aaatcagctc attttttaac caataggccg aaatcggcaa aatcccttat  7020
aaatcaaaag aatagaccga gatagggttg agtgttgttc cagtttggaa caagagtcca  7080
ctattaaaga acgtggactc caacgtcaaa gggcgaaaaa ccgtctatca gggcgatggc  7140
ccactacgtg aaccatcacc ctaatcaagt tttttggggt cgaggtgccg taaagcacta  7200
aatcggaacc ctaaagggag cccccgattt agagcttgac ggggaaagcc ggcgaacgtg  7260
```

```
gcgagaaagg aagggaagaa agcgaaagga gcgggcgcta gggcgctggc aagtgtagcg  7320
gtcacgctgc gcgtaaccac cacacccgcc gcgcttaatg cgccgctaca gggcgcgtcc  7380
cattcgccat tcaggctgcg caactgttgg gaagggcgat cggtgcgggc ctcttcgcta  7440
ttacgccagc tggcgaaagg gggatgtgct gcaaggcgat taagttgggt aacgccaggg  7500
ttttcccagt cacgacgttg taaaacgacg gccagtgagc gcgcggcgaa ttgggtaccg  7560
ggccccc                                                            7567

SEQ ID NO: 26          moltype = DNA  length = 11801
FEATURE                Location/Qualifiers
misc_feature           1..11801
                       note = Description of Artificial Sequence: Synthetic
                        polynucleotide
source                 1..11801
                       mol_type = other DNA
                       organism = synthetic construct
SEQUENCE: 26
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcgtttaaac ttaagcttgg taccgagctc ggatccacta  1560
gtccagtgtg gtggaattcc tgcttcgcga tgtacgggcc agatatacgc gttgacattg  1620
attattgact agttattaat agtaatcaat tacggggtca ttagttcata gcccatatat  1680
ggagttccgc gttacataac ttacggtaaa tggcccgcct ggctgaccgc ccaacgaccc  1740
ccgcccattg acgtcaataa tgacgtatgt tcccatagta acgccaatag ggactttcca  1800
ttgacgtcaa tgggtggagt atttacggta aactgcccac ttggcagtac atcaagtgta  1860
tcatatgcca agtacgcccc ctattgacgt caatgacggt aaatggcccg cctggcatta  1920
tgcccagtac atgaccttat gggactttcc tacttggcag tacatctacg tattagtcat  1980
cgctattacc atggtgatgc ggttttggca gtacatcaat gggcgtggat agcggtttga  2040
ctcacgggga tttccaagtc tccaccccat tgacgtcaat gggagtttgt tttggaacca  2100
aaatcaacgg gactttccaa aatgtcgtaa caactccgcc ccattgacgc aaatgggcgg  2160
taggcgtgta cggtgggagg tctatataag cagagctctc cctatcagtg atagagatct  2220
ccctatcagt gatagagatc gtcgacgagc tcgtttagtg aaccgtcaga tcgcctggag  2280
acgccatcca cgctgttttg acctccatag aagacaccgg gaccgatcca gcctccggac  2340
tctagcgttt aaacttaagc ttgccaccat ggccagtcgg gaagaggagc agcgcgaaac  2400
cacccccgag cgcggacgcg gtgcggcgcg acgtccccca accatggagg acgtgtcgtc  2460
cccgtccccg tcgccgccgc ctccccgggc gcccccaaaa aagcggatga ggcggcgtat  2520
cgagtccgag gacgaggaag actcatcaca agacgcgctg gtgccgcgca cacccagccc  2580
gcggccatcg acctcggcgg cggatttggc cattgcgccc aagaagaaaa agaagcgccc  2640
ttctcccaag cccgagcgcc cgccatcacc agaggtaatc gtggacagcg aggaagaaag  2700
agaagatgtg gcgctacaaa tggtgggttt cagcaaccca ccggtgctaa tcaagcatgg  2760
caaaggaggt aagcgcacag tgcggcggct gaatgaagac gacccagtgg cgcgtggtat  2820
gcggacgcaa gaggaagagg aagagcccag cgaagcggaa agtgaaatta cggtgatgaa  2880
cccgctgagt gtgccgatcg tgtctgcgtg ggagaagggc atggaggctg cgcgcgcgct  2940
gatggacaag taccacgtgg ataacgatct aaaggcgaac ttcaaactac tgcctgacca  3000
agtggaagct ctggcggccg tatgcaagac ctggctgaac gaggagcacc gcgggttgca  3060
gctgaccttc accagcaaca agacctttgt gacgatgatg gggcgattcc tgcaggcgta  3120
cctgcagtcg tttgcagagg tgacctacaa gcatcacgag cccacgggct gcgcgttgtg  3180
gctgcaccgc tgcgctgaga tcgaaggcga gcttaagtgt ctacacggaa gcattatgat  3240
aaataaggag cacgtgattg aaatggatgt gacgagcgaa aacgggcagc gcgcgctgaa  3300
ggagcagtct agcaaggcca agatcgtgaa gaaccggtgg ggccgaaatg tggtgcagat  3360
ctccaacacc gacgcaaggt gctgcgtgca cgacgcggcc tgtccggcca atcagttttc  3420
cggcaagtct tgcggcatgt tcttctctga aggcgcaaag gctcaggtgg cttttaagca  3480
gatcaaggct tttatgcagg cgctgtatcc taacgcccag accgggcacg gtcacctttt  3540
gatgccacta cggtgcgagt gcaactcaaa gcctgggcac gcgccctttt tgggaaggca  3600
gctaccaaag ttgactccgt tcgccctgag caacgcggag gacctggacg cggatctgat  3660
ctccgacaag agcgtgctgg ccagcgtgca ccacccggcg ctgatagtgt tccagtgctg  3720
caaccctgtg tatcgcaact cgcgcgcgca gggcggaggc cccaactgcg acttcaagat  3780
```

```
atcggcgccc gacctgctaa acgcgttggt gatggtgcgc agcctgtgga gtgaaaactt 3840
caccgagctg ccgcggatgg ttgtgcctga gtttaagtgg agcactaaac accagtatcg 3900
caacgtgtcc ctgccagtgg cgcatagcga tgcgcggcag aacccctttg atttttaacc 3960
cgggagttct agggatctgc cctctccct cccccccccc taacgttact ggccgaagcc 4020
gcttggaata aggccggtgt gcgtttgtct atatgttatt ttccaccata ttgccgtctt 4080
ttggcaatgt gagggcccgg aaacctggcc ctgtcttctt gacgagcatt cctaggggtc 4140
tttcccctct cgccaaagga atgcaaggtc tgttgaatgt cgtgaaggaa gcagttcctc 4200
tggaagcttc ttgaagacaa acaacgtctg tagcgaccct ttgcaggcag cggaaccccc 4260
cacctggcga caggtgcctc tgcggccaaa agccacgtgt ataagataca cctgcaaagg 4320
cggcacaacc ccagtgccac gttgtgagtt ggatagttgt ggaaagagtc aaatggctct 4380
cctcaagcgt attcaacaag gggctgaagg atgcccagaa ggtaccccat tgtatgggat 4440
ctgatctggg gcctcggtgc acatgcttta catgtgttta gtcgaggtta aaaaaacgtc 4500
taggcccccc gaaccacggg gacgtggttt tcctttgaaa aacacgatga taaggatcca 4560
ccggaggcca ccatgactac gtccggcgtt ccatttggca tgacactacg accaacacga 4620
tctcggttgt ctcggcgcac tccgtacagt agggatcgtc tacctccttt tgagacagaa 4680
acccgcgcta ccatactgga ggatcatccg ctgctgcccg aatgtaacac tttgacaatg 4740
cacaacgtga gttacgtgcg aggtcttccc tgcagtgtgg gatttacgct gattcaggaa 4800
tgggttgttc cctgggatat ggttctaacg cgggaggagc ttgtaatcct gaggaagtgt 4860
atgcacgtgt gcctgtgttg tgccaacatt gatatcatga cgagcatgat gatccatggt 4920
tacgagtcct gggctctcca ctgtcattgt tccagtcccg gttccctgca gtgtatagcc 4980
ggcgggcagg ttttggccag ctggtttagg atggtggtgg atggcgccat gtttaatcag 5040
aggtttatat ggtaccggga ggtggtgaat tacaacatgc caaaagaggt aatgtttatg 5100
tccagcgtgt ttatgagggg tcgccactta atctacctgc gcttgtggta tgatggccac 5160
gtgggttctg tggtccccgc catgagcttt ggatacagcg ccttgcactg tgggattttg 5220
aacaatattg tggtgctgtg ctgcagttac tgtgctgatt taagtgagat cagggtgcgc 5280
tgctgtgccc ggaggacaag gcgccttatg ctgcgggcgg tgcgaatcat cgctgaggag 5340
accactgcca tgttgtattc ctgcaggacg gagcggcggc ggcagcagtt tattcgcgcg 5400
ctgctgcagc accaccgccc tatcctgatg cacgattatg actctacccc catgtaggcg 5460
gccgtcgagt ctagagggcc cgtttaaacc cgctgatcag cctcgactgt gccttctagt 5520
tgccagccat ctgttgtttg cccctccccc gtgccttcct tgaccctgga aggtgccact 5580
cccactgtcc tttcctaata aaatgaggaa attgcatcgc attgtctgag taggtgtcat 5640
tctattctgg ggggtggggt ggggcaggac agcaaggggg aggattggga agacaatagc 5700
aggcatgctg gggatgcggt gggctctatg gcttctgagg cggaaagaac cagctggggc 5760
tctagggggt atccccggcg cgccggggtt gagctattcc agaagtagtg aagaggcttt 5820
tttggaggcc taggcttttg caaaaagctc cggatcgatt ggggttgcgc cttttccaag 5880
gcttttcccc gtatcccccc aggtgtctgc aggctcaaag agcagcgaga agcgttcaga 5940
ggaaagcgat cccgtgccac cttccccgtg cccgggctgt ccccgcacgc tgccggctcg 6000
gggatgcggg gggagcgccg gaccggagcg gagccccggg cggctcgctg ctgcccccta 6060
gcgggggagg gacgtaatta catccctggg ggctttgggg gggggctgtc cctctagggg 6120
atcctctagg gcctctgagc tattccagaa gtagtgaaga ggcttttttg gaggcctagg 6180
cttttgcaaa aagctccgga tcgatcgagc ggatccagca cagtggcggc cgcaatattt 6240
gcatgtcgct atgtgttctg ggaaatcacc ataaacgtga aatccctatc agtgatagag 6300
acttataagt tccctatcag tgatagagaa ccggtgggca ctcttccgtg gtctggtgga 6360
taaattcgca agggtatcat ggcggacgac cggggttcga gccccgtatc cggccgtccg 6420
ccgtgatcca tgcggttacc gcccgcgtgt cgaacccagg tgtgcgacgt cagacaacgg 6480
gggagtgctc ctttttgaat tccactttgg ccgcggctcg agtgagctat tccagaagta 6540
gtgaagaggc ttttttggag gcctaggctt ttgcaaaaag ctccggatcg atgcccgggg 6600
gatccactag ttctagaggg acagcccccc cccaaagccc ccagggatgt aattacgtcc 6660
ctcccccgct agggggcagc agcgagccgc ccggggctcc gctccggtcc ggcgctcccc 6720
ccgcatcccc gagccggcag cgtgcgggga cagcccgggc acggggaagg tggcacggga 6780
tcgctttcct ctgaacgctt ctcgctgctc tttgagcctg cagacacctg gggggatacg 6840
gggaaaaggc ctccaaggcc agcttcccac aataagttgg gtgaattttg gctgagctat 6900
tccagaagta gtgaagaggc ttttttggag gcctaggctt ttgcaaaaag ctccggatcg 6960
atcatatatg gcagatatac gcgttgacat tgattattga ctagttatta atagtaatca 7020
attacggggt cattagttca tagcccatat atggagttcc gcgttacata acttacggta 7080
aatggcccgc ctggctgacc gcccaacgac ccccgcccat tgacgtcaat aatgacgtat 7140
gttcccatag taacgccaat agggactttc cattgacgtc aatgggtgga gtatttacgg 7200
taaactgccc acttggcagt acatcaagtg tatcatatgc caagtacgcc ccctattgac 7260
gtcaatgacg gtaaatggcc cgcctggcat tatgcccagt acatgacctt atgggacttt 7320
cctacttggc agtacatcta cgtattagtc atcgctatta ccatggtgat gcggttttgg 7380
cagtacatca atgggcgtgg atagcggttt gactcacggg gatttccaag tctccacccc 7440
attgacgtca atgggagttt gttttggcac caaaatcaac gggactttcc aaaatgtcgt 7500
aacaactccg ccccattgac gcaaatgggc ggtaggcgtg tacggtggga ggtctatata 7560
agcagagctc tctggctaac tatcgtcgac gagctcgttt agtgaaccgt cagatcgcct 7620
ggagacgcca tccacgctgt tttgacctcc atagaagaca ccgggaccga tccagcctcc 7680
ggactctagc gtttaaactt aagcttgcca ccatgaccga gtacaagccc acggtgcgcc 7740
tcgccacccg cgacgacgtc cccagggccg tacgcaccct cgccgccgcg ttcgccgact 7800
accccgccac gcgccacacc gtcgatccgg accgccacat cgagcgggtc accgagctgc 7860
aagaactctt cctcacgcgc gtcgggctcg acatcggcaa ggtgtgggtc gcggacgacg 7920
gcgccgcggt ggcggtctgg accacgccgg agagcgtcga agcgggggcg gtgttcgccg 7980
agatcggccc gcgcatggcc gagttgagcg gttcccggct ggccgcgcag caacagatgg 8040
aaggcctcct ggcgccgcac cggcccaagg agcccgcgtg gttcctggcc accgtcggcg 8100
tctcgcccga ccaccagggc aagggtctgg gcagcgccgt cgtgctcccc ggagtggagg 8160
cggccgagcg cgccggggtg cccgccttcc tggagacctc cgcgccccgc aacctcccct 8220
tctacgagcg gctcggcttc accgtcaccg ccgacgtcga ggtgcccgaa ggaccgcgca 8280
cctggtgcat gacccgcaag cccggtgcct gaagcgcggg gatctcatgc tggagttctt 8340
cgcccacccc aacttgttta ttgcagctta taatggttac aaataaagca atagcatcac 8400
aaatttcaca aataaagcat ttttttcact gcattctagt tgtggtttgt ccaaactcat 8460
caatgtatct tatcatgtct gtagctgatg tatacctagg atccggccgg cctgcaggtg 8520
```

```
tcctcacagg aacgaagtcc ctaaagaaac agtggcagcc aggtttagcc ccggaattga  8580
ctggattcct tttttagggc ccattggtat ggctttttcc ccgtatcccc ccaggtgtct  8640
gcaggctcaa agagcagcga gaagcgttca gaggaaagcg atcccgtgcc accttccccg  8700
tgcccgggct gtccccgcac gctgccggct cggggatgcg gggggagcgc cggaccggag  8760
cggagccccg ggcggctcgc tgctgccccc tagcggggga gggacgtaat tacatccctg  8820
ggggctttgg ggggggggctg tccctctaga gcggccgcca ccgcggtgga gctccagctt  8880
ttgttccctt tagtgagggt taattagatc ttaatacgac tcactatagg gcgaattggg  8940
taccgggccc cccctcgagg tcgacggtat cgataagctt gatatctata acaagaaaat  9000
atatatataa taagttatca cgtaagtaga acatgaaata acaatataat tatcgtatga  9060
gttaaatctt aaaagtcacg taaaagataa tcatgcgtca ttttgactca cgcggtcgtt  9120
atagttcaaa atcagtgaca cttaccgcat tgacaagcac gcctcacggg agctccaagc  9180
ggcgactgag atgtcctaaa tgcacagcga cggattcgcg ctatttagaa agagagagca  9240
atatttcaag aatgcatgcg tcaattttac gcagactatc tttctagggt taatctagct  9300
gcatcaggat catatcgtcg ggtctttttt ccggctcagt catcgcccaa gctggcgcta  9360
tctgggcatc ggggaggaag aagcccgtgc cttttcccgc gaggttgaag cggcatggaa  9420
agagtttgcc gaggatgact gctgctgcat tgacgttgag cgaaaacgca cgtttaccat  9480
gatgattcgg gaaggtgtgg ccatgcacgc ctttaacggt gaactgttcg ttcaggccac  9540
ctgggatacc agttcgtcgc ggcttttccg gacacagttc cggatggtca gcccgaagcg  9600
catcagcaac ccgaacaata ccggcgacag ccggaactgc cgtgccggtg tgcagattaa  9660
tgacagcggt gcggcgctgg gatattacgt cagcgaggac gggtatcctg gctggatgcc  9720
gcagaaatgg acatggatac cccgtgagtt acccggcggg cgcgcttggc gtaatcatgg  9780
tcatagctgt ttcctgtgtg aaattgttat ccgctcacaa ttccacacaa catacgagcc  9840
ggaagcataa agtgtaaagc ctggggtgcc taatgagtga gctaactcac attaattgcg  9900
ttgcgctcac tgcccgcttt ccagtcggga aacctgtcgt gccagctgca ttaatgaatc  9960
ggccaacgcg cggggagagg cggtttgcgt attgggcgct cttccgcttc ctcgctcact  10020
gactcgctgc gctcggtcgt tcggctgcgg cgagcggtat cagctcactc aaaggcggta  10080
atacggttat ccacagaatc aggggataac gcaggaaaga acatgtgagc aaaaggccag  10140
caaaaggcca ggaaccgtaa aaaggccgcg ttgctggcgt ttttccatag gctccgcccc  10200
cctgacgagc atcacaaaaa tcgacgctca agtcagaggt ggcgaaaccc gacaggacta  10260
taaagatacc aggcgtttcc ccctggaagc tccctcgtgc gctctcctgt tccgaccctg  10320
ccgcttaccg gatacctgtc cgcctttctc ccttcgggaa gcgtggcgct ttctcatagc  10380
tcacgctgta ggtatctcag ttcggtgtag gtcgttcgct ccaagctggg ctgtgtgcac  10440
gaaccccccg ttcagcccga ccgctgcgcc ttatccggta actatcgtct tgagtccaac  10500
ccggtaagac acgacttatc gccactggca gcagccactg gtaacaggat tagcagagcg  10560
aggtatgtag gcggtgctac agagttcttg aagtggtggc ctaactacgg ctacactaga  10620
aggacagtat ttggtatctg cgctctgctg aagccagtta ccttcggaaa aagagttggt  10680
agctcttgat ccggcaaaca aaccaccgct ggtagcggtg gtttttttgt ttgcaagcag  10740
cagattacgc gcagaaaaaa aggatctcaa gaagatcctt tgatcttttc tacggggtct  10800
gacgctcagt ggaacgaaaa ctcacgttaa gggattttgg tcatgagatt atcaaaaagg  10860
atcttcacct agatcctttt aaattaaaaa tgaagtttta aatcaatcta aagtatatat  10920
gagtaaactt ggtctgacag ttaccaatgc ttaatcagtg aggcacctat ctcagcgatc  10980
tgtctatttc gttcatccat agttgcctga ctccccgtcg tgtagataac tacgatacgg  11040
gagggcttac catctggccc cagtgctgca atgataccgc gagacccacg ctcaccggct  11100
ccagatttat cagcaataaa ccagccagcc ggaagggccg agcgcagaag tggtcctgca  11160
actttatccg cctccatcca gtctattaat tgttgccggg aagctagagt aagtagttcg  11220
ccagttaata gtttgcgcaa cgttgttgcc attgctacag gcatcgtggt gtcacgctcg  11280
tcgtttggta tggcttcatt cagctccggt tcccaacgat caaggcgagt tacatgatcc  11340
cccatgttgt gcaaaaaagc ggttagctcc ttcggtcctc cgatcgttgt cagaagtaag  11400
ttggccgcag tgttatcact catggttatg gcagcactgc ataattctct tactgtcatg  11460
ccatccgtaa gatgcttttc tgtgactggt gagtactcaa ccaagtcatt ctgagaatag  11520
tgtatgcggc gaccgagttg ctcttgcccg gcgtcaatac gggataatac cgcgccacat  11580
agcagaactt taaaagtgct catcattgga aaacgttctt cggggcgaaa actctcaagg  11640
atcttaccgc tgttgagatc cagttcgatg taacccactc gtgcacccaa ctgatcttca  11700
gcatctttta ctttcaccag cgtttctggg tgagcaaaaa caggaaggca aaatgccgca  11760
aaaaagggaa taagggcgac acggaaatgt tgaatactca t                      11801
```

```
SEQ ID NO: 27           moltype = DNA  length = 7798
FEATURE                 Location/Qualifiers
misc_feature            1..7798
                        note = Description of Artificial Sequence: Synthetic
                         polynucleotide
source                  1..7798
                        mol_type = other DNA
                        organism = synthetic construct
SEQUENCE: 27
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
```

```
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcaaacgcca gcaacgcggc ctttttacgg ttcctggcct  1560
tttgctggcc ttttgctcac atgtcctgca ggcagctgcg cgctcgctcg ctcactgagg  1620
ccgcccgggc aaagcccggg cgtcgggcga cctttggtcg cccggcctca gtgagcgagc  1680
gagcgcgcag agagggagtg gccaactcca tcactagggg ttcctgcggc cgcacgcgtg  1740
gagctagtta ttaatagtaa tcaattacgg ggtcattagt tcatagccca tatatggagt  1800
tccgcgttac ataacttacg gtaaatggcc cgcctggctg accgcccaac gacccccgcc  1860
cattgacgtc aataatgacg tatgttccca tagtaacgtc aatagggact ttccattgac  1920
gtcaatgggt ggagtattta cggtaaactg cccacttggc agtacatcaa gtgtatcata  1980
tgccaagtac gccccctatt gacgtcaatg acggtaaatg gcccgcctgg cattatgccc  2040
agtacatgac cttatgggac tttcctactt ggcagtacat ctacgtatta gtcatcgcta  2100
ttaccatggt gatgcggttt tggcagtaca tcaatgggcg tggatagcgg tttgactcac  2160
ggggatttcc aagtctccac cccattgacg tcaatgggag tttgttttgc accaaaatca  2220
acgggacttt ccaaaatgtc gtaacaactc cgccccattg acgcaaatgg gcggtaggcg  2280
tgtacggtgg gaggtctata taagcagagc tcgtttagtg aaccgtcaga tcgcctggag  2340
acgccatcca cgctgttttg acctccatag aagacaccgg gaccgatcca gcctccgcgg  2400
attcgaatcc cggccgggaa cggtgcattg gaacgcggat tccccgtgcc aagagtgacg  2460
taagtaccgc ctatagagtc tataggccca caaaaaatgc tttcttcttt taatatactt  2520
ttttgtttat cttatttcta atactttccc taatctcttt ctttcagggc aataatgata  2580
caatgtatca tgcctctttg caccattcta aagaataaca gtgataattt ctgggttaag  2640
gcaatagcaa tatttctgca tataaatatt tctgcatata aattgtaact gatgtaagag  2700
gtttcatatt gctaatagca gctacaatcc agctaccatt ctgcttttat tttatggttg  2760
ggataaggct ggattattct gagtccaagc taggcccttt tgctaatcat gttcatacct  2820
cttatcttcc tcccacagct cctgggcaac gtgctggtct gtgtgctggc ccatcacttt  2880
ggcaaagaat tgggattcga acatcgattg aattctgaat ggtgagcaag ggcgaggagc  2940
tgttcaccgg ggtggtgccc atcctggtcg agctggacgg cgacgtaaac ggccacaagt  3000
tcagcgtgtc cggcgagggc gagggcgatg ccacctacgg caagctgacc ctgaagttca  3060
tctgcaccac cggcaagctg cccgtgccct ggcccaccct cgtgaccacc ctgacctacg  3120
gcgtgcagtg cttcagccgc taccccgacc acatgaagca gcacgacttc ttcaagtccg  3180
ccatgcccga aggctacgtc caggagcgca ccatcttctt caaggacgac ggcaactaca  3240
agacccgcgc cgaggtgaag ttcgagggcg acaccctggt gaaccgcatc gagctgaagg  3300
gcatcgactt caaggaggac ggcaacatcc tggggcacaa gctggagtac aactacaaca  3360
gccacaacgt ctatatcatg gccgacaagc agaagaacgg catcaaggtg aacttcaaga  3420
tccgccacaa catcgaggac ggcagcgtgc agctcgccga ccactaccag cagaacaccc  3480
ccatcggcga cggccccgtg ctgctgcccg acaaccacta cctgagcacc cagtccgccc  3540
tgagcaaaga ccccaacgag aagcgcgatc acatggtcct gctggagttc gtgaccgccg  3600
ccgggatcac tctcggcatg gacgagctgt acaagtactc agatctcgag ctcaagtagg  3660
gatcctctag agtcgacctg cagaagcttg cctcgagcag cgctgctcga gagatctacg  3720
ggtggcatcc ctgtgacccc tccccagtgc ctctcctggc cctggaagtt gccactccag  3780
tgcccaccag ccttgtccta ataaaattaa gttgcatcat tttgtctgac taggtgtcct  3840
tctataatat tatggggtgg aggggggtgg tatggagcaa ggggcaagtt gggaagacaa  3900
cctgtagggc ctgcggggtc tattgggaac caagctggag tgcagtggca caatcttggc  3960
tcactgcaat ctccgcctcc tgggttcaag cgattctcct gcctcagcct cccgagttgt  4020
tgggattcca ggcatgcatg accaggctca gctaattttt gtttttttgg tagagacggg  4080
gtttcaccat attggccagg ctggtctcca actcctaatc tcaggtgatc tacccacctt  4140
ggcctcccaa attgctggga ttacaggcgt gaaccactgc tcccttccct gtccttctga  4200
ttttgtaggt aaccacgtgc ggaccgagcg gccgcaggaa cccctagtga tggagttggc  4260
cactccctct ctgcgcgctc gctcgctcac tgaggccggg cgaccaaagg tcgcccgacg  4320
cccgggcttt gcccgggcgg cctcagtgag cgagcgagcg cgcagctgcc tgcaggggcg  4380
cctgatgcgg tattttctcc ttacgcatct gtgcggtatt tcacaccgca tacgtcgtag  4440
ctgatcaatt ggcgcgccga attcgttaac aagctttaat taacgcgtat acctaggatc  4500
cggccggcct gcaggtgtcc tcacaggaac gaagtcccta aagaaacagt ggcagccagg  4560
tttagccccg gaattgactg gattcctttt ttagggccca ttggtatggc tttttccccg  4620
tatcccccca ggtgtctgca ggctcaaaga gcagcgagaa gcgttcagag gaaagcgatc  4680
ccgtgccacc ttccccgtgc ccgggctgtc cccgcacgct gccggctcgg ggatgcgggg  4740
ggagcgccgg accggagcgg agccccgggc ggctcgctgc tgccccctag cgggggaggg  4800
acgtaattac atccctgggg gctttggggg ggggctgtcc ctctagagcg gccgccaccg  4860
cggtggagct ccagcttttg ttccctttag tgagggttaa ttagatctta atacgactca  4920
ctatagggcg aattgggtac cgggcccccc ctcgaggtcg acggtatcga taagcttgat  4980
atctataaca agaaaatata tatataataa gttatcacgt aagtagaaca tgaaataaca  5040
atataattat cgtatgagtt aaatcttaaa agtcacgtaa aagataatca tgcgtcattt  5100
tgactcacgc ggtcgttata gttcaaaatc agtgacactt accgcattga caagcacgcc  5160
tcacgggagc tccaagcggc gactgagatg tcctaaatgc acagcgacgg attcgcgcta  5220
tttagaaaga gagagcaata tttcaagaat gcatgcgtca attttacgca gactatcttt  5280
ctagggttaa tctagctgca tcaggatcat atcgtcgggt cttttttccg gctcagtcat  5340
cgcccaagct ggcgctatct gggcatcggg gaggaagaag cccgtgcctt ttcccgcgag  5400
gttgaagcgg catggaaaga gtttgccgag gatgactgct gctgcattga cgttgagcga  5460
aaacgcacgt ttaccatgat gattcgggaa ggtgtggcca tgcacgcctt taacggtgaa  5520
ctgttcgttc aggccacctg ggataccagt tcgtcgcggc ttttccggac acagttccgg  5580
```

```
atggtcagcc cgaagcgcat cagcaacccg aacaataccg gcgacagccg gaactgccgt  5640
gccggtgtgc agattaatga cagcggtgcg gcgctgggat attacgtcag cgaggacggg  5700
tatcctggct ggatgccgca gaaatggaca tggataccc gtgagttacc cggcgggcgc  5760
gcttggcgta atcatggtca tagctgtttc ctgtgtgaaa ttgttatccg ctcacaattc  5820
cacacaacat acgagccgga agcataaagt gtaaagcctg gggtgcctaa tgagtgagct  5880
aactcacatt aattgcgttg cgctcactgc ccgctttcca gtcgggaaac ctgtcgtgcc  5940
agctgcatta atgaatcggc caacgcgcgg ggagaggcgg tttgcgtatt gggcgctctt  6000
ccgcttcctc gctcactgac tcgctgcgct cggtcgttcg gctgcggcga gcggtatcag  6060
ctcactcaaa ggcggtaata cggttatcca cagaatcagg ggataacgca ggaaagaaca  6120
tgtgagcaaa aggccagcaa aaggccagga accgtaaaaa ggccgcgttg ctggcgtttt  6180
tccataggct ccgcccccct gacgagcatc acaaaaatcg acgctcaagt cagaggtggc  6240
gaaacccgac aggactataa agataccagg cgtttccccc tggaagctcc ctcgtgcgct  6300
ctcctgttcc gaccctgccg cttaccggat acctgtccgc ctttctccct tcgggaagcg  6360
tggcgctttc tcatagctca cgctgtaggt atctcagttc ggtgtaggtc gttcgctcca  6420
agctgggctg tgtgcacgaa ccccccgttc agcccgaccg ctgcgcctta tccggtaact  6480
atcgtcttga gtccaacccg gtaagacacg acttatcgcc actggcagca gccactggta  6540
acaggattag cagagcgagg tatgtaggcg gtgctacaga gttcttgaag tggtggccta  6600
actacggcta cactagaagg acagtatttg gtatctgcgc tctgctgaag ccagttacct  6660
tcggaaaaag agttggtagc tcttgatccg gcaaacaaac caccgctggt agcggtggtt  6720
tttttgtttg caagcagcag attacgcgca gaaaaaaagg atctcaagaa gatcctttga  6780
tcttttctac ggggtctgac gctcagtgga acgaaaactc acgttaaggg attttggtca  6840
tgagattatc aaaaaggatc ttcacctaga tccttttaaa ttaaaaatga agttttaaat  6900
caatctaaag tatatatgag taaacttggt ctgacagtta ccaatgctta atcagtgagg  6960
cacctatctc agcgatctgt ctatttcgtt catccatagt tgcctgactc cccgtcgtgt  7020
agataactac gatacgggag ggcttaccat ctggccccag tgctgcaatg ataccgcgag  7080
acccacgctc accggctcca gatttatcag caataaacca gccagccgga agggccgagc  7140
gcagaagtgg tcctgcaact ttatccgcct ccatccagtc tattaattgt tgccgggaag  7200
ctagagtaag tagttcgcca gttaatagtt tgcgcaacgt tgttgccatt gctacaggca  7260
tcgtggtgtc acgctcgtcg tttggtatgg cttcattcag ctccggttcc caacgatcaa  7320
ggcgagttac atgatccccc atgttgtgca aaaaagcggt tagctccttc ggtcctccga  7380
tcgttgtcag aagtaagttg gccgcagtgt tatcactcat ggttatggca gcactgcata  7440
attctcttac tgtcatgcca tccgtaagat gcttttctgt gactggtgag tactcaacca  7500
agtcattctg agaatagtgt atgcggcgac cgagttgctc ttgcccggcg tcaatacggg  7560
ataataccgc gccacatagc agaactttaa aagtgctcat cattggaaaa cgttcttcgg  7620
ggcgaaaact ctcaaggatc ttaccgctgt tgagatccag ttcgatgtaa cccactcgtg  7680
cacccaactg atcttcagca tcttttactt tcaccagcgt ttctgggtga gcaaaaacag  7740
gaaggcaaaa tgccgcaaaa aagggaataa gggcgacacg gaaatgttga atactcat    7798
```

```
SEQ ID NO: 28          moltype = DNA  length = 9399
FEATURE                Location/Qualifiers
misc_feature           1..9399
                       note = Description of Artificial Sequence: Synthetic
                        polynucleotide
source                 1..9399
                       mol_type = other DNA
                       organism = synthetic construct
SEQUENCE: 28
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcttaagcgc tgatcaattg gcgcgccgaa ttcgttatct  1560
gcagaattcg gcttggcggc tgcgcgttca aacctcccgc ttcaaaatgg agaccctgcg  1620
tgctcactcg ggcttaaata cccagcgtga ccacatggtg tcgcaaaatg tcgcaaaaca  1680
ctcacgtgac ctctaataca ggacctctag agcatggaaa ctagataaga aagaaatacg  1740
cagagaccaa agttcaactg aaacgaatta aacggtttat tgattaacaa gcaaactagt  1800
ttacagatta cgggtgaggt aacgggtgcc aatggggcgg ggttcagagt acacgccttc  1860
tgtattaaca gcaaagtcca cacttgtaga tttgtagtag ttggaggtgt actggatctc  1920
```

```
ggggttccag cgcttgctgt tttccttctg cagctcccat tcaatttcca cgctgacctg  1980
tccggtgctg tattgcgtga tgaaagagtt cagctttgac tggttgaagg tggtcggagg  2040
atccgcaggt acaggcgtgt tcttgatcag gatctgaggc ggaggatgtt tcaggccaaa  2100
gccgcccatc agcggagacg ggtggaagtt gccgtccgtg tgaggaatct tggcccagat  2160
gggaccctgc aggtacacgt cccggttctg ccagaccata ccgggtaagg ccccctggct  2220
gttgacagtt ccaatttgag gagccgtgtt ttgctgctgc aagttatctg ccacgatacc  2280
gtattcctct gtagccacag ggttagtggt tttgatttct tcctcgctgg tgagcatgac  2340
atcgctgtaa tccgcattgt ctctggcagc attttgtttg ccaaaaatca ggatcccgtt  2400
actgggaaaa aaacgctcct cgtcgtcttt gtgtgttgcc atagcgatgc caggattagc  2460
caatgaattt cttccattca gatggtattt ggtcccagca gtccaggcaa agttgctatt  2520
gttgttttgc ccggttgtcg ttgagacgcg ttgttggcgg taacagggtc ctggcagcca  2580
gttctttgcc tgattggcca ttgtattagg cccaccttgg ctgaagccca gagtctgcgt  2640
atttgccgtg cctcctgttg tttgagtccg agacaagtag tacaggtact ggtcaatcag  2700
aggattcatc agccggtcca agctctggct gtgggcgtag ctgctgtgga aaggcacgtc  2760
ctcgaaggtg taagtaaact ggaagttgtt gccggttctc agcatctgcg aaggaaagta  2820
ttccaggcag tagaaggagg agcgtcccac ggcctgacta ccgttgttga gtgttaggta  2880
gccgtactgg ggaatcatga acacgtccgc cgggaacgga ggcaggcagc cctggtgggc  2940
agagccgaga acgtacggca gctggtactc cgagtccgta aacacctgga tggtgctggt  3000
gaggttattg gcgatggtct tggtgccttc attctgcgtg acctccttga cctggatgtt  3060
gaagagcttg aagctgagtc tcttgggccg gaatccccag ttgttgttga tgagtcgctg  3120
ccagtcacgt ggtgaaaagt ggcagtggaa tctgttaaag tcaaaatacc cccagggggt  3180
gctgtagccg aagtaggtgt tgtcgttggt ggctcctccc gatgtcccgt tggagatttg  3240
cttgtagagg tggttgttgt aggtgggcag ggcccaggtt cgggtgctgg tggtgatgac  3300
tctgtcgccc agccatgtgg aatcgcaatg ccaatttccc gaggaactac ccactccgtc  3360
ggcgccttcg ttattgtctg ccattggtgc gccaccgcct gcagccattg tattaggtcc  3420
cacaccagag ggcgctgctg gaggttctcc gagaggttga gggtctggaa ctgactctga  3480
gtcgccagtc tgaccaaaat tgagtctttt tctggcgggc tgttggcctt tcttgccgat  3540
gcccgtagag gagtctggag aacgctgggg tgatggctct accggtctct tctttccagg  3600
agccgtctta gcgccttcct caaccagacc gagaggttcg agaacccgct tcttggcctg  3660
gaagactgct cgcccgaggt tgcccccaaa agacgtatct tcttgcagac gctcctgaaa  3720
ctcggcgtcg gcgtggttat accgcaggta cggattgtca cccgcctgca gctgctggtc  3780
gtaggccttg tcgtgctcga gggccgctgc gtccgccgcg ttgacgggct ccccccttgtc  3840
gagtccgttg aagggtccga ggtacttgta gccaggaagc accagacccc ggccgtcgtc  3900
ctgcttttgc tggttggctt tgggcttcgg ggctccaggt ttcagcgccc accactcgcg  3960
aatgccctca gagaggttgt cctcgagcca atctggaaga taaccatcgg cagccatacc  4020
tgatttaaat catttattgt tcaaagatgc agtcatccaa atccacattg accagatcgc  4080
aggcagtgca agcgtctggc acctttccca tgatatgatg aatgtagcac agtttctgat  4140
acgccttttt gacgacagaa acgggttgag attctgacac gggaaagcac tctaaacagt  4200
ctttctgtcc gtgagtgaag cagatatttg aattctgatt cattctctcg cattgtctgc  4260
agggaaacag catcagattc atgcccacgt gacgagaaca tttgttttgg tacctgtctg  4320
cgtagttgat cgaagcttcc gcgtctgacg tcgatggctg cgcaactgac tcgcgcaccc  4380
gtttgggctc acttatatct gcgtcactgg gggcgggtct tttcttggct ccaccctttt  4440
tgacgtagaa ttcatgctcc acctcaacca cgtgatcctt tgcccaccgg aaaaagtctt  4500
tgacttcctg cttggtgacc ttcccaaagt catgatccag acggcgggtg agttcaaatt  4560
tgaacatccg gtcttgcaac ggctgctggt gttcgaaggt cgttgagttc ccgtcaatca  4620
cggcgcacat gttggtgttg gaggtgacga tcacgggagt cgggtctatc tgggccgagg  4680
acttgcattt ctggtccacg cgcaccttgc ttcctccgag aatggctttg gccgactcca  4740
cgaccttggc ggtcatcttc ccctcctccc accagatcac catcttgtcg acacagtcgt  4800
tgaagggaaa gttctcattg gtccagttta cgcacccgta gaagggcaca gtgtgggcta  4860
tggcctccgc gatgttggtc ttcccggtag ttgcaggccc aaacagccag atggtgttcc  4920
tcttgccgaa ctttttcgtg gcccatccca gaaagacgga agccgcatat tggggatcgt  4980
acccgtttag ttccaaaatt ttataaatcc gattgctgga aatgtcctcc acgggctgct  5040
ggcccaccag gtagtcgggg gcggttttag tcaggctcat aatctttccc gcattgtcca  5100
aggcagcctt gatttgggac cgcgagttgg aggccgcatt gaaggagatg tatgaggcct  5160
ggtcctcctg gatccactgc ttctccgagg taatcccctt gtccacgagc cacccgacca  5220
gctccatgta cctggctgaa gtttttgatc tgatcaccgg cgcatcagaa ttgggattct  5280
gattctcttt gttctgctcc tgcgtctgcg acacgtgcgt cagatgctgc gccaccaacc  5340
gtttacgctc cgtgagattc aaacaggcgc tgtggagaga aaggcaaagt ggatgtcagt  5400
atctctatca ctgataggga gatctctatc actgataggg aacttacctt aaatactgtt  5460
ccatattagt ccacgcccac tggagctcag gctgggtttt ggggagcaag taattgggga  5520
tgtagcactc atccaccacc ttgttcccgc ctccggcgcc atttctggtc tttgtgaccg  5580
cgaaccagtt tggcaaagtc ggctcgatcc cgcggtaaat tctctgaatc agtttttcgc  5640
gaatctgact caggaaacgt cccaaaacca tggatttcac cccggtggtt tccacgagca  5700
cgtgcatgtg gaagtagctc tctcccttct caaattgcac aaagaaaaga gcctccgggg  5760
ccttactcac acggcgccat tccgtcagaa agtcgcgctg cagcttctcg gccacggtca  5820
ggggtgcctg ctcaatcaga ttcagatcca tgtcagaatc tggcggcaac tcccattcct  5880
tctcggccac ccagttcaca aagctgtcag aaatgccggg cagatgctcg tcaaggtcgc  5940
tggggacctt aatcacaatc tcgtaaaacc ccggcatggc ggctgcgcgt tcaaacctcc  6000
cgcttcaaaa tggagaccct gcgtgctcac tcgggcgatc tctatcactg atagggagat  6060
ctctatcact gatagggaga ttaaatagaa tggctaggat ccggccggcc tgcaggtgtc  6120
ctcacaggaa cgaagtccct aaagaaacag tggcagccag gtttagcccc ggaattgact  6180
ggattccttt tttagggccc attggtatgg ctttttcccc gtatccccccc aggtgtctgc  6240
aggctcaaag agcagcgaga agcgttcaga ggaaagcgat cccgtgccac cttccccgtg  6300
cccgggctgt ccccgcacgc tgccggctcg gggatgcggg gggagcgccg gaccggagcg  6360
gagccccggg cggctcgctg ctgcccccta gcgggggagg gacgtaatta catccctggg  6420
ggctttgggg gggggctgtc cctctagagc ggccgccacc gcggtggagc tccagctttt  6480
gttcccttta gtgagggtta attagatctt aatacgactc actatagggc gaattgggta  6540
ccgggccccc cctcgaggtc gacggtatcg ataagcttga tatctataac aagaaaatat  6600
atatataata agttatcacg taagtagaac atgaaataac aatataatta tcgtatgagt  6660
```

```
taaatcttaa aagtcacgta aaagataatc atgcgtcatt ttgactcacg cggtcgttat  6720
agttcaaaat cagtgacact taccgcattg acaagcacgc ctcacgggag ctccaagcgg  6780
cgactgagat gtcctaaatg cacagcgacg gattcgcgct atttagaaag agagagcaat  6840
atttcaagaa tgcatgcgtc aattttacgc agactatctt tctagggtta atctagctgc  6900
atcaggatca tatcgtcggg tctttttttcc ggctcagtca tcgcccaagc tggcgctatc  6960
tgggcatcgg ggaggaagaa gcccgtgcct tttcccgcga ggttgaagcg gcatggaaag  7020
agtttgccga ggatgactgc tgctgcattg acgttgagcg aaaacgcacg tttaccatga  7080
tgattcggga aggtgtggcc atgcacgcct ttaacggtga actgttcgtt caggccacct  7140
gggataccag ttcgtcgcgg cttttccgga cacagttccg gatggtcagc ccgaagcgca  7200
tcagcaaccc gaacaatacc ggcgacagcc ggaactgccg tgccggtgtg cagattaatg  7260
acagcggtgc ggcgctggga tattacgtca gcgaggacgg gtatcctggc tggatgccgc  7320
agaaatggac atggataccc cgtgagttac ccggcgggcg cgcttggcgt aatcatggtc  7380
atagctgttt cctgtgtgaa attgttatcc gctcacaatt ccacacaaca tacgagccgg  7440
aagcataaag tgtaaagcct ggggtgccta atgagtgagc taactcacat taattgcgtt  7500
gcgctcactg cccgctttcc agtcgggaaa cctgtcgtgc cagctgcatt aatgaatcgg  7560
ccaacgcgcg gggagaggcg gtttgcgtat tgggcgctct tccgcttcct cgctcactga  7620
ctcgctgcgc tcggtcgttc ggctgcggcg agcggtatca gctcactcaa aggcggtaat  7680
acggttatcc acagaatcag gggataacgc aggaaagaac atgtgagcaa aaggccagca  7740
aaaggccagg aaccgtaaaa aggccgcgtt gctggcgttt ttccataggc tccgcccccc  7800
tgacgagcat cacaaaaatc gacgctcaag tcagaggtgg cgaaacccga caggactata  7860
aagataccag gcgtttcccc ctggaagctc cctcgtgcgc tctcctgttc cgaccctgcc  7920
gcttaccgga tacctgtccg cctttctccc ttcgggaagc gtggcgcttt ctcatagctc  7980
acgctgtagg tatctcagtt cggtgtaggt cgttcgctcc aagctgggct gtgtgcacga  8040
accccccgtt cagcccgacc gctgcgcctt atccggtaac tatcgtcttg agtccaaccc  8100
ggtaagacac gacttatcgc cactggcagc agccactggt aacaggatta gcagagcgag  8160
gtatgtaggc ggtgctacag agttcttgaa gtggtggcct aactacggct acactagaag  8220
gacagtattt ggtatctgcg ctctgctgaa gccagttacc ttcggaaaaa gagttggtag  8280
ctcttgatcc ggcaaacaaa ccaccgctgg tagcggtggt ttttttgttt gcaagcagca  8340
gattacgcgc agaaaaaaag gatctcaaga agatcctttg atcttttcta cggggtctga  8400
cgctcagtgg aacgaaaact cacgttaagg gattttggtc atgagattat caaaaaggat  8460
cttcacctag atccttttaa attaaaaatg aagttttaaa tcaatctaaa gtatatatga  8520
gtaaacttgg tctgacagtt accaatgctt aatcagtgag gcacctatct cagcgatctg  8580
tctatttcgt tcatccatag ttgcctgact ccccgtcgtg tagataacta cgatacggga  8640
gggcttacca tctggcccca gtgctgcaat gataccgcga gacccacgct caccggctcc  8700
agatttatca gcaataaacc agccagccgg aagggccgag cgcagaagtg gtcctgcaac  8760
tttatccgcc tccatccagt ctattaattg ttgccgggaa gctagagtaa gtagttcgcc  8820
agttaatagt ttgcgcaacg ttgttgccat tgctacaggc atcgtggtgt cacgctcgtc  8880
gtttggtatg gcttcattca gctccggttc ccaacgatca aggcgagtta catgatcccc  8940
catgttgtgc aaaaaagcgg ttagctcctt cggtcctccg atcgttgtca gaagtaagtt  9000
ggccgcagtg ttatcactca tggttatggc agcactgcat aattctctta ctgtcatgcc  9060
atccgtaaga tgcttttctg tgactggtga gtactcaacc aagtcattct gagaatagtg  9120
tatgcggcga ccgagttgct cttgcccggc gtcaatacgg gataataccg cgccacatag  9180
cagaacttta aaagtgctca tcattggaaa acgttcttcg gggcgaaaac tctcaaggat  9240
cttaccgctg ttgagatcca gttcgatgta acccactcgt gcacccaact gatcttcagc  9300
atcttttact ttcaccagcg tttctgggtg agcaaaaaca ggaaggcaaa atgccgcaaa  9360
aaagggaata agggcgacac ggaaatgttg aatactcat                         9399
```

```
SEQ ID NO: 29          moltype = DNA  length = 9393
FEATURE                Location/Qualifiers
misc_feature           1..9393
                       note = Description of Artificial Sequence: Synthetic
                        polynucleotide
source                 1..9393
                       mol_type = other DNA
                       organism = synthetic construct
SEQUENCE: 29
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tggggggata cggggaaaag  1380
```

```
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcttaagcgc tgatcaattg gcgcgccgaa ttcgttatct  1560
gcagaattcg gcttggcggc tgcgcgttca aacctcccgc ttcaaaatgg agaccctgcg  1620
tgctcactcg ggcttaaata cccagcgtga ccacatggtg tcgcaaaatg tcgcaaaaca  1680
ctcacgtgac ctctaataca ggacctctag agcatggaaa ctagataaga aagaaatacg  1740
cagagaccaa agttcaactg aaacgaatta aacggtttat tgattaacaa gcaaactagt  1800
ttacagatta cgagtcaggt atctggtgcc aatggggcgg ggttcactat atacaccttc  1860
agtattaaca gcaaattcaa cattattaga cttgtaatag ttggaagtgt actggatctc  1920
cgggttccag cgcttgctgt tttccttctg cagctcccac tcgatctcca cgctgacttg  1980
gccagtagaa tactgggtga tgaaagagtt cagcttgtcc ttgttgaagg ccgttggagg  2040
atccgcaggt acaggtgtgt ttttgatgag gatctgagga ggcgggtgct tcattccaaa  2100
ccctcccatc agcggagaag ggtgaaagtt gccgtccgtg tgaggaattt tggcccaaat  2160
gggtccttgc aggtacacat ctctgtcctg ccaaaccata cccggaagta ttccttggtt  2220
ttgaacccag ccggtctgcg cctgtgcttg ggcactctgg tggtttgtgg ccacttgtcc  2280
ataggactcc gttgctaccg ggttagtagt tttaatttct tcttcgttgg ttatcatgac  2340
tttgtccgca tccacgttgt ctcttccagt tccttgtttg ccaaaaaatta aagatccaga  2400
caaaggaaag aaacggtcct ctccttcttt gtggctggcc atagcaggtc caggattcat  2460
caagctatta cgtccattga gagcccaaga agaagctcca ggccaagcaa attcgctgtt  2520
gttgttttga gtcacagtgg ttgagacacg ttgttgtcgg tagctgggtc caggtatgta  2580
gtttcttccc tggacagcca tgttgctggg tccggccaca ctgaatttta gcgtttgttg  2640
attctgtcca gaaccgttaa tagtctttga gagatagtac aagtattggt cgatgagtgg  2700
attcattagt cggtccaggc tttggctgtg agcgtagctg ctatggaaag gtacgttctc  2760
aaactcgtag ctgaactgga agttgttacc cgttcttagc atttgcgacg ggaaatattc  2820
caggcagtaa aaggacgaac gacccacggc ctggcttcca tcattaagcg tcagataccc  2880
gtactgagga atcatgaaaa cgtccgctgg gaacggcggg aggcagccct cgtgagccga  2940
cccgagcacg tacgggagct gatagtctga gtccgtgaag acctggaccg tgctggtaag  3000
gttattggcg atggtcttga ctccattgtt gtccgtaacc tctttgacct gaatgttgaa  3060
gagcttgaag ttgagtcgct taggccggaa tccccagttg ttgttgatga gtcgctgcca  3120
gtcacgtggt gagaagtggc agtggaatct gttgaagtca aaataccccc agggggtgct  3180
gtagccgaag taggcgttgt catttgaaga tcctccagat gtgctgttgg agatttgctt  3240
gtagaggtga ttgttgtagg tgggcagggc ccaggttcgg gtgctggtgg tgatgactct  3300
gtcccccagc cattgggaat cgcaatgcca atttcccgag gaactaccca ctccatcggc  3360
accttcgtta ttgtctgcca ctggtgcgcc accacctgaa gccattgtaa gagatcccac  3420
acctgagggg gctgcgggag gttctccgat tggttgaggg tctgggactg actctgtgtc  3480
gccagtctga ccgaaattga gtctcttttt agcgggctgt gcacccgatt tgccaatacc  3540
cgcggaggag tccggttcct gaggagactg ctctacaggc ctcttctttc caggagccgt  3600
cttagccgct tcctcaacca gaccaagagg ttcaagaagc ctctttttgg cctggaagac  3660
tgctcgcccg aggttgcccc caaaagacgt atcttctttg agccgctcct ggaactcggc  3720
gtcggcgtgg ttgtacttga ggtacgggtt gtctccggcc ttgagctgct ggtcgtaggc  3780
cttgtcgtgc tcgagggccg ccgcgtctgc tgcgttgacc ggctccccct tgtcgagtcc  3840
gttgccgggt ccaaggtatt tgtaacccgg aagcacaaga cctcgagcgt tgtcttgatg  3900
ttgttgattt gccttgggtt gaggggctcc aggtttcaaa gcccaccact cgcgaattcc  3960
ttcactaagg ttgtcctcga gccaatctgg aagataacca tcggcagcca tacctgattt  4020
aaatcattta ttgttcaaag atgcagtcat ccaaatccac attgaccaga tcgcaggcag  4080
tgcaagcgtc tggcaccttt cccatgatat gatgaatgta gcacagtttc tgatacgcct  4140
ttttgacgac agaaacgggt tgagattctg acacgggaaa gcactctaaa cagtctttct  4200
gtccgtgagt gaagcagata tttgaattct gattcattct ctcgcattgt ctgcagggaa  4260
acagcatcag attcatgccc acgtgacgag aacatttgtt ttggtacctg tctgcgtagt  4320
tgatcgaagc ttccgcgtct gacgtcgatg gctgcgcaac tgactcgcgc acccgtttgg  4380
gctcacttat atctgcgtca ctgggggcgg gtcttttctt ggctccaccc tttttgacgt  4440
agaattcatg ctccacctca accacgtgat cctttgccca ccggaaaaag tctttgactt  4500
cctgcttggt gaccttccca aagtcatgat ccagacggcg ggtgagttca aatttgaaca  4560
tccggtcttg caacggctgc tggtgttcga aggtcgttga gttcccgtca atcacggcgc  4620
acatgttggt gttggaggtg acgatcacgg gagtcgggtc tatctgggcc gaggacttgc  4680
atttctggtc cacgcgcacc ttgcttcctc cgagaatggc tttggccgac tccacgacct  4740
tggcggtcat cttcccctcc tcccaccaga tcaccatctt gtcgacacag tcgttgaagg  4800
gaaagttctc attggtccag tttacgcacc cgtagaaggg cacagtgtgg gctatggcct  4860
ccgcgatgtt ggtcttcccg gtagttgcag gcccaaacag ccagatggtg ttcctcttgc  4920
cgaacttttt cgtggcccat cccagaaaga cggaagccgc atattgggga tcgtacccgt  4980
ttagttccaa aattttataa atccgattgc tggaaatgtc ctccacgggc tgctggccca  5040
ccaggtagtc gggggcggtt ttagtcaggc tcataatctt tcccgcattg tccaaggcag  5100
ccttgatttg ggaccgcgag ttggaggccg cattgaagga gatgtatgag gcctggtcct  5160
cctggatcca ctgcttctcc gaggtaatcc ccttgtccac gagccacccg accagctcca  5220
tgtacctggc tgaagttttt gatctgatca ccggcgcatc agaattggga ttctgattct  5280
ctttgttctg ctcctgcgtc tgcgacacgt gcgtcagatg ctgcgccacc aaccgtttac  5340
gctccgtgag attcaaacag gcgctgtgga gagaaaggca aagtggatgt cagtatctct  5400
atcactgata gggagatctc tatcactgat agggaactta ccttaaatac tgttccatat  5460
tagtccacgc ccactggagc tcaggctggg ttttggggag caagtaattg gggatgtagc  5520
actcatccac caccttgttc ccgcctccgg cgccatttct ggtctttgtg accgcgaacc  5580
agtttggcaa agtcggctcg atcccgcggt aaattctctg aatcagtttt tcgcgaatct  5640
gactcaggaa acgtcccaaa accatggatt tcaccccggt ggtttccacg agcacgtgca  5700
tgtggaagta gctctctccc ttctcaaatt gcacaaagaa aagagcctcc ggggccttac  5760
tcacacggcg ccattccgtc agaaagtcgc gctgcagctt ctcggccacg gtcaggggtg  5820
cctgctcaat cagattcaga tccatgtcag aatctggcgg caactcccat tccttctcgg  5880
ccacccagtt cacaaagctg tcagaaatgc cgggcagatg ctcgtcaagg tcgctgggga  5940
ccttaatcac aatctcgtaa aaccccggca tggcggctgc gcgttcaaac ctcccgcttc  6000
aaaatggaga ccctgcgtgc tcactcgggc gatctctatc actgataggg agatctctat  6060
cactgatagg gagattaaat agaatggcta ggatccggcc ggcctgcagg tgtcctcaca  6120
```

```
ggaacgaagt ccctaaagaa acagtggcag ccaggtttag ccccggaatt gactggattc  6180
cttttttagg gcccattggt atggcttttt ccccgtatcc ccccaggtgt ctgcaggctc  6240
aaagagcagc gagaagcgtt cagaggaaag cgatcccgtg ccaccttccc cgtgcccggg  6300
ctgtccccgc acgctgccgg ctcggggatg cggggggagc gccggaccgg agcggagccc  6360
cgggcggctc gctgctgccc cctagcgggg gagggacgta attacatccc tgggggcttt  6420
gggggggggc tgtccctcta gagcggccgc caccgcggtg gagctccagc ttttgttccc  6480
tttagtgagg gttaattaga tcttaatacg actcactata gggcgaattg ggtaccgggc  6540
ccccctcga ggtcgacggt atcgataagc ttgatatcta taacaagaaa atatatatat  6600
aataagttat cacgtaagta gaacatgaaa taacaatata attatcgtat gagttaaatc  6660
ttaaaagtca cgtaaaagat aatcatgcgt cattttgact cacgcggtcg ttatagttca  6720
aaatcagtga cacttaccgc attgacaagc acgcctcacg ggagctccaa gcggcgactg  6780
agatgtccta aatgcacagc gacggattcg cgctatttag aaagagagag caatatttca  6840
agaatgcatg cgtcaatttt acgcagacta tctttctagg gttaatctag ctgcatcagg  6900
atcatatcgt cggtctttt ttccggctca gtcatcgccc aagctggcgc tatctgggca  6960
tcggggagga agaagcccgt gccttttccc gcgaggttga agcggcatgg aaagagtttg  7020
ccgaggatga ctgctgctgc attgacgttg agcgaaaacg cacgtttacc atgatgattc  7080
gggaaggtgt ggccatgcac gcctttaacg gtgaactgtt cgttcaggcc acctgggata  7140
ccagttcgtc gcggcttttc cggacacagt tccggatggt cagcccgaag cgcatcagca  7200
acccgaacaa taccggcgac agccggaact gccgtgccgg tgtgcagatt aatgacagcg  7260
gtgcggcgct gggatattac gtcagcgagg acgggtatcc tggctggatg ccgcagaaat  7320
ggacatggat accccgtgag ttacccggcg ggcgcgcttg gcgtaatcat ggtcatagct  7380
gtttcctgtg tgaaattgtt atccgctcac aattccacac aacatacgag ccggaagcat  7440
aaagtgtaaa gcctggggtg cctaatgagt gagctaactc acattaattg cgttgcgctc  7500
actgcccgct ttccagtcgg gaaacctgtc gtgccagctg cattaatgaa tcggccaacg  7560
cgcgggggaga ggcggtttgc gtattgggcg ctcttccgct tcctcgctca ctgactcgct  7620
gcgctcggtc gttcggctgc ggcgagcggt atcagctcac tcaaaggcgg taatacggtt  7680
atccacagaa tcaggggata acgcaggaaa gaacatgtga gcaaaaggcc agcaaaaggc  7740
caggaaccgt aaaaaggccg cgttgctggc gtttttccat aggctccgcc cccctgacga  7800
gcatcacaaa aatcgacgct caagtcagag gtggcgaaac ccgacaggac tataaagata  7860
ccaggcgttt ccccctggaa gctccctcgt gcgctctcct gttccgaccc tgccgcttac  7920
cggatacctg tccgcctttc tcccttcggg aagcgtggcg ctttctcata gctcacgctg  7980
taggtatctc agttcggtgt aggtcgttcg ctccaagctg ggctgtgtgc acgaaccccc  8040
cgttcagccc gaccgctgcg ccttatccgg taactatcgt cttgagtcca acccggtaag  8100
acacgactta tcgccactgg cagcagccac tggtaacagg attagcagag cgaggtatgt  8160
aggcggtgct acagagttct tgaagtggtg gcctaactac ggctacacta gaaggacagt  8220
atttggtatc tgcgctctgc tgaagccagt taccttcgga aaaagagttg gtagctcttg  8280
atccggcaaa caaaccaccg ctggtagcgg tggttttttt gtttgcaagc agcagattac  8340
gcgcagaaaa aaaggatctc aagaagatcc tttgatcttt tctacggggt ctgacgctca  8400
gtggaacgaa aactcacgtt aagggatttt ggtcatgaga ttatcaaaaa ggatcttcac  8460
ctagatcctt ttaaattaaa aatgaagttt taaatcaatc taaagtatat atgagtaaac  8520
ttggtctgac agttaccaat gcttaatcag tgaggcacct atctcagcga tctgtctatt  8580
tcgttcatcc atagttgcct gactccccgt cgtgtagata actacgatac gggagggctt  8640
accatctggc cccagtgctg caatgatacc gcgagaccca cgctcaccgg ctccagattt  8700
atcagcaata aaccagccag ccggaagggc cgagcgcaga agtggtcctg caactttatc  8760
cgcctccatc cagtctatta attgttgccg ggaagctaga gtaagtagtt cgccagttaa  8820
tagtttgcgc aacgttgttg ccattgctac aggcatcgtg gtgtcacgct cgtcgtttgg  8880
tatggcttca ttcagctccg gttcccaacg atcaaggcga gttacatgat cccccatgtt  8940
gtgcaaaaaa gcggttagct ccttcggtcc tccgatcgtt gtcagaagta agttggccgc  9000
agtgttatca ctcatggtta tggcagcact gcataattct cttactgtca tgccatccgt  9060
aagatgcttt tctgtgactg gtgagtactc aaccaagtca ttctgagaat agtgtatgcg  9120
gcgaccgagt tgctcttgcc cggcgtcaat acgggataat accgcgccac atagcagaac  9180
tttaaaagtg ctcatcattg gaaaacgttc ttcggggcga aaactctcaa ggatcttacc  9240
gctgttgaga tccagttcga tgtaacccac tcgtgcaccc aactgatctt cagcatcttt  9300
tactttcacc agcgtttctg ggtgagcaaa aacaggaagg caaaatgccg caaaaaaggg  9360
aataagggcg acacggaaat gttgaatact cat                                9393

SEQ ID NO: 30          moltype = DNA  length = 9393
FEATURE                Location/Qualifiers
misc_feature           1..9393
                       note = Description of Artificial Sequence: Synthetic
                        polynucleotide
source                 1..9393
                       mol_type = other DNA
                       organism = synthetic construct
SEQUENCE: 30
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
```

```
ctcgacacgc tgcagaacac gcagctagat taaccctaga aagataatca tattgtgacg  900
tacgttaaag ataatcatgc gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaaa caaaaactca  1080
aaatttcttc tataaagtaa caaaactttt atcgaattcc tgcagcccgg gggatccact  1140
agttctagag ggacagcccc cccccaaagc ccccagggat gtaattacgt ccctcccccg  1200
ctagggggca gcagcgagcc gcccggggct ccgctccggt ccggcgctcc ccccgcatcc  1260
ccgagccggc agcgtgcggg gacagcccgg gcacggggaa ggtggcacgg gatcgctttc  1320
ctctgaacgc ttctcgctgc tctttgagcc tgcagacacc tgggggggata cggggaaaag  1380
gcctccaagg ccagcttccc acaataagtt gggtgaattt tggctcattc ctcctttcta  1440
taggattgag gtcagagctt tgtgatggga attctgtgga atgtgtgtca gttagggtgt  1500
ggaaagtccc gcgatcgcta gcttaagcgc tgatcaattg gcgcgccgaa ttcgttatct  1560
gcagaattcg gcttggcggc tgcgcgttca aacctcccgc ttcaaaatgg agaccctgcg  1620
tgctcactcg ggcttaaata cccagcgtga ccacatggtg tcgcaaaatg tcgcaaaaca  1680
ctcacgtgac ctctaataca ggacctctag agcatggaaa ctagataaga aagaaatacg  1740
cagagaccaa agttcaactg aaacgaatta aacggtttat tgattaacaa gcaaactagt  1800
ttacagatta cgggtgaggt aacgggtgcc gatggggcga ggctcagaat aaacgccatt  1860
tgtgtcaaca gcaaagtcca catttgtaga tttgttgtag ttggaagtgt attgaatctc  1920
tgggttccag cgtttgctgt tttctttctg cagctcccat tcaatttcca cgctgacctg  1980
tccggtgctg tactgcgtga tgaacgacgc aaacttagct ggactgaagg tagttggagg  2040
attcgcggga acaggtgtat tcttaatcag gatctgagga ggcgggtgtt tcagtccaaa  2100
gcctcccatc agcggcgagg gatgaaagtg tccgtccgtg tgaggaatct tggcccagat  2160
aggaccctgc aggtacacgt cccggtcctg ccagaccatg ccaggtaagg ctccttgact  2220
gttgacggtc cctgtagcag gagcggtgtt ggccgattgc aggttagtgg ccaccgtgcc  2280
gtactcttct gtggccactg ggttggtggt tttaatttct tcctcgttgg ttatcataac  2340
gttgtcaagg tccacgttgc tatttccagc tccctgtttc ccaaatatta agactccgct  2400
catcggaaaa aatttgtctt cgtcgtcctt gtgggttgcc atagcgggac cgggatttac  2460
cagagagtct ctgccattca gatgatactt ggtggcaccg gtccaggcaa agttgctgtt  2520
gttattttga ttggttgtct tggagacgcg ttgctgccgg tagcagggcc cgggtagcca  2580
gtttttggcc tgattcgcca tgctactagg cccggcctga gaaaattgca acgtccgatt  2640
tcctgcggta ccactcgtgg tctgagtccg agacaggtag tacaggtact ggtcgatgag  2700
ggggttcatc agccggtcca ggctttggct gtgcgcgtag ctgctgtgaa aaggcacgtc  2760
ctcaaacgtg tagctgaact gaaagttgtt gcccgttctc agcatttgag aaggaaagta  2820
ttccaggcag tagaaggagg aacggcccac ggcctgactg ccattgttca gagtcaggta  2880
cccgtactga ggaatcatga agacgtccgc cgggaacgga ggcaggcagc cctggtgcgc  2940
agagccgagg acgtacggga gctggtattc cgagtccgta aagacctgaa ccgtgctggt  3000
aaggttattg gcgatggtcg tggtgccatc attcgtcgtg acctccttga cctggatgtt  3060
gaagagcttg aagttgagct tcttgggccg gaatccccag ttgttgttga tgagtcgctg  3120
ccagtcacgt ggtgagaagt ggcagtggaa tctgttaaag tcaaaatacc cccagggggt  3180
gctgtagccg aagtaggtgt tgtcgttggt gctgcctccc gattggctgg agatttgctt  3240
gtagaggtgg ttgttgtagg tggggagggc ccaggttcgg gtgctggtgg tgatgactct  3300
gtcgcccagc catgtggaat cgcaatgcca atttcctgag gcgttaccca ctccgtcggc  3360
gccttcgtta ttgtctgcca ttggagcgcc accgcctgca gccattgtat tagatcccac  3420
accagagggg gctgcggggg gttctccgag tggttgaggg tcgggcactg actctgagtc  3480
gccagtctgc ccaaagttga gtctctttct cgcgggctgc tggcctttct tgccgatgcc  3540
cgaagaggag tctggttcct ggggtgattg ctctaccggt ctcttctttc caggagccgt  3600
cttagcgcct tcctcaacca gaccgagagg ttcgagaacc cgcttcttgg cctggaagac  3660
tgctcgcccg aggttgcccc caaaagacgt atcttcttgc agacgctcct gaaactcggc  3720
gtcggcgtgg ttataccgca ggtacggatt gtcacccgct ttgagctgct ggtcgtaggc  3780
cttgtcgtgc tcgagggccg ctgcgtccgc cgcgttgacg ggctcccccct tgtcgagtcc  3840
gttgaagggt ccgaggtact tgtagccagg aagcaccaga ccccggccgt cgtcctgctt  3900
ttgctggttg gctttgggtt tcggggctcc aggtttcaag tcccaccact cgcgaatgcc  3960
ctcagagagg ttgtcctcga gccaatctgg aagataacca tcggcagcca tacctgattt  4020
aaatcattta ttgttcaaag atgcagtcat ccaaatccac attgaccaga tcgcaggcag  4080
tgcaagcgtc tggcaccttt cccatgatat gatgaatgta gcacagtttc tgatacgcct  4140
ttttgacgac agaaacgggt tgagattctg acacgggaaa gcactctaaa cagtctttct  4200
gtccgtgagt gaagcagata tttgaattct gattcattct ctcgcattgt ctgcagggaa  4260
acagcatcag attcatgccc acgtgacgag aacatttgtt ttggtacctg tctgcgtagt  4320
tgatcgaagc ttccgcgtct gacgtcgatg gctgcgcaac tgactcgcgc acccgtttgg  4380
gctcacttat atctgcgtca ctgggggcgg gtcttttctt ggctccaccc tttttgacgt  4440
agaattcatg ctccacctca accacgtgat cctttgccca ccggaaaaag tctttgactt  4500
cctgcttggt gaccttccca aagtcatgat ccagacggcg ggtgagttca aatttgaaca  4560
tccggtcttg caacggctgc tggtgttcga aggtcgttga gttcccgtca atcacggcgc  4620
acatgttggt gttggaggtg acgatcacgg gagtcgggtc tatctgggcc gaggacttgc  4680
atttctggtc cacgcgcacc ttgcttcctc cgagaatggc tttggccgac tccacgacct  4740
tggcggtcat cttcccctcc tcccaccaga tcaccatctt gtcgacacag tcgttgaagg  4800
gaaagttctc attggtccag tttacgcacc cgtagaaggg cacagtgtgg gctatggcct  4860
ccgcgatgtt ggtcttcccg gtagttgcag gcccaaacag ccagatggtg ttcctcttgc  4920
cgaacttttt cgtggcccat cccagaaaga cggaagccgc atattgggga tcgtacccgt  4980
ttagttccaa aattttataa atccgattgc tggaaatgtc ctccacgggc tgctggccca  5040
ccaggtagtc gggggcggtt ttagtcaggc tcataatctt tcccgcattg tccaaggcag  5100
ccttgatttg ggaccgcgag ttggaggccg cattgaagga gatgtatgag gcctggtcct  5160
cctggatcca ctgcttctcc gaggtaatcc ccttgtccac gagccacccg accagctcca  5220
tgtacctggc tgaagttttt gatctgatca ccggcgcatc agaattggga ttctgattct  5280
ctttgttctg ctcctgcgtc tgcgacacgt gcgtcagatg ctgcgccacc aaccgtttac  5340
gctccgtgag attcaaacag gcgctgtgga gagaaaggca aagtggatgt cagtatctct  5400
atcactgata gggagatctc tatcactgat agggaactta ccttaaatac tgttccatat  5460
tagtccacgc ccactggagc tcaggctggg ttttggggag caagtaattg gggatgtagc  5520
actcatccac caccttgttc ccgcctccgg cgccatttct ggtctttgtg accgcgaacc  5580
```

```
agtttggcaa agtcggctcg atcccgcggt aaattctctg aatcagtttt tcgcgaatct  5640
gactcaggaa acgtcccaaa accatggatt tcaccccggt ggtttccacg agcacgtgca  5700
tgtggaagta gctctctccc ttctcaaatt gcacaaagaa aagagcctcc ggggccttac  5760
tcacacggcg ccattccgtc agaaagtcgc gctgcagctt ctcggccacg gtcaggggtg  5820
cctgctcaat cagattcaga tccatgtcag aatctggcgg caactcccat tccttctcgg  5880
ccacccagtt cacaaagctg tcagaaatgc cgggcagatg ctcgtcaagg tcgctgggga  5940
ccttaatcac aatctcgtaa aaccccggca tggcggctgc gcgttcaaac ctcccgcttc  6000
aaaatggaga ccctgcgtgc tcactcgggc gatctctatc actgataggg agatctctat  6060
cactgatagg gagattaaat agaatggcta ggatccggcc ggcctgcagg tgtcctcaca  6120
ggaacgaagt ccctaaagaa acagtggcag ccaggtttag ccccggaatt gactggattc  6180
ctttttttagg gcccattggt atggcttttt ccccgtatcc ccccaggtgt ctgcaggctc  6240
aaagagcagc gagaagcgtt cagaggaaag cgatcccgtg ccaccttccc cgtgcccggg  6300
ctgtccccgc acgctgccgg ctcggggatg cggggggagc gccggaccgg agcggagccc  6360
cgggcggctc gctgctgccc cctagcgggg gagggacgta attacatccc tgggggcttt  6420
gggggggggc tgtccctcta gagcggccgc caccgcggtg gagctccagc ttttgttccc  6480
tttagtgagg gttaattaga tcttaatacg actcactata gggcgaattg ggtaccgggc  6540
ccccctcga ggtcgacggt atcgataagc ttgatatcta taacaagaaa atatatatat  6600
aataagttat cacgtaagta gaacatgaaa taacaatata attatcgtat gagttaaatc  6660
ttaaaagtca cgtaaaagat aatcatgcgt cattttgact cacgcggtcg ttatagttca  6720
aaatcagtga cacttaccgc attgacaagc acgcctcacg ggagctccaa gcggcgactg  6780
agatgtccta aatgcacagc gacggattcg cgctatttag aaagagagag caatatttca  6840
agaatgcatg cgtcaatttt acgcagacta tctttctagg gttaatctag ctgcatcagg  6900
atcatatcgt cgggtctttt ttccggctca gtcatcgccc aagctggcgc tatctgggca  6960
tcggggagga agaagcccgt gccttttccc gcgaggttga agcggcatgg aaagagtttg  7020
ccgaggatga ctgctgctgc attgacgttg agcgaaaacg cacgtttacc atgatgattc  7080
gggaaggtgt ggccatgcac gcctttaacg gtgaactgtt cgttcaggcc acctgggata  7140
ccagttcgtc gcggcttttc cggacacagt tccggatggt cagcccgaag cgcatcagca  7200
acccgaacaa taccggcgac agccggaact gccgtgccgg tgtgcagatt aatgacagcg  7260
gtgcggcgct gggatattac gtcagcgagg acgggtatcc tggctggatg ccgcagaaat  7320
ggacatggat accccgtgag ttacccggcg ggcgcgcttg gcgtaatcat ggtcatagct  7380
gtttcctgtg tgaaattgtt atccgctcac aattccacac aacatacgag ccggaagcat  7440
aaagtgtaaa gcctggggtg cctaatgagt gagctaactc acattaattg cgttgcgctc  7500
actgcccgct ttccagtcgg gaaacctgtc gtgccagctg cattaatgaa tcggccaacg  7560
cgcggggaga ggcggtttgc gtattgggcg ctcttccgct tcctcgctca ctgactcgct  7620
gcgctcggtc gttcggctgc ggcgagcggt atcagctcac tcaaaggcgg taatacggtt  7680
atccacagaa tcaggggata acgcaggaaa gaacatgtga gcaaaaggcc agcaaaaggc  7740
caggaaccgt aaaaaggccg cgttgctggc gtttttccat aggctccgcc cccctgacga  7800
gcatcacaaa aatcgacgct caagtcagag gtggcgaaac ccgacaggac tataaagata  7860
ccaggcgttt ccccctggaa gctccctcgt gcgctctcct gttccgaccc tgccgcttac  7920
cggatacctg tccgcctttc tcccttcggg aagcgtggcg ctttctcata gctcacgctg  7980
taggtatctc agttcggtgt aggtcgttcg ctccaagctg ggctgtgtgc acgaaccccc  8040
cgttcagccc gaccgctgcg ccttatccgg taactatcgt cttgagtcca acccggtaag  8100
acacgactta tcgccactgg cagcagccac tggtaacagg attagcagag cgaggtatgt  8160
aggcggtgct acagagttct tgaagtggtg gcctaactac ggctacacta gaaggacagt  8220
atttggtatc tgcgctctgc tgaagccagt taccttcgga aaaagagttg gtagctcttg  8280
atccggcaaa caaaccaccg ctggtagcgg tggttttttt gtttgcaagc agcagattac  8340
gcgcagaaaa aaaggatctc aagaagatcc tttgatcttt tctacggggt ctgacgctca  8400
gtggaacgaa aactcacgtt aagggatttt ggtcatgaga ttatcaaaaa ggatcttcac  8460
ctagatcctt ttaaattaaa aatgaagttt taaatcaatc taaagtatat atgagtaaac  8520
ttggtctgac agttaccaat gcttaatcag tgaggcacct atctcagcga tctgtctatt  8580
tcgttcatcc atagttgcct gactccccgt cgtgtagata actacgatac gggagggctt  8640
accatctggc cccagtgctg caatgatacc gcgagaccca cgctcaccgg ctccagattt  8700
atcagcaata aaccagccag ccggaagggc cgagcgcaga agtggtcctg caactttatc  8760
cgcctccatc cagtctatta attgttgccg ggaagctaga gtaagtagtt cgccagttaa  8820
tagtttgcgc aacgttgttg ccattgctac aggcatcgtg gtgtcacgct cgtcgtttgg  8880
tatggcttca ttcagctccg gttcccaacg atcaaggcga gttacatgat cccccatgtt  8940
gtgcaaaaaa gcggttagct ccttcggtcc tccgatcgtt gtcagaagta agttggccgc  9000
agtgttatca ctcatggtta tggcagcact gcataattct cttactgtca tgccatccgt  9060
aagatgcttt tctgtgactg gtgagtactc aaccaagtca ttctgagaat agtgtatgcg  9120
gcgaccgagt tgctcttgcc cggcgtcaat acgggataat accgcgccac atagcagaac  9180
tttaaaagtg ctcatcattg gaaaacgttc ttcggggcga aaactctcaa ggatcttacc  9240
gctgttgaga tccagttcga tgtaacccac tcgtgcaccc aactgatctt cagcatcttt  9300
tactttcacc agcgtttctg ggtgagcaaa aacaggaagg caaaatgccg caaaaaaggg  9360
aataagggcg acacggaaat gttgaatact cat                              9393

SEQ ID NO: 31          moltype = DNA  length = 7147
FEATURE                Location/Qualifiers
misc_feature           1..7147
                       note = Description of Artificial Sequence: Synthetic
                        polynucleotide
source                 1..7147
                       mol_type = other DNA
                       organism = synthetic construct
SEQUENCE: 31
gacggatcgg gagatctgag ctcacgggga cagcccccc ccaaagcccc cagggatgta  60
attacgtccc tcccccgcta gggggcagca gcgagccgcc cggggctccg ctccggtccg  120
gcgctccccc cgcatccccg agccggcagc gtgcggggac agcccgggca cggggaaggt  180
ggcacgggat cgctttcctc tgaacgcttc tcgctgctct ttgagcctgc agacacctgg  240
ggggatacgg ggaaaaagct ttaggctgaa agagagattt agaatgacag aatcatagaa  300
```

```
cggcctgggt tgcaaaggag cacagtgctc atccagatcc aaccccctgc tatgtgcagg  360
gtcatcaacc agcagcccag gctgcccaga gccacatcca gcctggcctt gaatgcctgc  420
aggcccgatc ccctatggtc gactctcagt acaatctgct ctgatgccgc atagttaagc  480
cagtatctgc tccctgcttg tgtgttggag gtcgctgagt agtgcgcgag caaaatttaa  540
gctacaacaa ggcaaggctt gaccgacaat tgcatgaaga atctgcttag ggttaggcgt  600
tttgcgctgc ttcgcgatgt acgggccaga tatacgcgtt gacattgatt attgactagt  660
tattaatagt aatcaattac ggggtcatta gttcatagcc catatatgga gttccgcgtt  720
acataactta cggtaaatgg cccgcctggc tgaccgccca acgacccccg cccattgacg  780
tcaataatga cgtatgttcc catagtaacg ccaataggga ctttccattg acgtcaatgg  840
gtggactatt tacggtaaac tgcccacttg gcagtacatc aagtgtatca tatgccaagt  900
acgcccccta ttgacgtcaa tgacggtaaa tggcccgcct ggcattatgc ccagtacatg  960
accttatggg actttcctac ttggcagtac atctacgtat tagtcatcgc tattaccatg  1020
gtgatgcggt tttggcagta catcaatggg cgtggatagc ggtttgactc acggggattt  1080
ccaagtctcc accccattga cgtcaatggg agtttgtttt ggcaccaaaa tcaacgggac  1140
tttccaaaat gtcgtaacaa ctccgcccca ttgacgcaaa tgggcggtag gcgtgtacgg  1200
tgggaggtct atataagcag agctctctgg ctaactagag aacccactgc ttactggctt  1260
atcgaaatta atacgactca ctatagggag acccaagctg gctagcgttt aaacttaagc  1320
tttctgtgag tttggggacc cttgattgtt ctttcttttt cgctattgta aaattcatgt  1380
tatatggagg gggcaaagtt ttcagggtgt tgtttagaat gggaagatgt cccttgtatc  1440
accatggacc ctcatgataa ttttgtttct ttcactttct actctgttga caaccattgt  1500
ctcctcttat tttcttttca ttttctgtaa ctttttcgtt aaactttagc ttgcatttgt  1560
aacgaatttt taaattcact tttgtttatt tgtcagattg taagtacttt ctctaatcac  1620
ttttttttca aggcaatcag ggtatattat attgtacttc agcacagttt tagagaacaa  1680
ttgttataat taaatgataa ggtagaatat ttctgcatat aaattctggc tggcgtggaa  1740
atattcttat tggtagaaac aactacatcc tggtcatcat cctgcctttc tctttatggt  1800
tacaatgata tacactgttt gagatgagga taaaatactc tgagtccaaa ccgggcccct  1860
ctgctaacca tgttcatgcc ttcttctttt tcctacagct cctgggcaac gtgctggtta  1920
ttgtgctgtc tcatcatttt ggcaaagaat tgtaatacga ctcactatag ggcgagccac  1980
catggctaga ttagataaaa gtaaagtgat taacagcgca ttagagctgc ttaatgaggt  2040
cggaatcgaa ggtttaacaa cccgtaaact cgcccagaag ctaggtgtag agcagcctac  2100
attgtattgg catgtaaaaa ataagcgggc tttgctcgac gccttagcca ttgagatgtt  2160
agataggcac catactcact tttgcccttt agaaggggaa agctggcaag attttttacg  2220
taataacgct aaaagtttta gatgtgcttt actaagtcat cgcgatggag caaaagtaca  2280
tttaggtaca cggcctacag aaaaacagta tgaaactctc gaaaatcaat tagccttttt  2340
atgccaacaa ggtttttcac tagagaatgc cttatatgca ctcagcgccg tggggcattt  2400
tactttaggt tgcgtattgg aagatcaaga gcatcaagtc gctaaagaag aaagggaaac  2460
acctactact gatagtatgc cgccattatt acgacaagct atcgaattat ttgatcacca  2520
aggtgcagag ccagccttct tattcggcct tgaattgatc atatgcggat tagaaaaaca  2580
acttaaatgt gaaagtgggt ccccaaaaaa gaagagaaag gtcgacggcg gtggttcagt  2640
ttaagcgtac agcgggatcc actagtccag tgtggtggaa ttctgcagat atccagcaca  2700
gtggcggccg ctcgagtcta gagggcccgt ttaaacccgc tgatcagcct cgactgtgcc  2760
ttctagttgc cagccatctg ttgtttgccc ctcccccgtg ccttccttga ccctggaagg  2820
tgccactccc actgtccttt cctaataaaa tgaggaaatt gcatcgcatt gtctgagtag  2880
gtgtcattct attctggggg gtggggtggg gcaggacagc aagggggagg attgggaaga  2940
caatagcagg catgctgggg atgcggtggg ctctatggct tctgaggcgg aaagaaccag  3000
ctggggctct agggggtatc cccacgcgcc ctgtagcggc gcattaagcg cggcgggtgt  3060
ggtggttacg cgcagcgtga ccgctacact tgccagcgcc ctagcgcccg ctcctttcgc  3120
tttcttccct tcctttctcg ccacgttcgc cggctttccc cgtcaagctc taaatcgggg  3180
catcccttta gggttccgat ttagtgcttt acggcacctc gaccccaaaa aacttgatta  3240
gggtgatggt tcacgtagtg ggccatcgcc ctgatagacg gtttttcgcc ctttgacgtt  3300
ggagtccacg ttctttaata gtggactctt gttccaaact ggaacaacac tcaaccctat  3360
ctcggtctat tcttttgatt tataagggat tttggggatt tcggcctatt ggttaaaaaa  3420
tgagctgatt taacaaaaat ttaacgcgaa ttaattctgt ggaatgtgtg tcagttaggg  3480
tgtggaaagt ccccaggctc cccaggcagg cagaagtatg caaagcatgc atctcaatta  3540
gtcagcaacc aggtgtggaa agtccccagg ctccccagca ggcagaagta tgcaaagcat  3600
gcatctcaat tagtcagcaa ccatagtccc gcccctaact ccgcccatcc cgcccctaac  3660
tccgcccagt tccgcccatt ctccgcccca tggctgacta attttttttta tttatgcaga  3720
ggccgaggcc gcctctgcct ctgagctatt ccagaagtag tgaggaggct tttttggagg  3780
cctaggcttt tgcaaaaagc tcccgggagc ttgtatatcc attttcggat ctgatcagca  3840
cgtgttgaca attaatcatc ggcatagtat atcggcatag tataatacga caaggtgagg  3900
aactaaacca tggccaagtt gaccagtgcc gttccggtgc tcaccgcgcg cgacgtcgcc  3960
ggagcggtcg agttctggac cgaccggctc gggttctccc gggacttcgt ggaggacgac  4020
ttcgccggtg tggtccggga cgacgtgacc ctgttcatca gcgcggtcca ggaccaggtg  4080
gtgccggaca acaccctggc ctgggtgtgg gtgcgcggcc tggacgagct gtacgccgag  4140
tggtcggagg tcgtgtccac gaacttccgg gacgcctccg ggccggccat gaccgagatc  4200
ggcgagcagc cgtgggggcg ggagttcgcc ctgcgcgacc cggccggcaa ctgcgtgcac  4260
ttcgtggccg aggagcagga ctgacacgtg ctacgagatt tcgattccac cgccgccttc  4320
tatgaaaggt tgggcttcgg aatcgttttc cgggacgccg gctggatgat cctccagcgc  4380
ggggatctca tgctggagtt cttcgcccac cccaacttgt ttattgcagc ttataatggt  4440
tacaaataaa gcaatagcat cacaaatttc acaaataaag catttttttc actgcattct  4500
agttgtggtt tgtccaaact catcaatgta tcttatcatg tctgtatacc gtcgacctct  4560
agctagagct tggcgtaatc atggtcatag ctgtttcctg tgtgaaattg ttatccgctc  4620
acaattccac acaacatacg agccggaagc ataaagtgta aagcctgggg tgcctaatga  4680
gtgagctaac tcacattaat tgcgttgcgc tcactgcccg ctttccagtc gggaaacctg  4740
tcgtgccagc tgcattaatg aatcggccaa cgcgcgggga gaggcggttt gcgtattggg  4800
cgctcttccg cttcctcgct cactgactcg ctgcgctcgg tcgttcggct gcggcgagcg  4860
gtatcagctc actcaaaggc ggtaatacgg ttatccacag aatcagggga taacgcagga  4920
aagagagctc acggggacag cccccccccca aagcccccag ggatgtaatt acgtccctcc  4980
cccgctaggg ggcagcagcg agccgcccgg ggctccgctc cggtccggcg ctccccccgc  5040
```

```
atccccgagc cggcagcgtg cggggacagc ccgggcacgg ggaaggtggc acgggatcgc  5100
tttcctctga acgcttctcg ctgctctttg agcctgcaga cacctggggg gatacgggga  5160
aaaagcttta ggctgaaaga gagatttaga atgacagaat catagaacgg cctgggttgc  5220
aaaggagcac agtgctcatc cagatccaac cccctgctat gtgcagggtc atcaaccagc  5280
agcccaggct gcccagagcc acatccagcc tggccttgaa tgcctgcagg acatgtgagc  5340
aaaaggccag caaaaggcca ggaaccgtaa aaaggccgcg ttgctggcgt ttttccatag  5400
gctccgcccc cctgacgagc atcacaaaaa tcgacgctca agtcagaggt ggcgaaaccc  5460
gacaggacta taaagatacc aggcgtttcc ccctggaagc tccctcgtgc gctctcctgt  5520
tccgaccctg ccgcttaccg gatacctgtc cgcctttctc ccttcgggaa gcgtggcgct  5580
ttctcaatgc tcacgctgta ggtatctcag ttcggtgtag gtcgttcgct ccaagctggg  5640
ctgtgtgcac gaaccccccg ttcagcccga ccgctgcgcc ttatccggta actatcgtct  5700
tgagtccaac ccggtaagac acgacttatc gccactggca gcagccactg gtaacaggat  5760
tagcagagcg aggtatgtag gcggtgctac agagttcttg aagtggtggc ctaactacgg  5820
ctacactaga aggacagtat ttggtatctg cgctctgctg aagccagtta ccttcggaaa  5880
aagagttggt agctcttgat ccggcaaaca aaccaccgct ggtagcggtg gtttttttgt  5940
ttgcaagcag cagattacgc gcagaaaaaa aggatctcaa gaagatcctt tgatcttttc  6000
tacggggtct gacgctcagt ggaacgaaaa ctcacgttaa gggattttgg tcatgagatt  6060
atcaaaaagg atcttcacct agatcctttt aaattaaaaa tgaagtttta aatcaatcta  6120
aagtatatat gagtaaactt ggtctgacag ttaccaatgc ttaatcagtg aggcacctat  6180
ctcagcgatc tgtctatttc gttcatccat agttgcctga ctccccgtcg tgtagataac  6240
tacgatacgg gagggcttac catctggccc cagtgctgca atgataccgc gagacccacg  6300
ctcaccggct ccagatttat cagcaataaa ccagccagcc ggaagggccg agcgcagaag  6360
tggtcctgca actttatccg cctccatcca gtctattaat tgttgccggg aagctagagt  6420
aagtagttcg ccagttaata gtttgcgcaa cgttgttgcc attgctacag gcatcgtggt  6480
gtcacgctcg tcgtttggta tggcttcatt cagctccggt tcccaacgat caaggcgagt  6540
tacatgatcc cccatgttgt gcaaaaaagc ggttagctcc ttcggtcctc cgatcgttgt  6600
cagaagtaag ttggccgcag tgttatcact catggttatg gcagcactgc ataattctct  6660
tactgtcatg ccatccgtaa gatgcttttc tgtgactggt gagtactcaa ccaagtcatt  6720
ctgagaatag tgtatgcggc gaccgagttg ctcttgcccg gcgtcaatac gggataatac  6780
cgcgccacat agcagaactt taaaagtgct catcattgga aaacgttctt cggggcgaaa  6840
actctcaagg atcttaccgc tgttgagatc cagttcgatg taacccactc gtgcacccaa  6900
ctgatcttca gcatctttta ctttcaccag cgtttctggg tgagcaaaaa caggaaggca  6960
aaatgccgca aaaaagggaa taagggcgac acggaaatgt tgaatactca tactcttcct  7020
ttttcaatat tattgaagca tttatcaggg ttattgtctc atgagcggat acatatttga  7080
atgtatttag aaaaataaac aaataggggt tccgcgcaca tttccccgaa aagtgccacc  7140
tgacgtc                                                            7147

SEQ ID NO: 32           moltype = DNA  length = 7493
FEATURE                 Location/Qualifiers
misc_feature            1..7493
                        note = Description of Artificial Sequence: Synthetic
                         polynucleotide
source                  1..7493
                        mol_type = other DNA
                        organism = synthetic construct
SEQUENCE: 32
gacggatcgg gagatctgag ctcacgggga cagcccccc ccaaagcccc cagggatgta  60
attacgtccc tcccccgcta gggggcagca gcgagccgcc cggggctccg ctccggtccg  120
gcgctccccc cgcatccccg agccggcagc gtgcggggac agcccgggca cggggaaggt  180
ggcacgggat cgctttcctc tgaacgcttc tcgctgctct ttgagcctgc agacacctgg  240
ggggatacgg ggaaaaagct ttaggctgaa agagagattt agaatgacag aatcatagaa  300
cggcctgggt tgcaaaggag cacagtgctc atccagatcc aaccccctgc tatgtgcagg  360
gtcatcaacc agcagcccag gctgcccaga gccacatcca gcctggcctt gaatgcctgc  420
aggcccgatc ccctatggtc gactctcagt acaatctgct ctgatgccgc atagttaagc  480
cagtatctgc tccctgcttg tgtgttggag gtcgctgagt agtgcgcgag caaaatttaa  540
gctacaacaa ggcaaggctt gaccgacaat tgcatgaaga atctgcttag ggttaggcgt  600
tttgcgctgc ttcgcgatgt acgggccaga tatacgcgtt gacattgatt attgactagt  660
tattaatagt aatcaattac ggggtcatta gttcatagcc catatatgga gttccgcgtt  720
acataactta cggtaaatgg cccgcctggc tgaccgccca acgacccccg cccattgacg  780
tcaataatga cgtatgttcc catagtaacg ccaataggga ctttccattg acgtcaatgg  840
gtggactatt tacggtaaac tgcccacttg gcagtacatc aagtgtatca tatgccaagt  900
acgcccccta ttgacgtcaa tgacggtaaa tggcccgcct ggcattatgc ccagtacatg  960
accttatggg actttcctac ttggcagtac atctacgtat tagtcatcgc tattaccatg  1020
gtgatgcggt tttggcagta catcaatggg cgtggatagc ggtttgactc acggggattt  1080
ccaagtctcc accccattga cgtcaatggg agtttgtttt ggcaccaaaa tcaacgggac  1140
tttccaaaat gtcgtaacaa ctccgcccca ttgacgcaaa tgggcggtag gcgtgtacgg  1200
tgggaggtct atataagcag agctctctgg ctaactagag aacccactgc ttactggctt  1260
atcgaaatta atacgactca ctatagggag acccaagctg gctagcgttt aaacttaagc  1320
tttctgtgag tttggggacc cttgattgtt ctttcttttt cgctattgta aaattcatgt  1380
tatatggagg gggcaaagtt ttcagggtgt tgtttagaat gggaagatgt cccttgtatc  1440
accatggacc ctcatgataa ttttgtttct ttcactttct actctgttga caaccattgt  1500
ctcctcttat tttcttttca ttttctgtaa ctttttcgtt aaactttagc ttgcatttgt  1560
aacgaatttt taaattcact tttgtttatt tgtcagattg taagtacttt ctctaatcac  1620
tttttttca aggcaatcag ggtatattat attgtacttc agcacagttt tagagaacaa  1680
ttgttataat taaatgataa ggtagaatat ttctgcatat aaattctggc tggcgtggaa  1740
atattcttat tggtagaaac aactacatcc tggtcatcat cctgcctttc tctttatggt  1800
tacaatgata tacactgttt gagatgagga taaaatactc tgagtccaaa ccgggcccct  1860
ctgctaacca tgttcatgcc ttcttctttt tcctacagct cctgggcaac gtgctggtta  1920
ttgtgctgtc tcatcatttt ggcaaagaat tgtaatacga ctcactatag ggcgagccac  1980
```

```
catggctaga ttagataaaa gtaaagtgat taacagcgca ttagagctgc ttaatgaggt  2040
cggaatcgaa ggtttaacaa cccgtaaact cgcccagaag ctaggtgtag agcagcctac  2100
attgtattgg catgtaaaaa ataagcgggc tttgctcgac gccttagcca ttgagatgtt  2160
agataggcac catactcact tttgcccttt agaaggggaa agctggcaag attttttacg  2220
taataacgct aaaagtttta gatgtgcttt actaagtcat cgcgatggag caaaagtaca  2280
tttaggtaca cggcctacag aaaaacagta tgaaactctc gaaaatcaat tagccttttt  2340
atgccaacaa ggtttttcac tagagaatgc cttatatgca ctcagcgccg tggggcattt  2400
tactttaggt tgcgtattgg aagatcaaga gcatcaagtc gctaaagaag aaagggaaac  2460
acctactact gatagtatgc cgccattatt acgacaagct atcgaattat ttgatcacca  2520
aggtgcagag ccagccttct tattcggcct tgaattgatc atatgcggat tagaaaaaca  2580
acttaaatgt gaaagtgggt ccccaaaaaa gaagagaaag gtcgacggcg gtggtgcttt  2640
gtctcctcag cactctgctg tcactcaagg aagtatcatc aagaacaagg agggcatgga  2700
tgctaagtca ctaactgcct ggtcccggac actggtgacc ttcaaggatg tatttgtgga  2760
cttcaccagg gaggagtgga agctgctgga cactgctcag cagatcgtgt acagaaatgt  2820
gatgctggag aactataaga acctggtttc cttgggttat cagcttacta agccagatgt  2880
gatcctccgg ttggagaagg gagaagagcc ctggctggtg gagagagaaa ttcaccaaga  2940
gacccatcct gattcagaga ctgcatttga aatcaaatca tcagtttaag cgtacagcgg  3000
ggatccacta gtccagtgtg gtggaattct gcagatatcc agcacagtgg cggccgctcg  3060
agtctagagg gcccgtttaa acccgctgat cagcctcgac tgtgccttct agttgccagc  3120
catctgttgt ttgcccctcc cccgtgcctt ccttgaccct ggaaggtgcc actcccactg  3180
tcctttccta ataaaatgag gaaattgcat cgcattgtct gagtaggtgt cattctattc  3240
tggggggtgg ggtggggcag gacagcaagg gggaggattg ggaagacaat agcaggcatg  3300
ctggggatgc ggtgggctct atggcttctg aggcggaaag aaccagctgg ggctctaggg  3360
ggtatcccca cgcgccctgt agcggcgcat taagcgcggc gggtgtggtg gttacgcgca  3420
gcgtgaccgc tacacttgcc agcgccctag cgcccgctcc tttcgctttc ttcccttcct  3480
ttctcgccac gttcgccggc tttccccgtc aagctctaaa tcgggggcatc cctttagggt  3540
tccgatttag tgctttacgg cacctcgacc ccaaaaaact tgattagggt gatggttcac  3600
gtagtgggcc atcgccctga tagacggttt ttcgcccttt gacgttggag tccacgttct  3660
ttaatagtgg actcttgttc caaactggaa caacactcaa ccctatctcg gtctattctt  3720
ttgatttata agggattttg gggatttcgg cctattggtt aaaaaatgag ctgatttaac  3780
aaaaatttaa cgcgaattaa ttctgtggaa tgtgtgtcag ttagggtgtg gaaagtcccc  3840
aggctcccca ggcaggcaga agtatgcaaa gcatgcatct caattagtca gcaaccaggt  3900
gtggaaagtc cccaggctcc ccagcaggca gaagtatgca aagcatgcat ctcaattagt  3960
cagcaaccat agtcccgccc ctaactccgc ccatcccgcc cctaactccg cccagttccg  4020
cccattctcc gccccatggc tgactaattt tttttattta tgcagaggcc gaggccgcct  4080
ctgcctctga gctattccag aagtagtgag gaggcttttt tggaggccta ggcttttgca  4140
aaaagctccc gggagcttgt atatccattt tcggatctga tcagcacgtg ttgacaatta  4200
atcatcggca tagtatatcg gcatagtata atacgacaag gtgaggaact aaaccatggc  4260
caagttgacc agtgccgttc cggtgctcac cgcgcgcgac gtcgccggag cggtcgagtt  4320
ctggaccgac cggctcgggt tctcccggga cttcgtggag gacgacttcg ccggtgtggt  4380
ccgggacgac gtgaccctgt tcatcagcgc ggtccaggac caggtggtgc cggacaacac  4440
cctggcctgg gtgtgggtgc gcggcctgga cgagctgtac gccgagtggt cggaggtcgt  4500
gtccacgaac ttccgggacg cctccgggcc ggccatgacc gagatcggcg agcagccgtg  4560
ggggcgggag ttcgccctgc gcgacccggc cggcaactgc gtgcacttcg tggccgagga  4620
gcaggactga cacgtgctac gagatttcga ttccaccgcc gccttctatg aaaggttggg  4680
cttcggaatc gttttccggg acgccggctg gatgatcctc cagcgcgggg atctcatgct  4740
ggagttcttc gcccacccca acttgtttat tgcagcttat aatggttaca aataaagcaa  4800
tagcatcaca aatttcacaa ataaagcatt tttttcactg cattctagtt gtggtttgtc  4860
caaactcatc aatgtatctt atcatgtctg tataccgtcg acctctagct agagcttggc  4920
gtaatcatgg tcatagctgt ttcctgtgtg aaattgttat ccgctcacaa ttccacacaa  4980
catacgagcc ggaagcataa agtgtaaagc ctggggtgcc taatgagtga gctaactcac  5040
attaattgcg ttgcgctcac tgcccgcttt ccagtcggga aacctgtcgt gccagctgca  5100
ttaatgaatc ggccaacgcg cggggagagg cggtttgcgt attgggcgct cttccgcttc  5160
ctcgctcact gactcgctgc gctcggtcgt tcggctgcgg cgagcggtat cagctcactc  5220
aaaggcggta atacggttat ccacagaatc aggggataac gcaggaaaga gagctcacgg  5280
ggacagcccc cccccaaagc ccccagggat gtaattacgt ccctcccccg ctagggggca  5340
gcagcgagcc gcccggggct ccgctccggt ccggcgctcc ccccgcatcc ccgagccggc  5400
agcgtgcggg gacagcccgg gcacggggaa ggtggcacgg gatcgctttc ctctgaacgc  5460
ttctcgctgc tctttgagcc tgcagacacc tgggggggata cggggaaaaa gctttaggct  5520
gaaagagaga tttagaatga cagaatcata gaacggcctg ggttgcaaag gagcacagtg  5580
ctcatccaga tccaacccc tgctatgtgc agggtcatca accagcagcc caggctgccc  5640
agagccacat ccagcctggc cttgaatgcc tgcaggacat gtgagcaaaa ggccagcaaa  5700
aggccaggaa ccgtaaaaag gccgcgttgc tggcgttttt ccataggctc cgcccccctg  5760
acgagcatca caaaaatcga cgctcaagtc agaggtggcg aaacccgaca ggactataaa  5820
gataccaggc gtttccccct ggaagctccc tcgtgcgctc tcctgttccg accctgccgc  5880
ttaccggata cctgtccgcc tttctccctt cgggaagcgt ggcgctttct caatgctcac  5940
gctgtaggta tctcagttcg gtgtaggtcg ttcgctccaa gctgggctgt gtgcacgaac  6000
cccccgttca gcccgaccgc tgcgccttat ccggtaacta tcgtcttgag tccaacccgg  6060
taagacacga cttatcgcca ctggcagcag ccactggtaa caggattagc agagcgaggt  6120
atgtaggcgg tgctacagag ttcttgaagt ggtggcctaa ctacggctac actagaagga  6180
cagtatttgg tatctgcgct ctgctgaagc cagttacctt cggaaaaaga gttggtagct  6240
cttgatccgg caaacaaacc accgctggta gcggtggttt ttttgtttgc aagcagcaga  6300
ttacgcgcag aaaaaaagga tctcaagaag atcctttgat cttttctacg gggtctgacg  6360
ctcagtggaa cgaaaactca cgttaaggga ttttggtcat gagattatca aaaaggatct  6420
tcacctagat ccttttaaat taaaaatgaa gttttaaatc aatctaaagt atatatgagt  6480
aaacttggtc tgacagttac caatgcttaa tcagtgaggc acctatctca gcgatctgtc  6540
tatttcgttc atccatagtt gcctgactcc ccgtcgtgta gataactacg atacgggagg  6600
gcttaccatc tggccccagt gctgcaatga taccgcgaga cccacgctca ccggctccag  6660
atttatcagc aataaaccag ccagccggaa gggccgagcg cagaagtggt cctgcaactt  6720
```

-continued

```
tatccgcctc catccagtct attaattgtt gccgggaagc tagagtaagt agttcgccag  6780
ttaatagttt gcgcaacgtt gttgccattg ctacaggcat cgtggtgtca cgctcgtcgt  6840
ttggtatggc ttcattcagc tccggttccc aacgatcaag gcgagttaca tgatccccca  6900
tgttgtgcaa aaaagcggtt agctccttcg gtcctccgat cgttgtcaga agtaagttgg  6960
ccgcagtgtt atcactcatg gttatggcag cactgcataa ttctcttact gtcatgccat  7020
ccgtaagatg cttttctgtg actggtgagt actcaaccaa gtcattctga gaatagtgta  7080
tgcggcgacc gagttgctct tgcccggcgt caatacggga taataccgcg ccacatagca  7140
gaactttaaa agtgctcatc attggaaaac gttcttcggg gcgaaaactc tcaaggatct  7200
taccgctgtt gagatccagt tcgatgtaac ccactcgtgc acccaactga tcttcagcat  7260
cttttacttt caccagcgtt tctgggtgag caaaaacagg aaggcaaaat gccgcaaaaa  7320
agggaataag ggcgacacgg aaatgttgaa tactcatact cttccttttt caatattatt  7380
gaagcattta tcagggttat tgtctcatga gcggatacat atttgaatgt atttagaaaa  7440
ataaacaaat aggggttccg cgcacatttc cccgaaaagt gccacctgac gtc         7493
```

ADENO-ASSOCIATED VIRUS (AAV) PRODUCER CELL LINE AND RELATED METHODS

CROSS-REFERENCE TO RELATED APPLICATIONS

The present application claims priority to U.S. Provisional Patent Application Nos. 62/783,589, filed Dec. 21, 2018, and 62/866,092, filed Jun. 25, 2019, the disclosures of each of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Dec. 17, 2019, is named 0132-0049US1_SL.txt and is 364,567 bytes in size.

FIELD OF THE INVENTION

The present disclosure relates to mammalian cell lines for producing adeno-associated virus (AAV). The cells suitably include nucleic acids encoding helper genes and AAV genes, under the control of derepressible promoters. The disclosure also relates to isolated nucleic acid molecules that encode such genes, as well as methods of using the mammalian cells for producing AAVs.

BACKGROUND OF THE INVENTION

The safety profile and long-term expression capacity make adeno-associated virus (AAV) an excellent viral vector for gene therapy in humans. The wildtype AAV genome is composed of a 4.7 kb single-stranded DNA that includes regulatory genes for replication (Rep) and structural genes for Capsid (Cap), flanked by inverted terminal repeats (ITR) for virus replication and packaging. As a dependent virus, AAV replication in host cells requires the coinfection of helper viruses, such as Adenovirus (Ad) and Herpes Simplex virus. Alternatively, the expression of cloned helper genes can also support AAV replication. For instance, recombinant AAV can be produced in HEK293 cells by the co-transfection of three plasmids: pHelper plasmids expressing E2A, E4Orf6 and VA from Adenovirus, pRep-Cap plasmids for Rep and Cap proteins, and AAV transfer plasmids carrying the desired gene of interest (GOI).

Currently, AAV manufacturing relies on several bridging platforms. Besides the triple transfection in HEK293 cells noted above, AAV can be produced by co-infection of two baculoviruses expressing Rep-Cap and the GOI, respectively, into insect cells. However, these baculoviruses are unstable at higher passage and are time-consuming to prepare (see, e.g., Urabe et al., “Insect Cells as a Factory to Produce Adeno-Associated Virus Type 2 Vectors,” *Human Gene Therapy* 13:1935-1943 (2002)). HeLa packaging cells with stably integrated Rep-Cap and GOI have also been developed. These systems, nevertheless, still require the wildtype Adenovirus as a helper virus, which poses risks of contamination of replicative adenovirus in AAV products (see, e.g., Robert et al., “Manufacturing of recombinant adeno-associated viruses using mammalian expression platforms,” *Biotechnology Journal* 12:1600193 (1-16) (2017).

What are needed, are cell lines and related methods for production of AAV that are easily scalable to large volume production, to provide reproducible and stable results, while limiting contamination and reducing cost.

SUMMARY OF THE INVENTION

In some embodiments, provided herein is a mammalian cell for producing an adeno-associated virus (AAV), comprising a nucleic acid molecule encoding a viral helper gene under control of a first derepressible promoter, a nucleic acid molecule encoding an AAV gene under control of a second derepressible promoter, and a nucleic acid molecule encoding a repressor element of the first and the second derepressible promoters.

In additional embodiments, provided herein is a mammalian cell for producing an adeno-associated virus (AAV), comprising a nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

In further embodiments, provided herein is an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

In still further embodiments, provided herein is a method of producing an adeno-associated virus (AAV) in a mammalian cell comprising transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, and harvesting the AAV.

In further embodiments, provided herein is a method of treatment with an adeno-associated virus (AAV) comprising: transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, harvesting the AAV and administering the AAV to a mammalian patient.

In still further embodiments, provided herein is a method of producing an adeno-associated virus (AAV) comprising: transfecting a mammalian cell stably expressing one or more nucleic acids encoding TetR and/or TetR-KRAB with a first nucleic acid encoding an adenovirus helper gene comprising an E2A gene, a E4Orf gene and a viral-associated non-coding RNA under control of a first derepressible promoter, a second nucleic acid encoding an AAV gene comprising Rep and Cap genes under control of a second derepressible promoter, and, optionally, a third nucleic acid encoding a gene of interest under control of a third derepressible promoter, treating the mammalian cell with a binding partner of the TetR and/or TetR-KRAB, activating the first, second, and third derepressible promoters, producing the AAV, and harvesting the AAV.

In still further embodiments, provided herein is a method for producing an adeno-associated virus (AAV), comprising: stably transfecting a mammalian cell with a nucleic acid encoding a TetR and/or TetR-KRAB repressor, chicken hypersensitive site-4 (cHS4) sequences flanking the TetR and/or TetR-KRAB repressor, and a selection gene, transfecting the stably transfected mammalian cell with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the mammalian cell with a binding partner of the TetR; activating the first, second and third derepressible promoters; producing the AAV; and harvesting the AAV.

DETAILED DESCRIPTION OF THE INVENTION

Figure 1:
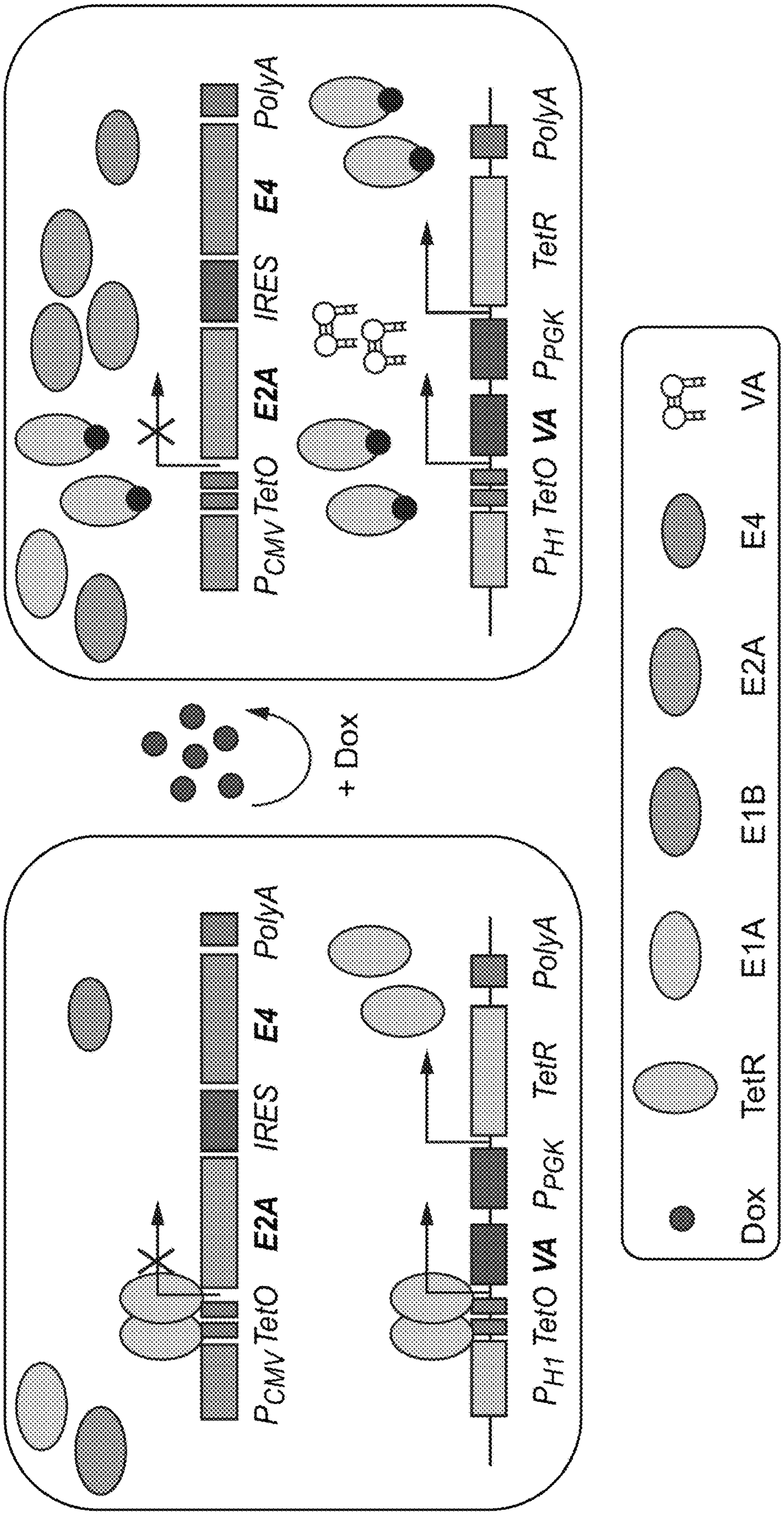
FIG. 1 shows a schematic of the use of derepressible promoters to control the expression of helper and VA genes in accordance with embodiments hereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

Adeno-associated virus (AAV) has emerged as the vector of choice for gene therapy in over 120 clinical trials worldwide. The fast-growing demand of recombinant AAV requires highly efficient and robust manufacturing platforms. However, current methods for AAV production, including transient transfection and helper virus systems, are extremely costly and lab-intensive. Described herein is a plasmid/helper virus-free AAV producer cell line, and methods of use thereof, that provides efficient AAV manufacturing for a long-term solution at significantly reduced cost. The AAV producer cell line described herein represents a next generation platform for both clinical and commercial AAV manufacturing.

Thus, in embodiments, provided herein is a mammalian cell for producing an adeno-associated virus (AAV).

As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g. POTELLIGENT®, Lonza, Slough, UK), a CHOK1SV GS-KO (glutamine synthetase knockout) cell including all variants (e.g., XCEED™ Lonza, Slough, UK). Exemplary human cells include human embryonic kidney (HEK) cells, such as HEK293, a HeLa cell, or a HT1080 cell.

Mammalian cells include mammalian cell cultures which can be either adherent cultures or suspension cultures. Adherent cultures refer to cells that are grown on a substrate surface, for example a plastic plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

As used herein, the term "adeno-associated virus (AAV)" refers to a small sized, replicative-defective nonenveloped virus containing a single stranded DNA of the family Parvoviridae and the genus Dependoparvovirus. Over 10 adeno-associated virus serotypes have been identified so far, with serotype AAV2 being the best characterized. Other non-limiting examples of AAV serotypes are ANC80, AAV1, AAV3, AAV4, AAV5, AAV6, AAV7, AAV8, AAV9, AAV10, and AAV11. In addition to these serotypes, AAV pseudotypes have been developed. An AAV pseudotype contains the capsid of a first serotype and the genome of a second serotype (e.g. the pseudotype AAV2/5 would correspond to an AAV with the genome of serotype AAV2 and the capsid of AAV5).

As referred to herein, the term "adenovirus" refers to a nonenveloped virus with an icosahedral nucleocapsid containing a double stranded DNA of the family Adenoviridae. Over 50 adenoviral subtypes have been isolated from humans and many additional subtypes have been isolated from other mammals and birds. Birds. See, e.g., Ishibashi et al., "Adenoviruses of animals," In *The Adenoviruses*, Ginsberg, ed., Plenum Press, New York, N.Y., pp. 497-562 (1984); Strauss, "Adenovirus infections in humans," In *The Adenoviruses*, Ginsberg, ed., Plenum Press, New York, N.Y., pp. 451-596 (1984). These subtypes belong to the family Adenoviridae, which is currently divided into two genera, namely Mastadenovirus and Aviadenovirus. All adenoviruses are morphologically and structurally similar. In humans, however, adenoviruses show diverging immunological properties and are, therefore, divided into serotypes. Two human serotypes of adenovirus, namely AV2 and AVS, have been studied intensively and have provided the majority of general information about adenoviruses.

In embodiments, the mammalian cell provided herein suitably includes a nucleic acid molecule encoding a viral helper gene under control of a first derepressible promoter, a nucleic acid molecule encoding an AAV gene under control of a second derepressible promoter, and a nucleic acid molecule encoding a repressor element of the first and the second derepressible promoters.

In exemplary embodiments, the nucleic acid molecules encoding the various components for producing an AAV are contained within the mammalian cell in separate nucleic acid molecules, for example separate plasmids or vectors. In other embodiments, the nucleic acid molecules encoding the various components for producing an AAV are included on the same plasmid or vector. In further embodiments, certain of the components are contained on the same nucleic acid molecule (e.g., helper genes and AAV genes), while other genes are contained on separate nucleic acid molecules (e.g., gene encoding the repressor element).

A "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

In the various embodiments described herein, the nucleic acid molecules are capable of encoding the various genes. That is the nucleic acid molecules, when transcribed, produce mRNA for the genes described herein, which is then translated to the desired or required proteins.

As described herein, suitably the mammalian cells include a nucleic acid molecule encoding a viral helper gene. Viral helper genes include various adenoviral virus genes, herpes virus genes and bocavirus genes (see, e.g., Guido et al., "Human bocavirus: Current knowledge and future challenges," *World J. Gateroenterol* 22:8684-8697, the disclosure of which is incorporated by reference herein in its entirety). In exemplary embodiments, the viral helper gene is an adenovirus helper gene. As referred to herein, the term "adenovirus helper gene" or "AV helper gene" refers to a gene that is composed of one or more nucleic acid sequences derived from one or more adenovirus subtypes or serotypes that contributes to Adeno-associated virus replication and packaging. In some embodiments, the Adenovirus helper gene is E1A, E1B, E2A, E4 (including E4Orf6), VA, or a combination thereof or any other adenovirus helper gene. In exemplary embodiments, the adenovirus helper gene comprises both E2A and E4Orf6 genes. Suitably, an internal ribosome entry site (IRES) element is included between the E2A and E4Orf6 genes. The IRES element initiates translation of the E4Orf6 gene after the E2A gene in a single expression cassette, providing stability to the construct.

The various nucleic acid molecules encoding the various genes described herein are suitably under control of a derepressible promoter. As used herein "under control" refers to a gene being regulated by a "promoter," "promoter sequence," or "promoter region," which refers to a DNA regulatory region/sequence capable of binding RNA polymerase and initiating transcription of a downstream coding or non-coding gene sequence. In other words, the promoter and the gene are in operable combination or operably linked. As referred to herein, the terms "in operable combination", "in operable order" and "operably linked" refer to the linkage of nucleic acid sequences in such a manner that a promoter capable of directing the transcription of a given gene and/or the synthesis of a desired protein molecule is produced. The term also refers to the linkage of amino acid sequences in such a manner so that a functional protein is produced.

In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any of the gene products as described herein. In other embodiments as described herein, the promoter is a constitutive promoter, which initiates mRNA synthesis independent of the influence of an external regulation.

Suitably, the promoters used to control the transcription of the various genes for producing the AAVs described herein are derepressible promoters. As used herein, a "derepressible promoter" refers to a structure that includes a functional promoter and additional elements or sequences capable of binding to a repressor element to cause repression of the functional promoter. "Repression" refers to the decrease or inhibition of the initiation of transcription of a downstream coding or non-coding gene sequence by a promoter. A "repressor element" refers to a protein or polypeptide that is capable of binding to a promoter (or near a promoter) so as to decrease or inhibit the activity of the promoter. A repressor element can interact with a substrate or binding partner of the repressor element, such that the repressor element undergoes a conformation change. This conformation change in the repressor element takes away the ability of the repressor element to decrease or inhibit the promoter, resulting in the "derepression" of the promoter, thereby allowing the promoter to proceed with the initiation of transcription. A "functional promoter" refers to a promoter, that absent the action of the repressor element, would be capable of initiation transcription. Various functional promoters that can be used in the practice of the present invention are known in the art, and include for example, $P_{CMV}$, $P_{H1}$, P19, P5, P40 and promoters of Adenovirus helper genes (e.g., E1A, E1B, E2A, E4Orf6, and VA).

Exemplary repressor elements and their corresponding binding partners that can be used as derepressible promoters are known in the art, and include systems such as the cumate gene-switch system (CuO operator, CymR repressor and cumate binding partner) (see, e.g., Mullick et al., "The cumate gene-switch: a system for regulated expression in mammalian cells," *BMC Biotechnology* 6:43 (1-18) (2006), the disclosure of which is incorporated by reference herein in its entirety, including the disclosure of the derepressible promoter system described therein) and the TetO/TetR system described herein (see, e.g., Yao et al., "Tetracycline Repressor, tetR, rather than the tetR-Mammalian Cell Transcription Factor Fusion Derivatives, Regulates Inducible Gene Expression in Mammalian Cells," *Human Gene Therapy* 9:1939-1950 (1998), the disclosure of which is incorporated by reference herein in its entirety).

In exemplary embodiments, the derepressible promoters comprise a functional promoter and two tetracycline operator sequences ($TetO_2$). A schematic showing an exemplary depressible promoter system is provided in FIG. 1. A derepressible promoter including the $P_{CMV}$ promoter, and a derepressible promoter including the $P_{H1}$ promoter, are shown, both including two TetO sequences ($TetO_2$). As illustrated schematically, upon binding of two tetracycline repressor proteins (TetR—the repressor elements for the $TetO_2$ sequences), to the $TetO_2$ sequences, both the $P_{CMV}$ promoter and the $P_{H1}$ promoter are repressed. That is, little or no transcription takes place from these promoters. Upon binding of a binding partner for TetR (suitably Doxycycline (Dox), the TetR proteins change conformation, release from the $TetO_2$ sequences, and the functional promoters begin their normal transcription processes, as they would naturally. As illustrated schematically in FIG. 1, this results in the change of the overall system from an "off" position (where suitably no transcription is taking place from the $P_{CMV}$ promoter and the $P_{H1}$ promoter), to an "on" position when Dox is added, allowing the $P_{CMV}$ promoter and the $P_{H1}$ promoter to return to their natural state of transcribing the genes under their control.

For example, as shown in FIG. 1, the $P_{CMV}$ promoter with $TetO_2$ sequences (suitably the pcDNA4/TO promotor; INVITROGEN®), is in an "off" position when bound by TetR. When Dox is added, the TetR changes conformation, release from the $TetO_2$ sequences of the depressible promoter, and the $P_{CMV}$ promotor proceeds to transcribe the adenoviral helper genes (e.g., E2A and E4).

As described herein, and as illustrated in FIG. 1, the mammalian cell can further comprise a nucleic acid encoding a viral-associated (VA), non-coding RNA under control of a fourth derepressible promoter. As shown in FIG. 1, this derepressible promoter can include the functional promoter $P_{H1}$, and the $TetO_2$ sequences controlling the expression of the non-coding RNA (see, e.g., Wiederschain et al., "Single-vector inducible lentiviral RNAi system for oncology target validation, *Cell Cycle* 8:498-504 (2009), the disclosure of which is incorporated by reference herein in its entirety, including for the disclosure of the promoter system and sequence). As shown in FIG. 1, the $P_{H1}$ promoter with $TetO_2$ sequences, is in an "off" position when bound by TetR. When Dox is added, the TetR changes conformation, release from the $TetO_2$ sequences of the depressible promoter, and the $P_{H1}$ promotor proceeds to transcribe the VA 1 non-coding RNA.

Figure 2A:
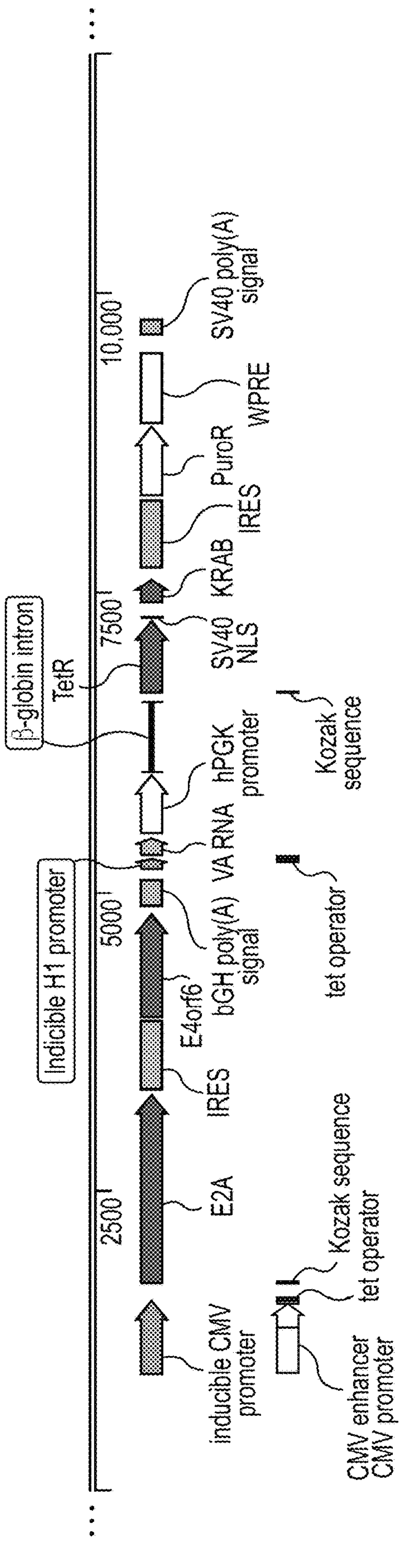
FIGS. 2A and 2B show exemplary nucleic acid molecules for production of helper and VA genes in accordance with embodiments hereof.

FIG. 2A shows an exemplary nucleic acid molecule that can be utilized in the various mammalian cells and methods described herein. As illustrated, a CMV promoter is used upstream of both E2A and E4Orf6 genes, linked via a IRES element. The CMV promoter includes the CMV enhancer and the tet operator ($TetO_2$), for control, via derepression. Also illustrated in FIG. 2A is an exemplary location for the H1 promotor, also including $TetO_2$ sequences, controlling the expression of the VA non-coding RNA.

FIG. 1 and FIG. 2A also illustrate that, in embodiments, the mammalian cells can include the repressor element under control of a constitutive promoter. As described herein, suitably the repressor element that is encoded is a tetracycline repressor protein (TetR). As illustrated in FIG. 1 and FIG. 2A, a suitable promotor for expression of the repressor element is an hPGK promotor. By placing the repressor element under the control of a constitutive promotor, production of the repressor element, suitably TetR, is always active. That is, TetR is being produced upon introduction of the nucleic acid molecule into the mammalian cell. This provides tight control of the various derepressible promoters that are repressed by the TetR binding to the $TetO_2$ sequences.

Figure 2B:
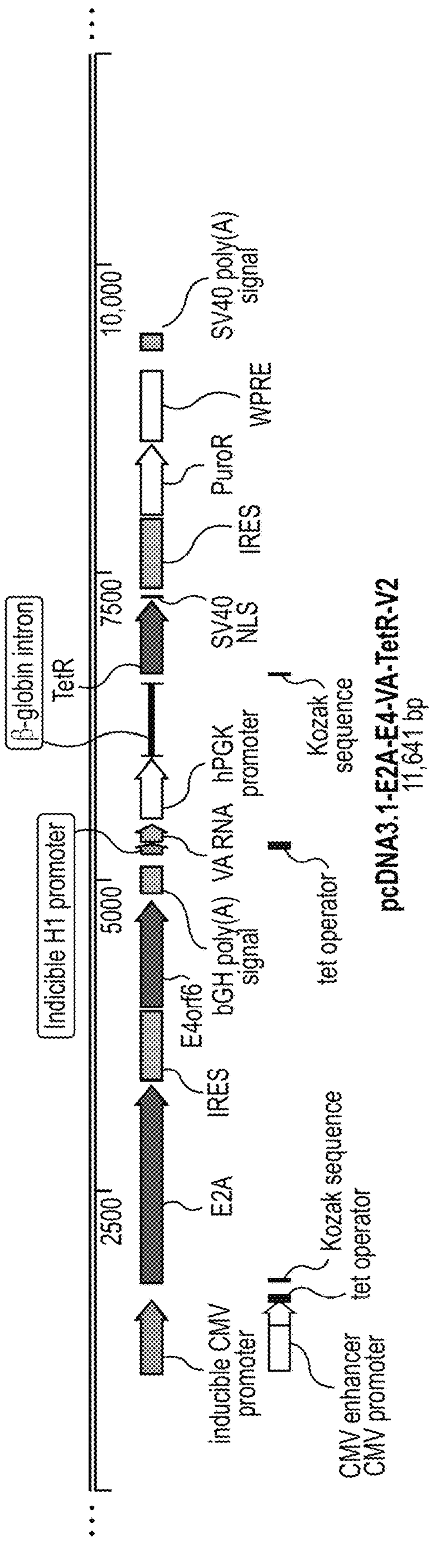
Figure 12A:
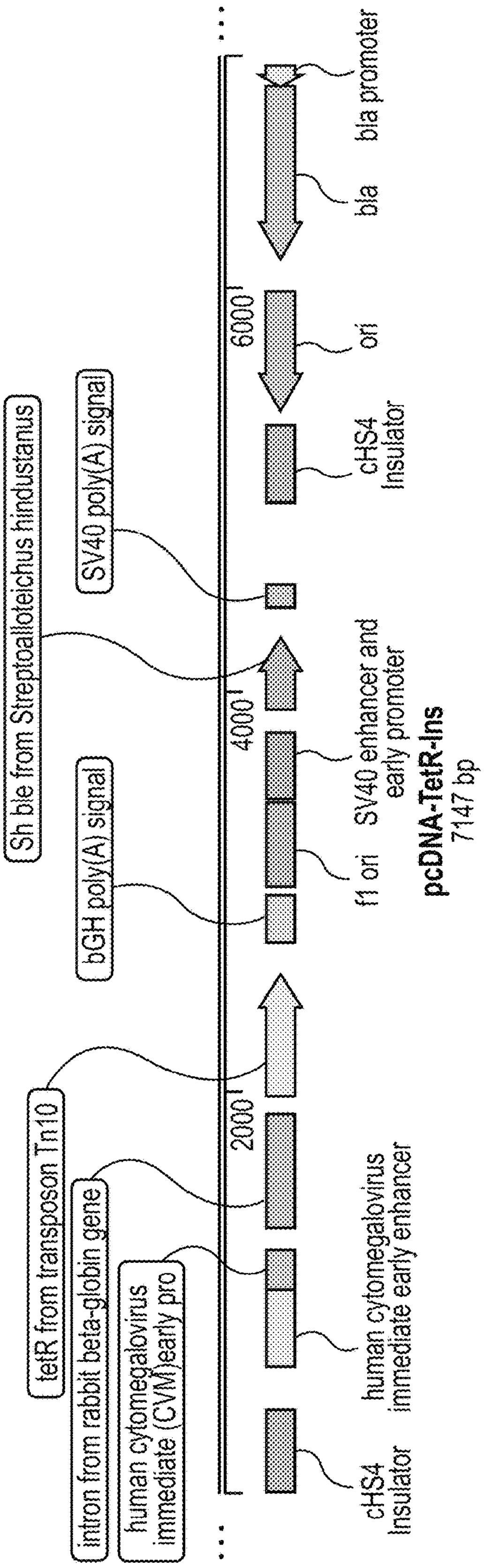
FIGS. 12A-12B show exemplary nucleic acid constructs encoding TetR and TetR-KRAB, in accordance with embodiments hereof.

As shown in FIG. 2A, in exemplary embodiments, a nucleic acid encoding a transcriptional repression domain in frame with the nucleic acid encoding the tetracycline repressor protein, can be included. In FIG. 2A, this transcriptional repression domain is a Krueppel-associated box (KRAB) sequence, fused in frame to the C-terminus of TetR (see, e.g., Szulc et al., "A versatile tool for conditional gene expression and knockdown," *Nature Methods* 3:109-116 (2006)). The use of a KRAB sequence, or other transcriptional repression domain, improves the repressive activity of the TetR when binding to $TetO_2$, thereby minimizing the amount of leakage or basal gene expression prior to derepression (i.e., prior to the addition of Dox). FIG. 2B and FIG. 12A shows an exemplary nucleic acid molecule that lacks the KRAB sequence.

Figure 12B:
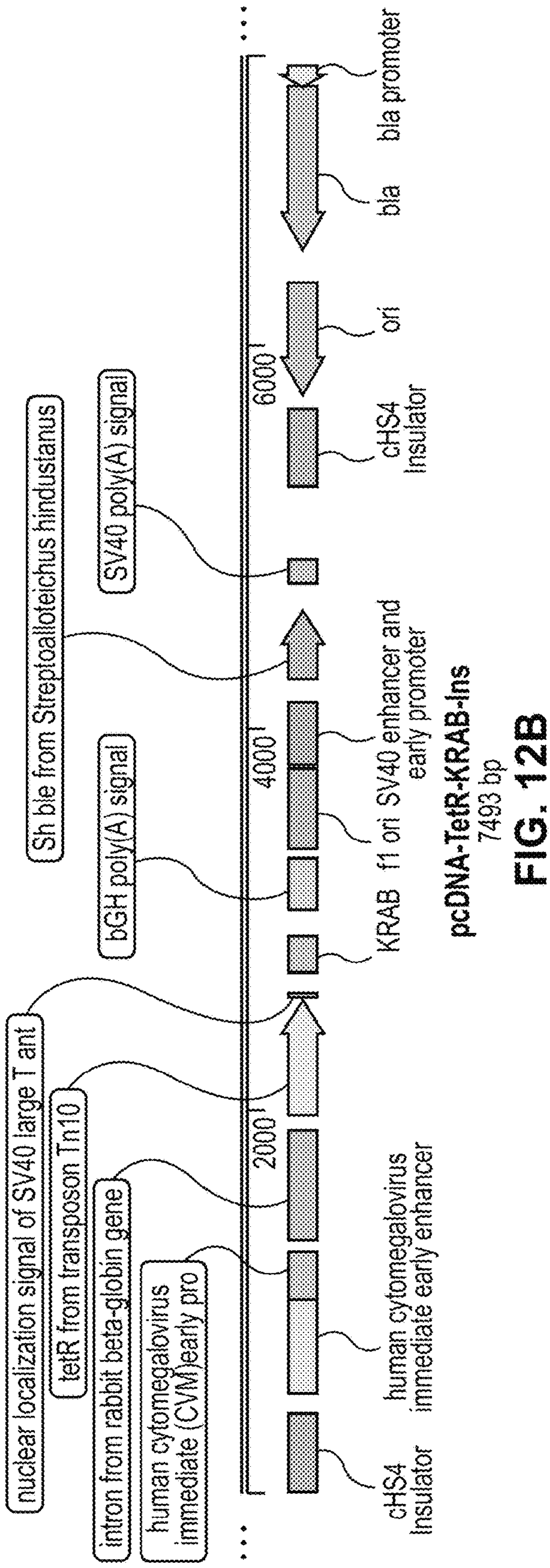

As shown in FIG. 12A, in exemplary embodiments, a nucleic acid encoding the tetracycline repressor protein, can be included or stably expressed within a mammalian cell. In FIG. 2A and FIG. 12B, this transcriptional repression domain is a Krueppel-associated box (KRAB) sequence, fused in frame to the C-terminus of TetR (see, e.g., Szulc et al., "A versatile tool for conditional gene expression and knockdown," *Nature Methods* 3:109-116 (2006)). The use of a KRAB sequence, or other transcriptional repression domain, improves the repressive activity of the TetR when binding to $TetO_2$, thereby minimizing the amount of leakage or basal gene expression prior to derepression (i.e., prior to the addition of Dox). FIG. 2B and FIG. 12A show an exemplary nucleic acid molecule that lacks the KRAB sequence.

In embodiments, the AAV gene that is encoded by the nucleic acid molecule comprises Rep and Cap genes. Other AAV genes that can be encoded by the nucleic acid molecules include any gene from any AAV serotype. In some embodiments, the AAV gene is Rep78, Rep68, Rep52, Rep40, VP1, VP2, VP3, or a combination thereof. In some embodiments, the AAV gene is from adeno-associated virus type 2. In some embodiments, the AAV gene is from the adeno-associated virus Anc80.

As referred to herein, the term "Rep" gene refers to the art-recognized region of the AAV genome which encodes the replication proteins of the virus which are collectively required for replicating the viral genome, or functional homologues thereof such as the human herpesvirus 6 (HHV-6) rep gene which is also known to mediate AAV-2 DNA replication. Thus, the rep coding region can include the genes encoding for AAV Rep78 and Rep68 (the "long forms of Rep"), and Rep52 and Rep40 (the "short forms of Rep"), or functional homologues thereof. The rep coding region, as used herein, can be derived from any viral serotype, such as the AAV serotypes described herein. The region need not include all wild-type genes but may be altered, (e.g., by insertion, deletion or substitution of nucleotides), so long as the rep genes present provide for sufficient integration functions when expressed in a suitable target cell. See, e.g. Muzyczka, N., *Current Topics in Microbiol. and Immunol.* 158:97-129 (1992); and Kotin, R. M., *Human Gene Therapy* 5:793-801 (1994).

As referred to herein, the term "Cap" gene refers to the art-recognized region of the AAV genome which encodes the capsid proteins of the virus. Illustrative (non-limiting) examples of these capsid proteins are the AAV capsid proteins VP1, VP2, and VP3. Cap genes used in this disclosure can come from any AAV serotype or a combination of AAV serotypes.

Figures 4A, 4B, 4C:
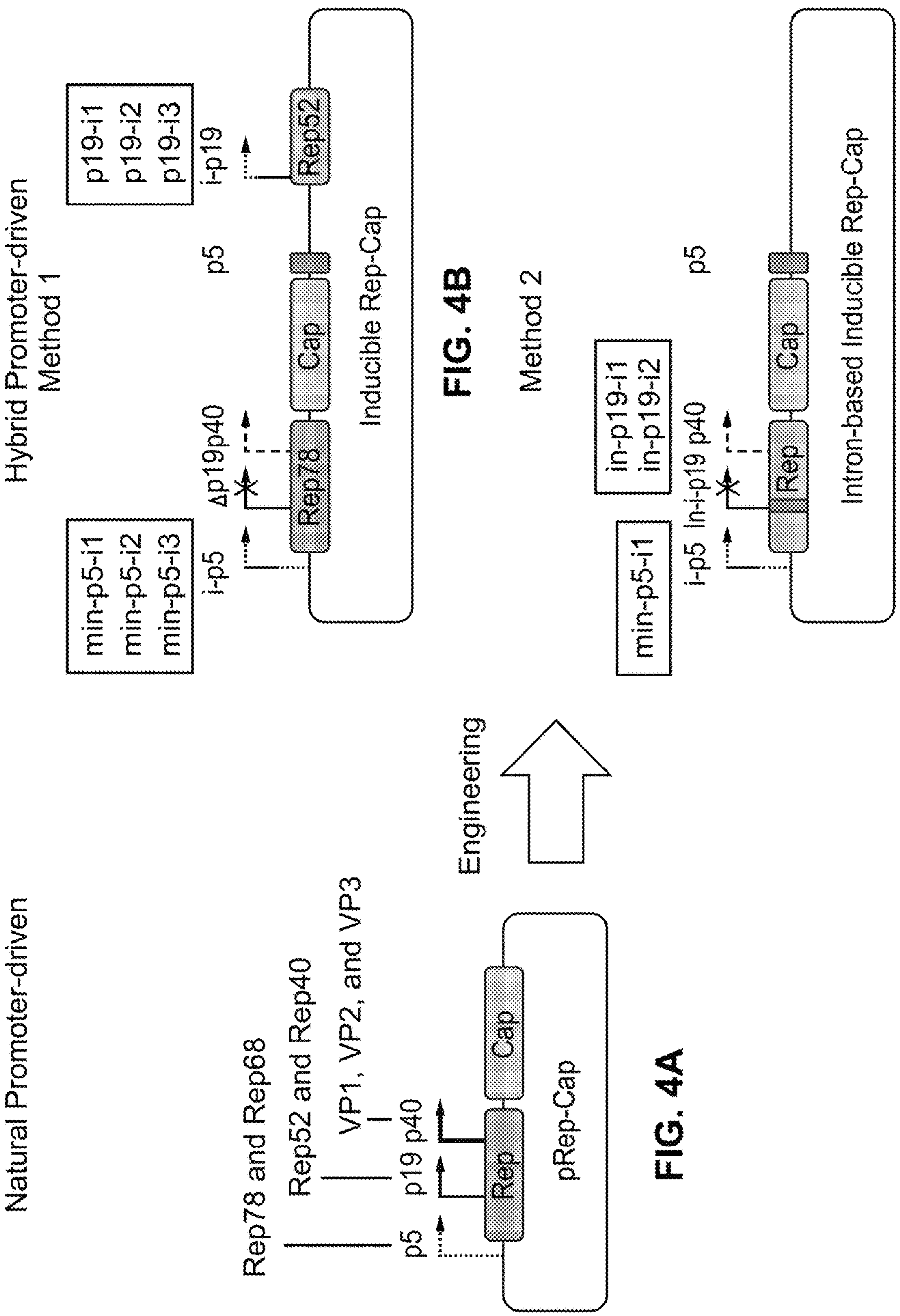
FIGS. 4A-4C shows schematics of derepressible constructs for expression of AAV genes in accordance with embodiments hereof.

FIG. 4A shows the natural location and promoter drivers of Rep and Cap genes. As known in the art, for successful production of AAV, the ratio of Rep78 and Rep52 genes must be maintained at optimum levels. For example, as discussed in Li et al., "Role for Highly Regulated rep Gene Expression in Adeno-Associated Virus Vector Production," *Journal of Virology* 71:5236-5243 (1997) (the disclosure of which is incorporated by reference herein in its entirety), control of the amount of Rep78 production can interference with DNA replication. In addition, Rep78 can be toxic if overly produced in mammalian cells. See, e.g., Clark et al., "Cell Lines for the Production of Recombinant Adeno-Associated Virus," *Human Gene Therapy* 6:1329-1341 (1995), the disclosure of which is incorporated by reference herein in its entirety, discussing that elevate rep protein levels can be associated with cytotoxicity. Also, the location of the promoter for Rep52 expression (p19) is located within the coding region for Rep78. As described herein, various modifications have been made to the natural locations of the Rep genes and promoters to overcome these challenges.

In exemplary embodiments, the mammalian cell can include a nucleic acid encoding a Rep78 gene under control of the second derepressible promoter and a Rep52 gene under control of a third derepressible promoter. As shown in FIG. 4B, one way to achieve this arrangement is to remove the Rep52 gene from within the Rep78 gene, and place it downstream of the Rep78 and Cap genes. The Rep78 gene can be under the control of a derepressible promoter (p5), that includes the $TetO_2$ sequences. In such embodiments, the natural p19 promoter within Rep78 is modified or mutated to be silenced. The removed Rep52 gene is also placed under the control of a derepressible promoter (p19) that includes $TetO_2$ sequences.

Figure 5:
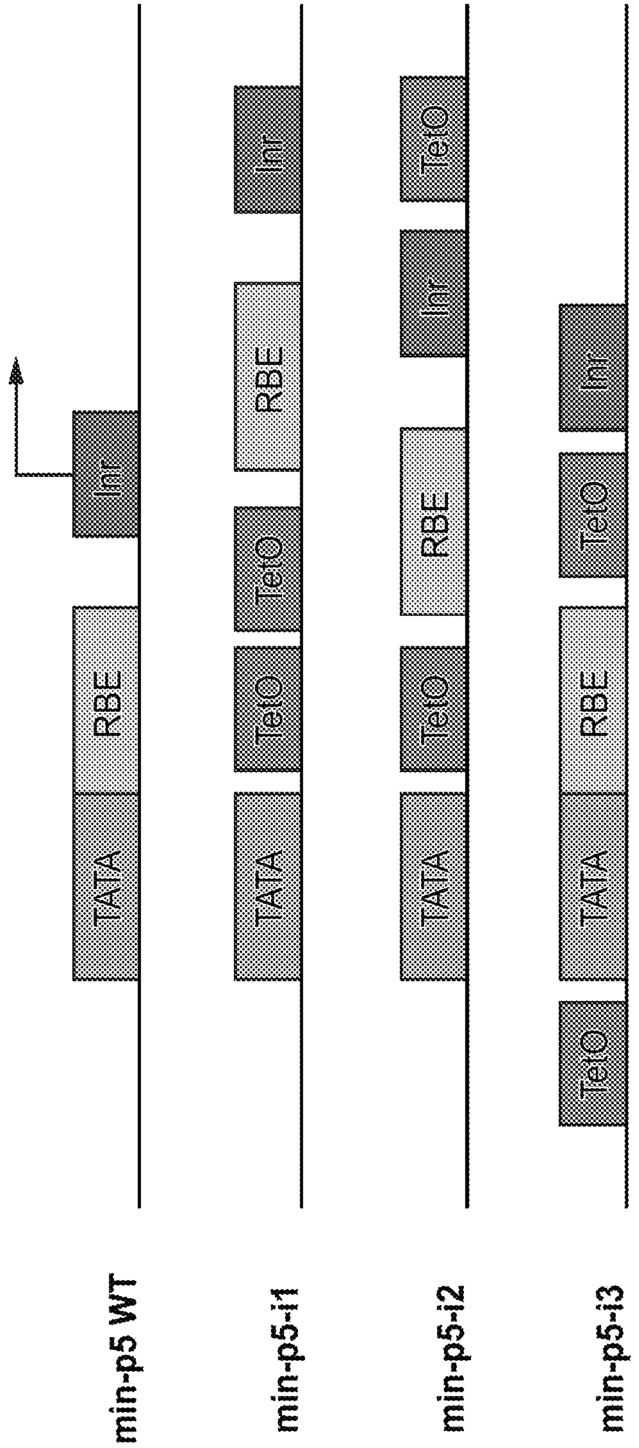
FIG. 5 shows exemplary derepressible p5 promoters in accordance with embodiments hereof.
Figure 6:
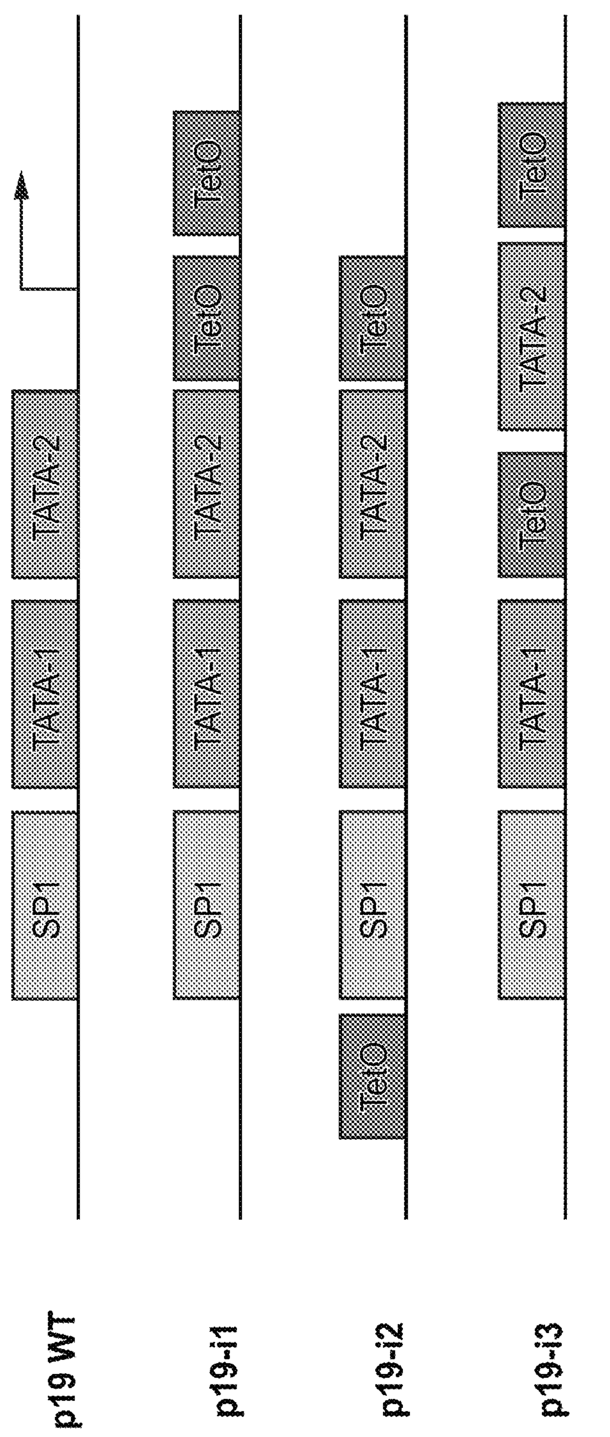
FIG. 6 shows exemplary derepressible p19 promoters in accordance with embodiments hereof.

FIG. 5 shows three potential locations for each of the TetO sequences, relative to the TATA box, rep-binding element (RBE) and initiator element (INR), for modification to the p5 promotor of Rep78. The wild-type p5 promotor is also illustrated schematically. FIG. 6 shows three potential locations for each of the TetO sequences, relative to the TATA boxes and the Sp1 transcription factor, of the p19 promoter for Rep52. The wild-type p19 promotor is also illustrated schematically. Additional locations of the TetO sequences are also encompassed herein and can readily be envisioned by those of ordinary skill in the art.

In still further embodiments, the Rep78 gene can be under control of a derepressible promoter, and the Rep52 gene can be under control of a derepressible promoter that is contained within an artificial intron. Such an embodiment is represented schematically in FIG. 4C. As illustrated, a derepressible p5 promoter (e.g., including $TetO_2$ sequences as described herein) is placed upstream of a Rep78 gene. A derepressible p19 promoter (e.g., including $TetO_2$ sequences) contained within an intron (designated In-i-p19), controls the expression of Rep52. A schematic of this embodiment is provided in FIG. 7A, where the two tet operator sequences are illustrated within a chimeric intron. This chimeric intron can be inserted at various locations relative to the components of the p19 promoter. For example, as shown in FIG. 7B, the intron sequence is suitably placed downstream of the TATA-2 of the p19 promoter. Spacing can be, for example, between about 1 and 25 base pairs downstream from the TATA-2 sequence.

As described herein, in exemplary embodiments, the Cap gene that is encoded by the nucleic acid molecules is suitably under the control of a native promoter. That is, the Cap gene does not necessarily have to be under the control of a derepressible promoter, though a derepressible promoter can be used if desired. In suitable embodiments, the Cap gene is under the control of a p40 promoter.

In exemplary embodiments, the nucleic acid molecules include two inverted terminal repeat (ITR) sequences. As known in the art, these ITR sequences (i.e., AAV2 ITR) are single stranded sequence of nucleotides, followed downstream by its reverse compliment. ITR sequences represent the minimal sequence required for replication, rescue, packaging and integration of the AAV genome. Suitably, these ITR sequences flank a gene of interest. Thus, in embodiments, the nucleic acid molecules further encode a gene of interest. This gene of interest can be, for example, a reporter gene, a selection gene, or a gene of therapeutic interest, for example.

Figure 10A:
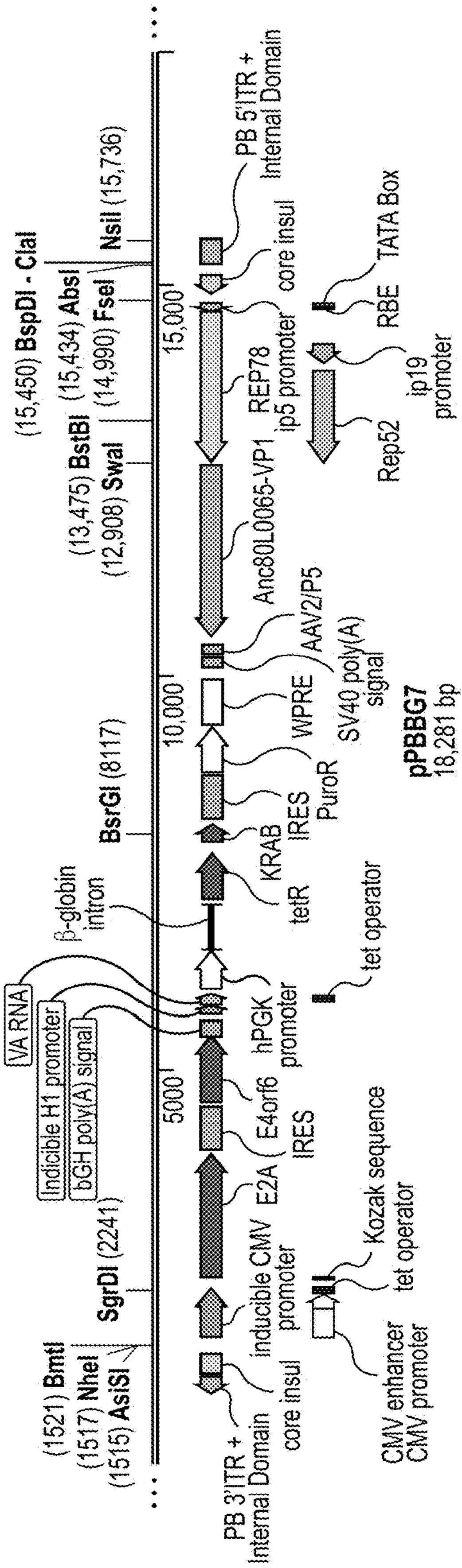
FIGS. 10A-10D show exemplary nucleic acid constructs encoding helper, AAV and VA genes, in accordance with embodiments hereof.
Figure 10B:
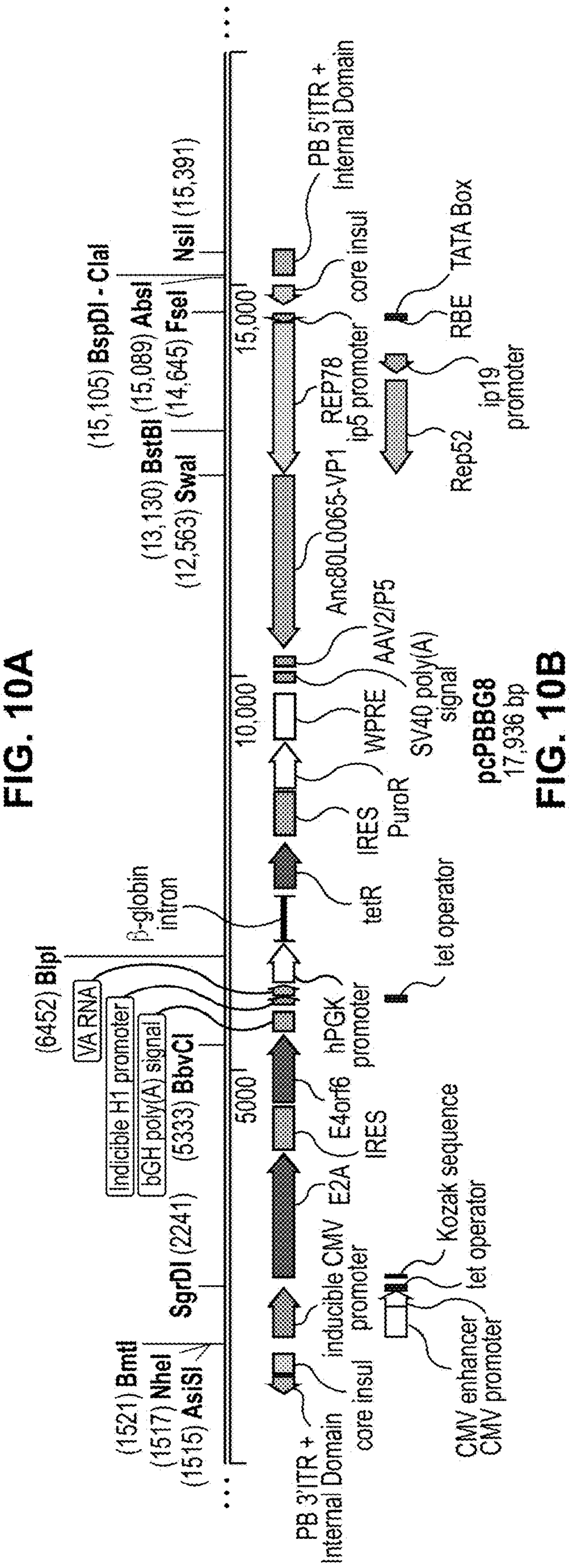
Figure 10C:
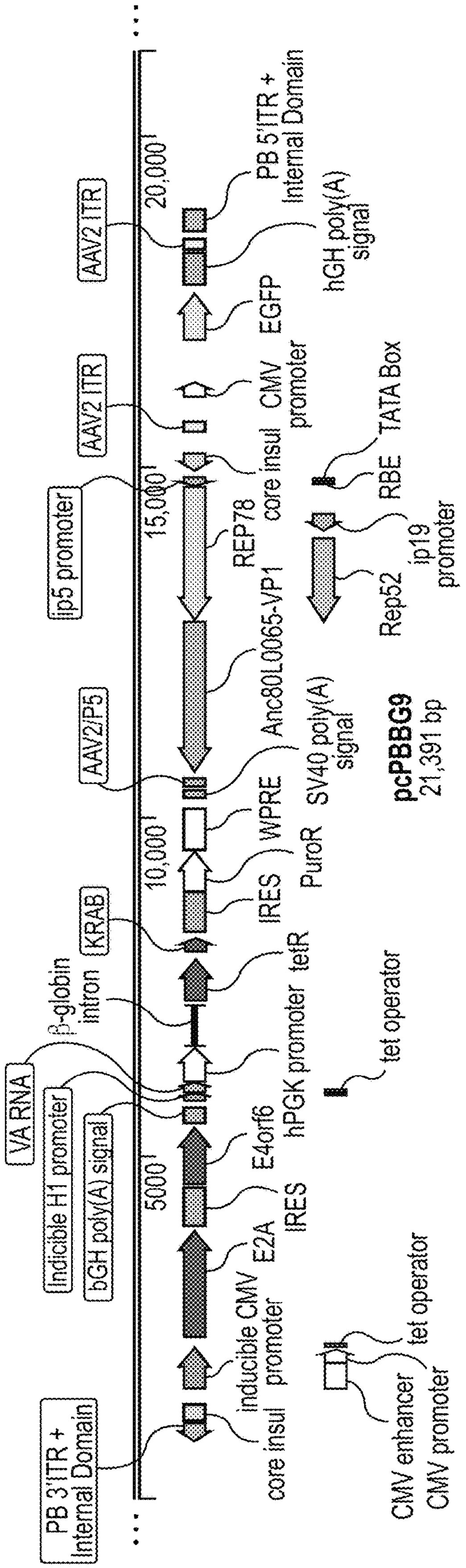

For example, as illustrated in FIG. 10C, a gene of interest, such as the gene encoding green fluorescent protein (EGFP) is flanked by two ITR sequences.

A "gene" refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

As referred to herein, the term "gene of interest" or "GOT" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

As referred to herein, a "reporter gene" is a gene whose expression confers a phenotype upon a cell that can be easily identified and measured. In some embodiments, the reporter gene comprises a fluorescent protein gene. In some embodiments, the reporter gene comprises a selection gene.

As referred to herein, the term "selection gene" refers to the use of a gene which encodes an enzymatic activity that confers the ability to grow in medium lacking what would otherwise be an essential nutrient; in addition, a selection gene may confer resistance to an antibiotic or drug upon the cell in which the selection gene is expressed. A selection gene may be used to confer a particular phenotype upon a host cell. When a host cell must express a selection gene to grow in selective medium, the gene is said to be a positive selection gene. A selection gene can also be used to select against host cells containing a particular gene; a selection gene used in this manner is referred to as a negative selection gene.

As referred to herein, the term "gene of therapeutic interest" refers to any functionally relevant nucleotide sequence. Thus, the gene of therapeutic interest of the present disclosure can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

In some embodiments, the mammalian cells provided herein are substantially free of helper virus. As referred to herein, a "helper virus" is any non-AAV virus that is added to enable the replication and packaging of adeno-associated virus. Representative (non-limiting) examples of helper viruses are adenovirus and herpes virus. In some embodiments, the term substantially free of helper virus refers to a cell that has fewer than 100, fewer than 10, or fewer than 1 helper virus per cell. In some embodiments, the term substantially free of helper virus refers to a cell in which no helper viruses are present or to a population of cells in which no helper viruses are present using detection methods known to those skilled in the art. In some embodiments, no wild-type helper virus is in the cell. In some embodiments, the term wild-type virus refers to any complete-non-AAV virus that can replicate in the cell independently of any other virus.

The AAV producer cells described herein provide a long-term and cost-effective solution for large scale AAV manufacturing. As constitutive expression of either helper or Rep proteins can be cytotoxic, the strategies described herein allow for control of their expression by engineered, derepressible promoters.

In still further embodiments, provided herein is a mammalian cell for producing an adeno-associated virus (AAV), comprising, in a single nucleic acid molecule, sequences encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters. In such embodiments, this single nucleic acid molecule includes all of the various sequences, along with other required elements, to enable the production of an AAV within the cell.

FIGS. 10A and 10B show exemplary nucleic acid molecules including these various sequences that can be utilized in mammalian cells to produce AAVs.

As described herein, suitably the mammalian cells are mammalian cell cultures, and in embodiments, can be suspension cultures. As described herein, the use of suspension cell cultures allows for increased scalability and production of AAV.

As described herein and as shown in FIGS. 1, 2A-2B, and 10A-10B, suitably the single nucleic acid molecule includes an internal ribosome entry site (IRES) element between the E2A and E4Orf6 genes.

Various constructs are described herein for encoding the Rep and Cap genes, including Rep78 and Rep52 genes. In embodiments, a Rep78 gene is under control of the second derepressible promoter and a Rep52 gene is under control of a fourth derepressible promoter (e.g., as shown in FIG. 4B, the Rep52 gene is separate from the Rep78 gene). In additional embodiments, for example as described herein with reference to FIGS. 4C and 7A-7B, a Rep78 gene can be placed under control of the second derepressible promoter and a Rep52 gene can be placed under control of a fourth derepressible promoter contained within an artificial intron. Suitably, the Cap gene is under control of a native promoter.

Various derepressible promoters are described herein, and in embodiments, the derepressible promoters comprise a functional promoter and two tetracycline operator sequences ($TetO_2$). In embodiments, the functional promoter of the first derepressible promoter (i.e., controlling the expression of the adenovirus helper gene comprising E2A and E4Orf6 genes) is a cytomegalovirus (CMV) promoter.

As described herein, in embodiments and as illustrated in FIGS. 1, 2A-2B, and 10A-10D, suitably the repressor element of the derepressible promoter is under control of a constitutive promoter, such that it is produced at all times to limit expression of other genes under the control of the derepressible promoters. Suitably, the repressor element that is encoded is a tetracycline repressor protein, for binding to $TetO_2$ sequences to act as the derepressible promoter. In embodiments, for example as shown in FIG. 2A, 10A and 10C, a nucleic acid encoding a transcriptional repression domain (e.g., a KRAB sequence) is included in frame with the nucleic acid encoding the tetracycline repressor protein. This transcriptional repression domain provides for improved repressive activity of the TetR when binding to $TetO_2$, thereby minimizing the amount of leakage or basal gene expression prior to derepression.

Exemplary mammalian cells that can be used in the embodiments and methods described herein are described throughout, and include for example, Chinese hamster ovary (CHO) cells, as well as human cells, including human embryonic kidney (HEK, such as HEK293) cells.

Figure 10D:
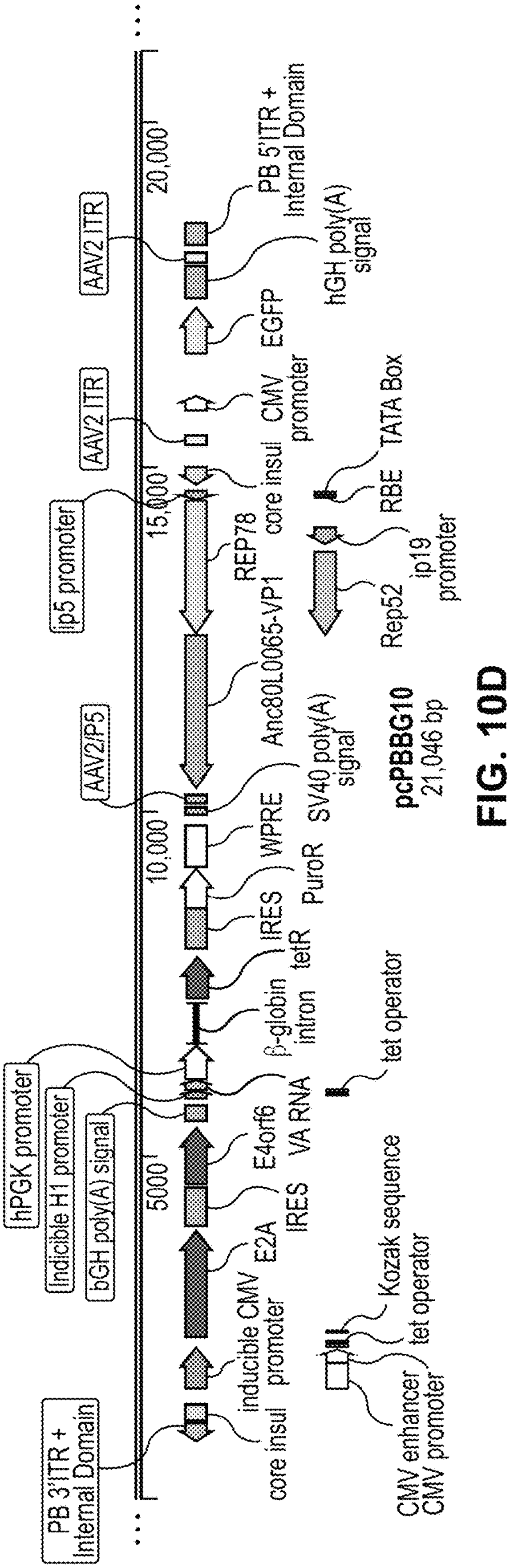

As described herein, suitably the mammalian cells further include a nucleic acid molecule encoding a gene of interest (GOI). As shown in FIGS. 10C-10D, suitably the GOI is included between two ITR sequences.

Also provided herein is an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

As used herein an "isolated nucleic acid molecule" includes vectors and plasmids that can contain the isolated nucleic acid molecule, as well as similar structures where the isolated nucleic acid molecule can be manipulated, stored, shipped, and ultimately utilized in various cell transfection systems. The isolated nucleic acid molecules described herein can be used for production of AAVs as described herein, but can also be utilized in various non-AAV producing cell lines (including transient transfection systems). The isolated nucleic acid molecules described herein suitably further include various additional elements and sequences as required to allow for use in the cellular systems, including mammalian cells, described herein.

For example, as shown in FIGS. 10A-10B, two plasmid constructs are shown. As indicated, in embodiments, an internal ribosome entry site (IRES) element can be included between the E2A and E4Orf6 genes. As described herein with reference to FIG. 4B in embodiments, a Rep78 gene is under control of the second derepressible promoter and a Rep52 gene is under control of a fourth derepressible promoter (i.e., separated from the Rep52 gene).

In further embodiments, as shown with reference to FIGS. 10A-10B, a Rep78 gene is under control of a derepressible promoter (ip5 promoter as shown, and various iterations described in FIG. 5) and a Rep52 gene is under control of a fourth derepressible promoter contained within an artificial intron, illustrated as ip19, and described with reference to FIGS. 7A-7B. The isolated nucleic acid further suitably includes the Cap gene under control of a native promoter (i.e., p40).

As described herein, various derepressible promoters can be included in the isolated nucleic acid molecules, and suitably include a functional promoter and two tetracycline operator sequences ($TetO_2$). As shown in FIGS. 10A and 10B, with regard to the helper genes E2 and E4, suitably this functional promoter is a CMV promoter, which includes the $TetO_2$ sequences. The derepressible promoter for use with the viral-associated, non-coding RNA suitably includes an H1 promoter, as well as the $TetO_2$ sequences.

As described herein and as shown in FIGS. 10A and 10B, the repressor element (e.g., a tetracycline repressor protein), is suitably under the control of a constitutive promoter, for example, a hPGK promoter. As shown in FIGS. 10A and 12B, the isolated nucleic acid molecules can further include a nucleic acid encoding a transcriptional repression domain (e.g., a KRAB sequence) in frame with the nucleic acid encoding the tetracycline repressor protein. As shown in FIGS. 10C-10D and FIG. 11B, the isolated nucleic acid molecules can further include a gene of interest (GOI, e.g., a GFP), suitably between the two ITR sequences.

As described herein and as shown in FIGS. 12A-12B, the repressor element is suitably flanked by an insulator, for example, a chicken hypersensitive site-4 (cHS4) sequence.

In embodiments, a nucleic acid encoding a transcriptional repression domain (such as KRAB) is included in frame with the nucleic acid encoding the tetracycline repressor protein (e.g., TetR-KRAB).

Additional genetic and sequence elements for inclusion in the isolated nucleic acid molecules described herein are known in the art and can be found illustrated schematically in FIGS. 10A-10D and FIGS. 11A-11E.

The terms "sequence identity" or "% identity" in the context of nucleic acid sequences described herein refers to the percentage of residues in the compared sequences that are the same when the sequences are aligned over a specified comparison window. A comparison window can be a segment of at least 10 to over 1000 residues in which the sequences can be aligned and compared. Methods of alignment for determination of sequence identity are well-known can be performed using publicly available databases such as BLAST (blast.ncbi.nlm.nih.gov/Blast. CGI.).

In some embodiments, nucleic acid molecules have at least about 70%, at least about 75%, at least about 80%, at least about 85%, at least about 90%, at least about 95%, at least about 97%, at least about 98%, at least about 99% or about 100% sequence identity with a reference nucleic acid molecule, respectively (or a fragment of the reference polypeptide or nucleic acid molecule). In certain embodiments of the disclosure, polypeptides or nucleic acid molecules have at least 70%, at least 75%, at least 80%, at least 85%, at least 90%, at least 95%, at least 97%, at least 98%, or at least 99% or 100% sequence identity with a reference nucleic acid molecule, respectively (or a fragment of the reference nucleic acid molecule). In some embodiments, nucleic acid molecules have about 90%, 91%, 92%, 93%, 94%, 95%, 96%, 97%, 98%, 99%, 99.5% sequence identity with a reference nucleic acid molecule, respectively.

A "vector" or "expression vector" is a replicon, such as a plasmid, phage, virus, or cosmid, to which a nucleic acid molecule described herein may be attached to bring about the replication and/or expression of the attached nucleic acid molecule in a cell. "Vector" includes episomal (e.g., plasmids) and non-episomal vectors. The term "vector" includes both viral and nonviral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters.

Also provided herein is a method of producing an adeno-associated virus (AAV) in a mammalian cell. Suitably, the methods described herein include transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., *Virology,* 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., *Gene* 13:197 (1981). Such techniques can be used to introduce one or more exogenous DNA moieties, such as an AAV vector cassette, AAV helper constructs, and other nucleic acid molecules, into suitable host cells.

Various methods of transfecting the mammalian cells with the isolated nucleic acid molecules described herein (i.e., vectors), are known in the art and include various chemical and physical methods, for example, electroporation, cell injection, calcium phosphate exposure, liposome or polymer-based carrier systems, etc.

In exemplary embodiments, a vectors such as the PIGGYBAC™ transposon can be used for the stable integration of these nucleic acid molecules, which allows one-step insertion of large nucleic acid sequences in multiple copies randomly in a cell genome. The system consists of a PIGGYBAC™ Vector and the Super PIGGYBAC™ Transposase which recognizes transposon-specific inverted terminal repeats (ITRs) and efficiently integrates the ITRs and intervening DNA into the genome at TTAA sites. The Super PIGGYBAC™ Transposase is delivered to the cell via the Super PIGGYBAC™ Transposase Expression Vector, which is co-transfected with one or more PIGGYBAC™ Vectors.

The methods further include treating the mammalian cell with a binding partner of the repressor element. As described herein, in the presence of a repressor element, the functional promoters of the derepressible promoters controlling the transcription of the various genes encoded by the nucleic acid molecules, are repressed. That is, the genes are not actively being transcribed, and are instead awaiting derepression. As noted herein, the repressor element of the derepressible promoters is suitably under control of constitutive promoter, such that the repressor element is being produced soon after transfection of the nucleic acid molecule into the mammalian cell. Upon treatment with the binding partner of the repressor element, the repressor element binds to the binding partner, changes conformation, and no longer represses the derepressible promoter. This results in the activating of the first, second and third (and additional as needed) derepressible promoters (i.e., the functional promoters of the derepressible promoters) within the mammalian cell.

Following the activation, the various elements are transcribed and translated within the mammalian cell, resulting in the production of the AAV. The AAV is then harvested using methods known in the art.

While the methods described herein can be utilized in any mammalian cell, including a mammalian cell culture, suitably the mammalian cell culture is a suspension culture, including a human cell such as an HEK suspension cell culture.

As described throughout the nucleic acid molecules can further include an internal ribosome entry site (IRES) element between the E2A and E4Orf6 genes. Exemplary constructs related to the Rep78 and Rep 52 genes are described herein, including where a Rep78 gene is under control of the second derepressible promoter and a Rep52 gene is under control of a fourth derepressible promoter. In additional embodiments of the methods, a Rep78 gene is under control of the second derepressible promoter and a Rep52 gene is under control of a fourth derepressible promoter contained within an artificial intron.

As described herein, the use of an artificial intron allows for removal of the fourth derepressible promoter following activating the derepressible promoters and prior to the producing the AAV. As described herein, the derepressible promoter within the intron ensures the repression of Rep52 gene expression before activation, while still allowing for the expression of the Rep78 protein following the removal of the intron during mRNA splicing. In exemplary embodiments of the methods, the Cap gene is under control of a native promoter, such as p40.

In embodiments, the functional promoter of the derepressible promoter controlling the expression of the helper genes is a cytomegalovirus (CMV) promoter. Suitably, the repressor element that is encoded in the methods described herein is a tetracycline repressor protein, and suitably the derepressible promoters comprise a functional promoter and two tetracycline operator sequences (TetO2). In embodiments, the repressor element is under control of a constitutive promoter, such as hPGK, for example when the repressor element that is encoded is a tetracycline repressor protein.

As described herein, in embodiments utilizing the TetR and/or TetR-KRAB repressor element, treating the cells with doxycycline changes the conformation of the TetR and activates the transcription of the various genes.

Various mammalian cells can be utilized in the methods described herein, including human cells such as human embryonic kidney (HEK) cells, or other mammalian cells including Chinese hamster ovary (CHO) cells.

As described throughout, in embodiments, the AAV comprises a nucleic acid molecule encoding a gene of interest. This GOI can be a reporter gene, a selection gene, or any other gene of interest, including a gene of therapeutic interest.

The methods of producing the AAVs can be used in a continuous manufacturing system. In exemplary embodiments, the use of a suspension cell culture allows for the production of large volumes of AAV, with high productivity and prolonged culture conditions to allow for multiple harvests of AAV for each batch of starting cells.

Production methods can utilize any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

In further embodiments, provided herein is a method of treatment with an adeno-associated virus (AAV) comprising: transfecting the mammalian cell with an isolated nucleic acid molecule encoding: an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, harvesting the AAV, and administering the AAV to a mammalian patient.

Suitably, the methods are used to treat a human patient with a gene of interest, including a gene of therapeutic interest. Administration to a human patient can include, for example, inhalation, injection, or intravenous administration, as well as other administration methods known in the art.

The methods of producing the AAV and the use of various derepressible promoters are described herein.

In further embodiments, a method of producing an adeno-associated virus (AAV) is provided and includes transfecting a mammalian cell stably expressing one or more nucleic acids encoding TetR and/or TetR-KRAB with: a first nucleic acid encoding an adenovirus helper gene comprising an E2A gene, a E4Orf gene and a viral-associated non-coding RNA, under control of a first derepressible promoter, a second nucleic acid encoding an AAV gene comprising Rep and Cap genes under control of a second derepressible promoter, optionally, a third nucleic acid encoding a gene of interest under control of a third derepressible promoter; treating the mammalian cell with a binding partner of the TetR; activating the first, second and third derepressible promoters; producing the AAV; and harvesting the AAV.

As described herein, suitably the mammalian cell is a mammalian cell culture, including a suspension culture As described herein, suitably the mammalian cell is a Chinese hamster ovary (CHO) cell or a human cell including a human embryonic kidney (HEK) cell.

As described herein, using 2 or 3 different nucleic acids or transposons to transfect mammalian cells offers advantages over combining the nucleic acids in one plasmid, including the ability to optimize the ratio of separate AAV-producing and packaging components and to exert temporal control over expression of each transposon.

As described herein, suitably the nucleic acid encoding the E2A and E4Orf genes further comprises an internal ribosome entry site (IRES) element between the E2A and E4Orf genes.

As described herein, suitably the derepressible promoters comprise a functional promoter and two tetracycline operator sequences ($TetO_2$).

As described herein, suitably the functional promoter of the first derepressible promoter is a cytomegalovirus (CMV) promoter.

In some embodiments, the mammalian cell used to produce adeno-associated virus (AAV) is stably expressing one or more nucleic acids encoding TetR and/or TetR-KRAB under control of a constitutive promoter.

As described herein, stable expression of a TetR and/or TetR-KRAB in a mammalian cell (prior to insertion of nucleic acids carrying the components of the virus, suitably via transposons) maximizes the repression of potentially cytotoxic AAV genes introduced by transfection and confers increased temporal control over the derepressible promoter elements.

In some embodiments, a KRAB repressor domain is fused in frame with the TetR.

As described herein, fusing a KRAB repressor domain in frame with the TetR ensures that "leaky" expression of the potentially cytotoxic AAV-packaging nucleic acids is less likely to occur. A KRAB repressor domain fused in frame with the TetR repressor domain provides an additional mechanism to accomplish high levels of repression of derepressible promoters.

In some embodiments, the mammalian cell produces a sufficient amounts of TetR. As used herein, a "sufficient" of TetR is defined as the level of amount and/or activity of a repressor (e.g., TetR) to stop expression and/or activity of a repressible and/or derepressible element (i.e., prior to addition of doxycycline).

As described herein, producing sufficient amounts of TetR is necessary for repression of the derepressible promoters under normal conditions (e.g., before addition of doxycycline). If sufficient amounts of TetR are not produced by the mammalian cell, the cell may prematurely transcribe and translate potentially cytotoxic AAV-packaging nucleic acids.

In further embodiments, the mammalian cell further comprises stable expression of one or more nucleic acids encoding chicken hypersensitive site-4 (cHS4) flanking the TetR and/or TetR-KRAB repressor sequences. As described herein, expression of cHS4 sequences flanking the TetR and/or TetR-KRAB repressor sequences prevent the silencing of TetR expression and further improve the stability of integrated repressors in the mammalian cell genome.

In further embodiments, the treating comprises treating with doxycycline to remove repression of derepressible promoters.

In further embodiments, each of the first, second and third nucleic acids are flanked by transposon-specific inverted terminal repeats (ITRs).

In further embodiments, a method for producing an adeno-associated virus (AAV) comprises stably transfecting a mammalian cell with: a nucleic acid encoding a TetR and/or TetR-KRAB repressor, chicken hypersensitive site-4 (cHS4) sequences flanking the TetR and/or TetR-KRAB repressor, and a selection gene; transfecting the stably transfected mammalian cell with a first nucleic acid encoding an adenovirus helper gene comprising an E2A gene, a E4Orf gene and a viral-associated non-coding RNA, under control of a first derepressible promoter, a second nucleic acid encoding an AAV gene comprising Rep and Cap genes under control of a second derepressible promoter, and optionally, a third nucleic acid encoding a gene of interest under control of a third derepressible promoter; treating the mammalian cell with a binding partner of the TetR; activating the first, second and third derepressible promoters; producing the AAV; and harvesting the AAV.

In some embodiments, the mammalian cell further comprises a selection gene, such asa zeocin resistance gene. Additional selection genes include other antibiotic resistance genes, such as kanamycin and geneticin resistance genes. As described herein, expression of a zeocin resistance gene allows for efficient selection of correctly integrated repressors in the mammalian cell genome.

Additional Exemplary Embodiments

Embodiment 1 is a mammalian cell for producing an adeno-associated virus (AAV), comprising a nucleic acid molecule encoding a viral helper gene under control of a first derepressible promoter, a nucleic acid molecule encoding an AAV gene under control of a second derepressible promoter, and a nucleic acid molecule encoding a repressor element of the first and the second derepressible promoters.

Embodiment 2 includes the mammalian cell of embodiment 1, wherein the mammalian cell is a mammalian cell culture.

Embodiment 3 includes the mammalian cell of embodiment 2, wherein the mammalian cell culture is a suspension culture.

Embodiment 4 includes the mammalian cell of any one of embodiments 1-3, wherein the viral helper gene is an adenovirus helper gene.

Embodiment 5 includes the mammalian cell of embodiment 4, wherein the adenovirus helper gene comprises E2A and E4Orf6 genes.

Embodiment 6 includes the mammalian cell of embodiment 5, further comprising an internal ribosome entry site (IRES) element between the E2A and E4Orf6 genes.

Embodiment 7 includes the mammalian cell of any one of embodiments 1-6, wherein the AAV gene comprises Rep and Cap genes.

Embodiment 8 includes the mammalian cell of embodiment 7, wherein a Rep78 gene is under control of the second derepressible promoter and a Rep52 gene is under control of a third derepressible promoter.

Embodiment 9 includes the mammalian cell of embodiment 7, wherein a Rep78 gene is under control of the second derepressible promoter and a Rep52 gene is under control of a third derepressible promoter contained within an artificial intron.

Embodiment 10 includes the mammalian cell of any one of embodiments 8 or 9, wherein the Cap gene is under control of a native promoter.

Embodiment 11 includes the mammalian cell of any one of embodiments 1-10, wherein each of the derepressible promoters comprise a functional promoter and two tetracycline operator sequences ($TetO_2$).

Embodiment 12 includes the mammalian cell of embodiment 11, wherein the functional promoter of the first derepressible promoter is a cytomegalovirus (CMV) promoter.

Embodiment 13 includes the mammalian cell of any one of embodiments 1-12, wherein the repressor element is under control of a constitutive promoter.

Embodiment 14 includes the mammalian cell of any one of embodiments 1-13, wherein the repressor element is a tetracycline repressor protein.

Embodiment 15 includes the mammalian cell of embodiment 14, further comprising a nucleic acid encoding a transcriptional repression domain in frame with the nucleic acid encoding the tetracycline repressor protein.

Embodiment 16 includes the mammalian cell of any one of embodiments 1-15, wherein the mammalian cell is a Chinese hamster ovary (CHO) cell.

Embodiment 17 includes the mammalian cell of any one of embodiments 1-15, wherein the mammalian cell is a human cell.

Embodiment 18 includes the mammalian cell of embodiment 17, wherein the human cell is a human embryonic kidney (HEK) cell.

Embodiment 19 includes the mammalian cell of any one of embodiments 1-18, further comprising a nucleic acid molecule including two inverted terminal repeat (ITR) sequences.

Embodiment 20 includes the mammalian cell of any one of embodiments 1-19, further comprising a nucleic acid molecule encoding a gene of interest.

Embodiment 21 includes the mammalian cell of any one of embodiments 1-20, further comprising a nucleic acid encoding a viral-associated, non-coding RNA under control of a fourth derepressible promoter.

Embodiment 22 is a mammalian cell for producing an adeno-associated virus (AAV), comprising a nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

Embodiment 23 includes mammalian cell of embodiment 22, wherein the mammalian cell is a mammalian cell culture.

Embodiment 24 includes the mammalian cell of embodiment 23, wherein the mammalian cell culture is a suspension culture.

Embodiment 25 includes the mammalian cell of any one of embodiments 22-24, further comprising an internal ribosome entry site (IRES) element between the E2A and E4Orf6 genes.

Embodiment 26 includes the mammalian cell of any one of embodiments 22-25, wherein a Rep78 gene is under control of the second derepressible promoter and a Rep52 gene is under control of a fourth derepressible promoter.

Embodiment 27 includes the mammalian cell of any one of embodiments 22-25, wherein a Rep78 gene is under control of the second derepressible promoter and a Rep52 gene is under control of a fourth derepressible promoter contained within an artificial intron.

Embodiment 28 includes the mammalian cell of any one of embodiments 26 or 27, wherein the Cap gene is under control of a native promoter.

Embodiment 29 includes the mammalian cell of any one of embodiments 22-28, wherein each of the derepressible promoters comprise a functional promoter and two tetracycline operator sequences (TetO2).

Embodiment 30 includes the mammalian cell of embodiment 29, wherein the functional promoter of the first derepressible promoter is a cytomegalovirus (CMV) promoter.

Embodiment 31 includes the mammalian cell of any one of embodiments 22-30, wherein the repressor element is under control of a constitutive promoter.

Embodiment 32 includes the mammalian cell of any one of embodiments 22-31, wherein the repressor element is a tetracycline repressor protein.

Embodiment 33 includes the mammalian cell of embodiment 25, further comprising a nucleic acid encoding a transcriptional repression domain in frame with the nucleic acid encoding the tetracycline repressor protein.

Embodiment 34 includes the mammalian cell of any one of embodiments 22-33, wherein the mammalian cell is a Chinese hamster ovary (CHO) cell.

Embodiment 35 includes the mammalian cell of any one of embodiments 22-33, wherein the mammalian cell is a human cell.

Embodiment 36 includes the mammalian cell embodiment 35, wherein the human cell is a human embryonic kidney (HEK) cell.

Embodiment 37 includes the mammalian cell of any one of embodiments 22-36, further comprising a nucleic acid molecule encoding a gene of interest.

Embodiment 38 is an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters.

Embodiment 39 includes the isolated nucleic acid of embodiment 38, further comprising an internal ribosome entry site (IRES) element between the E2A and E4Orf6 genes.

Embodiment 40 includes the isolated nucleic acid of any of embodiments 38-39, wherein a Rep78 gene is under control of the second derepressible promoter and a Rep52 gene is under control of a fourth derepressible promoter.

Embodiment 41 includes the isolated nucleic acid of any of embodiments 38-39 wherein a Rep78 gene is under control of the second derepressible promoter and a Rep52 gene is under control of a fourth derepressible promoter contained within an artificial intron.

Embodiment 42 includes the isolated nucleic acid of any of embodiments 40 or 41, wherein the Cap gene is under control of a native promoter.

Embodiment 43 includes the isolated nucleic acid of any of embodiments 38-42, wherein each of the derepressible promoters comprise a functional promoter and two tetracycline operator sequences (TetO2).

Embodiment 44 includes the isolated nucleic acid of embodiment 43, wherein the functional promoter of the first derepressible promoter is a cytomegalovirus (CMV) promoter.

Embodiment 45 includes the isolated nucleic acid of any of embodiments 38-44, wherein the repressor element is under control of a constitutive promoter.

Embodiment 46 includes the isolated nucleic acid of any of embodiments 38-45, wherein the repressor element is a tetracycline repressor protein.

Embodiment 47 includes the isolated nucleic acid of embodiment 46, further comprising a nucleic acid encoding a transcriptional repression domain in frame with the nucleic acid encoding the tetracycline repressor protein.

Embodiment 48 includes the isolated nucleic acid of any of embodiments 38-47, further comprising a gene of interest.

Embodiment 49 is a method of producing an adeno-associated virus (AAV) in a mammalian cell comprising transfecting the mammalian cell with an isolated nucleic acid molecule encoding an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences, and a repressor element of the first, second and third derepressible promoters, treating the mammalian cell with a binding partner of the repressor element, activating the first, second and third derepressible promoters, producing the AAV, and harvesting the AAV.

Embodiment 50 includes the method of embodiment 49, wherein the mammalian cell is a mammalian cell culture.

Embodiment 51 includes the method of embodiment 50, wherein the mammalian cell culture is a suspension culture.

Embodiment 52 includes the method of any of embodiments 49-51, further comprising an internal ribosome entry site (IRES) element between the E2A and E4Orf6 genes.

Embodiment 53 includes the method of any of embodiments 49-52, wherein a Rep78 gene is under control of the second derepressible promoter and a Rep52 gene is under control of a fourth derepressible promoter.

Embodiment 54 includes the method of any of embodiments 49-52, wherein a Rep78 gene is under control of the second derepressible promoter and a Rep52 gene is under control of a fourth derepressible promoter contained within an artificial intron.

Embodiment 55 includes the method of embodiment 54, wherein the fourth derepressible promoter is removed following the activating the derepressible promoters and prior to the producing the AAV.

Embodiment 56 includes the method of any of embodiments 53 or 54, wherein the Cap gene is under control of a native promoter.

Embodiment 57 includes the method of any of embodiments 49-56, wherein each of the derepressible promoters comprise a functional promoter and two tetracycline operator sequences (TetO2).

Embodiment 58 includes the method of embodiment 57, wherein the functional promoter of the first derepressible promoter is a cytomegalovirus (CMV) promoter.

Embodiment 59 includes the method of any of embodiments 49-58, wherein the repressor element is under control of a constitutive promoter.

Embodiment 60 includes the method of any of embodiments 49-59, wherein the repressor element that is a tetracycline repressor protein.

Embodiment 61 includes the method of embodiment 60, wherein the nucleic acid further comprises a nucleic acid encoding a transcriptional repression domain in frame with the nucleic acid encoding the tetracycline repressor protein.

Embodiment 62 includes the method of any of embodiments 60 or 61, wherein the treating comprises treating with doxycycline.

Embodiment 63 includes the method of any of embodiments 49-62, wherein the mammalian cell is a Chinese hamster ovary (CHO) cell.

Embodiment 64 includes the method of any of embodiments 49-63, wherein the mammalian cell is a human cell.

Embodiment 65 includes the method of embodiment 64, wherein the human cell is a human embryonic kidney (HEK) cell.

Embodiment 66 includes the method of any of embodiments 49-65, wherein the AAV comprises a nucleic acid molecule encoding a gene of interest.

Embodiment 67 includes the method of embodiment 66, wherein the AAV comprises a gene of therapeutic interest.

Embodiment 68 is a method of treatment with an adeno-associated virus (AAV) comprising transfecting the mammalian cell with an isolated nucleic acid molecule encoding, an adenovirus helper gene comprising E2A and E4Orf6 genes under control of a first derepressible promoter, an AAV gene comprising Rep and Cap genes under control of a second derepressible promoter, a viral-associated, non-coding RNA under control of a third depressible promoter, two inverted terminal repeat (ITR) sequences; and a repressor element of the first, second and third derepressible promoters; treating the mammalian cell with a binding partner of the repressor element; activating the first, second and third derepressible promoters; producing the AAV; harvesting the AAV; and administering the AAV to a mammalian patient.

Embodiment 69 includes the method of embodiment 68, wherein the mammalian cell is a mammalian cell culture.

Embodiment 70 includes the method of embodiment 69, wherein the mammalian cell culture is a suspension culture.

Embodiment 71 includes the method of any of embodiments 68-70, further comprising an internal ribosome entry site (IRES) element between the E2A and E4Orf6 genes.

Embodiment 72 includes the method of any of embodiments 68-71, wherein a Rep78 gene is under control of the second derepressible promoter and a Rep52 gene is under control of a fourth derepressible promoter.

Embodiment 73 includes the method of any of embodiments 68-72, wherein a Rep78 gene is under control of the second derepressible promoter and a Rep52 gene is under control of a fourth derepressible promoter contained within an artificial intron.

Embodiment 74 includes the method of embodiment 73, wherein the fourth derepressible promoter is removed following the activating the derepressible promoters and prior to the producing the AAV.

Embodiment 75 includes the method of any of embodiments 73 or 74, wherein the Cap gene is under control of a native promoter.

Embodiment 76 includes the method of any of embodiments 68-75, wherein each of the derepressible promoters comprise a functional promoter and two tetracycline operator sequences ($TetO_2$).

Embodiment 77 includes the method of embodiment 76, wherein the functional promoter of the first derepressible promoter is a cytomegalovirus (CMV) promoter.

Embodiment 78 includes the method of any of embodiments 68-77, wherein the repressor element is under control of a constitutive promoter.

Embodiment 79 includes the method of any of embodiments 68-78, wherein the repressor element that is a tetracycline repressor protein.

Embodiment 80 includes the method of embodiment 79, wherein the nucleic acid further comprises a nucleic acid encoding a transcriptional repression domain in frame with the nucleic acid encoding the tetracycline repressor protein.

Embodiment 81 includes the method of any of embodiments 79 or 80, wherein the treating comprises treating with doxycycline.

Embodiment 82 includes the method of any of embodiments 68-81, wherein the mammalian cell is a Chinese hamster ovary (CHO) cell.

Embodiment 83 includes the method of any of embodiments 68-82, wherein the mammalian cell is a human cell.

Embodiment 84 includes the method of embodiment 83, wherein the human cell is a human embryonic kidney (HEK) cell.

Embodiment 85 includes the method of any of embodiments 68-84, wherein the AAV comprises a nucleic acid molecule encoding a gene of interest.

Embodiment 86 includes the method of embodiment 87, wherein the AAV comprises a gene of therapeutic interest.

Embodiment 87 includes the method of any of embodiments 68-86, wherein the administering comprises inhalation, injection or intravenous administration.

Embodiment 88 is a method of producing an adeno-associated (AAV) virus, comprising: transfecting a mammalian cell stably expressing one or more nucleic acids encoding TetR and/or TetR with a first nucleic acid encoding an adenovirus helper gene comprising an E2A gene, a E4Orf gene and a viral-associated non-coding RNA under control of a first derepressible promoter, a second nucleic acid encoding an AAV gene comprising Rep and Cap genes under control of a second derepressible promoter, and, optionally, a third nucleic acid encoding a gene of interest under control of a third derepressible promoter; treating the mammalian cell with a binding partner of the TetR and/or TetR-KRAB; activating the first, second and third derepressible promoters; producing the AAV; and harvesting the AAV.

Embodiment 89 includes the method of embodiment 88, wherein the mammalian cell is a mammalian cell culture.

Embodiment 90 includes the method of any of embodiments 88-89, wherein the mammalian cell is a Chinese hamster ovary (CHO) cell.

Embodiment 91 includes the method of any of embodiments 88-90, wherein the mammalian cell is a human cell.

Embodiment 92 includes the method of embodiment 91, wherein the human cell is a human embryonic kidney (HEK) cell.

Embodiment 93 includes the method of embodiment 89, wherein the mammalian cell culture is a suspension culture.

Embodiment 94 includes the method of any of embodiments 88-90, wherein the mammalian cell further comprises an internal ribosome entry site (IRES) element between the E2A and E4Orf6 genes.

Embodiment 95 includes the method of any of embodiments 88-91, wherein each of the derepressible promoters comprise a functional promoter and two tetracycline operator sequences ($TetO_2$).

Embodiment 96 includes the method of embodiment 92, wherein the functional promoter of the first derepressible promoter is a cytomegalovirus (CMV) promoter.

Embodiment 97 includes the method of any of embodiments 88-96, wherein the stably expressed TetR and/or TetR-KRAB is under control of a constitutive promoter.

Embodiment 98 includes the method of embodiment 97, wherein the nucleic acid encoding the TetR-KRAB comprises KRAB fused in frame with the TetR.

Embodiment 99 includes the method of any one of embodiments 88-98, wherein the treating comprises treating with doxycycline.

Embodiment 100 includes the method of any one of embodiments 88-99, wherein each of the first, second and third nucleic acids are flanked by transposon-specific inverted terminal repeats (ITRs).

Embodiment 101 includes the method of any of embodiments 88-100, wherein the mammalian cell expresses sufficient amounts of TetR and/or TetR-KRAB.

Embodiment 102 includes the method of any of embodiments 88-101, wherein the AAV comprises a gene of therapeutic interest.

Embodiment 103 includes the method of any of embodiments 88-102, wherein the mammalian cell further comprises stable expression of one or more nucleic acids encoding chicken hypersensitive site-4 (cHS4) flanking the TetR and/or TetR-KRAB repressor sequences.

Embodiment 104 includes the method of any of embodiments 88-103, wherein the mammalian cell further comprises a zeocin resistance gene.

Embodiment 105 is a method for producing an adeno-associated virus (AAV), comprising: stably transfecting a mammalian cell with: a nucleic acid encoding a TetR and/or TetR-KRAB repressor; chicken hypersensitive site-4 (cHS4) sequences flanking the TetR and/or TetR-KRAB repressor; and a selection gene; transfecting the stably transfected mammalian cell with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the stably transfected mammalian cell with a binding partner of the TetR; activating the first, second and third derepressible promoters; producing the AAV; and harvesting the AAV.

Embodiment 106 includes the method of embodiment 105, wherein the stably transfected mammalian cell produces a sufficient amounts of TetR.

Embodiment 107 includes the method of any of embodiments 106 and 107, wherein the KRAB repressor domain is fused in frame with the TetR.

EXAMPLES

Example 1: Design and Validation of Derepressible Helper Genes

To drive the expression of E2A and E4Orf6 genes, a derepressible promoter from the pcDNA4/TO vector (INVITROGEN) was utilized. This promoter includes the complete CMV promoter with an insertion of two Tetracycline operator sequences ($TetO_2$) between the TATA box and transcriptional start site (TSS). In the presence of tetracycline repressor protein (TetR), transcription initiation was blocked by the binding of TetR onto the $TetO_2$ sites. When Tetracycline or Doxycycline is added into the medium, it binds to TetR and changes its conformation. This leads to the release of TetR and derepression/activation of the CMV promoter and results in induced gene expression (FIG. 1 showing OFF and ON conformations of TetR/$TetO_2$ derepressible promoter system).

To simplify the design and improve the stability, an Internal Ribosome Entry Site (IRES) element was used to initiate the translation of E4Orf6 after E2A in a single expression cassette, driven by a single inducible CMV promoter (FIG. 1).

To induce the VA I non-coding RNA, an H1 promoter with $TetO_2$ insertion was applied (see, e.g., Wiederschain et al., "Single-vector inducible lentiviral RNAi system for oncology target validation, *Cell Cycle* 8:498-504 (2009)). Similarly, the addition of Doxycycline releases TetR and turns on VA I expression (FIG. 1).

As mentioned, a TetR gene expression cassette is included for the control of the derepressible promoters (see FIG. 1). A constitutive human PGK promoter is used to drive the expression of TetR, followed by an IRES that directs the expression of puromycin N-acetyltransferase used to select the transposon integrated cells (see FIG. 2A).

To reduce the potential leaky expression from the derepressible promoters, an enhanced version of TetR was also included (see, e.g., Szulc et al., "A versatile tool for conditional gene expression and knockdown," *Nature Methods* 3:109-116 (2006)). Briefly, a strong repressive domain of KRAB was fused in-frame to the C-terminal of original TetR, which improves its repressive activity and minimizes basal gene expression before induction. An SV40 Nuclear Localization Signal (NLS) was inserted as well to facilitate the nuclear entry of the larger TetR-KRAB fusion protein (FIG. 2A, FIGS. 12A-12B).

The sequence of the pcDNA3.1-E2A-E4-VA-TetR vector shown in FIG. 2A is provided below:

iHelper 1/ pcDNA3.1-E2A-E4-VA-TetR (11,986 bp)

(SEQ ID NO: 1)

GACGGATCGGGAGATCTCCCGATCCCCTATGGTGCACTCTCAGTACAATC

TGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAAT

TGCATGAAGAATCTGCTTAGGGTTAGGCGTTTTGCGCTGCTTCGCGATGTACGGGCC

AGATATACGCGTTGACATTGATTATTGACTAGTTATTAATAGTAATCAATTACGGGG

TCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATT

GACGTCAATGACGGTAAATGGCCCGCCTGGCATTATGCCCAGTACATGACCTTATGG

-continued

GACTTTCCTACTTGGCAGTACATCTACGTATTAGTCATCGCTATTACCATGGTGATGC

GGTTTTGGCAGTACATCAATGGGCGTGGATAGCGGTTTGACTCACGGGGATTTCCAA

GTCTCCACCCCATTGACGTCAATGGGAGTTTGTTTTGGCACCAAAATCAACGGGACT

TTCCAAAATGTCGTAACAACTCCGCCCCATTGACGCAAATGGGCGGTAGGCGTGTAC

GGTGGGAGGTCTATATAAGCAGAGCTCTCTGGCTAACTAGAGAACCCACTGCTTACT

GGCTTATCGAAATTAATACGACTCACTATAGGGAGACCCAAGCTGGCTAGCGTTTAA

ACTTAAGCTTGGTACCGAGCTCGGATCCACTAGTCCAGTGTGGTGGAATTCCTGCTT

CGCGATGTACGGGCCAGATATACGCGTTGACATTGATTATTGACTAGTTATTAATAG

TAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCA

ATAATGACGTATGTTCCCATAGTAACGCCAATAGGGACTTTCCATTGACGTCAATGG

GTGGAGTATTTACGGTAAACTGCCCACTTGGCAGTACATCAAGTGTATCATATGCCA

AGTACGCCCCCTATTGACGTCAATGACGGTAAATGGCCCGCCTGGCATTATGCCCAG

TACATGACCTTATGGGACTTTCCTACTTGGCAGTACATCTACGTATTAGTCATCGCTA

TTACCATGGTGATGCGGTTTTGGCAGTACATCAATGGGCGTGGATAGCGGTTTGACT

CACGGGGATTTCCAAGTCTCCACCCCATTGACGTCAATGGGAGTTTGTTTTGGAACC

AAAATCAACGGGACTTTCCAAAATGTCGTAACAACTCCGCCCCATTGACGCAAATG

GGCGGTAGGCGTGTACGGTGGGAGGTCTATATAAGCAGAGCTCTCCCTATCAGTGAT

AGAGATCTCCCTATCAGTGATAGAGATCGTCGACGAGCTCGTTTAGTGAACCGTCAG

ATCGCCTGGAGACGCCATCCACGCTGTTTTGACCTCCATAGAAGACACCGGGACCG

ATCCAGCCTCCGGACTCTAGCGTTTAAACTTAAGCTTGCCACCatggccagtcgggaagaggagc agcgcgaaaccacccccgagcgcggacgcggtgcggcgcgacgtcccccaaccatggaggacgtgtcgtccccgtccccgtcgccgc cgcctccccgggcgcccccaaaaaagcggatgaggcggcgtatcgagtccgaggacgaggaagactcatcacaagacgcgctggtgc cgcgcacacccagcccgcggccatcgacctcggcggcggatttggccattgcgcccaagaagaaaaagaagcgcccttctcccaagcc cgagcgcccgccatcaccagaggtaatcgtggacagcgaggaagaaagagaagatgtggcgctacaaatggtgggtttcagcaaccca ccggtgctaatcaagcatggcaaaggaggtaagcgcacagtgcggcggctgaatgaagacgacccagtggcgcgtggtatgcggacgc aagaggaagaggaagagcccagcgaagcggaaagtgaaattacggtgatgaacccgctgagtgtgccgatcgtgtctgcgtgggagaa gggcatggaggctgcgcgcgcgctgatggacaagtaccacgtggataacgatctaaaggcgaacttcaaactactgcctgaccaagtgg aagctctggcggccgtatgcaagacctggctgaacgaggagcaccgcgggttgcagctgaccttcaccagcaacaagacctttgtgacga tgatggggcgattcctgcaggcgtacctgcagtcgtttgcagaggtgacctacaagcatcacgagcccacgggctgcgcgttgtggctgca ccgctgcgctgagatcgaaggcgagcttaagtgtctacacggaagcattatgataaataaggagcacgtgattgaaatggatgtgacgagc gaaaacgggcagcgcgcgctgaaggagcagtctagcaaggccaagatcgtgaagaaccggtggggccgaaatgtggtgcagatctcc aacaccgacgcaaggtgctgcgtgcacgacgcggcctgtccggccaatcagttttccggcaagtcttgcggcatgttcttctctgaaggcg caaaggctcaggtggcttttaagcagatcaaggcttttatgcaggcgctgtatcctaacgcccagaccgggcacggtcaccttttgatgccac tacggtgcgagtgcaactcaaagcctgggcacgcgcccttttttgggaaggcagctaccaaagttgactccgttcgccctgagcaacgcgg aggacctggacgcggatctgatctccgacaagagcgtgctggccagcgtgcaccacccggcgctgatagtgttccagtgctgcaaccctg tgtatcgcaactcgcgcgcgcagggcggaggccccaactgcgacttcaagatatcggcgcccgacctgctaaacgcgttggtgatggtgc gcagcctgtggagtgaaaacttcaccgagctgccgcggatggttgtgcctgagtttaagtggagcactaaacaccagtatcgcaacgtgtc cctgccagtggcgcatagcgatgcgcggcagaaccccttgatttttaacccgggagttctagggatctgcccctctccctccccccccccta acgttactggccgaagccgcttggaataaggccggtgtgcgtttgtctatatgttattttccaccatattgccgtcttttggcaatgtgagggccc ggaaacctggccctgtcttcttgacgagcattcctaggggtctttcccctctcgccaaaggaatgcaaggtctgttgaatgtcgtgaaggaag -continued cagttcctctggaagcttcttgaagacaaacaacgtctgtagcgaccctttgcaggcagcggaacccccacctggcgacaggtgcctctg cggccaaaagccacgtgtataagatacacctgcaaaggcggcacaaccccagtgccacgttgtgagttggatagttgtggaaagagtcaa atggctctcctcaagcgtattcaacaaggggctgaaggatgcccagaaggtaccccattgtatgggatctgatctggggcctcggtgcacat gctttacatgtgtttagtcgaggttaaaaaaacgtctaggccccccgaaccacggggacgtggttttcctttgaaaaacacgatgataaggat ccaccggaggccaccatgactacgtccggcgttccatttggcatgacactacgaccaacacgatctcggttgtctcggcgcactccgtaca gtagggatcgtctacctccttttgagacagaaacccgcgctaccatactggaggatcatccgctgctgcccgaatgtaacactttgacaatgc acaacgtgagttacgtgcgaggtcttccctgcagtgtgggatttacgctgattcaggaatgggttgttccctgggatatggttctaacgcggga ggagcttgtaatcctgaggaagtgtatgcacgtgtgcctgtgttgtgccaacattgatatcatgacgagcatgatgatccatggttacgagtcc tgggctctccactgtcattgttccagtcccggttccctgcagtgtatagccggcgggcaggttttggccagctggtttaggatggtggtggatg gcgccatgtttaatcagaggtttatatggtaccgggaggtggtgaattacaacatgccaaaagaggtaatgtttatgtccagcgtgtttatgag gggtcgccacttaatctacctgcgcttgtggtatgatggccacgtgggttctgtggtccccgccatgagctttggatacagcgccttgcactgt gggattttgaacaatattgtggtgctgtgctgcagttactgtgctgatttaagtgagatcagggtgcgctgctgtgcccggaggacaaggcgc cttatgctgcgggcggtgcgaatcatcgctgaggagaccactgccatgttgtattcctgcaggacggagcggcggcggcagcagtttattc gcgcgctgctgcagcaccaccgccctatcctgatgcacgattatgactctacccccatgtagGCGGCCGCTCGAGTCTAG

AGGGCCCGTTTAAACCCGCTGATCAGCCTCGACTGTGCCTTCTAGTTGCCAGCCATC

TGTTGTTTGCCCCTCCCCCGTGCCTTCCTTGACCCTGGAAGGTGCCACTCCCACTGTC

CTTTCCTAATAAAATGAGGAAATTGCATCGCATTGTCTGAGTAGGTGTCATTCTATTC

TGGGGGGTGGGGTGGGGCAGGACAGCAAGGGGGAGGATTGGGAAGACAATAGCAG

GCATGCTGGGGATGCGGTGGGCTCTATGGCTTCTGAGGCGGAAAGAACCAGCTGGG

GCTCTAGGGGGTATCCCCggggttggggttgcgccttttccaaggcATCCAGCACAGTGGCGGCCGCa atatttgcatgtcgctatgtgttctgggaaatcaccataaacgtgaaatccctatcagtgatagagacttataagttccctatcagtgatagagaa ccggtgggcactcttccgtggtctggtggataaattcgcaagggtatcatggcggacgaccggggttcgagccccgtatccggccgtccg ccgtgatccatgcggttaccgcccgcgtgtcgaacccaggtgtgcgacgtcagacaacgggggagtgctccttttgaattccactttggcc gcggctcgaggggggttggggttgcgccttttccaaggcagccctgggtttgcgcagggacgcggctgctctgggcgtggttccgggaaac gcagcggcgccgaccctgggtctcgcacattcttcacgtccgttcgcagcgtcacccggatcttcgccgctacccttgtgggccccccggc gacgcttcctgctccgccccctaagtcgggaaggttccttgcggttcgcggcgtgccggacgtgacaaacggaagccgcacgtctcactagt accctcgcagacggacagcgccagggagcaatggcagcgcgccgaccgcgatgggctgtggccaatagcggctgctcagcagggcg cgccgagagcagcggccgggaaggggcggtgcgggaggcggggtgtggggcggtagtgtgggccctgttcctgcccgcgcggtgttc cgcattctgcaagcctccggagcgcacgtcggcagtcggctccctcgttgaccgaatcaccgacctctctccccagggggatctgtgagttt ggggacccttgattgttctttctttttcgctattgtaaaattcatgttatatggagggggcaaagttttcagggtgttgtttagaatgggaagatgtc ccttgtatcaccatggaccctcatgataatttgtttctttcactttctactctgttgacaaccattgtctcctcttattttcttttcattttctgtaactttt tcgttaaactttagcttgcatttgtaacgaatttttaaattcacttttgtttatttgtcagattgtaagtactttctctaatcactttttttcaaggcaatca gggtatattatattgtacttcagcacagttttagagaacaattgttataattaaatgataaggtagaatatttctgcatataaattctggctggcgtgga aatattcttattggtagaaacaactacatcctggtcatcatcctgcctttctctttatggttacaatgatatacactgtttgagatgaggataaaatac tctgagtccaaaccgggcccctctgctaaccatgttcatgccttcttctttttcctacagctcctgggcaacgtgctggttattgtgctgtctcatc attttggcaaagaattgtaatacgactcactatagggcgaGCCACCatggctagattagataaaagtaaagtgattaacagcgcattaga gctgcttaatgaggtcggaatcgaaggtttaacaacccgtaaactcgcccagaagctaggtgtagagcagcctacattgtattggcatgtaaa aaataagcgggctttgctcgacgccttagccattgagatgttagataggcaccatactcacttttgccctttagaaggggaaagctggcaaga ttttttacgtaataacgctaaaagttttagatgtgctttactaagtcatcgcgatggagcaaaagtacatttaggtacacggcctacagaaaaaca gtatgaaactctcgaaaatcaattagcctttttatgccaacaaggtttttcactagagaatgcCttatatgcactcagcgcCgtggggcatttta -continued ctttaggttgcgtattggaagatcaagagcatcaagtcgctaaagaagaaagggaaacacctactactgatagtatgccgccattattacgac aagctatcgaattatttgatcaccaaggtgcagagccagccttcttattcggccttgaattgatcatatgcggattagaaaaacaacttaaatgt gaaagtgggtccccaaaaaagaagagaaaggtcgacggcggtggtgctttgtctcctcagcactctgctgtcactcaaggaagtatcatca agaacaaggagggcatggatgctaagtcactaactgcctggtcccggacactggtgaccttcaaggatgtatttgtggacttcaccaggga ggagtggaagctgctggacactgctcagcagatcgtgtacagaaatgtgatgctggagaactataagaacctggtttccttgggttatcagct tactaagccagatgtgatcctccggttggagaagggagaagagccctggctggtggagagagaaattcaccaagagacccatcctgattc agagactgcatttgaaatcaaatcatcagtttaagcgtacagcggctcccgggagttctagggatctgcccctctccctcccccccccctaac gttactggccgaagccgcttggaataaggccggtgtgcgtttgtctatatgttattttccaccatattgccgtcttttggcaatgtgagggcccg gaaacctggccctgtcttcttgacgagcattcctaggggtctttcccctctcgccaaaggaatgcaaggtctgttgaatgtcgtgaaggaagc agttcctctggaagcttcttgaagacaaacaacgtctgtagcgaccctttgcaggcagcggaacccccacctggcgacaggtgcctctgc ggccaaaagccacgtgtataagatacacctgcaaaggcggcacaaccccagtgccacgttgtgagttggatagttgtggaaagagtcaaat ggctctcctcaagcgtattcaacaaggggctgaaggatgcccagaaggtaccccattgtatgggatctgatctggggcctcggtgcacatg ctttacatgtgtttagtcgaggttaaaaaaacgtctaggccccccgaaccacggggacgtggttttcctttgaaaaacacgatgataaggatcc accggagGCCACCatgaccgagtacaagcccacggtgcgcctcgccacccgcgacgacgtccccagggccgtacgcaccctcgc cgccgcgttcgccgactaccccgccacgcgccacaccgtcgatccggaccgccacatcgagcgggtcaccgagctgcaagaactcttcc tcacgcgcgtcgggctcgacatcggcaaggtgtgggtcgcggacgacggcgccgcggtggcggtctggaccacgccggagagcgtcg aagcgggggcggtgttcgccgagatcggcccgcgcatggccgagttgagcggttcccggctggccgcgcagcaacagatggaaggcc tcctggcgccgcaccggcccaaggagcccgcgtggttcctggccaccgtcggcgtctcgcccgaccaccagggcaagggtctgggcag cgccgtcgtgctccccggagtggaggcggccgagcgcgccggggtgcccgccttcctggagacctccgcgccccgcaacctccccttct acgagcggctcggcttcaccgtcaccgccgacgtcgaggtgcccgaaggaccgcgcacctggtgcatgacccgcaagcccggtgcctg aCCGCGTCTGGAACAATCAACCTCTGGATTACAAAATTTGTGAAAGATTGACTGGTA

TTCTTAACTATGTTGCTCCTTTTACGCTATGTGGATACGCTGCTTTAATGCCTTTGTAT

CATGCTATTGCTTCCCGTATGGCTTTCATTTTCTCCTCCTTGTATAAATCCTGGTTGCT

GTCTCTTTATGAGGAGTTGTGGCCCGTTGTCAGGCAACGTGGCGTGGTGTGCACTGT

GTTTGCTGACGCAACCCCCACTGGTTGGGGCATTGCCACCACCTGTCAGCTCCTTTC

CGGGACTTTCGCTTTCCCCCTCCCTATTGCCACGGCGGAACTCATCGCCGCCTGCCTT

GCCCGCTGCTGGACAGGGGCTCGGCTGTTGGGCACTGACAATTCCGTGGTGTTGTCG

GGGAAGCTGACGTCCTTTCCATGGCTGCTCGCCTGTGTTGCCACCTGGATTCTGCGC

GGGACGTCCTTCTGCTACGTCCCTTCGGCCCTCAATCCAGCGGACCTTCCTTCCCGCG

GCCTGCTGCCGGCTCTGCGGCCTCTTCCGCGTCTTCGCCTTCGCCCTCAGACGAGTCG

GATCTCCCTTTGGGCCGCCTCCCCGCaAAATGACCGACCAAGCGACGCCCAACCTGC

CATCACGAGATTTCGATTCCACCGCCGCCTTCTATGAAAGGTTGGGCTTCGGAATCG

TTTTCCGGGACGCCGGCTGGATGATCCTCCAGCGCGGGGATCTCATGCTGGAGTTCT

TCGCCCACCCCAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAA

ACTCATCAATGTATCTTATCATGTCTGTATACCGTCGACCTCTAGCTAGAGCTTGGCG

TAATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCTGTCGTGC

CAGCTGCATTAATGAATCGGCCAACGCGCGGGGAGAGGCGGTTTGCGTATTGGGCG

CTCTTCCGCTTCCTCGCTCACTGACTCGCTGCGCTCGGTCGTTCGGCTGCGGCGAGCG

-continued

GTATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACAAAAATCGA

CGCTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGG

TAGCTCTTGATCCGGCAAACAAACCACCGCTGGTAGCGGTTTTTTTGTTTGCAAGCA

GCAGATTACGCGCAGAAAAAAAGGATCTCAAGAAGATCCTTTGATCTTTTCTACGGG

GTCTGACGCTCAGTGGAACGAAAACTCACGTTAAGGGATTTTGGTCATGAGATTATC

AAAAAGGATCTTCACCTAGATCCTTTTAAATTAAAAATGAAGTTTTAAATCAATCTA

AAGTATATATGAGTAAACTTGGTCTGACAGTTACCAATGCTTAATCAGTGAGGCACC

TATCTCAGCGATCTGTCTATTTCGTTCATCCATAGTTGCCTGACTCCCCGTCGTGTAG

ATAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAGGG

CCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATTCAGCTCCGG

TTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATG

GTTATGGCAGCACTGCATAATTCTCTTACTGTCATGCCATCCGTAAGATGCTTTTCTG

TGACTGGTGAGTACTCAACCAAGTCATTCTGAGAATAGTGTATGCGGCGACCGAGTT

GCTCTTGCCCGGCGTCAATACGGGATAATACCGCGCCACATAGCAGAACTTTAAAA

GTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTA

CTTTCACCAGCGTTTCTGGGTGAGCAAAAACAGGAAGGCAAAATGCCGCAAAAAAG

GGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAG

AAAAATAAACAAATAGGGGTTCCGCGCACATTTCCCCGAAAAGTGCCACCTGACGT

C

The sequence of the pcDNA3.1-E2A-E4-VA-TetR-V2 vector shown in FIG. 2B is provided below:

iHelper2/pcDNA3.1-E2A-E4-VA-TetR-V2 (11,641 bp)
(SEQ ID NO: 2)

GACGGATCGGGAGATCTCCCGATCCCCTATGGTGCACTCTCAGTACAA

TCTGCTCTGATGCCGCATAGTTAAGCCAGTATCTGCTCCCTGCTTGT

-continued

GTGTTGGAGGTCGCTGAGTAGTGCGCGAGCAAAATTTAAGCTACAACA

AGGCAAGGCTTGACCGACAATTGCATGAAGAATCTGCTTAGGGTTAGG

CGTTTTGCGCTGCTTCGCGATGTACGGGCCAGATATACGCGTTGACAT

TGATTATTGACTAGTTATTAATAGTAATCAATTACGGGGTCATTAGTT

CATAGCCCATATATGGAGTTCCGCGTTACATAACTTACGGTAAATGGC

-continued

CCGCCTGGCTGACCGCCCAACGACCCCCGCCCATTGACGTCAATAATG

ACGTATGTTCCCATAGTAACGCCAATAGGGACTTTCCATTGACGTCAA

TGGGTGGAGTATTTACGGTAAACTGCCCACTTGGCAGTACATCAAGTG

TATCATATGCCAAGTACGCCCCCTATTGACGTCAATGACGGTAAATGG

CCCGCCTGGCATTATGCCCAGTACATGACCTTATGGGACTTTCCTACT

TGGCAGTACATCTACGTATTAGTCATCGCTATTACCATGGTGATGCGG

TTTTGGCAGTACATCAATGGGCGTGGATAGCGGTTTGACTCACGGGGA

TTTCCAAGTCTCCACCCCATTGACGTCAATGGGAGTTTGTTTTGGCAC

CAAAATCAACGGGACTTTCCAAAATGTCGTAACAACTCCGCCCCATTG

ACGCAAATGGGCGGTAGGCGTGTACGGTGGGAGGTCTATATAAGCAGA

GCTCTCTGGCTAACTAGAGAACCCACTGCTTACTGGCTTATCGAAATT

AATACGACTCACTATAGGGAGACCCAAGCTGGCTAGCGTTTAAACTTA

AGCTTGGTACCGAGCTCGGATCCACTAGTCCAGTGTGGTGGAATTCCT

GCTTCGCGATGTACGGGCCAGATATACGCGTTGACATTGATTATTGAC

TAGTTATTAATAGTAATCAATTACGGGGTCATTAGTTCATAGCCCATA

TATGGAGTTCCGCGTTACATAACTTACGGTAAATGGCCCGCCTGGCTG

ACCGCCCAACGACCCCCGCCCATTGACGTCAATAATGACGTATGTTCC

CATAGTAACGCCAATAGGGACTTTCCATTGACGTCAATGGGTGGAGTA

TTTACGGTAAACTGCCCACTTGGCAGTACATCAAGTGTATCATATGCC

AAGTACGCCCCCTATTGACGTCAATGACGGTAAATGGCCCGCCTGGCA

TTATGCCCAGTACATGACCTTATGGGACTTTCCTACTTGGCAGTACAT

CTACGTATTAGTCATCGCTATTACCATGGTGATGCGGTTTTGGCAGTA

CATCAATGGGCGTGGATAGCGGTTTGACTCACGGGGATTTCCAAGTCT

CCACCCCATTGACGTCAATGGGAGTTTGTTTTGGAACCAAAATCAACG

GGACTTTCCAAAATGTCGTAACAACTCCGCCCCATTGACGCAAATGGG

CGGTAGGCGTGTACGGTGGGAGGTCTATATAAGCAGAGCTCTCCCTAT

CAGTGATAGAGATCTCCCTATCAGTGATAGAGATCGTCGACGAGCTCG

TTTAGTGAACCGTCAGATCGCCTGGAGACGCCATCCACGCTGTTTTGA

CCTCCATAGAAGACACCGGGACCGATCCAGCCTCCGGACTCTAGCGTT

Figure 3:
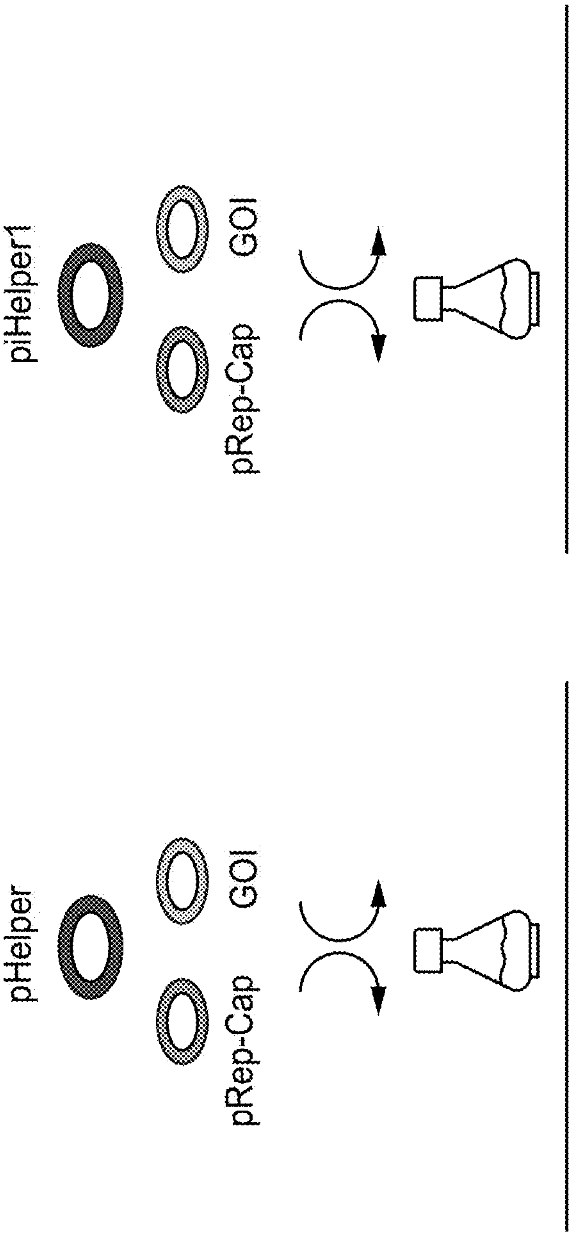
FIG. 3 shows the results of induction of helper and AAV genes in accordance with embodiments hereof.

TAAACTTAAGCTTGCCACCatggccagtcgggaagaggagcagcgcga aaccacccccgagcgcggacgcggtgcggcgcgacgtcccccaaccat ggaggacgtgtcgtccccgtccccgtcgccgccgcctccccgggcgcc cccaaaaaagcggatgaggcggcgtatcgagtccgaggacgaggaaga ctcatcacaagacgcgctggtgccgcgcacacccagcccgcggccatc gacctcggcggcggatttggccattgcgcccaagaagaaaaagaagcg cccttctcccaagcccgagcgcccgccatcaccagaggtaatcgtgga cagcgaggaagaaagagaagatgtggcgctacaaatggtgggtttcag caacccaccggtgctaatcaagcatggcaaaggaggtaagcgcacagt gcggcggctgaatgaagacgacccagtggcgcgtggtatgcggacgca agaggaagaggaagagcccagcgaagcggaaagtgaaattacggtgat -continued gaacccgctgagtgtgccgatcgtgtctgcgtgggagaagggcatgga ggctgcgcgcgcgctgatggacaagtaccacgtggataacgatctaaa ggcgaacttcaaactactgcctgaccaagtggaagctctggcggccgt atgcaagacctggctgaacgaggagcaccgcgggttgcagctgacctt caccagcaacaagacctttgtgacgatgatggggcgattcctgcaggc gtacctgcagtcgtttgcagaggtgacctacaagcatcacgagcccac gggctgcgcgttgtggctgcaccgctgcgctgagatcgaaggcgagct taagtgtctacacggaagcattatgataaataaggagcacgtgattga aatggatgtgacgagcgaaaacgggcagcgcgcgctgaaggagcagtc tagcaaggccaagatcgtgaagaaccggtggggccgaaatgtggtgca gatctccaacaccgacgcaaggtgctgcgtgcacgacgcggcctgtcc ggccaatcagttttccggcaagtcttgcggcatgttcttctctgaagg cgcaaaggctcaggtggcttttaagcagatcaaggcttttatgcaggc gctgtatcctaacgcccagaccgggcacggtcaccttttgatgccact acggtgcgagtgcaactcaaagcctgggcacgcgcccttttttgggaag gcagctaccaaagttgactccgttcgccctgagcaacgcggaggacct ggacgcggatctgatctccgacaagagcgtgctggccagcgtgcacca cccggcgctgatagtgttccagtgctgcaaccctgtgtatcgcaactc gcgcgcgcagggcggaggccccaactgcgacttcaagatatcggcgcc cgacctgctaaacgcgttggtgatggtgcgcagcctgtggagtgaaaa cttcaccgagctgccgcggatggttgtgcctgagtttaagtggagcac taaacaccagtatcgcaacgtgtccctgccagtggcgcatagcgatgc gcggcagaacccctttgatttttaacccgggagttctagggatctgcc cctctccctccccccccctaacgttactggccgaagccgcttggaat aaggccggtgtgcgtttgtctatatgttattttccaccatattgccgt cttttggcaatgtgagggcccggaaacctggccctgtcttcttgacga gcattcctaggggtctttcccctctcgccaaaggaatgcaaggtctgt tgaatgtcgtgaaggaagcagttcctctggaagcttcttgaagacaaa caacgtctgtagcgaccctttgcaggcagcggaacccccacctggcg acaggtgcctctgcggccaaaagccacgtgtataagatacacctgcaa aggcggcacaaccccagtgccacgttgtgagttggatagttgtggaaa gagtcaaatggctctcctcaagcgtattcaacaaggggctgaaggatg cccagaaggtaccccattgtatgggatctgatctggggcctcggtgca catgctttacatgtgtttagtcgaggttaaaaaaacgtctaggccccc cgaaccacggggacgtggttttcctttgaaaaacacgatgataaggat ccaccggaggccaccatgactacgtccggcgttccatttggcatgaca ctacgaccaacacgatctcggttgtctcggcgcactccgtacagtagg gatcgtctacctccttttgagacagaaacccgcgctaccatactggag gatcatccgctgctgcccgaatgtaacactttgacaatgcacaacgtg agttacgtgcgaggtcttccctgcagtgtgggatttacgctgattcag gaatgggttgttccctgggatatggttctaacgcgggaggagcttgta -continued atcctgaggaagtgtatgcacgtgtgcctgtgttgtgccaacattgat
atcatgacgagcatgatgatccatggttacgagtcctgggctctccac
tgtcattgttccagtcccggttccctgcagtgtatagccggcgggcag
gttttggccagctggtttaggatggtggtggatggcgccatgtttaat
cagaggtttatatggtaccgggaggtggtgaattacaacatgccaaaa
gaggtaatgtttatgtccagcgtgtttatgaggggtcgccacttaatc
tacctgcgcttgtggtatgatggccacgtgggttctgtggtccccgcc
atgagctttggatacagcgccttgcactgtgggattttgaacaatatt
gtggtgctgtgctgcagttactgtgctgatttaagtgagatcagggtg
cgctgctgtgcccggaggacaaggcgccttatgctgcgggcggtgcga
atcatcgctgaggagaccactgccatgttgtattcctgcaggacggag
cggcggcggcagcagtttattcgcgcgctgctgcagcaccaccgccct
atcctgatgcacgattatgactctacccccatgtagGCGGCCGCTCGA
GTCTAGAGGGCCCGTTTAAACCCGCTGATCAGCCTCGACTGTGCCTTC
TAGTTGCCAGCCATCTGTTGTTTGCCCCTCCCCCGTGCCTTCCTTGAC
CCTGGAAGGTGCCACTCCCACTGTCCTTTCCTAATAAAATGAGGAAAT
TGCATCGCATTGTCTGAGTAGGTGTCATTCTATTCTGGGGGGTGGGGT
GGGGCAGGACAGCAAGGGGGAGGATTGGGAAGACAATAGCAGGCATGC
TGGGGATGCGGTGGGCTCTATGGCTTCTGAGGCGGAAAGAACCAGCTG
GGGCTCTAGGGGGTATCCCCggggttggggttgcgccttttccaaggc
ATCCAGCACAGTGGCGGCCGCaatatttgcatgtcgctatgtgttctg
ggaaatcaccataaacgtgaaatccctatcagtgatagagacttataa
gttccctatcagtgatagagaaccggtgggcactcttccgtggtctgg
tggataaattcgcaagggtatcatggcggacgaccggggttcgagccc
cgtatccggccgtccgccgtgatccatgcggttaccgcccgcgtgtcg
aacccaggtgtgcgacgtcagacaacgggggagtgctccttttgaat
tccactttggccgcggctcgaggggggttggggttgcgccttttccaag
gcagccctgggtttgcgcagggacgcggctgctctgggcgtggttccg
ggaaacgcagcggcgccgaccctgggtctcgcacattcttcacgtccg
ttcgcagcgtcacccggatcttcgccgctacccttgtgggccccccgg
cgacgcttcctgctccgcccctaagtcgggaaggttccttgcggttcg
cggcgtgccggacgtgacaaacggaagccgcacgtctcactagtaccc
tcgcagacggacagcgccagggagcaatggcagcgcgccgaccgcgat
gggctgtggccaatagcggctgctcagcagggcgcgccgagagcagcg
gccgggaaggggcggtgcgggaggcggggtgtggggcggtagtgtggg
ccctgttcctgcccgcgcggtgttccgcattctgcaagcctccggagc
gcacgtcggcagtcggctccctcgttgaccgaatcaccgacctctctc
cccaggggggatctgtgagtttggggacccttgattgttctttcttttt
cgctattgtaaaattcatgttatatggagggggcaaagttttcagggt
gttgtttagaatgggaagatgtcccttgtatcaccatggaccctcatg -continued ataattttgtttctttcactttctactctgttgacaaccattgtctcc
tcttattttcttttcatttctgtaacttttcgttaaactttagctt
gcatttgtaacgaattttaaattcacttttgtttatttgtcagattg
taagtactttctctaatcactttttttcaaggcaatcagggtatatt
atattgtacttcagcacagttttagagaacaattgttataattaaatg
ataaggtagaatatttctgcatataaattctggctggcgtggaaatat
tcttattggtagaaacaactacatcctggtcatcatcctgcctttctc
tttatggttacaatgatatacactgtttgagatgaggataaaatactc
tgagtccaaaccgggcccctctgctaaccatgttcatgccttcttctt
tttcctacagctcctgggcaacgtgctggttattgtgctgtctcatca
ttttggcaaagaattgtaatacgactcactatagggcgaGCCACCatg
gctagattagataaaagtaaagtgattaacagcgcattagagctgctt
aatgaggtcggaatcgaaggtttaacaacccgtaaactcgcccagaag
ctaggtgtagagcagcctacattgtattggcatgtaaaaaataagcgg
gctttgctcgacgccttagccattgagatgttagataggcaccatact
cacttttgccctttagaaggggaaagctggcaagattttttacgtaat
aacgctaaaagttttagatgtgctttactaagtcatcgcgatggagca
aaagtacatttaggtacacggcctacagaaaaacagtatgaaactctc
gaaaatcaattagcctttttatgccaacaaggtttttcactagagaat
gcCttatatgcactcagcgcCgtggggcattttactttaggttgcgta
ttggaagatcaagagcatcaagtcgctaaagaagaaagggaaacacct
actactgatagtatgccgccattattacgacaagctatcgaattattt
gatcaccaaggtgcagagccagccttcttattcggccttgaattgatc
atatgcggattagaaaaacaacttaaatgtgaaagtgggtccccaaaa
aagaagagaaaggtcgacggcggtggttcagtttaagcgtacagcggc
tcccgggagttctagggatctgcccctctccctcccccccccctaacg
ttactggccgaagccgcttggaataaggccggtgtgcgtttgtctata
tgttattttccaccatattgccgtcttttggcaatgtgagggcccgga
aacctggccctgtcttcttgacgagcattcctaggggtctttcccctc
tcgccaaaggaatgcaaggtctgttgaatgtcgtgaaggaagcagttc
ctctggaagcttcttgaagacaaacaacgtctgtagcgaccctttgca
ggcagcggaaccccccacctggcgacaggtgcctctgcggccaaaagc
cacgtgtataagatacacctgcaaaggcggcacaaccccagtgccacg
ttgtgagttggatagttgtggaaagagtcaaatggctctcctcaagcg
tattcaacaaggggctgaaggatgcccagaaggtaccccattgtatgg
gatctgatctggggcctcggtgcacatgctttacatgtgtttagtcga
ggttaaaaaaacgtctaggccccccgaaccacggggacgtggttttcc
tttgaaaaacacgatgataaggatccaccggagGCCACCatgaccgag
tacaagcccacggtgcgcctcgccacccgcgacgacgtccccagggcc
gtacgcaccctcgccgccgcgttcgccgactaccccgccacgcgccac
accgtcgatccggaccgccacatcgagcgggtcaccgagctgcaagaa -continued ctcttcctcacgcgcgtcgggctcgacatcggcaaggtgtgggtcgcg
gacgacggcgccgcggtggcggtctggaccacgccggagagcgtcgaa
gcgggggcggtgttcgccgagatcggcccgcgcatggccgagttgagc
ggttcccggctggccgcgcagcaacagatggaaggcctcctggcgccg
caccggcccaaggagcccgcgtggttcctggccaccgtcggcgtctcg
cccgaccaccagggcaagggtctgggcagcgccgtcgtgctccccgga
gtggaggcggccgagcgcgccggggtgcccgccttcctggagacctcc
gcgccccgcaacctccccttctacgagcggctcggcttcaccgtcacc
gccgacgtcgaggtgcccgaaggaccgcgcacctggtgcatgacccgc
aagcccggtgcctgaCCGCGTCTGGAACAATCAACCTCTGGATTACAA
AATTTGTGAAAGATTGACTGGTATTCTTAACTATGTTGCTCCTTTTAC
GCTATGTGGATACGCTGCTTTAATGCCTTTGTATCATGCTATTGCTTC
CCGTATGGCTTTCATTTTCTCCTCCTTGTATAAATCCTGGTTGCTGTC
TCTTTATGAGGAGTTGTGGCCCGTTGTCAGGCAACGTGGCGTGGTGTG
CACTGTGTTTGCTGACGCAACCCCCACTGGTTGGGGCATTGCCACCAC
CTGTCAGCTCCTTTCCGGGACTTTCGCTTTCCCCCTCCCTATTGCCAC
GGCGGAACTCATCGCCGCCTGCCTTGCCCGCTGCTGGACAGGGGCTCG
GCTGTTGGGCACTGACAATTCCGTGGTGTTGTCGGGGAAGCTGACGTC
CTTTCCATGGCTGCTCGCCTGTGTTGCCACCTGGATTCTGCGCGGGAC
GTCCTTCTGCTACGTCCCTTCGGCCCTCAATCCAGCGGACCTTCCTTC
CCGCGGCCTGCTGCCGGCTCTGCGGCCTCTTCCGCGTCTTCGCCTTCG
CCCTCAGACGAGTCGGATCTCCCTTTGGGCCGCCTCCCCGCaAAATGA
CCGACCAAGCGACGCCCAACCTGCCATCACGAGATTTCGATTCCACCG
CCGCCTTCTATGAAAGGTTGGGCTTCGGAATCGTTTTCCGGGACGCCG
GCTGGATGATCCTCCAGCGCGGGGATCTCATGCTGGAGTTCTTCGCCC
ACCCCAACTTGTTTATTGCAGCTTATAATGGTTACAAATAAAGCAATA
GCATCACAAATTTCACAAATAAAGCATTTTTTTCACTGCATTCTAGTT
GTGGTTTGTCCAAACTCATCAATGTATCTTATCATGTCTGTATACCGT
CGACCTCTAGCTAGAGCTTGGCGTAATCATGGTCATAGCTGTTTCCTG
TGTGAAATTGTTATCCGCTCACAATTCCACACAACATACGAGCCGGAA
GCATAAAGTGTAAAGCCTGGGGTGCCTAATGAGTGAGCTAACTCACAT
TAATTGCGTTGCGCTCACTGCCCGCTTTCCAGTCGGGAAACCTGTCGT
GCCAGCTGCATTAATGAATCGGCCAACGCGCGGGGAGAGGCGGTTTGC
GTATTGGGCGCTCTTCCGCTTCCTCGCTCACTGACTCGCTGCGCTCGG
TCGTTCGGCTGCGGCGAGCGGTATCAGCTCACTCAAAGGCGGTAATAC
GGTTATCCACAGAATCAGGGGATAACGCAGGAAAGAACATGTGAGCAA
AAGGCCAGCAAAAGGCCAGGAACCGTAAAAAGGCCGCGTTGCTGGCGT
TTTTCCATAGGCTCCGCCCCCCTGACGAGCATCACAAAAATCGACGCT
CAAGTCAGAGGTGGCGAAACCCGACAGGACTATAAAGATACCAGGCGT
TTCCCCCTGGAAGCTCCCTCGTGCGCTCTCCTGTTCCGACCCTGCCGC -continued TTACCGGATACCTGTCCGCCTTTCTCCCTTCGGGAAGCGTGGCGCTTT
CTCATAGCTCACGCTGTAGGTATCTCAGTTCGGTGTAGGTCGTTCGCT
CCAAGCTGGGCTGTGTGCACGAACCCCCCGTTCAGCCCGACCGCTGCG
CCTTATCCGGTAACTATCGTCTTGAGTCCAACCCGGTAAGACACGACT
TATCGCCACTGGCAGCAGCCACTGGTAACAGGATTAGCAGAGCGAGGT
ATGTAGGCGGTGCTACAGAGTTCTTGAAGTGGTGGCCTAACTACGGCT
ACACTAGAAGAACAGTATTTGGTATCTGCGCTCTGCTGAAGCCAGTTA
CCTTCGGAAAAAGAGTTGGTAGCTCTTGATCCGGCAAACAAACCACCG
CTGGTAGCGGTTTTTTTGTTTGCAAGCAGCAGATTACGCGCAGAAAAA
AAGGATCTCAAGAAGATCCTTTGATCTTTTCTACGGGGTCTGACGCTC
AGTGGAACGAAAACTCACGTTAAGGGATTTTGGTCATGAGATTATCAA
AAAGGATCTTCACCTAGATCCTTTTAAATTAAAAATGAAGTTTTAAAT
CAATCTAAAGTATATATGAGTAAACTTGGTCTGACAGTTACCAATGCT
TAATCAGTGAGGCACCTATCTCAGCGATCTGTCTATTTCGTTCATCCA
TAGTTGCCTGACTCCCCGTCGTGTAGATAACTACGATACGGGAGGGCT
TACCATCTGGCCCCAGTGCTGCAATGATACCGCGAGACCCACGCTCAC
CGGCTCCAGATTTATCAGCAATAAACCAGCCAGCCGGAAGGGCCGAGC
GCAGAAGTGGTCCTGCAACTTTATCCGCCTCCATCCAGTCTATTAATT
GTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTG
GTATGGCTTCATTCAGCTCCGGTTCCCAACGATCAAGGCGAGTTACAT
GATCCCCCATGTTGTGCAAAAAAGCGGTTAGCTCCTTCGGTCCTCCGA
TCGTTGTCAGAAGTAAGTTGGCCGCAGTGTTATCACTCATGGTTATGG
CAGCACTGCATAATTCTCTTACTGTCATGCCATCCGTAAGATGCTTTT
CTGTGACTGGTGAGTACTCAACCAAGTCATTCTGAGAATAGTGTATGC
GGCGACCGAGTTGCTCTTGCCCGGCGTCAATACGGGATAATACCGCGC
CACATAGCAGAACTTTAAAAGTGCTCATCATTGGAAAACGTTCTTCGG
GGCGAAAACTCTCAAGGATCTTACCGCTGTTGAGATCCAGTTCGATGT
AACCCACTCGTGCACCCAACTGATCTTCAGCATCTTTTACTTTCACCA
GCGTTTCTGGGTGAGCAAAAACAGGAAGGCAAAATGCCGCAAAAAAGG
GAATAAGGGCGACACGGAAATGTTGAATACTCATACTCTTCCTTTTTC
AATATTATTGAAGCATTTATCAGGGTTATTGTCTCATGAGCGGATACA
TATTTGAATGTATTTAGAAAAATAAACAAATAGGGGTTCCGCGCACAT
TTCCCCGAAAAGTGCCACCTGACGTC The entire transfer plasmid including the derepressible Helper (piHelper1) and TetR expression cassettes was tested for use in AAV production by transient transfection. As shown in FIG. 3, when the plasmids were co-transfected with control pRep-Cap and pAAV-GOI plasmids, the addition of Dox activated the production of AAV to the level of approximately 30% of control Helper vectors that supports constitutive helper gene expression. Therefore, the derepressible helper construct was functional for AAV production upon induction.

Example 2: Design and Validation of Derepressible Rep-Cap Genes

Challenges for producing Rep proteins are two-fold. First, the ratio of Rep78 and Rep52 needs to be maintained during induction for high titer AAV production. Second, the p19 promoter required for Rep52 expression is located inside the coding region of Rep78, which creates challenges for including a derepressible promoter. To overcome these challenges, two strategies were developed (FIGS. 4A-4C).

First, to retain the natural regulation of Rep gene expression (see FIG. 4A), the original viral promoters were retained but modified by inserting two TetO sites surround the TATA box and TSS. Two copies of TetO sites was inserted into the upstream truncated p5 promoter with core elements including TATA box, Rep Binding Element (RBE), and YY1 site. In addition, a wildtype copy of p5 promoter, serving as an enhancer, was placed downstream of cap gene to support both Rep and Cap expression (FIG. 5) (See, e.g., U.S. Pat. No. 5,622,856).

The sequences for the derepressible p5 promoters set forth in FIG. 5 are as follows

```
min-p5-i1
                                        (SEQ ID NO: 3)
TATTTAATCTCCCTATCAGTGATAGAGATCTCCCTATCAGTGATAGAG

ATCGCCCGAGTGAGCACGCAGGGTCTCCATTTTGAAGCGGGAGGTTT

GAACGCGCAGCCGCC

min-p5-i2
                                        (SEQ ID NO: 4)
TATTTAAtcTCCCTATCAGTGATAGAGAtcGCCCGAGTGAGCACGCAG

GGTCTCCATTTTGATCCCTATCAGTGATAGAGAAGCGGGAGGTTTGAA

CGCGCAGCCGCC

min-p5-i3
                                        (SEQ ID NO: 5)
TCCCTATCAGTGATAGAGAtcTATTTAAGCCCGAGTGAGCACGCAGTC

CCTATCAGTGATAGAGAGGTCTCCATTTTGAAGCGGGAGGTTTGAACG

CGCAGCCGCC
```

Similarly, two copies of TetO sites were also inserted into the p19 promoter next to TSS site (FIG. 6). In order to minimize the interference of such insertion and maximize the original activity of these viral promoters, three ways of insertion of TetO sites were designed for each promoter for best performance. Thus, a total of 9 variations were examined (iRepCap1 to iRepCap9).

The sequences for the derepressible promoters including p19 illustrated schematically in FIG. 6 are provided below:

```
p19-i1
                                        (SEQ ID NO: 6)
ccagaaatggcgccggaggcgggaacaaggtggtggatgagtgctaca

tccccaattacttgctccccaaaacccagcctgagctccagtgggcgt

ggactaatatggaacagtatttaagcgcctgTCCCTATCAGTGATAGA

GATCTCCCTATCAGTGATAGAGAtttgaatctcacggag

p19-i2
                                        (SEQ ID NO: 7)
ccagaaatggcgccggaggcgggaacaaggtggtggatgagtgctaca

tccccaattacttgctccccaaaacccagcctgagTCCCTATCAGTG
```

-continued

```
ATAGAGActccagtgggcgtggactaatatggaacagtatttaagcgc

ctgTCCCTATCAGTGATAGAGAtttgaatctcacggag

p19-i3
                                        (SEQ ID NO: 8)
ccagaaatggcgccggaggcgggaacaaggtggtggatgagtgctaca

tccccaattacttgctccccaaaacccagcctgagctccagtgggcg

tggactaatatggaaTCCCTATCAGTGATAGAGAcagtatttaagcgc

ctgTCCCTATCAGTGATAGAGAtttgaatctcacggag
```

Two methods were developed for the placement of the derepressible p19 promoters. In the first method, a separate expression cassette for Rep52 was generated, driven by the derepressible p19 promoters. In the first method shown in FIG. 4B, the original p19 promoter in the Rep78 ORF was silenced by changing six nucleotides in three core regulatory elements required for p19 activity (SP1, TATA-1, and TATA-2 sites). These changes did not alter the Rep78 protein sequence. Rep78 was controlled by a derepressible p5 promoter.

In a second method, an artificial intron was created for the insertion of TetO sites in the Rep78 ORF (FIG. 4C). The chimeric intron between introns from human β-globin and immunoglobulin heavy chain genes was adopted by replacing the non-essential internal sequence with the $TetO_2$ sites (FIG. 7A). The new artificial intron was inserted 1 bp or 25 bp downstream of TATA-2 of p19 promoter in situ (iRepCap-10 and iRepCap11) (FIG. 4B and FIG. 7B). The new p19 promoter with adjacent TetO-containing intron ensured the repression of Rep52 gene expression before induction, while still allowing for the expression of the Rep78 protein after the removal of the intron during mRNA splicing. The efficiency of splicing is evaluated by PCR analysis for the cDNA.

Figure 7A:
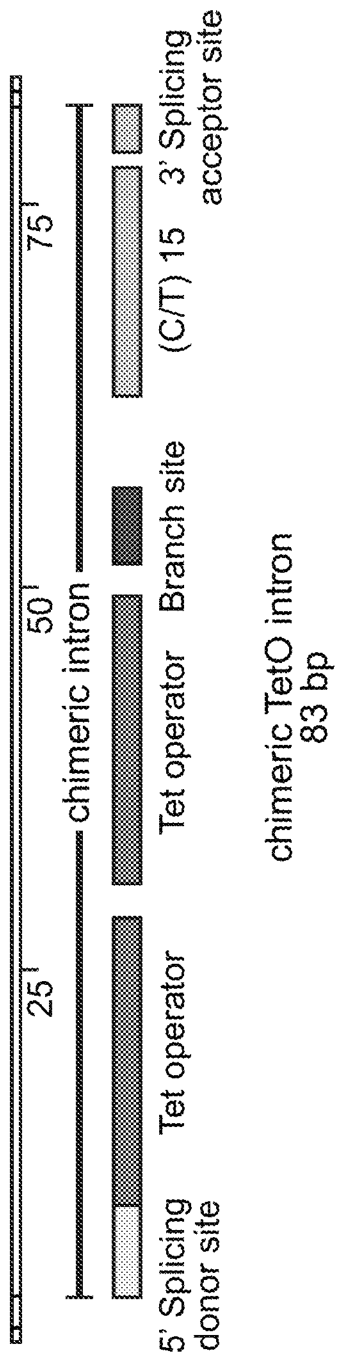
FIG. 7A-7B shows exemplary derepressible p19 promoters, including an artificial intron, in accordance with embodiments hereof.
Figure 7B:
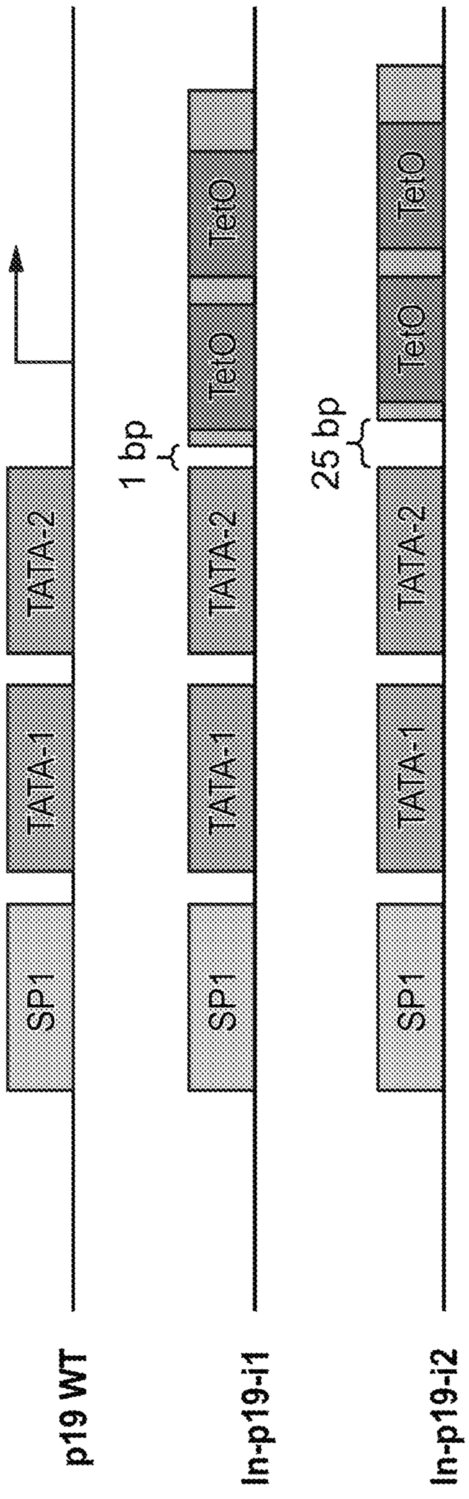

The nucleic acid sequences for the intron-based p19 promoters illustrated in FIGS. 7A-7B are provided below.

```
In-p19-i1
                                        (SEQ ID NO: 9)
ccagaaatggcgccggaggcgggaacaaggtggtggatgagtgctaca

tccccaattacttgctccccaaaacccagcctgagctccagtgggcg

tggactaatatggaacagtatttaaggtaagtTCCCTATCAGTGATAG

AGATCTCCCTATCAGTGATAGAGAtactgacatccactttgcctttct

ctccacagcgcctgtttgaatctcacggag

In-p19-i2
                                        (SEQ ID NO: 10)
ccagaaatggcgccggaggcgggaacaaggtggtggatgagtgctaca

tccccaattacttgctccccaaaacccagcctgagctccagtgggcg

tggactaatatggaacagtatttaagcgcctgtttgaatctcacggaa

aggtaagtTCCCTATCAGTGATAGAGATCTCCCTATCAGTGATAGAGA

tactgacatccactttgcctttctctccacag
```

Figure 8A:
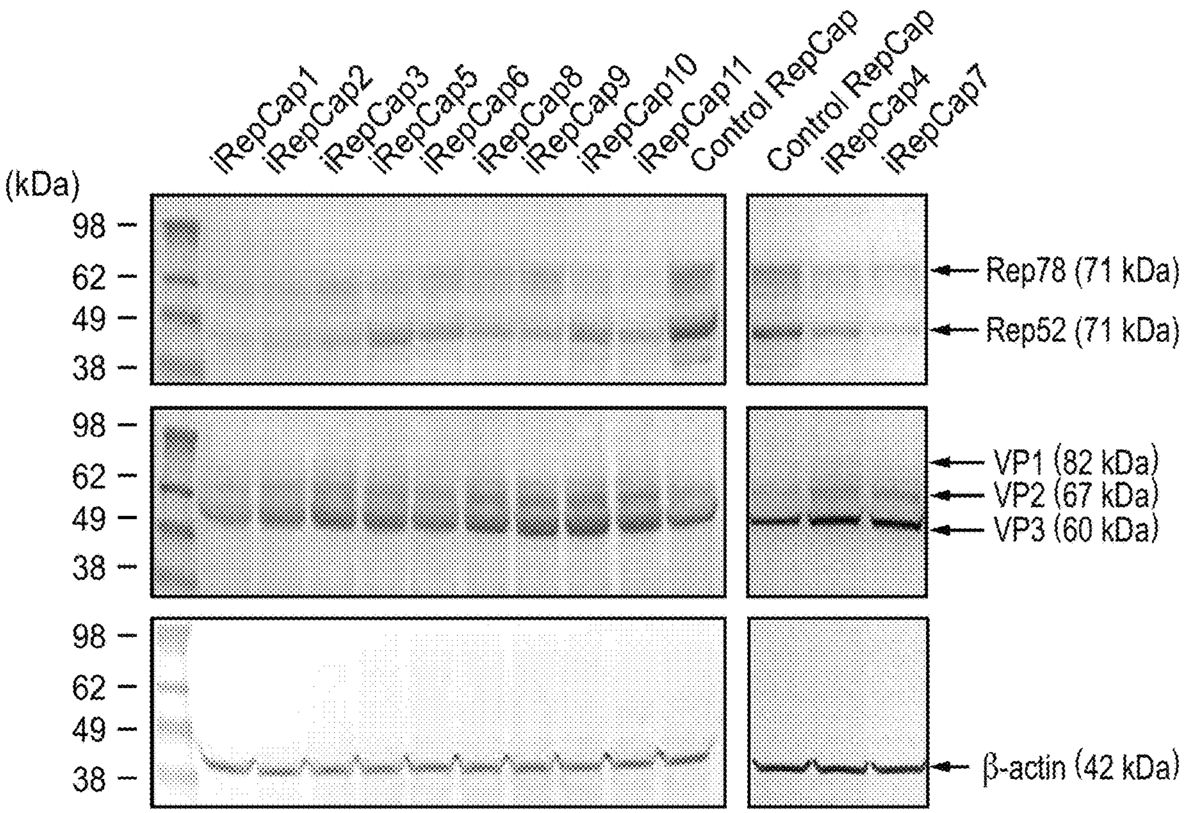
FIGS. 8A-8B show the results of Rep-Cap expression and AAV titers using the Rep-Cap vectors, in accordance with embodiments hereof.
Figure 8B:
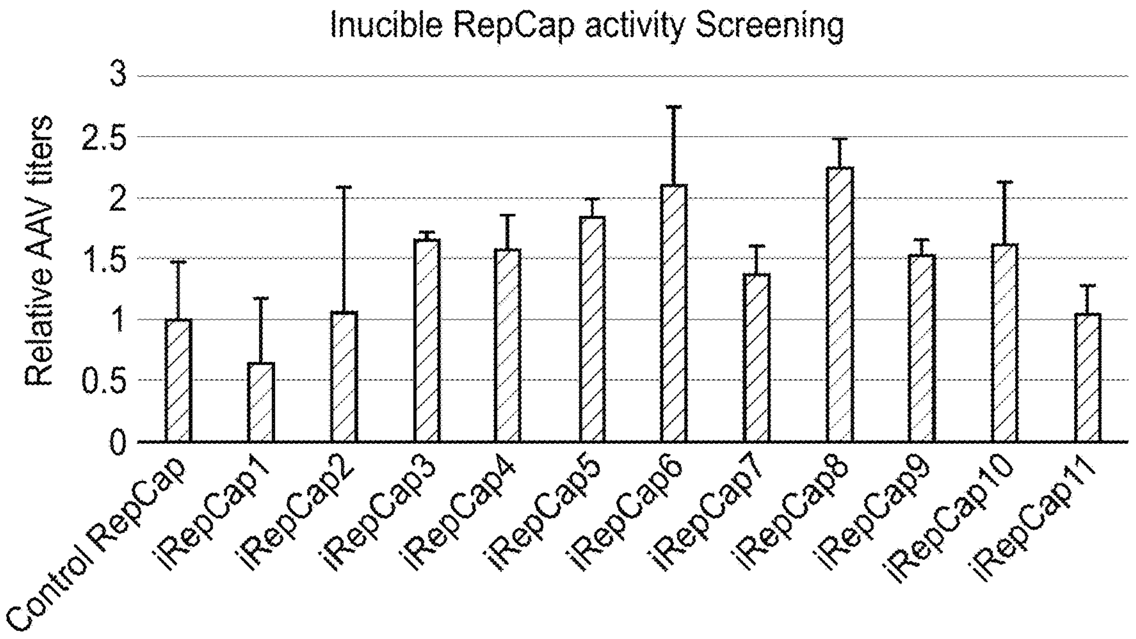

To test the activity of the 11 inducible Rep-Cap designs, HEK293 cells were transfected with one of the vectors plus standard pHelper and pAAV-GFP for AAV production. Three days after transfection, cells were harvested for Rep-Cap protein expression and AAV titer analysis. Western blot analysis revealed various expression levels of Rep and Cap proteins; many maintained similar ratios of Rep78 vs Rep52 as control RepCap vector (FIG. 8A). qPCR analysis of the AAV titer showed that the designs performed similarly or had higher titers compared to control triple transfection (FIG. 8B).

Figure 9A:
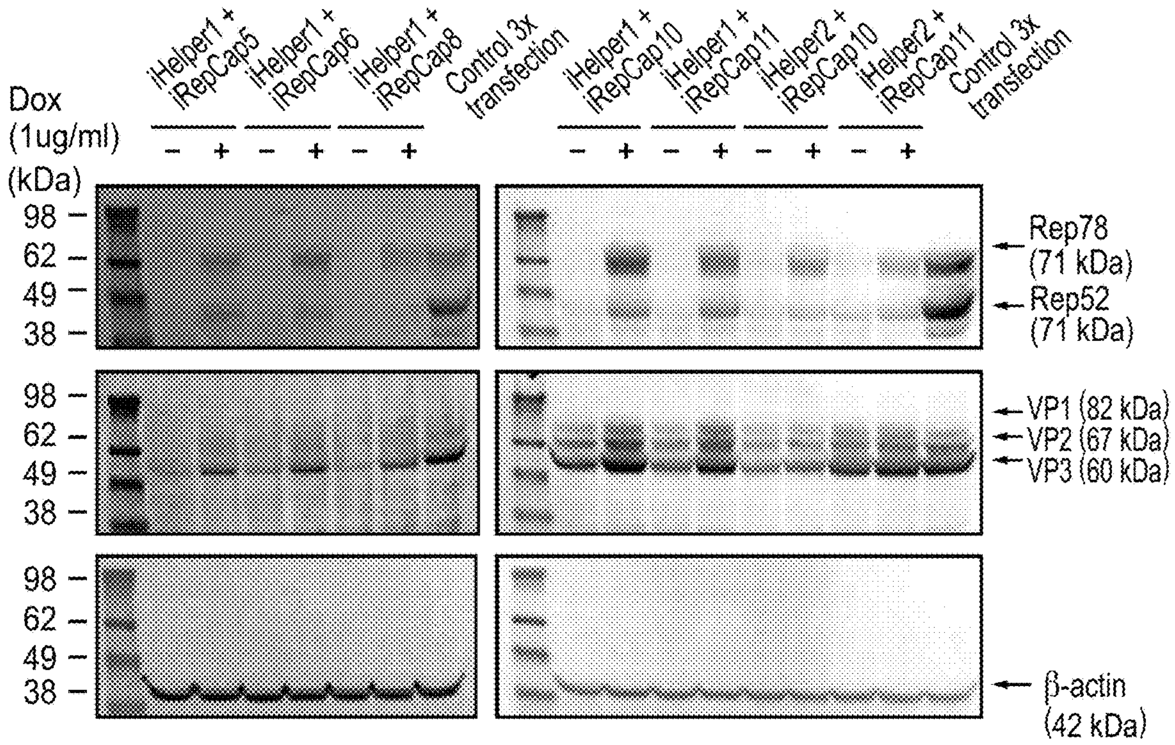
FIGS. 9A-9B show additional results of Rep-Cap expression and AAV titers using the Helpers and Rep-Cap vectors, in accordance with embodiments hereof.
Figure 9B:
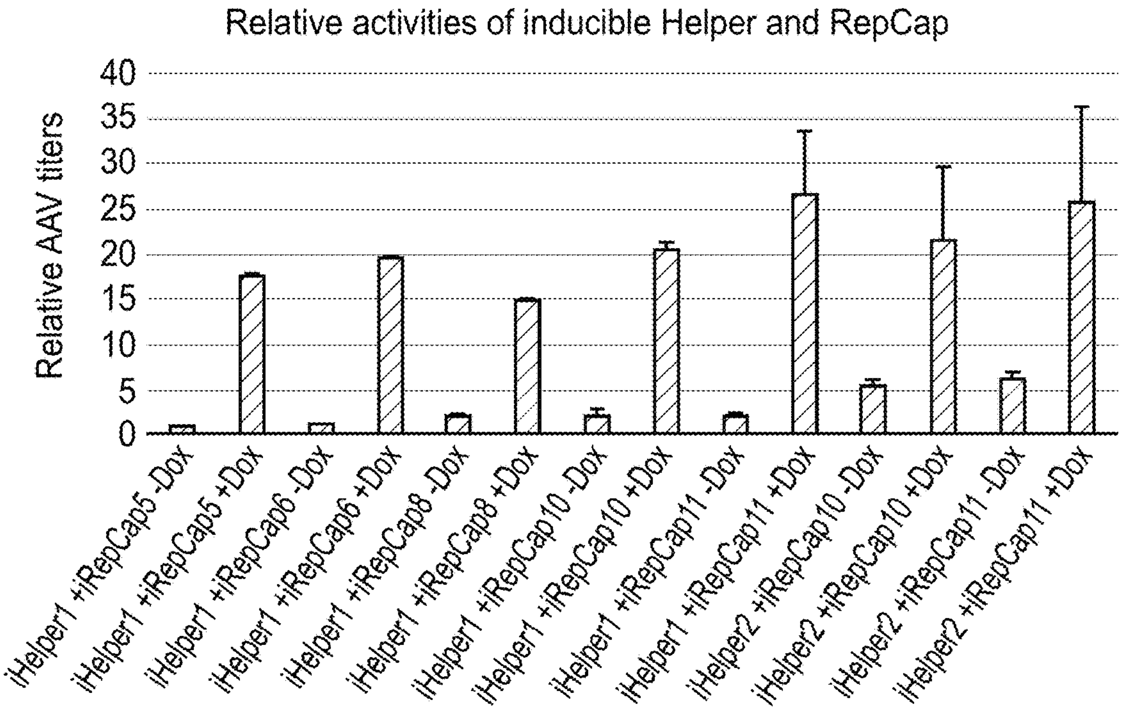

To test the performance of both inducible helpers and inducible Rep-Cap designs together, HEK293 cells were transfected with selected iRepCap vectors, iHelperl/2, and pAAV-GFP, and left untreated or treated with Doxycycline for three days. As shown in FIG. 9A, the protein expression of Rep and Cap was only induced by the addition of Dox, and the derepression of the derepressible promoters. Accordingly, the AAV titer was significantly increased over 10 to 25 fold upon derepression (FIG. 9B).

To stably integrate the iHelper and iRepCap, iHelperl/2 and iRepCap10 were chosen with AAV-GFP to assemble the functional cassettes into a single PIGGYBAC™ transposon transfer vector PB007 (Transposagen, Inc., Lexington, KY). FIGS. 10A-10D show the plasmid constructs used for integration into mammalian cells, suitably HEK293 cells. To facilitate the future addition of specific AAV genes of interest, the AAV-GFP was not included in some of the transfer vectors (FIGS. 10A and 10B). HEK293 cells will be transfected with both the transfer vectors and transposase mRNA and the integrated cell pool will be enriched by puromycin selection. The single cell clones will be isolated and screened for AAV production with and without Dox treatment to activate derepression.

The nucleic acid sequence of the vector illustrated in FIG. 10A is provided below:

```
PB007-iHelper1-iRepCap10/PBBG7 (18,281 bp)
                                    (SEQ ID NO: 11)
ACTCTTCCTTTTTCAATATTATTGAAGCATTTATCAGGGTTATTGTCT
CATGAGCGGATACATATTTGAATGTATTTAGAAAAATAAACAAATAG
GGGTTCCGCGCACATTTCCCCGAAAAGTGCCACCTAAATTGTAAGCGT
TAATATTTTGTTAAAATTCGCGTTAAATTTTTGTTAAATCAGCTCATT
TTTTAACCAATAGGCCGAAATCGGCAAAATCCCTTATAAATCAAAAGA
ATAGACCGAGATAGGGTTGAGTGTTGTTCCAGTTTGGAACAAGAGTCC
ACTATTAAAGAACGTGGACTCCAACGTCAAAGGGCGAAAAACCGTCTA
TCAGGGCGATGGCCCACTACGTGAACCATCACCCTAATCAAGTTTTTT
GGGGTCGAGGTGCCGTAAAGCACTAAATCGGAACCCTAAAGGGAGCCC
CCGATTTAGAGCTTGACGGGGAAAGCCGGCGAACGTGGCGAGAAAGGA
AGGGAAGAAAGCGAAAGGAGCGGGCGCTAGGGCGCTGGCAAGTGTAGC
GGTCACGCTGCGCGTAACCACCACACCCGCCGCGCTTAATGCGCCGCT
ACAGGGCGCGTCCCATTCGCCATTCAGGCTGCGCAACTGTTGGGAAGG
GCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTC
ACGACGTTGTAAAACGACGGCCAGTGAGCGCGCCTCGTTCATTCACGT
TTTTGAACCCGTGGAGGACGGGCAGACTCGCGGTGCAAATGTGTTTTA
CAGCGTGATGGAGCAGATGAAGATGCTCGACACGCTGCAGAACACGCA
GCTAGATTAACCCTAGAAAGATAATCATATTGTGACGTACGTTAAAGA
TAATCATGCGTAAAATTGACGCATGTGTTTTATCGGTCTGTATATCGA
GGTTTATTTATTAATTTGAATAGATATTAAGTTTTATTATATTTACAC
```

-continued

```
TTACATACTAATAATAAATTCAACAAACAATTTATTTATGTTTATTTA
TTTATTAAAAAAAAACAAAAACTCAAAATTTCTTCTATAAAGTAACAA
AACTTTTATCGAATTCCTGCAGCCCGGGGGATCCACTAGTTCTAGAGG
GACAGCCCCCCCCCAAAGCCCCCAGGGATGTAATTACGTCCCTCCCCC
GCTAGGGGGCAGCAGCGAGCCGCCCGGGGCTCCGCTCCGGTCCGGCGC
TCCCCCCGCATCCCCGAGCCGGCAGCGTGCGGGGACAGCCCGGGCACG
GGGAAGGTGGCACGGGATCGCTTTCCTCTGAACGCTTCTCGCTGCTCT
TTGAGCCTGCAGACACCTGGGGGGATACGGGGAAAAGGCCTCCAAGGC
CAGCTTCCCACAATAAGTTGGGTGAATTTTGGCTCATTCCTCCTTTCT
ATAGGATTGAGGTCAGAGCTTTGTGATGGGAATTCTGTGGAATGTGTG
TCAGTTAGGGTGTGGAAAGTCCCgcGATCgcTAGcGTTTAAACTTAAG
CTTGGTACCGAGCTCGGATCCACTAGTCCAGTGTGGTGGAATTCCTGC
TTCGCGATGTACGGGCCAGATATACGCGTTGACATTGATTATTGACTA
GTTATTAATAGTAATCAATTACGGGGTCATTAGTTCATAGCCCATATA
TGGAGTTCCGCGTTACATAACTTACGGTAAATGGCCCGCCTGGCTGAC
CGCCCAACGACCCCCGCCCATTGACGTCAATAATGACGTATGTTCCCA
TAGTAACGCCAATAGGGACTTTCCATTGACGTCAATGGGTGGAGTATT
TACGGTAAACTGCCCACTTGGCAGTACATCAAGTGTATCATATGCCAA
GTACGCCCCCTATTGACGTCAATGACGGTAAATGGCCCGCCTGGCATT
ATGCCCAGTACATGACCTTATGGGACTTTCCTACTTGGCAGTACATCT
ACGTATTAGTCATCGCTATTACCATGGTGATGCGGTTTTGGCAGTACA
TCAATGGGCGTGGATAGCGGTTTGACTCACGGGGATTTCCAAGTCTCC
ACCCCATTGACGTCAATGGGAGTTTGTTTTGGAACCAAAATCAACGGG
ACTTTCCAAAATGTCGTAACAACTCCGCCCCATTGACGCAAATGGGCG
GTAGGCGTGTACGGTGGGAGGTCTATATAAGCAGAGCTCTCCCTATCA
GTGATAGAGATCTCCCTATCAGTGATAGAGATCGTCGACGAGCTCGTT
TAGTGAACCGTCAGATCGCCTGGAGACGCCATCCACGCTGTTTTGACC
TCCATAGAAGACACCGGGACCGATCCAGCCTCCGGACTCTAGCGTTTA
AACTTAAGCTTGCCACCatggccagtcgggaagaggagcagcgcgaaa
ccacccccgagcgcggacgcggtgcggcgcgacgtcccccaaccatgg
aggacgtgtcgtccccgtccccgtcgccgccgcctccccgggcgcccc
caaaaaagcggatgaggcggcgtatcgagtccgaggacgaggaagact
catcacaagacgcgctggtgccgcgcacacccagcccgcggccatcga
cctcggcggcggatttggccattgcgcccaagaagaaaaagaagcgcc
cttctcccaagcccgagcgcccgccatcaccagaggtaatcgtggaca
gcgaggaagaaagagaagatgtggcgctacaaatggtgggtttcagca
acccaccggtgctaatcaagcatggcaaaggaggtaagcgcacagtgc
ggcggctgaatgaagacgacccagtggcgcgtggtatgcggacgcaag
aggaagaggaagagcccagcgaagcggaaagtgaaattacggtgatga
acccgctgagtgtgccgatcgtgtctgcgtgggagaagggcatggagg
```

-continued ctgcgcgcgcgctgatggacaagtaccacgtggataacgatctaaagg
cgaacttcaaactactgcctgaccaagtggaagctctggcggccgtat
gcaagacctggctgaacgaggagcaccgcgggttgcagctgaccttca
ccagcaacaagacctttgtgacgatgatggggcgattcctgcaggcgt
acctgcagtcgtttgcagaggtgacctacaagcatcacgagcccacgg
gctgcgcgttgtggctgcaccgctgcgctgagatcgaaggcgagctta
agtgtctacacggaagcattatgataaataaggagcacgtgattgaaa
tggatgtgacgagcgaaaacgggcagcgcgcgctgaaggagcagtcta
gcaaggccaagatcgtgaagaaccggtggggccgaaatgtggtgcaga
tctccaacaccgacgcaaggtgctgcgtgcacgacgcggcctgtccgg
ccaatcagttttccggcaagtcttgcggcatgttcttctctgaaggcg
caaaggctcaggtggcttttaagcagatcaaggcttttatgcaggcgc
tgtatcctaacgcccagaccgggcacggtcaccttttgatgccactac
ggtgcgagtgcaactcaaagcctgggcacgcgcccttttgggaaggc
agctaccaaagttgactccgttcgccctgagcaacgcggaggacctgg
acgcggatctgatctccgacaagagcgtgctggccagcgtgcaccacc
cggcgctgatagtgttccagtgctgcaaccctgtgtatcgcaactcgc
gcgcgcagggcggaggccccaactgcgacttcaagatatcggcgcccg
acctgctaaacgcgttggtgatggtgcgcagcctgtggagtgaaaact
tcaccgagctgccgcggatggttgtgcctgagtttaagtggagcacta
aacaccagtatcgcaacgtgtccctgccagtggcgcatagcgatgcgc
ggcagaacccctttgattttaacccgggagttctagggatctgcccc
tctccctcccccccccctaacgttactggccgaagccgcttggaataa
ggccggtgtgcgtttgtctatatgttattttccaccatattgccgtct
tttggcaatgtgagggcccggaaacctggccctgtcttcttgacgagc
attcctaggggtctttcccctctcgccaaaggaatgcaaggtctgttg
aatgtcgtgaaggaagcagttcctctggaagcttcttgaagacaaaca
acgtctgtagcgaccctttgcaggcagcggaaccccccacctggcgac
aggtgcctctgcggccaaaagccacgtgtataagatacacctgcaaag
gcggcacaaccccagtgccacgttgtgagttggatagttgtggaaaga
gtcaaatggctctcctcaagcgtattcaacaaggggctgaaggatgcc
cagaaggtaccccattgtatgggatctgatctggggcctcggtgcaca
tgctttacatgtgtttagtcgaggttaaaaaaacgtctaggccccccg
aaccacggggacgtggttttcctttgaaaaacacgatgataaggatcc
accggaggccaccatgactacgtccggcgttccatttggcatgacact
acgaccaacacgatctcggttgtctcggcgcactccgtacagtaggga
tcgtctacctccttttgagacagaaacccgcgctaccatactggagga
tcatccgctgctgcccgaatgtaacactttgacaatgcacaacgtgag
ttacgtgcgaggtcttccctgcagtgtgggatttacgctgattcagga
atgggttgttccctgggatatggttctaacgcgggaggagcttgtaat
cctgaggaagtgtatgcacgtgtgcctgtgttgtgccaacattgatat -continued catgacgagcatgatgatccatggttacgagtcctgggctctccactg
tcattgttccagtcccggttccctgcagtgtatagccggcgggcaggt
tttggccagctggtttaggatggtggtggatggcgccatgtttaatca
gaggtttatatggtaccgggaggtggtgaattacaacatgccaaaaga
ggtaatgtttatgtccagcgtgtttatgaggggtcgccacttaatcta
cctgcgcttgtggtatgatggccacgtgggttctgtggtccccgccat
gagctttggatacagcgccttgcactgtgggatttgaacaatattgt
ggtgctgtgctgcagttactgtgctgatttaagtgagatcagggtgcg
ctgctgtgcccggaggacaaggcgccttatgctgcgggcggtgcgaat
catcgctgaggagaccactgccatgttgtattcctgcaggacggagcg
gcggcggcagcagtttattcgcgcgctgctgcagcaccaccgccctat
cctgatgcacgattatgactctaccccccatgtagGCGGCCGCTCGAGT
CTAGAGGGCCCGTTTAAACCCGCTGATCAGCCTCGACTGTGCCTTCTA
GTTGCCAGCCATCTGTTGTTTGCCCCTCCCCCGTGCCTTCCTTGACCC
TGGAAGGTGCCACTCCCACTGTCCTTTCCTAATAAAATGAGGAAATTG
CATCGCATTGTCTGAGTAGGTGTCATTCTATTCTGGGGGGTGGGGTGG
GGCAGGACAGCAAGGGGGAGGATTGGGAAGACAATAGCAGGCATGCTG
GGGATGCGGTGGGCTCTATGGCTTCTGAGGCGGAAAGAACCAGCTGGG
GCTCTAGGGGGTATCCCCggggttggggttgcgccttttccaaggcAT
CCAGCACAGTGGCGGCCGCaatatttgcatgtcgctatgtgttctggg
aaatcaccataaacgtgaaatccctatcagtgatagagacttataagt
tccctatcagtgatagagaaccggtgggcactcttccgtggtctggtg
gataaattcgcaagggtatcatggcggacgaccggggttcgagccccg
tatccggccgtccgccgtgatccatgcggttaccgcccgcgtgtcgaa
cccaggtgtgcgacgtcagacaacgggggagtgctcctttttgaattc
cactttggccgcggctcgaggggggttggggttgcgccttttccaaggc
agccctgggtttgcgcagggacgcggctgctctgggcgtggttccggg
aaacgcagcggcgccgaccctgggtctcgcacattcttcacgtccgtt
cgcagcgtcacccggatcttcgccgctacccttgtgggccccccggcg
acgcttcctgctccgcccctaagtcgggaaggttccttgcggttcgcg
gcgtgccggacgtgacaaacggaagccgcacgtctcactagtaccctc
gcagacggacagcgccagggagcaatggcagcgcgccgaccgcgatgg
gctgtggccaatagcggctgctcagcagggcgcgccgagagcagcggc
cgggaaggggcggtgcgggggggggtgtggggcggtagtgtgggccct
gttcctgcccgcgcggtgttccgcattctgcaagcctccggagcgcac
gtcggcagtcggctccctcgttgaccgaatcaccgacctctctcccca
gggggatctgtgagtttggggacccttgattgttctttctttttcgct
attgtaaaattcatgttatatggagggggcaaagttttcagggtgttg
tttagaatggggatgtcccttgtatcaccatggaccctcatgataatt
ttgtttctttcactttctactctgttgacaaccattgtctcctcttat -continued

```
tttcttttcattttctgtaactttttcgttaaactttagcttgcattt
gtaacgaatttttaaattcacttttgtttatttgtcagattgtaagta
ctttctctaatcacttttttttcaaggcaatcagggtatattatattg
tacttcagcacagttttagagaacaattgttataattaaatgataagg
tagaatatttctgcatataaattctggctggcgtggaaatattcttat
tggtagaaacaactacatcctggtcatcatcctgcctttctctttatg
gttacaatgatatacactgtttgagatgaggataaaatactctgagtc
caaaccgggcccctctgctaaccatgttcatgccttcttctttttcct
acagctcctgggcaacgtgctggttattgtgctgtctcatcattttgg
caaagaattgtaatacgactcactatagggcgaGCCACCatggctaga
ttagataaaagtaaagtgattaacagcgcattagagctgcttaatgag
gtcggaatcgaaggtttaacaacccgtaaactcgcccagaagetaggt
gtagagcagcctacattgtattggcatgtaaaaaataagcgggctttg
ctcgacgccttagccattgagatgttagataggcaccatactcacttt
tgccctttagaaggggaaagctggcaagatttttacgtaataacgct
aaaagttttagatgtgctttactaagtcatcgcgatggagcaaaagta
catttaggtacacggcctacagaaaaacagtatgaaactctcgaaaat
caattagcctttttatgccaacaaggtttttcactagagaatgcCtta
tatgcactcagcgcCgtggggcattttactttaggttgcgtattggaa
gatcaagagcatcaagtcgctaaagaagaaagggaaacacctactact
gatagtatgccgccattattacgacaagctatcgaattatttgatcac
caaggtgcagagccagccttcttattcggccttgaattgatcatatgc
ggattagaaaaacaacttaaatgtgaaagtgggtccccaaaaaagaag
agaaaggtcgacggcggtggtgctttgtctcctcagcactctgctgtc
actcaaggaagtatcatcaagaacaaggagggcatggatgctaagtca
ctaactgcctggtcccggacactggtgaccttcaaggatgtatttgtg
gacttcaccagggaggagtggaagctgctggacactgctcagcagatc
gtgtacagaaatgtgatgctggagaactataagaacctggtttccttg
ggttatcagcttactaagccagatgtgatcctccggttggagaaggga
gaagagccctggctggtggagagagaaattcaccaagagacccatcct
gattcagagactgcatttgaaatcaaatcatcagtttaagcgtacage
ggctcccgggagttctagggatctgcccctctccctcccccccccta
acgttactggccgaagccgcttggaataaggccggtgtgcgtttgtct
atatgttattttccaccatattgccgtcttttggcaatgtgagggccc
ggaaacctggccctgtcttcttgacgagcattcctaggggtctttccc
ctctcgccaaaggaatgcaaggtctgttgaatgtcgtgaaggaagcag
ttcctctggaagcttcttgaagacaaacaacgtctgtagcgaccettt
gcaggcagcggaacccccacctggcgacaggtgcctctgcggccaaa
agccacgtgtataagatacacctgcaaaggcggcacaaccccagtgcc
acgttgtgagttggatagttgtggaaagagtcaaatggctctcctcaa
gcgtattcaacaaggggctgaaggatgcccagaaggtaccccattgta
```

-continued

```
tgggatctgatctggggcctcggtgcacatgctttacatgtgtttagt
cgaggttaaaaaaacgtctaggccccccgaaccacggggacgtggttt
tcctttgaaaaacacgatgataaggatccaccggagGCCACCatgacc
gagtacaagcccacggtgcgcctcgccacccgcgacgacgtccccagg
gccgtacgcaccctcgccgccgcgttcgccgactaccccgccacgcgc
cacaccgtcgatccggaccgccacatcgagcgggtcaccgagctgcaa
gaactcttcctcacgcgcgtcgggctcgacatcggcaaggtgtgggtc
gcggacgacggcgccgcggtggcggtctggaccacgccggagagcgtc
gaagcgggggcggtgttcgccgagatcggcccgcgcatggccgagttg
agcggttcccggctggccgcgcagcaacagatggaaggcctcctggcg
ccgcaccggcccaaggagcccgcgtggttcctggccaccgtcggcgtc
tcgcccgaccaccagggcaagggtctgggcagcgccgtcgtgctcccc
ggagtggaggcggccgagcgcgccggggtgcccgccttcctggagacc
tccgcgccccgcaacctccccttctacgagcggctcggcttcaccgtc
accgccgacgtcgaggtgcccgaaggaccgcgcacctggtgcatgacc
cgcaagcccggtgcctgaCCGCGTCTGGAACAATCAACCTCTGGATTA
CAAAATTTGTGAAAGATTGACTGGTATTCTTAACTATGTTGCTCCTTT
TACGCTATGTGGATACGCTGCTTTAATGCCTTTGTATCATGCTATTGC
TTCCCGTATGGCTTTCATTTTCTCCTCCTTGTATAAATCCTGGTTGCT
GTCTCTTTATGAGGAGTTGTGGCCCGTTGTCAGGCAACGTGGCGTGGT
GTGCACTGTGTTTGCTGACGCAACCCCCACTGGTTGGGGCATTGCCAC
CACCTGTCAGCTCCTTTCCGGGACTTTCGCTTTCCCCCTCCCTATTGC
CACGGCGGAACTCATCGCCGCCTGCCTTGCCCGCTGCTGGACAGGGGC
TCGGCTGTTGGGCACTGACAATTCCGTGGTGTTGTCGGGGAAGCTGAC
GTCCTTTCCATGGCTGCTCGCCTGTGTTGCCACCTGGATTCTGCGCGG
GACGTCCTTCTGCTACGTCCCTTCGGCCCTCAATCCAGCGGACCTTCC
TTCCCGCGGCCTGCTGCCGGCTCTGCGGCCTCTTCCGCGTCTTCGCCT
TCGCCCTCAGACGAGTCGGATCTCCCTTTGGGCCGCCTCCCCGCaAAA
TGACCGACCAAGCGACGCCCAACCTGCCATCACGAGATTTCGATTCCA
CCGCCGCCTTCTATGAAAGGTTGGGCTTCGGAATCGTTTTCCGGGACG
CCGGCTGGATGATCCTCCAGCGCGGGGATCTCATGCTGGAGTTCTTCG
CCCACCCCAACTTGTTTATTGCAGCTTATAATGGTTACAAATAAAGCA
ATAGCATCACAAATTTCACAAATAAAGCATTTTTTTCACTGCATTCTA
GTTGTGGTTTGTCCAAACTCATCAATGTATCTTATCATGTCTGTAGCt
GATcaATTgGCGCGCCGAATTCGTTatctgcagaattcggcttggcgg
ctgcgcgttcaaacctcccgcttcaaaatggagaccctgcgtgctcac
tcgggcttaaatacccagcgtgaccacatggtgtcgcaaaatgtcgca
aaacactcacgtgacctctaatacaggacctctagagcatggaaacta
gataagaaagaaatacgcagagaccaaagttcaactgaaacgaattaa
acggtttattgattaacaagcaaactagtttacagattacgggtgagg
```

taacgggtgccgatggggcgaggctcagaataaacgccatttgtgtca acagcaaagtccacatttgtagatttgttgtagttggaagtgtattga atctctgggttccagcgtttgctgttttctttctgcagctcccattca atttccacgctgacctgtccggtgctgtactgcgtgatgaacgacgca aacttagctggactgaaggtagttggaggattcgcgggaacaggtgta ttcttaatcaggatctgaggaggcgggtgtttcagtccaaagcctccc atcagcggcgagggatgaaagtgtccgtccgtgtgaggaatcttggcc cagataggaccctgcaggtacacgtcccggtcctgccagaccatgcca ggtaaggctccttgactgttgacggtccctgtagcaggagcggtgttg gccgattgcaggttagtggccaccgtgccgtactcttctgtggccact gggttggtggttttaatttcttcctcgttggttatcataacgttgtca aggtccacgttgctatttccagctccctgtttcccaaatattaagact ccgctcatcggaaaaaatttgtcttcgtcgtccttgtgggttgccata gcgggaccgggatttaccagagagtctctgccattcagatgatacttg gtggcaccggtccaggcaaagttgctgttgttattttgattggttgtc ttggagacgcgttgctgccggtagcagggcccgggtagccagtttttg gcctgattcgccatgctactaggcccggcctgagaaaattgcaacgtc cgatttcctgcggtaccactcgtggtctgagtccgagacaggtagtac aggtactggtcgatgaggggttcatcagccggtccaggctttggctg tgcgcgtagctgctgtgaaaaggcacgtcctcaaacgtgtagctgaac tgaaagttgttgcccgttctcagcatttgagaaggaaagtattccagg cagtagaaggaggaacggcccacggcctgactgccattgttcagagtc aggtacccgtactgaggaatcatgaagacgtccgccgggaacggaggc aggcagccctggtgcgcagagccgaggacgtacgggagctggtattcc gagtccgtaaagacctgaaccgtgctggtaaggttattggcgatggtc gtggtgccatcattcgtcgtgacctccttgacctggatgttgaagagc ttgaagttgagcttcttgggccggaatccccagttgttgttgatgagt cgctgccagtcacgtggtgagaagtggcagtggaatctgttaaagtca aaatacccccaggggggtgctgtagccgaagtaggtgttgtcgttggtg ctgcctcccgattggctggagatttgcttgtagaggtggttgttgtag gtggggagggcccaggttcgggtgctggtggtgatgactctgtcgccc agccatgtggaatcgcaatgccaatttcctgaggcgttacccactccg tcggcgccttcgttattgtctgccattggagcgccaccgcctgcagcc attgtattagatcccacaccagaggggggctgcgggggggttctccgagt ggttgagggtcgggcactgactctgagtcgccagtctgcccaaagttg agtctctttctcgcgggctgctggcctttcttgccgatgcccgaagag gagtctggttcctggggtgattgctctaccggtctcttctttccagga gccgtcttagcgccttcctcaaccagaccgagaggttcgagaacccgc ttcttggcctggaagactgctcgcccgaggttgcccccaaaagacgta tcttcttgcagacgctcctgaaactcggcgtcggcgtggttataccgc aggtacggattgtcacccgctttgagctgctggtcgtaggccttgtcg tgctcgagggccgctgcgtccgccgcgttgacgggctccccccttgtcg agtccgttgaagggtccgaggtacttgtagccaggaagcaccagaccc cggccgtcgtcctgcttttgctggttggctttgggtttcggggctcca ggtttcaagtcccaccactcgcgaatgccctcagagaggttgtcctcg agccaatctggaagataaccatcggcagccatacctgatttaaatcat ttattgttcaaagatgcagtcatccaaatccacattgaccagatcgca ggcagtgcaagcgtctggcacctttcccatgatatgatgaatgtagca cagtttctgatacgcctttttgacgacagaaacgggttgagattctga cacgggaaagcactctaaacagtctttctgtccgtgagtgaagcagat atttgaattctgattcattctctcgcattgtctgcagggaaacagcat cagattcatgcccacgtgacgagaacatttgttttggtacctgtctgc gtagttgatcgaagcttccgcgtctgacgtcgatggctgcgcaactga ctcgcgcacccgtttgggctcacttatatctgcgtcactgggggggt cttttcttggctccacccttttttgacgtagaattcatgctccacctca accacgtgatcctttgcccaccggaaaaagtctttgacttcctgcttg gtgaccttcccaaagtcatgatccagacggcgggtgagttcaaatttg aacatccggtcttgcaacggctgctggtgttcgaaggtcgttgagttc ccgtcaatcacggcgcacatgttggtgttggaggtgacgatcacggga gtcgggtctatctgggccgaggacttgcatttctggtccacgcgcacc ttgcttcctccgagaatggctttggccgactccacgaccttggcggtc atcttcccctcctcccaccagatcaccatcttgtcgacacagtcgttg aagggaaagttctcattggtccagtttacgcacccgtagaagggcaca gtgtgggctatggcctccgcgatgttggtcttcccggtagttgcaggc ccaaacagccagatggtgttcctcttgccgaactttttcgtggcccat cccagaaagacggaagccgcatattggggatcgtacccgtttagttcc aaaattttataaatccgattgctggaaatgtcctccacgggctgctgg cccaccaggtagtcgggggcggttttagtcaggctcataatctttccc gcattgtccaaggcagccttgatttgggaccgcgagttggaggccgca ttgaaggagatgtatgaggcctggtcctcctggatccactgcttctcc gaggtaatccccttgtccacgagccacccgaccagctccatgtacctg gctgaagtttttgatctgatcaccggcgcatcagaattgggattctga ttctctttgttctgctcctgcgtctgcgacacgtgcgtcagatgctgc gccaccaaccgtttacgctccgtgagattcaaacaggcgctgtggaga gaaaggcaaagtggatgtcagtaTCTCTATCACTGATAGGGAGATCTC TATCACTGATAGGGAacttaccttaaatactgttccatattagtccac gcccactggagctcaggctgggttttggggagcaagtaattggggatg tagcactcatccaccaccttgttcccgcctccggcgccatttctggtc tttgtgaccgcgaaccagtttggcaaagtcggctcgatcccgcggtaa attctctgaatcagtttttcgcgaatctgactcaggaaacgtcccaaa accatggatttcaccccggtggtttccacgagcacgtgcatgtggaag -continued

```
tagctctctcccttctcaaattgcacaaagaaaagagcctccggggcc

ttactcacacggcgccattccgtcagaaagtcgcgctgcagcttctcg

gccacggtcaggggtgcctgctcaatcagattcagatccatgtcagaa

tctggcggcaactcccattccttctcggccacccagttcacaaagctg

tcagaaatgccgggcagatgctcgtcaaggtcgctggggaccttaatc

acaatctcgtaaaaccccggcatGGCGGCTGCGCGTTCAAACCTCCCG

CTTCAAAATGGAGACCCTGCGTGCTCACTCGGGCgaTCTCTATCACTG

ATAGGGAGATCTCTATCACTGATAGGGAgaTTAAATAgaatggCTAgg

ATCCGGCCGGccTGCAggTGTCCTCACAGGAACGAAGTCCCTAAAGAA

ACAGTGGCAGCCAGGTTTAGCCCCGGAATTGACTGGATTCCTTTTTTA

GGGCCCATTGGTATGGCTTTTTCCCCGTATCCCCCCAGGTGTCTGCAG

GCTCAAAGAGCAGCGAGAAGCGTTCAGAGGAAAGCGATCCCGTGCCAC

CTTCCCCGTGCCCGGGCTGTCCCCGCACGCTGCCGGCTCGGGGATGCG

GGGGGAGCGCCGGACCGGAGCGGAGCCCCGGGCGGCTCGCTGCTGCCC

CCTAGCGGGGGAGGGACGTAATTACATCCCTGGGGGCTTTGGGGGGGG

GCTGTCCCTCTAGAGCGGCCGCCACCGCGGTGGAGCTCCAGCTTTTGT

TCCCTTTAGTGAGGGTTAATTAGATCTTAATACGACTCACTATAGGGC

GAATTGGGTACCGGGCCCCCCCTCGAGGTCGACGGTATCGATAAGCTT

GATATCTATAACAAGAAAATATATATATAATAAGTTATCACGTAAGTA

GAACATGAAATAACAATATAATTATCGTATGAGTTAAATCTTAAAAGT

CACGTAAAAGATAATCATGCGTCATTTTGACTCACGCGGTCGTTATAG

TTCAAAATCAGTGACACTTACCGCATTGACAAGCACGCCTCACGGGAG

CTCCAAGCGGCGACTGAGATGTCCTAAATGCACAGCGACGGATTCGCG

CTATTTAGAAAGAGAGAGCAATATTTCAAGAATGCATGCGTCAATTTT

ACGCAGACTATCTTTCTAGGGTTAATCTAGCTGCATCAGGATCATATC

GTCGGGTCTTTTTTCCGGCTCAGTCATCGCCCAAGCTGGCGCTATCTG

GGCATCGGGGAGGAAGAAGCCCGTGCCTTTTCCCGCGAGGTTGAAGCG

GCATGGAAAGAGTTTGCCGAGGATGACTGCTGCTGCATTGACGTTGAG

CGAAAACGCACGTTTACCATGATGATTCGGGAAGGTGTGGCCATGCAC

GCCTTTAACGGTGAACTGTTCGTTCAGGCCACCTGGGATACCAGTTCG

TCGCGGCTTTTCCGGACACAGTTCCGGATGGTCAGCCCGAAGCGCATC

AGCAACCCGAACAATACCGGCGACAGCCGGAACTGCCGTGCCGGTGTG

CAGATTAATGACAGCGGTGCGGCGCTGGGATATTACGTCAGCGAGGAC

GGGTATCCTGGCTGGATGCCGCAGAAATGGACATGGATACCCCGTGAG

TTACCCGGCGGGCGCGCTTGGCGTAATCATGGTCATAGCTGTTTCCTG

TGTGAAATTGTTATCCGCTCACAATTCCACACAACATACGAGCCGGAA

GCATAAAGTGTAAAGCCTGGGGTGCCTAATGAGTGAGCTAACTCACAT

TAATTGCGTTGCGCTCACTGCCCGCTTTCCAGTCGGGAAACCTGTCGT

GCCAGCTGCATTAATGAATCGGCCAACGCGCGGGGAGAGGCGGTTTGC

GTATTGGGCGCTCTTCCGCTTCCTCGCTCACTGACTCGCTGCGCTCGG

TCGTTCGGCTGCGGCGAGCGGTATCAGCTCACTCAAAGGCGGTAATAC
```

-continued

```
GGTTATCCACAGAATCAGGGGATAACGCAGGAAAGAACATGTGAGCAA

AAGGCCAGCAAAAGGCCAGGAACCGTAAAAAGGCCGCGTTGCTGGCGT

TTTTCCATAGGCTCCGCCCCCCTGACGAGCATCACAAAAATCGACGCT

CAAGTCAGAGGTGGCGAAACCCGACAGGACTATAAAGATACCAGGCGT

TTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTT

CTCATAGCTCACGCTGTAGGTATCTCAGTTCGGTGTAGGTCGTTCGCT

CCAAGCTGGGCTGTGTGCACGAACCCCCCGTTCAGCCCGACCGCTGCG

CCTTATCCGGTAACTATCGTCTTGAGTCCAACCCGGTAAGACACGACT

TATCGCCACTGGCAGCAGCCACTGGTAACAGGATTAGCAGAGCGAGGT

ATGTAGGCGGTGCTACAGAGTTCTTGAAGTGGTGGCCTAACTACGGCT

ACACTAGAAGGACAGTATTTGGTATCTGCGCTCTGCTGAAGCCAGTTA

CCTTCGGAAAAAGAGTTGGTAGCTCTTGATCCGGCAAACAAACCACCG

CTGGTAGCGGTGGTTTTTTTGTTTGCAAGCAGCAGATTACGCGCAGAA

AAAAAGGATCTCAAGAAGATCCTTTGATCTTTTCTACGGGGTCTGACG

CTCAGTGGAACGAAAACTCACGTTAAGGGATTTTGGTCATGAGATTAT

CAAAAAGGATCTTCACCTAGATCCTTTTAAATTAAAAATGAAGTTTTA

AATCAATCTAAAGTATATATGAGTAAACTTGGTCTGACAGTTACCAAT

GCTTAATCAGTGAGGCACCTATCTCAGCGATCTGTCTATTTCGTTCAT

CCATAGTTGCCTGACTCCCCGTCGTGTAGATAACTACGATACGGGAGG

GCTTACCATCTGGCCCCAGTGCTGCAATGATACCGCGAGACCCACGCT

CACCGGCTCCAGATTTATCAGCAATAAACCAGCCAGCCGGAAGGGCCG

AGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGC

GCAACGTTGTTGCCATTGCTACAGGCATCGTGGTGTCACGCTCGTCGT

TTGGTATGGCTTCATTCAGCTCCGGTTCCCAACGATCAAGGCGAGTTA

CATGATCCCCCATGTTGTGCAAAAAAGCGGTTAGCTCCTTCGGTCCTC

CGATCGTTGTCAGAAGTAAGTTGGCCGCAGTGTTATCACTCATGGTTA

TGGCAGCACTGCATAATTCTCTTACTGTCATGCCATCCGTAAGATGCT

TTTCTGTGACTGGTGAGTACTCAACCAAGTCATTCTGAGAATAGTGTA

TGCGGCGACCGAGTTGCTCTTGCCCGGCGTCAATACGGGATAATACCG

CGCCACATAGCAGAACTTTAAAAGTGCTCATCATTGGAAAACGTTCTT

CGGGGCGAAAACTCTCAAGGATCTTACCGCTGTTGAGATCCAGTTCGA

TGTAACCCACTCGTGCACCCAACTGATCTTCAGCATCTTTTACTTTCA

CCAGCGTTTCTGGGTGAGCAAAAACAGGAAGGCAAAATGCCGCAAAAA

AGGGAATAAGGGCGACACGGAAATGTTGAATACTCAT
```

The sequence of the vector illustrated in FIG. 10B is provided below.

PB007-iHelper2-iRepCap10/PBBG8 (17,936 bp) (SEQ ID NO: 12)

```
ACTCTTCCTTTTTCAATATTATTGAAGCATTTATCAGGGTTATTGTCT
CATGAGCGGATACATATTTGAATGTATTTAGAAAAATAAACAAATAG
GGGTTCCGCGCACATTTCCCCGAAAAGTGCCACCTAAATTGTAAGCGT
TAATATTTTGTTAAAATTCGCGTTAAATTTTTGTTAAATCAGCTCATT
TTTTAACCAATAGGCCGAAATCGGCAAAATCCCTTATAAATCAAAAGA
ATAGACCGAGATAGGGTTGAGTGTTGTTCCAGTTTGGAACAAGAGTCC
ACTATTAAAGAACGTGGACTCCAACGTCAAAGGGCGAAAAACCGTCTA
TCAGGGCGATGGCCCACTACGTGAACCATCACCCTAATCAAGTTTTTT
GGGGTCGAGGTGCCGTAAAGCACTAAATCGGAACCCTAAAGGGAGCCC
CCGATTTAGAGCTTGACGGGGAAAGCCGGCGAACGTGGCGAGAAAGGA
AGGGAAGAAAGCGAAAGGAGCGGGCGCTAGGGCGCTGGCAAGTGTAGC
GGTCACGCTGCGCGTAACCACCACACCCGCCGCGCTTAATGCGCCGCT
ACAGGGCGCGTCCCATTCGCCATTCAGGCTGCGCAACTGTTGGGAAGG
GCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTC
ACGACGTTGTAAAACGACGGCCAGTGAGCGCGCCTCGTTCATTCACGT
TTTTGAACCCGTGGAGGACGGGCAGACTCGCGGTGCAAATGTGTTTTA
CAGCGTGATGGAGCAGATGAAGATGCTCGACACGCTGCAGAACACGCA
GCTAGATTAACCCTAGAAAGATAATCATATTGTGACGTACGTTAAAGA
TAATCATGCGTAAAATTGACGCATGTGTTTTATCGGTCTGTATATCGA
GGTTTATTTATTAATTTGAATAGATATTAAGTTTTATTATATTTACAC
TTACATACTAATAATAAATTCAACAAACAATTTATTTATGTTTATTTA
TTTATTAAAAAAAAACAAAAACTCAAAATTTCTTCTATAAAGTAACAA
AACTTTTATCGAATTCCTGCAGCCCGGGGGATCCACTAGTTCTAGAGG
GACAGCCCCCCCCCAAAGCCCCCAGGGATGTAATTACGTCCCTCCCCC
GCTAGGGGGCAGCAGCGAGCCGCCCGGGGCTCCGCTCCGGTCCGGCGC
TCCCCCCGCATCCCCGAGCCGGCAGCGTGCGGGGACAGCCCGGGCACG
GGGAAGGTGGCACGGGATCGCTTTCCTCTGAACGCTTCTCGCTGCTCT
TTGAGCCTGCAGACACCTGGGGGGATACGGGGAAAAGGCCTCCAAGGC
CAGCTTCCCACAATAAGTTGGGTGAATTTTGGCTCATTCCTCCTTTCT
ATAGGATTGAGGTCAGAGCTTTGTGATGGGAATTCTGTGGAATGTGTG
TCAGTTAGGGTGTGGAAAGTCCCgcGATCgcTAGcGTTTAAACTTAAG
CTTGGTACCGAGCTCGGATCCACTAGTCCAGTGTGGTGGAATTCCTGC
TTCGCGATGTACGGGCCAGATATACGCGTTGACATTGATTATTGACTA
GTTATTAATAGTAATCAATTACGGGGTCATTAGTTCATAGCCCATATA
TGGAGTTCCGCGTTACATAACTTACGGTAAATGGCCCGCCTGGCTGAC
CGCCCAACGACCCCCGCCCATTGACGTCAATAATGACGTATGTTCCCA
TAGTAACGCCAATAGGGACTTTCCATTGACGTCAATGGGTGGAGTATT
```

-continued

```
TACGGTAAACTGCCCACTTGGCAGTACATCAAGTGTATCATATGCCAA
GTACGCCCCCTATTGACGTCAATGACGGTAAATGGCCCGCCTGGCATT
ATGCCCAGTACATGACCTTATGGGACTTTCCTACTTGGCAGTACATCT
ACGTATTAGTCATCGCTATTACCATGGTGATGCGGTTTTGGCAGTACA
TCAATGGGCGTGGATAGCGGTTTGACTCACGGGGATTTCCAAGTCTCC
ACCCCATTGACGTCAATGGGAGTTTGTTTTGGAACCAAAATCAACGGG
ACTTTCCAAAATGTCGTAACAACTCCGCCCCATTGACGCAAATGGGCG
GTAGGCGTGTACGGTGGGAGGTCTATATAAGCAGAGCTCTCCCTATCA
GTGATAGAGATCTCCCTATCAGTGATAGAGATCGTCGACGAGCTCGTT
TAGTGAACCGTCAGATCGCCTGGAGACGCCATCCACGCTGTTTTGACC
TCCATAGAAGACACCGGGACCGATCCAGCCTCCGGACTCTAGCGTTTA
AACTTAAGCTTGCCACCatggccagtcgggaagaggagcagcgcgaaa
ccacccccgagcgcggacgcggtgcggcgcgacgtcccccaaccatgg
aggacgtgtcgtccccgtccccgtcgccgccgcctccccgggcgcccc
caaaaaagcggatgaggcggcgtatcgagtccgaggacgaggaagact
catcacaagacgcgctggtgccgcgcacacccagcccgcggccatcga
cctcggcggcggatttggccattgcgcccaagaagaaaaagaagcgcc
cttctcccaagcccgagegcccgccatcaccagaggtaatcgtggaca
gcgaggaagaaagagaagatgtggcgctacaaatggtgggtttcagca
acccaccggtgctaatcaagcatggcaaaggaggtaagcgcacagtgc
ggcggctgaatgaagacgacccagtggcgcgtggtatgcggacgcaag
aggaagaggaagagcccagcgaagcggaaagtgaaattacggtgatga
acccgctgagtgtgccgatcgtgtctgcgtgggagaagggcatggagg
ctgcgcgcgcgctgatggacaagtaccacgtggataacgatctaaagg
cgaacttcaaactactgcctgaccaagtggaagctctggcggccgtat
gcaagacctggctgaacgaggagcaccgcgggttgcagctgaccttca
ccagcaacaagacctttgtgacgatgatggggcgattcctgcaggcgt
acctgcagtcgtttgcagaggtgacctacaagcatcacgagcccacgg
gctgcgcgttgtggctgcaccgctgcgctgagatcgaaggcgagctta
agtgtctacacggaagcattatgataaataaggagcacgtgattgaaa
tggatgtgacgagcgaaaacgggcagcgcgcgctgaaggagcagtcta
gcaaggccaagatcgtgaagaaccggtggggccgaaatgtggtgcaga
tctccaacaccgacgcaaggtgctgcgtgcacgacgcggcctgtccgg
ccaatcagttttccggcaagtcttgcggcatgttcttctctgaaggcg
caaaggctcaggtggcttttaagcagatcaaggcttttatgcaggcgc
tgtatcctaacgcccagaccgggcacggtcaccttttgatgccactac
ggtgcgagtgcaactcaaagcctgggcacgcgcccttttttgggaaggc
agctaccaaagttgactccgttcgccctgagcaacgcggaggacctgg
acgcggatctgatctccgacaagagcgtgctggccagcgtgcaccacc
cggcgctgatagtgttccagtgctgcaaccctgtgtatcgcaactegc
```

-continued

```
gcgcgcagggcggaggccccaactgcgacttcaagatatcggcgcccg
acctgctaaacgcgttggtgatggtgcgcagcctgtggagtgaaaact
tcaccgagctgccgcggatggttgtgcctgagtttaagtggagcacta
aacaccagtatcgcaacgtgtccctgccagtggcgcatagcgatgcgc
ggcagaacccctttgattttaacccgggagttctagggatctgcccc
tctccctcccccccccctaacgttactggccgaagccgcttggaataa
ggccggtgtgcgtttgtctatatgttattttccaccatattgccgtct
tttggcaatgtgagggcccggaaacctggccctgtcttcttgacgagc
attcctaggggtctttcccctctcgccaaaggaatgcaaggtctgttg
aatgtcgtgaaggaagcagttcctctggaagcttcttgaagacaaaca
acgtctgtagcgaccctttgcaggcagcggaaccccccacctggcgac
aggtgcctctgcggccaaaagccacgtgtataagatacacctgcaaag
gcggcacaaccccagtgccacgttgtgagttggatagttgtggaaaga
gtcaaatggctctcctcaagcgtattcaacaaggggctgaaggatgcc
cagaaggtaccccattgtatgggatctgatctggggcctcggtgcaca
tgctttacatgtgtttagtcgaggttaaaaaaacgtctaggccccccg
aaccacggggacgtggttttcctttgaaaaacacgatgataaggatcc
accggaggccaccatgactacgtccggcgttccatttggcatgacact
acgaccaacacgatctcggttgtctcggcgcactccgtacagtaggga
tcgtctacctccttttgagacagaaacccgcgctaccatactggagga
tcatccgctgctgcccgaatgtaacactttgacaatgcacaacgtgag
ttacgtgcgaggtcttccctgcagtgtgggatttacgctgattcagga
atgggttgttccctgggatatggttctaacgcgggaggagcttgtaat
cctgaggaagtgtatgcacgtgtgcctgtgttgtgccaacattgatat
catgacgagcatgatgatccatggttacgagtcctgggctctccactg
tcattgttccagtcccggttccctgcagtgtatagccggcgggcaggt
tttggccagctggtttaggatggtggtggatggcgccatgtttaatca
gaggtttatatggtaccgggaggtggtgaattacaacatgccaaaaga
ggtaatgtttatgtccagcgtgtttatgaggggtcgccacttaatcta
cctgcgcttgtggtatgatggccacgtgggttctgtggtccccgccat
gagctttggatacagcgccttgcactgtgggattttgaacaatattgt
ggtgctgtgctgcagttactgtgctgatttaagtgagatcagggtgcg
ctgctgtgcccggaggacaaggcgccttatgctgcgggcggtgcgaat
catcgctgaggagaccactgccatgttgtattcctgcaggacggagcg
gcggcggcagcagtttattcgcgcgctgctgcagcaccaccgccctat
cctgatgcacgattatgactctaccccccatgtagGCGGCCGCTCGAGT
CTAGAGGGCCCGTTTAAACCCGCTGATCAGCCTCGACTGTGCCTTCTA
GTTGCCAGCCATCTGTTGTTTGCCCCTCCCCCGTGCCTTCCTTGACCC
TGGAAGGTGCCACTCCCACTGTCCTTTCCTAATAAAATGAGGAAATTG
CATCGCATTGTCTGAGTAGGTGTCATTCTATTCTGGGGGGTGGGGTGG
GGCAGGACAGCAAGGGGGAGGATTGGGAAGACAATAGCAGGCATGCTG
```

-continued

```
GGGATGCGGTGGGCTCTATGGCTTCTGAGGCGGAAAGAACCAGCTGGG
GCTCTAGGGGGTATCCCCggggttggggttgcgccttttccaaggcAT
CCAGCACAGTGGCGGCCGCaatatttgcatgtcgctatgtgttctggg
aaatcaccataaacgtgaaatccctatcagtgatagagacttataagt
tccctatcagtgatagagaaccggtgggcactcttccgtggtctggtg
gataaattcgcaagggtatcatggcggacgaccggggttcgagccccg
tatccggccgtccgccgtgatccatgcggttaccgcccgcgtgtcgaa
cccaggtgtgcgacgtcagacaacgggggagtgctccttttttgaattc
cactttggccgcggctcgaggggggttggggttgcgccttttccaaggc
agccctgggtttgcgcagggacgcggctgctctgggcgtggttccggg
aaacgcagcggcgccgaccctgggtctcgcacattcttcacgtccgtt
cgcagcgtcacccggatcttcgccgctacccttgtgggccccccggcg
acgcttcctgctccgcccctaagtcgggaaggttccttgcggttcgcg
gcgtgccggacgtgacaaacggaagccgcacgtctcactagtaccctc
gcagacggacagcgccagggagcaatggcagcgcgccgaccgcgatgg
gctgtggccaatagcggctgctcagcagggcgcgccgagagcagcggc
cgggaaggggcggtgcgggaggcggggtgtggggcggtagtgtgggcc
ctgttcctgcccgcgcggtgttccgcattctgcaagcctccggagcgc
acgtcggcagtcggctccctcgttgaccgaatcaccgacctctctccc
caggggggatctgtgagtttggggacccttgattgttctttctttttcg
ctattgtaaaattcatgttatatggagggggcaaagttttcagggtgt
tgtttagaatgggaagatgtcccttgtatcaccatggaccctcatgat
aattttgtttctttcactttctactctgttgacaaccattgtctcctc
ttattttcttttcatttctgtaactttttcgttaaactttagcttgc
atttgtaacgaatttttaaattcacttttgtttatttgtcagattgta
agtactttctctaatcactttttttcaaggcaatcagggtatattat
attgtacttcagcacagttttagagaacaattgttataattaaatgat
aaggtagaatatttctgcatataaattctggctggcgtggaaatattc
ttattggtagaaacaactacatcctggtcatcatcctgcctttctctt
tatggttacaatgatatacactgtttgagatgaggataaaatactctg
agtccaaaccgggcccctctgctaaccatgttcatgccttcttctttt
tcctacagctcctgggcaacgtgctggttattgtgctgtctcatcatt
ttggcaaagaattgtaatacgactcactatagggcgaGCCACCatggc
tagattagataaaagtaaagtgattaacagcgcattagagctgcttaa
tgaggtcggaatcgaaggtttaacaacccgtaaactcgcccagaagct
aggtgtagagcagcctacattgtattggcatgtaaaaaataagcgggc
tttgctcgacgccttagccattgagatgttagataggcaccatactca
cttttgccctttagaaggggaaagctggcaagatttttttacgtaataa
cgctaaaagttttagatgtgctttactaagtcatcgcgatggagcaaa
agtacatttaggtacacggcctacagaaaaacagtatgaaactctcga
```

-continued aaatcaattagccttttatgccaacaaggtttttcactagagaatgc
CttatatgcactcagcgcCgtggggcattttactttaggttgcgtatt
ggaagatcaagagcatcaagtcgctaaagaagaaagggaaacacctac
tactgatagtatgccgccattattacgacaagctatcgaattatttga
tcaccaaggtgcagagccagccttcttattcggccttgaattgatcat
atgcggattagaaaaacaacttaaatgtgaaagtgggtccccaaaaaa
gaagagaaaggtcgacggcggtggttcagtttaagcgtacagcggctc
ccgggagttctagggatctgcccctctccctccccccccctaacgtt
actggccgaagccgcttggaataaggccggtgtgcgtttgtctatatg
ttattttccaccatattgccgtcttttggcaatgtgagggcccggaaa
cctggccctgtcttcttgacgagcattcctaggggtctttcccctctc
gccaaaggaatgcaaggtctgttgaatgtcgtgaaggaagcagttcct
ctggaagcttcttgaagacaaacaacgtctgtagcgaccctttgcagg
cagcggaacccccacctggcgacaggtgcctctgcggccaaaagcca
cgtgtataagatacacctgcaaaggcggcacaaccccagtgccacgtt
gtgagttggatagttgtggaaagagtcaaatggctctcctcaagcgta
ttcaacaaggggctgaaggatgcccagaaggtaccccattgtatggga
tctgatctggggcctcggtgcacatgctttacatgtgtttagtcgagg
ttaaaaaaacgtctaggccccccgaaccacggggacgtggttttcctt
tgaaaaacacgatgataaggatccaccggagGCCACCatgaccgagta
caagcccacggtgcgcctcgccacccgcgacgacgtccccagggccgt
acgcaccctcgccgccgcgttcgccgactaccccgccacgcgccacac
cgtcgatccggaccgccacatcgagcgggtcaccgagctgcaagaact
cttcctcacgcgcgtcgggctcgacatcggcaaggtgtgggtcgcgga
cgacggcgccgcggtggcggtctggaccacgccggagagcgtcgaagc
gggggcggtgttcgccgagatcggcccgcgcatggccgagttgagcgg
ttcccggctggccgcgcagcaacagatggaaggcctcctggcgccgca
ccggcccaaggagcccgcgtggttcctggccaccgtcggcgtctcgcc
cgaccaccagggcaagggtctgggcagcgccgtcgtgctccccggagt
ggaggcggccgagcgcgccggggtgcccgccttcctggagacctccgc
gccccgcaacctccccttctacgagcggctcggcttcaccgtcaccgc
cgacgtcgaggtgcccgaaggaccgcgcacctggtgcatgacccgcaa
gcccggtgcctgaCCGCGTCTGGAACAATCAACCTCTGGATTACAAAA
TTTGTGAAAGATTGACTGGTATTCTTAACTATGTTGCTCCTTTTACGC
TATGTGGATACGCTGCTTTAATGCCTTTGTATCATGCTATTGCTTCCC
GTATGGCTTTCATTTTCTCCTCCTTGTATAAATCCTGGTTGCTGTCTC
TTTATGAGGAGTTGTGGCCCGTTGTCAGGCAACGTGGCGTGGTGTGCA
CTGTGTTTGCTGACGCAACCCCCACTGGTTGGGGCATTGCCACCACCT
GTCAGCTCCTTTCCGGGACTTTCGCTTTCCCCCTCCCTATTGCCACGG
CGGAACTCATCGCCGCCTGCCTTGCCCGCTGCTGGACAGGGGCTCGGC
TGTTGGGCACTGACAATTCCGTGGTGTTGTCGGGGAAGCTGACGTCCT -continued TTCCATGGCTGCTCGCCTGTGTTGCCACCTGGATTCTGCGCGGGACGT
CCTTCTGCTACGTCCCTTCGGCCCTCAATCCAGCGGACCTTCCTTCCC
GCGGCCTGCTGCCGGCTCTGCGGCCTCTTCCGCGTCTTCGCCTTCGCC
CTCAGACGAGTCGGATCTCCCTTTGGGCCGCCTCCCCGCaAAATGACC
GACCAAGCGACGCCCAACCTGCCATCACGAGATTTCGATTCCACCGCC
GCCTTCTATGAAAGGTTGGGCTTCGGAATCGTTTTCCGGGACGCCGGC
TGGATGATCCTCCAGCGCGGGGATCTCATGCTGGAGTTCTTCGCCCAC
CCCAACTTGTTTATTGCAGCTTATAATGGTTACAAATAAAGCAATAGC
ATCACAAATTTCACAAATAAAGCATTTTTTTCACTGCATTCTAGTTGT
GGTTTGTCCAAACTCATCAATGTATCTTATCATGTCTGTAGCtGATca
ATTgGCGCGCCGAATTCGTTatctgcagaattcggcttggcggctgcg
cgttcaaacctcccgcttcaaaatggagaccctgcgtgctcactcggg
cttaaatacccagcgtgaccacatggtgtcgcaaaatgtcgcaaaaca
ctcacgtgacctctaatacaggacctctagagcatggaaactagataa
gaaagaaatacgcagagaccaaagttcaactgaaacgaattaaacggt
ttattgattaacaagcaaactagtttacagattacgggtgaggtaacg
ggtgccgatggggcgaggctcagaataaacgccatttgtgtcaacagc
aaagtccacatttgtagatttgttgtagttggaagtgtattgaatctc
tgggttccagcgtttgctgttttctttctgcagctcccattcaatttc
cacgctgacctgtccggtgctgtactgcgtgatgaacgacgcaaactt
agctggactgaaggtagttggaggattcgcgggaacaggtgtattctt
aatcaggatctgaggaggcgggtgtttcagtccaaagcctcccatcag
cggcgagggatgaaagtgtccgtccgtgtgaggaatcttggcccagat
aggaccctgcaggtacacgtcccggtcctgccagaccatgccaggtaa
ggctccttgactgttgacggtccctgtagcaggagcggtgttggccga
ttgcaggttagtggccaccgtgccgtactcttctgtggccactgggtt
ggtggttttaatttcttcctcgttggttatcataacgttgtcaaggtc
cacgttgctatttccagctccctgtttcccaaatattaagactccgct
catcggaaaaaatttgtcttcgtcgtccttgtgggttgccatagcggg
accgggatttaccagagagtctctgccattcagatgatacttggtggc
accggtccaggcaaagttgctgttgttattttgattggttgtcttgga
gacgcgttgctgccggtagcagggcccgggtagccagtttttggcctg
attcgccatgctactaggcccggcctgagaaaattgcaacgtccgatt
tcctgcggtaccactcgtggtctgagtccgagacaggtagtacaggta
ctggtcgatgaggggggttcatcagccggtccaggctttggctgtgcgc
gtagctgctgtgaaaaggcacgtcctcaaacgtgtagctgaactgaaa
gttgttgcccgttctcagcatttgagaaggaaagtattccaggcagta
gaaggaggaacggcccacggcctgactgccattgttcagagtcaggta
cccgtactgaggaatcatgaagacgtccgccgggaacggaggcaggca
gccctggtgcgcagagccgaggacgtacgggagctggtattccgagtc -continued cgtaaagacctgaaccgtgctggtaaggttattggcgatggtcgtggt gccatcattcgtcgtgacctccttgacctggatgttgaagagcttgaa gttgagcttcttgggccggaatccccagttgttgttgatgagtcgctg ccagtcacgtggtgagaagtggcagtggaatctgttaaagtcaaaata cccccaggggggtgctgtagccgaagtaggtgttgtcgttggtgctgcc tcccgattggctggagatttgcttgtagaggtggttgttgtaggtggg gagggcccaggttcgggtgctggtggtgatgactctgtcgcccagcca tgtggaatcgcaatgccaatttcctgaggcgttacccactccgtcggc gccttcgttattgtctgccattggagcgccaccgcctgcagccattgt attagatcccacaccagaggggctgcgggggttctccgagtggttg agggtcgggcactgactctgagtcgccagtctgcccaaagttgagtct ctttctcgcgggctgctggcctttcttgccgatgcccgaagaggagtc tggttcctggggtgattgctctaccggtctcttctttccaggagccgt cttagcgccttcctcaaccagaccgagaggttcgagaacccgcttctt ggcctggaagactgctcgcccgaggttgcccccaaaagacgtatcttc ttgcagacgctcctgaaactcggcgtcggcgtggttataccgcaggta cggattgtcacccgctttgagctgctggtcgtaggccttgtcgtgctc gagggccgctgcgtccgccgcgttgacgggctccccccttgtcgagtcc gttgaagggtccgaggtacttgtagccaggaagcaccagaccccggcc gtcgtcctgcttttgctggttggctttgggtttcggggctccaggttt caagtcccaccactcgcgaatgccctcagagaggttgtcctcgagcca atctggaagataaccatcggcagccatacctgatttaaatcatttatt gttcaaagatgcagtcatccaaatccacattgaccagatcgcaggcag tgcaagcgtctggcacctttcccatgatatgatgaatgtagcacagtt tctgatacgcctttttgacgacagaaacgggttgagattctgacacgg gaaagcactctaaacagtctttctgtccgtgagtgaagcagatatttg aattctgattcattctctcgcattgtctgcagggaaacagcatcagat tcatgcccacgtgacgagaacatttgttttggtacctgtctgcgtagt tgatcgaagcttccgcgtctgacgtcgatggctgcgcaactgactcgc gcacccgtttgggctcacttatatctgcgtcactgggggcgggtcttt tcttggctccaccctttttgacgtagaattcatgctccacctcaacca cgtgatcctttgcccaccggaaaaagtctttgacttcctgcttggtga ccttcccaaagtcatgatccagacggcgggtgagttcaaatttgaaca tccggtcttgcaacggctgctggtgttcgaaggtcgttgagttcccgt caatcacggcgcacatgttggtgttggaggtgacgatcacgggagtcg ggtctatctgggccgaggacttgcatttctggtccacgcgcaccttgc ttcctccgagaatggctttggccgactccacgaccttggcggtcatct tcccctcctcccaccagatcaccatcttgtcgacacagtcgttgaagg gaaagttctcattggtccagtttacgcacccgtagaagggcacagtgt gggctatggcctccgcgatgttggtcttcccggtagttgcaggcccaa acagccagatggtgttcctcttgccgaactttttcgtggcccatccca -continued gaaagacggaagccgcatattggggatcgtacccgtttagttccaaaa ttttataaatccgattgctggaaatgtcctccacgggctgctggccca ccaggtagtcgggggcggttttagtcaggctcataatctttcccgcat tgtccaaggcagccttgatttgggaccgcgagttggaggccgcattga aggagatgtatgaggcctggtcctcctggatccactgcttctccgagg taatccccttgtccacgagccacccgaccagctccatgtacctggctg aagtttttgatctgatcaccggcgcatcagaattgggattctgattct ctttgttctgctcctgcgtctgcgacacgtgcgtcagatgctgcgcca ccaaccgtttacgctccgtgagattcaaacaggcgctgtggagagaaa ggcaaagtggatgtcagtaTCTCTATCACTGATAGGGAGATCTCTATC ACTGATAGGGAacttaccttaaatactgttccatattagtccacgccc actggagctcaggctgggttttggggagcaagtaattggggatgtagc actcatccaccaccttgttcccgcctccggcgccatttctggtctttg tgaccgcgaaccagtttggcaaagtcggctcgatcccgcggtaaattc tctgaatcagtttttcgcgaatctgactcaggaaacgtcccaaaacca tggatttcaccccggtggtttccacgagcacgtgcatgtggaagtagc tctctcccttctcaaattgcacaaagaaaagagcctccggggccttac tcacacggcgccattccgtcagaaagtcgcgctgcagcttctcggcca cggtcaggggtgcctgctcaatcagattcagatccatgtcagaatctg gcggcaactcccattccttctcggccacccagttcacaaagctgtcag aaatgccgggcagatgctcgtcaaggtcgctggggaccttaatcacaa tctcgtaaaaccccggcatGGCGGCTGCGCGTTCAAACCTCCCGCTTC AAAATGGAGACCCTGCGTGCTCACTCGGGCgaTCTCTATCACTGATAG GGAGATCTCTATCACTGATAGGGAgaTTAAATAgaatggCTAggATCC GGCCGGccTGCAggTGTCCTCACAGGAACGAAGTCCCTAAAGAAACAG

TGGCAGCCAGGTTTAGCCCCGGAATTGACTGGATTCCTTTTTTAGGGC

CCATTGGTATGGCTTTTTCCCCGTATCCCCCCAGGTGTCTGCAGGCTC

AAAGAGCAGCGAGAAGCGTTCAGAGGAAAGCGATCCCGTGCCACCTTC

CCCGTGCCCGGGCTGTCCCCGCACGCTGCCGGCTCGGGGATGCGGGGG

GAGCGCCGGACCGGAGCGGAGCCCCGGGCGGCTCGCTGCTGCCCCCTA

GCGGGGGAGGGACGTAATTACATCCCTGGGGGCTTTGGGGGGGGGCTG

TCCCTCTAGAGCGGCCGCCACCGCGGTGGAGCTCCAGCTTTTGTTCCC

TTTAGTGAGGGTTAATTAGATCTTAATACGACTCACTATAGGGCGAAT

TGGGTACCGGGCCCCCCCTCGAGGTCGACGGTATCGATAAGCTTGATA

TCTATAACAAGAAAATATATATATAATAAGTTATCACGTAAGTAGAAC

ATGAAATAACAATATAATTATCGTATGAGTTAAATCTTAAAAGTCACG

TAAAAGATAATCATGCGTCATTTTGACTCACGCGGTCGTTATAGTTCA

AAATCAGTGACACTTACCGCATTGACAAGCACGCCTCACGGGAGCTCC

AAGCGGCGACTGAGATGTCCTAAATGCACAGCGACGGATTCGCGCTAT

TTAGAAAGAGAGAGCAATATTTCAAGAATGCATGCGTCAATTTTACGC

-continued

AGACTATCTTTCTAGGGTTAATCTAGCTGCATCAGGATCATATCGTCG
GGTCTTTTTTCCGGCTCAGTCATCGCCCAAGCTGGCGCTATCTGGGCA
TCGGGGAGGAAGAAGCCCGTGCCTTTTCCCGCGAGGTTGAAGCGGCAT
GGAAAGAGTTTGCCGAGGATGACTGCTGCTGCATTGACGTTGAGCGAA
AACGCACGTTTACCATGATGATTCGGGAAGGTGTGGCCATGCACGCCT
TTAACGGTGAACTGTTCGTTCAGGCCACCTGGGATACCAGTTCGTCGC
GGCTTTTCCGGACACAGTTCCGGATGGTCAGCCCGAAGCGCATCAGCA
ACCCGAACAATACCGGCGACAGCCGGAACTGCCGTGCCGGTGTGCAGA
TTAATGACAGCGGTGCGGCGCTGGGATATTACGTCAGCGAGGACGGGT
ATCCTGGCTGGATGCCGCAGAAATGGACATGGATACCCCGTGAGTTAC
CCGGCGGGCGCGCTTGGCGTAATCATGGTCATAGCTGTTTCCTGTGTG
AAATTGTTATCCGCTCACAATTCCACACAACATACGAGCCGGAAGCAT
AAAGTGTAAAGCCTGGGGTGCCTAATGAGTGAGCTAACTCACATTAAT
TGCGTTGCGCTCACTGCCCGCTTTCCAGTCGGGAAACCTGTCGTGCCA
GCTGCATTAATGAATCGGCCAACGCGCGGGGAGAGGCGGTTTGCGTAT
TGGGCGCTCTTCCGCTTCCTCGCTCACTGACTCGCTGCGCTCGGTCGT
TCGGCTGCGGCGAGCGGTATCAGCTCACTCAAAGGCGGTAATACGGTT
ATCCACAGAATCAGGGGATAACGCAGGAAAGAACATGTGAGCAAAAGG
CCAGCAAAAGGCCAGGAACCGTAAAAAGGCCGCGTTGCTGGCGTTTTT
CCATAGGCTCCGCCCCCCTGACGAGCATCACAAAAATCGACGCTCAAG
TCAGAGGTGGCGAAACCCGACAGGACTATAAAGATACCAGGCGTTTCC
CCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAA
GCTGGGCTGTGTGCACGAACCCCCCGTTCAGCCCGACCGCTGCGCCTT
ATCCGGTAACTATCGTCTTGAGTCCAACCCGGTAAGACACGACTTATC
GCCACTGGCAGCAGCCACTGGTAACAGGATTAGCAGAGCGAGGTATGT

-continued

AGGCGGTGCTACAGAGTTCTTGAAGTGGTGGCCTAACTACGGCTACAC
TAGAAGGACAGTATTTGGTATCTGCGCTCTGCTGAAGCCAGTTACCTT
CGGAAAAAGAGTTGGTAGCTCTTGATCCGGCAAACAAACCACCGCTGG
TAGCGGTGGTTTTTTTGTTTGCAAGCAGCAGATTACGCGCAGAAAAAA
AGGATCTCAAGAAGATCCTTTGATCTTTTCTACGGGGTCTGACGCTCA
GTGGAACGAAAACTCACGTTAAGGGATTTTGGTCATGAGATTATCAAA
AAGGATCTTCACCTAGATCCTTTTAAATTAAAAATGAAGTTTTAAATC
AATCTAAAGTATATATGAGTAAACTTGGTCTGACAGTTACCAATGCTT
AATCAGTGAGGCACCTATCTCAGCGATCTGTCTATTTCGTTCATCCAT
AGTTGCCTGACTCCCCGTCGTGTAGATAACTACGATACGGGAGGGCTT
ACCATCTGGCCCCAGTGCTGCAATGATACCGCGAGACCCACGCTCACC
GGCTCCAGATTTATCAGCAATAAACCAGCCAGCCGGAAGGGCCGAGCG
CAGAAGTGGTCCTGCAACTTTATCCGCCTCCATCCAGTCTATTAATTG
TTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGG
TATGGCTTCATTCAGCTCCGGTTCCCAACGATCAAGGCGAGTTACATG
ATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGC
AGCACTGCATAATTCTCTTACTGTCATGCCATCCGTAAGATGCTTTTC
TGTGACTGGTGAGTACTCAACCAAGTCATTCTGAGAATAGTGTATGCG
GCGACCGAGTTGCTCTTGCCCGGCGTCAATACGGGATAATACCGCGCC
ACATAGCAGAACTTTAAAAGTGCTCATCATTGGAAAACGTTCTTCGGG
GCGAAAACTCTCAAGGATCTTACCGCTGTTGAGATCCAGTTCGATGTA
ACCCACTCGTGCACCCAACTGATCTTCAGCATCTTTTACTTTCACCAG
CGTTTCTGGGTGAGCAAAAACAGGAAGGCAAAATGCCGCAAAAAAGGG
AATAAGGGCGACACGGAAATGTTGAATACTCAT

The sequence of the vector represented in FIG. 10C is provided below.

PB007-iHelper1-iRepCap10-AAV-GFP/PBBG9 (21, 391 bp)

(SEQ ID NO: 13)

ACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCAC
ATTTCCCCGAAAAGTGCCACCTAAATTGTAAGCGTTAATATTTTGTTAAAATTCGCG
TTAAATTTTTGTTAAATCAGCTCATTTTTTAACCAATAGGCCGAAATCGGCAAAATC
CCTTATAAATCAAAAGAATAGACCGAGATAGGGTTGAGTGTTGTTCCAGTTTGGAAC
AAGAGTCCACTATTAAAGAACGTGGACTCCAACGTCAAAGGGCGAAAAACCGTCTA
TCAGGGCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCACACCCGCC
GCGCTTAATGCGCCGCTACAGGGCGCGTCCCATTCGCCATTCAGGCTGCGCAACTGT

-continued

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct -continued gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcaccttttgatgc cactacggtgcgagtgcaactcaaagcctgggcacgcgcccttttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgattttaacccgggagttctagggatctgcccctctccctcccccccc cctaacgttactggccgaagccgcttggaataaggccggtgtgcgtttgtctatatgttattttccaccatattgccgtcttttggcaatgtgagg gcccggaaacctggccctgtcttcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaaccccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg ggaggagcttgtaatcctgaggaagtgtatgcacgtgtgcctgtgttgtgccaacattgatatcatgacgagcatgatgatccatggttacga gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGCTCGAGTCT

AGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACAATAGC

AGGCATGCTGGGGATGCGGTGGGCTCTATGGCTTCTGAGGCGGAAAGAACCAGCTG

GGGCTCTAGGGGGTATCCCCggggttggggttgcgccttttccaaggcATCCAGCACAGTGGCGGCC

GCaatatttgcatgtcgctatgtgttctgggaaatcaccataaacgtgaaatccctatcagtgatagagacttataagttccctatcagtgatag agaaccggtgggcactcttccgtggtctggtggataaattcgcaagggtatcatggcggacgaccggggttcgagccccgtatccggccg tccgccgtgatccatgcggttaccgcccgcgtgtcgaacccaggtgtgcgacgtcagacaacgggggagtgctccttttttgaattccactttg gccgcggctcgaggggggttggggttgcgccttttccaaggcagccctgggtttgcgcagggacgcggctgctctgggcgtggttccggg aaacgcagcggcgccgaccctgggtctcgcacattcttcacgtccgttcgcagcgtcacccggatcttcgccgctacccttgtgggccccc cggcgacgcttcctgctccgcccctaagtcgggaaggttccttgcggttcgcggcgtgccggacgtgacaaacggaagccgcacgtctca ctagtaccctcgcagacggacagcgccagggagcaatggcagcgcgccgaccgcgatgggctgtggccaatagcggctgctcagcag ggcgcgccgagagcagcggccgggaaggggcggtgcgggaggcggggtgtggggcggtagtgtgggccctgttcctgcccgcgcg gtgttccgcattctgcaagcctccggagcgcacgtcggcagtcggctccctcgttgaccgaatcaccgacctctctccccagggggatctgt gagtttggggacccttgattgttctttctttttcgctattgtaaaattcatgttatatggagggggcaaagttttcagggtgttgtttagaatgggaa -continued gatgtcccttgtatcaccatggaccctcatgataattttgtttctttcactttctactctgttgacaaccattgtctcctcttattttcttttcattttct gtaactttttcgttaaactttagcttgcatttgtaacgaatttttaaattcacttttgtttatttgtcagattgtaagtactttctctaatcacttttttt caaggcaatcagggtatattatattgtacttcagcacagttttagagaacaattgttataattaaatgataaggtagaatatttctgcatataaattctggc tggcgtggaaatattcttattggtagaaacaactacatcctggtcatcatcctgcctttctctttatggttacaatgatatacactgtttgagatgaggat aaaatactctgagtccaaaccgggcccctctgctaaccatgttcatgccttcttctttttcctacagctcctgggcaacgtgctggttattgtgctg tctcatcattttggcaaagaattgtaatacgactcactatagggcgaGCCACCatggctagattagataaaagtaaagtgattaacagcg cattagagctgcttaatgaggtcggaatcgaaggtttaacaacccgtaaactcgcccagaagctaggtgtagagcagcctacattgtattggc atgtaaaaaataagcgggctttgctcgacgccttagccattgagatgttagataggcaccatactcacttttgccctttagaaggggaaagctg gcaagatttttacgtaataacgctaaaagttttagatgtgctttactaagtcatcgcgatggagcaaaagtacatttaggtacacggcctacag aaaaacagtatgaaactctcgaaaatcaattagcctttttatgccaacaaggtttttcactagagaatgcCttatatgcactcagcgcCgtggg gcattttactttaggttgcgtattggaagatcaagagcatcaagtcgctaaagaagaaagggaaacacctactactgatagtatgccgccatta ttacgacaagctatcgaattatttgatcaccaaggtgcagagccagccttcttattcggccttgaattgatcatatgcggattagaaaaacaactt aaatgtgaaagtgggtccccaaaaaagaagagaaaggtcgacggcggtggtgctttgtctcctcagcactctgctgtcactcaaggaagtat catcaagaacaaggagggcatggatgctaagtcactaactgcctggtcccggacactggtgaccttcaaggatgtatttgtggacttcacca gggaggagtggaagctgctggacactgctcagcagatcgtgtacagaaatgtgatgctggagaactataagaacctggtttccttgggttat cagcttactaagccagatgtgatcctccggttggagaagggagaagagccctggctggtggagagagaaattcaccaagagacccatcct gattcagagactgcatttgaaatcaaatcatcagtttaagcgtacagcggctcccgggagttctagggatctgcccctctccctcccccccc ctaacgttactggccgaagccgcttggaataaggccggtgtgcgtttgtctatatgttattttccaccatattgccgtcttttggcaatgtgaggg cccggaaacctggccctgtcttcttgacgagcattcctaggggtctttcccctctcgccaaaggaatgcaaggtctgttgaatgtcgtgaagg aagcagttcctctggaagcttcttgaagacaaacaacgtctgtagcgaccctttgcaggcagcggaaccccccacctggcgacaggtgcct ctgcggccaaaagccacgtgtataagatacacctgcaaaggcggcacaaccccagtgccacgttgtgagttggatagttgtggaaagagt caaatggctctcctcaagcgtattcaacaaggggctgaaggatgcccagaaggtaccccattgtatgggatctgatctggggcctcggtgc acatgctttacatgtgtttagtcgaggttaaaaaaacgtctaggccccccgaaccacggggacgtggttttcctttgaaaaacacgatgataag gatccaccggagGCCACCatgaccgagtacaagcccacggtgcgcctcgccacccgcgacgacgtccccagggccgtacgcacc ctcgccgccgcgttcgccgactaccccgccacgcgccacaccgtcgatccggaccgccacatcgagcgggtcaccgagctgcaagaac tcttcctcacgcgcgtcgggctcgacatcggcaaggtgtgggtcgcggacgacggcgccgcggtggcggtctggaccacgccggagag cgtcgaagcgggggcggtgttcgccgagatcggcccgcgcatggccgagttgagcggttcccggctggccgcgcagcaacagatgga aggcctcctggcgccgcaccggcccaaggagcccgcgtggttcctggccaccgtcggcgtctcgcccgaccaccagggcaagggtctg ggcagcgccgtcgtgctccccggagtggaggcggccgagcgcgccggggtgcccgccttcctggagacctccgcgccccgcaacctc cccttctacgagcggctcggcttcaccgtcaccgccgacgtcgaggtgcccgaaggaccgcgcacctggtgcatgacccgcaagcccg gtgcctgaCCGCGTCTGGAACAATCAACCTCTGGATTACAAAATTTGTGAAAGATTGACT

GGTATTCTTAACTATGTTGCTCCTTTTACGCTATGTGGATACGCTGCTTTAATGCCTT

TGTATCATGCTATTGCTTCCCGTATGGCTTTCATTTTCTCCTCCTTGTATAAATCCTGG

TTGCTGTCTCTTTATGAGGAGTTGTGGCCCGTTGTCAGGCAACGTGGCGTGGTGTGC

ACTGTGTTTGCTGACGCAACCCCCACTGGTTGGGGCATTGCCACCACCTGTCAGCTC

CTTTCCGGGACTTTCGCTTTCCCCCTCCCTATTGCCACGGCGGAACTCATCGCCGCCT

GCCTTGCCCGCTGCTGGACAGGGGCTCGGCTGTTGGGCACTGACAATTCCGTGGTGT

TGTCGGGGAAGCTGACGTCCTTTCCATGGCTGCTCGCCTGTGTTGCCACCTGGATTCT

GCGCGGGACGTCCTTCTGCTACGTCCCTTCGGCCCTCAATCCAGCGGACCTTCCTTCC

CGCGGCCTGCTGCCGGCTCTGCGGCCTCTTCCGCGTCTTCGCCTTCGCCCTCAGACG

-continued

AGTCGGATCTCCCTTTGGGCCGCCTCCCCGCaAAATGACCGACCAAGCGACGCCCAA

CCTGCCATCACGAGATTTCGATTCCACCGCCGCCTTCTATGAAAGGTTGGGCTTCGG

AATCGTTTTCCGGGACGCCGGCTGGATGATCCTCCAGCGCGGGGATCTCATGCTGGA

GTTCTTCGCCCACCCCAACTTGTTTATTGCAGCTTATAATGGTTACAAATAAAGCAAT

AGCATCACAAATTTCACAAATAAAGCATTTTTTTCACTGCATTCTAGTTGTGGTTTGT

CCAAACTCATCAATGTATCTTATCATGTCTGTAGCtGATcaATTgGCGCGCCGAATTCG

TTatctgcagaattcggcttggcggctgcgcgttcaaacctcccgcttcaaaatggagaccctgcgtgctcactcgggcttaaataccccag cgtgaccacatggtgtcgcaaaatgtcgcaaaacactcacgtgacctctaatacaggacctctagagcatggaaactagataagaaagaaa tacgcagagaccaaagttcaactgaaacgaattaaacggtttattgattaacaagcaaactagtttacagattacgggtgaggtaacgggtgc cgatggggcgaggctcagaataaacgccatttgtgtcaacagcaaagtccacatttgtagatttgttgtagttggaagtgtattgaatctctgg gttccagcgtttgctgttttctttctgcagctcccattcaatttccacgctgacctgtccggtgctgtactgcgtgatgaacgacgcaaacttagct ggactgaaggtagttggaggattcgcgggaacaggtgtattcttaatcaggatctgaggaggcgggtgtttcagtccaaagcctcccatcag cggcgagggatgaaagtgtccgtccgtgtgaggaatcttggcccagataggaccctgcaggtacacgtcccggtcctgccagaccatgcc aggtaaggctccttgactgttgacggtccctgtagcaggagcggtgttggccgattgcaggttagtggccaccgtgccgtactcttctgtggc cactgggttggtggttttaatttcttcctcgttggttatcataacgttgtcaaggtccacgttgctatttccagctccctgtttcccaaatattaagact ccgctcatcggaaaaaatttgtcttcgtcgtccttgtgggttgccatagcgggaccgggatttaccagagagtctctgccattcagatgatactt ggtggcaccggtccaggcaaagttgctgttgttattttgattggttgtcttggagacgcgttgctgccggtagcagggcccgggtagccagttt ttggcctgattcgccatgctactaggcccggcctgagaaaattgcaacgtccgatttcctgcggtaccactcgtggtctgagtccgagacag gtagtacaggtactggtcgatgaggggggttcatcagccggtccaggctttggctgtgcgcgtagctgctgtgaaaaggcacgtcctcaaac gtgtagctgaactgaaagttgttgcccgttctcagcatttgagaaggaaagtattccaggcagtagaaggaggaacggcccacggcctgac tgccattgttcagagtcaggtacccgtactgaggaatcatgaagacgtccgccgggaacggaggcaggcagccctggtgcgcagagccg aggacgtacgggagctggtattccgagtccgtaaagacctgaaccgtgctggtaaggttattggcgatggtcgtggtgccatcattcgtcgt gacctccttgacctggatgttgaagagcttgaagttgagcttcttgggccggaatccccagttgttgttgatgagtcgctgccagtcacgtggt gagaagtggcagtggaatctgttaaagtcaaaatacccccaggggggtgctgtagccgaagtaggtgttgtcgttggtgctgcctcccgattg gctggagatttgcttgtagaggtggttgttgtaggtggggagggcccaggttcgggtgctggtggtgatgactctgtcgcccagccatgtgg aatcgcaatgccaatttcctgaggcgttacccactccgtcggcgccttcgttattgtctgccattggagcgccaccgcctgcagccattgtatt agatcccacaccagagggggctgcggggggttctccgagtggttgagggtcgggcactgactctgagtcgccagtctgcccaaagttga gtctctttctcgcgggctgctggcctttcttgccgatgcccgaagaggagtctggttcctggggtgattgctctaccggtctcttctttccagga gccgtcttagcgccttcctcaaccagaccgagaggttcgagaacccgcttcttggcctggaagactgctcgcccgaggttgcccccaaaag acgtatcttcttgcagacgctcctgaaactcggcgtcggcgtggttataccgcaggtacggattgtcacccgctttgagctgctggtcgtagg ccttgtcgtgctcgagggccgctgcgtccgccgcgttgacgggctccccccttgtcgagtccgttgaagggtccgaggtacttgtagccagg aagcaccagaccccggccgtcgtcctgcttttgctggttggctttgggtttcggggctccaggtttcaagtcccaccactcgcgaatgccctc agagaggttgtcctcgagccaatctggaagataaccatcggcagccatacctgatttaaatcatttattgttcaaagatgcagtcatccaaatc cacattgaccagatcgcaggcagtgcaagcgtctggcacctttcccatgatatgatgaatgtagcacagtttctgatacgccttttttgacgaca gaaacgggttgagattctgacacgggaaagcactctaaacagtctttctgtccgtgagtgaagcagatatttgaattctgattcattctctcgca ttgtctgcagggaaacagcatcagattcatgcccacgtgacgagaacatttgttttggtacctgtctgcgtagttgatcgaagcttccgcgtctg acgtcgatggctgcgcaactgactcgcgcacccgtttgggctcacttatatctgcgtcactgggggcgggtcttttcttggctccacccttttttg acgtagaattcatgctccacctcaaccacgtgatcctttgcccaccggaaaaagtctttgacttcctgcttggtgaccttcccaaagtcatgatc cagacggcgggtgagttcaaatttgaacatccggtcttgcaacggctgctggtgttcgaaggtcgttgagttcccgtcaatcacggcgcaca tgttggtgttggaggtgacgatcacgggagtcgggtctatctgggccgaggacttgcatttctggtccacgcgcaccttgcttcctccgagaa tggctttggccgactccacgaccttggcggtcatcttcccctcctcccaccagatcaccatcttgtcgacacagtcgttgaagggaaagttctc -continued attggtccagtttacgcacccgtagaagggcacagtgtgggctatggcctccgcgatgttggtcttcccggtagttgcaggcccaaacagcc
agatggtgttcctcttgccgaactttttcgtggcccatcccagaaagacggaagccgcatattggggatcgtacccgtttagttccaaaattta
taaatccgattgctggaaatgtcctccacgggctgctggcccaccaggtagtcgggggcggttttagtcaggctcataatctttcccgcattgt
ccaaggcagccttgatttgggaccgcgagttggaggccgcattgaaggagatgtatgaggcctggtcctcctggatccactgcttctccga
ggtaatccccttgtccacgagccacccgaccagctccatgtacctggctgaagtttttgatctgatcaccggcgcatcagaattgggattctga
ttctctttgttctgctcctgcgtctgcgacacgtgcgtcagatgctgcgccaccaaccgtttacgctccgtgagattcaaacaggcgctgtgga
gagaaaggcaaagtggatgtcagtaTCTCTATCACTGATAGGGAGATCTCTATCACTGATAGGGAac
ttaccttaaatactgttccatattagtccacgcccactggagctcaggctgggttttggggagcaagtaattggggatgtagcactcatccacc
accttgttcccgcctccggcgccatttctggtctttgtgaccgcgaaccagtttggcaaagtcggctcgatcccgcggtaaattctctgaatca
gtttttcgcgaatctgactcaggaaacgtcccaaaaccatggatttcaccccggtggtttccacgagcacgtgcatgtggaagtagctctctcc
cttctcaaattgcacaaagaaaagagcctccggggccttactcacacggcgccattccgtcagaaagtcgcgctgcagcttctcggccacg
gtcaggggtgcctgctcaatcagattcagatccatgtcagaatctggcggcaactcccattccttctcggccacccagttcacaaagctgtca
gaaatgccgggcagatgctcgtcaaggtcgctggggaccttaatcacaatctcgtaaaaccccggcatGGCGGCTGCGCGTT
CAAACCTCCCGCTTCAAAATGGAGACCCTGCGTGCTCACTCGGGCgaTCTCTATCACT
GATAGGGAGATCTCTATCACTGATAGGGAgaTTAAATAgaatggCTAggATCCGGCCGGc
cTGCAggTGTCCTCACAGGAACGAAGTCCCTAAAGAAACAGTGGCAGCCAGGTTTAG
CCCCGGAATTGACTGGATTCCTTTTTTAGGGCCCATTGGTATGGCTTTTTCCCCGTAT
CCCCCCAGGTGTCTGCAGGCTCAAAGAGCAGCGAGAAGCGTTCAGAGGAAAGCGAT
CCCGTGCCACCTTCCCCGTGCCCGGGCTGTCCCCGCACGCTGCCGGCTCGGGGATGC
GGGGGGAGCGCCGGACCGGAGCGGAGCCCCGGGCGGCTCGCTGCTGCCCCCTAGCG
GGGGAGGGACGTAATTACATCCCTGGGGGCTTTGGGGGGGGGCTGTCCCTCTAGAG
CGGCCGCCACCGCGGTGGAGCTCCAGCTTTTGTTCCCTTTAGTGAGGGTTAATTAGA
TCTTAATACGACTCACTATAGGGCGAATTGGGTACCGGGCCCCCCCTCGAGGTCGAC
GGTATCGCCTCCAAGGCCAGCTTCCCACAATAAGTTGGGTGAATTTTGGCTCATTCC
TCCTTTCTATAGGATTGAGGTCAGAGCTTTGTGATGGGAATTCTGTGGAATGTGTGT
CAGTTAGGGTGTGGAAAGTCCCgcGATCgcTAGcAAACGCCAGCAACGCGGCCTTTTT
ACGGTTCCTGGCCTTTTGCTGGCCTTTTGCTCACATGTCCTGCAGGCAGCTGCGCGCT
CGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGCCAACTCCATCACTA
GGGGTTCCTGCGGCCGCACGCGTGGAGCTAGTTATTAATAGTAATCAATTACGGGGT
CATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTC
CCATAGTAACGTCAATAGGGACTTTCCATTGACGTCAATGGGTGGAGTATTTACGGT
AAACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCG
GTTTTGGCAGTACATCAATGGGCGTGGATAGCGGTTTGACTCACGGGGATTTCCAAG
TCTCCACCCCATTGACGTCAATGGGAGTTTGTTTTGCACCAAAATCAACGGGACTTT
CCAAAATGTCGTAACAACTCCGCCCCATTGACGCAAATGGGCGGTAGGCGTGTACG
GTGGGAGGTCTATATAAGCAGAGCTCGTTTAGTGAACCGTCAGATCGCCTGGAGAC -continued

GCCATCCACGCTGTTTTGACCTCCATAGAAGACACCGGGACCGATCCAGCCTCCGCG

GATTCGAATCCCGGCCGGGAACGGTGCATTGGAACGCGGATTCCCCGTGCCAAGAG

TGACGTAAGTACCGCCTATAGAGTCTATAGGCCCACAAAAAATGCTTTCTTCTTTTA

ATATACTTTTTTGTTTATCTTATTTCTAATACTTTCCCTAATCTCTTTCTTTCAGGGCA

ATAATGATACAATGTATCATGCCTCTTTGCACCATTCTAAAGAATAACAGTGATAAT

TTCTGGGTTAAGGCAATAGCAATATTTCTGCATATAAATATTTCTGCATATAAATTGT

AACTGATGTAAGAGGTTTCATATTGCTAATAGCAGCTACAATCCAGCTACCATTCTG

CTTTTATTTTATGGTTGGGATAAGGCTGGATTATTCTGAGTCCAAGCTAGGCCCTTTT

GCTAATCATGTTCATACCTCTTATCTTCCTCCCACAGCTCCTGGGCAACGTGCTGGTC

TGTGTGCTGGCCCATCACTTTGGCAAAGAATTGGGATTCGAACATCGATTGAATTCT

GAATGGTGAGCAAGGGCGAGGAGCTGTTCACCGGGGTGGTGCCCATCCTGGTCGAG

CTGGACGGCGACGTAAACGGCCACAAGTTCAGCGTGTCCGGCGAGGGCGAGGGCGA

TGCCACCTACGGCAAGCTGACCCTGAAGTTCATCTGCACCACCGGCAAGCTGCCCGT

GCCCTGGCCCACCCTCGTGACCACCCTGACCTACGGCGTGCAGTGCTTCAGCCGCTA

CCCCGACCACATGAAGCAGCACGACTTCTTCAAGTCCGCCATGCCCGAAGGCTACGT

CCAGGAGCGCACCATCTTCTTCAAGGACGACGGCAACTACAAGACCCGCGCCGAGG

TGAAGTTCGAGGGCGACACCCTGGTGAACCGCATCGAGCTGAAGGGCATCGACTTC

AAGGAGGACGGCAACATCCTGGGGCACAAGCTGGAGTACAACTACAACAGCCACA

ACGTCTATATCATGGCCGACAAGCAGAAGAACGGCATCAAGGTGAACTTCAAGATC

CGCCACAACATCGAGGACGGCAGCGTGCAGCTCGCCGACCACTACCAGCAGAACAC

CCCCATCGGCGACGGCCCCGTGCTGCTGCCCGACAACCACTACCTGAGCACCCAGTC

CGCCCTGAGCAAAGACCCCAACGAGAAGCGCGATCACATGGTCCTGCTGGAGTTCG

TGACCGCCGCCGGGATCACTCTCGGCATGGACGAGCTGTACAAGTACTCAGATCTCG

AGCTCAAGTAGGGATCCTCTAGAGTCGACCTGCAGAAGCTTGCCTCGAGCAGCGCT

GCTCGAGAGATCTACGGGTGGCATCCCTGTGACCCCTCCCCAGTGCCTCTCCTGGCC

CTGGAAGTTGCCACTCCAGTGCCCACCAGCCTTGTCCTAATAAAATTAAGTTGCATC

ATTTTGTCTGACTAGGTGTCCTTCTATAATATTATGGGGTGGAGGGGGGTGGTATGG

AGCAAGGGGCAAGTTGGGAAGACAACCTGTAGGGCCTGCGGGGTCTATTGGGAACC

AAGCTGGAGTGCAGTGGCACAATCTTGGCTCACTGCAATCTCCGCCTCCTGGGTTCA

AGCGATTCTCCTGCCTCAGCCTCCCGAGTTGTTGGGATTCCAGGCATGCATGACCAG

GCTCAGCTAATTTTTGTTTTTTTGGTAGAGACGGGGTTTCACCATATTGGCCAGGCTG

GTCTCCAACTCCTAATCTCAGGTGATCTACCCACCTTGGCCTCCCAAATTGCTGGGA

TTACAGGCGTGAACCACTGCTCCCTTCCCTGTCCTTCTGATTTTGTAGGTAACCACGT

GCGGACCGAGCGGCCGCAGGAACCCCTAGTGATGGAGTTGGCCACTCCCTCTCTGC

GCGCTCGCTCGCTCACTGAGGCCGGGCGACCAAAGGTCGCCCGACGCCCGGGCTTT

GCCCGGGCGGCCTCAGTGAGCGAGCGAGCGCGCAGCTGCCTGCAGGGGCGCCTGAT

GCGGTATTTTCTCCTTACGCATCTGTGCGGTATTTCACACCGCATACGTCgtaGCtGATc aATTgGCGCGCCGAATTCGTTAACAAGCTtTAATTAaCGCgtAcgATAAGCTTGATATCT

ATAACAAGAAAATATATATATAATAAGTTATCACGTAAGTAGAACATGAAATAACA

ATATAATTATCGTATGAGTTAAATCTTAAAAGTCACGTAAAAGATAATCATGCGTCA

TTTTGACTCACGCGGTCGTTATAGTTCAAAATCAGTGACACTTACCGCATTGACAAG

-continued

CACGCCTCACGGGAGCTCCAAGCGGCGACTGAGATGTCCTAAATGCACAGCGACGG

ATTCGCGCTATTTAGAAAGAGAGAGCAATATTTCAAGAATGCATGCGTCAATTTTAC

GCAGACTATCTTTCTAGGGTTAATCTAGCTGCATCAGGATCATATCGTCGGGTCTTTT

TTCCGGCTCAGTCATCGCCCAAGCTGGCGCTATCTGGGCATCGGGGAGGAAGAAGC

CCGTGCCTTTTCCCGCGAGGTTGAAGCGGCATGGAAAGAGTTTGCCGAGGATGACTG

CTGCTGCATTGACGTTGAGCGAAAACGCACGTTTACCATGATGATTCGGGAAGGTGT

GGCCATGCACGCCTTTAACGGTGAACTGTTCGTTCAGGCCACCTGGGATACCAGTTC

GTCGCGGCTTTTCCGGACACAGTTCCGGATGGTCAGCCCGAAGCGCATCAGCAACCC

GAACAATACCGGCGACAGCCGGAACTGCCGTGCCGGTGTGCAGATTAATGACAGCG

GTGCGGCGCTGGGATATTACGTCAGCGAGGACGGGTATCCTGGCTGGATGCCGCAG

AAATGGACATGGATACCCCGTGAGTTACCCGGCGGGCGCGCTTGGCGTAATCATGG

TCATAGCTGTTTCCTGTGTGAAATTGTTATCCGCTCACAATTCCACACAACATACGA

GCCGGAAGCATAAAGTGTAAAGCCTGGGGTGCCTAATGAGTGAGCTAACTCACATT

AATTGCGTTGCGCTCACTGCCCGCTTTCCAGTCGGGAAACCTGTCGTGCCAGCTGCA

TTAATGAATCGGCCAACGCGCGGGGAGAGGCGGTTTGCGTATTGGGCGCTCTTCCGC

TTCCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCT

GGCGTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTT

TCTCCCTTCGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGGCGG

TGCTACAGAGTTCTTGAAGTGGTGGCCTAACTACGGCTACACTAGAAGGACAGTATT

TGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGGTCTGA

CGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTA

TATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGG

GAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACTCATGGTTA

-continued

TGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTC

TTGCCCGGCGTCAATACGGGATAATACCGCGCCACATAGCAGAACTTTAAAAGTGCT

CATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTC

ACCAGCGTTTCTGGGTGAGCAAAAACAGGAAGGCAAAATGCCGCAAAAAAGGGAA

TAAGGGCGACACGGAAATGTTGAATACTCAT

The sequence of the vector illustrated in FIG. 10D is provided below.

PB007-iHelper2-iRepCap10-AAV-GFP/PBBG10 (21, 046 bp)

(SEQ ID NO: 14)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT

-continued

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcaccttttgatgc cactacggtgcgagtgcaactcaaagcctgggcacgcgcccttttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgattttaacccgggagttctagggatctgcccctctccctcccccccc cctaacgttactggccgaagccgcttggaataaggccggtgtgcgtttgtctatatgttattttccaccatattgccgtcttttggcaatgtgagg gcccggaaacctggccctgtcttcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaaccccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg ggaggagcttgtaatcctgaggaagtgtatgcacgtgtgcctgtgttgtgccaacattgatatcatgacgagcatgatgatccatggttacga -continued gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGCTCGAGTCT

AGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACAATAGC

AGGCATGCTGGGGATGCGGTGGGCTCTATGGCTTCTGAGGCGGAAAGAACCAGCTG

GGGCTCTAGGGGGTATCCCCggggttggggttgcgccttttccaaggcATCCAGCACAGTGGCGGCC

GCaatatttgcatgtcgctatgtgttctgggaaatcaccataaacgtgaaatccctatcagtgatagagacttataagttccctatcagtgatag agaaccggtgggcactcttccgtggtctggtggataaattcgcaagggtatcatggcggacgaccggggttcgagccccgtatccggccg tccgccgtgatccatgcggttaccgcccgcgtgtcgaacccaggtgtgcgacgtcagacaacgggggagtgctccttttttgaattccactttg gccgcggctcgaggggggttggggttgcgccttttccaaggcagccctgggtttgcgcagggacgcggctgctctgggcgtggttccggg aaacgcagcggcgccgaccctgggtctcgcacattcttcacgtccgttcgcagcgtcacccggatcttcgccgctacccttgtgggccccc cggcgacgcttcctgctccgcccctaagtcgggaaggttccttgcggttcgcggcgtgccggacgtgacaaacggaagccgcacgtctca ctagtaccctcgcagacggacagcgccagggagcaatggcagcgcgccgaccgcgatgggctgtggccaatagcggctgctcagcag ggcgcgccgagagcagcggccgggaaggggcggtgcgggaggcggggtgtggggcggtagtgtgggccctgttcctgcccgcgcg gtgttccgcattctgcaagcctccggagcgcacgtcggcagtcggctccctcgttgaccgaatcaccgacctctctccccagggggatctgt gagtttggggacccttgattgttctttctttttcgctattgtaaaattcatgttatatggagggggcaaagttttcagggtgttgtttagaatgg gaagatgtcccttgtatcaccatggaccctcatgataatttgtttctttcactttctactctgttgacaaccattgtctcctcttattttcttt tcattttctgtaactttttcgttaaactttagcttgcatttgtaacgaatttttaaattcacttttgtttatttgtcagattgtaagtactttct ctaatcacttttttttcaaggcaatcagggtatattatattgtacttcagcacagttttagagaacaattgttataattaaatgataaggtagaa tatttctgcatataaattctggctggcgtggaaatattcttattggtagaaacaactacatcctggtcatcatcctgcctttctctttatggtta caatgatatacactgtttgagatgaggataaaatactctgagtccaaaccgggcccctctgctaaccatgttcatgccttcttctttttcctaca gctcctgggcaacgtgctggttattgtgctgtctcatcattttggcaaagaattgtaatacgactcactatagggcgaGCCACCatggctagatt agataaaagtaaagtgattaacagcgcattagagctgcttaatgaggtcggaatcgaaggtttaacaacccgtaaactcgcccagaagctaggtg tagagcagcctacattgtattggcatgtaaaaaataagcgggctttgctcgacgccttagccattgagatgttagataggcaccatactcacttt tgccctttagaaggggaaagctggcaagatttttttacgtaataacgctaaaagttttagatgtgctttactaagtcatcgcgatggagcaaaagt acatttaggtacacggcctacagaaaaacagtatgaaactctcgaaaatcaattagcctttttatgccaacaaggtttttcactagagaatgcCt tatatgcactcagcgcCgtggggcattttactttaggttgcgtattggaagatcaagagcatcaagtcgctaaagaagaaagggaaacacctact actgatagtatgccgccattattacgacaagctatcgaattatttgatcaccaaggtgcagagccagccttcttattcggccttgaattgatcat atgcggattagaaaaacaacttaaatgtgaaagtgggtccccaaaaaagaagagaaaggtcgacggcggtggttcagtttaagcgtacagcggct cccgggagttctagggatctgcccctctccctcccccccccctaacgttactggccgaagccgcttggaataaggccggtgtgcgtttgtctata tgttattttccaccatattgccgtcttttggcaatgtgagggcccggaaacctggccctgtcttcttgacgagcattcctaggggtctttcccct ctcgccaaaggaatgcaaggtctgttgaatgtcgtgaaggaagcagttcctctggaagcttcttgaagacaaacaacgtctgtagcgaccctttg caggcagcggaaccccccacctggcgacaggtgcctctgcggccaaaagccacgtgtataagatacacctgcaaaggcggcacaaccccagtgcc acgttgtgagttggatagttgtggaaagagtcaaatggctctcctcaagcgtattcaacaaggggctgaaggatgcccagaaggtaccccattgt atgggatctgatctggggcctcggtgcacatgctttacatgtgtttagtcgaggttaaaaaaacgtctaggccccccgaaccacggggacgtggt -continued tttcctttgaaaaacacgatgataaggatccaccggagGCCACCatgaccgagtacaagcccacggtgcgcctcgccacccgcgacga cgtccccagggccgtacgcaccctcgccgccgcgttcgccgactaccccgccacgcgccacaccgtcgatccggaccgccacatcgag cgggtcaccgagctgcaagaactcttcctcacgcgcgtcgggctcgacatcggcaaggtgtgggtcgcggacgacggcgccgcggtgg cggtctggaccacgccggagagcgtcgaagcgggggcggtgttcgccgagatcggcccgcgcatggccgagttgagcggttcccggct ggccgcgcagcaacagatggaaggcctcctggcgccgcaccggcccaaggagcccgcgtggttcctggccaccgtcggcgtctcgcc cgaccaccagggcaagggtctgggcagcgccgtcgtgctccccggagtggaggcggccgagcgcgccggggtgcccgccttcctgga gacctccgcgccccgcaacctccccttctacgagcggctcggcttcaccgtcaccgccgacgtcgaggtgcccgaaggaccgcgcacct ggtgcatgacccgcaagcccggtgcctgaCCGCGTCTGGAACAATCAACCTCTGGATTACAAAATTT

GTGAAAGATTGACTGGTATTCTTAACTATGTTGCTCCTTTTACGCTATGTGGATACGC

TGCTTTAATGCCTTTGTATCATGCTATTGCTTCCCGTATGGCTTTCATTTTCTCCTCCT

TGTATAAATCCTGGTTGCTGTCTCTTTATGAGGAGTTGTGGCCCGTTGTCAGGCAAC

GTGGCGTGGTGTGCACTGTGTTTGCTGACGCAACCCCCACTGGTTGGGGCATTGCCA

CCACCTGTCAGCTCCTTTCCGGGACTTTCGCTTTCCCCCTCCCTATTGCCACGGCGGA

ACTCATCGCCGCCTGCCTTGCCCGCTGCTGGACAGGGGCTCGGCTGTTGGGCACTGA

CAATTCCGTGGTGTTGTCGGGGAAGCTGACGTCCTTTCCATGGCTGCTCGCCTGTGTT

GCCACCTGGATTCTGCGCGGGACGTCCTTCTGCTACGTCCCTTCGGCCCTCAATCCA

GCGGACCTTCCTTCCCGCGGCCTGCTGCCGGCTCTGCGGCCTCTTCCGCGTCTTCGCC

TTCGCCCTCAGACGAGTCGGATCTCCCTTTGGGCCGCCTCCCCGCaAAATGACCGAC

CAAGCGACGCCCAACCTGCCATCACGAGATTTCGATTCCACCGCCGCCTTCTATGAA

AGGTTGGGCTTCGGAATCGTTTTCCGGGACGCCGGCTGGATGATCCTCCAGCGCGGG

GATCTCATGCTGGAGTTCTTCGCCCACCCCAACTTGTTTATTGCAGCTTATAATGGTT

ACAAATAAAGCAATAGCATCACAAATTTCACAAATAAAGCATTTTTTTCACTGCATT

CTAGTTGTGGTTTGTCCAAACTCATCAATGTATCTTATCATGTCTGTAGCtGATcaATTg

GCGCGCCGAATTCGTTatctgcagaattcggcttggcggctgcgcgttcaaacctcccgcttcaaaatggagaccctgcgtg ctcactcgggcttaaatacccagcgtgaccacatggtgtcgcaaaatgtcgcaaaacactcacgtgacctctaatacaggacctctagagca tggaaactagataagaaagaaatacgcagagaccaaagttcaactgaaacgaattaaacggtttattgattaacaagcaaactagtttacaga ttacgggtgaggtaacgggtgccgatggggcgaggctcagaataaacgccatttgtgtcaacagcaaagtccacatttgtagatttgttgtag ttggaagtgtattgaatctctgggttccagcgtttgctgttttctttctgcagctcccattcaatttccacgctgacctgtccggtgctgtactg cgtgatgaacgacgcaaacttagctggactgaaggtagttggaggattcgcgggaacaggtgtattcttaatcaggatctgaggaggcgggtgt ttcagtccaaagcctcccatcagcggcgagggatgaaagtgtccgtccgtgtgaggaatcttggcccagataggaccctgcaggtacacgt cccggtcctgccagaccatgccaggtaaggctccttgactgttgacggtccctgtagcaggagcggtgttggccgattgcaggttagtggc caccgtgccgtactcttctgtggccactgggttggtggttttaatttcttcctcgttggttatcataacgttgtcaaggtccacgttgctatttc cagctccctgtttcccaaatattaagactccgctcatcggaaaaaatttgtcttcgtcgtccttgtgggttgccatagcgggaccgggatttacc agagagtctctgccattcagatgatacttggtggcaccggtccaggcaaagttgctgttgttattttgattggttgtcttggagacgcgttgctg ccggtagcagggcccgggtagccagtttttggcctgattcgccatgctactaggcccggcctgagaaaattgcaacgtccgatttcctgcggtac cactcgtggtctgagtccgagacaggtagtacaggtactggtcgatgaggggggttcatcagccggtccaggctttggctgtgcgcgtagctg ctgtgaaaaggcacgtcctcaaacgtgtagctgaactgaaagttgttgcccgttctcagcatttgagaaggaaagtattccaggcagtagaa ggaggaacggcccacggcctgactgccattgttcagagtcaggtacccgtactgaggaatcatgaagacgtccgccgggaacggaggc aggcagccctggtgcgcagagccgaggacgtacgggagctggtattccgagtccgtaaagacctgaaccgtgctggtaaggttattggcg atggtcgtggtgccatcattcgtcgtgacctccttgacctggatgttgaagagcttgaagttgagcttcttgggccggaatccccagttgttgtt -continued gatgagtcgctgccagtcacgtggtgagaagtggcagtggaatctgttaaagtcaaaatacccccagggggtgctgtagccgaagtaggt gttgtcgttggtgctgcctcccgattggctggagatttgcttgtagaggtggttgttgtaggtggggagggcccaggttcgggtgctggtggt gatgactctgtcgcccagccatgtggaatcgcaatgccaatttcctgaggcgttacccactccgtcggcgccttcgttattgtctgccattgga gcgccaccgcctgcagccattgtattagatcccacaccagagggggctgcggggggttctccgagtggttgagggtcgggcactgactct gagtcgccagtctgcccaaagttgagtctctttctcgcgggctgctggcctttcttgccgatgcccgaagaggagtctggttcctggggtgatt gctctaccggtctcttctttccaggagccgtcttagcgccttcctcaaccagaccgagaggttcgagaacccgcttcttggcctggaagactg ctcgcccgaggttgcccccaaaagacgtatcttcttgcagacgctcctgaaactcggcgtcggcgtggttataccgcaggtacggattgtca cccgctttgagctgctggtcgtaggccttgtcgtgctcgagggccgctgcgtccgccgcgttgacgggctccccccttgtcgagtccgttgaa gggtccgaggtacttgtagccaggaagcaccagaccccggccgtcgtcctgcttttgctggttggctttgggtttcggggctccaggtttcaa gtcccaccactcgcgaatgccctcagagaggttgtcctcgagccaatctggaagataaccatcggcagccatacctgatttaaatcatttattg ttcaaagatgcagtcatccaaatccacattgaccagatcgcaggcagtgcaagcgtctggcacctttcccatgatatgatgaatgtagcacag tttctgatacgcctttttgacgacagaaacgggttgagattctgacacgggaaagcactctaaacagtctttctgtccgtgagtgaagcagatat ttgaattctgattcattctctcgcattgtctgcagggaaacagcatcagattcatgcccacgtgacgagaacatttgttttggtacctgtctgcgt agttgatcgaagcttccgcgtctgacgtcgatggctgcgcaactgactcgcgcacccgtttgggctcacttatatctgcgtcactgggggcgg gtcttttcttggctccaccctttttgacgtagaattcatgctccacctcaaccacgtgatcctttgcccaccggaaaaagtctttgacttcctgc ttggtgaccttcccaaagtcatgatccagacggcgggtgagttcaaatttgaacatccggtcttgcaacggctgctggtgttcgaaggtcgttga gttcccgtcaatcacggcgcacatgttggtgttggaggtgacgatcacgggagtcgggtctatctgggccgaggacttgcatttctggtccac gcgcaccttgcttcctccgagaatggctttggccgactccacgaccttggcggtcatcttcccctcctcccaccagatcaccatcttgtcgaca cagtcgttgaagggaaagttctcattggtccagtttacgcacccgtagaagggcacagtgtgggctatggcctccgcgatgttggtcttcccg gtagttgcaggcccaaacagccagatggtgttcctcttgccgaactttttcgtggcccatcccagaaagacggaagccgcatattggggatc gtacccgtttagttccaaaattttataaatccgattgctggaaatgtcctccacgggctgctggcccaccaggtagtcgggggcggttttagtc aggctcataatctttcccgcattgtccaaggcagccttgatttgggaccgcgagttggaggccgcattgaaggagatgtatgaggcctggtc ctcctggatccactgcttctccgaggtaatccccttgtccacgagccacccgaccagctccatgtacctggctgaagtttttgatctgatcacc ggcgcatcagaattgggattctgattctctttgttctgctcctgcgtctgcgacacgtgcgtcagatgctgcgccaccaaccgtttacgctccgt gagattcaaacaggcgctgtggagagaaaggcaaagtggatgtcagtaTCTCTATCACTGATAGGGAGATCTCT ATCACTGATAGGGAacttaccttaaatactgttccatattagtccacgcccactggagctcaggctgggttttggggagcaagta attggggatgtagcactcatccaccaccttgttcccgcctccggcgccatttctggtctttgtgaccgcgaaccagtttggcaaagtcggctcg atcccgcggtaaattctctgaatcagtttttcgcgaatctgactcaggaaacgtcccaaaaccatggatttcaccccggtggtttccacgagca cgtgcatgtggaagtagctctctcccttctcaaattgcacaaagaaaagagcctccggggccttactcacacggcgccattccgtcagaaag tcgcgctgcagcttctcggccacggtcaggggtgcctgctcaatcagattcagatccatgtcagaatctggcggcaactcccattccttctcg gccacccagttcacaaagctgtcagaaatgccgggcagatgctcgtcaaggtcgctggggaccttaatcacaatctcgtaaaaccccggca tGGCGGCTGCGCGTTCAAACCTCCCGCTTCAAAATGGAGACCCTGCGTGCTCACTCG GGCgaTCTCTATCACTGATAGGGAGATCTCTATCACTGATAGGGAgaTTAAATAgaatgg CTAggATCCGGCCGGccTGCAggTGTCCTCACAGGAACGAAGTCCCTAAAGAAACAGT

GGCAGCCAGGTTTAGCCCCGGAATTGACTGGATTCCTTTTTTAGGGCCCATTGGTAT

GGCTTTTTCCCCGTATCCCCCCAGGTGTCTGCAGGCTCAAAGAGCAGCGAGAAGCGT

TCAGAGGAAAGCGATCCCGTGCCACCTTCCCCGTGCCCGGGCTGTCCCCGCACGCTG

CCGGCTCGGGGATGCGGGGGGAGCGCCGGACCGGAGCGGAGCCCCGGGCGGCTCG

CTGCTGCCCCCCTAGCGGGGGAGGGACGTAATTACATCCCTGGGGGCTTTGGGGGGG

GGCTGTCCCTCTAGAGCGGCCGCCACCGCGGTGGAGCTCCAGCTTTTGTTCCCTTTA

GTGAGGGTTAATTAGATCTTAATACGACTCACTATAGGGCGAATTGGGTACCGGGCC

-continued

CCCCCTCGAGGTCGACGGTATCGCCTCCAAGGCCAGCTTCCCACAATAAGTTGGGTG

AATTTTGGCTCATTCCTCCTTTCTATAGGATTGAGGTCAGAGCTTTGTGATGGGAATT

CTGTGGAATGTGTGTCAGTTAGGGTGTGGAAAGTCCCgcGATCgcTAGcAAACGCCAG

CAACGCGGCCTTTTTACGGTTCCTGGCCTTTTGCTGGCCTTTTGCTCACATGTCCTGC

AGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGG

CCAACTCCATCACTAGGGGTTCCTGCGGCCGCACGCGTGGAGCTAGTTATTAATAGT

AATCAATTACGGGGTCATTAGTTCATAGCCCATATATGGAGTTCCGCGTTACATAAC

TTACGGTAAATGGCCCGCCTGGCTGACCGCCCAACGACCCCCGCCCATTGACGTCAA

TAATGACGTATGTTCCCATAGTAACGTCAATAGGGACTTTCCATTGACGTCAATGGG

TGGAGTATTTACGGTAAACTGCCCACTTGGCAGTACATCAAGTGTATCATATGCCAA

GTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTAT

TACCATGGTGATGCGGTTTTGGCAGTACATCAATGGGCGTGGATAGCGGTTTGACTC

ACGGGGATTTCCAAGTCTCCACCCCATTGACGTCAATGGGAGTTTGTTTTGCACCAA

AATCAACGGGACTTTCCAAAATGTCGTAACAACTCCGCCCCATTGACGCAAATGGG

CGGTAGGCGTGTACGGTGGGAGGTCTATATAAGCAGAGCTCGTTTAGTGAACCGTC

AGATCGCCTGGAGACGCCATCCACGCTGTTTTGACCTCCATAGAAGACACCGGGAC

CGATCCAGCCTCCGCGGATTCGAATCCCGGCCGGGAACGGTGCATTGGAACGCGGA

TTCCCCGTGCCAAGAGTGACGTAAGTACCGCCTATAGAGTCTATAGGCCCACAAAA

AATGCTTTCTTCTTTTAATATACTTTTTTGTTTATCTTATTTCTAATACTTTCCCTAATC

TCTTTCTTTCAGGGCAATAATGATACAATGTATCATGCCTCTTTGCACCATTCTAAAG

AATAACAGTGATAATTTCTGGGTTAAGGCAATAGCAATATTTCTGCATATAAATATT

TCTGCATATAAATTGTAACTGATGTAAGAGGTTTCATATTGCTAATAGCAGCTACAA

TCCAGCTACCATTCTGCTTTTATTTTATGGTTGGGATAAGGCTGGATTATTCTGAGTC

CAAGCTAGGCCCTTTTGCTAATCATGTTCATACCTCTTATCTTCCTCCCACAGCTCCT

GGGCAACGTGCTGGTCTGTGTGCTGGCCCATCACTTTGGCAAAGAATTGGGATTCGA

ACATCGATTGAATTCTGAATGGTGAGCAAGGGCGAGGAGCTGTTCACCGGGGTGGT

GCCCATCCTGGTCGAGCTGGACGGCGACGTAAACGGCCACAAGTTCAGCGTGTCCG

GCGAGGGCGAGGGCGATGCCACCTACGGCAAGCTGACCCTGAAGTTCATCTGCACC

ACCGGCAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGTCCGCC

ATGCCCGAAGGCTACGTCCAGGAGCGCACCATCTTCTTCAAGGACGACGGCAACTA

CAAGACCCGCGCCGAGGTGAAGTTCGAGGGCGACACCCTGGTGAACCGCATCGAGC

TGAAGGGCATCGACTTCAAGGAGGACGGCAACATCCTGGGGCACAAGCTGGAGTAC

AACTACAACAGCCACAACGTCTATATCATGGCCGACAAGCAGAAGAACGGCATCAA

GGTGAACTTCAAGATCCGCCACAACATCGAGGACGGCAGCGTGCAGCTCGCCGACC

ACTACCAGCAGAACACCCCCATCGGCGACGGCCCCGTGCTGCTGCCCGACAACCAC

TACCTGAGCACCCAGTCCGCCCTGAGCAAAGACCCCAACGAGAAGCGCGATCACAT

GGTCCTGCTGGAGTTCGTGACCGCCGCCGGGATCACTCTCGGCATGGACGAGCTGTA

-continued

CAAGTACTCAGATCTCGAGCTCAAGTAGGGATCCTCTAGAGTCGACCTGCAGAAGCT

TGCCTCGAGCAGCGCTGCTCGAGAGATCTACGGGTGGCATCCCTGTGACCCCTCCCC

AGTGCCTCTCCTGGCCCTGGAAGTTGCCACTCCAGTGCCCACCAGCCTTGTCCTAAT

AAAATTAAGTTGCATCATTTTGTCTGACTAGGTGTCCTTCTATAATATTATGGGGTGG

AGGGGGGTGGTATGGAGCAAGGGGCAAGTTGGGAAGACAACCTGTAGGGCCTGCG

GGGTCTATTGGGAACCAAGCTGGAGTGCAGTGGCACAATCTTGGCTCACTGCAATCT

CCGCCTCCTGGGTTCAAGCGATTCTCCTGCCTCAGCCTCCCGAGTTGTTGGGATTCCA

GGCATGCATGACCAGGCTCAGCTAATTTTTGTTTTTTTGGTAGAGACGGGGTTTCAC

CATATTGGCCAGGCTGGTCTCCAACTCCTAATCTCAGGTGATCTACCCACCTTGGCC

TCCCAAATTGCTGGGATTACAGGCGTGAACCACTGCTCCCTTCCCTGTCCTTCTGATT

TTGTAGGTAACCACGTGCGGACCGAGCGGCCGCAGGAACCCCTAGTGATGGAGTTG

GCCACTCCCTCTCTGCGCGCTCGCTCGCTCACTGAGGCCGGGCGACCAAAGGTCGCC

CGACGCCCGGGCTTTGCCCGGGCGGCCTCAGTGAGCGAGCGAGCGCGCAGCTGCCT

GCAGGGGCGCCTGATGCGGTATTTTCTCCTTACGCATCTGTGCGGTATTTCACACCG

CATACGTCgtaGCtGATcaATTgGCGCGCCGAATTCGTTAACAAGCTtTAATTAaCGCgtAc gATAAGCTTGATATCTATAACAAGAAAATATATATATAATAAGTTATCACGTAAGTA

GAACATGAAATAACAATATAATTATCGTATGAGTTAAATCTTAAAAGTCACGTAAA

AGATAATCATGCGTCATTTTGACTCACGCGGTCGTTATAGTTCAAAATCAGTGACAC

TTACCGCATTGACAAGCACGCCTCACGGGAGCTCCAAGCGGCGACTGAGATGTCCT

GCATGCGTCAATTTTACGCAGACTATCTTTCTAGGGTTAATCTAGCTGCATCAGGAT

CATATCGTCGGGTCTTTTTTCCGGCTCAGTCATCGCCCAAGCTGGCGCTATCTGGGCA

TCGGGGAGGAAGAAGCCCGTGCCTTTTCCCGCGAGGTTGAAGCGGCATGGAAAGAG

TTTGCCGAGGATGACTGCTGCTGCATTGACGTTGAGCGAAAACGCACGTTTACCATG

ATGATTCGGGAAGGTGTGGCCATGCACGCCTTTAACGGTGAACTGTTCGTTCAGGCC

ACCTGGGATACCAGTTCGTCGCGGCTTTTCCGGACACAGTTCCGGATGGTCAGCCCG

AAGCGCATCAGCAACCCGAACAATACCGGCGACAGCCGGAACTGCCGTGCCGGTGT

GCAGATTAATGACAGCGGTGCGGCGCTGGGATATTACGTCAGCGAGGACGGGTATC

CTGGCTGGATGCCGCAGAAATGGACATGGATACCCCGTGAGTTACCCGGCGGGCGC

GCTTGGCGTAATCATGGTCATAGCTGTTTCCTGTGTGAAATTGTTATCCGCTCACAAT

TCCACACAACATACGAGCCGGAAGCATAAAGTGTAAAGCCTGGGGTGCCTAATGAG

TGAGCTAACTCACATTAATTGCGTTGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTTCCGCTTCCTCGCTCACTGACTCGCTGCGCTCGGTCGTTCGGCTGC

GGCGAGCGGTATCAGCTCACTCAAAGGCGGTAATACGGTTATCCACAGAATCAGGG

GATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACA

AAAATCGACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGTCCAACCC

-continued

GGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACA

CTAGAAGGACAGTATTTGGTATCTGCGCTCTGCTGAAGCCAGTTACCTTCGGAAAAA

GAGTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAA

TGATACCGCGAGACCCACGCTCACCGGCTCCAGATTTATCAGCAATAAACCAGCCA

GCCGGAAGGGCCGAGCGCAGAAGTGGTCCTGCAACTTTATCCGCCTCCATCCAGTCT

ATTAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTCAT

TCAGCTCCGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCCGCAGTGT

TATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAAGGGAATAAGGGCGACACGGAAATGTTGAATACTCAT

Sequences of additional vectors for use in the practice of the present invention:

iRepCap1/pKan-Anc80-RepCap-p5i1-p19i1
(10,497 bp)

(SEQ ID NO: 15)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccaAtgggcAtggacCaaCatggaaca gtaCCtCagcgcctgtttgaatctcacggagcgtaaacggttggtggcgcagcatctgacgcacgtgtcgcagacgcaggagcagaac aaagagaatcagaatcccaattctgatgcgccggtgatcagatcaaaaacttcagccaggtacatggagctggtcgggtggctcgtggaca aggggattacctcggagaagcagtggatccaggaggaccaggcctcatacatctccttcaatgcggcctccaactcgcggtcccaaatca aggctgccttggacaatgcgggaaagattatgagcctgactaaaaccgcccccgactacctggtgggccagcagcccgtggaggacattt ccagcaatcggatttataaaattttggaactaaacgggtacgatccccaatatgcggcttccgtctttctgggatgggccacgaaaaagttcg -continued gcaagaggaacaccatctggctgtttgggcctgcaactaccgggaagaccaacatcgcggaggccatagcccacactgtgcccttctacg
ggtgcgtaaactggaccaatgagaactttcccttcaacgactgtgtcgacaagatggtgatctggtgggaggaggggaagatgaccgcca
aggtcgtggagtcggccaaagccattctcggaggaagcaaggtgcgcgtggaccagaaatgcaagtcctcggcccagatagacccgact
cccgtgatcgtcacctccaacaccaacatgtgcgccgtgattgacgggaactcaacgaccttcgaacaccagcagccgttgcaagaccgg
atgttcaaatttgaactcacccgccgtctggatcatgactttgggaaggtcaccaagcaggaagtcaaagactttttccggtgggcaaggat
cacgtggttgaggtggagcatgaattctacgtcaaaaagggtggagccaagaaaagacccgcccccagtgacgcagatataagtgagcc
caaacgggtgcgcgagtcagttgcgcagccatcgacgtcagacgcggaagcttcgatcaactacgcagacaggtaccaaaacaaatgttc
tcgtcacgtgggcatgaatctgatgctgtttccctgcagacaatgcgagagaatgaatcagaattcaaatatctgcttcactcacggacagaa
agactgtttagagtgctttcccgtgtcagaatctcaacccgtttctgtcgtcaaaaaggcgtatcagaaactgtgctacattcatcatatcatggg
aaaggtgccagacgcttgcactgcctgcgatctggtcaatgtggatttggatgactgcatctttgaacaataaatgatttaaatcaggtatggct
gccgatggttatcttccagattggctcgaggacaacctctctgagggcattcgcgagtggtgggacttgaaacctggagccccgaaaccca
aagccaaccagcaaaagcaggacgacggccggggtctggtgcttcctggctacaagtacctcggacccttcaacggactcgacaaggg
ggagcccgtcaacgcggcggacgcagcggccctcgagcacgacaaggcctacgaccagcagctcaaagcgggtgacaatccgtacct
gcggtataaccacgccgacgccgagtttcaggagcgtctgcaagaagatacgtcttttgggggcaacctcgggcgagcagtcttccaggc
caagaagcgggttctcgaacctctcggtctggttgaggaaggcgctaagacggctcctggaaagaagagaccggtagagcaatcacccc
aggaaccagactcctcttcgggcatcggcaagaaaggccagcagcccgcgagaaagagactcaactttgggcagactggcgactcaga
gtcagtgcccgaccctcaaccactcggagaacccccgcagcccccctctggtgtgggatctaatacaatggctgcaggcggtggcgctcc
aatggcagacaataacgaaggcgccgacggagtgggtaacgcctcaggaaattggcattgcgattccacatggctgggcgacagagtca
tcaccaccagcacccgaacctgggccctccccacctacaacaaccacctctacaagcaaatctccagccaatcgggaggcagcaccaac
gacaacacctacttcggctacagcaccccctgggggtattttgactttaacagattccactgccacttctcaccacgtgactggcagcgactc
atcaacaacaactggggattccggcccaagaagctcaacttcaagctcttcaacatccaggtcaaggaggtcacgacgaatgatggcacc
acgaccatcgccaataaccttaccagcacggttcaggtctttacggactcggaataccagctcccgtacgtcctcggctctgcgcaccagg
gctgcctgcctccgttcccggcggacgtcttcatgattcctcagtacgggtacctgactctgaacaatggcagtcaggccgtgggccgttcct
ccttctactgcctggaatactttccttctcaaatgctgagaacgggcaacaactttcagttcagctacacgtttgaggacgtgccttttcacagca
gctacgcgcacagccaaagcctggaccggctgatgaacccccctcatcgaccagtacctgtactacctgtctcggactcagaccacgagtg
gtaccgcaggaaatcggacgttgcaattttctcaggccgggcctagtagcatggcgaatcaggccaaaaactggctacccgggccctgct
accggcagcaacgcgtctccaagacaaccaatcaaaataacaacagcaactttgcctggaccggtgccaccaagtatcatctgaatggca
gagactctctggtaaatcccggtcccgctatggcaacccacaaggacgacgaagacaaatttttttccgatgagcggagtcttaatatttggga
aacagggagctggaaatagcaacgtggaccttgacaacgttatgataaccaacgaggaagaaattaaaaccaccaacccagtggccaca
gaagagtacggcacggtggccactaacctgcaatcggccaacaccgctcctgctacagggaccgtcaacagtcaaggagccttacctgg
catggtctggcaggaccgggacgtgtacctgcagggtcctatctgggccaagattcctcacacggacggacacttttcatccctcgccgctg
atgggaggctttggactgaaacacccgcctcctcagatcctgattaagaatacacctgttcccgcgaatcctccaactaccttcagtccagct
aagtttgcgtcgttcatcacgcagtacagcaccggacaggtcagcgtggaaattgaatgggagctgcagaaagaaaacagcaaacgctgg
aacccagagattcaatacacttccaactacaacaaatctacaaatgtggactttgctgttgacacaaatggcgtttattctgagcctcgccccat
cggcacccgttacctcacccgtaatctgtaaactagtttgcttgttaatcaataaaccgtttaattcgtttcagttgaactttggtctctgcgtatttct
ttcttatctagtttccatgctctagaggtcctgtattagaggtcacgtgagtgttttgcgacattttgcgacaccatgtggtcacgctgggtatttaa
gcccgagtgagcacgcagggtctccattttgaagcgggaggtttgaacgcgcagccgccaagccgaattctgcagatatcggggttgggg
ttgcgccttttccaaggcagccctgggtttgcgcagggacgcggctgctctgggcgtggttccgggaaacgcagcggcgccgaccctgg
gtctcgcacattcttcacgtccgttcgcagcgtcacccggatcttcgccgctacccttgtgggccccccggcgacgcttcctgctccgcccct
aagtcgggaaggttccttgcggttcgcggcgtgccggacgtgacaaacggaagccgcacgtctcactagtaccctcgcagacggacagc -continued gccagggagcaatggcagcgcgccgaccgcgatgggctgtggccaatagcggctgctcagcagggcgcgccgagagcagcggccg ggaaggggcggtgcgggaggcggggtgtggggcggtagtgtgggccctgttcctgcccgcgcggtgttccgcattctgcaagcctccg gagcgcacgtcggcagtcggctccctcgttgaccgaatcaccgacctctctccccagAAGCTCCCGGGAGCTTGTATA

TCCATTTTCGGATCTGATCAGCACGTGTTGACAATTAATCATCGGCATAGTATATCG

GCATAGTATAATACGACAAGGTGAGGAACgccaccATGGCCAAGCCTTTGTCTCAAGA

AGAATCCACCCTCATTGAAAGAGCAACGGCTACAATCAACAGCATCCCCATCTCTG

AAGACTACAGCGTCGCCAGCGCAGCTCTCTCTAGCGACGGCCGCATCTTCACTGGTG

TCAATGTATATCATTTTACTGGGGGACCTTGTGCAGAACTCGTGGTGCTGGGCACTG

CTGCTGCTGCGGCAGCTGGCAACCTGACTTGTATCGTCGCGATCGGAAATGAGAACA

GGGGCATCTTGAGCCCCTGCGGACGGTGCCGACAGGTGCTTCTCGATCTGCATCCTG

GGATCAAAGCCATAGTGAAGGACAGTGATGGACAGCCGACGGCAGTTGGGATTCGT

GAATTGCTGCCCTCTGGTTATGTGTGGGAGGGCTAAGCACTTCGTGGCCGAGGAGCA

GGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCAT

GCTGGAGTTCTTCGCCCACCCCAACTTGTTTATTGCAGCTTATAATGGTTACAAATAA

AGCAATAGCATCACAAATTTCACAAATAAAGCATTTTTTTCACTGCATTCTAGTTGT

GGTTTGTCCAAACTCATCAATGTATCTTAGCGCTCACTGCCCGCTTTCCAGTCGGGA

AACCTGTCGTGCCAGCTGCATTAATGAATCGGCCAACGCGCGGGGAGAGGCGGTTT

GCGTATTGGGCGCTCTCCTAGGccagaaatggcgccggaggcgggaacaaggtggtggatgagtgctacatcccca attacttgctccccaaaacccagcctgagctccagtgggcgtggactaatatggaacagtatttaagcgcctgTCCCTATCAGTG ATAGAGATCTCCCTATCAGTGATAGAGAtttgaatctcacggagcgtaaacggttggtggcgcagcatctGTT TAAACgcagacgcaggagcagaacaaagagaatcagaatcccaattctgatgcgccggtgatcagatcaaaaacttcagccaggtac atggagctggtcgggtggctcgtggacaaggggattacctcggagaagcagtggattcaggaggaccaggcctcatacatctccttcaatg cggcctccaactcgcggtcccaaatcaaggctgccttggacaatgcgggaaagattatgagcctgactaaaaccgcccccgactacctggt gggccagcagcccgtggaggacatttccagcaatcggatttataaaattttggaactaaacgggtacgatccccaatatgcggcttccgtctt tctgggatgggccacgaaaaagttcggcaagaggaacaccatctggctgtttgggcctgcaactaccgggaagaccaacatcgcggagg ccatagcccacactgtgcccttctacgggtgcgtaaactggaccaatgagaactttcccttcaacgactgtgtcgacaagatggtgatctggt gggaggaggggaagatgaccgccaaggtcgtggagtcggccaaagccattctcggaggaagcaaggtgcgcgtggaccagaaatgca agtcctcggcccagatagacccgactcccgtgatcgtcacctccaacaccaacatgtgcgccgtgattgacgggaactcaacgaccttcga acaccagcagccgttgcaagaccggatgttcaaatttgaactcacccgccgtctggatcatgactttgggaaggtcaccaagcaggaagtc aaagactttttccggtgggcaaaggatcacgtggttgaggtggagcatgaattctacgtcaaaaagggtggagccaagaaaagacccgcc cccagtgacgcagatataagtgagcccaaacgggtgcgcgagtcagttgcgcagccatcgacgtcagacgcggaagcttcgatcaacta cgcagacaggtaccaaaacaaatgttctcgtcacgtgggcatgaatctgatgctgtttccctgcagacaatgcgagagaatgaatcagaatt caaatatctgcttcactcacggacagaaagactgtttagagtgctttcccgtgtcagaatctcaacccgtttctgtcgtcaaaaaggcgtatcag aaactgtgctacattcatcatatcatgggaaaggtgccagacgcttgcactgcctgcgatctggtcaatgtggatttggatgactgcatctttga acaataaACTAGTTTGCTTGTTAATCAATAAACCGTTTAATTCGTTTCAGTTGAACTTTGG TCTCTGCGTATTTCTTTCTTATCTAGTTTCCATGCTCTAGAGTATACgatatccatcacactggcg gccgctcgactagagcggccgccaccgcggtggagctccagcttttgttcgcgcgcttggcgtaatcatggtcatagctgtttcctgtgtgaa attccacagcctggggtgcctaattgcgttgcgctcactgcccgctttccagtcgggaaacctgtcgtgccagctgcattaatgaatcggcca acgcgcggggagaggcggtttgcgtattgggcgctcttccgcttcctcgctcactgactcgctgcgctcggtcgttcggctgcggcgagcg gtatcagctcactcaaaggcggtaatacggttatccacagaatcaggggataacgcaggaaagaacatgtgagcaaaaggccagcaaaa -continued ggccaggaaccgtaaaaaggccgcgttgctggcgtttttccataggctccgcccccctgacgagcatcacaaaaatcgacgctcaagtca gaggtggcgaaacccgacaggactataaagataccaggcgtttccccctggaagctccctcgtgcgctctcctgttccgaccctgccgctta ccggatacctgtccgcctttctcccttcgggaagcgtggcgctttctcatagctcacgctgtaggtatctcagttcggtgtaggtcgttcgctcc aagctgggctgtgtgcacgaaccccccgttcagcccgaccgctgcgccttatccggtaactatcgtcttgagtccaacccggtaagacacg acttatcgccactggcagcagccactggtaacaggattagcagagcgaggtatgtaggcggtgctacagagttcttgaagtggtggcctaa ctacggctacactagaagaacagtatttggtatctgcgctctgctgaagccagttaccttcggaaaaagagttggtagctcttgatccggcaa acaaaccaccgctggtagcggtggtttttttgtttgcaagcagcagattacgcgcagaaaaaaaggatctcaagaagatcctttgatcttttcta cggggtctgacgctcagtggaacgaaaactcacgttaagggattttggtcatgagattatcaaaaaggatcttcacctagatccttttaaattaa aaatgaagttttaaatcaatctaaagtatatatgagtaaacttggtctgacagaaataataaaaaagccggattaataatctggctttttatattctc tctctagtatataaacgcagaaaggcccacccgaaggtgagccagtgtgactctagtattattagaaaaactcatcgagcatcaaatgaaact gcaatttattcatatcaggattatcaataccatatttttgaaaaagccgtttctgtaatgaaggagaaaactcaccgaggcagttccaaagaatg gcaaggtcctggtaacggtctgcgattccgacccgtccaacatcaatacaacctattaatttcccctcgtcaaaaataaggttatcaagtgaga aatcaccatgagtgacgactgaatccggtgagaatggcaagagcttgtgcatttctttccagacttgttcaacaggccagccattacgctcgtc atcaaaatcactcgcatcaaccaaaccgttattcatgcgtgattgcgcctgagcaagacgaaatacacgatcgctgttaaaaggacaattaca aacaggaatcgaatgtaaccggcgcaggaacacggccagcgcatcaacaatattttcacctgaatcaggatattcttctaatacctggaagg ctgttttcccaggaatcgcggtggtgagtaaccacgcatcatcaggagtacggataaaatgcttgatggtcgggagaggcataaactccgtc agccagttgagacggaccatctcatctgtaacatcattggcaacgctacctttgccatgtttcagaaacaactctggcgcatcgggcttcccat acaagcgatagattgtcgcacctgattgcccgacattatcgcgagcccatttatacccatataaatcagcgtccatgttggagtttaagcgcgg acgggagcaagacgtttcccgttgaatatggctcataacaccccttgtattactgtttatgtaagcagacagttttattgttcatgatgatatatttt atcttgtgcaatgtaacatcagagattttgagacacaacgtggctttgttgaataaatcgaacttttgctgagttgaaggatcagctctagtaaaa taataaaaaagccggattaataatctggctttttatattctctctctagtatataaacgcagaaaggcccacccgaaggtgagccagtgtgacg gcacatttccccgaaaagtgccacctaaattgtaagcgttaatattttgttaaaattcgcgttaaatttttgttaaatcagctcattttttaaccaatag gccgaaatcggcaaaatcccttataaatcaaaagaatagaccgagatagggttgagtgttgttccagtttggaacaagagtccactattaaag aacgtggactccaacgtcaaagggcgaaaaaccgtctatcagggcgatggcccactacgtgaaccatcaccctaatcaagttttttggggtc gaggtgccgtaaagcactaaatcggaaccctaaagggagcccccgatttagagcttgacggggaaagccggcgaacgtggcgagaaag gaagggaagaaagcgaaaggagcgggcgctagggcgctggcaagtgtagcggtcacgctgcgcgtaaccaccacacccgccgcgctt aatgcgccgctacagggcgcgtcccattcgccattcaggctgcgcaactgttgggaagggcgatcggtgcgggcctcttcgctattacgcc agctggcgaaagggggatgtgctgcaaggcgattaagttgggtaacgccagggttttcccagtcacgacgttgtaaaacgacggccagtg agcgcgcggcgaattgggtaccgggccccc iRepCap2/pKan-Anc80-RepCap-p5i2-p19i1 (10,495 bp)

(SEQ ID NO: 16)

cctcgaggGCTAGCcattcTATTTAAtcTCCCTATCAGTGATAGAGAtcGCCCGAGT

GAGCACGCAGGGTCTCCATTTTGATCCCTATCAGTGATAGAGAAGCGGGAGGTTTGA

ACGCGCAGCCGCCatgccggggttttacgagattgtgattaaggtccccagcgaccttgacgagcatctgcccggcatttctgac agctttgtgaactgggtggccgagaaggaatgggagttgccgccagattctgacatggatctgaatctgattgagcaggcacccctgaccg tggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg -continued ggattacctcggagaagcagtggatccaggaggaccaggcctcatacatctccttcaatgcggcctccaactcgcggtcccaaatcaagg
ctgccttggacaatgcgggaaagattatgagcctgactaaaaccgcccccgactacctggtgggccagcagcccgtggaggacatttcca
gcaatcggatttataaaattttggaactaaacgggtacgatccccaatatgcggcttccgtctttctgggatgggccacgaaaaagttcggca
agaggaacaccatctggctgtttgggcctgcaactaccgggaagaccaacatcgcggaggccatagcccacactgtgcccttctacgggt
gcgtaaactggaccaatgagaactttcccttcaacgactgtgtcgacaagatggtgatctggtgggaggaggggaagatgaccgccaagg
tcgtggagtcggccaaagccattctcggaggaagcaaggtgcgcgtggaccagaaatgcaagtcctcggcccagatagacccgactccc
gtgatcgtcacctccaacaccaacatgtgcgccgtgattgacgggaactcaacgaccttcgaacaccagcagccgttgcaagaccggatgt
tcaaatttgaactcacccgccgtctggatcatgactttgggaaggtcaccaagcaggaagtcaaagactttttccggtgggcaaaggatcac
gtggttgaggtggagcatgaattctacgtcaaaaagggtggagccaagaaaagacccgcccccagtgacgcagatataagtgagcccaa
acgggtgcgcgagtcagttgcgcagccatcgacgtcagacgcggaagcttcgatcaactacgcagacaggtaccaaaacaaatgttctcg
tcacgtgggcatgaatctgatgctgtttccctgcagacaatgcgagagaatgaatcagaattcaaatatctgcttcactcacggacagaaaga
ctgtttagagtgctttcccgtgtcagaatctcaacccgtttctgtcgtcaaaaaggcgtatcagaaactgtgctacattcatcatatcatgggaaa
ggtgccagacgcttgcactgcctgcgatctggtcaatgtggatttggatgactgcatctttgaacaataaatgatttaaatcaggtatggctgcc
gatggttatcttccagattggctcgaggacaacctctctgagggcattcgcgagtggtgggacttgaaacctggagccccgaaacccaaag
ccaaccagcaaaagcaggacgacggccggggtctggtgcttcctggctacaagtacctcggacccttcaacggactcgacaaggggga
gcccgtcaacgcggcggacgcagcggccctcgagcacgacaaggcctacgaccagcagctcaaagcgggtgacaatccgtacctgcg
gtataaccacgccgacgccgagtttcaggagcgtctgcaagaagatacgtcttttgggggcaacctcgggcgagcagtcttccaggccaa
gaagcgggttctcgaacctctcggtctggttgaggaaggcgctaagacggctcctggaaagaagagaccggtagagcaatcaccccagg
aaccagactcctcttcgggcatcggcaagaaaggccagcagcccgcgagaaagagactcaactttgggcagactggcgactcagagtca
gtgcccgaccctcaaccactcggagaaccccccgcagcccctctggtgtgggatctaatacaatggctgcaggcggtggcgctccaatg
gcagacaataacgaaggcgccgacggagtgggtaacgcctcaggaaattggcattgcgattccacatggctgggcgacagagtcatcac
caccagcacccgaacctgggccctccccacctacaacaaccacctctacaagcaaatctccagccaatcgggaggcagcaccaacgaca
acacctacttcggctacagcaccccctgggggtattttgactttaacagattccactgccacttctcaccacgtgactggcagcgactcatcaa
caacaactggggattccggcccaagaagctcaacttcaagctcttcaacatccaggtcaaggaggtcacgacgaatgatggcaccacgac
catcgccaataaccttaccagcacggttcaggtctttacggactcggaataccagctcccgtacgtcctcggctctgcgcaccagggctgcc
tgcctccgttcccggcggacgtcttcatgattcctcagtacgggtacctgactctgaacaatggcagtcaggccgtgggccgttcctccttcta
ctgcctggaatactttccttctcaaatgctgagaacgggcaacaactttcagttcagctacacgtttgaggacgtgccttttcacagcagctacg
cgcacagccaaagcctggaccggctgatgaacccccctcatcgaccagtacctgtactacctgtctcggactcagaccacgagtggtaccg
caggaaatcggacgttgcaattttctcaggccgggcctagtagcatggcgaatcaggccaaaaactggctacccgggccctgctaccggc
agcaacgcgtctccaagacaaccaatcaaaataacaacagcaactttgcctggaccggtgccaccaagtatcatctgaatggcagagactc
tctggtaaatcccggtcccgctatggcaacccacaaggacgacgaagacaaatttttttccgatgagcggagtcttaatatttgggaaacagg
gagctggaaatagcaacgtggaccttgacaacgttatgataaccaacgaggaagaaattaaaaccaccaacccagtggccacagaagagt
acggcacggtggccactaacctgcaatcggccaacaccgctcctgctacagggaccgtcaacagtcaaggagccttacctggcatggtct
ggcaggaccgggacgtgtacctgcagggtcctatctgggccaagattcctcacacggacggacactttcatccctcgccgctgatgggag
gctttggactgaaacacccgcctcctcagatcctgattaagaatacacctgttcccgcgaatcctccaactaccttcagtccagctaagtttgc
gtcgttcatcacgcagtacagcaccggacaggtcagcgtggaaattgaatgggagctgcagaaagaaaacagcaaacgctggaacccag
agattcaatacacttccaactacaacaaatctacaaatgtggactttgctgttgacacaaatggcgtttattctgagcctcgccccatcggcacc
cgttacctcacccgtaatctgtaaactagtttgcttgttaatcaataaaccgtttaattcgtttcagttgaactttggtctctgcgtatttctttctta
tctagtttccatgctctagaggtcctgtattagaggtcacgtgagtgttttgcgacattttgcgacaccatgtggtcacgctgggtatttaagcccga
gtgagcacgcagggtctccattttgaagcgggaggtttgaacgcgcagccgccaagccgaattctgcagatatcggggttggggttgcgc
cttttccaaggcagccctgggtttgcgcagggacgcggctgctctgggcgtggttccgggaaacgcagcggcgccgaccctgggtctcg -continued cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaacagtatttaagcgcctgTCCCTATCAGTGATAG AGATCTCCCTATCAGTGATAGAGAtttgaatctcacggagcgtaaacggttggtggcgcagcatctGTTTAAA Cgcagacgcaggagcagaacaaagagaatcagaatcccaattctgatgcgccggtgatcagatcaaaaacttcagccaggtacatggag ctggtcgggtggctcgtggacaaggggattacctcggagaagcagtggattcaggaggaccaggcctcatacatctccttcaatgcggcct ccaactcgcggtcccaaatcaaggctgccttggacaatgcgggaaagattatgagcctgactaaaaccgcccccgactacctggtgggcc agcagcccgtggaggacatttccagcaatcggatttataaaattttggaactaaacgggtacgatccccaatatgcggcttccgtctttctggg atgggccacgaaaaagttcggcaagaggaacaccatctggctgtttgggcctgcaactaccgggaagaccaacatcgcggaggccatag cccacactgtgcccttctacgggtgcgtaaactggaccaatgagaactttcccttcaacgactgtgtcgacaagatggtgatctggtgggag gaggggaagatgaccgccaaggtcgtggagtcggccaaagccattctcggaggaagcaaggtgcgcgtggaccagaaatgcaagtcct cggcccagatagacccgactcccgtgatcgtcacctccaacaccaacatgtgcgccgtgattgacgggaactcaacgaccttcgaacacc agcagccgttgcaagaccggatgttcaaatttgaactcacccgccgtctggatcatgactttgggaaggtcaccaagcaggaagtcaaaga ctttttccggtgggcaaaggatcacgtggttgaggtggagcatgaattctacgtcaaaaagggtggagccaagaaaagacccgcccccagt gacgcagatataagtgagcccaaacgggtgcgcgagtcagttgcgcagccatcgacgtcagacgcggaagcttcgatcaactacgcaga caggtaccaaaacaaatgttctcgtcacgtgggcatgaatctgatgctgtttccctgcagacaatgcgagagaatgaatcagaattcaaatat ctgcttcactcacggacagaaagactgtttagagtgctttcccgtgtcagaatctcaacccgtttctgtcgtcaaaaaggcgtatcagaaactgt gctacattcatcatatcatgggaaaggtgccagacgcttgcactgcctgcgatctggtcaatgtggatttggatgactgcatctttgaacaataa

ACTAGTTTGCTTGTTAATCAATAAACCGTTTAATTCGTTTCAGTTGAACTTTGGTCTC

TGCGTATTTCTTTCTTATCTAGTTTCCATGCTCTAGAGTATACgatatccatcacactggcggccgct cgactagagcggccgccaccgcggtggagctccagcttttgttcgcgcgcttggcgtaatcatggtcatagctgtttcctgtgtgaaattcca -continued cagcctggggtgcctaattgcgttgcgctcactgcccgctttccagtcgggaaacctgtcgtgccagctgcattaatgaatcggccaacgcg cggggagaggcggtttgcgtattgggcgctcttccgcttcctcgctcactgactcgctgcgctcggtcgttcggctgcggcgagcggtatca gctcactcaaaggcggtaatacggttatccacagaatcaggggataacgcaggaaagaacatgtgagcaaaaggccagcaaaaggcca ggaaccgtaaaaaggccgcgttgctggcgtttttccataggctccgcccccctgacgagcatcacaaaaatcgacgctcaagtcagaggtg gcgaaacccgacaggactataaagataccaggcgtttccccctggaagctccctcgtgcgctctcctgttccgaccctgccgcttaccggat acctgtccgcctttctcccttcgggaagcgtggcgctttctcatagctcacgctgtaggtatctcagttcggtgtaggtcgttcgctccaagctg ggctgtgtgcacgaaccccccgttcagcccgaccgctgcgccttatccggtaactatcgtcttgagtccaacccggtaagacacgacttatc gccactggcagcagccactggtaacaggattagcagagcgaggtatgtaggcggtgctacagagttcttgaagtggtggcctaactacgg ctacactagaagaacagtatttggtatctgcgctctgctgaagccagttaccttcggaaaaagagttggtagctcttgatccggcaaacaaac caccgctggtagcggtggtttttttgtttgcaagcagcagattacgcgcagaaaaaaaggatctcaagaagatcctttgatcttttctacggggt ctgacgctcagtggaacgaaaactcacgttaagggattttggtcatgagattatcaaaaaggatcttcacctagatccttttaaattaaaaatga agttttaaatcaatctaaagtatatatgagtaaacttggtctgacagaaataataaaaaagccggattaataatctggcttttttatattctctctctag tatataaacgcagaaaggcccacccgaaggtgagccagtgtgactctagtattattagaaaaactcatcgagcatcaaatgaaactgcaattt tcctggtaacggtctgcgattccgacccgtccaacatcaatacaacctattaatttcccctcgtcaaaaataaggttatcaagtgagaaatcacc atgagtgacgactgaatccggtgagaatggcaagagcttgtgcatttctttccagacttgttcaacaggccagccattacgctcgtcatcaaaa tcactcgcatcaaccaaaccgttattcatgcgtgattgcgcctgagcaagacgaaatacacgatcgctgttaaaaggacaattacaaacagg aatcgaatgtaaccggcgcaggaacacggccagcgcatcaacaatattttcacctgaatcaggatattcttctaatacctggaaggctgttttc ccaggaatcgcggtggtgagtaaccacgcatcatcaggagtacggataaaatgcttgatggtcgggagaggcataaactccgtcagccag ttgagacggaccatctcatctgtaacatcattggcaacgctacctttgccatgtttcagaaacaactctggcgcatcgggcttcccatacaagc gatagattgtcgcacctgattgcccgacattatcgcgagcccatttatacccatataaatcagcgtccatgttggagtttaagcgcggacggg agcaagacgtttcccgttgaatatggctcataacaccccttgtattactgtttatgtaagcagacagttttattgttcatgatgatatatttttatcttgt gcaatgtaacatcagagattttgagacacaacgtggctttgttgaataaatcgaacttttgctgagttgaaggatcagctctagtaaaataataa aaaagccggattaataatctggcttttttatattctctctctagtatataaacgcagaaaggcccacccgaaggtgagccagtgtgacggcacat ttccccgaaaagtgccacctaaattgtaagcgttaatattttgttaaaattcgcgttaaatttttgttaaatcagctcattttttaaccaataggccga aatcggcaaaatcccttataaatcaaaagaatagaccgagatagggttgagtgttgttccagtttggaacaagagtccactattaaagaacgt ggactccaacgtcaaagggcgaaaaaccgtctatcagggcgatggcccactacgtgaaccatcaccctaatcaagttttttggggtcgagg tgccgtaaagcactaaatcggaaccctaaagggagcccccgatttagagcttgacggggaaagccggcgaacgtggcgagaaaggaag ggaagaaagcgaaaggagcgggcgctagggcgctggcaagtgtagcggtcacgctgcgcgtaaccaccacacccgccgcgcttaatg cgccgctacagggcgcgtcccattcgccattcaggctgcgcaactgttgggaagggcgatcggtgcgggcctcttcgctattacgccagct ggcgaaagggggatgtgctgcaaggcgattaagttgggtaacgccagggttttcccagtcacgacgttgtaaaacgacggccagtgagcg cgcggcgaattgggtaccgggccccc iRepCap3/pKan-Anc80-RepCap-p5i3-p19i1 (10,493 bp)

(SEQ ID NO: 17)

cctcgaggGCTAGCcattcTCCCTATCAGTGATAGAGAtcTATTTAAGCCCGAGTG

AGCACGCAGTCCCTATCAGTGATAGAGAGGTCTCCATTTTGAAGCGGGAGGTTTGAA

CGCGCAGCCGCCatgccggggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa -continued gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaacccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttctta tctagtttccatgctctagaggtcctgtattagaggtcacgtgagtgttttgcgacattttgcgacaccatgtggtcacgctgggtatttaagcccga -continued gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaacagtatttaagcgcctgTCCCTATCAGTGATAG AGATCTCCCTATCAGTGATAGAGAtttgaatctcacggagcgtaaacggttggtggcgcagcatctGTTTAAA Cgcagacgcaggagcagaacaaagagaatcagaatcccaattctgatgcgccggtgatcagatcaaaaacttcagccaggtacatggag ctggtcgggtggctcgtggacaaggggattacctcggagaagcagtggattcaggaggaccaggcctcatacatctccttcaatgcggcct ccaactcgcggtcccaaatcaaggctgccttggacaatgcgggaaagattatgagcctgactaaaaccgcccccgactacctggtgggcc agcagcccgtggaggacatttccagcaatcggatttataaaatttttggaactaaacgggtacgatccccaatatgcggcttccgtctttctggg atgggccacgaaaaagttcggcaagaggaacaccatctggctgtttgggcctgcaactaccgggaagaccaacatcgcggaggccatag cccacactgtgcccttctacgggtgcgtaaactggaccaatgagaactttcccttcaacgactgtgtcgacaagatggtgatctggtgggag gaggggaagatgaccgccaaggtcgtggagtcggccaaagccattctcggaggaagcaaggtgcgcgtggaccagaaatgcaagtcct cggcccagatagacccgactcccgtgatcgtcacctccaacaccaacatgtgcgccgtgattgacgggaactcaacgaccttcgaacacc agcagccgttgcaagaccggatgttcaaatttgaactcacccgccgtctggatcatgactttgggaaggtcaccaagcaggaagtcaaaga ctttttccggtgggcaaaggatcacgtggttgaggtggagcatgaattctacgtcaaaaagggtggagccaagaaaagacccgcccccagt gacgcagatataagtgagcccaaacgggtgcgcgagtcagttgcgcagccatcgacgtcagacgcggaagcttcgatcaactacgcaga caggtaccaaaacaaatgttctcgtcacgtgggcatgaatctgatgctgtttccctgcagacaatgcgagagaatgaatcagaattcaaatat ctgcttcactcacggacagaaagactgtttagagtgctttcccgtgtcagaatctcaacccgtttctgtcgtcaaaaaggcgtatcagaaactgt gctacattcatcatatcatgggaaaggtgccagacgcttgcactgcctgcgatctggtcaatgtggatttggatgactgcatctttgaacaataa

ACTAGTTTGCTTGTTAATCAATAAACCGTTTAATTCGTTTCAGTTGAACTTTGGTCTC

TGCGTATTTCTTTCTTATCTAGTTTCCATGCTCTAGAGTATACgatatccatcacactggcggccgct

-continued cgactagagcggccgccaccgcggtggagctccagcttttgttcgcgcgcttggcgtaatcatggtcatagctgtttcctgtgtgaaattcca cagcctggggtgcctaattgcgttgcgctcactgcccgctttccagtcgggaaacctgtcgtgccagctgcattaatgaatcggccaacgcg cggggagaggcggtttgcgtattgggcgctcttccgcttcctcgctcactgactcgctgcgctcggtcgttcggctgcggcgagcggtatca gctcactcaaaggcggtaatacggttatccacagaatcaggggataacgcaggaaagaacatgtgagcaaaaggccagcaaaaggcca ggaaccgtaaaaaggccgcgttgctggcgtttttccataggctccgcccccctgacgagcatcacaaaaatcgacgctcaagtcagaggtg gcgaaacccgacaggactataaagataccaggcgtttccccctggaagctccctcgtgcgctctcctgttccgaccctgccgcttaccggat acctgtccgcctttctcccttcgggaagcgtggcgctttctcatagctcacgctgtaggtatctcagttcggtgtaggtcgttcgctccaagctg ggctgtgtgcacgaaccccccgttcagcccgaccgctgcgccttatccggtaactatcgtcttgagtccaacccggtaagacacgacttatc gccactggcagcagccactggtaacaggattagcagagcgaggtatgtaggcggtgctacagagttcttgaagtggtggcctaactacgg ctacactagaagaacagtatttggtatctgcgctctgctgaagccagttaccttcggaaaaagagttggtagctcttgatccggcaaacaaac caccgctggtagcggtggtttttttgtttgcaagcagcagattacgcgcagaaaaaaaggatctcaagaagatcctttgatcttttctacggggt ctgacgctcagtggaacgaaaactcacgttaagggattttggtcatgagattatcaaaaaggatcttcacctagatccttttaaattaaaaatga agttttaaatcaatctaaagtatatatgagtaaacttggtctgacagaaataataaaaaagccggattaataatctggctttttatattctctctctag tatataaacgcagaaaggcccacccgaaggtgagccagtgtgactctagtattattagaaaaactcatcgagcatcaaatgaaactgcaattt attcatatcaggattatcaataccatatttttgaaaaagccgtttctgtaatgaaggagaaaactcaccgaggcagttccaaagaatggcaagg tcctggtaacggtctgcgattccgacccgtccaacatcaatacaacctattaatttcccctcgtcaaaaataaggttatcaagtgagaaatcacc atgagtgacgactgaatccggtgagaatggcaagagcttgtgcatttctttccagacttgttcaacaggccagccattacgctcgtcatcaaaa tcactcgcatcaaccaaaccgttattcatgcgtgattgcgcctgagcaagacgaaatacacgatcgctgttaaaaggacaattacaaacagg aatcgaatgtaaccggcgcaggaacacggccagcgcatcaacaatattttcacctgaatcaggatattcttctaatacctggaaggctgttttc ccaggaatcgcggtggtgagtaaccacgcatcatcaggagtacggataaaatgcttgatggtcgggagaggcataaactccgtcagccag ttgagacggaccatctcatctgtaacatcattggcaacgctacctttgccatgtttcagaaacaactctggcgcatcgggcttcccatacaagc gatagattgtcgcacctgattgcccgacattatcgcgagcccatttatacccatataaatcagcgtccatgttggagtttaagcgcggacggg agcaagacgtttcccgttgaatatggctcataacaccccttgtattactgtttatgtaagcagacagttttattgttcatgatgatatatttttatctt gtgcaatgtaacatcagagattttgagacacaacgtggctttgttgaataaatcgaacttttgctgagttgaaggatcagctctagtaaaataataa aaaagccggattaataatctggctttttatattctctctctagtatataaacgcagaaaggcccacccgaaggtgagccagtgtgacggcacat ttccccgaaaagtgccacctaaattgtaagcgttaatattttgttaaaattcgcgttaaatttttgttaaatcagctcattttttaaccaataggccga aatcggcaaaatcccttataaatcaaaagaatagaccgagatagggttgagtgttgttccagtttggaacaagagtccactattaaagaacgt ggactccaacgtcaaagggcgaaaaaccgtctatcagggcgatggcccactacgtgaaccatcaccctaatcaagttttttggggtcgagg tgccgtaaagcactaaatcggaaccctaaagggagcccccgatttagagcttgacggggaaagccggcgaacgtggcgagaaaggaag ggaagaaagcgaaaggagcgggcgctagggcgctggcaagtgtagcggtcacgctgcgcgtaaccaccacacccgccgcgcttaatg cgccgctacagggcgcgtcccattcgccattcaggctgcgcaactgttgggaagggcgatcggtgcgggcctcttcgctattacgccagct ggcgaaagggggatgtgctgcaaggcgattaagttgggtaacgccagggttttcccagtcacgacgttgtaaaacgacggccagtgagcg cgcggcgaattgggtaccgggccccc iRepCap4/pKan-Anc80-RepCap-p5i1-p19i2 (10,495 bp)

(SEQ ID NO: 18)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa -continued actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccaAtgggcAtggacCaaCatggaaca gtaCCtCagcgcctgtttgaatctcacggagcgtaaacggttggtggcgcagcatctgacgcacgtgtcgcagacgcaggagcagaac aaagagaatcagaatcccaattctgatgcgccggtgatcagatcaaaaacttcagccaggtacatggagctggtcgggtggctcgtggaca aggggattacctcggagaagcagtggatccaggaggaccaggcctcatacatctccttcaatgcggcctccaactcgcggtcccaaatca aggctgccttggacaatgcgggaaagattatgagcctgactaaaaccgcccccgactacctggtgggccagcagcccgtggaggacattt ccagcaatcggatttataaaattttggaactaaacgggtacgatccccaatatgcggcttccgtctttctgggatgggccacgaaaaagttcg gcaagaggaacaccatctggctgtttgggcctgcaactaccgggaagaccaacatcgcggaggccatagcccacactgtgcccttctacg ggtgcgtaaactggaccaatgagaactttcccttcaacgactgtgtcgacaagatggtgatctggtgggaggaggggaagatgaccgcca aggtcgtggagtcggccaaagccattctcggaggaagcaaggtgcgcgtggaccagaaatgcaagtcctcggcccagatagacccgact cccgtgatcgtcacctccaacaccaacatgtgcgccgtgattgacgggaactcaacgaccttcgaacaccagcagccgttgcaagaccgg atgttcaaatttgaactcacccgccgtctggatcatgactttgggaaggtcaccaagcaggaagtcaaagactttttccggtgggcaaaggat cacgtggttgaggtggagcatgaattctacgtcaaaaagggtggagccaagaaaagacccgcccccagtgacgcagatataagtgagcc caaacgggtgcgcgagtcagttgcgcagccatcgacgtcagacgcggaagcttcgatcaactacgcagacaggtaccaaaacaaatgttc tcgtcacgtgggcatgaatctgatgctgtttccctgcagacaatgcgagagaatgaatcagaattcaaatatctgcttcactcacggacagaa agactgtttagagtgctttcccgtgtcagaatctcaacccgtttctgtcgtcaaaaaggcgtatcagaaactgtgctacattcatcatatcatggg aaaggtgccagacgcttgcactgcctgcgatctggtcaatgtggatttggatgactgcatctttgaacaataaatgatttaaatcaggtatggct gccgatggttatcttccagattggctcgaggacaacctctctgagggcattcgcgagtggtgggacttgaaacctggagccccgaaaccca aagccaaccagcaaaagcaggacgacggccggggtctggtgcttcctggctacaagtacctcggacccttcaacggactcgacaaggg ggagcccgtcaacgcggcggacgcagcggccctcgagcacgacaaggcctacgaccagcagctcaaagcgggtgacaatccgtacct gcggtataaccacgccgacgccgagtttcaggagcgtctgcaagaagatacgtcttttgggggcaacctcgggcgagcagtcttccaggc caagaagcgggttctcgaacctctcggtctggttgaggaaggcgctaagacggctcctggaaagaagagaccggtagagcaatcacccc aggaaccagactcctcttcgggcatcggcaagaaaggccagcagcccgcgagaaagagactcaactttgggcagactggcgactcaga gtcagtgcccgaccctcaaccactcggagaacccccgcagcccccctctggtgtgggatctaatacaatggctgcaggcggtggcgctcc aatggcagacaataacgaaggcgccgacggagtgggtaacgcctcaggaaattggcattgcgattccacatggctgggcgacagagtca tcaccaccagcacccgaacctgggccctccccacctacaacaaccacctctacaagcaaatctccagccaatcgggaggcagcaccaac gacaacacctacttcggctacagcaccccctgggggtattttgactttaacagattccactgccacttctcaccacgtgactggcagcgactc atcaacaacaactggggattccggcccaagaagctcaacttcaagctcttcaacatccaggtcaaggaggtcacgacgaatgatggcacc acgaccatcgccaataaccttaccagcacggttcaggtctttacggactcggaataccagctcccgtacgtcctcggctctgcgcaccagg gctgcctgcctccgttcccggcggacgtcttcatgattcctcagtacgggtacctgactctgaacaatggcagtcaggccgtgggccgttcct ccttctactgcctggaatactttccttctcaaatgctgagaacgggcaacaactttcagttcagctacacgtttgaggacgtgccttttcacagca gctacgcgcacagccaaagcctggaccggctgatgaacccctcatcgaccagtacctgtactacctgtctcggactcagaccacgagtg gtaccgcaggaaatcggacgttgcaattttctcaggccgggcctagtagcatggcgaatcaggccaaaaactggctacccgggccctgct accggcagcaacgcgtctccaagacaaccaatcaaaataacaacagcaactttgcctggaccggtgccaccaagtatcatctgaatggca gagactctctggtaaatcccggtcccgctatggcaacccacaaggacgacgaagacaaatttttcccgatgagcggagtcttaatatttggga aacagggagctggaaatagcaacgtggaccttgacaacgttatgataaccaacgaggaagaaattaaaaccaccaacccagtggccaca gaagagtacggcacggtggccactaacctgcaatcggccaacaccgctcctgctacagggaccgtcaacagtcaaggagccttacctgg catggtctggcaggaccgggacgtgtacctgcagggtcctatctgggccaagattcctcacacggacggacactttcatccctcgccgctg atgggaggctttggactgaaacacccgcctcctcagatcctgattaagaatacacctgttcccgcgaatcctccaactaccttcagtccagct aagtttgcgtcgttcatcacgcagtacagcaccggacaggtcagcgtggaaattgaatgggagctgcagaaagaaaacagcaaacgctgg aacccagagattcaatacacttccaactacaacaaatctacaaatgtggactttgctgttgacacaaatggcgtttattctgagcctcgccccat -continued cggcacccgttacctcacccgtaatctgtaaactagtttgcttgttaatcaataaaccgtttaattcgtttcagttgaactttggtctctgcgtatttc
tttcttatctagtttccatgctctagaggtcctgtattagaggtcacgtgagtgttttgcgacattttgcgacaccatgtggtcacgctgggtatttaa
gcccgagtgagcacgcagggtctccattttgaagcgggaggtttgaacgcgcagccgccaagccgaattctgcagatatcggggttgggg
ttgcgccttttccaaggcagccctgggtttgcgcagggacgcggctgctctgggcgtggttccgggaaacgcagcggcgccgaccctgg
gtctcgcacattcttcacgtccgttcgcagcgtcacccggatcttcgccgctacccttgtgggccccccggcgacgcttcctgctccgcccct
aagtcgggaaggttccttgcggttcgcggcgtgccggacgtgacaaacggaagccgcacgtctcactagtaccctcgcagacggacagc
gccagggagcaatggcagcgcgccgaccgcgatgggctgtggccaatagcggctgctcagcagggcgcgccgagagcagcggccg
ggaaggggcggtgcgggaggcggggtgtggggcggtagtgtgggccctgttcctgcccgcgcggtgttccgcattctgcaagcctccg
gagcgcacgtcggcagtcggctccctcgttgaccgaatcaccgacctctctccccagAAGCTCCCGGGAGCTTGTATA
TCCATTTTCGGATCTGATCAGCACGTGTTGACAATTAATCATCGGCATAGTATATCG
GCATAGTATAATACGACAAGGTGAGGAACgccaccATGGCCAAGCCTTTGTCTCAAGA
AGAATCCACCCTCATTGAAAGAGCAACGGCTACAATCAACAGCATCCCCATCTCTG
AAGACTACAGCGTCGCCAGCGCAGCTCTCTCTAGCGACGGCCGCATCTTCACTGGTG
TCAATGTATATCATTTTACTGGGGGACCTTGTGCAGAACTCGTGGTGCTGGGCACTG
CTGCTGCTGCGGCAGCTGGCAACCTGACTTGTATCGTCGCGATCGGAAATGAGAACA
GGGGCATCTTGAGCCCCTGCGGACGGTGCCGACAGGTGCTTCTCGATCTGCATCCTG
GGATCAAAGCCATAGTGAAGGACAGTGATGGACAGCCGACGGCAGTTGGGATTCGT
GAATTGCTGCCCTCTGGTTATGTGTGGGAGGGCTAAGCACTTCGTGGCCGAGGAGCA
GGACTGACACGTGCTACGAGATTTCGATTCCACCGCCGCCTTCTATGAAAGGTTGGG
CTTCGGAATCGTTTTCCGGGACGCCGGCTGGATGATCCTCCAGCGCGGGGATCTCAT
GCTGGAGTTCTTCGCCCACCCCAACTTGTTTATTGCAGCTTATAATGGTTACAAATAA
AGCAATAGCATCACAAATTTCACAAATAAAGCATTTTTTTCACTGCATTCTAGTTGT
GGTTTGTCCAAACTCATCAATGTATCTTAGCGCTCACTGCCCGCTTTCCAGTCGGGA
AACCTGTCGTGCCAGCTGCATTAATGAATCGGCCAACGCGCGGGGAGAGGCGGTTT
GCGTATTGGGCGCTCTCCTAGGccagaaatggcgccggaggcgggaacaaggtggtggatgagtgctacatcccca
attacttgctccccaaaacccagcctgagTCCCTATCAGTGATAGAGActccagtgggcgtggactaatatggaacagtat
ttaagcgcctgTCCCTATCAGTGATAGAGAtttgaatctcacggagcgtaaacggttggtggcgcagcatctGTTTA
AACgcagacgcaggagcagaacaaagagaatcagaatcccaattctgatgcgccggtgatcagatcaaaaacttcagccaggtacatg
gagctggtcgggtggctcgtggacaaggggattacctcggagaagcagtggattcaggaggaccaggcctcatacatctccttcaatgcg
gcctccaactcgcggtcccaaatcaaggctgccttggacaatgcgggaaagattatgagcctgactaaaaccgcccccgactacctggtg
ggccagcagcccgtggaggacatttccagcaatcggatttataaaattttggaactaaacgggtacgatccccaatatgcggcttccgtctttc
tgggatgggccacgaaaaagttcggcaagaggaacaccatctggctgtttgggcctgcaactaccgggaagaccaacatcgcggaggcc
atagcccacactgtgcccttctacgggtgcgtaaactggaccaatgagaactttcccttcaacgactgtgtcgacaagatggtgatctggtgg
gaggaggggaagatgaccgccaaggtcgtggagtcggccaaagccattctcggaggaagcaaggtgcgcgtggaccagaaatgcaag
tcctcggcccagatagacccgactcccgtgatcgtcacctccaacaccaacatgtgcgccgtgattgacgggaactcaacgaccttcgaac
accagcagccgttgcaagaccggatgttcaaatttgaactcacccgccgtctggatcatgactttgggaaggtcaccaagcaggaagtcaa
agactttttccggtgggcaaaggatcacgtggttgaggtggagcatgaattctacgtcaaaaagggtggagccaagaaaagacccgcccc
cagtgacgcagatataagtgagcccaaacgggtgcgcgagtcagttgcgcagccatcgacgtcagacgcggaagcttcgatcaactacg
cagacaggtaccaaaacaaatgttctcgtcacgtgggcatgaatctgatgctgtttccctgcagacaatgcgagagaatgaatcagaattcaa
atatctgcttcactcacggacagaaagactgtttagagtgctttcccgtgtcagaatctcaacccgtttctgtcgtcaaaaaggcgtatcagaaa -continued ctgtgctacattcatcatatcatgggaaaggtgccagacgcttgcactgcctgcgatctggtcaatgtggatttggatgactgcatctttgaaca ataaACTAGTTTGCTTGTTAATCAATAAACCGTTTAATTCGTTTCAGTTGAACTTTGGTC TCTGCGTATTTCTTTCTTATCTAGTTTCCATGCTCTAGAGTATACgatatccatcacactggcggcc gctcgactagagcggccgccaccgcggtggagctccagcttttgttcgcgcgcttggcgtaatcatggtcatagctgtttcctgtgtgaaattc cacagcctggggtgcctaattgcgttgcgctcactgcccgctttccagtcgggaaacctgtcgtgccagctgcattaatgaatcggccaacg cgcggggagaggcggtttgcgtattgggcgctcttccgcttcctcgctcactgactcgctgcgctcggtcgttcggctgcggcgagcggtat cagctcactcaaaggcggtaatacggttatccacagaatcaggggataacgcaggaaagaacatgtgagcaaaaggccagcaaaaggc caggaaccgtaaaaaggccgcgttgctggcgtttttccataggctccgcccccctgacgagcatcacaaaaatcgacgctcaagtcagag gtggcgaaacccgacaggactataaagataccaggcgtttccccctggaagctccctcgtgcgctctcctgttccgaccctgccgcttaccg gatacctgtccgcctttctcccttcgggaagcgtggcgctttctcatagctcacgctgtaggtatctcagttcggtgtaggtcgttcgctccaag ctgggctgtgtgcacgaaccccccgttcagcccgaccgctgcgccttatccggtaactatcgtcttgagtccaacccggtaagacacgactt atcgccactggcagcagccactggtaacaggattagcagagcgaggtatgtaggcggtgctacagagttcttgaagtggtggcctaactac ggctacactagaagaacagtatttggtatctgcgctctgctgaagccagttaccttcggaaaaagagttggtagctcttgatccggcaaacaa accaccgctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaattaaaaa tgaagttttaaatcaatctaaagtatatatgagtaaacttggtctgacagaaataataaaaaagccggattaataatctggcttttttatattctctctc tagtatataaacgcagaaaggcccacccgaaggtgagccagtgtgactctagtattattagaaaaactcatcgagcatcaaatgaaactgca atttattcatatcaggattatcaataccatatttttgaaaaagccgtttctgtaatgaaggagaaaactcaccgaggcagttccaaagaatggca aggtcctggtaacggtctgcgattccgacccgtccaacatcaatacaacctattaatttcccctcgtcaaaaataaggttatcaagtgagaaat caccatgagtgacgactgaatccggtgagaatggcaagagcttgtgcatttctttccagacttgttcaacaggccagccattacgctcgtcatc aaaatcactcgcatcaaccaaaccgttattcatgcgtgattgcgcctgagcaagacgaaatacacgatcgctgttaaaaggacaattacaaa caggaatcgaatgtaaccggcgcaggaacacggccagcgcatcaacaatattttcacctgaatcaggatattcttctaatacctggaaggct gttttcccaggaatcgcggtggtgagtaaccacgcatcatcaggagtacggataaaatgcttgatggtcgggagaggcataaactccgtca gccagttgagacggaccatctcatctgtaacatcattggcaacgctacctttgccatgtttcagaaacaactctggcgcatcgggcttcccata caagcgatagattgtcgcacctgattgcccgacattatcgcgagcccatttatacccatataaatcagcgtccatgttggagtttaagcgcgga cgggagcaagacgtttcccgttgaatatggctcataacaccccttgtattactgtttatgtaagcagacagttttattgttcatgatgatatattttta tcttgtgcaatgtaacatcagagattttgagacacaacgtggctttgttgaataaatcgaacttttgctgagttgaaggatcagctctagtaaaat aataaaaaagccggattaataatctggcttttttatattctctctctagtatataaacgcagaaaggcccacccgaaggtgagccagtgtgacgg cacatttccccgaaaagtgccacctaaattgtaagcgttaatattttgttaaaattcgcgttaaatttttgttaaatcagctcattttttaaccaatag gccgaaatcggcaaaatcccttataaatcaaaagaatagaccgagatagggttgagtgttgttccagtttggaacaagagtccactattaaaga acgtggactccaacgtcaaagggcgaaaaaccgtctatcagggcgatggcccactacgtgaaccatcaccctaatcaagttttttggggtcg aggtgccgtaaagcactaaatcggaaccctaaagggagcccccgatttagagcttgacggggaaagccggcgaacgtggcgagaaagg aagggaagaaagcgaaaggagcgggcgctagggcgctggcaagtgtagcggtcacgctgcgcgtaaccaccacacccgccgcgctta atgcgccgctacagggcgcgtcccattcgccattcaggctgcgcaactgttgggaagggcgatcggtgcgggcctcttcgctattacgcca gctggcgaaagggggatgtgctgcaaggcgattaagttgggtaacgccagggttttcccagtcacgacgttgtaaaacgacggccagtga gcgcgcggcgaattgggtaccgggccccc iRepCap5/pKan-Anc80-RepCap-p5i2-p19i2 (10,493 bp)

(SEQ ID NO: 19)

cctcgaggGCTAGCcattcTATTTAAtcTCCCTATCAGTGATAGAGAtcGCCCGAGT

GAGCACGCAGGGTCTCCATTTTGATCCCTATCAGTGATAGAGAAGCGGGAGGTTTGA

ACGCGCAGCCGCCatgccggggttttacgagattgtgattaaggtccccagcgaccttgacgagcatctgcccggcatttctgac agctttgtgaactgggtggccgagaaggaatgggagttgccgccagattctgacatggatctgaatctgattgagcaggcacccctgaccg -continued tggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaacccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttcccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag -continued gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttctta tctagtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagTCCCTATCAGTGATAGAGActccagtgggcgtggactaatatggaacagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagactttttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag -continued gtaccaaaacaaatgttctcgtcacgtgggcatgaatctgatgctgtttccctgcagacaatgcgagagaatgaatcagaattcaaatatctgc
ttcactcacggacagaaagactgtttagagtgctttcccgtgtcagaatctcaacccgtttctgtcgtcaaaaaggcgtatcagaaactgtgcta
cattcatcatatcatgggaaaggtgccagacgcttgcactgcctgcgatctggtcaatgtggatttggatgactgcatctttgaacaataaAC
TAGTTTGCTTGTTAATCAATAAACCGTTTAATTCGTTTCAGTTGAACTTTGGTCTCTG
CGTATTTCTTTCTTATCTAGTTTCCATGCTCTAGAGTATACgatatccatcacactggcggccgctcga
ctagagcggccgccaccgcggtggagctccagcttttgttcgcgcgcttggcgtaatcatggtcatagctgtttcctgtgtgaaattccacag
cctggggtgcctaattgcgttgcgctcactgcccgctttccagtcgggaaacctgtcgtgccagctgcattaatgaatcggccaacgcgcgg
ggagaggcggtttgcgtattgggcgctcttccgcttcctcgctcactgactcgctgcgctcggtcgttcggctgcggcgagcggtatcagct
cactcaaaggcggtaatacggttatccacagaatcaggggataacgcaggaaagaacatgtgagcaaaaggccagcaaaaggccagga
accgtaaaaaggccgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacc
tgtccgcctttctcccttcgggaagcgtggcgctttctcatagctcacgctgtaggtatctcagttcggtgtaggtcgttcgctccaagctgggc
tgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaagaacagtatttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagttt
taaatcaatctaaagtatatatgagtaaacttggtctgacagaaataataaaaaagccggattaataatctggctttttatattctctctctagtatat
aaacgcagaaaggcccacccgaaggtgagccagtgtgactctagtattattagaaaaactcatcgagcatcaaatgaaactgcaatttattca
tatcaggattatcaataccatatttttgaaaaagccgtttctgtaatgaaggagaaaactcaccgaggcagttccaaagaatggcaaggtcctg
gtaacggtctgcgattccgacccgtccaacatcaatacaacctattaatttcccctcgtcaaaaataaggttatcaagtgagaaatcaccatga
gtgacgactgaatccggtgagaatggcaagagcttgtgcatttctttccagacttgttcaacaggccagccattacgctcgtcatcaaaatcac
tcgcatcaaccaaaccgttattcatgcgtgattgcgcctgagcaagacgaaatacacgatcgctgttaaaaggacaattacaaacaggaatc
gaatgtaaccggcgcaggaacacggccagcgcatcaacaatattttcacctgaatcaggatattcttctaatacctggaaggctgttttccca
ggaatcgcggtggtgagtaaccacgcatcatcaggagtacggataaaatgcttgatggtcgggagaggcataaactccgtcagccagttg
agacggaccatctcatctgtaacatcattggcaacgctacctttgccatgtttcagaaacaactctggcgcatcgggcttcccatacaagcgat
agattgtcgcacctgattgcccgacattatcgcgagcccatttatacccatataaatcagcgtccatgttggagtttaagcgcggacgggagc
aagacgtttcccgttgaatatggctcataacaccccttgtattactgtttatgtaagcagacagttttattgttcatgatgatatatttttatcttgt
gcaatgtaacatcagagatttgagacacaacgtggctttgttgaataaatcgaacttttgctgagttgaaggatcagctctagtaaaataataaaaa
agccggattaataatctggctttttatattctctctctagtatataaacgcagaaaggcccacccgaaggtgagccagtgtgacggcacatttcc
ccgaaaagtgccacctaaattgtaagcgttaatattttgttaaaattcgcgttaaatttttgttaaatcagctcattttttaaccaataggccgaaat
cggcaaaatcccttataaatcaaaagaatagaccgagatagggttgagtgttgttccagtttggaacaagagtccactattaaagaacgtggac
tccaacgtcaaagggcgaaaaaccgtctatcagggcgatggcccactacgtgaaccatcaccctaatcaagttttttggggtcgaggtgcc
gtaaagcactaaatcggaaccctaaagggagcccccgatttagagcttgacggggaaagccggcgaacgtggcgagaaaggaaggga
agaaagcgaaaggagcgggcgctagggcgctggcaagtgtagcggtcacgctgcgcgtaaccaccacacccgccgcgcttaatgcgc
cgctacagggcgcgtcccattcgccattcaggctgcgcaactgttgggaagggcgatcggtgcgggcctcttcgctattacgccagctggc
gaaagggggatgtgctgcaaggcgattaagttgggtaacgccagggttttcccagtcacgacgttgtaaaacgacggccagtgagcgcgc
ggcgaattgggtaccgggccccc -continued iRepCap6/pKan-Anc80-RepCap-p5i3-p19i2 (10,491 bp)

(SEQ ID NO: 20)

cctcgaggGCTAGCcattcTCCCTATCAGTGATAGAGAtcTATTTAAGCCCGAGTG

AGCACGCAGTCCCTATCAGTGATAGAGAGGTCTCCATTTTGAAGCGGGAGGTTTGAA

CGCGCAGCCGCCatgccggggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaaccccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc -continued agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttcttatct agtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggcccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagTCCCTATCAGTGATAGAGActccagtgggcgtggactaatatggaacagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg -continued ggaagatgaccgccaaggtcgtggagtcggccaaagccattctcggaggaagcaaggtgcgcgtggaccagaaatgcaagtcctcggc
ccagatagacccgactcccgtgatcgtcacctccaacaccaacatgtgcgccgtgattgacgggaactcaacgaccttcgaacaccagca
gccgttgcaagaccggatgttcaaatttgaactcacccgccgtctggatcatgactttgggaaggtcaccaagcaggaagtcaaagactttttt
ccggtgggcaaaggatcacgtggttgaggtggagcatgaattctacgtcaaaaagggtggagccaagaaaagacccgcccccagtgac
gcagatataagtgagcccaaacgggtgcgcgagtcagttgcgcagccatcgacgtcagacgcggaagcttcgatcaactacgcagacag
gtaccaaaacaaatgttctcgtcacgtgggcatgaatctgatgctgtttccctgcagacaatgcgagagaatgaatcagaattcaaatatctgc
ttcactcacggacagaaagactgtttagagtgctttcccgtgtcagaatctcaacccgtttctgtcgtcaaaaaggcgtatcagaaactgtgcta
cattcatcatatcatgggaaaggtgccagacgcttgcactgcctgcgatctggtcaatgtggatttggatgactgcatctttgaacaataaAC
TAGTTTGCTTGTTAATCAATAAACCGTTTAATTCGTTTCAGTTGAACTTTGGTCTCTG
CGTATTTCTTTCTTATCTAGTTTCCATGCTCTAGAGTATACgatatccatcacactggcggccgctcga
ctagagcggccgccaccgcggtggagctccagcttttgttcgcgcgcttggcgtaatcatggtcatagctgtttcctgtgtgaaattccacag
cctggggtgcctaattgcgttgcgctcactgcccgctttccagtcgggaaacctgtcgtgccagctgcattaatgaatcggccaacgcgcgg
ggagaggcggtttgcgtattgggcgctcttccgcttcctcgctcactgactcgctgcgctcggtcgttcggctgcggcgagcggtatcagct
cactcaaaggcggtaatacggttatccacagaatcaggggataacgcaggaaagaacatgtgagcaaaaggccagcaaaaggccagga
accgtaaaaaggccgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacc
tgtccgcctttctcccttcgggaagcgtggcgctttctcatagctcacgctgtaggtatctcagttcggtgtaggtcgttcgctccaagctgggc
tgtgtgcacgaaccccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcctaactacggctac
actagaagaacagtatttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagttt
taaatcaatctaaagtatatatgagtaaacttggtctgacagaaataataaaaaagccggattaataatctggctttttatattctctctctagtatat
aaacgcagaaaggcccacccgaaggtgagccagtgtgactctagtattattagaaaaactcatcgagcatcaaatgaaactgcaatttattca
tatcaggattatcaataccatatttttgaaaaagccgtttctgtaatgaaggagaaaactcaccgaggcagttccaaagaatggcaaggtcctg
gtaacggtctgcgattccgacccgtccaacatcaatacaacctattaatttcccctcgtcaaaaataaggttatcaagtgagaaatcaccatga
gtgacgactgaatccggtgagaatggcaagagcttgtgcatttctttccagacttgttcaacaggccagccattacgctcgtcatcaaaatcac
tcgcatcaaccaaaccgttattcatgcgtgattgcgcctgagcaagacgaaatacacgatcgctgttaaaaggacaattacaaacaggaatc
gaatgtaaccggcgcaggaacacggccagcgcatcaacaatattttcacctgaatcaggatattcttctaatacctggaaggctgttttccca
ggaatcgcggtggtgagtaaccacgcatcatcaggagtacggataaaatgcttgatggtcgggagaggcataaactccgtcagccagttg
agacggaccatctcatctgtaacatcattggcaacgctacctttgccatgtttcagaaacaactctggcgcatcgggcttcccatacaagcgat
agattgtcgcacctgattgcccgacattatcgcgagcccatttatacccatataaatcagcgtccatgttggagtttaagcgcggacgggagc
aagacgtttcccgttgaatatggctcataacaccccttgtattactgtttatgtaagcagacagttttattgttcatgatgatatatttttatcttgt
gcaatgtaacatcagagattttgagacacaacgtggctttgttgaataaatcgaacttttgctgagttgaaggatcagctctagtaaaataataaaaa
agccggattaataatctggctttttatattctctctctagtatataaacgcagaaaggcccacccgaaggtgagccagtgtgacggcacatttcc
ccgaaaagtgccacctaaattgtaagcgttaatattttgttaaaattcgcgttaaatttttgttaaatcagctcattttttaaccaataggccgaaat
cggcaaaatcccttataaatcaaaagaatagaccgagatagggttgagtgttgttccagtttggaacaagagtccactattaaagaacgtggac
tccaacgtcaaagggcgaaaaaccgtctatcagggcgatggcccactacgtgaaccatcaccctaatcaagttttttggggtcgaggtgcc
gtaaagcactaaatcggaaccctaaagggagcccccgatttagagcttgacggggaaagccggcgaacgtggcgagaaaggaaggga
agaaagcgaaaggagcgggcgctagggcgctggcaagtgtagcggtcacgctgcgcgtaaccaccacacccgccgcgcttaatgcgc -continued cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap7/pKan-Anc80-RepCap-p5i1-p19i3 (10,495 bp)

(SEQ ID NO: 21)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccaAtgggcAtggacCaaCatggaaca gtaCCtCagcgcctgtttgaatctcacggagcgtaaacggttggtggcgcagcatctgacgcacgtgtcgcagacgcaggagcagaac aaagagaatcagaatcccaattctgatgcgccggtgatcagatcaaaaacttcagccaggtacatggagctggtcgggtggctcgtggaca aggggattacctcggagaagcagtggatccaggaggaccaggcctcatacatctccttcaatgcggcctccaactcgcggtcccaaatca aggctgccttggacaatgcgggaaagattatgagcctgactaaaaccgcccccgactacctggtgggccagcagcccgtggaggacattt ccagcaatcggatttataaaattttggaactaaacgggtacgatccccaatatgcggcttccgtctttctgggatgggccacgaaaaagttcg gcaagaggaacaccatctggctgtttgggcctgcaactaccgggaagaccaacatcgcggaggccatagcccacactgtgcccttctacg ggtgcgtaaactggaccaatgagaactttcccttcaacgactgtgtcgacaagatggtgatctggtgggaggaggggaagatgaccgcca aggtcgtggagtcggccaaagccattctcggaggaagcaaggtgcgcgtggaccagaaatgcaagtcctcggcccagatagacccgact cccgtgatcgtcacctccaacaccaacatgtgcgccgtgattgacgggaactcaacgaccttcgaacaccagcagccgttgcaagaccgg atgttcaaatttgaactcacccgccgtctggatcatgactttgggaaggtcaccaagcaggaagtcaaagactttttccggtgggcaaaggat cacgtggttgaggtggagcatgaattctacgtcaaaaagggtggagccaagaaaagacccgcccccagtgacgcagatataagtgagcc caaacgggtgcgcgagtcagttgcgcagccatcgacgtcagacgcggaagcttcgatcaactacgcagacaggtaccaaaacaaatgttc tcgtcacgtgggcatgaatctgatgctgtttccctgcagacaatgcgagagaatgaatcagaattcaaatatctgcttcactcacggacagaa agactgtttagagtgctttcccgtgtcagaatctcaacccgtttctgtcgtcaaaaaggcgtatcagaaactgtgctacattcatcatatcatggg aaaggtgccagacgcttgcactgcctgcgatctggtcaatgtggatttggatgactgcatctttgaacaataaatgatttaaatcaggtatggct gccgatggttatcttccagattggctcgaggacaacctctctgagggcattcgcgagtggtgggacttgaaacctggagccccgaaaccca aagccaaccagcaaaagcaggacgacggccggggtctggtgcttcctggctacaagtacctcggacccttcaacggactcgacaaggg ggagcccgtcaacgcggcggacgcagcggccctcgagcacgacaaggcctacgaccagcagctcaaagcgggtgacaatccgtacct gcggtataaccacgccgacgccgagtttcaggagcgtctgcaagaagatacgtcttttgggggcaacctcgggcgagcagtcttccaggc caagaagcgggttctcgaacctctcggtctggttgaggaaggcgctaagacggctcctggaaagaagagaccggtagagcaatcacccc aggaaccagactcctcttcgggcatcggcaagaaaggccagcagcccgcgagaaagagactcaactttgggcagactggcgactcaga gtcagtgcccgaccctcaaccactcggagaacccccgcagcccccctctggtgtgggatctaatacaatggctgcaggcggtggcgctcc aatggcagacaataacgaaggcgccgacggagtgggtaacgcctcaggaaattggcattgcgattccacatggctgggcgacagagtca tcaccaccagcacccgaacctgggccctccccacctacaacaaccacctctacaagcaaatctccagccaatcgggaggcagcaccaac gacaacacctacttcggctacagcacccccctgggggtattttgactttaacagattccactgccacttctcaccacgtgactggcagcgactc atcaacaacaactggggattccggcccaagaagctcaacttcaagctcttcaacatccaggtcaaggaggtcacgacgaatgatggcacc acgaccatcgccaataaccttaccagcacggttcaggtctttacggactcggaataccagctcccgtacgtcctcggctctgcgcaccagg gctgcctgcctccgttcccggcggacgtcttcatgattcctcagtacgggtacctgactctgaacaatggcagtcaggccgtgggccgttcct ccttctactgcctggaatactttccttctcaaatgctgagaacgggcaacaactttcagttcagctacacgtttgaggacgtgccttttcacagca -continued gctacgcgcacagccaaagcctggaccggctgatgaacccccctcatcgaccagtacctgtactacctgtctcggactcagaccacgagtg gtaccgcaggaaatcggacgttgcaattttctcaggccgggcctagtagcatggcgaatcaggccaaaaactggctacccgggccctgct accggcagcaacgcgtctccaagacaaccaatcaaaataacaacagcaactttgcctggaccggtgccaccaagtatcatctgaatggca gagactctctggtaaatcccggtcccgctatggcaacccacaaggacgacgaagacaaatttttttccgatgagcggagtcttaatatttggga aacagggagctggaaatagcaacgtggaccttgacaacgttatgataaccaacgaggaagaaattaaaaccaccaacccagtggccaca gaagagtacggcacggtggccactaacctgcaatcggccaacaccgctcctgctacagggaccgtcaacagtcaaggagccttacctgg catggtctggcaggaccgggacgtgtacctgcagggtcctatctgggccaagattcctcacacggacggacactttcatccctcgccgctg atgggaggctttggactgaaacacccgcctcctcagatcctgattaagaatacacctgttcccgcgaatcctccaactaccttcagtccagct aagtttgcgtcgttcatcacgcagtacagcaccggacaggtcagcgtggaaattgaatgggagctgcagaaagaaaacagcaaacgctgg aacccagagattcaatacacttccaactacaacaaatctacaaatgtggactttgctgttgacacaaatggcgtttattctgagcctcgccccat cggcacccgttacctcacccgtaatctgtaaactagtttgcttgttaatcaataaaccgtttaattcgtttcagttgaactttggtctctgcgtattt ctttcttatctagtttccatgctctagaggtcctgtattagaggtcacgtgagtgttttgcgacattttgcgacaccatgtggtcacgctgggtattt aagcccgagtgagcacgcagggtctccattttgaagcgggaggtttgaacgcgcagccgccaagccgaattctgcagatatcggggttgggg ttgcgccttttccaaggcagccctgggtttgcgcagggacgcggctgctctgggcgtggttccgggaaacgcagcggcgccgaccctgg gtctcgcacattcttcacgtccgttcgcagcgtcacccggatcttcgccgctacccttgtgggccccccggcgacgcttcctgctccgcccct aagtcgggaaggttccttgcggttcgcggcgtgccggacgtgacaaacggaagccgcacgtctcactagtaccctcgcagacggacagc gccagggagcaatggcagcgcgccgaccgcgatgggctgtggccaatagcggctgctcagcagggcgcgccgagagcagcggccg ggaaggggcggtgcgggaggcggggtgtggggcggtagtgtgggccctgttcctgcccgcgcggtgttccgcattctgcaagcctccg gagcgcacgtcggcagtcggctccctcgttgaccgaatcaccgacctctctccccagAAGCTCCCGGGAGCTTGTATA

TCCATTTTCGGATCTGATCAGCACGTGTTGACAATTAATCATCGGCATAGTATATCG

GCATAGTATAATACGACAAGGTGAGGAACgccaccATGGCCAAGCCTTTGTCTCAAGA

AGAATCCACCCTCATTGAAAGAGCAACGGCTACAATCAACAGCATCCCCATCTCTG

AAGACTACAGCGTCGCCAGCGCAGCTCTCTCTAGCGACGGCCGCATCTTCACTGGTG

TCAATGTATATCATTTTACTGGGGGACCTTGTGCAGAACTCGTGGTGCTGGGCACTG

CTGCTGCTGCGGCAGCTGGCAACCTGACTTGTATCGTCGCGATCGGAAATGAGAACA

GGGGCATCTTGAGCCCCTGCGGACGGTGCCGACAGGTGCTTCTCGATCTGCATCCTG

GGATCAAAGCCATAGTGAAGGACAGTGATGGACAGCCGACGGCAGTTGGGATTCGT

GAATTGCTGCCCTCTGGTTATGTGTGGGAGGGCTAAGCACTTCGTGGCCGAGGAGCA

GGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCAT

GCTGGAGTTCTTCGCCCACCCCAACTTGTTTATTGCAGCTTATAATGGTTACAAATAA

AGCAATAGCATCACAAATTTCACAAATAAAGCATTTTTTTCACTGCATTCTAGTTGT

GGTTTGTCCAAACTCATCAATGTATCTTAGCGCTCACTGCCCGCTTTCCAGTCGGGA

AACCTGTCGTGCCAGCTGCATTAATGAATCGGCCAACGCGCGGGGAGAGGCGGTTT

GCGTATTGGGCGCTCTCCTAGGccagaaatggcgccggaggcgggaacaaggtggtggatgagtgctacatcccca attacttgctccccaaaacccagcctgagctccagtgggcgtggactaatatggaaTCCCTATCAGTGATAGAGAcagtat ttaagcgcctgTCCCTATCAGTGATAGAGAtttgaatctcacggagcgtaaacggttggtggcgcagcatctGTTTA AACgcagacgcaggagcagaacaaagagaatcagaatcccaattctgatgcgccggtgatcagatcaaaaacttcagccaggtacatg gagctggtcgggtggctcgtggacaaggggattacctcggagaagcagtggattcaggaggaccaggcctcatacatctccttcaatgcg gcctccaactcgcggtcccaaatcaaggctgccttggacaatgcgggaaagattatgagcctgactaaaaccgcccccgactacctggtg -continued ggccagcagcccgtggaggacatttccagcaatcggatttataaaattttggaactaaacgggtacgatccccaatatgcggcttccgtctttc tgggatgggccacgaaaaagttcggcaagaggaacaccatctggctgtttgggcctgcaactaccgggaagaccaacatcgcggaggcc atagcccacactgtgcccttctacgggtgcgtaaactggaccaatgagaactttcccttcaacgactgtgtcgacaagatggtgatctggtgg gaggaggggaagatgaccgccaaggtcgtggagtcggccaaagccattctcggaggaagcaaggtgcgcgtggaccagaaatgcaag tcctcggcccagatagacccgactcccgtgatcgtcacctccaacaccaacatgtgcgccgtgattgacgggaactcaacgaccttcgaac accagcagccgttgcaagaccggatgttcaaatttgaactcacccgccgtctggatcatgactttgggaaggtcaccaagcaggaagtcaa agactttttccggtgggcaaaggatcacgtggttgaggtggagcatgaattctacgtcaaaaagggtggagccaagaaaagacccgcccc cagtgacgcagatataagtgagcccaaacgggtgcgcgagtcagttgcgcagccatcgacgtcagacgcggaagcttcgatcaactacg cagacaggtaccaaaacaaatgttctcgtcacgtgggcatgaatctgatgctgtttccctgcagacaatgcgagagaatgaatcagaattcaa atatctgcttcactcacggacagaaagactgtttagagtgctttcccgtgtcagaatctcaacccgtttctgtcgtcaaaaaggcgtatcagaaa ctgtgctacattcatcatatcatgggaaaggtgccagacgcttgcactgcctgcgatctggtcaatgtggatttggatgactgcatctttgaaca ataaACTAGTTTGCTTGTTAATCAATAAACCGTTTAATTCGTTTCAGTTGAACTTTGGTC TCTGCGTATTTCTTTCTTATCTAGTTTCCATGCTCTAGAGTATACgatatccatcacactggcggcc gctcgactagagcggccgccaccgcggtggagctccagcttttgttcgcgcgcttggcgtaatcatggtcatagctgtttcctgtgtgaaattc cacagcctggggtgcctaattgcgttgcgctcactgcccgctttccagtcgggaaacctgtcgtgccagctgcattaatgaatcggccaacg cgcggggagaggcggtttgcgtattgggcgctcttccgcttcctcgctcactgactcgctgcgctcggtcgttcggctgcggcgagcggtat cagctcactcaaaggcggtaatacggttatccacagaatcaggggataacgcaggaaagaacatgtgagcaaaaggccagcaaaaggc caggaaccgtaaaaaggccgcgttgctggcgtttttccataggctccgcccccctgacgagcatcacaaaaatcgacgctcaagtcagag gtggcgaaacccgacaggactataaagataccaggcgtttccccctggaagctccctcgtgcgctctcctgttccgaccctgccgcttaccg gatacctgtccgcctttctcccttcgggaagcgtggcgctttctcatagctcacgctgtaggtatctcagttcggtgtaggtcgttcgctccaag ctgggctgtgtgcacgaaccccccgttcagcccgaccgctgcgccttatccggtaactatcgtcttgagtccaacccggtaagacacgactt atcgccactggcagcagccactggtaacaggattagcagagcgaggtatgtaggcggtgctacagagttcttgaagtggtggcctaactac ggctacactagaagaacagtatttggtatctgcgctctgctgaagccagttaccttcggaaaaagagttggtagctcttgatccggcaaacaa accaccgctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaattaaaaa tgaagttttaaatcaatctaaagtatatatgagtaaacttggtctgacagaaataataaaaaagccggattaataatctggctttttatattctctctc tagtatataaacgcagaaaggcccacccgaaggtgagccagtgtgactctagtattattagaaaaactcatcgagcatcaaatgaaactgca atttattcatatcaggattatcaataccatatttttgaaaaagccgtttctgtaatgaaggagaaaactcaccgaggcagttccaaagaatggca aggtcctggtaacggtctgcgattccgacccgtccaacatcaatacaacctattaatttcccctcgtcaaaaataaggttatcaagtgagaaat caccatgagtgacgactgaatccggtgagaatggcaagagcttgtgcatttctttccagacttgttcaacaggccagccattacgctcgtcatc aaaatcactcgcatcaaccaaaccgttattcatgcgtgattgcgcctgagcaagacgaaatacacgatcgctgttaaaaggacaattacaaa caggaatcgaatgtaaccggcgcaggaacacggccagcgcatcaacaatattttcacctgaatcaggatattcttctaatacctggaaggct gttttcccaggaatcgcggtggtgagtaaccacgcatcatcaggagtacggataaaatgcttgatggtcgggagaggcataaactccgtca gccagttgagacggaccatctcatctgtaacatcattggcaacgctacctttgccatgtttcagaaacaactctggcgcatcgggcttcccata caagcgatagattgtcgcacctgattgcccgacattatcgcgagcccatttatacccatataaatcagcgtccatgttggagtttaagcgcgga cgggagcaagacgtttcccgttgaatatggctcataacaccccttgtattactgtttatgtaagcagacagttttattgttcatgatgatatatttt aaataaaaaagccggattaataatctggctttttatattctctctctagtatataaacgcagaaaggcccacccgaaggtgagccagtgtgacgg cacatttccccgaaaagtgccacctaaattgtaagcgttaatattttgttaaaattcgcgttaaatttttgttaaatcagctcattttttaaccaata ggccgaaatcggcaaaatcccttataaatcaaaagaatagaccgagatagggttgagtgttgttccagtttggaacaagagtccactattaaaga acgtggactccaacgtcaaagggcgaaaaaccgtctatcagggcgatggcccactacgtgaaccatcaccctaatcaagttttttggggtcg aggtgccgtaaagcactaaatcggaaccctaaagggagcccccgatttagagcttgacggggaaagccggcgaacgtggcgagaaagg -continued aagggaagaaagcgaaaggagcgggcgctagggcgctggcaagtgtagcggtcacgctgcgcgtaaccaccacacccgccgcgctta atgcgccgctacagggcgcgtcccattcgccattcaggctgcgcaactgttgggaagggcgatcggtgcgggcctcttcgctattacgcca gctggcgaaagggggatgtgctgcaaggcgattaagttgggtaacgccagggttttcccagtcacgacgttgtaaaacgacggccagtga gcgcgcggcgaattgggtaccgggccccc iRepCap8/pKan-Anc80-RepCap-p5i2-p19i3
(10,493 bp)

(SEQ ID NO: 22)

cctcgaggGCTAGCcattcTATTTAAtcTCCCTATCAGTGATAGAGAtcGCCCGAGT

GAGCACGCAGGGTCTCCATTTTGATCCCTATCAGTGATAGAGAAGCGGGAGGTTTGA

ACGCGCAGCCGCCatgccggggttttacgagattgtgattaaggtccccagcgaccttgacgagcatctgcccggcatttctgac agctttgtgaactgggtggccgagaaggaatgggagttgccgccagattctgacatggatctgaatctgattgagcaggcacccctgaccg tggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaaccccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcaccccctgggggtattttgactttaacagattccactgccacttctcaccacgtgactggcagcgactcatcaa caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc -continued tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaacccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttctta tctagtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaaTCCCTATCAGTGATAGAGAcagtatttaagc gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg -continued tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagactttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag gtaccaaaacaaatgttctcgtcacgtgggcatgaatctgatgctgtttccctgcagacaatgcgagagaatgaatcagaattcaaatatctgc ttcactcacggacagaaagactgtttagagtgctttcccgtgtcagaatctcaacccgtttctgtcgtcaaaaaggcgtatcagaaactgtgcta cattcatcatatcatgggaaaggtgccagacgcttgcactgcctgcgatctggtcaatgtggatttggatgactgcatctttgaacaataaAC

TAGTTTGCTTGTTAATCAATAAACCGTTTAATTCGTTTCAGTTGAACTTTGGTCTCTG

CGTATTTCTTTCTTATCTAGTTTCCATGCTCTAGAGTATACgatatccatcacactggcggccgctcga ctagagcggccgccaccgcggtggagctccagcttttgttcgcgcgcttggcgtaatcatggtcatagctgtttcctgtgtgaaattccacag cctggggtgcctaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggtatcagct cactcaaaggcggtaatacggttatccacagaatcaggggataacgcaggaaagaacatgtgagcaaaaggccagcaaaaggccagga accgtaaaaaggccgcgttgctggcgtttttccataggctccgcccccctgacgagcatcacaaaaatcgacgctcaagtcagaggtggcg aaacccgacaggactataaagataccaggcgtttccccctggaagctccctcgtgcgctctcctgttccgaccctgccgcttaccggatacc tgtccgcctttctcccttcgggaagcgtggcgctttctcatagctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcctaactacggctac actagaagaacagtatttggtatctgcgctctgctgaagccagttaccttcggaaaaagagttggtagctcttgatccggcaaacaaaccacc cgctcagtggaacgaaaactcacgttaagggattttggtcatgagattatcaaaaaggatcttcacctagatccttttaaattaaaaatgaagttt taaatcaatctaaagtatatatgagtaaacttggtctgacagaaataataaaaaagccggattaataatctggctttttatattctctctctagtatat aaacgcagaaaggcccacccgaaggtgagccagtgtgactctagtattattagaaaaactcatcgagcatcaaatgaaactgcaatttattca tatcaggattatcaataccatatttttgaaaaagccgtttctgtaatgaaggagaaaactcaccgaggcagttccaaagaatggcaaggtcctg gtaacggtctgcgattccgacccgtccaacatcaatacaacctattaatttcccctcgtcaaaaataaggttatcaagtgagaaatcaccatga gtgacgactgaatccggtgagaatggcaagagcttgtgcatttctttccagacttgttcaacaggccagccattacgctcgtcatcaaaatcac tcgcatcaaccaaaccgttattcatgcgtgattgcgcctgagcaagacgaaatacacgatcgctgttaaaaggacaattacaaacaggaatc gaatgtaaccggcgcaggaacacggccagcgcatcaacaatattttcacctgaatcaggatattcttctaatacctggaaggctgttttccca ggaatcgcggtggtgagtaaccacgcatcatcaggagtacggataaaatgcttgatggtcgggagaggcataaactccgtcagccagttg agacggaccatctcatctgtaacatcattggcaacgctacctttgccatgtttcagaaacaactctggcgcatcgggcttcccatacaagcgat agattgtcgcacctgattgcccgacattatcgcgagcccatttatacccatataaatcagcgtccatgttggagtttaagcgcggacgggagc aagacgtttcccgttgaatatggctcataacaccccttgtattactgtttatgtaagcagacagttttattgttcatgatgatatatttttatcttgt gcaatgtaacatcagagattttgagacacaacgtggctttgttgaataaatcgaacttttgctgagttgaaggatcagctctagtaaaataataaaaa agccggattaataatctggctttttatattctctctctagtatataaacgcagaaaggcccacccgaaggtgagccagtgtgacggcacatttcc ccgaaaagtgccacctaaattgtaagcgttaatattttgttaaaattcgcgttaaatttttgttaaatcagctcattttttaaccaataggccgaaat cggcaaaatcccttataaatcaaaagaatagaccgagatagggttgagtgttgttccagtttggaacaagagtccactattaaagaacgtggac -continued tccaacgtcaaagggcgaaaaaccgtctatcagggcgatggcccactacgtgaaccatcaccctaatcaagttttttggggtcgaggtgcc gtaaagcactaaatcggaaccctaaagggagcccccgatttagagcttgacggggaaagccggcgaacgtggcgagaaaggaaggga agaaagcgaaaggagcgggcgctagggcgctggcaagtgtagcggtcacgctgcgcgtaaccaccacacccgccgcgcttaatgcgc cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap9/pKan-Anc80-RepCap-p5i3-p19i3
(10,491 bp)

(SEQ ID NO: 23)

cctcgaggGCTAGCcattcTCCCTATCAGTGATAGAGAtcTATTTAAGCCCGAGTG

AGCACGCAGTCCCTATCAGTGATAGAGAGGTCTCCATTTTGAAGCGGGAGGTTTGAA

CGCGCAGCCGCCatgccggggttttacgagattgtgattaaggtccccagcgaccttgacgagcatctgcccggcatttctgaca gctttgtgaactgggtggccgagaaggaatgggagttgccgccagattctgacatggatctgaatctgattgagcaggcacccctgaccgt ggccgagaagctgcagcgcgactttctgacggaatggcgccgtgtgagtaaggccccggaggctcttttctttgtgcaatttgagaaggga gagagctacttccacatgcacgtgctcgtggaaaccaccggggtgaaatccatggttttgggacgtttcctgagtcagattcgcgaaaaact gattcagagaatttaccgcgggatcgagccgactttgccaaactggttcgcggtcacaaagaccagaaatggcgccggaggcgggaaca aggtggtggatgagtgctacatccccaattacttgctccccaaaacccagcctgagctccaAtgggcAtggacCaaCatggaacagta CCtCagcgcctgtttgaatctcacggagcgtaaacggttggtggcgcagcatctgacgcacgtgtcgcagacgcaggagcagaacaaa gagaatcagaatcccaattctgatgcgccggtgatcagatcaaaaacttcagccaggtacatggagctggtcgggtggctcgtggacaagg ggattacctcggagaagcagtggatccaggaggaccaggcctcatacatctccttcaatgcggcctccaactcgcggtcccaaatcaagg ctgccttggacaatgcgggaaagattatgagcctgactaaaaccgcccccgactacctggtgggccagcagcccgtggaggacatttcca gcaatcggatttataaaattttggaactaaacgggtacgatccccaatatgcggcttccgtctttctgggatgggccacgaaaaagttcggca agaggaacaccatctggctgtttgggcctgcaactaccgggaagaccaacatcgcggaggccatagcccacactgtgcccttctacgggt gcgtaaactggaccaatgagaactttcccttcaacgactgtgtcgacaagatggtgatctggtgggaggaggggaagatgaccgccaagg tcgtggagtcggccaaagccattctcggaggaagcaaggtgcgcgtggaccagaaatgcaagtcctcggcccagatagacccgactccc gtgatcgtcacctccaacaccaacatgtgcgccgtgattgacgggaactcaacgaccttcgaacaccagcagccgttgcaagaccggatgt tcaaatttgaactcacccgccgtctggatcatgactttgggaaggtcaccaagcaggaagtcaaagactttttccggtgggcaaaggatcac gtggttgaggtggagcatgaattctacgtcaaaaagggtggagccaagaaaagacccgcccccagtgacgcagatataagtgagcccaa acgggtgcgcgagtcagttgcgcagccatcgacgtcagacgcggaagcttcgatcaactacgcagacaggtaccaaaacaaatgttctcg tcacgtgggcatgaatctgatgctgtttccctgcagacaatgcgagagaatgaatcagaattcaaatatctgcttcactcacggacagaaaga ctgtttagagtgctttcccgtgtcagaatctcaacccgtttctgtcgtcaaaaaggcgtatcagaaactgtgctacattcatcatatcatgggaaa ggtgccagacgcttgcactgcctgcgatctggtcaatgtggatttggatgactgcatctttgaacaataaatgatttaaatcaggtatggctgcc gatggttatcttccagattggctcgaggacaacctctctgagggcattcgcgagtggtgggacttgaaacctggagccccgaaacccaaag ccaaccagcaaaagcaggacgacggccggggtctggtgcttcctggctacaagtacctcggacccttcaacggactcgacaaggggga gcccgtcaacgcggcggacgcagcggccctcgagcacgacaaggcctacgaccagcagctcaaagcgggtgacaatccgtacctgcg gtataaccacgccgacgccgagtttcaggagcgtctgcaagaagatacgtcttttgggggcaacctcgggcgagcagtcttccaggccaa gaagcgggttctcgaacctctcggtctggttgaggaaggcgctaagacggctcctggaaagaagagaccggtagagcaatcaccccagg aaccagactcctcttcgggcatcggcaagaaaggccagcagcccgcgagaaagagactcaactttgggcagactggcgactcagagtca gtgcccgaccctcaaccactcggagaaccccccgcagcccctctggtgtgggatctaatacaatggctgcaggcggtggcgctccaatg gcagacaataacgaaggcgccgacggagtgggtaacgcctcaggaaattggcattgcgattccacatggctgggcgacagagtcatcac caccagcacccgaacctgggccctccccacctacaacaaccacctctacaagcaaatctccagccaatcgggaggcagcaccaacgaca acacctacttcggctacagcacccccctgggggtattttgactttaacagattccactgccacttctcaccacgtgactggcagcgactcatcaa -continued caacaactggggattccggcccaagaagctcaacttcaagctcttcaacatccaggtcaaggaggtcacgacgaatgatggcaccacgac catcgccaataaccttaccagcacggttcaggtctttacggactcggaataccagctcccgtacgtcctcggctctgcgcaccagggctgcc tgcctccgttcccggcggacgtcttcatgattcctcagtacgggtacctgactctgaacaatggcagtcaggccgtgggccgttcctccttcta ctgcctggaatactttccttctcaaatgctgagaacgggcaacaactttcagttcagctacacgtttgaggacgtgccttttcacagcagctacg cgcacagccaaagcctggaccggctgatgaaccccctcatcgaccagtacctgtactacctgtctcggactcagaccacgagtggtaccg caggaaatcggacgttgcaattttctcaggccgggcctagtagcatggcgaatcaggccaaaaactggctacccgggccctgctaccggc agcaacgcgtctccaagacaaccaatcaaaataacaacagcaactttgcctggaccggtgccaccaagtatcatctgaatggcagagactc tctggtaaatcccggtcccgctatggcaacccacaaggacgacgaagacaaatttttttccgatgagcggagtcttaatatttgggaaacagg gagctggaaatagcaacgtggaccttgacaacgttatgataaccaacgaggaagaaattaaaaccaccaacccagtggccacagaagagt acggcacggtggccactaacctgcaatcggccaacaccgctcctgctacagggaccgtcaacagtcaaggagccttacctggcatggtct ggcaggaccgggacgtgtacctgcagggtcctatctgggccaagattcctcacacggacggacactttcatccctcgccgctgatgggag gctttggactgaaacacccgcctcctcagatcctgattaagaatacacctgttcccgcgaatcctccaactaccttcagtccagctaagtttgc gtcgttcatcacgcagtacagcaccggacaggtcagcgtggaaattgaatgggagctgcagaaagaaaacagcaaacgctggaacccag agattcaatacacttccaactacaacaaatctacaaatgtggactttgctgttgacacaaatggcgtttattctgagcctcgccccatcggcacc cgttacctcacccgtaatctgtaaactagtttgcttgttaatcaataaaccgtttaattcgtttcagttgaactttggtctctgcgtatttctttctta tctagtttccatgctctagaggtcctgtattagaggtcacgtgagtgttttgcgacattttgcgacaccatgtggtcacgctgggtatttaagcccga gtgagcacgcagggtctccattttgaagcgggaggtttgaacgcgcagccgccaagccgaattctgcagatatcggggttggggttgcgc cttttccaaggcagccctgggtttgcgcagggacgcggctgctctgggcgtggttccgggaaacgcagcggcgccgaccctgggtctcg cacattcttcacgtccgttcgcagcgtcacccggatcttcgccgctacccttgtgggccccccggcgacgcttcctgctccgcccctaagtcg ggaaggttccttgcggttcgcggcgtgccggacgtgacaaacggaagccgcacgtctcactagtaccctcgcagacggacagcgccag ggagcaatggcagcgcgccgaccgcgatgggctgtggccaatagcggctgctcagcagggcgcgccgagagcagcggccgggaag gggcggtgcgggaggcggggtgtggggcggtagtgtgggccctgttcctgcccgcgcggtgttccgcattctgcaagcctccggagcgc acgtcggcagtcggctccctcgttgaccgaatcaccgacctctctccccagAAGCTCCCGGGAGCTTGTATATCCA

TTTTCGGATCTGATCAGCACGTGTTGACAATTAATCATCGGCATAGTATATCGGCAT

AGTATAATACGACAAGGTGAGGAACgccaccATGGCCAAGCCTTTGTCTCAAGAAGAA

TCCACCCTCATTGAAAGAGCAACGGCTACAATCAACAGCATCCCCATCTCTGAAGAC

TACAGCGTCGCCAGCGCAGCTCTCTCTAGCGACGGCCGCATCTTCACTGGTGTCAAT

GTATATCATTTTACTGGGGGACCTTGTGCAGAACTCGTGGTGCTGGGCACTGCTGCT

GCTGCGGCAGCTGGCAACCTGACTTGTATCGTCGCGATCGGAAATGAGAACAGGGG

CATCTTGAGCCCCTGCGGACGGTGCCGACAGGTGCTTCTCGATCTGCATCCTGGGAT

CAAAGCCATAGTGAAGGACAGTGATGGACAGCCGACGGCAGTTGGGATTCGTGAAT

TGCTGCCCTCTGGTTATGTGTGGGAGGGCTAAGCACTTCGTGGCCGAGGAGCAGGAC

TGACACGTGCTACGAGATTTCGATTCCACCGCCGCCTTCTATGAAAGGTTGGGCTTC

GGAATCGTTTTCCGGGACGCCGGCTGGATGATCCTCCAGCGCGGGGATCTCATGCTG

GAGTTCTTCGCCCACCCCAACTTGTTTATTGCAGCTTATAATGGTTACAAATAAAGC

AATAGCATCACAAATTTCACAAATAAAGCATTTTTTTCACTGCATTCTAGTTGTGGTT

TGTCCAAACTCATCAATGTATCTTAGCGCTCACTGCCCGCTTTCCAGTCGGGAAACC

TGTCGTGCCAGCTGCATTAATGAATCGGCCAACGCGCGGGGAGAGGCGGTTTGCGT

ATTGGGCGCTCTCCTAGGccagaaatggcgccggaggcgggaacaaggtggtggatgagtgctacatccccaattactt gctccccaaaacccagcctgagctccagtgggcgtggactaatatggaaTCCCTATCAGTGATAGAGAcagtatttaagc -continued gcctgTCCCTATCAGTGATAGAGAtttgaatctcacggagcgtaaacggttggtggcgcagcatctGTTTAAACgc agacgcaggagcagaacaaagagaatcagaatcccaattctgatgcgccggtgatcagatcaaaaacttcagccaggtacatggagctgg tcgggtggctcgtggacaaggggattacctcggagaagcagtggattcaggaggaccaggcctcatacatctccttcaatgcggcctccaa ctcgcggtcccaaatcaaggctgccttggacaatgcgggaaagattatgagcctgactaaaaccgcccccgactacctggtgggccagca gcccgtggaggacatttccagcaatcggatttataaaattttggaactaaacgggtacgatccccaatatgcggcttccgtctttctgggatgg gccacgaaaaagttcggcaagaggaacaccatctggctgtttgggcctgcaactaccgggaagaccaacatcgcggaggccatagccca cactgtgcccttctacgggtgcgtaaactggaccaatgagaactttcccttcaacgactgtgtcgacaagatggtgatctggtgggaggagg ggaagatgaccgccaaggtcgtggagtcggccaaagccattctcggaggaagcaaggtgcgcgtggaccagaaatgcaagtcctcggc ccagatagacccgactcccgtgatcgtcacctccaacaccaacatgtgcgccgtgattgacgggaactcaacgaccttcgaacaccagca gccgttgcaagaccggatgttcaaatttgaactcacccgccgtctggatcatgactttgggaaggtcaccaagcaggaagtcaaagactttttt ccggtgggcaaaggatcacgtggttgaggtggagcatgaattctacgtcaaaaagggtggagccaagaaaagacccgcccccagtgac gcagatataagtgagcccaaacgggtgcgcgagtcagttgcgcagccatcgacgtcagacgcggaagcttcgatcaactacgcagacag gtaccaaaacaaatgttctcgtcacgtgggcatgaatctgatgctgtttccctgcagacaatgcgagagaatgaatcagaattcaaatatctgc ttcactcacggacagaaagactgtttagagtgctttcccgtgtcagaatctcaacccgtttctgtcgtcaaaaaggcgtatcagaaactgtgcta cattcatcatatcatgggaaaggtgccagacgcttgcactgcctgcgatctggtcaatgtggatttggatgactgcatctttgaacaataaAC

TAGTTTGCTTGTTAATCAATAAACCGTTTAATTCGTTTCAGTTGAACTTTGGTCTCTG

CGTATTTCTTTCTTATCTAGTTTCCATGCTCTAGAGTATACgatatccatcacactggcggccgctcga ctagagcggccgccaccgcggtggagctccagcttttgttcgcgcgcttggcgtaatcatggtcatagctgtttcctgtgtgaaattccacag cctggggtgcctaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggtatcagct cactcaaaggcggtaatacggttatccacagaatcaggggataacgcaggaaagaacatgtgagcaaaaggccagcaaaaggccagga accgtaaaaaggccgcgttgctggcgtttttccataggctccgcccccctgacgagcatcacaaaaatcgacgctcaagtcagaggtggcg aaacccgacaggactataaagataccaggcgtttccccctggaagctccctcgtgcgctctcctgttccgaccctgccgcttaccggatacc tgtccgcctttctcccttcgggaagcgtggcgctttctcatagctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcctaactacggctac actagaagaacagtatttggtatctgcgctctgctgaagccagttaccttcggaaaaagagttggtagctcttgatccggcaaacaaaccacc gctggtagcggtggtttttttgtttgcaagcagcagattacgcgcagaaaaaaaggatctcaagaagatcctttgatcttttctacggggtctga cgctcagtggaacgaaaactcacgttaagggattttggtcatgagattatcaaaaaggatcttcacctagatccttttaaattaaaaatgaagttt taaatcaatctaaagtatatatgagtaaacttggtctgacagaaataataaaaaagccggattaataatctggctttttatattctctctctagtatat aaacgcagaaaggcccacccgaaggtgagccagtgtgactctagtattattagaaaaactcatcgagcatcaaatgaaactgcaatttattca tatcaggattatcaataccatatttttgaaaaagccgtttctgtaatgaaggagaaaactcaccgaggcagttccaaagaatggcaaggtcctg gtaacggtctgcgattccgacccgtccaacatcaatacaacctattaatttcccctcgtcaaaaataaggttatcaagtgagaaatcaccatga gtgacgactgaatccggtgagaatggcaagagcttgtgcatttctttccagacttgttcaacaggccagccattacgctcgtcatcaaaatcac tcgcatcaaccaaaccgttattcatgcgtgattgcgcctgagcaagacgaaatacacgatcgctgttaaaaggacaattacaaacaggaatc gaatgtaaccggcgcaggaacacggccagcgcatcaacaatattttcacctgaatcaggatattcttctaatacctggaaggctgttttccca ggaatcgcggtggtgagtaaccacgcatcatcaggagtacggataaaatgcttgatggtcgggagaggcataaactccgtcagccagttg agacggaccatctcatctgtaacatcattggcaacgctacctttgccatgtttcagaaacaactctggcgcatcgggcttcccatacaagcgat agattgtcgcacctgattgcccgacattatcgcgagcccatttatacccatataaatcagcgtccatgttggagtttaagcgcggacgggagc aagacgtttcccgttgaatatggctcataacaccccttgtattactgtttatgtaagcagacagttttattgttcatgatgatatatttttatcttgt gcaatgtaacatcagagattttgagacacaacgtggctttgttgaataaatcgaacttttgctgagttgaaggatcagctctagtaaaataataaaaa -continued agccggattaataatctggctttttatattctctctctagtatataaacgcagaaaggcccacccgaaggtgagccagtgtgacggcacatttcc ccgaaaagtgccacctaaattgtaagcgttaatattttgttaaaattcgcgttaaatttttgttaaatcagctcattttttaaccaataggccgaaa tcggcaaaatcccttataaatcaaaagaatagaccgagatagggttgagtgttgttccagtttggaacaagagtccactattaaagaacgtggac tccaacgtcaaagggcgaaaaaccgtctatcagggcgatggcccactacgtgaaccatcaccctaatcaagttttttggggtcgaggtgcc gtaaagcactaaatcggaaccctaaagggagcccccgatttagagcttgacggggaaagccggcgaacgtggcgagaaaggaaggga agaaagcgaaaggagcgggcgctagggcgctggcaagtgtagcggtcacgctgcgcgtaaccaccacacccgccgcgcttaatgcgc cgctacagggcgcgtcccattcgccattcaggctgcgcaactgttgggaagggcgatcggtgcgggcctcttcgctattacgccagctggc gaaagggggatgtgctgcaaggcgattaagttgggtaacgccagggttttcccagtcacgacgttgtaaaacgacggccagtgagcgcgc ggcgaattgggtaccgggccccc iRepCap10/pKan-Anc80-intron-inducibleRepCap (7,567 bp)

(SEQ ID NO: 24)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccagtgggcgtggactaatatggaacagtat ttaaggtaagtTCCCTATCAGTGATAGAGATCTCCCTATCAGTGATAGAGAtactgacatccactttgc ctttctctccacagcgcctgtttgaatctcacggagcgtaaacggttggtggcgcagcatctgacgcacgtgtcgcagacgcaggagcaga acaaagagaatcagaatcccaattctgatgcgccggtgatcagatcaaaaacttcagccaggtacatggagctggtcgggtggctcgtgga caaggggattacctcggagaagcagtggatccaggaggaccaggcctcatacatctccttcaatgcggcctccaactcgcggtcccaaat caaggctgccttggacaatgcgggaaagattatgagcctgactaaaaccgcccccgactacctggtgggccagcagcccgtggaggaca tttccagcaatcggatttataaaattttggaactaaacgggtacgatccccaatatgcggcttccgtctttctgggatgggccacgaaaaagttc ggcaagaggaacaccatctggctgtttgggcctgcaactaccgggaagaccaacatcgcggaggccatagcccacactgtgcccttctac gggtgcgtaaactggaccaatgagaactttcccttcaacgactgtgtcgacaagatggtgatctggtgggaggaggggaagatgaccgcc aaggtcgtggagtcggccaaagccattctcggaggaagcaaggtgcgcgtggaccagaaatgcaagtcctcggcccagatagacccga ctcccgtgatcgtcacctccaacaccaacatgtgcgccgtgattgacgggaactcaacgaccttcgaacaccagcagccgttgcaagacc ggatgttcaaatttgaactcacccgccgtctggatcatgactttgggaaggtcaccaagcaggaagtcaaagactttttccggtgggcaaag gatcacgtggttgaggtggagcatgaattctacgtcaaaaagggtggagccaagaaaagacccgcccccagtgacgcagatataagtga gcccaaacgggtgcgcgagtcagttgcgcagccatcgacgtcagacgcggaagcttcgatcaactacgcagacaggtaccaaaacaaat gttctcgtcacgtgggcatgaatctgatgctgtttccctgcagacaatgcgagagaatgaatcagaattcaaatatctgcttcactcacggaca gaaagactgtttagagtgctttcccgtgtcagaatctcaacccgtttctgtcgtcaaaaaggcgtatcagaaactgtgctacattcatcatatcat gggaaaggtgccagacgcttgcactgcctgcgatctggtcaatgtggatttggatgactgcatctttgaacaataaatgatttaaatcaggtat ggctgccgatggttatcttccagattggctcgaggacaacctctctgagggcattcgcgagtggtgggacttgaaacctggagccccgaaa cccaaagccaaccagcaaaagcaggacgacggccggggtctggtgcttcctggctacaagtacctcggacccttcaacggactcgacaa gggggagcccgtcaacgcggcggacgcagcggccctcgagcacgacaaggcctacgaccagcagctcaaagcgggtgacaatccgt acctgcggtataaccacgccgacgccgagtttcaggagcgtctgcaagaagatacgtcttttgggggcaacctcgggcgagcagtcttcca ggccaagaagcgggttctcgaacctctcggtctggttgaggaaggcgctaagacggctcctggaaagaagagaccggtagagcaatcac cccaggaaccagactcctcttcgggcatcggcaagaaaggccagcagcccgcgagaaagagactcaactttgggcagactggcgactc -continued agagtcagtgcccgaccctcaaccactcggagaaccccccgcagccccctctggtgtgggatctaatacaatggctgcaggcggtggcg ctccaatggcagacaataacgaaggcgccgacggagtgggtaacgcctcaggaaattggcattgcgattccacatggctgggcgacaga gtcatcaccaccagcacccgaacctgggccctccccacctacaacaaccacctctacaagcaaatctccagccaatcgggaggcagcac caacgacaacacctacttcggctacagcaccccctgggggtattttgactttaacagattccactgccacttctcaccacgtgactggcagcg actcatcaacaacaactggggattccggcccaagaagctcaacttcaagctcttcaacatccaggtcaaggaggtcacgacgaatgatggc accacgaccatcgccaataaccttaccagcacggttcaggtctttacggactcggaataccagctcccgtacgtcctcggctctgcgcacca gggctgcctgcctccgttcccggcggacgtcttcatgattcctcagtacgggtacctgactctgaacaatggcagtcaggccgtgggccgtt cctccttctactgcctggaatactttccttctcaaatgctgagaacgggcaacaactttcagttcagctacacgtttgaggacgtgcctttttcaca gcagctacgcgcacagccaaagcctggaccggctgatgaacccccctcatcgaccagtacctgtactacctgtctcggactcagaccacga gtggtaccgcaggaaatcggacgttgcaattttctcaggccgggcctagtagcatggcgaatcaggccaaaaactggctacccgggccct gctaccggcagcaacgcgtctccaagacaaccaatcaaaataacaacagcaactttgcctggaccggtgccaccaagtatcatctgaatgg cagagactctctggtaaatcccggtcccgctatggcaacccacaaggacgacgaagacaaatttttttccgatgagcggagtcttaatatttgg gaaacagggagctggaaatagcaacgtggaccttgacaacgttatgataaccaacgaggaagaaattaaaaccaccaacccagtggcca cagaagagtacggcacggtggccactaacctgcaatcggccaacaccgctcctgctacagggaccgtcaacagtcaaggagccttacct ggcatggtctggcaggaccgggacgtgtacctgcagggtcctatctgggccaagattcctcacacggacggacactttcatccctcgccgc tgatgggaggctttggactgaaacacccgcctcctcagatcctgattaagaatacacctgttcccgcgaatcctccaactaccttcagtccag ctaagtttgcgtcgttcatcacgcagtacagcaccggacaggtcagcgtggaaattgaatgggagctgcagaaagaaaacagcaaacgct ggaacccagagattcaatacacttccaactacaacaaatctacaaatgtggactttgctgttgacacaaatggcgtttattctgagcctcgccc catcggcacccgttacctcacccgtaatctgtaaactagtttgcttgttaatcaataaaccgtttaattcgtttcagttgaactttggtctctgcgtat ttctttcttatctagtttccatgctctagaggtcctgtattagaggtcacgtgagtgttttgcgacattttgcgacaccatgtggtcacgctgggtatt taagcccgagtgagcacgcagggtctccattttgaagcgggaggtttgaacgcgcagccgccaagccgaattctgcagatatccatcacac tggcggccgctcgactagagcggccgccaccgcggtggagctccagcttttgttcgcgcgcttggcgtaatcatggtcatagctgtttcctgt gtgaaattccacagcctggggtgcctaattgcgttgcgctcactgcccgctttccagtcgggaaacctgtcgtgccagctgcattaatgaatc ggccaacgcgcggggagaggcggtttgcgtattgggcgctcttccgcttcctcgctcactgactcgctgcgctcggtcgttcggctgcggc gagcggtatcagctcactcaaaggcggtaatacggttatccacagaatcaggggataacgcaggaaagaacatgtgagcaaaaggccag caaaaggccaggaaccgtaaaaaggccgcgttgctggcgtttttccataggctccgcccccctgacgagcatcacaaaaatcgacgctca agtcagaggtggcgaaacccgacaggactataaagataccaggcgtttccccctggaagctccctcgtgcgctctcctgttccgaccctgc cgcttaccggatacctgtccgcctttctcccttcgggaagcgtggcgctttctcatagctcacgctgtaggtatctcagttcggtgtaggtcgtt cgctccaagctgggctgtgtgcacgaaccccccgttcagcccgaccgctgcgccttatccggtaactatcgtcttgagtccaacccggtaag acacgacttatcgccactggcagcagccactggtaacaggattagcagagcgaggtatgtaggcggtgctacagagttcttgaagtggtgg cctaactacggctacactagaagaacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaagaagatcctttgatctt ttctacggggtctgacgctcagtggaacgaaaactcacgttaagggattttggtcatgagattatcaaaaaggatcttcacctagatccttttaa attaaaaatgaagttttaaatcaatctaaagtatatatgagtaaacttggtctgacagaaataataaaaaagccggattaataatctggctttttata ttctctctctagtatataaacgcagaaaggcccacccgaaggtgagccagtgtgactctagtattattagaaaaactcatcgagcatcaaatga aactgcaatttattcatatcaggattatcaataccatatttttgaaaaagccgtttctgtaatgaaggagaaaactcaccgaggcagttccaaag aatggcaaggtcctggtaacggtctgcgattccgacccgtccaacatcaatacaacctattaatttcccctcgtcaaaaataaggttatcaagt gagaaatcaccatgagtgacgactgaatccggtgagaatggcaagagcttgtgcatttctttccagacttgttcaacaggccagccattacgc tcgtcatcaaaatcactcgcatcaaccaaaccgttattcatgcgtgattgcgcctgagcaagacgaaatacacgatcgctgttaaaaggacaa ttacaaacaggaatcgaatgtaaccggcgcaggaacacggccagcgcatcaacaatattttcacctgaatcaggatattcttctaatacctgg aaggctgttttcccaggaatcgcggtggtgagtaaccacgcatcatcaggagtacggataaaatgcttgatggtcgggagaggcataaact -continued ccgtcagccagttgagacggaccatctcatctgtaacatcattggcaacgctacctttgccatgtttcagaaacaactctggcgcatcgggctt cccatacaagcgatagattgtcgcacctgattgcccgacattatcgcgagcccatttatacccatataaatcagcgtccatgttggagtttaag cgcggacgggagcaagacgtttcccgttgaatatggctcataacaccccttgtattactgtttatgtaagcagacagttttattgttcatgatgat atatttttatcttgtgcaatgtaacatcagagattttgagacacaacgtggctttgttgaataaatcgaacttttgctgagttgaaggatcagctcta gtaaaataataaaaaagccggattaataatctggctttttatattctctctctagtatataaacgcagaaaggcccacccgaaggtgagccagt gtgacggcacatttccccgaaaagtgccacctaaattgtaagcgttaatattttgttaaaattcgcgttaaatttttgttaaatcagctcatttttaa ccaataggccgaaatcggcaaaatcccttataaatcaaaagaatagaccgagatagggttgagtgttgttccagtttggaacaagagtccact attaaagaacgtggactccaacgtcaaagggcgaaaaaccgtctatcagggcgatggcccactacgtgaaccatcaccctaatcaagtttt tggggtcgaggtgccgtaaagcactaaatcggaaccctaaagggagcccccgatttagagcttgacggggaaagccggcgaacgtggc gagaaaggaagggaagaaagcgaaaggagcgggcgctagggcgctggcaagtgtagcggtcacgctgcgcgtaaccaccacacccg ccgcgcttaatgcgccgctacagggcgcgtcccattcgccattcaggctgcgcaactgttgggaagggcgatcggtgcgggcctcttcgct attacgccagctggcgaaagggggatgtgctgcaaggcgattaagttgggtaacgccagggttttcccagtcacgacgttgtaaaacgacg gccagtgagcgcgcggcgaattgggtaccgggccccc iRepCap11/pKan-Anc80-intron-inducibleRepCap-d2 (7,567 bp)

(SEQ ID NO: 25)

cctcgaggGCTAGCcattcTATTTAAtcTCCCTATCAGTGATAGAGATCTCCCTATC

AGTGATAGAGAtcGCCCGAGTGAGCACGCAGGGTCTCCATTTTGAAGCGGGAGGTTT

Figure 11A:
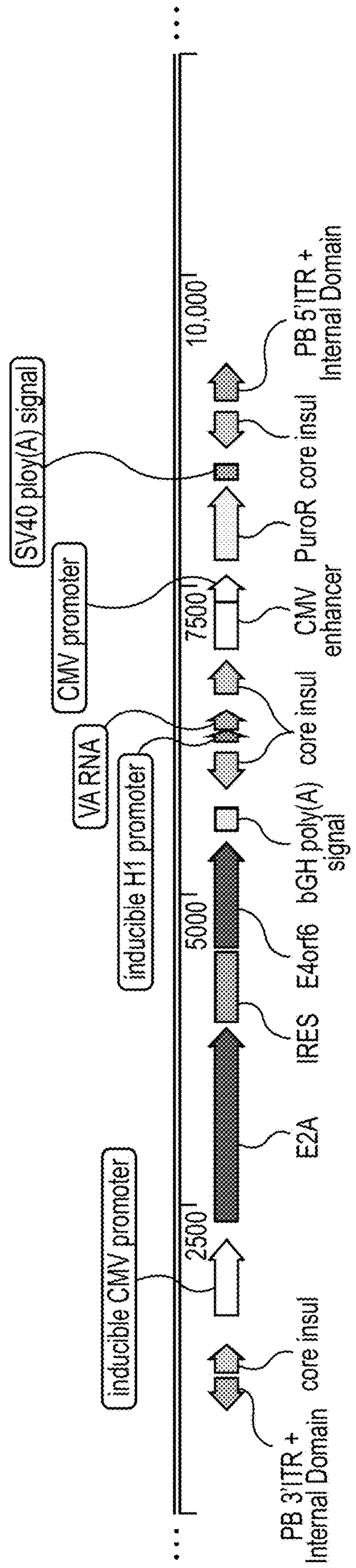
FIGS. 11A-11E show exemplary nucleic acid constructs encoding helper, AAV, gene of interest, and Rep-Cap vectors, in accordance with embodiments hereof.
Figure 11B:
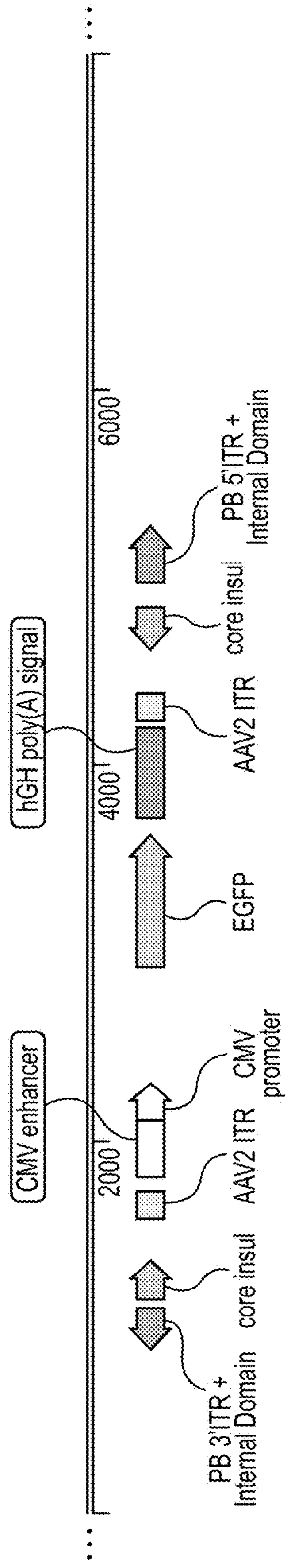

GAACGCGCAGCCGCCatgccggggttttacgagattgtgattaaggtccccagcgaccttgacgagcatctgcccggcatttct gacagctttgtgaactgggtggccgagaaggaatgggagttgccgccagattctgacatggatctgaatctgattgagcaggcacccctga ccgtggccgagaagctgcagcgcgactttctgacggaatggcgccgtgtgagtaaggccccggaggctcttttctttgtgcaatttgagaag ggagagagctacttccacatgcacgtgctcgtggaaaccaccggggtgaaatccatggttttgggacgtttcctgagtcagattcgcgaaaa actgattcagagaatttaccgcgggatcgagccgactttgccaaactggttcgcggtcacaaagaccagaaatggcgccggaggcggga acaaggtggtggatgagtgctacatccccaattacttgctccccaaaacccagcctgagctccagtgggcgtggactaatatggaacagtat ttaagcgcctgtttgaatctcacggaaaggtaagtTCCCTATCAGTGATAGAGATCTCCCTATCAGTGATA GAGAtactgacatccactttgcctttctctccacaggaaacggttggtggcgcagcatctgacgcacgtgtcgcagacgcaggagcaga acaaagagaatcagaatcccaattctgatgcgccggtgatcagatcaaaaacttcagccaggtacatggagctggtcgggtggctcgtgga caaggggattacctcggagaagcagtggatccaggaggaccaggcctcatacatctccttcaatgcggcctccaactcgcggtcccaaat caaggctgccttggacaatgcgggaaagattatgagcctgactaaaaccgcccccgactacctggtgggccagcagcccgtggaggaca tttccagcaatcggatttataaaattttggaactaaacgggtacgatccccaatatgcggcttccgtctttctgggatgggccacgaaaaagttc ggcaagaggaacaccatctggctgtttgggcctgcaactaccgggaagaccaacatcgcggaggccatagcccacactgtgcccttctac gggtgcgtaaactggaccaatgagaactttcccttcaacgactgtgtcgacaagatggtgatctggtgggaggaggggaagatgaccgcc aaggtcgtggagtcggccaaagccattctcggaggaagcaaggtgcgcgtggaccagaaatgcaagtcctcggcccagatagacccga ctcccgtgatcgtcacctccaacaccaacatgtgcgccgtgattgacgggaactcaacgaccttcgaacaccagcagccgttgcaagacc ggatgttcaaatttgaactcacccgccgtctggatcatgactttgggaaggtcaccaagcaggaagtcaaagactttttccggtgggcaaag gatcacgtggttgaggtggagcatgaattctacgtcaaaaagggtggagccaagaaaagacccgcccccagtgacgcagatataagtga gcccaaacgggtgcgcgagtcagttgcgcagccatcgacgtcagacgcggaagcttcgatcaactacgcagacaggtaccaaaacaaat gttctcgtcacgtgggcatgaatctgatgctgtttccctgcagacaatgcgagagaatgaatcagaattcaaatatctgcttcactcacggaca gaaagactgtttagagtgctttcccgtgtcagaatctcaacccgtttctgtcgtcaaaaaggcgtatcagaaactgtgctacattcatcatatcat gggaaaggtgccagacgcttgcactgcctgcgatctggtcaatgtggatttggatgactgcatctttgaacaataaatgatttaaatcaggtat ggctgccgatggttatcttccagattggctcgaggacaacctctctgagggcattcgcgagtggtgggacttgaaacctggagccccgaaa cccaaagccaaccagcaaaagcaggacgacggccggggtctggtgcttcctggctacaagtacctcggacccttcaacggactcgacaa -continued gggggagcccgtcaacgcggcggacgcagcggccctcgagcacgacaaggcctacgaccagcagctcaaagcgggtgacaatccgt acctgcggtataaccacgccgacgccgagtttcaggagcgtctgcaagaagatacgtcttttgggggcaacctcgggcgagcagtcttcca ggccaagaagcgggttctcgaacctctcggtctggttgaggaaggcgctaagacggctcctggaaagaagagaccggtagagcaatcac cccaggaaccagactcctcttcgggcatcggcaagaaaggccagcagcccgcgagaaagagactcaactttgggcagactggcgactc agagtcagtgcccgaccctcaaccactcggagaacccccgcagcccccctctggtgtgggatctaatacaatggctgcaggcggtggcg ctccaatggcagacaataacgaaggcgccgacggagtgggtaacgcctcaggaaattggcattgcgattccacatggctgggcgacaga gtcatcaccaccagcacccgaacctgggccctccccacctacaacaaccacctctacaagcaaatctccagccaatcgggaggcagcac caacgacaacacctacttcggctacagcaccccctgggggtattttgactttaacagattccactgccacttctcaccacgtgactggcagcg actcatcaacaacaactggggattccggcccaagaagctcaacttcaagctcttcaacatccaggtcaaggaggtcacgacgaatgatggc accacgaccatcgccaataaccttaccagcacggttcaggtctttacggactcggaataccagctcccgtacgtcctcggctctgcgcacca gggctgcctgcctccgttcccggcggacgtcttcatgattcctcagtacgggtacctgactctgaacaatggcagtcaggccgtgggccgtt cctccttctactgcctggaatactttccttctcaaatgctgagaacgggcaacaactttcagttcagctacacgtttgaggacgtgccttttcaca gcagctacgcgcacagccaaagcctggaccggctgatgaacccccctcatcgaccagtacctgtactacctgtctcggactcagaccacga gtggtaccgcaggaaatcggacgttgcaattttctcaggccgggcctagtagcatggcgaatcaggccaaaaactggctacccgggccct gctaccggcagcaacgcgtctccaagacaaccaatcaaaataacaacagcaactttgcctggaccggtgccaccaagtatcatctgaatgg cagagactctctggtaaatcccggtcccgctatggcaacccacaaggacgacgaagacaaatttttttccgatgagcggagtcttaatatttgg gaaacagggagctggaaatagcaacgtggaccttgacaacgttatgataaccaacgaggaagaaattaaaaccaccaacccagtggcca cagaagagtacggcacggtggccactaacctgcaatcggccaacaccgctcctgctacagggaccgtcaacagtcaaggagccttacct ggcatggtctggcaggaccgggacgtgtacctgcagggtcctatctgggccaagattcctcacacggacggacactttcatccctcgccgc tgatgggaggctttggactgaaacacccgcctcctcagatcctgattaagaatacacctgttcccgcgaatcctccaactaccttcagtccag ctaagtttgcgtcgttcatcacgcagtacagcaccggacaggtcagcgtggaaattgaatgggagctgcagaaagaaaacagcaaacgct ggaacccagagattcaatacacttccaactacaacaaatctacaaatgtggactttgctgttgacacaaatggcgtttattctgagcctcgccc catcggcacccgttacctcacccgtaatctgtaaactagtttgcttgttaatcaataaaccgtttaattcgtttcagttgaactttggtctctgcgtat ttctttcttatctagtttccatgctctagaggtcctgtattagaggtcacgtgagtgttttgcgacattttgcgacaccatgtggtcacgctgggtatt taagcccgagtgagcacgcagggtctccattttgaagcgggaggtttgaacgcgcagccgccaagccgaattctgcagatatccatcacac tggcggccgctcgactagagcggccgccaccgcggtggagctccagcttttgttcgcgcgcttggcgtaatcatggtcatagctgtttcctgt gtgaaattccacagcctggggtgcctaattgcgttgcgctcactgcccgctttccagtcgggaaacctgtcgtgccagctgcattaatgaatc ggccaacgcgcggggagaggcggtttgcgtattgggcgctcttccgcttcctcgctcactgactcgctgcgctcggtcgttcggctgcggc gagcggtatcagctcactcaaaggcggtaatacggttatccacagaatcaggggataacgcaggaaagaacatgtgagcaaaaggccag caaaaggccaggaaccgtaaaaaggccgcgttgctggcgtttttccataggctccgcccccctgacgagcatcacaaaaatcgacgctca agtcagaggtggcgaaacccgacaggactataaagataccaggcgtttccccctggaagctccctcgtgcgctctcctgttccgaccctgc cgcttaccggatacctgtccgcctttctcccttcgggaagcgtggcgctttctcatagctcacgctgtaggtatctcagttcggtgtaggtcgtt cgctccaagctgggctgtgtgcacgaaccccccgttcagcccgaccgctgcgccttatccggtaactatcgtcttgagtccaacccggtaag acacgacttatcgccactggcagcagccactggtaacaggattagcagagcgaggtatgtaggcggtgctacagagttcttgaagtggtgg cctaactacggctacactagaagaacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaagaagatcctttgatctt ttctacggggtctgacgctcagtggaacgaaaactcacgttaagggattttggtcatgagattatcaaaaaggatcttcacctagatccttttaa attaaaaatgaagttttaaatcaatctaaagtatatatgagtaaacttggtctgacagaaataataaaaaagccggattaataatctggcttttata ttctctctctagtatataaacgcagaaaggcccacccgaaggtgagccagtgtgactctagtattattagaaaaactcatcgagcatcaaatga aactgcaatttattcatatcaggattatcaataccatatttttgaaaaagccgtttctgtaatgaaggagaaaactcaccgaggcagttccaaag aatggcaaggtcctggtaacggtctgcgattccgacccgtccaacatcaatacaacctattaatttcccctcgtcaaaaataaggttatcaagt -continued gagaaatcaccatgagtgacgactgaatccggtgagaatggcaagagcttgtgcatttctttccagacttgttcaacaggccagccattacgc tcgtcatcaaaatcactcgcatcaaccaaaccgttattcatgcgtgattgcgcctgagcaagacgaaatacacgatcgctgttaaaaggacaa ttacaaacaggaatcgaatgtaaccggcgcaggaacacggccagcgcatcaacaatattttcacctgaatcaggatattcttctaatacctgg aaggctgttttcccaggaatcgcggtggtgagtaaccacgcatcatcaggagtacggataaaatgcttgatggtcgggagaggcataaact ccgtcagccagttgagacggaccatctcatctgtaacatcattggcaacgctacctttgccatgtttcagaaacaactctggcgcatcgggctt cccatacaagcgatagattgtcgcacctgattgcccgacattatcgcgagcccatttatacccatataaatcagcgtccatgttggagtttaag cgcggacgggagcaagacgtttcccgttgaatatggctcataacaccccttgtattactgtttatgtaagcagacagttttattgttcatgatgat atatttttatcttgtgcaatgtaacatcagagattttgagacacaacgtggctttgttgaataaatcgaacttttgctgagttgaaggatcagctcta gtaaaataataaaaaagccggattaataatctggctttttatattctctctctagtatataaacgcagaaaggcccacccgaaggtgagccagt gtgacggcacatttccccgaaaagtgccacctaaattgtaagcgttaatattttgttaaaattcgcgttaaatttttgttaaatcagctcattttttaa ccaataggccgaaatcggcaaaatcccttataaatcaaaagaatagaccgagatagggttgagtgttgttccagtttggaacaagagtccact attaaagaacgtggactccaacgtcaaagggcgaaaaaccgtctatcagggcgatggcccactacgtgaaccatcaccctaatcaagttttt tggggtcgaggtgccgtaaagcactaaatcggaaccctaaagggagcccccgatttagagcttgacggggaaagccggcgaacgtggc gagaaaggaagggaagaaagcgaaaggagcgggcgctagggcgctggcaagtgtagcggtcacgctgcgcgtaaccaccacacccg ccgcgcttaatgcgccgctacagggcgcgtcccattcgccattcaggctgcgcaactgttgggaagggcgatcggtgcgggcctcttcgct attacgccagctggcgaaagggggatgtgctgcaaggcgattaagttgggtaacgccagggttttcccagtcacgacgttgtaaaacgacg gccagtgagcgcgcggcgaattgggtaccgggccccc The sequence for the PBBG-iHelper-Puro construct illustrated in in FIG. 11A is shown below:

PBBG-iHelper-Puro (11,801 bp)

(SEQ ID NO: 26)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

-continued

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcGTTT

AAACTTAAGCTTGGTACCGAGCTCGGATCCACTAGTCCAGTGTGGTGGAATTCCTGC

TTCGCGATGTACGGGCCAGATATACGCGTTGACATTGATTATTGACTAGTTATTAAT

AGTAATCAATTACGGGGTCATTAGTTCATAGCCCATATATGGAGTTCCGCGTTACAT

AACTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCAAT

GGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGC

TATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGAA

CCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCCCTATCAGTG

ATAGAGATCTCCCTATCAGTGATAGAGATCGTCGACGAGCTCGTTTAGTGAACCGTC

AGATCGCCTGGAGACGCCATCCACGCTGTTTTGACCTCCATAGAAGACACCGGGAC

CGATCCAGCCTCCGGACTCTAGCGTTTAAACTTAAGCTTGCCACCatggccagtcgggaagagg agcagcgcgaaaccacccccgagcgcggacgcggtgcggcgcgacgtcccccaaccatggaggacgtgtcgtccccgtccccgtcgc cgccgcctccccgggcgcccccaaaaaagcggatgaggcggcgtatcgagtccgaggacgaggaagactcatcacaagacgcgctgg tgccgcgcacacccagcccgcggccatcgacctcggcggcggatttggccattgcgcccaagaagaaaaagaagcgcccttctcccaa gcccgagcgcccgccatcaccagaggtaatcgtggacagcgaggaagaaagagaagatgtggcgctacaaatggtgggtttcagcaac ccaccggtgctaatcaagcatggcaaaggaggtaagcgcacagtgcggcggctgaatgaagacgacccagtggcgcgtggtatgcgga cgcaagaggaagaggaagagcccagcgaagcggaaagtgaaattacggtgatgaacccgctgagtgtgccgatcgtgtctgcgtggga gaagggcatggaggctgcgcgcgcgctgatggacaagtaccacgtggataacgatctaaaggcgaacttcaaactactgcctgaccaagt ggaagctctggcggccgtatgcaagacctggctgaacgaggagcaccgcgggttgcagctgaccttcaccagcaacaagacctttgtga cgatgatggggcgattcctgcaggcgtacctgcagtcgtttgcagaggtgacctacaagcatcacgagcccacgggctgcgcgttgtggct gcaccgctgcgctgagatcgaaggcgagcttaagtgtctacacggaagcattatgataaataaggagcacgtgattgaaatggatgtgacg agcgaaaacgggcagcgcgcgctgaaggagcagtctagcaaggccaagatcgtgaagaaccggtggggccgaaatgtggtgcagatc tccaacaccgacgcaaggtgctgcgtgcacgacgcggcctgtccggccaatcagttttccggcaagtcttgcggcatgttcttctctgaagg cgcaaaggctcaggtggcttttaagcagatcaaggcttttatgcaggcgctgtatcctaacgcccagaccgggcacggtcaccttttgatgc cactacggtgcgagtgcaactcaaagcctgggcacgcgcccttttgggaaggcagctaccaaagttgactccgttcgccctgagcaacgc ggaggacctggacgcggatctgatctccgacaagagcgtgctggccagcgtgcaccacccggcgctgatagtgttccagtgctgcaacc ctgtgtatcgcaactcgcgcgcgcagggcggaggccccaactgcgacttcaagatatcggcgcccgacctgctaaacgcgttggtgatgg tgcgcagcctgtggagtgaaaacttcaccgagctgccgcggatggttgtgcctgagtttaagtggagcactaaacaccagtatcgcaacgt gtccctgccagtggcgcatagcgatgcgcggcagaacccctttgatttttaacccgggagttctagggatctgcccctctccctcccccccc -continued cctaacgttactggccgaagccgcttggaataaggccggtgtgcgtttgtctatatgttattttccaccatattgccgtcttttggcaatgtgagg gcccggaaacctggccctgtcttcttgacgagcattcctaggggtctttcccctctcgccaaaggaatgcaaggtctgttgaatgtcgtgaag gaagcagttcctctggaagcttcttgaagacaaacaacgtctgtagcgaccctttgcaggcagcggaaccccccacctggcgacaggtgc ctctgcggccaaaagccacgtgtataagatacacctgcaaaggcggcacaaccccagtgccacgttgtgagttggatagttgtggaaaga gtcaaatggctctcctcaagcgtattcaacaaggggctgaaggatgcccagaaggtaccccattgtatgggatctgatctggggcctcggtg cacatgctttacatgtgtttagtcgaggttaaaaaaacgtctaggccccccgaaccacggggacgtggttttcctttgaaaaacacgatgataa ggatccaccggaggccaccatgactacgtccggcgttccatttggcatgacactacgaccaacacgatctcggttgtctcggcgcactccgt acagtagggatcgtctacctccttttgagacagaaacccgcgctaccatactggaggatcatccgctgctgcccgaatgtaacactttgacaa tgcacaacgtgagttacgtgcgaggtcttccctgcagtgtgggatttacgctgattcaggaatgggttgttccctgggatatggttctaacgcg ggaggagcttgtaatcctgaggaagtgtatgcacgtgtgcctgtgttgtgccaacattgatatcatgacgagcatgatgatccatggttacga gtcctgggctctccactgtcattgttccagtcccggttccctgcagtgtatagccggcgggcaggttttggccagctggtttaggatggtggtg gatggcgccatgtttaatcagaggtttatatggtaccgggaggtggtgaattacaacatgccaaaagaggtaatgtttatgtccagcgtgtttat gaggggtcgccacttaatctacctgcgcttgtggtatgatggccacgtgggttctgtggtccccgccatgagctttggatacagcgccttgca ctgtgggattttgaacaatattgtggtgctgtgctgcagttactgtgctgatttaagtgagatcagggtgcgctgctgtgcccggaggacaagg cgccttatgctgcgggcggtgcgaatcatcgctgaggagaccactgccatgttgtattcctgcaggacggagcggcggcggcagcagttt attcgcgcgctgctgcagcaccaccgccctatcctgatgcacgattatgactctacccccatgtagGCGGCCGTCGAGTCTA

GAGGGCCCGTTTAAACCCGCTGATCAGCCTCGACTGTGCCTTCTAGTTGCCAGCCAT

CTGTTGTTTGCCCCTCCCCCGTGCCTTCCTTGACCCTGGAAGGTGCCACTCCCACTGT

CCTTTCCTAATAAAATGAGGAAATTGCATCGCATTGTCTGAGTAGGTGTCATTCTATT

CTGGGGGGTGGGGTGGGGCAGGACAGCAAGGGGGAGGATTGGGAAGACAATAGCA

GGCATGCTGGGGATGCGGTGGGCTCTATGGCTTCTGAGGCGGAAAGAACCAGCTGG

GGCTCTAGGGGGTATCCCCGGCGCGCCggggtTGAGCTATTCCAGAAGTAGTGAAGAG

GCTTTTTTGGAGGCCTAGGCTTTTGCAAAAAGCTCCGGATCGATtggggttgcgccttttccaagg cTTTTCCCCGTATCCCCCCAGGTGTCTGCAGGCTCAAAGAGCAGCGAGAAGCGTTCA

GAGGAAAGCGATCCCGTGCCACCTTCCCCGTGCCCGGGCTGTCCCCGCACGCTGCCG

GCTCGGGGATGCGGGGGGAGCGCCGGACCGGAGCGGAGCCCCGGGCGGCTCGCTG

CTGCCCCCTAGCGGGGGAGGGACGTAATTACATCCCTGGGGGCTTTGGGGGGGGGC

TGTCCCTCTAGGGGATCCTCTAGGGCCTCTGAGCTATTCCAGAAGTAGTGAAGAGGC

TTTTTTGGAGGCCTAGGCTTTTGCAAAAAGCTCCGGATCGATCGAGCGGATCCAGCA

CAGTGGCGGCCGCaatatttgcatgtcgctatgtgttctgggaaatcaccataaacgtgaaatccctatcagtgatagagacttata agttccctatcagtgatagagaaccggtgggcactcttccgtggtctggtggataaattcgcaagggtatcatggcggacgaccggggttcg agccccgtatccggccgtccgccgtgatccatgcggttaccgcccgcgtgtcgaacccaggtgtgcgacgtcagacaacgggggagtgc tcctttttgaattccactttggccgcggctcgagTGAGCTATTCCAGAAGTAGTGAAGAGGCTTTTTTGGA

GGCCTAGGCTTTTGCAAAAAGCTCCGGATCGATGCCCGGGGGATCCACTAGTTCTAG

AGGGACAGCCCCCCCCCAAAGCCCCCAGGGATGTAATTACGTCCCTCCCCCGCTAG

GGGGCAGCAGCGAGCCGCCCGGGGCTCCGCTCCGGTCCGGCGCTCCCCCCGCATCC

CCGAGCCGGCAGCGTGCGGGGACAGCCCGGGCACGGGGAAGGTGGCACGGGATCG

CTTTCCTCTGAACGCTTCTCGCTGCTCTTTGAGCCTGCAGACACCTGGGGGGATACG

GGGAAAAGGCCTCCAAGGCCAGCTTCCCACAATAAGTTGGGTGAATTTTGGCTGAG

CTATTCCAGAAGTAGTGAAGAGGCTTTTTTGGAGGCCTAGGCTTTTGCAAAAAGCTC

-continued

CGGATCGATCATATATGGCAGATATACGCGTTGACATTGATTATTGACTAGTTATTA

ATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGAC

GTCAATAATGACGTATGTTCCCATAGTAACGCCAATAGGGACTTTCCATTGACGTCA

ATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATGC

CCAGTACATGACCTTATGGGACTTTCCTACTTGGCAGTACATCTACGTATTAGTCATC

GCTATTACCATGGTGATGCGGTTTTGGCAGTACATCAATGGGCGTGGATAGCGGTTT

GACTCACGGGGATTTCCAAGTCTCCACCCCATTGACGTCAATGGGAGTTTGTTTTGG

CACCAAAATCAACGGGACTTTCCAAAATGTCGTAACAACTCCGCCCCATTGACGCA

AATGGGCGGTAGGCGTGTACGGTGGGAGGTCTATATAAGCAGAGCTCTCTGGCTAA

CTATCGTCGACGAGCTCGTTTAGTGAACCGTCAGATCGCCTGGAGACGCCATCCACG

CTGTTTTGACCTCCATAGAAGACACCGGGACCGATCCAGCCTCCGGACTCTAGCGTT

TAAACTTAAGCTTGCCACCatgaccgagtacaagcccacggtgcgcctcgccacccgcgacgacgtccccagggccgt acgcaccctcgccgccgcgttcgccgactaccccgccacgcgccacaccgtcgatccggaccgccacatcgagcgggtcaccgagctg caagaactcttcctcacgcgcgtcgggctcgacatcggcaaggtgtgggtcgcggacgacggcgccgcggtggcggtctggaccacgc cggagagcgtcgaagcgggggcggtgttcgccgagatcggcccgcgcatggccgagttgagcggttcccggctggccgcgcagcaac agatggaaggcctcctggcgccgcaccggcccaaggagcccgcgtggttcctggccaccgtcggcgtctcgcccgaccaccagggca agggtctgggcagcgccgtcgtgctccccggagtggaggcggccgagcgcgccggggtgcccgccttcctggagacctccgcgcccc gcaacctccccttctacgagcggctcggcttcaccgtcaccgccgacgtcgaggtgcccgaaggaccgcgcacctggtgcatgacccgc aagcccggtgcctgaAGCGCGGGGATCTCATGCTGGAGTTCTTCGCCCACCCCAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGTAGCtGATgtATAcCTAggATCCGGCCGGccTGCAggTGTCCTCACAGGAACGAA

GTCCCTAAAGAAACAGTGGCAGCCAGGTTTAGCCCCGGAATTGACTGGATTCCTTTT

TTAGGGCCCATTGGTATGGCTTTTTCCCCGTATCCCCCCAGGTGTCTGCAGGCTCAAA

GAGCAGCGAGAAGCGTTCAGAGGAAAGCGATCCCGTGCCACCTTCCCCGTGCCCGG

GCTGTCCCCGCACGCTGCCGGCTCGGGGATGCGGGGGGAGCGCCGGACCGGAGCGG

AGCCCCGGGCGGCTCGCTGCTGCCCCCTAGCGGGGGAGGGACGTAATTACATCCCT

GGGGGCTTTGGGGGGGGGCTGTCCCTCTAGAGCGGCCGCCACCGCGGTGGAGCTCC

AGCTTTTGTTCCCTTTAGTGAGGGTTAATTAGATCTTAATACGACTCACTATAGGGCG

AATTGGGTACCGGGCCCCCCCTCGAGGTCGACGGTATCGATAAGCTTGATATCTATA

ACAAGAAAATATATATATAATAAGTTATCACGTAAGTAGAACATGAAATAACAATA

TAATTATCGTATGAGTTAAATCTTAAAAGTCACGTAAAAGATAATCATGCGTCATTT

TGACTCACGCGGTCGTTATAGTTCAAAATCAGTGACACTTACCGCATTGACAAGCAC

GCCTCACGGGAGCTCCAAGCGGCGACTGAGATGTCCTAAATGCACAGCGACGGATT

CGCGCTATTTAGAAAGAGAGAGCAATATTTCAAGAATGCATGCGTCAATTTTACGCA

GACTATCTTTCTAGGGTTAATCTAGCTGCATCAGGATCATATCGTCGGGTCTTTTTTC

CGGCTCAGTCATCGCCCAAGCTGGCGCTATCTGGGCATCGGGGAGGAAGAAGCCCG

TGCCTTTTCCCGCGAGGTTGAAGCGGCATGGAAAGAGTTTGCCGAGGATGACTGCTG

CTGCATTGACGTTGAGCGAAAACGCACGTTTACCATGATGATTCGGGAAGGTGTGGC

-continued

CATGCACGCCTTTAACGGTGAACTGTTCGTTCAGGCCACCTGGGATACCAGTTCGTC

GCGGCTTTTCCGGACACAGTTCCGGATGGTCAGCCCGAAGCGCATCAGCAACCCGA

ACAATACCGGCGACAGCCGGAACTGCCGTGCCGGTGTGCAGATTAATGACAGCGGT

GCGGCGCTGGGATATTACGTCAGCGAGGACGGGTATCCTGGCTGGATGCCGCAGAA

ATGGACATGGATACCCCGTGAGTTACCCGGCGGGCGCGCTTGGCGTAATCATGGTCA

TAGCTGTTTCCTGTGTGAAATTGTTATCCGCTCACAATTCCACACAACATACGAGCC

GGAAGCATAAAGTGTAAAGCCTGGGGTGCCTAATGAGTGAGCTAACTCACATTAAT

TGCGTTGCGCTCACTGCCCGCTTTCCAGTCGGGAAACCTGTCGTGCCAGCTGCATTA

ATGAATCGGCCAACGCGCGGGGAGAGGCGGTTTGCGTATTGGGCGCTCTTCCGCTTC

CTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGC

GTTTTTCCATAGGCTCCGCCCCCCTGACGAGCATCACAAAAATCGACGCTCAAGTCA

GAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCT

CCCTTCGGGAAGCGTGGCGCTTTCTCATAGCTCACGCTGTAGGTATCTCAGTTCGGT

GTAGGTCGTTCGCTCCAAGCTGGGCTGTGTGCACGAACCCCCCGTTCAGCCCGACCG

CTGCGCCTTATCCGGTAACTATCGTCTTGAGTCCAACCCGGTAAGACACGACTTATC

GCCACTGGCAGCAGCCACTGGTAACAGGATTAGCAGAGCGAGGTATGTAGGCGGTG

CTACAGAGTTCTTGAAGTGGTGGCCTAACTACGGCTACACTAGAAGGACAGTATTTG

GTATCTGCGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAGCAGATTA

CGCGCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAAAGG

ATCTTCACCTAGATCCTTTTAAATTAAAAATGAAGTTTTAAATCAATCTAAAGTATAT

ATGAGTAAACTTGGTCTGACAGTTACCAATGCTTAATCAGTGAGGCACCTATCTCAG

CGATCTGTCTATTTCGTTCATCCATAGTTGCCTGACTCCCCGTCGTGTAGATAACTAC

GATACGGGAGGGCTTACCATCTGGCCCCAGTGCTGCAATGATACCGCGAGACCCAC

GCTCACCGGCTCCAGATTTATCAGCAATAAACCAGCCAGCCGGAAGGGCCGAGCGC

AGAAGTGGTCCTGCAACTTTATCCGCCTCCATCCAGTCTATTAATTGTTGCCGGGAA

GCTAGAGTAAGTAGTTCGCCAGTTAATAGTTTGCGCAACGTTGTTGCCATTGCTACA

GGCATCGTGGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGG

CAGCACTGCATAATTCTCTTACTGTCATGCCATCCGTAAGATGCTTTTCTGTGACTGG

TGAGTACTCAACCAAGTCATTCTGAGAATAGTGTATGCGGCGACCGAGTTGCTCTTG

CCCGGCGTCAATACGGGATAATACCGCGCCACATAGCAGAACTTTAAAAGTGCTCA

TCATTGGAAAACGTTCTTCGGGGCGAAAACTCTCAAGGATCTTACCGCTGTTGAGAT

CCAGTTCGATGTAACCCACTCGTGCACCCAACTGATCTTCAGCATCTTTTACTTTCAC

-continued

CAGCGTTTCTGGGTGAGCAAAAACAGGAAGGCAAAATGCCGCAAAAAAGGGAATA

AGGGCGACACGGAAATGTTGAATACTCAT

The sequence for the PBBG-ITRGFP construct illustrated in in FIG. 11B is shown below:

PBBG-ITRGFP (7,798 bp)

(SEQ ID NO: 27)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcAAA

CGCCAGCAACGCGGCCTTTTTACGGTTCCTGGCCTTTTGCTGGCCTTTTGCTCACATG

TCCTGCAGGCAGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCAGAGAGG

GAGTGGCCAACTCCATCACTAGGGGTTCCTGCGGCCGCACGCGTGGAGCTAGTTATT

AATAGTAATCAATTACGGGGTCATTAGTTCATAGCCCATATATGGAGTTCCGCGTTA

CATAACTTACGGTAAATGGCCCGCCTGGCTGACCGCCCAACGACCCCCGCCCATTGA

CGTCAATAATGACGTATGTTCCCATAGTAACGTCAATAGGGACTTTCCATTGACGTC

-continued

AATGGGTGGAGTATTTACGGTAAACTGCCCACTTGGCAGTACATCAAGTGTATCATA

TGCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCAT

CGCTATTACCATGGTGATGCGGTTTTGGCAGTACATCAATGGGCGTGGATAGCGGTT

TGACTCACGGGGATTTCCAAGTCTCCACCCCATTGACGTCAATGGGAGTTTGTTTTG

CACCAAAATCAACGGGACTTTCCAAAATGTCGTAACAACTCCGCCCCATTGACGCA

AATGGGCGGTAGGCGTGTACGGTGGGAGGTCTATATAAGCAGAGCTCGTTTAGTGA

ACCGTCAGATCGCCTGGAGACGCCATCCACGCTGTTTTGACCTCCATAGAAGACACC

GGGACCGATCCAGCCTCCGCGGATTCGAATCCCGGCCGGGAACGGTGCATTGGAAC

GCGGATTCCCCGTGCCAAGAGTGACGTAAGTACCGCCTATAGAGTCTATAGGCCCA

CAAAAAATGCTTTCTTCTTTTAATATACTTTTTTGTTTATCTTATTTCTAATACTTTCC

CTAATCTCTTTCTTTCAGGGCAATAATGATACAATGTATCATGCCTCTTTGCACCATT

CTAAAGAATAACAGTGATAATTTCTGGGTTAAGGCAATAGCAATATTTCTGCATATA

AATATTTCTGCATATAAATTGTAACTGATGTAAGAGGTTTCATATTGCTAATAGCAG

CTACAATCCAGCTACCATTCTGCTTTTATTTTATGGTTGGGATAAGGCTGGATTATTC

TGAGTCCAAGCTAGGCCCTTTTGCTAATCATGTTCATACCTCTTATCTTCCTCCCACA

GCTCCTGGGCAACGTGCTGGTCTGTGTGCTGGCCCATCACTTTGGCAAAGAATTGGG

ATTCGAACATCGATTGAATTCTGAATGGTGAGCAAGGGCGAGGAGCTGTTCACCGG

GGTGGTGCCCATCCTGGTCGAGCTGGACGGCGACGTAAACGGCCACAAGTTCAGCG

TGTCCGGCGAGGGCGAGGGCGATGCCACCTACGGCAAGCTGACCCTGAAGTTCATC

TGCACCACCGGCAAGCTGCCCGTGCCCTGGCCCACCCTCGTGACCACCCTGACCTAC

GGCGTGCAGTGCTTCAGCCGCTACCCCGACCACATGAAGCAGCACGACTTCTTCAAG

TCCGCCATGCCCGAAGGCTACGTCCAGGAGCGCACCATCTTCTTCAAGGACGACGG

CAACTACAAGACCCGCGCCGAGGTGAAGTTCGAGGGCGACACCCTGGTGAACCGCA

TCGAGCTGAAGGGCATCGACTTCAAGGAGGACGGCAACATCCTGGGGCACAAGCTG

GAGTACAACTACAACAGCCACAACGTCTATATCATGGCCGACAAGCAGAAGAACGG

CATCAAGGTGAACTTCAAGATCCGCCACAACATCGAGGACGGCAGCGTGCAGCTCG

CCGACCACTACCAGCAGAACACCCCCATCGGCGACGGCCCCGTGCTGCTGCCCGAC

AACCACTACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCATGGACGA

GCTGTACAAGTACTCAGATCTCGAGCTCAAGTAGGGATCCTCTAGAGTCGACCTGCA

GAAGCTTGCCTCGAGCAGCGCTGCTCGAGAGATCTACGGGTGGCATCCCTGTGACCC

CTCCCCAGTGCCTCTCCTGGCCCTGGAAGTTGCCACTCCAGTGCCCACCAGCCTTGT

CCTAATAAAATTAAGTTGCATCATTTTGTCTGACTAGGTGTCCTTCTATAATATTATG

GGGTGGAGGGGGGTGGTATGGAGCAAGGGGCAAGTTGGGAAGACAACCTGTAGGG

CCTGCGGGGTCTATTGGGAACCAAGCTGGAGTGCAGTGGCACAATCTTGGCTCACTG

CAATCTCCGCCTCCTGGGTTCAAGCGATTCTCCTGCCTCAGCCTCCCGAGTTGTTGGG

ATTCCAGGCATGCATGACCAGGCTCAGCTAATTTTTGTTTTTTTGGTAGAGACGGGG

TTTCACCATATTGGCCAGGCTGGTCTCCAACTCCTAATCTCAGGTGATCTACCCACCT

TGGCCTCCCAAATTGCTGGGATTACAGGCGTGAACCACTGCTCCCTTCCCTGTCCTTC

TGATTTTGTAGGTAACCACGTGCGGACCGAGCGGCCGCAGGAACCCCTAGTGATGG

-continued

AGTTGGCCACTCCCTCTCTGCGCGCTCGCTCGCTCACTGAGGCCGGGCGACCAAAGG

TCGCCCGACGCCCGGGCTTTGCCCGGGCGGCCTCAGTGAGCGAGCGAGCGCGCAGC

TGCCTGCAGGGGCGCCTGATGCGGTATTTTCTCCTTACGCATCTGTGCGGTATTTCAC

ACCGCATACGTCgtaGCtGATcaATTgGCGCGCCGAATTCGTTAACAAGCTtTAATTAaCG

CgtATAcCTAggATCCGGCCGGccTGCAggTGTCCTCACAGGAACGAAGTCCCTAAAGA

AACAGTGGCAGCCAGGTTTAGCCCCGGAATTGACTGGATTCCTTTTTTAGGGCCCAT

TGGTATGGCTTTTTCCCCGTATCCCCCCAGGTGTCTGCAGGCTCAAAGAGCAGCGAG

AAGCGTTCAGAGGAAAGCGATCCCGTGCCACCTTCCCCGTGCCCGGGCTGTCCCCGC

ACGCTGCCGGCTCGGGGATGCGGGGGGAGCGCCGGACCGGAGCGGAGCCCCGGGC

GGCTCGCTGCTGCCCCCTAGCGGGGGAGGGACGTAATTACATCCCTGGGGGCTTTGG

GGGGGGGCTGTCCCTCTAGAGCGGCCGCCACCGCGGTGGAGCTCCAGCTTTTGTTCC

CTTTAGTGAGGGTTAATTAGATCTTAATACGACTCACTATAGGGCGAATTGGGTACC

GGGCCCCCCCTCGAGGTCGACGGTATCGATAAGCTTGATATCTATAACAAGAAAAT

ATATATATAATAAGTTATCACGTAAGTAGAACATGAAATAACAATATAATTATCGTA

TGAGTTAAATCTTAAAAGTCACGTAAAAGATAATCATGCGTCATTTTGACTCACGCG

GTCGTTATAGTTCAAAATCAGTGACACTTACCGCATTGACAAGCACGCCTCACGGGA

GCTCCAAGCGGCGACTGAGATGTCCTAAATGCACAGCGACGGATTCGCGCTATTTAG

AAAGAGAGAGCAATATTTCAAGAATGCATGCGTCAATTTTACGCAGACTATCTTTCT

AGGGTTAATCTAGCTGCATCAGGATCATATCGTCGGGTCTTTTTTCCGGCTCAGTCAT

CGCCCAAGCTGGCGCTATCTGGGCATCGGGGAGGAAGAAGCCCGTGCCTTTTCCCG

CGAGGTTGAAGCGGCATGGAAAGAGTTTGCCGAGGATGACTGCTGCTGCATTGACG

TTGAGCGAAAACGCACGTTTACCATGATGATTCGGGAAGGTGTGGCCATGCACGCCT

TTAACGGTGAACTGTTCGTTCAGGCCACCTGGGATACCAGTTCGTCGCGGCTTTTCC

GGACACAGTTCCGGATGGTCAGCCCGAAGCGCATCAGCAACCCGAACAATACCGGC

GACAGCCGGAACTGCCGTGCCGGTGTGCAGATTAATGACAGCGGTGCGGCGCTGGG

ATATTACGTCAGCGAGGACGGGTATCCTGGCTGGATGCCGCAGAAATGGACATGGA

TACCCCGTGAGTTACCCGGCGGGCGCGCTTGGCGTAATCATGGTCATAGCTGTTTCC

TGTGTGAAATTGTTATCCGCTCACAATTCCACACAACATACGAGCCGGAAGCATAAA

GTGTAAAGCCTGGGGTGCCTAATGAGTGAGCTAACTCACATTAATTGCGTTGCGCTC

ACTGCCCGCTTTCCAGTCGGGAAACCTGTCGTGCCAGCTGCATTAATGAATCGGCCA

ACGCGCGGGGAGAGGCGGTTTGCGTATTGGGCGCTCTTCCGCTTCCTCGCTCACTGA

CTCGCTGCGCTCGGTCGTTCGGCTGCGGCGAGCGGTATCAGCTCACTCAAAGGCGGT

AATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCA

-continued

GCCACTGGTAACAGGATTAGCAGAGCGAGGTATGTAGGCGGTGCTACAGAGTTCTT

GAAGTGGTGGCCTAACTACGGCTACACTAGAAGGACAGTATTTGGTATCTGCGCTCT

GCTGAAGCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGCAGAAAAA

AAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTT

GGTCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGAGG

GCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCT

GCAACTTTATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCATCGTGGTG

TCACGCTCGTCGTTTGGTATGGCTTCATTCAGCTCCGGTTCCCAACGATCAAGGCGA

GTTACATGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGCAT

AATTCTCTTACTGTCATGCCATCCGTAAGATGCTTTTCTGTGACTGGTGAGTACTCAA

CCAAGTCATTCTGAGAATAGTGTATGCGGCGACCGAGTTGCTCTTGCCCGGCGTCAA

TACGGGATAATACCGCGCCACATAGCAGAACTTTAAAAGTGCTCATCATTGGAAAA

CGTTCTTCGGGGCGAAAACTCTCAAGGATCTTACCGCTGTTGAGATCCAGTTCGATG

TAACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACACG

GAAATGTTGAATACTCAT

Figure 11C:
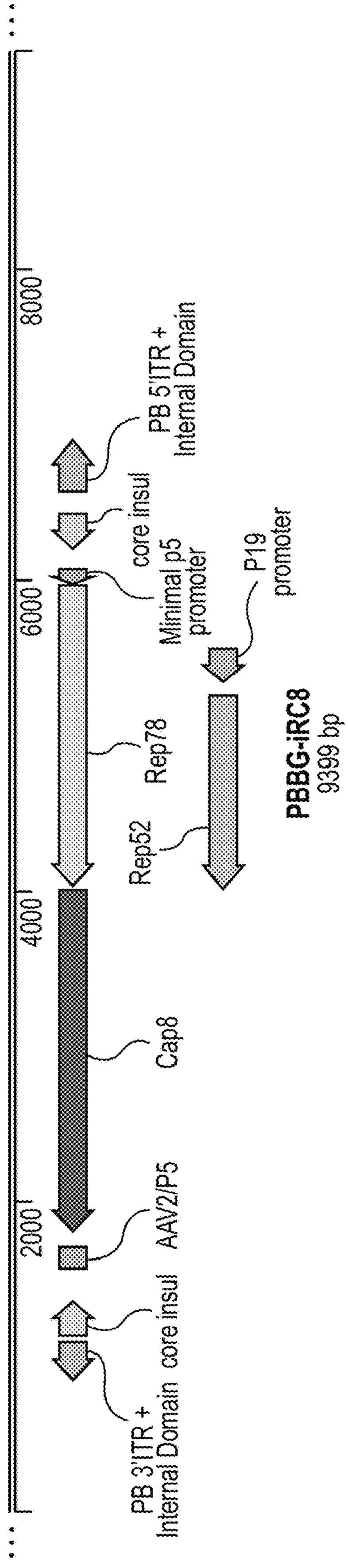

The sequence for the PBBG-iRC8 construct illustrated in in FIG. 11C is shown below:

PBBG-iRC8 (9,399 bp)

(SEQ ID NO: 28)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

-continued

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcTTAa gCGCtGATcaATTgGCGCGCCGAATTCGTTatctgcagaattcggcttggcggctgcgcgttcaaacctcccgcttc aaaatggagaccctgcgtgctcactcgggcttaaatacccagcgtgaccacatggtgtcgcaaaatgtcgcaaaacactcacgtgacctcta atacaggacctctagagcatggaaactagataagaaagaaatacgcagagaccaaagttcaactgaaacgaattaaacggtttattgattaa caagcaaactagtttacagattacgggtgaggtaacgggtgccaatggggggggttcagagtacacgccttctgtattaacagcaaagtc cacacttgtagatttgtagtagttggaggtgtactggatctcggggttccagcgcttgctgttttccttctgcagctcccattcaatttccacgc tgacctgtccggtgctgtattgcgtgatgaaagagttcagctttgactggttgaaggtggtcggaggatccgcaggtacaggcgtgttcttgatc aggatctgaggcggaggatgtttcaggccaaagccgcccatcagcggagacgggtggaagttgccgtccgtgtgaggaatcttggccca gatgggaccctgcaggtacacgtcccggttctgccagaccataccgggtaaggccccctggctgttgacagttccaatttgaggagccgtg ttttgctgctgcaagttatctgccacgataccgtattcctctgtagccacagggttagtggttttgatttcttcctcgctggtgagcatgacatc gctgtaatccgcattgtctctggcagcattttgtttgccaaaaatcaggatcccgttactgggaaaaaaacgctcctcgtcgtctttgtgtgttg ccatagcgatgccaggattagccaatgaatttcttccattcagatggtatttggtcccagcagtccaggcaaagttgctattgttgttttgcccg gttgtcgttgagacgcgttgttggcggtaacagggtcctggcagccagttctttgcctgattggccattgtattaggcccaccttggctgaagcc cagagtctgcgtatttgccgtgcctcctgttgtttgagtccgagacaagtagtacaggtactggtcaatcagaggattcatcagccggtccaagc tctggctgtgggcgtagctgctgtggaaaggcacgtcctcgaaggtgtaagtaaactggaagttgttgccggttctcagcatctgcgaaggaaa gtattccaggcagtagaaggaggagcgtcccacggcctgactaccgttgttgagtgttaggtagccgtactggggaatcatgaacacgtcc gccgggaacggaggcaggcagccctggtgggcagagccgagaacgtacggcagctggtactccgagtccgtaaacacctggatggtg ctggtgaggttattggcgatggtcttggtgccttcattctgcgtgacctccttgacctggatgttgaagagcttgaagctgagtctcttgggccg gaatccccagttgttgttgatgagtcgctgccagtcacgtggtgaaaagtggcagtggaatctgttaaagtcaaaatacccccaggggggtgc tgtagccgaagtaggtgttgtcgttggtggctcctcccgatgtcccgttggagatttgcttgtagaggtggttgttgtaggtgggcagggccca ggttcgggtgctggtggtgatgactctgtcgcccagccatgtggaatcgcaatgccaatttcccgaggaactacccactccgtcggcgcctt cgttattgtctgccattggtgcgccaccgcctgcagccattgtattaggtcccacaccagagggcgctgctggaggttctccgagaggttga gggtctggaactgactctgagtcgccagtctgaccaaaattgagtctttttctggcgggctgttggcctttcttgccgatgcccgtagaggagt ctggagaacgctggggtgatggctctaccggtctcttctttccaggagccgtcttagcgccttcctcaaccagaccgagaggttcgagaacc cgcttcttggcctggaagactgctcgcccgaggttgcccccaaaagacgtatcttcttgcagacgctcctgaaactcggcgtcggcgtggtt ataccgcaggtacggattgtcacccgcctgcagctgctggtcgtaggccttgtcgtgctcgagggccgctgcgtccgccgcgttgacggg ctccccccttgtcgagtccgttgaagggtccgaggtacttgtagccaggaagcaccagaccccggccgtcgtcctgcttttgctggttggcttt gggcttcggggctccaggtttcagcgcccaccactcgcgaatgccctcagagaggttgtcctcgagccaatctggaagataaccatcggc -continued agccatacctgatttaaatcatttattgttcaaagatgcagtcatccaaatccacattgaccagatcgcaggcagtgcaagcgtctggcaccttt cccatgatatgatgaatgtagcacagtttctgatacgccttttgacgacagaaacgggttgagattctgacacgggaaagcactctaaacagt ctttctgtccgtgagtgaagcagatatttgaattctgattcattctctcgcattgtctgcagggaaacagcatcagattcatgcccacgtgacga gaacatttgttttggtacctgtctgcgtagttgatcgaagcttccgcgtctgacgtcgatggctgcgcaactgactcgcgcacccgtttgggct cacttatatctgcgtcactgggggggtcttttcttggctccacccttttgacgtagaattcatgctccacctcaaccacgtgatcctttgccc accggaaaaagtctttgacttcctgcttggtgaccttcccaaagtcatgatccagacggcgggtgagttcaaatttgaacatccggtcttgcaac ggctgctggtgttcgaaggtcgttgagttcccgtcaatcacggcgcacatgttggtgttggaggtgacgatcacgggagtcgggtctatctg ggccgaggacttgcatttctggtccacgcgcaccttgcttcctccgagaatggctttggccgactccacgaccttggcggtcatcttcccctc ctcccaccagatcaccatcttgtcgacacagtcgttgaagggaaagttctcattggtccagtttacgcacccgtagaagggcacagtgtggg ctatggcctccgcgatgttggtcttcccggtagttgcaggcccaaacagccagatggtgttcctcttgccgaacttttcgtggcccatcccag aaagacggaagccgcatattggggatcgtacccgtttagttccaaaattttataaatccgattgctggaaatgtcctccacgggctgctggcc caccaggtagtcgggggcggttttagtcaggctcataatctttcccgcattgtccaaggcagccttgatttgggaccgcgagttggaggccg cattgaaggagatgtatgaggcctggtcctcctggatccactgcttctccgaggtaatccccttgtccacgagccacccgaccagctccatgt acctggctgaagtttttgatctgatcaccggcgcatcagaattgggattctgattctctttgttctgctcctgcgtctgcgacacgtgcgtcaga tgctgcgccaccaaccgtttacgctccgtgagattcaaacaggcgctgtggagagaaaggcaaagtggatgtcagtaTCTCTATCA CTGATAGGGAGATCTCTATCACTGATAGGGAacttaccttaaatactgttccatattagtccacgcccactggag ctcaggctgggttttggggagcaagtaattggggatgtagcactcatccaccaccttgttcccgcctccggcgccatttctggtctttgtgacc gcgaaccagtttggcaaagtcggctcgatcccgcggtaaattctctgaatcagtttttcgcgaatctgactcaggaaacgtcccaaaaccatg gatttcaccccggtggtttccacgagcacgtgcatgtggaagtagctctctcccttctcaaattgcacaaagaaaagagcctccggggcctta ctcacacggcgccattccgtcagaaagtcgcgctgcagcttctcggccacggtcaggggtgcctgctcaatcagattcagatccatgtcag aatctggcggcaactcccattccttctcggccacccagttcacaaagctgtcagaaatgccgggcagatgctcgtcaaggtcgctggggac cttaatcacaatctcgtaaaaccccggcatGGCGGCTGCGCGTTCAAACCTCCCGCTTCAAAATGGAG ACCCTGCGTGCTCACTCGGGCgaTCTCTATCACTGATAGGGAGATCTCTATCACTGAT AGGGAgaTTAAATAgaatggCTAggATCCGGCCGGccTGCAggTGTCCTCACAGGAACGAA

GTCCCTAAAGAAACAGTGGCAGCCAGGTTTAGCCCCGGAATTGACTGGATTCCTTTT

TTAGGGCCCATTGGTATGGCTTTTTCCCCGTATCCCCCCAGGTGTCTGCAGGCTCAAA

GAGCAGCGAGAAGCGTTCAGAGGAAAGCGATCCCGTGCCACCTTCCCCGTGCCCGG

GCTGTCCCCGCACGCTGCCGGCTCGGGGATGCGGGGGGAGCGCCGGACCGGAGCGG

AGCCCCGGGCGGCTCGCTGCTGCCCCCTAGCGGGGGAGGGACGTAATTACATCCCT

GGGGGCTTTGGGGGGGGGCTGTCCCTCTAGAGCGGCCGCCACCGCGGTGGAGCTCC

AGCTTTTGTTCCCTTTAGTGAGGGTTAATTAGATCTTAATACGACTCACTATAGGGCG

AATTGGGTACCGGGCCCCCCCTCGAGGTCGACGGTATCGATAAGCTTGATATCTATA

ACAAGAAAATATATATATAATAAGTTATCACGTAAGTAGAACATGAAATAACAATA

TAATTATCGTATGAGTTAAATCTTAAAAGTCACGTAAAAGATAATCATGCGTCATTT

TGACTCACGCGGTCGTTATAGTTCAAAATCAGTGACACTTACCGCATTGACAAGCAC

GCCTCACGGGAGCTCCAAGCGGCGACTGAGATGTCCTAAATGCACAGCGACGGATT

CGCGCTATTTAGAAAGAGAGAGCAATATTTCAAGAATGCATGCGTCAATTTTACGCA

GACTATCTTTCTAGGGTTAATCTAGCTGCATCAGGATCATATCGTCGGGTCTTTTTTC

CGGCTCAGTCATCGCCCAAGCTGGCGCTATCTGGGCATCGGGGAGGAAGAAGCCCG

TGCCTTTTCCCGCGAGGTTGAAGCGGCATGGAAAGAGTTTGCCGAGGATGACTGCTG

CTGCATTGACGTTGAGCGAAAACGCACGTTTACCATGATGATTCGGGAAGGTGTGGC

-continued

CATGCACGCCTTTAACGGTGAACTGTTCGTTCAGGCCACCTGGGATACCAGTTCGTC
GCGGCTTTTCCGGACACAGTTCCGGATGGTCAGCCCGAAGCGCATCAGCAACCCGA
ACAATACCGGCGACAGCCGGAACTGCCGTGCCGGTGTGCAGATTAATGACAGCGGT
GCGGCGCTGGGATATTACGTCAGCGAGGACGGGTATCCTGGCTGGATGCCGCAGAA
ATGGACATGGATACCCCGTGAGTTACCCGGCGGGCGCGCTTGGCGTAATCATGGTCA
TAGCTGTTTCCTGTGTGAAATTGTTATCCGCTCACAATTCCACACAACATACGAGCC
GGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTA
ATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACA
TGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAGCAGATTA
CGCGCAGAAAAAAAGGATCTCAAGAAGATCCTTTGATCTTTTCTACGGGGTCTGACG
CTCAGTGGAACGAAAACTCACGTTAAGGGATTTTGGTCATGAGATTATCAAAAAGG
ATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAG
CGATCTGTCTATTTCGTTCATCCATAGTTGCCTGACTCCCCGTCGTGTAGATAACTAC
GATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAA
GCTAGAGTAAGTAGTTCGCCAGTTAATAGTTTGCGCAACGTTGTTGCCATTGCTACA
GGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGG
TGAGTACTCAACCAAGTCATTCTGAGAATAGTGTATGCGGCGACCGAGTTGCTCTTG
CCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGAT

-continued

CCAGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAATA

AGGGCGACACGGAAATGTTGAATACTCAT

Figure 11D:
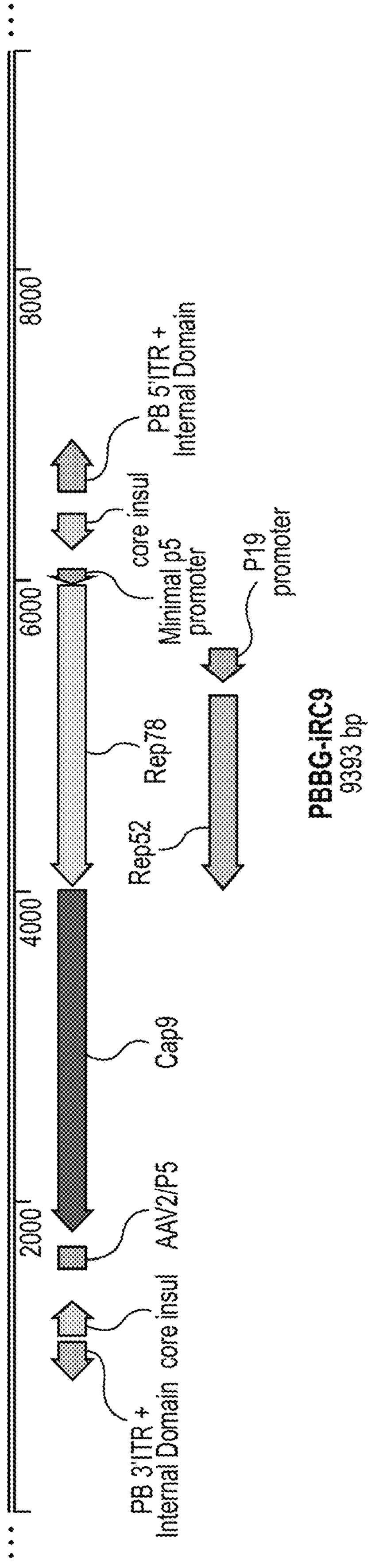

The sequence for the PBBG-iRC9 construct illustrated in in FIG. 11D is shown below:

PBBG-iRC9 (9,393 bp)

(SEQ ID NO: 29)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcTTAa gCGCtGATcaATTgGCGCGCCGAATTCGTTatctgcagaattcggcttggcggctgcgcgttcaaacctcccgcttc aaaatggagaccctgcgtgctcactcgggcttaaatacccagcgtgaccacatggtgtcgcaaaatgtcgcaaaacactcacgtgacctcta atacaggacctctagagcatggaaactagataagaaagaaatacgcagagaccaaagttcaactgaaacgaattaaacggtttattgattaa caagcaaactagtTTACAGATTACGAGTCAGGTATCTGGTGCCAATGGGGCGGGGTTCACTA

TATACACCTTCAGTATTAACAGCAAATTCAACATTATTAGACTTGTAATAGTTGGAA

GTGTACTGGATCTCCGGGTTCCAGCGCTTGCTGTTTTCCTTCTGCAGCTCCCACTCGA

-continued

TCTCCACGCTGACTTGGCCAGTAGAATACTGGGTGATGAAAGAGTTCAGCTTGTCCT

TGTTGAAGGCCGTTGGAGGATCCGCAGGTACAGGTGTGTTTTTGATGAGGATCTGAG

GAGGCGGGTGCTTCATTCCAAACCCTCCCATCAGCGGAGAAGGGTGAAAGTTGCCG

TCCGTGTGAGGAATTTTGGCCCAAATGGGTCCTTGCAGGTACACATCTCTGTCCTGC

CAAACCATACCCGGAAGTATTCCTTGGTTTTGAACCCAGCCGGTCTGCGCCTGTGCT

TGGGCACTCTGGTGGTTTGTGGCCACTTGTCCATAGGACTCCGTTGCTACCGGGTTA

GTAGTTTTAATTTCTTCTTCGTTGGTTATCATGACTTTGTCCGCATCCACGTTGTCTCT

TCCAGTTCCTTGTTTGCCAAAAATTAAAGATCCAGACAAAGGAAAGAAACGGTCCTC

TCCTTCTTTGTGGCTGGCCATAGCAGGTCCAGGATTCATCAAGCTATTACGTCCATTG

AGAGCCCAAGAAGAAGCTCCAGGCCAAGCAAATTCGCTGTTGTTGTTTTGAGTCACA

GTGGTTGAGACACGTTGTTGTCGGTAGCTGGGTCCAGGTATGTAGTTTCTTCCCTGG

ACAGCCATGTTGCTGGGTCCGGCCACACTGAATTTTAGCGTTTGTTGATTCTGTCCAG

AACCGTTAATAGTCTTTGAGAGATAGTACAAGTATTGGTCGATGAGTGGATTCATTA

GTCGGTCCAGGCTTTGGCTGTGAGCGTAGCTGCTATGGAAAGGTACGTTCTCAAACT

CGTAGCTGAACTGGAAGTTGTTACCCGTTCTTAGCATTTGCGACGGGAAATATTCCA

GGCAGTAAAAGGACGAACGACCCACGGCCTGGCTTCCATCATTAAGCGTCAGATAC

CCGTACTGAGGAATCATGAAAACGTCCGCTGGGAACGGCGGGAGGCAGCCCTCGTG

AGCCGACCCGAGCACGTACGGGAGCTGATAGTCTGAGTCCGTGAAGACCTGGACCG

TGCTGGTAAGGTTATTGGCGATGGTCTTGACTCCATTGTTGTCCGTAACCTCTTTGAC

CTGAATGTTGAAGAGCTTGAAGTTGAGTCGCTTAGGCCGGAATCCCCAGTTGTTGTT

GATGAGTCGCTGCCAGTCACGTGGTGAGAAGTGGCAGTGGAATCTGTTGAAGTCAA

AATACCCCCAGGGGGTGCTGTAGCCGAAGTAGGCGTTGTCATTTGAAGATCCTCCAG

ATGTGCTGTTGGAGATTTGCTTGTAGAGGTGATTGTTGTAGGTGGGCAGGGCCCAGG

TTCGGGTGCTGGTGGTGATGACTCTGTCCCCCAGCCATTGGGAATCGCAATGCCAAT

TTCCCGAGGAACTACCCACTCCATCGGCACCTTCGTTATTGTCTGCCACTGGTGCGC

CACCACCTGAAGCCATTGTAAGAGATCCCACACCTGAGGGGGCTGCGGGAGGTTCT

CCGATTGGTTGAGGGTCTGGGACTGACTCTGTGTCGCCAGTCTGACCGAAATTGAGT

CTCTTTTTAGCGGGCTGTGCACCCGATTTGCCAATACCCGCGGAGGAGTCCGGTTCC

TGAGGAGACTGCTCTACAGGCCTCTTCTTTCCAGGAGCCGTCTTAGCCGCTTCCTCA

ACCAGACCAAGAGGTTCAAGAAGCCTCTTTTTGGCCTGGAAGACTGCTCGCCCGAG

GTTGCCCCCAAAAGACGTATCTTCTTTGAGCCGCTCCTGGAACTCGGCGTCGGCGTG

GTTGTACTTGAGGTACGGGTTGTCTCCGGCCTTGAGCTGCTGGTCGTAGGCCTTGTC

GTGCTCGAGGGCCGCCGCGTCTGCTGCGTTGACCGGCTCCCCCTTGTCGAGTCCGTT

GCCGGGTCCAAGGTATTTGTAACCCGGAAGCACAAGACCTCGAGCGTTGTCTTGATG

TTGTTGATTTGCCTTGGGTTGAGGGGCTCCAGGTTTCAAAGCCCACCACTCGCGAAT

TCCTTCACTAAGGTTGTCCTCGAGCCAATCTGGAAGATAACCATCGGCAGCCATacctg atttaaatcatttattgttcaaagatgcagtcatccaaatccacattgaccagatcgcaggcagtgcaagcgtctggcacctttcccatgatatg atgaatgtagcacagtttctgatacgccttttttgacgacagaaacgggttgagattctgacacgggaaagcactctaaacagtctttctgtccgt gagtgaagcagatatttgaattctgattcattctctcgcattgtctgcagggaaacagcatcagattcatgcccacgtgacgagaacatttgtttt ggtacctgtctgcgtagttgatcgaagcttccgcgtctgacgtcgatggctgcgcaactgactcgcgcacccgtttgggctcacttatatctgc gtcactgggggggtcttttcttggctccacccttttgacgtagaattcatgctccacctcaaccacgtgatcctttgcccaccggaaaaagt -continued ctttgacttcctgcttggtgaccttcccaaagtcatgatccagacggcgggtgagttcaaatttgaacatccggtcttgcaacggctgctggtgt tcgaaggtcgttgagttcccgtcaatcacggcgcacatgttggtgttggaggtgacgatcacgggagtcgggtctatctgggccgaggactt gcatttctggtccacgcgcaccttgcttcctccgagaatggctttggccgactccacgaccttggcggtcatcttcccctcctcccaccagatc accatcttgtcgacacagtcgttgaagggaaagttctcattggtccagtttacgcacccgtagaagggcacagtgtgggctatggcctccgc gatgttggtcttcccggtagttgcaggcccaaacagccagatggtgttcctcttgccgaactttttcgtggcccatcccagaaagacggaagc cgcatattggggatcgtacccgtttagttccaaaattttataaatccgattgctggaaatgtcctccacgggctgctggcccaccaggtagtcg ggggcggttttagtcaggctcataatctttcccgcattgtccaaggcagccttgatttgggaccgcgagttggaggccgcattgaaggagat gtatgaggcctggtcctcctggatccactgcttctccgaggtaatccccttgtccacgagccacccgaccagctccatgtacctggctgaagt ttttgatctgatcaccggcgcatcagaattgggattctgattctctttgttctgctcctgcgtctgcgacacgtgcgtcagatgctgcgccaccaa ccgtttacgctccgtgagattcaaacaggcgctgtggagagaaaggcaaagtggatgtcagtaTCTCTATCACTGATAGG GAGATCTCTATCACTGATAGGGAacttaccttaaatactgttccatattagtccacgcccactggagctcaggctgggtt ttggggagcaagtaattggggatgtagcactcatccaccaccttgttcccgcctccggcgccatttctggtctttgtgaccgcgaaccagtttg gcaaagtcggctcgatcccgcggtaaattctctgaatcagtttttcgcgaatctgactcaggaaacgtcccaaaaccatggatttcaccccgg tggtttccacgagcacgtgcatgtggaagtagctctctcccttctcaaattgcacaaagaaaagagcctccggggccttactcacacggcgc cattccgtcagaaagtcgcgctgcagcttctcggccacggtcaggggtgcctgctcaatcagattcagatccatgtcagaatctggcggcaa ctcccattccttctcggccacccagttcacaaagctgtcagaaatgccgggcagatgctcgtcaaggtcgctggggaccttaatcacaatctc gtaaaaccccggcatGGCGGCTGCGCGTTCAAACCTCCCGCTTCAAAATGGAGACCCTGCGT GCTCACTCGGGCgaTCTCTATCACTGATAGGGAGATCTCTATCACTGATAGGGAgaTT AAATAgaatggCTAggATCCGGCCGGccTGCAggTGTCCTCACAGGAACGAAGTCCCTAA

AGAAACAGTGGCAGCCAGGTTTAGCCCCGGAATTGACTGGATTCCTTTTTTAGGGCC

CATTGGTATGGCTTTTTCCCCGTATCCCCCCAGGTGTCTGCAGGCTCAAAGAGCAGC

GAGAAGCGTTCAGAGGAAAGCGATCCCGTGCCACCTTCCCCGTGCCCGGGCTGTCC

CCGCACGCTGCCGGCTCGGGGATGCGGGGGGAGCGCCGGACCGGAGCGGAGCCCC

GGGCGGCTCGCTGCTGCCCCCTAGCGGGGGAGGGACGTAATTACATCCCTGGGGGC

TTTGGGGGGGGGCTGTCCCTCTAGAGCGGCCGCCACCGCGGTGGAGCTCCAGCTTTT

GTTCCCTTTAGTGAGGGTTAATTAGATCTTAATACGACTCACTATAGGGCGAATTGG

GTACCGGGCCCCCCCTCGAGGTCGACGGTATCGATAAGCTTGATATCTATAACAAGA

AAATATATATATAATAAGTTATCACGTAAGTAGAACATGAAATAACAATATAATTAT

CGTATGAGTTAAATCTTAAAAGTCACGTAAAAGATAATCATGCGTCATTTTGACTCA

CGCGGTCGTTATAGTTCAAAATCAGTGACACTTACCGCATTGACAAGCACGCCTCAC

GGGAGCTCCAAGCGGCGACTGAGATGTCCTAAATGCACAGCGACGGATTCGCGCTA

TTTAGAAAGAGAGAGCAATATTTCAAGAATGCATGCGTCAATTTTACGCAGACTATC

TTTCTAGGGTTAATCTAGCTGCATCAGGATCATATCGTCGGGTCTTTTTTCCGGCTCA

GTCATCGCCCAAGCTGGCGCTATCTGGGCATCGGGGAGGAAGAAGCCCGTGCCTTTT

CCCGCGAGGTTGAAGCGGCATGGAAAGAGTTTGCCGAGGATGACTGCTGCTGCATT

GACGTTGAGCGAAAACGCACGTTTACCATGATGATTCGGGAAGGTGTGGCCATGCA

CGCCTTTAACGGTGAACTGTTCGTTCAGGCCACCTGGGATACCAGTTCGTCGCGGCT

TTTCCGGACACAGTTCCGGATGGTCAGCCCGAAGCGCATCAGCAACCCGAACAATA

CCGGCGACAGCCGGAACTGCCGTGCCGGTGTGCAGATTAATGACAGCGGTGCGGCG

CTGGGATATTACGTCAGCGAGGACGGGTATCCTGGCTGGATGCCGCAGAAATGGAC

-continued

ATGGATACCCCGTGAGTTACCCGGCGGGCGCGCTTGGCGTAATCATGGTCATAGCTG

TTTCCTGTGTGAAATTGTTATCCGCTCACAATTCCACACAACATACGAGCCGGAAGC

ATAAAGTGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAATGAATC

GGCCAACGCGCGGGGAGAGGCGGTTTGCGTATTGGGCGCTCTTCCGCTTCCTCGCTC

ACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGC

AAAAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGTGG

CGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGTGTAGGTC

GTTCGCTCCAAGCTGGGCTGTGTGCACGAACCCCCCGTTCAGCCCGACCGCTGCGCC

TTATCCGGTAACTATCGTCTTGAGTCCAACCCGGTAAGACACGACTTATCGCCACTG

GCAGCAGCCACTGGTAACAGGATTAGCAGAGCGAGGTATGTAGGCGGTGCTACAGA

GTTCTTGAAGTGGTGGCCTAACTACGGCTACACTAGAAGGACAGTATTTGGTATCTG

CGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCTG

TCTATTTCGTTCATCCATAGTTGCCTGACTCCCCGTCGTGTAGATAACTACGATACGG

GAGGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAAGCTAGAGT

AAGTAGTTCGCCAGTTAATAGTTTGCGCAACGTTGTTGCCATTGCTACAGGCATCGT

GGTGTCACGCTCGTCGTTTGGTATGGCTTCATTCAGCTCCGGTTCCCAACGATCAAG

GCGAGTTACATGATCCCCCATGTTGTGCAAAAAAGCGGTTAGCTCCTTCGGTCCTCC

GATCGTTGTCAGAAGTAAGTTGGCCGCAGTGTTATCACTCATGGTTATGGCAGCACT

GCATAATTCTCTTACTGTCATGCCATCCGTAAGATGCTTTTCTGTGACTGGTGAGTAC

TCAACCAAGTCATTCTGAGAATAGTGTATGCGGCGACCGAGTTGCTCTTGCCCGGCG

TCAATACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCG

ATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGAC

ACGGAAATGTTGAATACTCAT

Figure 11E:
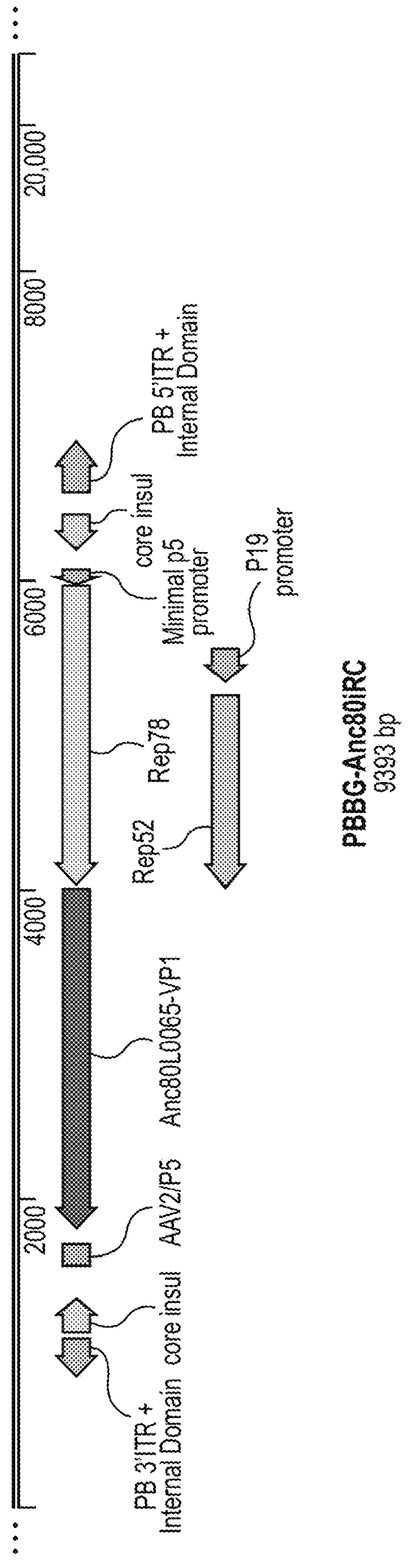

The sequence for the PBBG-Anc80iRC construct illustrated in in FIG. 11E is shown below:

PBBG-Anc80iRC (9,393 bp)

(SEQ ID NO: 30)

ACTCTTCCTTTTTCAATATTATTGAAGCATTTATCAGGGTTATTGTCTCATG

AGCGGATACATATTTGAATGTATTTAGAAAAATAAACAAATAGGGGTTCCGCGCAC

ATTTCCCCGAAAAGTGCCACCTAAATTGTAAGCGTTAATATTTTGTTAAAATTCGCG

TTAAATTTTTGTTAAATCAGCTCATTTTTTAACCAATAGGCCGAAATCGGCAAAATC

CCTTATAAATCAAAAGAATAGACCGAGATAGGGTTGAGTGTTGTTCCAGTTTGGAAC

AAGAGTCCACTATTAAAGAACGTGGACTCCAACGTCAAAGGGCGAAAAACCGTCTA

TCAGGGCGATGGCCCACTACGTGAACCATCACCCTAATCAAGTTTTTTGGGGTCGAG

GTGCCGTAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCC

GCGCTTAATGCGCCGCTACAGGGCGCGTCCCATTCGCCATTCAGGCTGCGCAACTGT

TGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTG

TAAAACGACGGCCAGTGAGCGCGCCTCGTTCATTCACGTTTTTGAACCCGTGGAGGA

CGGGCAGACTCGCGGTGCAAATGTGTTTTACAGCGTGATGGAGCAGATGAAGATGC

TCGACACGCTGCAGAACACGCAGCTAGATTAACCCTAGAAAGATAATCATATTGTG

ACGTACGTTAAAGATAATCATGCGTAAAATTGACGCATGTGTTTTATCGGTCTGTAT

ATCGAGGTTTATTTATTAATTTGAATAGATATTAAGTTTTATTATATTTACACTTACA

TACTAATAATAAATTCAACAAACAATTTATTTATGTTTATTTATTTATTAAAAAAAAA

CAAAAACTCAAAATTTCTTCTATAAAGTAACAAAACTTTTATCGAATTCCTGCAGCC

CGGGGGATCCACTAGTTCTAGAGGGACAGCCCCCCCCCAAAGCCCCCAGGGATGTA

ATTACGTCCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGGGCACGG

GGAAGGTGGCACGGGATCGCTTTCCTCTGAACGCTTCTCGCTGCTCTTTGAGCCTGC

AGACACCTGGGGGGATACGGGGAAAAGGCCTCCAAGGCCAGCTTCCCACAATAAGT

TGGGTGAATTTTGGCTCATTCCTCCTTTCTATAGGATTGAGGTCAGAGCTTTGTGATG

GGAATTCTGTGGAATGTGTGTCAGTTAGGGTGTGGAAAGTCCCgcGATCgcTAGcTTAa gCGCtGATcaATTgGCGCGCCGAATTCGTTatctgcagaattcggcttggcggctgcgcgttcaaacctcccgcttc aaaatggagaccctgcgtgctcactcgggcttaaatacccagcgtgaccacatggtgtcgcaaaatgtcgcaaaacactcacgtgacctcta atacaggacctctagagcatggaaactagataagaaagaaatacgcagagaccaaagttcaactgaaacgaattaaacggtttattgattaa caagcaaactagtttacagattacgggtgaggtaacgggtgccgatggggcgaggctcagaataaacgccatttgtgtcaacagcaaagtc cacatttgtagatttgttgtagttggaagtgtattgaatctctgggttccagcgtttgctgttttctttctgcagctcccattcaatttccacgctg acctgtccggtgctgtactgcgtgatgaacgacgcaaacttagctggactgaaggtagttggaggattcgcgggaacaggtgtattcttaatcag gatctgaggaggcgggtgtttcagtccaaagcctcccatcagcggcgagggatgaaagtgtccgtccgtgtgaggaatcttggcccagata ggaccctgcaggtacacgtcccggtcctgccagaccatgccaggtaaggctccttgactgttgacggtccctgtagcaggagcggtgttgg ccgattgcaggttagtggccaccgtgccgtactcttctgtggccactgggttggtggttttaatttcttcctcgttggttatcataacgttgtcaag gtccacgttgctatttccagctccctgtttcccaaatattaagactccgctcatcggaaaaaatttgtcttcgtcgtccttgtgggttgccatagcg ggaccgggatttaccagagagtctctgccattcagatgatacttggtggcaccggtccaggcaaagttgctgttgttatttgattggttgtcttg -continued gagacgcgttgctgccggtagcagggcccgggtagccagtttttggcctgattcgccatgctactaggcccggcctgagaaaattgcaacg tccgatttcctgcggtaccactcgtggtctgagtccgagacaggtagtacaggtactggtcgatgaggggggttcatcagccggtccaggcttt ggctgtgcgcgtagctgctgtgaaaaggcacgtcctcaaacgtgtagctgaactgaaagttgttgcccgttctcagcatttgagaaggaaag tattccaggcagtagaaggaggaacggcccacggcctgactgccattgttcagagtcaggtacccgtactgaggaatcatgaagacgtcc gccgggaacggaggcaggcagccctggtgcgcagagccgaggacgtacgggagctggtattccgagtccgtaaagacctgaaccgtg ctggtaaggttattggcgatggtcgtggtgccatcattcgtcgtgacctccttgacctggatgttgaagagcttgaagttgagcttcttgggccg gaatccccagttgttgttgatgagtcgctgccagtcacgtggtgagaagtggcagtggaatctgttaaagtcaaaatacccccaggggggtgc tgtagccgaagtaggtgttgtcgttggtgctgcctcccgattggctggagatttgcttgtagaggtggttgttgtaggtggggagggcccagg ttcgggtgctggtggtgatgactctgtcgcccagccatgtggaatcgcaatgccaatttcctgaggcgttacccactccgtcggcgccttcgtt attgtctgccattggagcgccaccgcctgcagccattgtattagatcccacaccagaggggggctgcggggggttctccgagtggttgaggg tcgggcactgactctgagtcgccagtctgcccaaagttgagtctctttctcgcgggctgctggcctttcttgccgatgcccgaagaggagtct ggttcctggggtgattgctctaccggtctcttctttccaggagccgtcttagcgccttcctcaaccagaccgagaggttcgagaacccgcttct tggcctggaagactgctcgcccgaggttgcccccaaaagacgtatcttcttgcagacgctcctgaaactcggcgtcggcgtggttataccgc aggtacggattgtcacccgctttgagctgctggtcgtaggccttgtcgtgctcgagggccgctgcgtccgccgcgttgacgggctccccctt gtcgagtccgttgaagggtccgaggtacttgtagccaggaagcaccagaccccggccgtcgtcctgcttttgctggttggctttgggtttcgg ggctccaggtttcaagtcccaccactcgcgaatgccctcagagaggttgtcctcgagccaatctggaagataaccatcggcagccatacct gatttaaatcatttattgttcaaagatgcagtcatccaaatccacattgaccagatcgcaggcagtgcaagcgtctggcacctttcccatgatat gatgaatgtagcacagtttctgatacgccttttttgacgacagaaacgggttgagattctgacacgggaaagcactctaaacagtctttctgtcc gtgagtgaagcagatatttgaattctgattcattctctcgcattgtctgcagggaaacagcatcagattcatgcccacgtgacgagaacatttgt tttggtacctgtctgcgtagttgatcgaagcttccgcgtctgacgtcgatggctgcgcaactgactcgcgcacccgtttgggctcacttatatct gcgtcactggggggggtcttttcttggctccacccttttgacgtagaattcatgctccacctcaaccacgtgatcctttgcccaccggaaaa agtctttgacttcctgcttggtgaccttcccaaagtcatgatccagacggcgggtgagttcaaatttgaacatccggtcttgcaacggctgctg gtgttcgaaggtcgttgagttcccgtcaatcacggcgcacatgttggtgttggaggtgacgatcacgggagtcgggtctatctgggccgagg acttgcatttctggtccacgcgcaccttgcttcctccgagaatggctttggccgactccacgaccttggcggtcatcttcccctcctcccacca gatcaccatcttgtcgacacagtcgttgaagggaaagttctcattggtccagtttacgcacccgtagaagggcacagtgtgggctatggcctc cgcgatgttggtcttcccggtagttgcaggcccaaacagccagatggtgttcctcttgccgaactttttcgtggcccatcccagaaagacgga agccgcatattggggatcgtacccgtttagttccaaaattttataaatccgattgctggaaatgtcctccacgggctgctggcccaccaggtag tcgggggcggttttagtcaggctcataatctttcccgcattgtccaaggcagccttgatttgggaccgcgagttggaggccgcattgaagga gatgtatgaggcctggtcctcctggatccactgcttctccgaggtaatccccttgtccacgagccacccgaccagctccatgtacctggctga agtttttgatctgatcaccggcgcatcagaattgggattctgattctctttgttctgctcctgcgtctgcgacacgtgcgtcagatgctgcgccac caaccgtttacgctccgtgagattcaaacaggcgctgtggagagaaaggcaaagtggatgtcagtaTCTCTATCACTGATAG GGAGATCTCTATCACTGATAGGGAacttaccttaaatactgttccatattagtccacgcccactggagctcaggctggg ttttggggagcaagtaattggggatgtagcactcatccaccaccttgttcccgcctccggcgccatttctggtctttgtgaccgcgaaccagttt ggcaaagtcggctcgatcccgcggtaaattctctgaatcagtttttcgcgaatctgactcaggaaacgtcccaaaaccatggatttcaccccg gtggtttccacgagcacgtgcatgtggaagtagctctctcccttctcaaattgcacaaagaaaagagcctccggggccttactcacacggcg ccattccgtcagaaagtcgcgctgcagcttctcggccacggtcaggggtgcctgctcaatcagattcagatccatgtcagaatctggcggca actcccattccttctcggccacccagttcacaaagctgtcagaaatgccgggcagatgctcgtcaaggtcgctggggaccttaatcacaatct cgtaaaaccccggcatGGCGGCTGCGCGTTCAAACCTCCCGCTTCAAAATGGAGACCCTGCGT GCTCACTCGGGCgaTCTCTATCACTGATAGGGAGATCTCTATCACTGATAGGGAgaTT AAATAgaatggCTAggATCCGGCCGGccTGCAggTGTCCTCACAGGAACGAAGTCCCTAA

AGAAACAGTGGCAGCCAGGTTTAGCCCCGGAATTGACTGGATTCCTTTTTTAGGGCC

-continued

CATTGGTATGGCTTTTTCCCCGTATCCCCCCAGGTGTCTGCAGGCTCAAAGAGCAGC

GAGAAGCGTTCAGAGGAAAGCGATCCCGTGCCACCTTCCCCGTGCCCGGGCTGTCC

CCGCACGCTGCCGGCTCGGGGATGCGGGGGGAGCGCCGGACCGGAGCGGAGCCCC

GGGCGGCTCGCTGCTGCCCCCTAGCGGGGGAGGGACGTAATTACATCCCTGGGGGC

TTTGGGGGGGGGCTGTCCCTCTAGAGCGGCCGCCACCGCGGTGGAGCTCCAGCTTTT

GTTCCCTTTAGTGAGGGTTAATTAGATCTTAATACGACTCACTATAGGGCGAATTGG

GTACCGGGCCCCCCCTCGAGGTCGACGGTATCGATAAGCTTGATATCTATAACAAGA

AAATATATATATAATAAGTTATCACGTAAGTAGAACATGAAATAACAATATAATTAT

CGTATGAGTTAAATCTTAAAAGTCACGTAAAAGATAATCATGCGTCATTTTGACTCA

CGCGGTCGTTATAGTTCAAAATCAGTGACACTTACCGCATTGACAAGCACGCCTCAC

GGGAGCTCCAAGCGGCGACTGAGATGTCCTAAATGCACAGCGACGGATTCGCGCTA

TTTAGAAAGAGAGAGCAATATTTCAAGAATGCATGCGTCAATTTTACGCAGACTATC

TTTCTAGGGTTAATCTAGCTGCATCAGGATCATATCGTCGGGTCTTTTTTCCGGCTCA

GTCATCGCCCAAGCTGGCGCTATCTGGGCATCGGGGAGGAAGAAGCCCGTGCCTTTT

CCCGCGAGGTTGAAGCGGCATGGAAAGAGTTTGCCGAGGATGACTGCTGCTGCATT

GACGTTGAGCGAAAACGCACGTTTACCATGATGATTCGGGAAGGTGTGGCCATGCA

CGCCTTTAACGGTGAACTGTTCGTTCAGGCCACCTGGGATACCAGTTCGTCGCGGCT

TTTCCGGACACAGTTCCGGATGGTCAGCCCGAAGCGCATCAGCAACCCGAACAATA

CCGGCGACAGCCGGAACTGCCGTGCCGGTGTGCAGATTAATGACAGCGGTGCGGCG

CTGGGATATTACGTCAGCGAGGACGGGTATCCTGGCTGGATGCCGCAGAAATGGAC

ATGGATACCCCGTGAGTTACCCGGCGGGCGCGCTTGGCGTAATCATGGTCATAGCTG

TTTCCTGTGTGAAATTGTTATCCGCTCACAATTCCACACAACATACGAGCCGGAAGC

ATAAAGTGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAATGAATC

GGCCAACGCGCGGGGAGAGGCGGTTTGCGTATTGGGCGCTCTTCCGCTTCCTCGCTC

ACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGC

AAAAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGTGG

CGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGTGTAGGTC

GTTCGCTCCAAGCTGGGCTGTGTGCACGAACCCCCCGTTCAGCCCGACCGCTGCGCC

TTATCCGGTAACTATCGTCTTGAGTCCAACCCGGTAAGACACGACTTATCGCCACTG

GCAGCAGCCACTGGTAACAGGATTAGCAGAGCGAGGTATGTAGGCGGTGCTACAGA

GTTCTTGAAGTGGTGGCCTAACTACGGCTACACTAGAAGGACAGTATTTGGTATCTG

CGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCAC

-continued

CTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCTG

TCTATTTCGTTCATCCATAGTTGCCTGACTCCCCGTCGTGTAGATAACTACGATACGG

GAGGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAAGCTAGAGT

AAGTAGTTCGCCAGTTAATAGTTTGCGCAACGTTGTTGCCATTGCTACAGGCATCGT

GGTGTCACGCTCGTCGTTTGGTATGGCTTCATTCAGCTCCGGTTCCCAACGATCAAG

GCGAGTTACATGATCCCCCATGTTGTGCAAAAAAGCGGTTAGCTCCTTCGGTCCTCC

GATCGTTGTCAGAAGTAAGTTGGCCGCAGTGTTATCACTCATGGTTATGGCAGCACT

GCATAATTCTCTTACTGTCATGCCATCCGTAAGATGCTTTTCTGTGACTGGTGAGTAC

TCAACCAAGTCATTCTGAGAATAGTGTATGCGGCGACCGAGTTGCTCTTGCCCGGCG

TCAATACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCG

ATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGAC

ACGGAAATGTTGAATACTCAT

The sequence for the pcDNA-TetR-Ins construct illustrated in in FIG. 12A is shown below:

pcDNA-TetR-Ins (7147 bp)

(SEQ ID NO: 31)

gacggatcgggagatctgagctcacggggacagcccccccccaaagcccccagggatgtaattacgtccctcccccgct agggggcagcagcgagccgcccggggctccgctccggtccggcgctccccccgcatccccgagccggcagcgtgcggggacagcc cgggcacggggaaggtggcacgggatcgctttcctctgaacgcttctcgctgctctttgagcctgcagacacctgggggggatacggggaa aaagctttaggctgaaagagagatttagaatgacagaatcatagaacggcctgggttgcaaaggagcacagtgctcatccagatccaaccc cctgctatgtgcagggtcatcaaccagcagcccaggctgcccagagccacatccagcctggccttgaatgcctgcaggcccgatcccctat ggtcgactctcagtacaatctgctctgatgccgcatagttaagccagtatctgctccctgcttgtgtgttggaggtcgctgagtagtgcgcgag caaaatttaagctacaacaaggcaaggcttgaccgacaattgcatgaagaatctgcttagggttaggcgttttgcgctgcttcgcgatgtacg ggccagatatacgcgttgacattgattattgactagttattaatagtaatcaattacggggtcattagttcatagcccatatatggagttccgcgtt acataacttacggtaaatggcccgcctggctgaccgcccaacgacccccgcccattgacgtcaataatgacgtatgttcccatagtaacgcc aatagggactttccattgacgtcaatgggtggactatttacggtaaactgcccacttggcagtacatcaagtgtatcatatgccaagtacgccc cctattgacgtcaatgacggtaaatggcccgcctggcattatgcccagtacatgaccttatgggactttcctacttggcagtacatctacgtatt agtcatcgctattaccatggtgatgcggttttggcagtacatcaatgggcgtggatagcggtttgactcacggggatttccaagtctccacccc attgacgtcaatgggagtttgttttggcaccaaaatcaacgggactttccaaaatgtcgtaacaactccgccccattgacgcaaatgggcggt aggcgtgtacggtgggaggtctatataagcagagctctctggctaactagagaacccactgcttactggcttatcgaaattaatacgactcac tatagggagacccaagctggctagcgtttaaacttaagctttctgtgagtttggggacccttgattgttctttctttttcgctattgtaaaattcatgt tatatggagggggcaaagttttcagggtgttgtttagaatgggaagatgtcccttgtatcaccatggaccctcatgataattttgtttctttcactttc tactctgttgacaaccattgtctcctcttattttcttttcattttctgtaactttttcgttaaactttagcttgcatttgtaacgaattttaaattca cttttgtttatttgtcagattgtaagtactttctctaatcactttttttcaaggcaatcagggtatattatattgtacttcagcacagttttagagaa caattgttataattaaatgataaggtagaatatttctgcatataaattctggctggcgtggaaatattcttattggtagaaacaactacatcctggtca tcatcctgcctttctctttatggttacaatgatatacactgtttgagatgaggataaaatactctgagtccaaaccgggcccctctgctaaccatgttc -continued atgccttcttctttttcctacagctcctgggcaacgtgctggttattgtgctgtctcatcattttggcaaagaattgtaatacgactcactatagggcg agccaccatggctagattagataaaagtaaagtgattaacagcgcattagagctgcttaatgaggtcggaatcgaaggtttaacaacccgtaaactcg cccagaagctaggtgtagagcagcctacattgtattggcatgtaaaaaataagcgggctttgctcgacgccttagccattgagatgttagata ggcaccatactcacttttgccctttagaaggggaaagctggcaagatttttacgtaataacgctaaaagttttagatgtgctttactaagtcatc gcgatggagcaaaagtacatttaggtacacggcctacagaaaaacagtatgaaactctcgaaaatcaattagcctttttatgccaacaaggttt ttcactagagaatgccttatatgcactcagcgccgtggggcattttactttaggttgcgtattggaagatcaagagcatcaagtcgctaaagaa gaaagggaaacacctactactgatagtatgccgccattattacgacaagctatcgaattatttgatcaccaaggtgcagagccagccttcttat tcggccttgaattgatcatatgcggattagaaaaacaacttaaatgtgaaagtgggtccccaaaaaagaagagaaaggtcgacggcggtgg ttcagtttaagcgtacagcgggatccactagtccagtgtggtggaattctgcagatatccagcacagtggcggccgctcgagtctagagggc ccgtttaaacccgctgatcagcctcgactgtgccttctagttgccagccatctgttgtttgcccctcccccgtgccttccttgaccctggaaggt gccactcccactgtcctttcctaataaaatgaggaaattgcatcgcattgtctgagtaggtgtcattctattctggggggtggggtggggcagg acagcaagggggaggattgggaagacaatagcaggcatgctggggatgcggtgggctctatggcttctgaggcggaaagaaccagctg gggctctagggggtatccccacgcgccctgtagcggcgcattaagcgcggcgggtgtggtggttacgcgcagcgtgaccgctacacttg ccagcgccctagcgcccgctcctttcgctttcttcccttcctttctcgccacgttcgccggctttccccgtcaagctctaaatcgggcatccctt tagggttccgatttagtgctttacggcacctcgaccccaaaaaacttgattagggtgatggttcacgtagtgggccatcgccctgatagacgg tttttcgccctttgacgttggagtccacgttctttaatagtggactcttgttccaaactggaacaacactcaaccctatctcggtctattcttttgatt tataagggattttggggatttcggcctattggttaaaaaatgagctgatttaacaaaaatttaacgcgaattaattctgtggaatgtgtgtcagttag ggtgtggaaagtccccaggctccccaggcaggcagaagtatgcaaagcatgcatctcaattagtcagcaaccaggtgtggaaagtcccca ggctccccagcaggcagaagtatgcaaagcatgcatctcaattagtcagcaaccatagtcccgcccctaactccgcccatcccgcccctaa ctccgcccagttccgcccattctccgccccatggctgactaattttttttatttatgcagaggccgaggccgcctctgcctctgagctattccag aagtagtgaggaggcttttttggaggcctaggcttttgcaaaaagctcccgggagcttgtatatccatttcggatctgatcagcacgtgttgac aattaatcatcggcatagtatatcggcatagtataatacgacaaggtgaggaactaaaccatggccaagttgaccagtgccgttccggtgctc accgcgcgcgacgtcgccggagcggtcgagttctggaccgaccggctcgggttctcccgggacttcgtggaggacgacttcgccggtgt ggtccgggacgacgtgaccctgttcatcagcgcggtccaggaccaggtggtgccggacaacaccctggcctgggtgtgggtgcgcggc ctggacgagctgtacgccgagtggtcggaggtcgtgtccacgaacttccgggacgcctccgggccggccatgaccgagatcggcgagc agccgtgggggcgggagttcgccctgcgcgacccggccggcaactgcgtgcacttcgtggccgaggagcaggactgacacgtgctac gagatttcgattccaccgccgccttctatgaaaggttgggcttcggaatcgttttccgggacgccggctggatgatcctccagcgcggggat ctcatgctggagttcttcgcccaccccaacttgtttattgcagcttataatggttacaaataaagcaatagcatcacaaatttcacaaataaagca tttttttcactgcattctagttgtggtttgtccaaactcatcaatgtatcttatcatgtctgtataccgtcgacctctagctagagcttggcgtaatca tggtcatagctgtttcctgtgtgaaattgttatccgctcacaattccacacaacatacgagccggaagcataaagtgtaaagcctggggtgccta atgagtgagctaactcacattaattgcgttgcgctcactgcccgctttccagtcgggaaacctgtcgtgccagctgcattaatgaatcggccaa cgcgcggggagaggcggtttgcgtattgggcgctcttccgcttcctcgctcactgactcgctgcgctcggtcgttcggctgcggcgagcgg tatcagctcactcaaaggcggtaatacggttatccacagaatcaggggataacgcaggaaagagagctcacggggacagcccccccca aagcccccagggatgtaattacgtccctcccccgctagggggcagcagcgagccgcccggggctccgctccggtccggcgctcccccc gcatccccgagccggcagcgtgcggggacagcccgggcacggggaaggtggcacgggatcgctttcctctgaacgcttctcgctgctct ttgagcctgcagacacctgggggatacggggaaaaagctttaggctgaaagagagatttagaatgacagaatcatagaacggcctgggt tgcaaaggagcacagtgctcatccagatccaacccccctgctatgtgcagggtcatcaaccagcagcccaggctgcccagagccacatcca gcctggccttgaatgcctgcaggacatgtgagcaaaaggccagcaaaaggccaggaaccgtaaaaaggccgcgttgctggcgtttttcca taggctccgcccccctgacgagcatcacaaaaatcgacgctcaagtcagaggtggcgaaacccgacaggactataaagataccaggcgt ttcccccctggaagctccctcgtgcgctctcctgttccgaccctgccgcttaccggatacctgtccgcctttctcccttcgggaagcgtggcgct -continued ttctcaatgctcacgctgtaggtatctcagttcggtgtaggtcgttcgctccaagctgggctgtgtgcacgaaccccccgttcagcccgaccg ctgcgccttatccggtaactatcgtcttgagtccaacccggtaagacacgacttatcgccactggcagcagccactggtaacaggattagca gagcgaggtatgtaggcggtgctacagagttcttgaagtggtggcctaactacggctacactagaaggacagtatttggtatctgcgctctgc tgaagccagttaccttcggaaaaagagttggtagctcttgatccggcaaacaaaccaccgctggtagcggtggtttttttgtttgcaagcagca gattacgcgcagaaaaaaaggatctcaagaagatcctttgatcttttctacggggtctgacgctcagtggaacgaaaactcacgttaagggat tttggtcatgagattatcaaaaaggatcttcacctagatccttttaaattaaaaatgaagttttaaatcaatctaaagtatatatgagtaaacttggtc tgacagttaccaatgcttaatcagtgaggcacctatctcagcgatctgtctatttcgttcatccatagttgcctgactccccgtcgtgtagataact acgatacgggagggcttaccatctggccccagtgctgcaatgataccgcgagacccacgctcaccggctccagatttatcagcaataaacc agccagccggaagggccgagcgcagaagtggtcctgcaactttatccgcctccatccagtctattaattgttgccgggaagctagagtaagt agttcgccagttaatagtttgcgcaacgttgttgccattgctacaggcatcgtggtgtcacgctcgtcgtttggtatggcttcattcagctccggt tcccaacgatcaaggcgagttacatgatcccccatgttgtgcaaaaaagcggttagctccttcggtcctccgatcgttgtcagaagtaagttg gccgcagtgttatcactcatggttatggcagcactgcataattctcttactgtcatgccatccgtaagatgcttttctgtgactggtgagtactcaa ccaagtcattctgagaatagtgtatgcggcgaccgagttgctcttgcccggcgtcaatacgggataataccgcgccacatagcagaacttta aaagtgctcatcattggaaaacgttcttcggggcgaaaactctcaaggatcttaccgctgttgagatccagttcgatgtaacccactcgtgcac ccaactgatcttcagcatcttttactttcaccagcgtttctgggtgagcaaaaacaggaaggcaaaatgccgcaaaaaagggaataagggcg tacacggaaatgttgaatactcatactcttcctttttcaatattattgaagcatttatcagggttattgtctcatgagcggatacatatttgaatgtatt agaaaaataaacaaataggggttccgcgcacatttccccgaaaagtgccacctgacgtc The sequence for the pcDNA-TetR-KRAB-Ins construct illustrated in in FIG. 12B is shown below:

pcDNA-TetR-KRAB-Ins (7493 bp)

(SEQ ID NO: 32)

gacggatcgggagatctgagctcacggggacagcccccccccaaagcccccagggatgtaattacgtccctcccccgct agggggcagcagcgagccgcccggggctccgctccggtccggcgctccccccgcatccccgagccggcagcgtgcggggacagcc cgggcacggggaaggtggcacgggatcgctttcctctgaacgcttctcgctgctctttgagcctgcagacacctgggggggatacggggaa aaagctttaggctgaaagagagatttagaatgacagaatcatagaacggcctgggttgcaaaggagcacagtgctcatccagatccaaccc cctgctatgtgcagggtcatcaaccagcagcccaggctgcccagagccacatccagcctggccttgaatgcctgcaggcccgatcccctat ggtcgactctcagtacaatctgctctgatgccgcatagttaagccagtatctgctccctgcttgtgtgttggaggtcgctgagtagtgcgcgag caaaatttaagctacaacaaggcaaggcttgaccgacaattgcatgaagaatctgcttagggttaggcgttttgcgctgcttcgcgatgtacg ggccagatatacgcgttgacattgattattgactagttattaatagtaatcaattacggggtcattagttcatagcccatatatggagttccgcgtt acataacttacggtaaatggcccgcctggctgaccgcccaacgacccccgcccattgacgtcaataatgacgtatgttcccatagtaacgcc aatagggactttccattgacgtcaatgggtggactatttacggtaaactgcccacttggcagtacatcaagtgtatcatatgccaagtacgccc cctattgacgtcaatgacggtaaatggcccgcctggcattatgcccagtacatgaccttatgggactttcctacttggcagtacatctacgtatt agtcatcgctattaccatggtgatgcggttttggcagtacatcaatgggcgtggatagcggtttgactcacggggatttccaagtctccacccc attgacgtcaatgggagtttgttttggcaccaaaatcaacgggactttccaaaatgtcgtaacaactccgccccattgacgcaaatgggcggt aggcgtgtacggtgggaggtctatataagcagagctctctggctaactagagaacccactgcttactggcttatcgaaattaatacgactcac tatagggagacccaagctggctagcgtttaaacttaagctttctgtgagtttggggacccttgattgttctttctttttcgctattgtaaaattcatgtt atatggagggggcaaagttttcagggtgttgtttagaatgggaagatgtcccttgtatcaccatggaccctcatgataatttgtttctttcactttc tactctgttgacaaccattgtctcctcttattttcttttcattttctgtaactttttcgttaaactttagcttgcatttgtaacgaattttaaattcactttt gtttatttgtcagattgtaagtactttctctaatcactttttttcaaggcaatcagggtatattatattgtacttcagcacagttttagagaacaattgttat aattaaatgataaggtagaatatttctgcatataaattctggctggcgtggaaatattcttattggtagaaacaactacatcctggtcatcatcctgc ctttctctttatggttacaatgatatacactgtttgagatgaggataaaatactctgagtccaaaccgggcccctctgctaaccatgttcatgcctt -continued cttctttttcctacagctcctgggcaacgtgctggttattgtgctgtctcatcattttggcaaagaattgtaatacgactcactatagggcgagcca ccatggctagattagataaaagtaaagtgattaacagcgcattagagctgcttaatgaggtcggaatcgaaggtttaacaacccgtaaactcg cccagaagctaggtgtagagcagcctacattgtattggcatgtaaaaaataagcgggctttgctcgacgccttagccattgagatgttagata ggcaccatactcacttttgccctttagaaggggaaagctggcaagatttttacgtaataacgctaaaagttttagatgtgctttactaagtcatc gcgatggagcaaaagtacatttaggtacacggcctacagaaaaacagtatgaaactctcgaaaatcaattagcctttttatgccaacaaggttt ttcactagagaatgccttatatgcactcagcgccgtggggcattttactttaggttgcgtattggaagatcaagagcatcaagtcgctaaagaa gaaagggaaacacctactactgatagtatgccgccattattacgacaagctatcgaattatttgatcaccaaggtgcagagccagccttcttat tcggccttgaattgatcatatgcggattagaaaaacaacttaaatgtgaaagtgggtccccaaaaaagaagagaaaggtcgacggcggtgg tgctttgtctcctcagcactctgctgtcactcaaggaagtatcatcaagaacaaggagggcatggatgctaagtcactaactgcctggtcccg gacactggtgaccttcaaggatgtatttgtggacttcaccagggaggagtggaagctgctggacactgctcagcagatcgtgtacagaaatg tgatgctggagaactataagaacctggtttccttgggttatcagcttactaagccagatgtgatcctccggttggagaagggagaagagccct ggctggtggagagagaaattcaccaagagacccatcctgattcagagactgcatttgaaatcaaatcatcagtttaagcgtacagcggggat ccactagtccagtgtggtggaattctgcagatatccagcacagtggcggccgctcgagtctagagggcccgtttaaacccgctgatcagcct cgactgtgccttctagttgccagccatctgttgtttgcccctcccccgtgccttccttgaccctggaaggtgccactcccactgtcctttcctaat aaaatgaggaaattgcatcgcattgtctgagtaggtgtcattctattctggggggtggggtggggcaggacagcaagggggaggattggg aagacaatagcaggcatgctggggatgcggtgggctctatggcttctgaggcggaaagaaccagctggggctctagggggtatccccac gcgccctgtagcggcgcattaagcgcggcgggtgtggtggttacgcgcagcgtgaccgctacacttgccagcgccctagcgcccgctcc tttcgctttcttcccttcctttctcgccacgttcgccggctttccccgtcaagctctaaatcggggcatccctttagggttccgatttagtgctttac ggcacctcgaccccaaaaaacttgattagggtgatggttcacgtagtgggccatcgccctgatagacggtttttcgccctttgacgttggagt ccacgttctttaatagtggactcttgttccaaactggaacaacactcaaccctatctcggtctattcttttgatttataagggattttggggatttcg gcctattggttaaaaaatgagctgatttaacaaaaatttaacgcgaattaattctgtggaatgtgtgtcagttagggtgtggaaagtccccaggc tccccaggcaggcagaagtatgcaaagcatgcatctcaattagtcagcaaccaggtgtggaaagtccccaggctccccagcaggcagaa gtatgcaaagcatgcatctcaattagtcagcaaccatagtcccgcccctaactccgcccatcccgcccctaactccgcccagttccgcccatt ctccgccccatggctgactaattttttttatttatgcagaggccgaggccgcctctgcctctgagctattccagaagtagtgaggaggcttttttg gaggcctaggcttttgcaaaaagctcccgggagcttgtatatccattttcggatctgatcagcacgtgttgacaattaatcatcggcatagtata tcggcatagtataatacgacaaggtgaggaactaaaccatggccaagttgaccagtgccgttccggtgctcaccgcgcgcgacgtcgccg gagcggtcgagttctggaccgaccggctcgggttctcccgggacttcgtggaggacgacttcgccggtgtggtccgggacgacgtgacc ctgttcatcagcgcggtccaggaccaggtggtgccggacaacaccctggcctgggtgtgggtgcgcggcctggacgagctgtacgccga gtggtcggaggtcgtgtccacgaacttccgggacgcctccgggccggccatgaccgagatcggcgagcagccgtgggggcgggagttc gccctgcgcgacccggccggcaactgcgtgcacttcgtggccgaggagcaggactgacacgtgctacgagatttcgattccaccgccgc cttctatgaaaggttgggcttcggaatcgttttccgggacgccggctggatgatcctccagcgcggggatctcatgctggagttcttcgccca ccccaacttgtttattgcagcttataatggttacaaataaagcaatagcatcacaaatttcacaaataaagcatttttttcactgcattctagttgtg gtttgtccaaactcatcaatgtatcttatcatgtctgtataccgtcgacctctagctagagcttggcgtaatcatggtcatagctgtttcctgtgtga aattgttatccgctcacaattccacacaacatacgagccggaagcataaagtgtaaagcctggggtgcctaatgagtgagctaactcacatta attgcgttgcgctcactgcccgctttccagtcgggaaacctgtcgtgccagctgcattaatgaatcggccaacgcgcggggagaggcggttt gcgtattgggcgctcttccgcttcctcgctcactgactcgctgcgctcggtcgttcggctgcggcgagcggtatcagctcactcaaaggcgg taatacggttatccacagaatcaggggataacgcaggaaagagagctcacggggacagccccccccaaagcccccagggatgtaatta cgtccctcccccgctagggggcagcagcgagccgcccggggctccgctccggtccggcgctccccccgcatccccgagccggcagcg tgcggggacagcccgggcacggggaaggtggcacgggatcgctttcctctgaacgcttctcgctgctctttgagcctgcagacacctggg gggatacggggaaaaagctttaggctgaaagagagatttagaatgacagaatcatagaacggcctgggttgcaaaggagcacagtgctca -continued

```
tccagatccaacccccctgctatgtgcagggtcatcaaccagcagcccaggctgcccagagccacatccagcctggccttgaatgcctgca

ggacatgtgagcaaaaggccagcaaaaggccaggaaccgtaaaaaggccgcgttgctggcgtttttccataggctccgcccccctgacg

agcatcacaaaaatcgacgctcaagtcagaggtggcgaaacccgacaggactataaagataccaggcgtttccccctggaagctccctcg

tgcgctctcctgttccgaccctgccgcttaccggatacctgtccgcctttctcccttcgggaagcgtggcgctttctcaatgctcacgctgtagg

tatctcagttcggtgtaggtcgttcgctccaagctgggctgtgtgcacgaaccccccgttcagcccgaccgctgcgccttatccggtaactat

cgtcttgagtccaacccggtaagacacgacttatcgccactggcagcagccactggtaacaggattagcagagcgaggtatgtaggcggt

gctacagagttcttgaagtggtggcctaactacggctacactagaaggacagtatttggtatctgcgctctgctgaagccagttaccttcggaa

aaagagttggtagctcttgatccggcaaacaaaccaccgctggtagcggtggtttttttgtttgcaagcagcagattacgcgcagaaaaaaa

ggatctcaagaagatcctttgatcttttctacggggtctgacgctcagtggaacgaaaactcacgttaagggattttggtcatgagattatcaaa

aaggatcttcacctagatccttttaaattaaaaatgaagttttaaatcaatctaaagtatatatgagtaaacttggtctgacagttaccaatgcttaa

tcagtgaggcacctatctcagcgatctgtctatttcgttcatccatagttgcctgactccccgtcgtgtagataactacgatacgggagggctta

ccatctggccccagtgctgcaatgataccgcgagacccacgctcaccggctccagatttatcagcaataaaccagccagccggaagggcc

gagcgcagaagtggtcctgcaactttatccgcctccatccagtctattaattgttgccgggaagctagagtaagtagttcgccagttaatagttt

gcgcaacgttgttgccattgctacaggcatcgtggtgtcacgctcgtcgtttggtatggcttcattcagctccggttcccaacgatcaaggcga

gttacatgatcccccatgttgtgcaaaaaagcggttagctccttcggtcctccgatcgttgtcagaagtaagttggccgcagtgttatcactcat

ggttatggcagcactgcataattctcttactgtcatgccatccgtaagatgcttttctgtgactggtgagtactcaaccaagtcattctgagaata

gtgtatgcggcgaccgagttgctcttgcccggcgtcaatacgggataataccgcgccacatagcagaactttaaaagtgctcatcattggaa

aacgttcttcggggcgaaaactctcaaggatcttaccgctgttgagatccagttcgatgtaacccactcgtgcacccaactgatcttcagcatc

ttttactttcaccagcgtttctgggtgagcaaaaacaggaaggcaaaatgccgcaaaaaagggaataagggcgacacggaaatgttgaata

ctcatactcttcctttttcaatattattgaagcatttatcagggttattgtctcatgagcggatacatatttgaatgtatttagaaaaataaacaaatag

gggttccgcgcacatttccccgaaaagtgccacctgacgtc
```

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. An isolated Chinese hamster ovary (CHO) cell or an isolated human embryonic kidney (HEK) cell for producing an adeno-associated virus (AAV), comprising:

a nucleic acid sequence comprising:

i) a nucleotide sequence encoding the adenovirus helper E2A and E4Orf6 proteins under control of a first derepressible promoter comprising a functional promoter and two tetracycline operator sequences ($TetO_2$);

ii) a nucleotide sequence encoding the AAV gene comprising a) a rep78 protein coding region under control of a second derepressible promoter comprising a p5 promoter and $TetO_2$; b) a cap protein coding region under control of the second derepressible promoter or a p40 native promoter; and c) a rep52 coding region under control of a third derepressible promoter comprised of a p19 promoter and $TetO_2$;

iii) a nucleotide sequence encoding adenovirus viral-associated (VA I) non-coding RNA under control of a fourth depressible promoter comprising a functional promoter and $TetO_2$;

iv) two adenovirus inverted terminal repeat (ITR) sequences; and v) a repressor element of the first, second, third, and fourth derepressible promoters under the control of a constitutive promoter, wherein the nucleic acid molecule is integrated into the isolated CHO or isolated HEK cell's genomic DNA and/or is maintained by the isolated CHO or isolated HEK cell extra-chromosomally.

2. The isolated CHO or isolated HEK cell of claim 1, wherein the isolated CHO or isolated HEK cell is an isolated CHO or isolated HEK cell culture.

3. The isolated CHO or isolated HEK cell of claim 2, wherein the isolated CHO or isolated HEK cell culture is a suspension culture.

4. The isolated CHO or isolated HEK cell of claim 1, further comprising an internal ribosome entry site (IRES) element between the e2a and e4orf6 encoding regions.

5. The isolated CHO or isolated HEK cell of claim 1, wherein the rep52 coding region is under control of the third derepressible promoter comprising the p19 promoter and $TetO_2$ contained within an artificial intron.

6. The isolated CHO or isolated HEK cell of claim 1, wherein the functional promoter of the first derepressible promoter is a cytomegalovirus (CMV) promoter.

7. The isolated CHO or isolated HEK cell of claim 1, wherein the repressor element is a tetracycline repressor protein.

8. The isolated CHO or isolated HEK cell of claim 7, further comprising a nucleic acid encoding a transcriptional repression domain in frame with the nucleic acid encoding the tetracycline repressor protein.

9. The isolated CHO or isolated HEK cell of claim 1, further comprising a nucleic acid molecule encoding a gene of interest.

* * * * *